(12) United States Patent
Qian et al.

(10) Patent No.: US 7,795,448 B2
(45) Date of Patent: *Sep. 14, 2010

(54) IMIDAZOYL-BENZAMIDE ANTI-CANCER AGENTS

(75) Inventors: Xiangping Qian, South San Francisco, CA (US); Andrew I. McDonald, South San Francisco, CA (US); Han-Jie Zhou, South San Francisco, CA (US); Luke W. Ashcraft, South San Francisco, CA (US); Bing Yao, South San Francisco, CA (US); Hong Jiang, South San Francisco, CA (US); Jennifer Kuo Chen Huang, South San Francisco, CA (US); Jianchao Wang, South San Francisco, CA (US); David J. Morgans, Jr., South San Francisco, CA (US); Bradley P. Morgan, South San Francisco, CA (US); Gustave Bergnes, South San Francisco, CA (US); Dashyant Dhanak, Philadelphia, PA (US); Steven D. Knight, Philadelphia, PA (US); Nicholas D. Adams, Philadelphia, PA (US); Cynthia A. Parrish, Philadelphia, PA (US); Kevin Duffy, Philadelphia, PA (US); Duke Fitch, Philadelphia, PA (US); Rosanna Tedesco, Philadelphia, PA (US)

(73) Assignee: Cytokinetics, Incorporated, South San Francisco, CA (US)

( * ) Notice: Subject to any disclaimer, the term of this patent is extended or adjusted under 35 U.S.C. 154(b) by 871 days.

This patent is subject to a terminal disclaimer.

(21) Appl. No.: 11/124,608

(22) Filed: May 6, 2005
(Under 37 CFR 1.47)

(65) Prior Publication Data
US 2007/0197481 A1 Aug. 23, 2007

Related U.S. Application Data

(63) Continuation-in-part of application No. 11/121,709, filed on May 3, 2005.

(60) Provisional application No. 60/569,510, filed on May 6, 2004.

(51) Int. Cl.
C07D 233/64 (2006.01)
C07D 231/12 (2006.01)
A61K 31/415 (2006.01)
A61K 31/4164 (2006.01)

(52) U.S. Cl. .................. 548/338.1; 548/375.1; 514/399; 514/406

(58) Field of Classification Search .................. 514/396, 514/406, 399; 548/338.1, 375.1
See application file for complete search history.

(56) References Cited

U.S. PATENT DOCUMENTS

| | | |
|---|---|---|
| 3,978,071 A | 8/1976 | Nakanishi et al. |
| 4,431,851 A | 2/1984 | Moinet et al. |
| 4,579,866 A | 4/1986 | Stevenson et al. |
| 5,158,959 A | 10/1992 | Geiger et al. |
| 5,401,766 A | 3/1995 | Geiger et al. |

(Continued)

FOREIGN PATENT DOCUMENTS

| | | |
|---|---|---|
| DE | 2 905 883 A1 | 8/1980 |
| FR | 8.005 M | 7/1970 |
| JP | 52113992 | 9/1977 |
| JP | 61-000054 | 1/1986 |
| WO | WO 97/08133 A1 | 3/1997 |
| WO | WO 98/56756 A1 | 12/1998 |
| WO | WO 99/10312 A1 | 3/1999 |
| WO | WO 99/61410 A1 | 12/1999 |

(Continued)

OTHER PUBLICATIONS

Cox et. al. "Kinesin spindle protein (KSP) inhibitors. Part 1: The discovery of 3,5-diaryl-4,5-dihydropyrazoles as potent and selective inhibitors of the mitotic kinesin KSP" Bioorganic & Medicinal Chemistry Letters 2005 15, 2041-2045.*

(Continued)

*Primary Examiner*—Janet L Andres
*Assistant Examiner*—David K O'Dell
(74) *Attorney, Agent, or Firm*—Finnegan, Henderson, Farabow, Garrett & Dunner LLP

(57) ABSTRACT

Provided are compounds of Formula V and pharmaceutically acceptable salts thereof which may be useful for the treatment of cancer or other proliferative disorders.

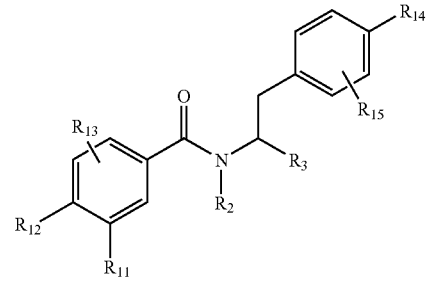

Formula V

10 Claims, No Drawings

U.S. PATENT DOCUMENTS

| | | | |
|---|---|---|---|
| 6,204,282 | B1 | 3/2001 | Neustadt et al. |
| 6,214,877 | B1 | 4/2001 | Butera et al. |
| 6,545,004 | B1 | 4/2003 | Finer et al. |
| 6,908,929 | B2 | 6/2005 | Breitenbucher et al. |
| 7,504,413 | B2 | 3/2009 | Qian et al. |
| 2002/0183249 | A1 | 12/2002 | Taylor et al. |
| 2005/0075356 | A1 | 4/2005 | Di Francesco et al. |
| 2006/0094708 | A1 | 5/2006 | Qian et al. |
| 2006/0247289 | A1 | 11/2006 | Qian et al. |
| 2007/0149516 | A1 | 6/2007 | Qian et al. |
| 2007/0197640 | A1 | 8/2007 | Qian et al. |
| 2008/0255182 | A1 | 10/2008 | Qian et al. |

FOREIGN PATENT DOCUMENTS

| | | |
|---|---|---|
| WO | WO 00/39077 A2 | 7/2000 |
| WO | WO 01/44154 A1 | 6/2001 |
| WO | WO 01/68619 A1 | 9/2001 |
| WO | WO 02/18327 A2 | 3/2002 |
| WO | WO 02/096864 A1 | 12/2002 |
| WO | WO 2004/004652 A2 | 1/2004 |
| WO | WO 2004/056784 A1 | 7/2004 |
| WO | WO 2004/071448 A1 | 8/2004 |
| WO | WO 2004/087720 A1 | 10/2004 |

OTHER PUBLICATIONS

Tarby et. al. "Inhibitors of human mitotic kinesin Eg5: Characterization of the 4-phenyl-tetrahydroisoquinoline lead series" Bioorganic & Medicinal Chemistry Letters 2006, 16, 2095-2100.*

Sunder-Plassman et. al."Synthesis and biological evaluation of new tetrahydro-b-carbolines as inhibitors of the mitotic kinesin Eg5" Bioorganic & Medicinal Chemistry 2005, 13, 6094-6111.*

Dorwald, F.A. Side Reactions in Organic Synthesis, 2005, Wiley: VCH, Weinheim p. IX of Preface.

Hyun, et al. "Improved Chiral Stationary Phase Derived from (S)-Naproxen for the Liquid Chromatographic Resolution of Enantiomers," J. Chromatogr. A, 732: 209-214 (1996).

Jackson, et al. Journal of Organic Chemistry, 1998, 63, 7875-7884.

Kim et al. "Synthesis and SAR of pyrrolotriazine-4-one based Eg5 Inhibitors," Bioorganic & Medicinal Chemistry Letters, 2006, 16, 3937-3942.

Kosolapoff, G.M. Journal of the American Chemical Society, 1953, 75, 3596-3597.

"Lithium Aluminium Hydride" Paquette, L. In Encyclopedia of Reagents for Organic Synthesis Online Posting Date: Oct. 15, 2004 2004 John Wiley & Sons, Ltd. "http://www.mrw.interscience.wiley.com/eros/articles/rl036/frame.html".

Office Action dated May 29, 2007 for U.S. Appl. No. 11/271,147.

Notice of Allowance dated Oct. 29, 2007 for U.S. Appl. No. 11/271,147.

International Search Report and Written Opinion, mailed May 4, 2006, for International Application No. PCT/US05/15666, filed May 6, 2005.

International Search Report and Written Opinion, mailed Sep. 24, 2007 for International Application No. PCT/US06/43514, filed Nov. 8, 2006.

International Search Report, dated Sep. 7, 2007, for International Application No. PCT/US2006/042801, filed Nov. 2, 2005.

Supplemental Partial European Search Report completed Nov. 27, 2007 for European application No. EP 05 76 2665.

Arndts et al., "Evaluation of clonidine plasma levels in man using a highly sensitive radioimmunoassay," Methods Clin. Pharmacol., Proc. Int. Symp., Meeting Date 1979, 279-86 (1980).

Bebernitz et al., "Anilides of (R)-trifluoro-2-hydroxy-2-methylpropionic acid as inhibitors of pyruvate dehydrogenase kinase," Journal of Medicinal Chemistry, 43(11), 2248-57 (2000).

Breysse et al., "Potential psychotropic agents. V. Synthesis and pharmacological study of 4-alkoxy-3,5-dihalobenzoyl hydrazines inhibiting monoamine oxidase," Chimica Therapeutica, 4(3), 157-66 (1969).

Gombar et al., "Quantitative structure-activity relationship studies: β-adrenergic blocking activity of 1-(2,4-disubstituted phenoxy)-3-aminopropan-2-ols," European Journal of Medicinal Chemistry, 25(8), 689-95 (1990).

Iwamura et al., "Prophylactic effect of JTE-607 on LPS-induced acute lung injury in rats with CINC-1 inhibition," Inflammation Research, 51(3), 160-66 (2002).

Kakutani et al, "JTE-607, a novel inflammatory cytokine synthesis inhibitor without immunosuppression, protects from endotoxin shock in mice," Inflammation Research, 48(8), 461-468 (1999).

Smith, "β-Adrenergic blocking agents. 13. (3-Amino-2-hydroxypropoxy)benzamides," Journal of Medicinal Chemistry, 19(9), 1119-23 (1976).

Qian et al., U.S. Appl. No. 11/121,709, filed May 3, 2005, entitled "Certain Chemical Entities, Compositions, and Methods," 312 pages.

Chemical Abstracts Registry No. 22476-72-8.

Chemical Abstracts Registry No. 315675-64-0.

Chemical Abstracts Registry No. 356550-38-4.

Chemical Abstracts Registry No. 506428-81-5.

Office Action dated May 20, 2008 for U.S. Appl. No. 11/598,250, filed Nov. 8, 2006.

Notice of Allowance dated Apr. 23, 2008, for U.S. Appl. No. 11/217,147.

Office Action dated May 29, 2008, for U.S. Appl. No. 11/121,709.

Notice of Allowance dated Oct. 10, 2008, for U.S. Appl. No. 11/271,147.

Office Action dated Nov. 20, 2008 for.U.S. Appl. No. 11/598,250, filed Nov. 8, 2006.

Office Action dated Dec. 3, 2008, for U.S. Appl. No. 11/121,709.

Advisory Action dated Apr. 3, 2009 for U.S. Appl. No. 11/121,709.

Notice of Allowance dated Apr. 10, 2009 for U.S. Appl. No. 11/598,250.

Notice of Allowance dated Jul. 6, 2009, for U.S. Appl. No. 11/121,709.

* cited by examiner

IMIDAZOYL-BENZAMIDE ANTI-CANCER AGENTS

This application claims the benefit of U.S. Patent Application No. 60/569,510, filed May 6, 2004, and is a continuation-in-part of U.S. patent application Ser. No. 11/121,709, filed May 3, 2005, both of which are hereby incorporated by reference.

This invention relates to chemical entities which are inhibitors of one or more mitotic kinesins and are useful in the treatment of cellular proliferative diseases, for example cancer, hyperplasias, restenosis, cardiac hypertrophy, immune disorders, fungal disorders, and inflammation.

Among the therapeutic agents used to treat cancer are the taxanes and vinca alkaloids, which act on microtubules. Microtubules are the primary structural element of the mitotic spindle. The mitotic spindle is responsible for distribution of replicate copies of the genome to each of the two daughter cells that result from cell division. It is presumed that disruption of the mitotic spindle by these drugs results in inhibition of cancer cell division, and induction of cancer cell death. However, microtubules form other types of cellular structures, including tracks for intracellular transport in nerve processes. Because these agents do not specifically target mitotic spindles, they have side effects that limit their usefulness.

Improvements in the specificity of agents used to treat cancer is of considerable interest because of the therapeutic benefits which would be realized if the side effects associated with the administration of these agents could be reduced. Traditionally, dramatic improvements in the treatment of cancer are associated with identification of therapeutic agents acting through novel mechanisms. Examples of this include not only the taxanes, but also the camptothecin class of topoisomerase I inhibitors. From both of these perspectives, mitotic kinesins are attractive targets for new anti-cancer agents.

Mitotic kinesins are enzymes essential for assembly and function of the mitotic spindle, but are not generally part of other microtubule structures, such as in nerve processes. Mitotic kinesins play essential roles during all phases of mitosis. These enzymes are "molecular motors" that transform energy released by hydrolysis of ATP into mechanical force which drives the directional movement of cellular cargoes along microtubules. The catalytic domain sufficient for this task is a compact structure of approximately 340 amino acids. During mitosis, kinesins organize microtubules into the bipolar structure that is the mitotic spindle. Kinesins mediate movement of chromosomes along spindle microtubules, as well as structural changes in the mitotic spindle associated with specific phases of mitosis. Experimental perturbation of mitotic kinesin function causes malformation or dysfunction of the mitotic spindle, frequently resulting in cell cycle arrest and cell death.

In one aspect, the invention relates to methods for treating cellular proliferative diseases, and for treating disorders by inhibiting the activity of one or more mitotic kinesins.

Provided is at least one chemical entity chosen from compounds of Formula I

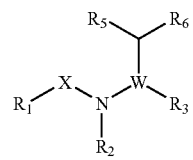

Formula I and pharmaceutically acceptable salts, solvates, chelates, non-covalent complexes, prodrugs, and mixtures thereof, wherein $R_1$ is optionally substituted aryl, optionally substituted heterocycloalkyl, or optionally substituted heteroaryl;

X is —CO— or —$SO_2$—;

$R_2$ is hydrogen or optionally substituted lower alkyl;

W is —$CR_4$—, —$CH_2CR_4$—, or N;

$R_3$ is —CO—$R_7$, hydrogen, optionally substituted alkyl, optionally substituted heterocyclyl, cyano, optionally substituted sulfonyl, or optionally substituted aryl;

$R_4$ is hydrogen or optionally substituted alkyl;

$R_5$ is hydrogen, hydroxyl, optionally substituted amino, optionally substituted heterocyclyl; or optionally substituted lower alkyl;

$R_6$ is hydrogen, optionally substituted alkyl, optionally substituted alkoxy, optionally substituted aryloxy, optionally substituted hetararyloxy, optionally substituted alkoxycarbonyl-, optionally substituted aminocarbonyl-, optionally substituted aryl, optionally substituted heteroaryl, optionally substituted heterocyclyl, or optionally substituted aralkyl; and $R_7$ is optionally substituted lower alkyl, optionally substituted aryl, hydroxyl, optionally substituted amino, optionally substituted aralkoxy, or optionally substituted alkoxy.

In some embodiments, if W is N, then $R_5$ is not hydroxyl or optionally substituted amino, and $R_6$ is not optionally substituted alkoxy, optionally substituted aralkoxy, optionally substituted heteroaralkoxy, or optionally substituted amino.

Also provided is at least one chemical entity chosen from compounds of Formula II

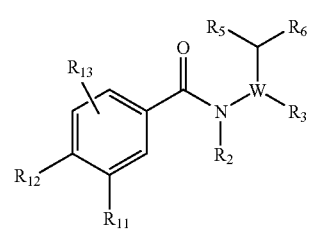

(Formula II)

and pharmaceutically acceptable salts, solvates, chelates, non-covalent complexes, prodrugs, and mixtures thereof, wherein $R_2$, $R_3$, $R_5$, $R_6$, and W are as described for compounds of Formula I and wherein $R_{11}$ is optionally substituted heterocyclyl, optionally substituted lower alkyl, nitro, cyano, hydrogen, sulfonyl, or halo;

$R_{12}$ is hydrogen, halo, optionally substituted alkyl, optionally substituted amino, optionally substituted sulfanyl, optionally substituted alkoxy, optionally substituted aryloxy, optionally substituted heterocyclyl, or optionally substituted heteroaryloxy; and $R_{13}$ is hydrogen, acyl, optionally substituted alkyl-, optionally substituted alkoxy, halo, hydroxyl, nitro, cyano, optionally substituted amino, alkylsulfonyl-, alkylsulfonamido-, alkylsulfonyl-, carboxyalkyl-, aminocarbonyl-, optionally substituted aryl or optionally substituted heteroaryl-.

Also provided is at least one chemical entity chosen from compounds of Formula III

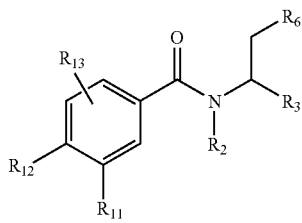

(Formula III)

and pharmaceutically acceptable salts, solvates, chelates, non-covalent complexes, prodrugs, and mixtures thereof, wherein $R_2$, $R_3$, $R_6$, $R_{11}$, $R_{12}$, and $R_{13}$ are as described for compounds of Formula II.

Also provided is at least one chemical entity chosen from compounds of Formula IV

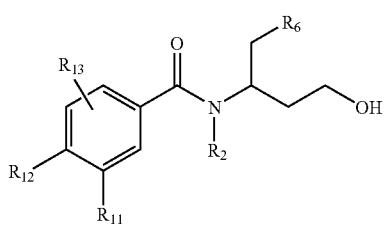

(Formula IV)

and pharmaceutically acceptable salts, solvates, chelates, non-covalent complexes, prodrugs, and mixtures thereof, wherein $R_2$, $R_6$, $R_{11}$, $R_{12}$, and $R_{13}$ are as described for compounds of Formula III.

Also provided is at least one chemical entity chosen from compounds of Formula V

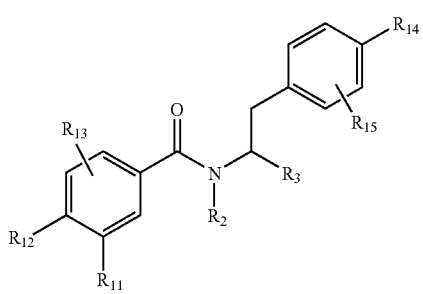

(Formula V)

and pharmaceutically acceptable salts, solvates, chelates, non-covalent complexes, prodrugs, and mixtures thereof, wherein $R_2$, $R_3$, $R_{11}$, $R_{12}$, and $R_{13}$ are as described for compounds of Formula III and wherein $R_{14}$ is optionally substituted heteroaryl; and
$R_{15}$ is chosen from hydrogen, halo, hydroxyl, and lower alkyl.

Also provided is at least one chemical entity chosen from compounds of Formula VI

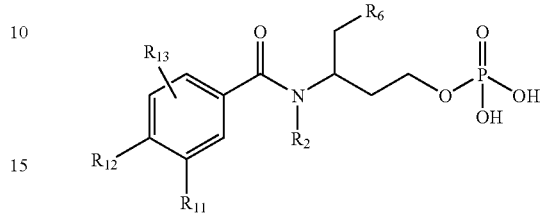

(Formula VI)

and pharmaceutically acceptable salts, solvates, chelates, non-covalent complexes, prodrugs, and mixtures thereof, wherein $R_2$, $R_6$, $R_{11}$, $R_{12}$, and $R_{13}$ are as described for compounds of Formula III.

Also provided is at least one chemical entity chosen from compounds of Formula VII

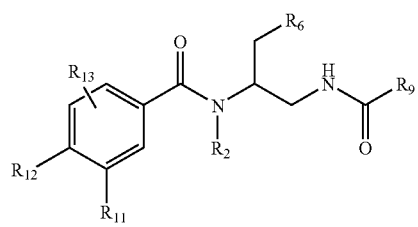

(Formula VII)

and pharmaceutically acceptable salts, solvates, chelates, non-covalent complexes, prodrugs, and mixtures thereof, wherein $R_2$, $R_6$, $R_{11}$, $R_{12}$, and $R_{13}$ are as described for compounds of Formula III and wherein $R_9$ is chosen from optionally substituted alkoxy, optionally substituted cycloalkoxy, optionally substituted arylalkoxy, optionally substituted amino and optionally substituted lower alkyl.

Also provided is composition comprising a pharmaceutical excipient and at least one chemical entity described herein.

Also provided is a method of modulating CENP-E kinesin activity which comprises contacting said kinesin with an effective amount of at least one chemical entity described herein.

Also provided is a method of inhibiting CENP-E which comprises contacting said kinesin with an effective amount of at least one chemical entity described herein.

Also provided is a method for the treatment of a cellular proliferative disease comprising administering to a subject in need thereof at least one chemical entity described herein.

Also provided is a method for the treatment of a cellular proliferative disease comprising administering to a subject in need thereof a composition comprising a pharmaceutical excipient and at least one chemical entity described herein.

Also provided is the use, in the manufacture of a medicament for treating cellular proliferative disease, of at least one chemical entity of described herein.

Also provided is the use of at least one chemical entity described herein for the manufacture of a medicament for treating a disorder associated with CENP-E kinesin activity.

As used in the present specification, the following words and phrases are generally intended to have the meanings as set forth below, except to the extent that the context in which they are used indicates otherwise. The following abbreviations and terms have the indicated meanings throughout:

As used herein, when any variable occurs more than one time in a chemical formula, its definition on each occurrence is independent of its definition at every other occurrence.

The following abbreviations and terms have the indicated meanings throughout:

Ac=acetyl
Boc=t-butyloxy carbonyl
Bu=butyl
c-=cyclo
CBZ=carbobenzoxy=benzyloxycarbonyl
DCM=dichloromethane=methylene chloride=$CH_2Cl_2$
DCE=dichloroethane
DEAD=diethyl azodicarboxylate
DIC=diisopropylcarbodiimide
DIEA=N,N-diisopropylethylamine
DMAP=4-N,N-dimethylaminopyridine
DMF=N,N-dimethylformamide
DMSO=dimethyl sulfoxide
Et=ethyl
Fmoc=9-fluorenylmethoxycarbonyl
GC=gas chromatography
HATU=O-(7-Azabenzotriazol-1-yl)-1,1,3,3-tetramethyluronium hexafluorophosphate
HOAc=acetic acid
HOBt=hydroxybenzotriazole
LAH=lithium aluminum hydride
Me=methyl
mesyl=methanesulfonyl
NCS=N-chlorosuccinimide
Ph=phenyl
Py=pyridine
rt=room temperature
sat'd=saturated
s-=secondary
t-=tertiary
TES=triethylsilyl
TFA=trifluoroacetic acid
THF=tetrahydrofuran
TMS=trimethylsilyl
tosyl=p-toluenesulfonyl A dash ("-") that is not between two letters or symbols is used to indicate a point of attachment for a substituent. For example, —$CONH_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to four carbons.

"Cycloalkyl" indicates a saturated hydrocarbon ring group, having the specified number of carbon atoms, usually from 3 to 7 ring carbon atoms. Examples of cycloalkyl groups include cyclopropyl, cyclobutyl, cyclopentyl, and cyclohexyl as well as bridged and caged saturated ring groups such as norbornane.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like. Alkoxy groups will usually have from 1 to 6 carbon atoms attached through the oxygen bridge. "Lower alkoxy" refers to alkoxy groups having one to four carbons.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3(C=O)$—.

By "alkoxycarbonyl" is meant an ester group of the formula (alkoxy)(C=O)— attached through the carbonyl carbon wherein the alkoxy group has the indicated number of carbon atoms. Thus a $C_1$-$C_6$alkoxycarbonyl group is an alkoxy group having from 1 to 6 carbon atoms attached through its oxygen to a carbonyl linker.

By "amino" is meant the group —$NH_2$.

The term "aminocarbonyl" refers to the group —CON$R^aR^b$, where
  $R^b$ is chosen from H, optionally substituted $C_1$-$C_6$ alkyl, optionally substituted aryl, and optionally substituted heteroaryl; and
  $R^c$ is chosen from hydrogen and optionally substituted $C_1$-$C_4$ alkyl; or
  $R^b$ and $R^c$ taken together with the nitrogen to which they are bound, form an optionally substituted 5- to 7-membered nitrogen-containing heterocycloalkyl which optionally includes 1 or 2 additional heteroatoms selected from O, N, and S in the heterocycloalkyl ring;
where each substituted group is independently substituted with one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N(C₁-C₄ alkyl)C(O)(phenyl), —C(O)C₁-C₄ alkyl, —C(O)C₁-C₄ phenyl, —C(O)C₁-C₄ haloalkyl, —OC(O)C₁-C₄ alkyl, —SO₂(C₁-C₄ alkyl), —SO₂(phenyl), —SO₂(C₁-C₄ haloalkyl), —SO₂NH₂, —SO₂NH(C₁-C₄ alkyl), —SO₂NH(phenyl), —NHSO₂(C₁-C₄ alkyl), —NHSO₂(phenyl), and —NHSO₂(C₁-C₄ haloalkyl).

"Aryl" encompasses:
5- and 6-membered carbocyclic aromatic rings, for example, benzene;
bicyclic ring systems wherein at least one ring is carbocyclic and aromatic, for example, naphthalene, indane, and tetralin; and
tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "aryloxy" refers to the group —O-aryl.

The term "aralkyl" refers to a residue in which an aryl moiety is attached to the parent structure via an alkyl residue. Examples include benzyl-, phenethyl-, phenylvinyl-, phenylallyl and the like.

The term "heteroaralkyl" refers to a residue in which a heteroaryl moiety is attached to the parent structure via an alkyl residue. Examples include furanylmethyl-, pyridinylmethyl-, pyrimidinylethyl and the like.

The term "halo" includes fluoro, chloro, bromo, and iodo, and the term "halogen" includes fluorine, chlorine, bromine, and iodine.

"Haloalkyl" indicates alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Heteroaryl" encompasses:
5- to 7-membered aromatic, monocyclic rings containing one or more, for example, from 1 to 4, or in certain embodiments, from 1 to 3, heteroatoms chosen from N, O, and S, with the remaining ring atoms being carbon; and
bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, imidazopyridinyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

In the term "heteroaralkyl," heteroaryl and alkyl are as defined herein, and the point of attachment is on the alkyl group. This term encompasses, but is not limited to, pyridylmethyl, thiophenylmethyl, and (pyrrolyl) 1-ethyl.

A "leaving group" or "atom" is any group or atom that will, under the reaction conditions, cleave from the starting material, thus promoting reaction at a specified site. Suitable examples of such groups unless otherwise specified are halogen atoms, mesyloxy, p-nitrobenzensulphonyloxy and tosyloxy groups.

"Optional" or "optionally" means that the subsequently described event or circumstance may or may not occur, and that the description includes instances where said event or circumstances occurs and instances in which it does not. For example, "optionally substituted alkyl" includes "alkyl" and "substituted alkyl" as defined herein. It will be understood by those skilled in the art with respect to any group containing one or more substituents that such groups are not intended to introduce any substitution or substitution patterns that are sterically impractical and/or synthetically non-feasible and/or inherently unstable.

"Protecting group" has the meaning conventionally associated with it in organic synthesis, i.e. a group that selectively blocks one or more reactive sites in a multifunctional compound such that a chemical reaction can be carried out selectively on another unprotected reactive site and such that the group can readily be removed after the selective reaction is complete. A variety of protecting groups are disclosed, for example, in T. H. Greene and P. G. M. Wuts, Protective Groups in Organic Synthesis, Third Edition, John Wiley & Sons, New York (1999), which is incorporated herein by reference in its entirety. For example, a hydroxyl protected form is where at least one of the hydroxyl groups present in a compound is protected with a hydroxyl protecting group. Likewise, amines and other reactive groups may similarly be protected.

By "heterocycloalkyl" is meant a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. Suitable heterocycloalkyl groups include, for example (as numbered from the linkage position assigned priority 1), 2-pyrrolinyl, 2,4-imidazolidinyl, 2,3-pyrazolidinyl, 2-piperidyl, 3-piperidyl, 4-piperdyl, and 2,5-piperzinyl. Morpholinyl groups are also contemplated, including 2-morpholinyl and 3-morpholinyl (numbered wherein the oxygen is assigned priority 1).

As used herein, "modulation" refers to a change in CENP-E activity as a direct or indirect response to the presence at least one chemical entity described herein, relative to the activity of CENP-E in the absence of the chemical entity. The change may be an increase in activity or a decrease in activity, and may be due to the direct interaction of the chemical entity with CENP-E, or due to the interaction of the compound with one or more other factors that in turn affect CENP-E activity.

The term "sulfanyl" includes the groups: —S-(optionally substituted ($C_1$-$C_6$)alkyl), —S-(optionally substituted aryl), —S-(optionally substituted heteroaryl), and —S-(optionally substituted heterocycloalkyl). Hence, sulfanyl includes the group $C_1$-$C_6$ alkylsulfanyl.

The term "sulfinyl" includes the groups: —S(O)—H, —S(O)-(optionally substituted ($C_1$-$C_6$)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups: —S($O_2$)—H, —S($O_2$)-(optionally substituted ($C_1$-$C_6$)alkyl), —S($O_2$)-optionally substituted aryl), —S($O_2$)-optionally substituted heteroaryl), —S($O_2$)-(optionally substituted heterocycloalkyl), —S($O_2$)-(optionally substituted alkoxy), —S($O_2$)-optionally substituted aryloxy), —S($O_2$)-optionally substituted heteroaryloxy), —S($O_2$)-(optionally substituted heterocyclyloxy); and —S($O_2$)-(optionally substituted amino).

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, —O($C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$CO_2R^b$, —$CONR^bR^c$, —$NR^cCOR^b$, —$SOR^a$, —$SO_2R^a$, —$SO_2NR^bR^c$, and —$NR^cSO_2R^a$, where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl;

where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ phenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2NH$($C_1$-$C_4$ alkyl), —$SO_2NH$(phenyl), —$NHSO_2$($C_1$-$C_4$ alkyl), —$NHSO_2$(phenyl), and —$NHSO_2$($C_1$-$C_4$ haloalkyl).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl, refer respectively to alkyl, cycloalkyl, aryl, heteroaryl, and heterocycloalkyl wherein one or more (such as up to 5, for example, up to 3) hydrogen atoms are replaced by a substituent independently chosen from:

—$R^a$, —$OR^b$, —O($C_1$-$C_2$ alkyl)O— (e.g., methylenedioxy-), —$SR^b$, guanidine, guanidine wherein one or more of the guanidine hydrogens are replaced with a lower-alkyl group, —$NR^bR^c$, halo, cyano, nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$CO_2R^b$, —$CONR^bR^c$, —$NR^cCOR^b$, —$SOR^a$, $SO_2R^a$, —$SO_2NR^bR^c$, and —$NR^cSO_2R^a$, where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is chosen from hydrogen and optionally substituted $C_1$-$C_4$ alkyl;

where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substitutent for heteroaryl), —$CO_2H$, —C(O)O$C_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O) (phenyl), —C(O)$C_1$-$C_4$ alkyl, —C(O)$C_1$-$C_4$ phenyl, —C(O) $C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

The term "substituted alkoxy" refers to alkoxy wherein the alkyl constituent is substituted (i.e., —O-(substituted alkyl)) wherein "substituted alkyl" refers to alkyl wherein one or more (such as up to 5, for example, up to 3) hydrogen atoms are replaced by a substituent independently chosen from:

—R$^a$, —OR$^b$, —O(C$_1$-C$_2$ alkyl)O— (e.g., methylenedioxy-), —SR$^b$, guanidine, guanidine wherein one or more of the guanidine hydrogens are replaced with a lower-alkyl group, —NR$^b$R$^c$, halo, cyano, nitro, —COR$^b$, —CO$_2$R$^b$, —CONR$^b$R$^c$, —OCOR$^b$, —OCO$_2$R$^a$, —OCONR$^b$R$^c$, —NR$^c$COR$^b$, —NR$^c$CO$_2$R$^a$, —NR$^c$CONR$^b$R$^c$, —CO$_2$R$^b$, —CONR$^b$R$^c$, —NR$^c$COR$^b$, —SOR$^a$, SO$_2$R$^a$, —SO$_2$NR$^b$R$^c$, and —NR$^c$SO$_2$R$^a$, where R$^a$ is chosen from optionally substituted C$_1$-C$_6$ alkyl, optionally substituted aryl, and optionally substituted heteroaryl;

R$^b$ is chosen from H, optionally substituted C$_1$-C$_6$ alkyl, optionally substituted aryl, and optionally substituted heteroaryl; and R$^c$ is chosen from hydrogen and optionally substituted C$_1$-C$_4$ alkyl;

where each optionally substituted group is unsubstituted or independently substituted with one or more, such as one, two, or three, substituents independently selected from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl-, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substitutent for heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ phenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl). In some embodiments, a substituted alkoxy group is "polyalkoxy" or —O-(optionally substituted alkylene)-(optionally substituted alkoxy), and includes groups such as —OCH$_2$CH$_2$OCH$_3$, and residues of glycol ethers such as polyethyleneglycol, and —O(CH$_2$CH$_2$O)$_x$CH$_3$, where x is an integer of 2-20, such as 2-10, and for example, 2-5. Another substituted alkoxy group is hydroxyalkoxy or —OCH$_2$(CH$_2$)$_y$OH, where y is an integer of 1-10, such as 1-4.

The term "substituted alkoxycarbonyl" refers to the group (substituted alkyl)-O—C(O)— wherein the group is attached to the parent structure through the carbonyl functionality and wherein substituted refers to alkyl wherein one or more (such as up to 5, for example, up to 3) hydrogen atoms are replaced by a substituent independently chosen from:

—R$^a$, —OR$^b$, —O(C$_1$-C$_2$ alkyl)O— (e.g., methylenedioxy-), —SR$^b$, guanidine, guanidine wherein one or more of the guanidine hydrogens are replaced with a lower-alkyl group, —NR$^b$R$^c$, halo, cyano, nitro, —COR$^b$, —CO$_2$R$^b$, —CONR$^b$R$^c$, —OCOR$^b$, —OCO$_2$R$^a$, —OCONR$^b$R$^c$, —NR$^c$COR$^b$, —NR$^c$CO$_2$R$^a$, —NR$^c$CONR$^b$R$^c$, —CO$_2$R$^b$, —CONR$^b$R$^c$, —NR$^c$COR$^b$, —SOR$^a$, —SO$_2$R$^a$, —SO$_2$NR$^b$R$^c$, and —NR$^c$SO$_2$R$^a$, where R$^a$ is chosen from optionally substituted C$_1$-C$_6$ alkyl, optionally substituted aryl, and optionally substituted heteroaryl;

R$^b$ is chosen from H, optionally substituted C$_1$-C$_6$ alkyl, optionally substituted aryl, and optionally substituted heteroaryl; and R$^c$ is chosen from hydrogen and optionally substituted C$_1$-C$_4$ alkyl;

where each optionally substituted group is unsubstituted or independently substituted with one or more, such as one, two, or three, substituents independently selected from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl-, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substitutent for heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ phenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

The term "substituted amino" refers to the group —NHR$^d$ or —NR$^d$R$^d$ where each R$^d$ is independently chosen from: optionally substituted alkyl, optionally substituted cycloalkyl, optionally substituted acyl, optionally substituted aryl, optionally substituted heteroaryl, optionally substituted heterocycloalkyl, alkoxycarbonyl, sulfinyl and sulfonyl, wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

—R$^a$, —OR$^b$, —O(C$_1$-C$_2$ alkyl)O— (e.g., methylenedioxy-), —SR$^b$, guanidine, guanidine wherein one or more of the guanidine hydrogens are replaced with a lower-alkyl group, —NR$^b$R$^c$, halo, cyano, nitro, —COR$^b$, —CO$_2$R$^b$, —CONR$^b$R$^c$, —OCOR$^b$, —OCO$_2$R$^a$, —OCONR$^b$R$^c$, —NR$^c$COR$^b$, —NR$^c$CO$_2$R$^a$, —NR$^c$CONR$^b$R$^c$, —CO$_2$R$^b$, —CONR$^b$R$^c$, —NR$^c$COR$^b$, —SOR$^a$, —SO$_2$R$^a$, —SO$_2$NR$^b$R$^c$, and —NR$^c$SO$_2$R$^a$, where R$^a$ is chosen from optionally substituted C$_1$-C$_6$ alkyl, optionally substituted aryl, and optionally substituted heteroaryl;

R$^b$ is chosen from H, optionally substituted C$_1$-C$_6$ alkyl, optionally substituted aryl, and optionally substituted heteroaryl; and R$^c$ is chosen from hydrogen and optionally substituted C$_1$-C$_4$ alkyl;

where each optionally substituted group is unsubstituted or independently substituted with one or more, such as one, two, or three, substituents independently selected from C$_1$-C$_4$ alkyl, aryl, heteroaryl, aryl-C$_1$-C$_4$ alkyl-, heteroaryl-C$_1$-C$_4$ alkyl-, C$_1$-C$_4$ haloalkyl-, —OC$_1$-C$_4$ alkyl, —OC$_1$-C$_4$ alkylphenyl, —C$_1$-C$_4$ alkyl-OH, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substitutent for heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ phenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl); and wherein optionally substituted acyl, alkoxycarbonyl, sulfinyl and sulfonyl are as defined herein.

The term "substituted amino" also refers to the group —NR$^e$R$^f$ wherein R$^e$ and R$^f$, together with the nitrogen to which they are bound, form an optionally substituted 5- to 7-membered nitrogen-containing, non-aromatic, heterocycle which optionally contains 1 or 2 additional heteroatoms chosen from nitrogen, oxygen, and sulfur.

Compounds of Formula I-XIII include, but are not limited to, optical isomers of compounds of Formula I-XIII, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I-XIII include Z- and E-forms (or cis- and trans-forms) of compounds with carbon-carbon double bonds. Where compounds of Formula I-XIII exists in various tautomeric forms, chemical entities of the present invention include all tautomeric forms of the compound. Compounds of Formula I-XIII also includes crystal forms such as polymorphs and clathrates.

Chemical entities of the present invention include, but are not limited to compounds of Formula I-XIII and all pharmaceutically acceptable forms thereof. Pharmaceutically acceptable forms of the compounds recited herein include pharmaceutically acceptable salts, solvates, chelates, non-covalent complexes, prodrugs, and mixtures thereof. In certain embodiments, the compounds described herein are in the form of pharmaceutically acceptable salts. Hence, the terms "chemical entity" and "chemical entities" also encompass pharmaceutically acceptable salts, solvates, chelates, non-covalent complexes, prodrugs, and mixtures.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—(CH$_2$)$_n$—COOH where n is 0-4, and like salts. Similarly, pharmaceutically acceptable cations include, but are not limited to sodium, potassium, calcium, aluminum, lithium, and ammonium.

In addition, if the compound of Formula I-XIII is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of chemical entities, for example ester or amide derivatives of the compounds of Formula I-XIII. The term "prodrug" includes any compound that becomes a compound of Formula I-XIII when administered to a patient, e.g., upon metabolic processing of the prodrug. Examples of prodrugs include, but are not limited to, acetate, formate, and benzoate and like derivatives of functional groups (such as alcohol or amine groups) in the compounds of Formula I-XIII. In some embodiments, the prodrug is a phosphate ester. A thorough discussion of prodrugs is provided in T. Higuchi and V. Stella, Pro-drugs as Novel Delivery Systems, Vol. 14 of the A.C.S. Symposium Series, in Edward B. Roche, ed., Bioreversible Carriers in Drug Design, American Pharmaceutical Association and Pergamon Press, 1987, and in Design of Prodrugs, ed. H. Bundgaard, Elsevier, 1985, each of which are incorporated herein by reference.

The term "solvate" refers to the chemical entity formed by the interaction of a solvent and a compound. Suitable solvates are pharmaceutically acceptable solvates, such as hydrates, including monohydrates and hemi-hydrates.

The term "chelate" refers to the chemical entity formed by the coordination of a compound to a metal ion at two (or more) points.

The term "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

The term "active agent" is used to indicate a chemical entity which has biological activity. In certain embodiments, an "active agent" is a compound having pharmaceutical utility. For example an active agent may be an anti-cancer therapeutic.

The term "antimitotic" refers to a drug for inhibiting or preventing mitosis, for example, by causing metaphase arrest. Some antitumour drugs block proliferation and are considered antimitotics.

The term "therapeutically effective amount" of a chemical entity of this invention means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to CENP-E inhibition. In some embodiments, a therapeutically effective amount is an amount sufficient to reduce cancer symptoms. In some embodiments a therapeutically effective amount is an amount sufficient to decrease the number of detectable cancerous cells in an organism, detectably slow, or stop the growth of a cancerous tumor. In some embodiments, a therapeutically effective amount is an amount sufficient to shrink a cancerous tumor.

The term "inhibition" indicates a significant decrease in the baseline activity of a biological activity or process. "Inhibition of CENP-E activity" refers to a decrease in CENP-E activity as a direct or indirect response to the presence of at least one chemical entity described herein, relative to the activity of CENP-E in the absence of the at least one chemical entity. The decrease in activity may be due to the direct interaction of the chemical entity with CENP-E, or due to the interaction of the chemical entity(ies) described herein with one or more other factors that in turn affect CENP-E activity. For example, the presence of the chemical entity(ies) may decrease CENP-E activity by directly binding to CENP-E, by causing (directly or indirectly) another factor to decrease CENP-E activity, or by (directly or indirectly) decreasing the amount of CENP-E present in the cell or organism.

A "disease responsive to CENP-E inhibition" is a disease in which inhibiting CENP-E provides a therapeutic benefit such as an amelioration of symptoms, decrease in disease progression, prevention or delay of disease onset, or inhibition of aberrant activity of certain cell-types.

"Treatment or treating means any treatment of a disease in a patient, including:
a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

"Patient" refers to an animal, such as a mammal, that has been or will be the object of treatment, observation or experiment. The methods of the invention can be useful in both human therapy and veterinary applications. In some embodiments, the patient is a mammal; in some embodiments the patient is human; and in some embodiments the patient is chosen from cats and dogs.

The present invention is directed to a class of novel chemical entities that are inhibitors of one or more mitotic kinesins. According to some embodiments, the chemical entities described herein inhibit the mitotic kinesin, CENP-E, particularly human CENP-E. CENP-E is a plus end-directed microtubule motor essential for achieving metaphase chromosome alignment. CENP-E accumulates during interphase and is degraded following completion of mitosis. Microinjection of antibody directed against CENP-E or overexpression of a dominant negative mutant of CENP-E causes mitotic arrest with prometaphase chromosomes scattered on a bipolar spindle. The tail domain of CENP-E mediates localization to kinetochores and also interacts with the mitotic checkpoint kinase hBubR1. CENP-E also associates with active forms of MAP kinase. Cloning of human (Yen, et al., Nature, 359 (6395):536-9 (1992)) CENP-E has been reported. In Thrower, et al., EMBO J., 14:918-26 (1995) partially purified native human CENP-E was reported on. Moreover, the study reported that CENP-E was a minus end-directed microtubule motor. Wood, et al., Cell, 91:357-66 (1997)) discloses expressed *Xenopus* CENP-E in *E. coli* and that XCENP-E has motility as a plus end directed motor in vitro. CENP-E See, PCT Publication No. WO 99/13061, which is incorporated herein by reference.

In some embodiments, the chemical entities inhibit the mitotic kinesin, CENP-E, as well as modulating one or more of the human mitotic kinesins selected from HSET (see, U.S. Pat. No. 6,361,993, which is incorporated herein by reference); MCAK (see, U.S. Pat. No. 6,331,424, which is incorporated herein by reference); RabK-6 (see U.S. Pat. No. 6,544,766, which is incorporated herein by reference); Kif4 (see, U.S. Pat. No. 6,440,684, which is incorporated herein by reference); MKLPI (see, U.S. Pat. No. 6,448,025, which is incorporated herein by reference); Kifl5 (see, U.S. Pat. No. 6,355,466, which is incorporated herein by reference); Kid (see, U.S. Pat. No. 6,387,644, which is incorporated herein by reference); Mpp1, CMKrp, KinI-3 (see, U.S. Pat. No. 6,461,855, which is incorporated herein by reference); Kip3a (see, PCT Publication No. WO 01/96593, which is incorporated herein by reference); Kip3d (see, U.S. Pat. No. 6,492,151, which is incorporated herein by reference); and KSP (see, U.S. Pat. No. 6,617,115, which is incorporated herein by reference).

The methods of inhibiting a mitotic kinesin comprise contacting an inhibitor of the invention with one or more mitotic kinesin, particularly a human kinesin; or fragments and variants thereof. The inhibition can be of the ATP hydrolysis activity of the mitotic kinesin and/or the mitotic spindle formation activity, such that the mitotic spindles are disrupted.

The present invention provides inhibitors of one or more mitotic kinesins, in particular, one or more human mitotic kinesins, for the treatment of disorders associated with cell proliferation. The chemical entities compositions and methods described herein can differ in their selectivity and are used to treat diseases of cellular proliferation, including, but not limited to cancer, hyperplasias, restenosis, cardiac hypertrophy, immune disorders, fungal disorders and inflammation.

Accordingly, the present invention provides at least one chemical entity chosen from compounds of Formula I

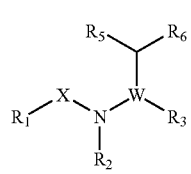

Formula I and pharmaceutically acceptable salts, solvates, chelates, non-covalent complexes, prodrugs, and mixtures thereof, wherein $R_1$ is optionally substituted aryl, optionally substituted heterocycloalkyl, or optionally substituted heteroaryl;

X is —CO or —SO$_2$—;

$R_2$ is hydrogen or optionally substituted lower alkyl;

W is —CR$_4$—, —CH$_2$CR$_4$—, or N;

$R_3$ is —CO—R$_7$, hydrogen, optionally substituted alkyl, optionally substituted heterocyclyl, cyano, optionally substituted sulfonyl, or optionally substituted aryl;

$R_4$ is hydrogen or optionally substituted alkyl;

$R_5$ is hydrogen, hydroxyl, optionally substituted amino, optionally substituted heterocyclyl; or optionally substituted lower alkyl;

$R_6$ is hydrogen, optionally substituted alkyl, optionally substituted alkoxy, optionally substituted aryloxy, optionally substituted heterayloxy, optionally substituted alkoxycarbonyl-, optionally substituted aminocarbonyl-, optionally substituted aryl, optionally substituted heteroaryl, optionally substituted heterocyclyl, or optionally substituted aralkyl; and $R_7$ is optionally substituted lower alkyl, optionally substituted aryl, hydroxyl, optionally substituted amino, optionally substituted aralkoxy, or optionally substituted alkoxy;

provided that if W is N, then $R_5$ is not hydroxyl or optionally substituted amino, and $R_6$ is not optionally substituted alkoxy, optionally substituted aralkoxy, optionally substituted heteroaralkoxy, or optionally substituted amino.

In some embodiments, $R_1$ is optionally substituted aryl, or optionally substituted heteroaryl. In some embodiments, $R_1$ is optionally substituted aryl. In some embodiments, $R_1$ is optionally substituted phenyl. In some embodiments, $R_1$ is phenyl substituted with one, two or three groups independently selected from optionally substituted heterocyclyl, optionally substituted alkyl, sulfonyl, halo, optionally substituted amino, optionally substituted sulfanyl, optionally substituted alkoxy, optionally substituted aryloxy, optionally substituted heteroaryloxy; acyl, hydroxyl, nitro, cyano, optionally substituted aryl, and optionally substituted heteroaryl-. In some embodiments, $R_1$ is chosen from 3-halo-4-isopropoxy-phenyl, 3-cyano-4-isopropoxy-phenyl, 3-cyano-4-isopropylamino-phenyl, 3-chloro-4-isopropylamino-phenyl, 3-cyano-4-trifluoroisopropyloxyphenyl, 3-chloro-4-trifluoroisopropyloxyphenyl, 3-cyano-4-cylobutyloxyphenyl, 3-chloro-4-cylobutyloxyphenyl, 3-cyano-4-cylopropyloxyphenyl, and 3-chloro-4-cylopropyloxyphenyl. In some embodiments, $R_1$ is 3-halo-4-isopropoxy-phenyl or 3-cyano-4-isopropoxy-phenyl.

In some embodiments, $R_2$ is hydrogen.

In some embodiments, X is —CO—.

In some embodiments, W is —CR$_4$— and $R_4$ is hydrogen.

In some embodiments, the compounds described herein possess a potentially chiral center, for example, when W is —CR$_4$—. The invention contemplates the use of pure enantiomers and mixtures of enantiomers, including racemic mixtures, although the use of a substantially optically pure enantiomer will generally be preferred. The term "substantially optically pure" or "enantiomerically pure" means having at least about 95% of the described enantiomer with no single impurity greater than about 1% and particularly, at least about 97.5% enantiomeric excess. In some embodiments, the stereogenic center at W is as shown below:

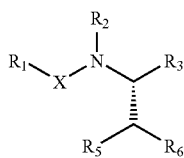

In some embodiments, $R_3$ is —CO—$R_7$; hydrogen; optionally substituted lower alkyl; cyano; optionally substituted sulfonyl; optionally substituted aryl; or optionally substituted heterocyclyl. In some embodiments, $R_3$ is optionally substituted lower alkyl. In some embodiments, $R_3$ is lower alkyl that is optionally substituted with a hydroxyl or a phosphate ester thereof, lower alkyl that is optionally substituted with a lower alkoxy, lower alkyl that is optionally substituted with an optionally substituted amino group, or lower alkyl that is optionally substituted with CO—$R_8$ where $R_8$ is hydroxyl or optionally substituted amino.

In some embodiments, $R_5$ is hydrogen, hydroxyl, or optionally substituted lower alkyl. In some embodiments, $R_5$ is hydrogen.

In some embodiments, the compounds described herein possess a potentially chiral center when $R_5$ is not hydrogen. The invention contemplates the use of pure enantiomers and mixtures of enantiomers, including racemic mixtures, although the use of a substantially optically pure enantiomer will generally be preferred. The term "substantially optically pure" or "enantiomerically pure" means having at least about 95% of the described enantiomer with no single impurity greater than about 1% and particularly, at least about 97.5% enantiomeric excess.

In some embodiments, $R_6$ is optionally substituted aryl, optionally substituted heteroaryl, optionally substituted heterocyclyl, or optionally substituted alkyl (such as wherein the alkyl group is substituted with an optionally substituted amino group or wherein the alkyl group is optionally substituted cycloalkyl-). In some embodiments, $R_6$ is phenyl substituted with one or two of the following substituents: optionally substituted heteroaryl, optionally substituted amino, aralkoxy, halo, hydroxymethyl-, hydroxy, cyano, alkoxy, phenyl, phenoxy, methylenedioxy, ethylenedioxy, sulfonyl, aminocarbonyl, carboxy, alkoxycarbonyl, nitro, heteroaralkoxy, aralkoxy, and optionally substituted heterocyclyl.

Also provided is at least one chemical entity chosen from compounds of Formula II

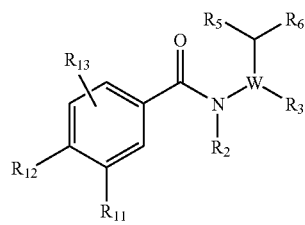

(Formula II)

and pharmaceutically acceptable salts, solvates, chelates, non-covalent complexes, prodrugs, and mixtures thereof, wherein $R_2$, $R_3$, $R_5$, $R_6$, and W are as described for compounds of Formula I and wherein $R_{11}$ is optionally substituted heterocyclyl, optionally substituted lower alkyl, nitro, cyano, hydrogen, sulfonyl, or halo;

$R_{12}$ is hydrogen, halo, optionally substituted alkyl, optionally substituted amino, optionally substituted sulfanyl, optionally substituted alkoxy, optionally substituted aryloxy, optionally substituted heterocyclyl, or optionally substituted heteroaryloxy; and $R_{13}$ is hydrogen, acyl, optionally substituted alkyl-, optionally substituted alkoxy, halo, hydroxyl, nitro, cyano, optionally substituted amino, alkylsulfonyl-, alkylsulfonamido-, alkylsulfonyl-, carboxyalkyl-, aminocarbonyl-, optionally substituted aryl or optionally substituted heteroaryl-.

In some embodiments, $R_{11}$ is hydrogen, cyano, nitro, or halo. In some embodiments, $R_{11}$ is chloro or cyano.

In some embodiments, $R_{12}$ is optionally substituted lower alkoxy, optionally substituted lower alkyl, or optionally substituted amino-. In some embodiments, $R_{12}$ is chosen from isopropoxy, isopropylamino, trifluoroisopropyloxy, cylobutyloxy, and cylopropyloxy. In some embodiments, $R_{12}$ is lower alkoxy (such as propoxy) or 2,2,2-trifluoro-1-methylethoxy. In some embodiments, $R_{12}$ is propoxy or 2,2,2-trifluoro-1-methyl-ethoxy. In some embodiments, $R_{12}$ is not —(CH$_2$)$_n$NH$_2$ or —(CH$_2$)$_4$NH(CH$_3$) wherein n is 4 or 5.

In some embodiments $R_{11}$ and $R_{12}$, taken together, form an optionally substituted carbocyclic or heterocyclic ring. In some embodiments, $R_{11}$ and $R_{12}$, taken together, form a methylenedioxy or ethylenedioxy ring. In some embodiments, $R_{12}$ and $R_{13}$, taken together, form an optionally substituted carbocyclic or heterocyclic ring. In some embodiments, $R_{11}$ and $R_{13}$, taken together, form an optionally substituted carbocyclic or heterocyclic ring.

In some embodiments, $R_{13}$ is hydrogen.

In some embodiments, $R_2$ and $R_{13}$, taken together, form an optionally substituted carbocyclic or heterocyclic ring, i.e., $R_1$, X, N, and $R_2$, taken together, form an optionally substituted carbocyclic or heterocyclic ring. In certain embodiments, a substituted 2,4-dioxo-1,4-dihydro-2H-quinazolin-3-yl ring is formed, e.g.,

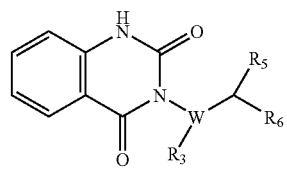

wherein the phenyl ring is optionally substituted. In other embodiments, a 4-oxo-4H-quinazolin-3-yl ring is formed, e.g.,

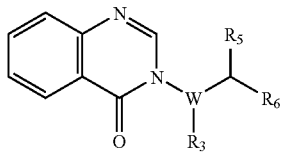

wherein the phenyl ring is optionally substituted. In certain embodiments, a 4-oxo-4H-pyridopyrimidin-3-yl ring is formed, e.g.,

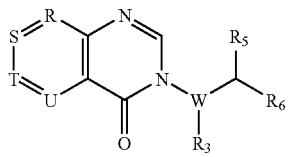

wherein one of R, S, T, and U is nitrogen with the others being —CH and wherein the pyridine ring is optionally substituted.

Also provided is at least one chemical entity chosen from compounds of Formula III

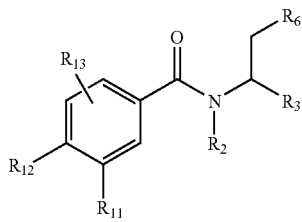

(Formula III)

and pharmaceutically acceptable salts, solvates, chelates, non-covalent complexes, prodrugs, and mixtures thereof, wherein $R_2$, $R_3$, $R_6$, $R_{11}$, $R_{12}$, and $R_{13}$ are as described for compounds of Formula II.

Also provided is at least one chemical entity chosen from compounds of Formula IV

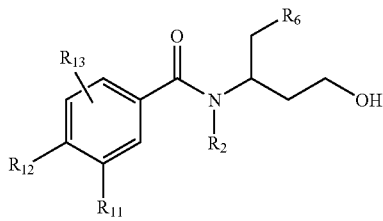

(Formula IV)

and pharmaceutically acceptable salts, solvates, chelates, non-covalent complexes, prodrugs, and mixtures thereof, wherein $R_2$, $R_6$, $R_{11}$, $R_{12}$, and $R_{13}$ are as described for compounds of Formula III.

Also provided is at least one chemical entity chosen from compounds of Formula V

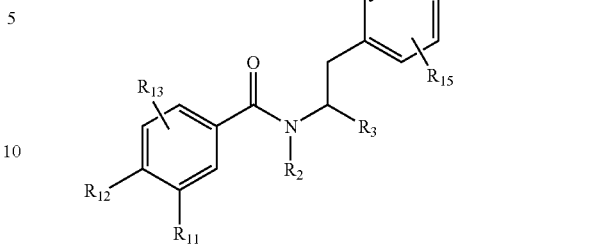

(Formula V)

and pharmaceutically acceptable salts, solvates, chelates, non-covalent complexes, prodrugs, and mixtures thereof, wherein $R_2$, $R_3$, $R_{11}$, $R_{12}$, and $R_{13}$ are as described for compounds of Formula III and wherein $R_{14}$ is optionally substituted heteroaryl; and $R_{15}$ is chosen from hydrogen, halo, hydroxyl, and lower alkyl.

In some embodiments, $R_{14}$ is chosen from
7,8-dihydro-imidazo[1,2-c][1,3]oxazin-2-yl,
3a,7a-dihydro-1H-benzoimidazol-2-yl,
imidazo[2,1-b]oxazol-6-yl,
oxazol-4-yl,
5,6,7,8-tetrahydro-imidazo[1,2-a]pyridin-2-yl,
1H-[1,2,4]triazol-3-yl,
2,3-dihydro-imidazol-4-yl,
1H-imidazol-2-yl,
imidazo[1,2-a]pyridin-2-yl,
thiazol-2-yl,
thiazol-4-yl,
pyrazol-3-yl, and
1H-imidazol-4-yl, each of which is optionally substituted with one, two, or three groups chosen from optionally substituted lower alkyl, halo, acyl, sulfonyl, cyano, nitro, optionally substituted amino, and optionally substituted heteroaryl.

In some embodiments, $R_{14}$ is chosen from
1H-imidazol-2-yl,
imidazo[1,2-a]pyridin-2-yl; and
1H-imidazol-4-yl, each of which is optionally substituted with one or two groups chosen from optionally substituted lower alkyl, halo, and acyl.

In some embodiments, $R_{15}$ is hydrogen.

Also provided is at least one chemical entity chosen from compounds of Formula VI

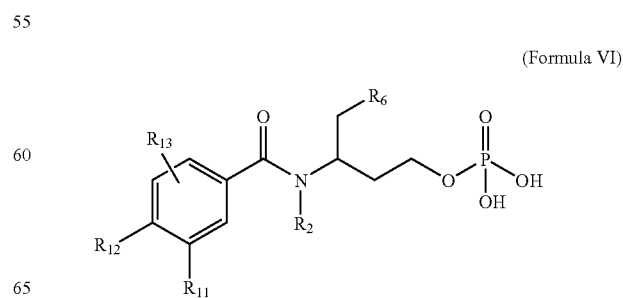

(Formula VI)

and pharmaceutically acceptable salts, solvates, chelates, non-covalent complexes, prodrugs, and mixtures thereof, wherein $R_2$, $R_6$, $R_{11}$, $R_{12}$, and $R_{13}$ are as described for compounds of Formula III.

Also provided is at least one chemical entity chosen from compounds of Formula VII

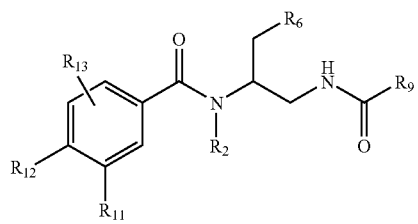

(Formula VII)

and pharmaceutically acceptable salts, solvates, chelates, non-covalent complexes, prodrugs, and mixtures thereof, wherein $R_2$, $R_6$, $R_{11}$, $R_{12}$, and $R_{13}$ are as described for compounds of Formula III and wherein $R_9$ is chosen from optionally substituted alkoxy, optionally substituted cycloalkoxy, optionally substituted arylalkoxy, optionally substituted amino and optionally substituted lower alkyl.

In some embodiments, $R_9$ is lower alkyl substituted with hydroxyl or optionally substituted amino. In some embodiments, $R_9$ is lower alkyl substituted with hydroxyl, amino, N-methylamino, or N,N-dimethylamino.

Also provided is at least one chemical entity chosen from compounds of Formula VIII

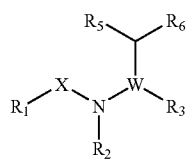

(Formula VIII)

and pharmaceutically acceptable salts, solvates, chelates, non-covalent complexes, prodrugs, and mixtures thereof, wherein $R_1$, X, W, $R_3$, $R_4$, $R_6$, and $R_7$ are as defined for compounds of Formula I and wherein $R_2$ and $R_5$, together with the atoms to which they are bound, form an optionally substituted 5-7 membered heterocycle which optionally may include one or two additional heteroatoms.

In some embodiments, $R_2$ taken together with $R_5$, form an optionally substituted pyrrolidinyl ring or optionally substituted piperidinyl ring.

Also provided is at least one chemical entity chosen from compounds of Formula IX

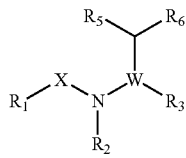

(Formula IX)

and pharmaceutically acceptable salts, solvates, chelates, non-covalent complexes, prodrugs, and mixtures thereof, wherein $R_1$, X, W, $R_2$, $R_3$, $R_4$, and $R_7$ are as defined for compounds of Formula I and wherein $R_5$ and $R_6$, together with the atoms to which they are bound, form an optionally substituted 5-7 membered heterocycle which optionally may include one or two heteroatoms.

In some embodiments, $R_5$ and $R_6$, together with the atoms to which they are attached, form an optionally substituted 2H-[1,2,3]triazol-4-yl; an optionally substituted 1H-benzoimidazol-2-yl; an optionally substituted piperazinyl ring; an optionally substituted morpholinyl ring; or an optionally substituted 1H-Imidazol-4-yl ring; an optionally substituted isoxazol-4-yl ring.

Also provided is at least one chemical entity chosen from compounds of Formula X

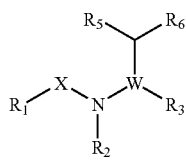

(Formula X)

and pharmaceutically acceptable salts, solvates, chelates, non-covalent complexes, prodrugs, and mixtures thereof, wherein $R_1$, X, W, $R_4$, $R_5$, $R_6$ and $R_7$ are as defined for compounds of Formula I and wherein $R_2$ and $R_3$, taken together with the atoms to which they are attached, form an optionally substituted 3- to 7-membered heterocyclic ring.

In some embodiments, $R_2$ and $R_3$, taken together with the atoms to which they are attached, form an optionally substituted 3- to 7-membered heterocyclic ring. In some embodiments, they form an aziridinyl ring.

Also provided is at least one chemical entity chosen from compounds of Formula XI

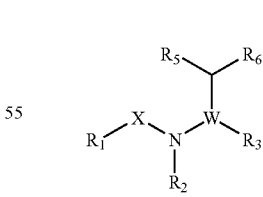

(Formula XI)

and pharmaceutically acceptable salts, solvates, chelates, non-covalent complexes, prodrugs, and mixtures thereof, wherein W, $R_3$, $R_4$, $R_5$, $R_6$ and $R_7$ are as defined for compounds of Formula I and wherein $R_1$, X, N, and $R_2$, taken together, form a substituted 2,4-dioxo-1,4-dihydro-2H-quinazolin-3-yl, 4-oxo-4H-quinazolin-3-yl, or 4-oxo-4H-pyridopyrimidin-3-yl ring.

Also provided is at least one chemical entity chosen from compounds of Formula XII

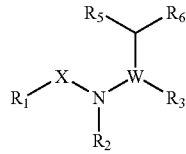

(Formula XII)

and pharmaceutically acceptable salts, solvates, chelates, non-covalent complexes, prodrugs, and mixtures thereof, wherein $R_1$, W, $R_4$, $R_5$, and $R_6$ are as defined for compounds of Formula I and wherein
—X—N($R_2$)— is —C=N—; and
X taken together with $R_3$ forms an optionally substituted heterocyclic ring;
in each case, provided that if W is N, then $R_5$ is not hydroxyl or optionally substituted amino, and $R_6$ is not optionally substituted alkoxy, optionally substituted aralkoxy, optionally substituted heteroaralkoxy, or optionally substituted amino.

In certain embodiments, —X—N($R_2$)— is —C=N—; and X taken together with $R_3$ forms an optionally substituted heterocyclic ring, including but not limited to 3H-[1,3,4] oxadiazol-2-one; 4,5-dihydro-oxazole; thiazole; imidazole; 3,5-dihydro-imidazol-4-one; or 3H-pyrimidin-4-one, each of which is optionally substituted.

Also provided is at least one chemical entity chosen from compounds of Formula XIII

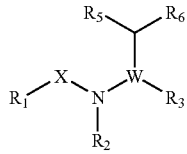

(Formula XIII)

and pharmaceutically acceptable salts, solvates, chelates, non-covalent complexes, prodrugs, and mixtures thereof,
wherein $R_1$, X, W, $R_2$, $R_4$, $R_5$, and $R_7$ are as defined for compounds of Formula I and wherein
$R_3$ and $R_6$, together with the atoms to which they are bound, form an optionally substituted 5-7 membered heterocycle which optionally may include one or two additional heteroatoms.

In some embodiments, $R_3$ and $R_6$, together with the atoms to which they are attached, form an optionally substituted pyrrolidinyl ring, an optionally substituted piperidinyl ring, or an optionally substituted 1,2,3,4-tetrahydro-quinolin-3-yl ring.

Also provided is at least one chemical entity chosen from compounds recited in Table 1, 2, 3, 4, 5, or 6, and pharmaceutically acceptable salts, solvates, chelates, non-covalent complexes, prodrugs, and mixtures thereof.

The compounds can be named and numbered using AutoNom version 2.1, ChemDraw Ultra 6.0, Cambridgesoft, Cambridge, Mass.; Struct<=>Name algorithm of ChemDraw Ultra 9.0, Cambridgesoft, Cambridge, Mass. or ISIS-DRAW.

TABLE 1

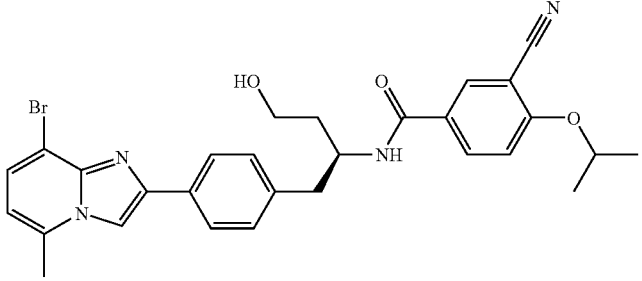

N-{1-[4-(8-Bromo-5-methyl-imidazo[1,2-a]pyridin-2-yl)-benzyl]-3-hydroxy-propyl}-3-cyano-4-isopropoxy-benzamide

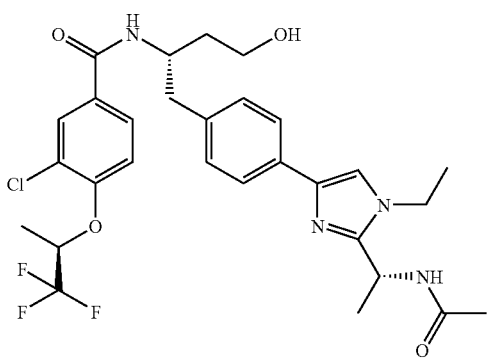

N-(1-{4-[2-(1-Acetylamino-ethyl)-1-ethyl-1H-imidazol-4-yl]-benzyl}-3-hydroxy-propyl)-3-chloro-4-(2,2,2-trifluoro-1-methyl-ethoxy)-benzamide TABLE 1-continued

| Structure | Name |
|---|---|
| ABS 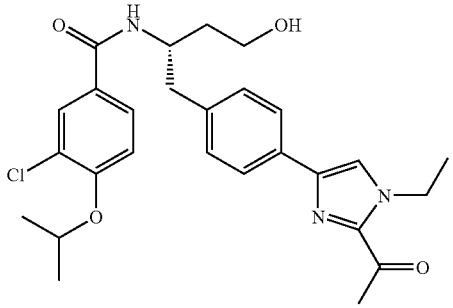 | N-(1-{4-[2-acetyl-1-ethyl-1H-imidazol-4-yl]-benzyl}-3-hydroxy-propyl)-3-chloro-4-(isopropoxy)-benzamide |
| ABS 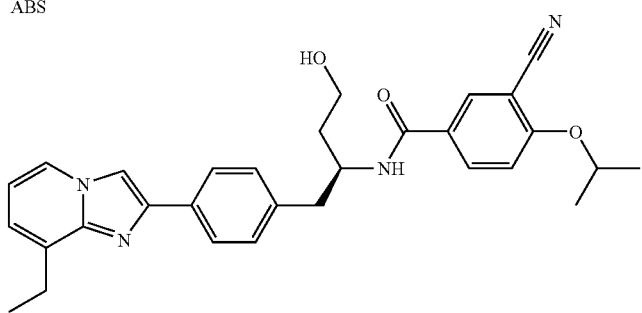 | N-{1-[4-(8-ethyl-imidazo[1,2-a]pyridin-2-yl)-benzyl]-3-hydroxy-propyl}-3-cyano-4-isopropoxy-benzamide |
| ABS 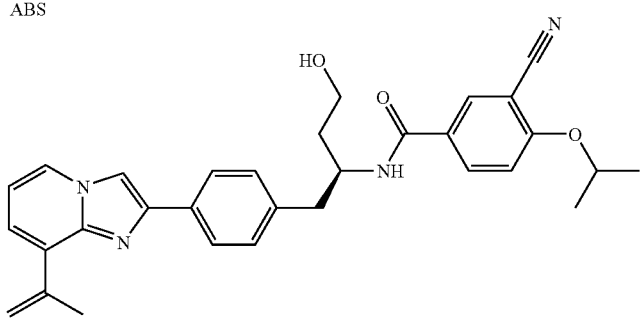 | N-{1-[4-(8-isopropenyl-imidazo[1,2-a]pyridin-2-yl)-benzyl]-3-hydroxy-propyl}-3-cyano-4-isopropoxy-benzamide |
| ABS 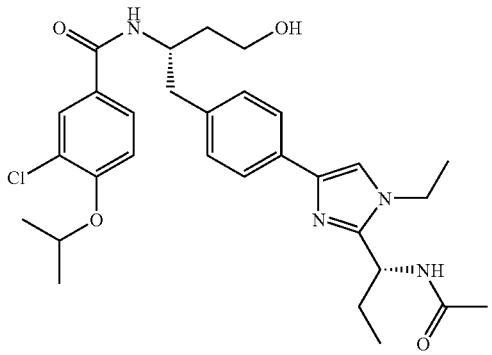 | N-(1-{4-[2-(1-Acetylamino-propyl)-1-ethyl-1H-imidazol-4-yl]-benzyl}-3-hydroxy-propyl)-3-chloro-4-(isopropoxy)-benzamide |

TABLE 1-continued
| | |
|---|---|
| ABS 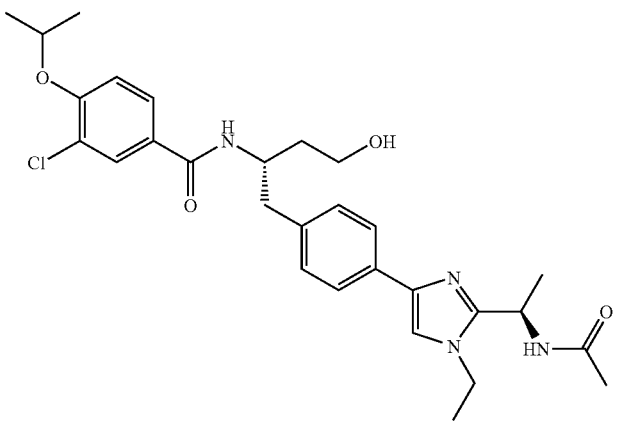 | N-(1-{4-[2-(1-Acetylamino-ethyl)-1-ethyl-1H-imidazol-4-yl]-benzyl}-3-hydroxy-propyl)-3-chloro-4-isopropoxy-benzamide |
| ABS 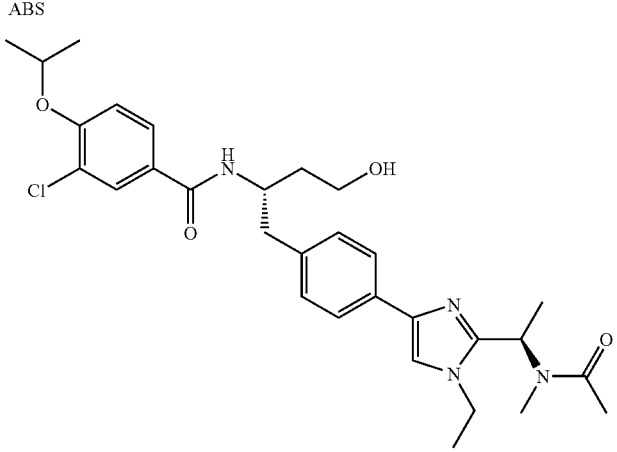 | N-[1-(4-{2-[1-(Acetyl-methyl-amino)-ethyl]-1-ethyl-1H-imidazol-4-yl}-benzyl)-3-hydroxy-propyl]-3-chloro-4-(2,2,2-trifluoro-1-methyl-ethoxy)-benzamide |
| ABS 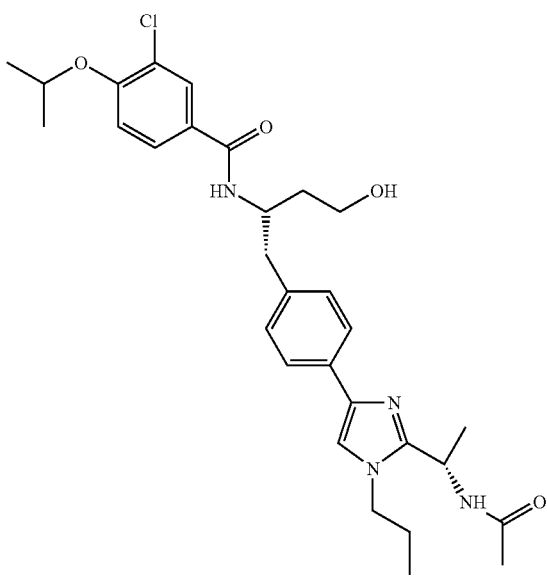 | N-(1-{4-[2-(1-Acetylamino-ethyl)-1-propyl-1H-imidazol-4-yl]-benzyl}-3-hydroxy-propyl)-3-chloro-4-isopropoxy-benzamide |

TABLE 1-continued

| | | |
|---|---|---|
| ABS | 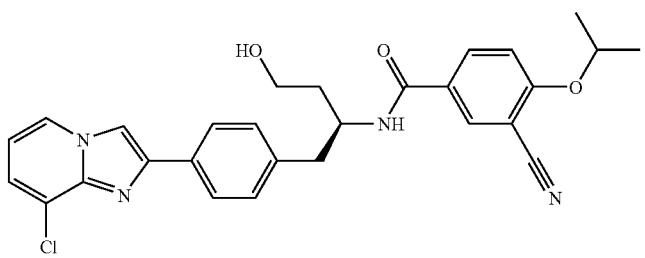 | N-{1-[4-(8-chloro-imidazo[1,2-a]pyridin-2-yl)-benzyl]-3-hydroxy-propyl}-3-cyano-4-isopropoxy-benzamide |
| ABS | 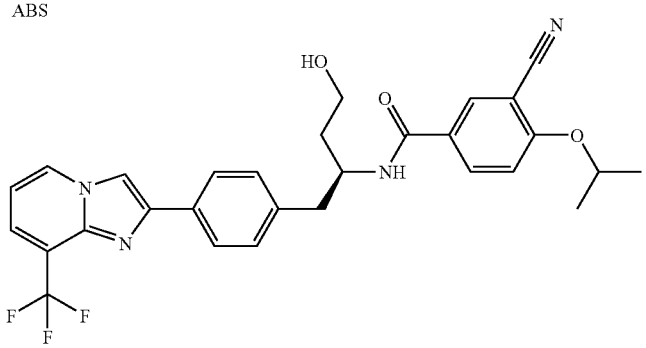 | N-{1-[4-(8-trifluoromethyl-imidazo[1,2-a]pyridin-2-yl)-benzyl]-3-hydroxy-propyl}-3-cyano-4-isopropoxy-benzamide |
| ABS | 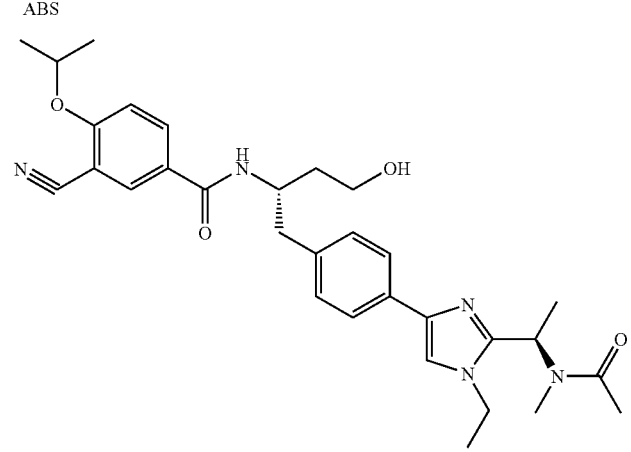 | N-(1-{4-[2-[1-(Acetyl-methyl-amino)-ethyl]-1-ethyl-1H-imidazol-4-yl]-benzyl}-3-hydroxy-propyl)-3-cyano-4-isopropoxy-benzamide |
| RAC | 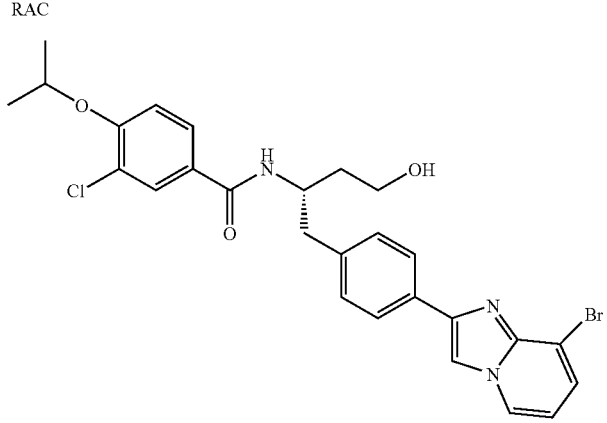 | N-{1-[4-(8-Bromo-imidazo[1,2-a]pyridin-2-yl)-benzyl]-3-hydroxy-propyl}-3-chloro-4-isopropoxy-benzamide |

TABLE 1-continued

| Structure | Name |
|---|---|
| ABS | N-(1-{4-[2-(1-Acetylamino-ethyl)-1-isopropyl-1H-imidazol-4-yl]-benzyl}-3-hydroxy-propyl)-3-chloro-4-isopropoxy-benzamide |
| RAC | N-(1-{4-[2-(1-Acetylamino-ethyl)-1-ethyl-1H-imidazol-4-yl]-benzyl}-3-hydroxy-propyl)-3-chloro-4-(2,2,2-trifluoro-1-methyl-ethoxy)-benzamide |
| ABS | N-(2-(2-amino-2-methyl-propionylamino)-1-{4-[8-(1-hydroxy-ethyl)-imidazo[1,2-a]pyridin-2-yl]-benzyl}-ethyl)-3-chloro-4-isopropoxy-benzamide |
| ABS | N-(1-{4-[2-[1-(3-methyl-ureido)-ethyl]-1-ethyl-1H-imidazol-4-yl]-benzyl}-3-hydroxy-propyl)-3-chloro-4-(2,2,2-trifluoro-1-methyl-ethoxy)-benzamide |

TABLE 1-continued

| | | |
|---|---|---|
| ABS 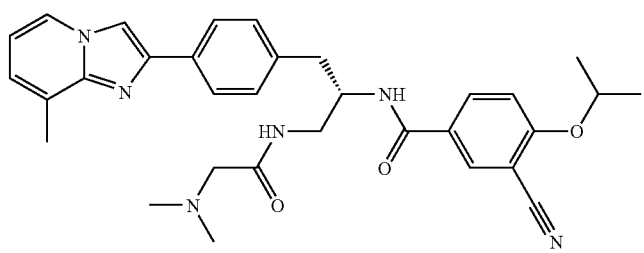 | | N-(2-(2-dimethylamino-acetylamino)-1-{4-[8-methyl-imidazo [1,2-a]pyridin-2-yl]-benzyl}-ethyl)-3-cyano-4-isopropoxy-benzamide |
| ABS 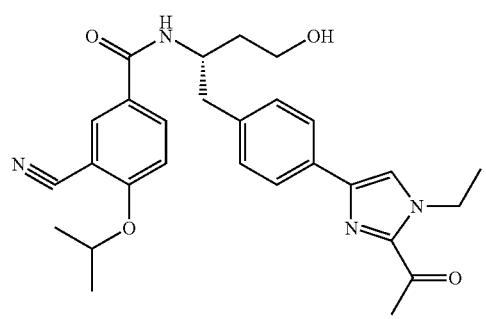 | | N-(1-{4-[2-Acetyl-1-ethyl-1H-imidazol-4-yl]-benzyl}-3-hydroxy-propyl)-3-cyano-4-isopropoxy-benzamide |
| ABS 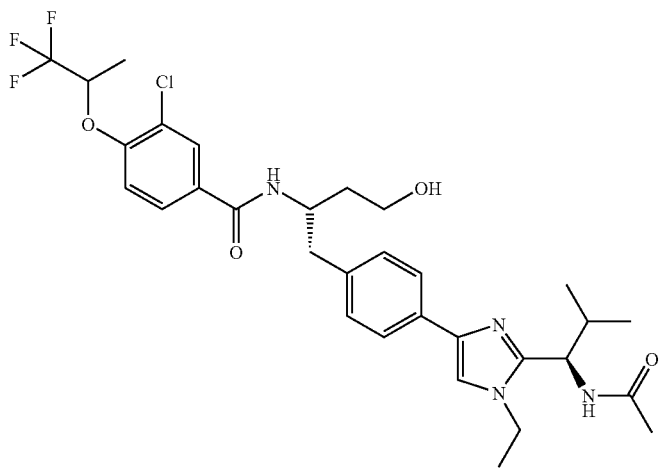 | | N-(1-{4-[2-(1-Acetylamino-2-methyl-propyl)-1-ethyl-1H-imidazol-4-yl]-benzyl}-3-hydroxy-propyl)-3-chloro-4-(2,2,2-trifluoro-1-methyl-ethoxy)-benzamide |
| ABS 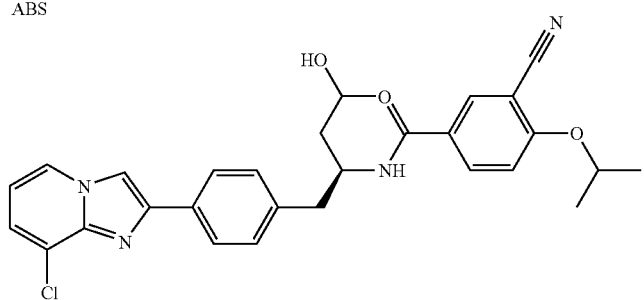 | | N-(1-[4-(8-chloro-imidazo[1,2-a]pyridin-2-yl)-benzyl]-3-hydroxy-butyl}-3-cyano-4-isopropoxy-benzamide |

TABLE 1-continued

| | | |
|---|---|---|
| ABS | 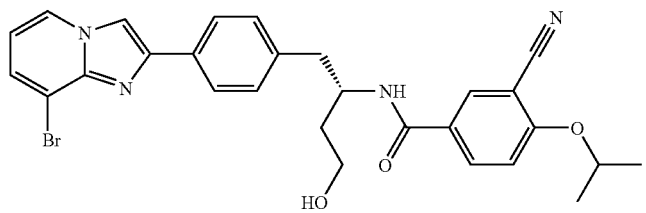 | N-{1-[4-(8-Bromo-imidazo[1,2-a]pyridin-2-yl)-benzyl]-3-hydroxy-propyl}-3-cyano-4-isopropoxy-benzamide |
| ABS | 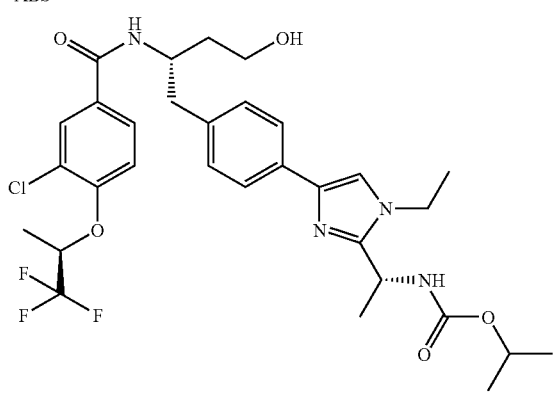 | N-(1-{4-[2-(1-(isopropoxycarbonylamino)-ethyl)-1-ethyl-1H-imidazol-4-yl]-benzyl}-3-hydroxy-propyl)-3-chloro-4-(2,2,2-trifluoro-1-methyl-ethoxy)-benzamide |
| RAC | 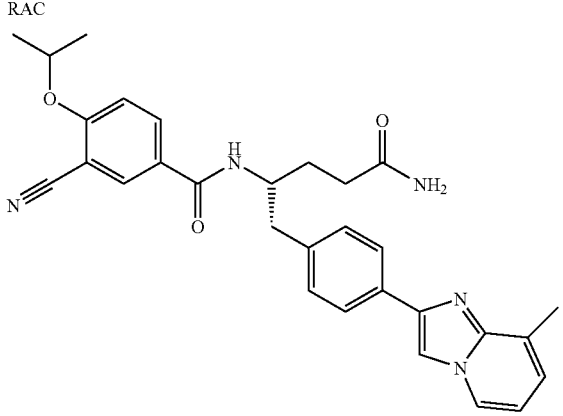 | N-{1-[4-(8-methyl-imidazo[1,2-a]pyridin-2-yl)-benzyl]-3-carbamoyl-propyl}-3-cyano-4-isopropoxy-benzamide |
| ABS | 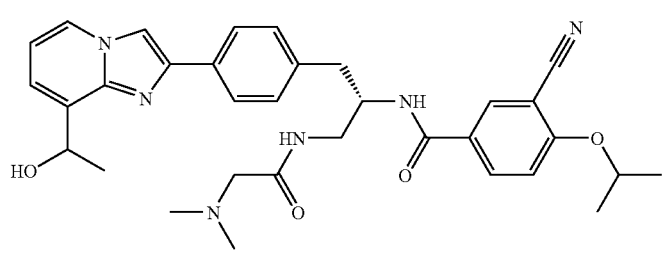 | N-(2-(2-dimethylamino-acetylamino)-1-{4-[8-(1-hydroxy-ethyl)-imidazo[1,2-a]pyridin-2-yl]-benzyl}-ethyl)-3-cyano-4-isopropoxy-benzamide |

TABLE 1-continued

| ABS | | |
|---|---|---|
| | 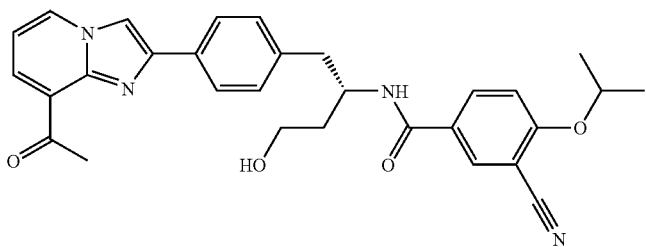 | N-{1-[4-(8-acetyl-imidazo[1,2-a]pyridin-2-yl)-benzyl]-3-hydroxy-propyl}-3-cyano-4-isopropoxy-benzamide |
| ABS | 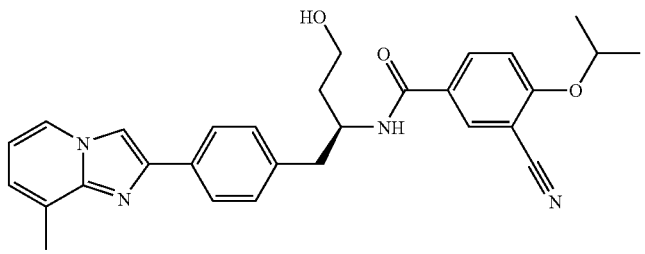 | N-{1-[4-(8-methyl-imidazo[1,2-a]pyridin-2-yl)-benzyl]-3-hydroxy-propyl}-3-cyano-4-isopropoxy-benzamide |
| ABS | 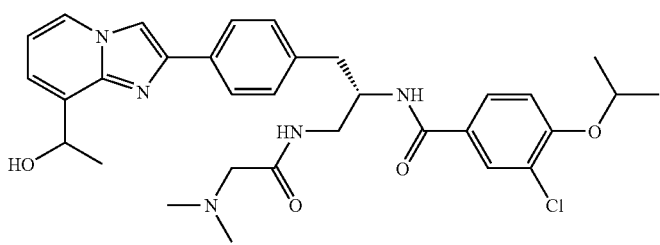 | N-(2-(2-dimethylamino-acetylamino)-1-{4-[8-(1-hydroxy-ethyl)-imidazo[1,2-a]pyridin-2-yl]-benzyl}-ethyl)-3-chloro-4-isopropoxy-benzamide |
| ABS | 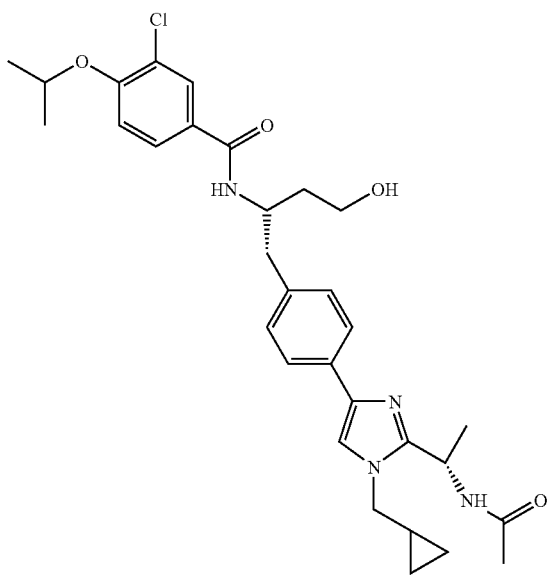 | N-(1-{4-[2-(1-Acetylamino-ethyl)-1-cyclopropylmethyl-1H-imidazol-4-yl]-benzyl}-3-hydroxy-propyl)-3-chloro-4-isopropoxy-benzamide |

TABLE 1-continued

| | | |
|---|---|---|
| ABS | 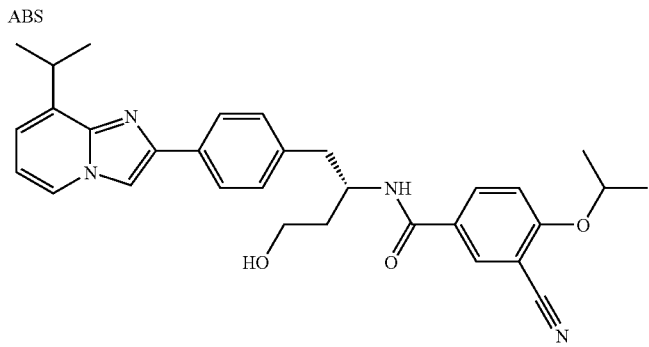 | N-{1-[4-(8-isopropyl-imidazo[1,2-a]pyridin-2-yl)-benzyl]-3-hydroxy-propyl}-3-cyano-4-isopropoxy-benzamide |
| ABS | 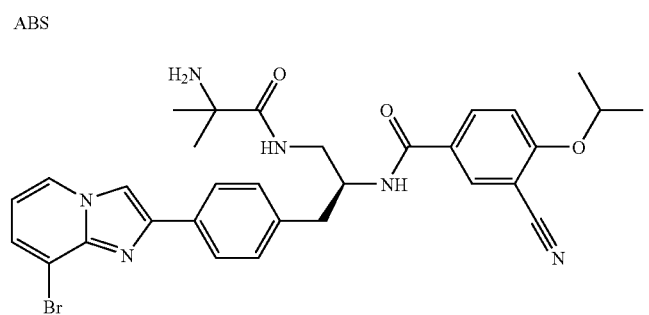 | N-(2-(2-amino-2-methyl-propionylamino)-1-{4-[8-bromo-imidazo[1,2-a]pyridin-2-yl]-benzyl}-ethyl)-3-cyano-4-isopropoxy-benzamide |
| ABS | 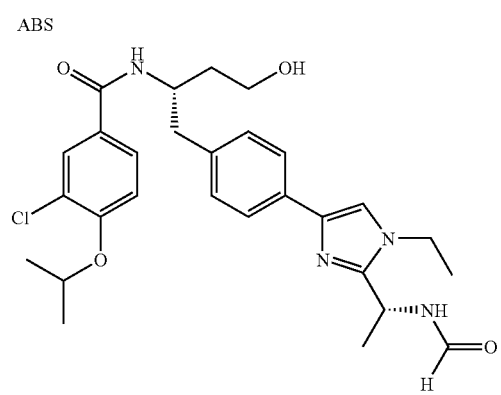 | N-(1-{4-[2-(1-formylamino-ethyl)-1-ethyl-1H-imidazol-4-yl]-benzyl}-3-hydroxy-propyl)-3-chloro-4-isopropoxy-benzamide |
| ABS | 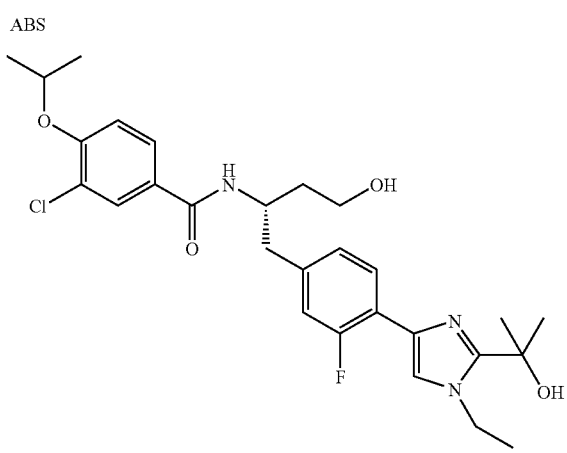 | N-(1-{3-fluoro-4-[2-(1-methyl-hydroxy-ethyl)-1-ethyl-1H-imidazol-4-yl]-benzyl}-3-hydroxy-propyl)-3-chloro-4-isopropoxy-benzamide |

TABLE 1-continued

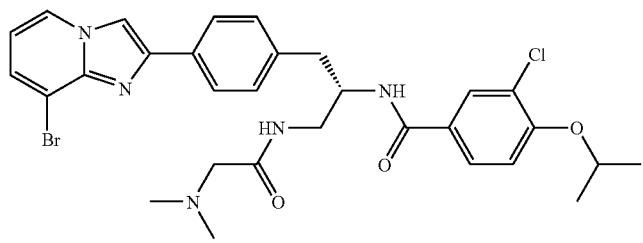

N-(2-(2-dimethylamino-acetylamino)-1-{4-[8-bromo-imidazo[1,2-a]pyridin-2-yl]-benzyl}-ethyl)-3-chloro-4-isopropoxy-benzamide

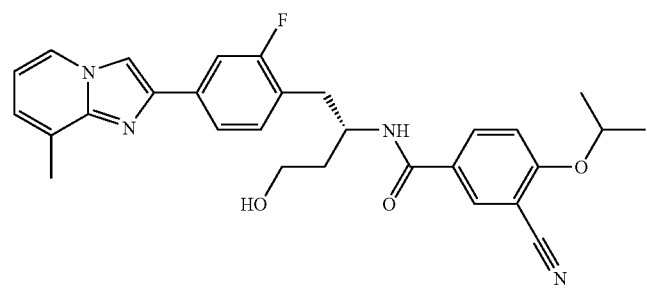

N-{1-[2-fluoro-4-(8-methyl-imidazo[1,2-a]pyridin-2-yl)-benzyl]-3-hydroxy-propyl}-3-cyano-4-isopropoxy-benzamide

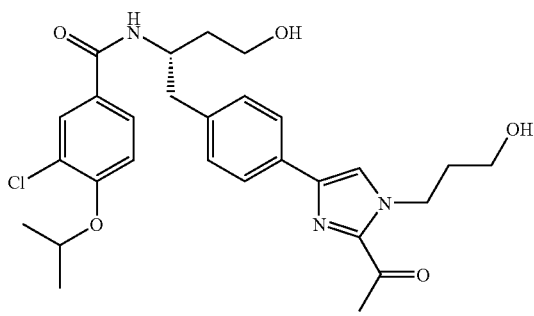

N-(1-{4-[2-acetyl-1-(3-hydroxypropyl)-1H-imidazol-4-yl]-benzyl}-3-hydroxy-propyl)-3-chloro-4-isopropoxy-benzamide

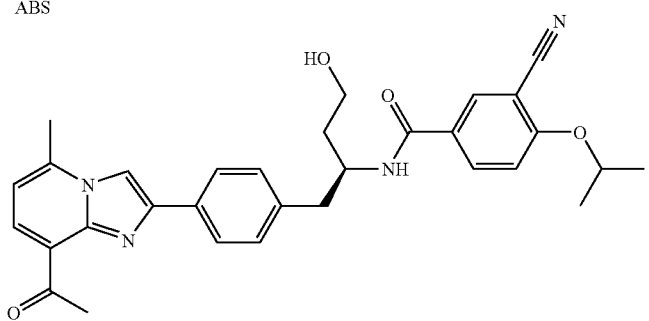

N-{1-[4-(8-acetyl-5-methyl-imidazo[1,2-a]pyridin-2-yl)-benzyl]-3-hydroxy-propyl}-3-cyano-4-isopropoxy-benzamide TABLE 1-continued

| ABS (structure) | Name |
|---|---|
| | N-(1-{4-[2-(1-Acetylamino-2-methyl-propyl)-1-ethyl-1H-imidazol-4-yl]-benzyl}-3-hydroxy-propyl)-3-chloro-4-isopropoxy-benzamide |
| | N-[1-[4-(2-acetyl-1-ethyl-1H-imidazol-4-yl)-benzyl]-2-(2-hydroxy-acetylamino)-ethyl]-3-chloro-4-(2,2,2-trifluoro-1-methyl-ethoxy)-benzamide |
| | N-(1-{4-[2-butyl-1-ethyl-1H-imidazol-4-yl]-benzyl}-3-hydroxy-propyl)-3-cyano-4-isopropoxy-benzamide |
| | N-(2-(2-dimethylamino-acetylamino)-1-{4-[8-bromo-imidazo[1,2-a]pyridin-2-yl]-benzyl}-ethyl)-3-cyano-4-isopropoxy-benzamide |

TABLE 1-continued

| | |
|---|---|
| 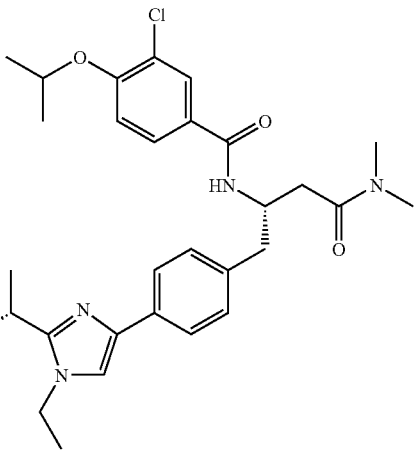 ABS | N-(1-{4-[2-(1-acetylamino-ethyl)-1-ethyl-1H-imidazol-4-yl]-benzyl}-2-dimethylcarbamoyl-ethyl)-3-chloro-4-isopropoxy-benzamide |
| 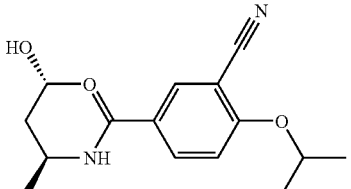 ABS | N-{1-[4-(8-methyl-imidazo[1,2-a]pyridin-2-yl)-benzyl]-3-hydroxy-butyl}-3-cyano-4-isopropoxy-benzamide |
| 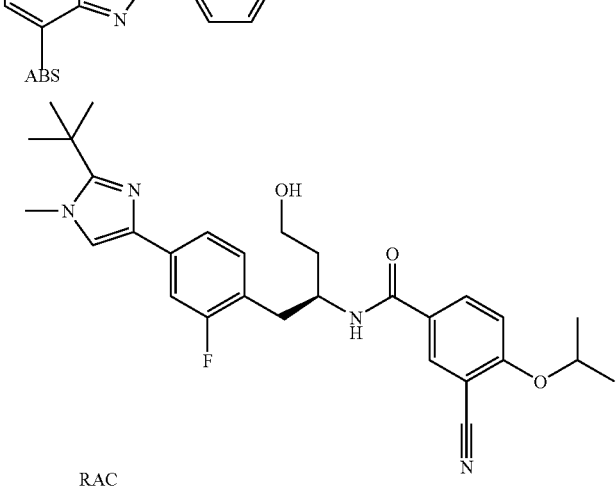 ABS | N-(1-{2-fluoro-4-[2-t-butyl-1-methyl-1H-imidazol-4-yl]-benzyl}-3-hydroxy-propyl)-3-cyano-4-isopropoxy-benzamide |
| 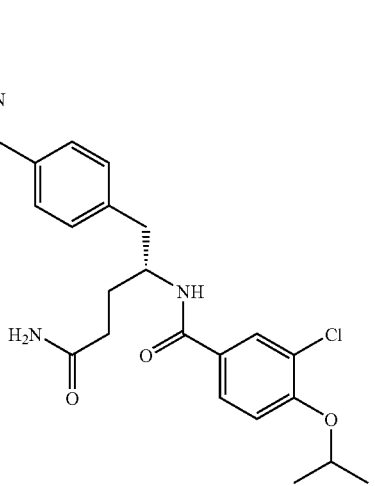 RAC | N-(1-{4-[2-acetyl-1-methyl-1H-imidazol-4-yl]-benzyl}-3-carbamoyl-propyl)-3-chloro-4-isopropoxy-benzamide |

TABLE 1-continued

| ABS | | |
|---|---|---|
| | 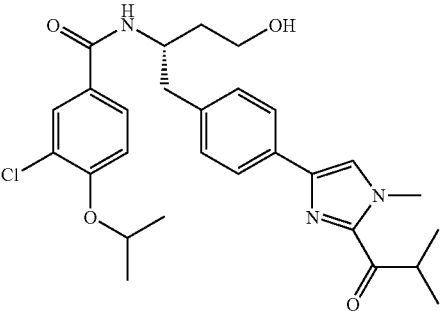 | N-(1-{4-[2-isobutyryl-1-methyl-1H-imidazol-4-yl]-benzyl}-3-hydroxy-propyl)-3-chloro-4-isopropoxy-benzamide |
| ABS | 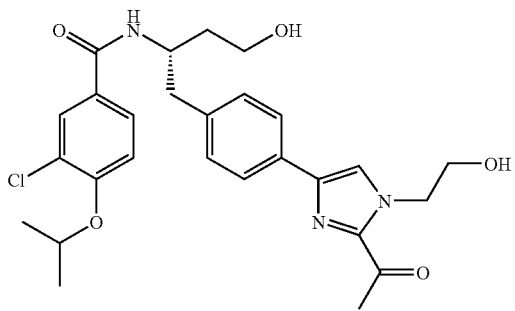 | N-(1-{4-[2-acetyl-1-(2-hydroxy-ethyl)-1H-imidazol-4-yl]-benzyl}-3-hydroxy-propyl)-3-chloro-4-isopropoxy-benzamide |
| ABS | 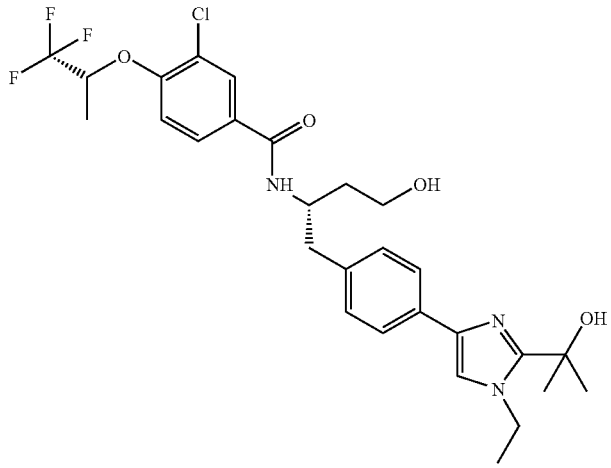 | N-(1-{4-[2-(1-methyl-1-hydroxy-ethyl)-1-ethyl-1H-imidazol-4-yl]-benzyl}-3-hydroxy-propyl)-3-chloro-4-(2,2,2-trifluoro-1-methyl-ethoxy)-benzamide |
| ABS | 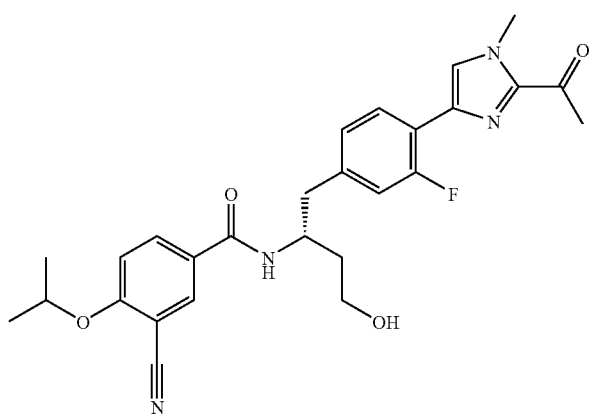 | N-(1-{3-fluoro-4-[2-acetyl-1-methyl-1H-imidazol-4-yl]-benzyl}-3-hydroxy-propyl)-3-cyano-4-isopropoxy-benzamide |

TABLE 1-continued

| | | |
|---|---|---|
| ABS | 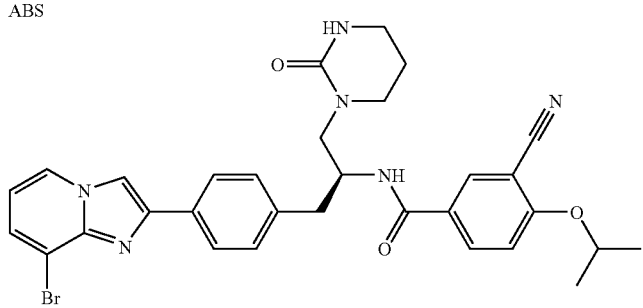 | N-[1-[4-(8-Bromo-imidazo[1,2-a]pyridin-2-yl)-benzyl]-2-(2-oxo-tetrahydro-pyrimidin-1-yl)-ethyl]-3-cyano-4-isopropoxy-benzamide |
| RAC | 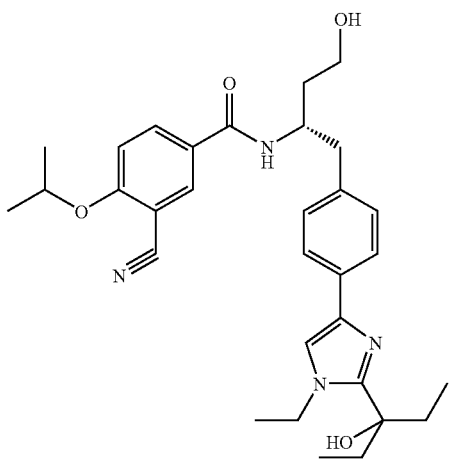 | N-(1-{4-[2-(3-hydroxy-pent-3-yl)-1-ethyl-1H-imidazol-4-yl]-benzyl}-3-hydroxy-propyl)-3-cyano-4-isopropoxy-benzamide |
| RAC | 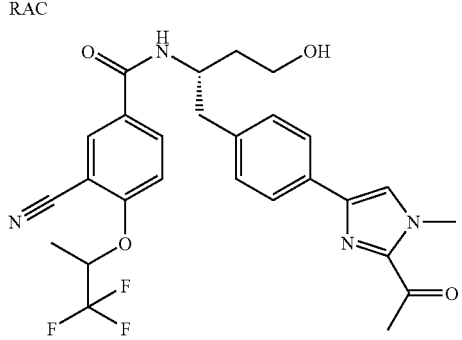 | N-(1-{4-[2-acetyl-1-methyl-1H-imidazol-4-yl]-benzyl}-3-hydroxy-propyl)-3-cyano-4-(2,2,2-trifluoro-1-methyl-ethoxy)-benzamide |
| RAC | 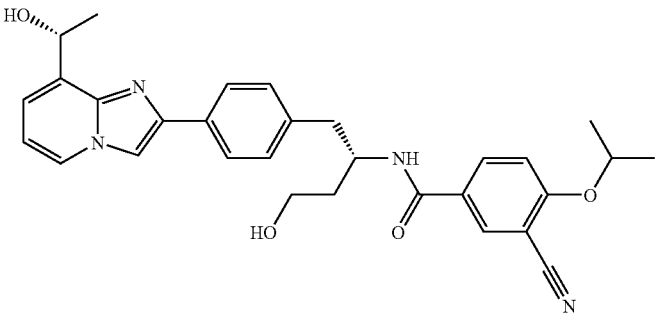 | N-{1-[4-(8-(1-hydroxy-ethyl)-imidazo[1,2-a]pyridin-2-yl)-benzyl]-3-hydroxy-propyl}-3-cyano-4-isopropoxy-benzamide |

TABLE 1-continued

| ABS (structure) | Name |
|---|---|
| 3-chloro-4-isopropoxy-benzamide linked to CH2-CH(NHC(O)Ar)-CH2-CH2-OH with para-phenyl bearing 2-(1-hydroxy-1-methylethyl)-1-(2,2,2-trifluoroethyl)-1H-imidazol-4-yl | N-(1-{4-[2-(1-hydroxy-1-methyl-ethyl)-1-(2,2,2-trifluoroethyl)-1H-imidazol-4-yl]-benzyl}-3-hydroxy-propyl)-3-chloro-4-isopropoxy-benzamide |
| 3-chloro-4-isopropoxy-benzamide linked to CH2-CH(NH-)-C(O)-CH2-OH with para-phenyl bearing 2-acetyl-1-ethyl-1H-imidazol-4-yl | N-[1-[4-(2-acetyl-1-ethyl-1H-imidazol-4-yl)-benzyl]-2-(2-hydroxy-acetylamino)-ethyl]-3-chloro-4-isopropoxy-benzamide |
| 3-chloro-4-isopropoxy-benzamide linked to CH2-CH(NHC(O)Ar)-CH2-CH2-OH with para-phenyl bearing 2-acetyl-1-(2-methoxyethyl)-1H-imidazol-4-yl | N-(1-{4-[2-acetyl-1-(2-methoxyethyl)-1H-imidazol-4-yl]-benzyl}-3-hydroxy-propyl)-3-chloro-4-isopropoxy-benzamide |
| 3-cyano-4-isopropoxy-benzamide linked to CH2-CH(NH-)-CH2-NHC(O)C(CH3)2NH2 with para-phenyl bearing 8-(1-hydroxyethyl)-imidazo[1,2-a]pyridin-2-yl | N-(2-(2-amino-2-methyl-propionylamino)-1-{4-[8-(1-hydroxy-ethyl)-imidazo[1,2-a]pyridin-2-yl]-benzyl}-ethyl)-3-cyano-4-isopropoxy-benzamide |

TABLE 1-continued

| | |
|---|---|
| 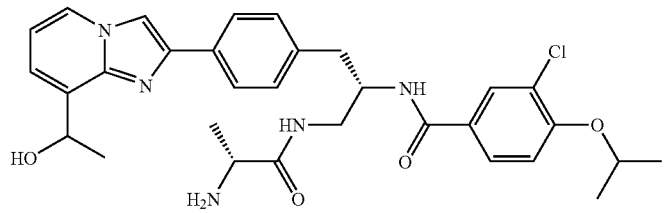 | N-(2-(2-amino-propionylamino)-1-{4-[8-(1-hydroxy-ethyl)-imidazo[1,2-a]pyridin-2-yl]-benzyl}-ethyl)-3-chloro-4-isopropoxy-benzamide |
| 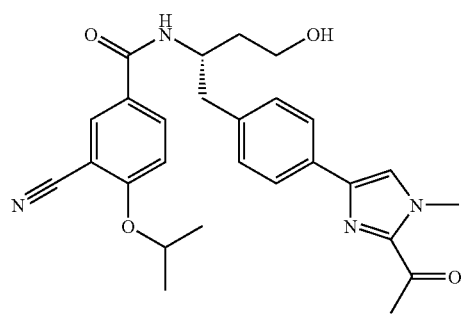 | N-(1-{4-[2-acetyl-1-methyl-1H-imidazol-4-yl]-benzyl}-3-hydroxy-propyl)-3-cyano-4-isopropoxy-benzamide |
| 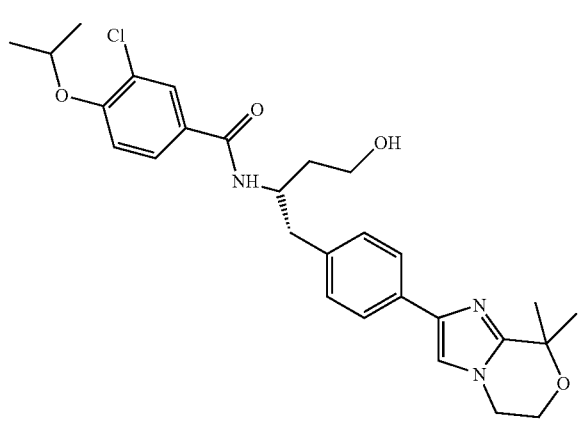 | N-(1-{4-(5,5-dimethyl-7,8-dihydro-imidazo[1,2-c][1,3]oxazin-2-yl)-benzyl}-3-hydroxy-propyl)-3-chloro-4-isopropoxy-benzamide |
| 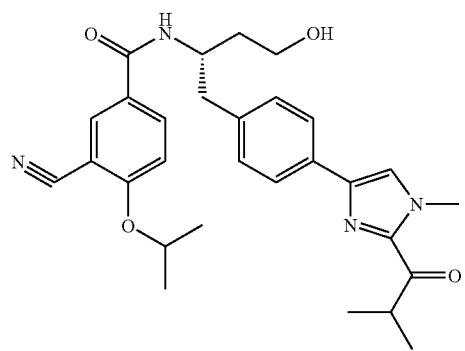 | N-(1-{4-[2-isobutyryl-1-methyl-1H-imidazol-4-yl]-benzyl}-3-hydroxy-propyl)-3-cyano-4-isopropoxy-benzamide |

TABLE 1-continued

| | | |
|---|---|---|
| ABS | 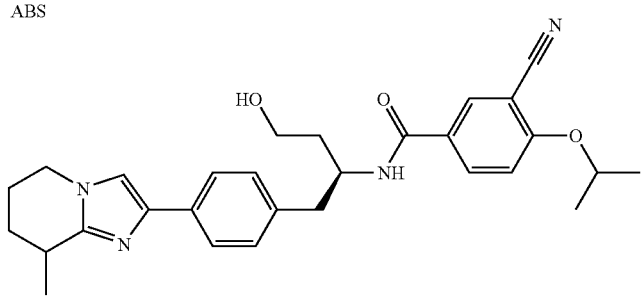 | N-(1-{4-(8-methyl-5,6,7,8-tetrahydro-imidazo[1,2-a]pyridin-2-yl)-benzyl}-3-hydroxy-propyl)-3-cyano-4-isopropoxy-benzamide |
| ABS | 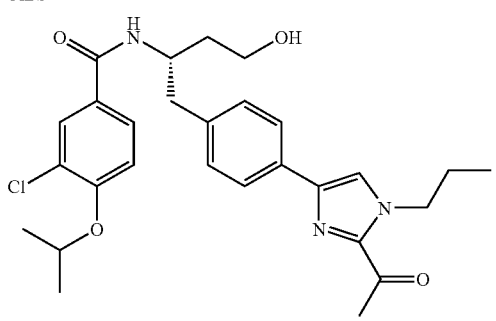 | N-(1-{4-[2-acetyl-1-propyl-1H-imidazol-4-yl]-benzyl}-3-hydroxy-propyl)-3-chloro-4-isopropoxy-benzamide |
| ABS | 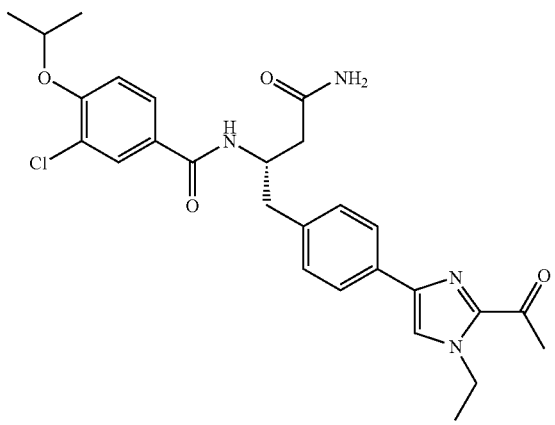 | N-(1-{4-[2-acetyl-1-ethyl-1H-imidazol-4-yl]-benzyl}-2-carbamoyl-ethyl)-3-chloro-4-isopropoxy-benzamide |
| ABS | 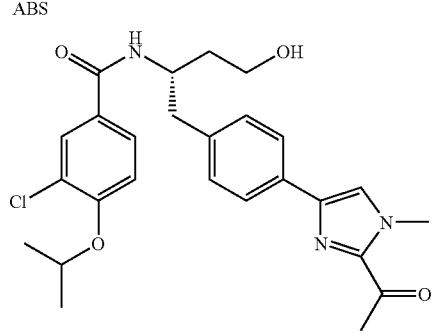 | N-(1-{4-[2-acetyl-1-methyl-1H-imidazol-4-yl]-benzyl}-3-hydroxy-propyl)-3-chloro-4-isopropoxy-benzamide |

TABLE 1-continued

| | | |
|---|---|---|
| ABS | 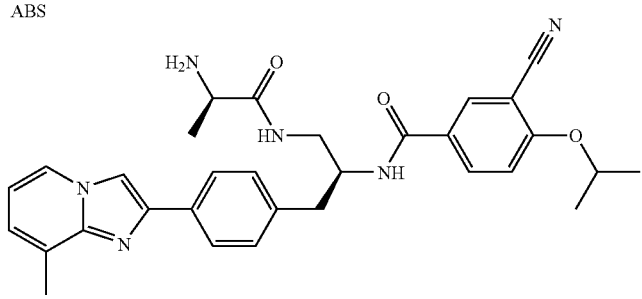 | N-(2-(2-amino-propionylamino)-1-[8-methyl-imidazo[1,2-a]pyridin-2-yl]-benzyl}-ethyl)-3-cyano-4-isopropoxy-benzamide |
| ABS | 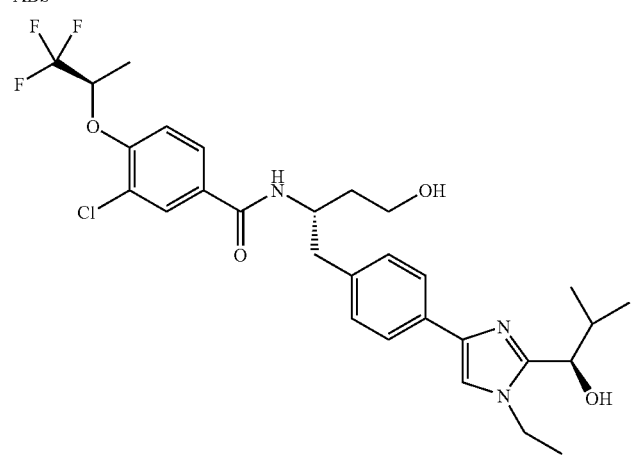 | N-(1-{4-[2-(1-hydroxy-2-methyl-propyl)-1-ethyl-1H-imidazol-4-yl]-benzyl}-3-hydroxy-propyl)-3-chloro-4-(2,2,2-trifluoro-1-methyl-ethoxy)-benzamide |
| ABS | 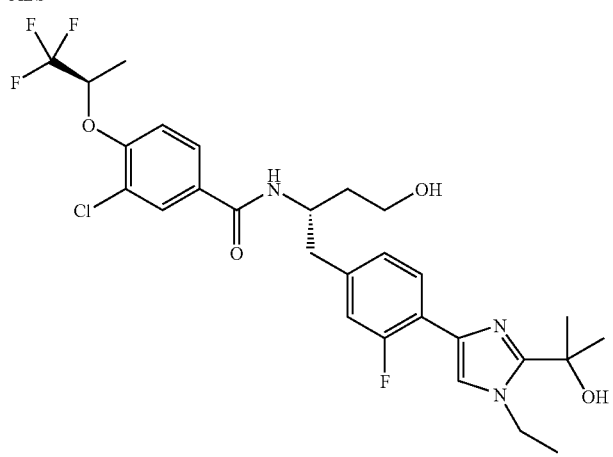 | N-(1-{3-fluoro-4-[2-(1-hydroxy-1-methyl-ethyl)-1-ethyl-1H-imidazol-4-yl]-benzyl}-3-hydroxy-propyl)-3-chloro-4-(2,2,2-trifluoro-1-methyl-ethoxy)-benzamide |
| ABS | 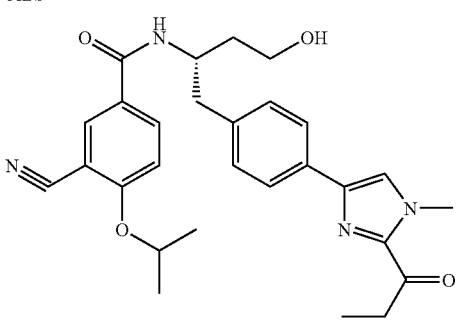 | N-(1-{4-[2-propionyl-1-methyl-1H-imidazol-4-yl]-benzyl}-3-hydroxy-propyl)-3-cyano-4-isopropoxy-benzamide |

TABLE 1-continued
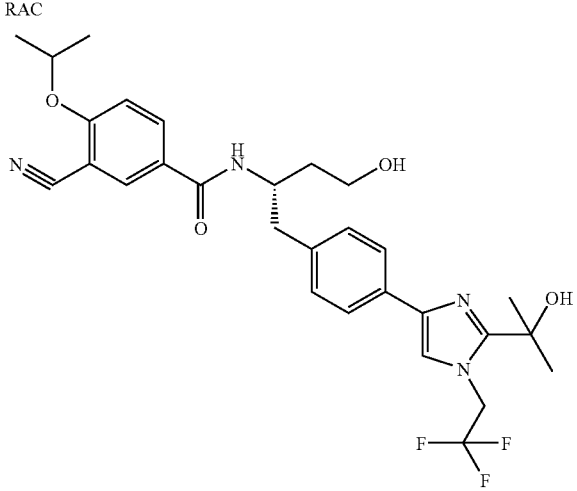
N-(1-{4-[2-(1-hydroxy-1-methyl-ethyl)-1-(2,2,2-trifluoroethyl)-1H-propyl)-3-cyano-4-isopropoxy-benzamide
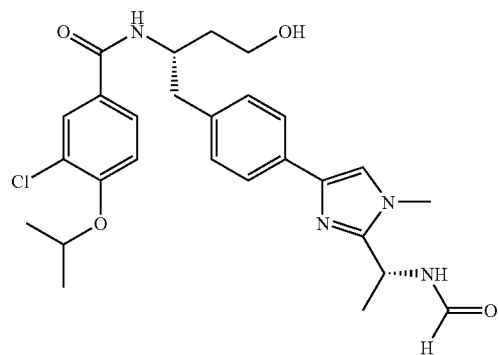
N-(1-{4-[2-(1-formylamino-ethyl)-1-methyl-1H-imidazol-4-yl]-benzyl}-3-hydroxy-propyl)-3-chloro-4-isopropoxy-benzamide
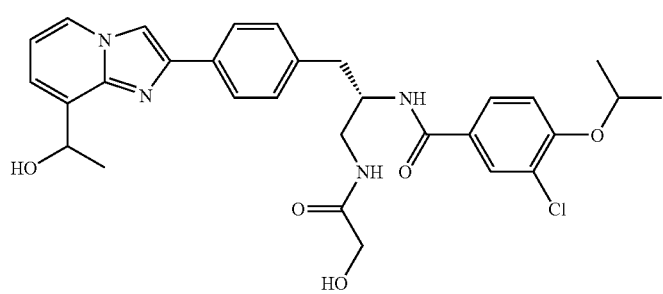
N-(2-(2-hydroxy-acetylamino)-1-{4-[8-(1-hydroxy-ethyl)-imidazo[1,2-a]pyridin-2-yl]-benzyl}-ethyl)-3-chloro-4-isopropoxy-benzamide TABLE 1-continued

| | |
|---|---|
| ABS | N-(3-fluoro-1-{4-[2-(1-hydroxy-1-methyl-ethyl)-1-methyl-1H-imidazol-4-yl]-benzyl}-3-hydroxy-propyl)-3-cyano-4-isopropoxy-benzamide |
| ABS | N-(1-{4-[2-(1-acetylamino-ethyl)-1-methyl-1H-imidazol-4-yl]-benzyl}-3-hydroxy-propyl)-3-chloro-4-isopropoxy-benzamide |
| ABS | N-{1-[4-(8-chloro-imidazo[1,2-a]pyridin-2-yl)-benzyl]-3-hydroxy-propyl}-3-chloro-4-isopropoxy-benzamide |
| ABS | N-(2-(2-amino-2-methyl-propionylamino)-1-{4-[8-methyl-imidazo[1,2-a]pyridin-2-yl]-benzyl}-ethyl)-3-cyano-4-isopropoxy-benzamide |

TABLE 1-continued
| | | |
|---|---|---|
| ABS | 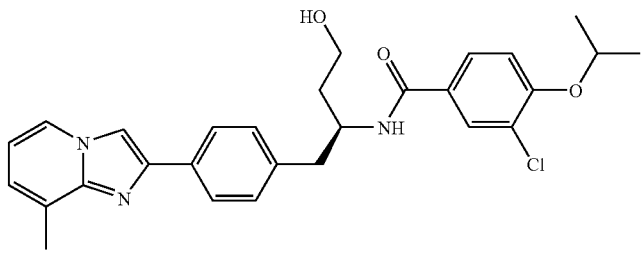 | N-{1-[4-(8-methyl-imidazo[1,2-a]pyridin-2-yl)-benzyl]-3-hydroxy-propyl}-3-chloro-4-isopropoxy-benzamide |
| ABS | 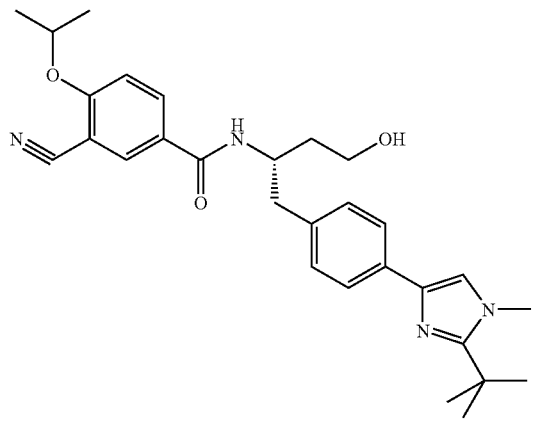 | N-(1-{4-[2-t-butyl-1-methyl-1H-imidazol-4-yl]-benzyl}-3-hydroxy-propyl)-3-cyano-4-isopropoxy-benzamide |
| RAC | 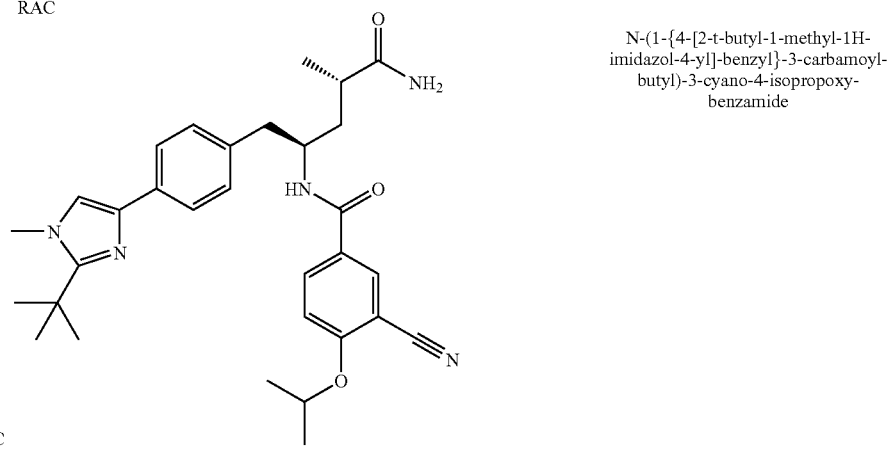 | N-(1-{4-[2-t-butyl-1-methyl-1H-imidazol-4-yl]-benzyl}-3-carbamoyl-butyl)-3-cyano-4-isopropoxy-benzamide |
| RAC | 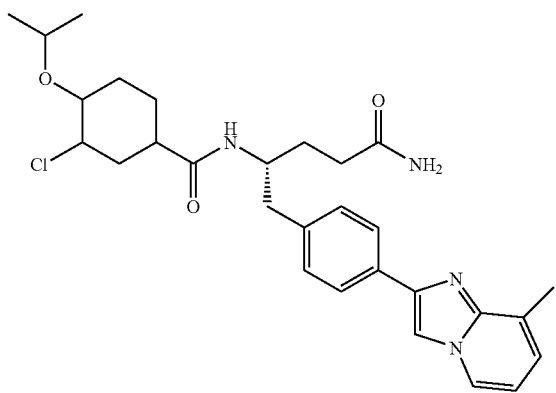 | N-{1-[4-(8-methyl-imidazo[1,2-a]pyridin-2-yl)-benzyl]-3-carbamoyl-propyl}-3-chloro-4-isopropoxy-benzamide |

TABLE 1-continued
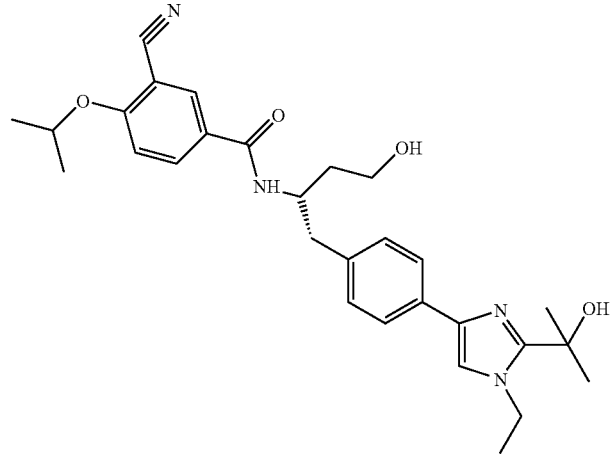
N-(1-{4-[2-(1-hydroxy-1-methyl-ethyl)-1-ethyl-1H-imidazol-4-yl]-benzyl}-3-hydroxy-propyl)-3-cyano-4-isopropoxy-benzamide
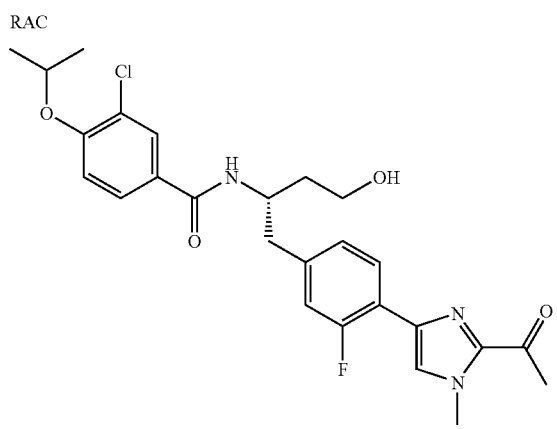
N-(1-{3-fluoro-4-[2-acetyl-1-methyl-1H-imidazol-4-yl]-benzyl}-3-hydroxy-propyl)-3-chloro-4-isopropoxy-benzamide
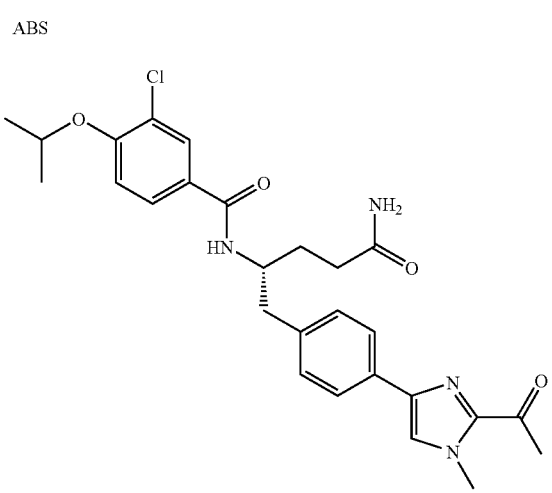
N-(1-{4-[2-acetyl-1-methyl-1H-imidazol-4-yl]-benzyl}-3-carbamoyl-propyl)-3-chloro-4-isopropoxy-benzamide TABLE 1-continued

| ABS | |
|---|---|
| 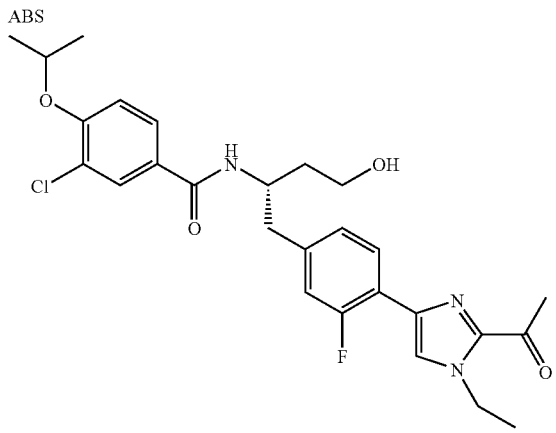 | N-(1-{3-fluoro-4-[2-acetyl-1-ethyl-1H-imidazol-4-yl]-benzyl}-3-hydroxy-propyl)-3-chloro-4-isopropoxy-benzamide |
| 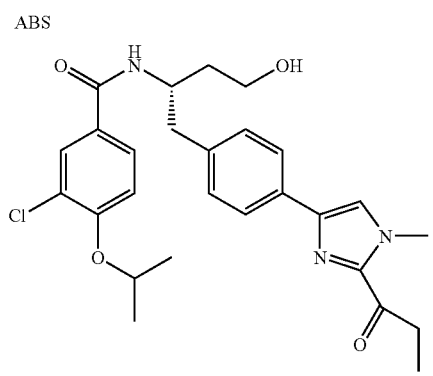 | N-(1-{4-[2-propionyl-1-methyl-1H-imidazol-4-yl]-benzyl}-3-hydroxy-propyl)-3-chloro-4-isopropoxy-benzamide |
| 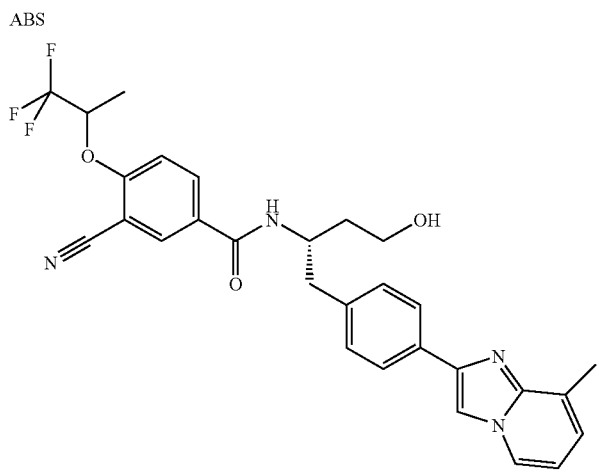 | N-{1-[4-(8-methyl-imidazo[1,2-a]pyridin-2-yl)-benzyl]-3-hydroxy-propyl}-3-cyano-4-(2,2,2-trifluoro-1-methyl-ethoxy)-benzamide |
| 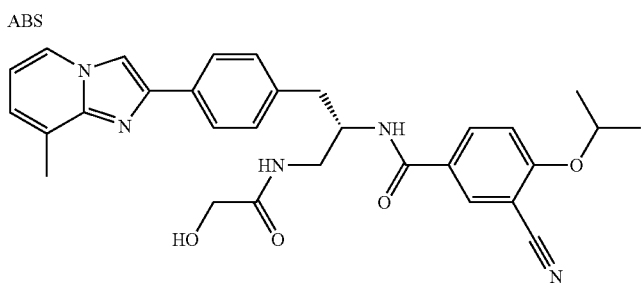 | N-(2-(2-hydroxy-acetylamino)-1-{4-[8-methyl-imidazo[1,2-a]pyridin-2-yl]-benzyl}-ethyl)-3-cyano-4-isopropoxy-benzamide |

TABLE 1-continued

| | | |
|---|---|---|
| ABS | 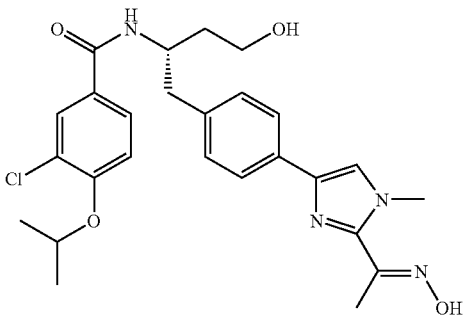 | N-(1-{4-[2-(1-hydroxyimino-ethyl)-1-methyl-1H-imidazol-4-yl]-benzyl}-3-hydroxy-propyl)-3-chloro-4-isopropoxy-benzamide |
| RAC | 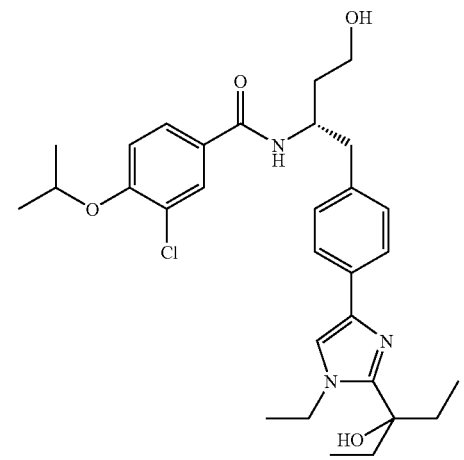 | N-(1-{4-[2-(3-hydroxy-pent-3-yl)-1-ethyl-1H-imidazol-4-yl]-benzyl}-3-hydroxy-propyl)-3-chloro-4-isopropoxy-benzamide |
| ABS | 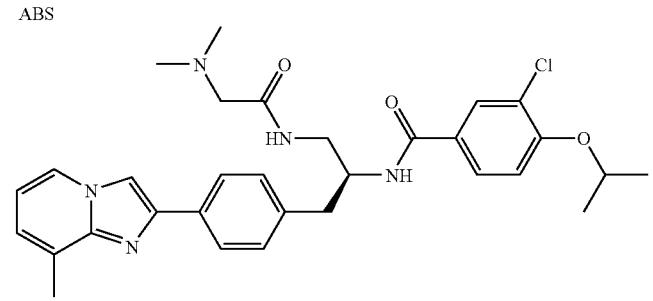 | N-(2-(2-dimethylamino-acetylamino)-1-{4-[8-methyl-imidazo[1,2-a]pyridin-2-yl]-benzyl}-ethyl)-3-chloro-4-isopropoxy-benzamide |
| ABS | 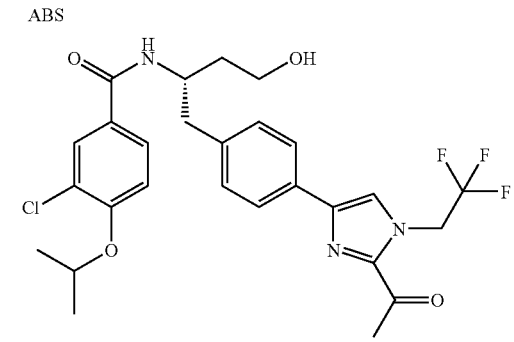 | N-(1-{4-[2-acetyl-1-(2,2,2-trifluoro-ethyl)-1H-imidazol-4-yl]-benzyl}-3-hydroxy-propyl)-3-chloro-4-isopropoxy-benzamide |

TABLE 1-continued

| | | |
|---|---|---|
| ABS | 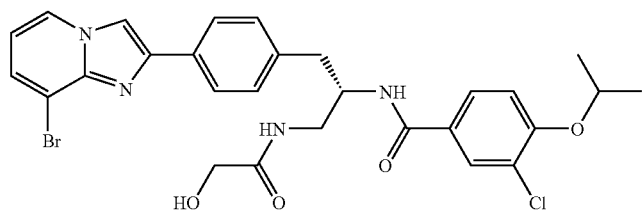 | N-(2-(3-hydroxy-propionylamino)-1-{4-[8-bromo-imidazo[1,2-a]pyridin-2-yl]-benzyl}-ethyl)-3-chloro-4-isopropoxy-benzamide |
| ABS | 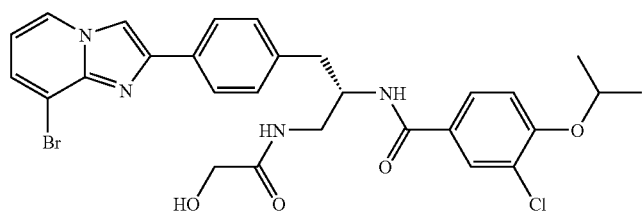 | N-(2-(2-hydroxy-acetylamino)-1-{4-[8-bromo-imidazo[1,2-a]pyridin-2-yl]-benzyl}-ethyl)-3-chloro-4-isopropoxy-benzamide |
| ABS | 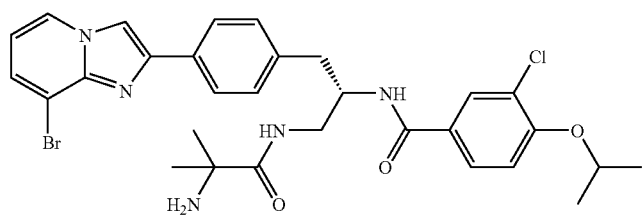 | N-(2-(2-amino-2-methyl-propionylamino)-1-{4-[8-bromo-imidazo[1,2-a]pyridin-2-yl]-benzyl}-ethyl)-3-chloro-4-isopropoxy-benzamide |
| ABS | 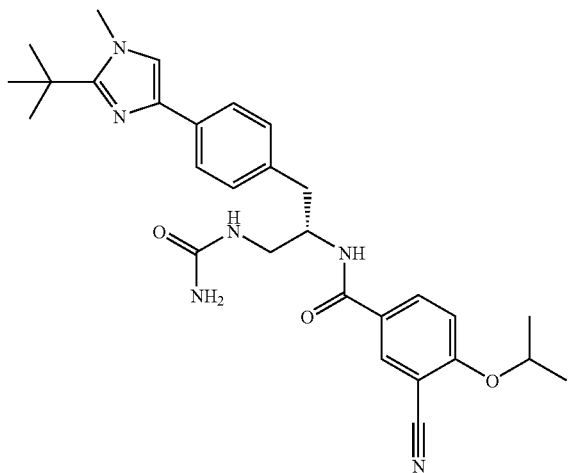 | N-[1-[4-(2-t-butyl-1-methyl-1H-imidazol-4-yl)-benzyl]-2-ureido-ethyl]-3-cyano-4-isopropoxy-benzamide |
| ABS | 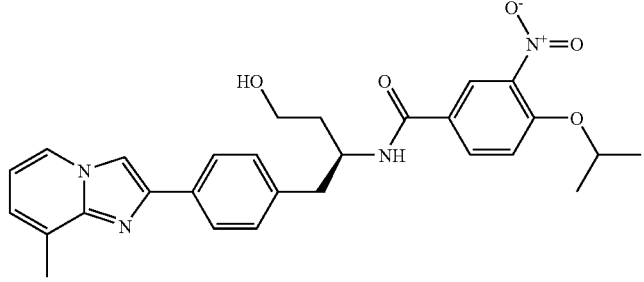 | N-{1-[4-(8-methyl-imidazo[1,2-a]pyridin-2-yl)-benzyl]-3-carbamoyl-propyl}-3-chloro-4-isopropoxy-benzamide |

TABLE 1-continued

| | |
|---|---|
| RAC 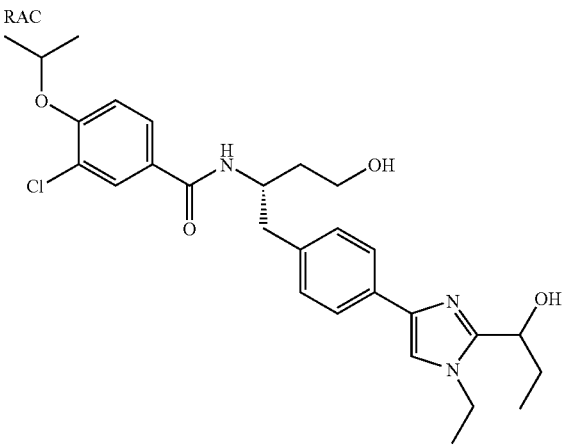 | N-(1-{4-[2-(1-hydroxypropyl)-1-ethyl-1H-imidazol-4-yl]-benzyl}-3-hydroxy-propyl)-3-chloro-4-isopropoxy-benzamide |
| ABS 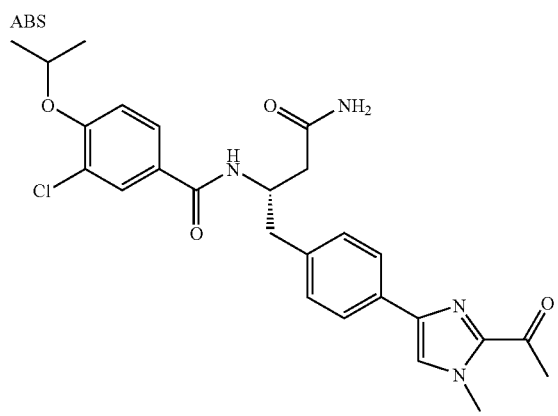 | N-(1-{4-[2-acetyl-1-methyl-1H-imidazol-4-yl]-benzyl}-2-carbamoyl-ethyl)-3-chloro-4-isopropoxy-benzamide |
| ABS 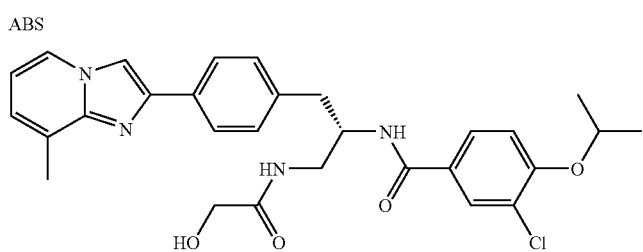 | N-(2-(2-hydroxy-acetylamino)-1-{4-[8-methyl-imidazo[1,2-a]pyridin-2-yl]-benzyl}-ethyl)-3-chloro-4-isopropoxy-benzamide |
| RAC 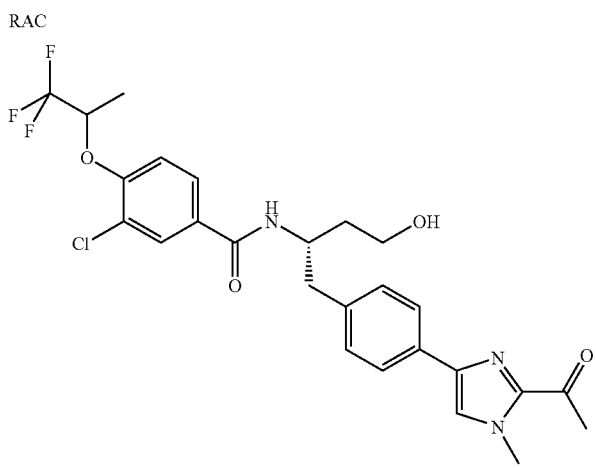 | N-(1-{4-[2-acetyl-1-methyl-1H-imidazol-4-yl]-benzyl}-3-hydroxy-propyl)-3-chloro-4-(2,2,2-trifluoro-1-methyl-ethoxy)-benzamide |

TABLE 1-continued

| | | |
|---|---|---|
| RAC | 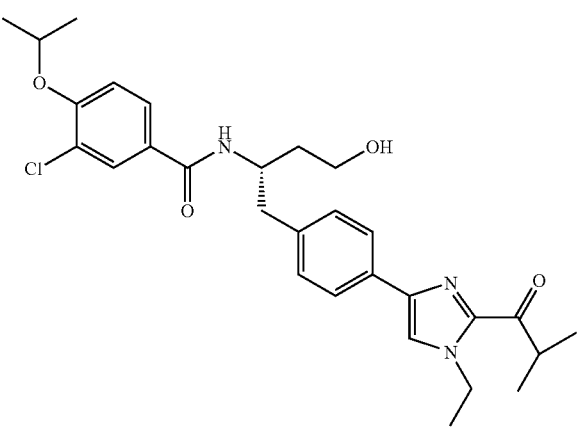 | N-(1-{4-[2-isobutyryl-1-ethyl-1H-imidazol-4-yl]-benzyl}-3-hydroxy-propyl)-3-chloro-4-isopropoxy-benzamide |
| ABS | 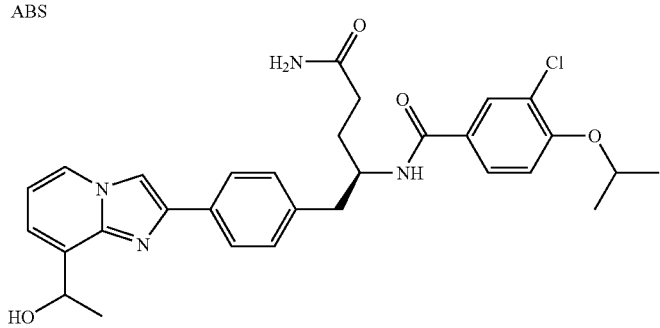 | N-{1-[4-(8-(1-hydroxy-ethyl)-imidazo[1,2-a]pyridin-2-yl)-benzyl]-3-carbamoyl-propyl}-3-chloro-4-isopropoxy-benzamide |
| ABS | 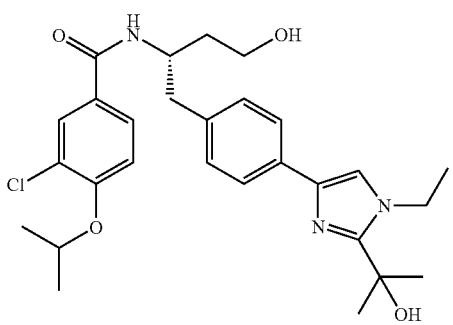 | N-(1-{4-[2-(1-hydroxy-1-methyl-ethyl)-1-ethyl-1H-imidazol-4-yl]-benzyl}-3-hydroxy-propyl)-3-chloro-4-isopropoxy-benzamide |
| ABS | 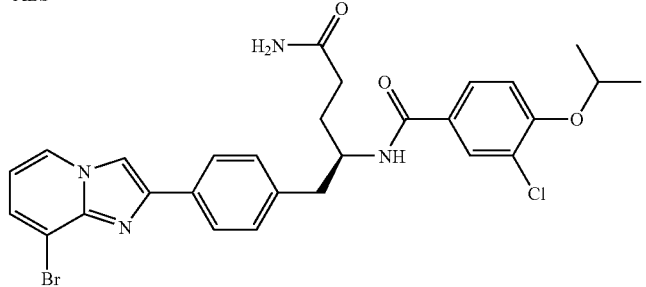 | N-{1-[4-(8-bromo-imidazo[1,2-a]pyridin-2-yl)-benzyl]-3-carbamoyl-propyl}-3-chloro-4-isopropoxy-benzamide |

TABLE 1-continued

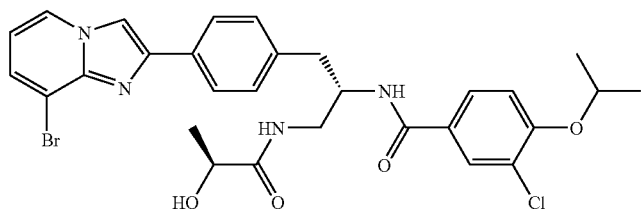

N-(2-(2-hydroxy-propionylamino)-1-{4-[8-bromo-imidazo [1,2-a]pyridin-2-yl]-benzyl}-ethyl)-3-chloro-4-isopropoxy-benzamide

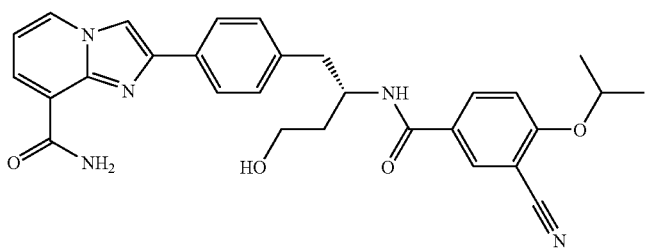

N-{1-[4-(8-(carbamoyl)-imidazo[1,2-a]pyridin-2-yl)-benzyl]-3-hydroxy-propyl}-3-cyano-4-isopropoxy-benzamide

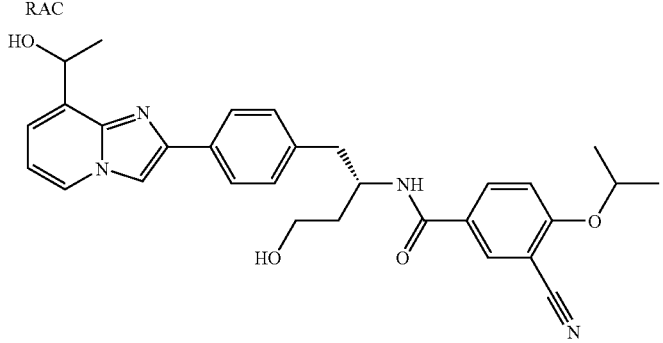

N-{1-[4-(8-(1-hydroxy-ethyl)-imidazo[1,2-a]pyridin-2-yl)-benzyl]-3-hydroxy-propyl}-3-cyano-4-isopropoxy-benzamide

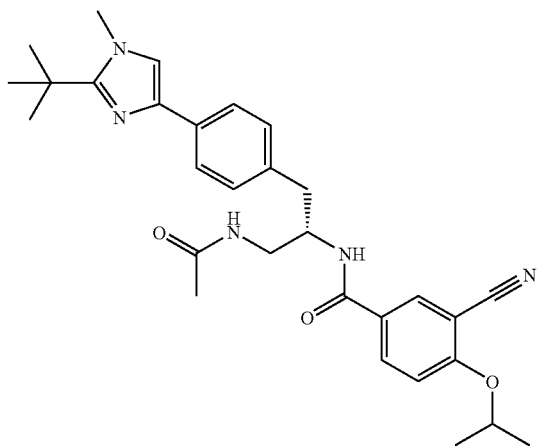

N-[1-[4-(2-t-butyl-1-methyl-1H-imidazol-4-yl)-benzyl]-2-(acetylamino)-ethyl]-3-cyano-4-isopropoxy-benzamide

TABLE 1-continued

| | | |
|---|---|---|
| ABS | 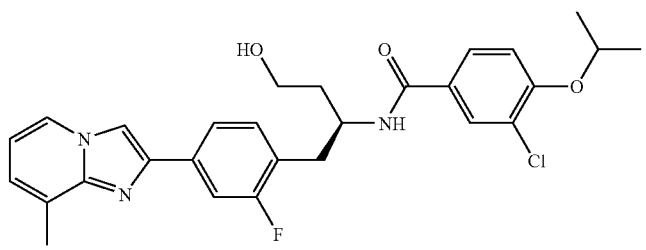 | N-{1-[2-fluoro-4-(8-methyl-imidazo[1,2-a]pyridin-2-yl)-benzyl]-3-hydroxy-propyl}-3-chloro-4-isopropoxy-benzamide |
| ABS | 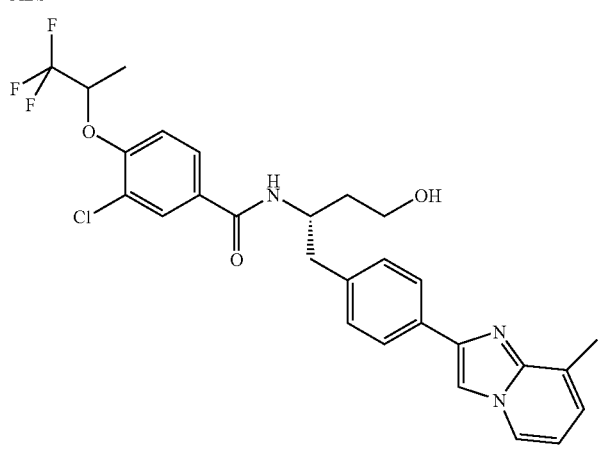 | N-{1-[4-(8-methyl-imidazo[1,2-a]pyridin-2-yl)-benzyl]-3-hydroxy-propyl}-3-chloro-4-(2,2,2-trifluoro-1-methyl-ethoxy)-benzamide |
| | 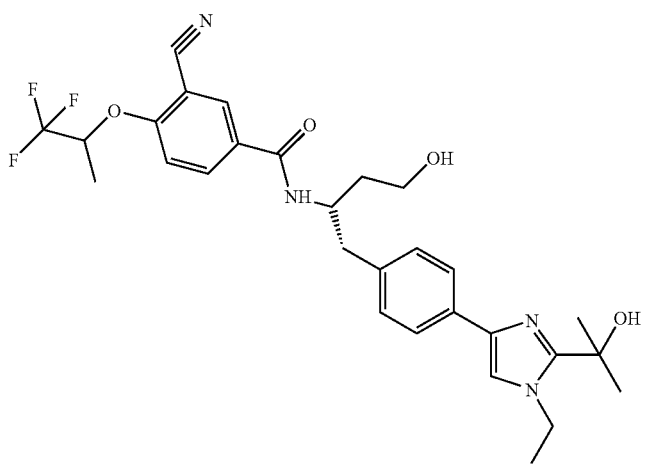 | N-(1-{4-[2-(1-hydroxy-1-methyl-ethyl)-1-ethyl-1H-imidazol-4-yl]-benzyl}-3-hydroxy-propyl)-3-cyano-4-(2,2,2-trifluoro-1-methyl-ethoxy)-benzamide |
| ABS | 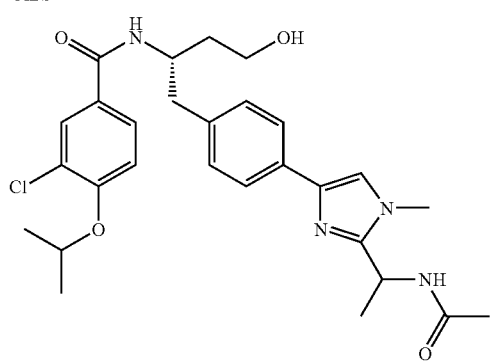 | N-(1-{4-[2-(1-Acetylamino-ethyl)-1-methyl-1H-imidazol-4-yl]-benzyl}-3-hydroxy-propyl)-3-chloro-4-isopropoxy-benzamide |

TABLE 1-continued
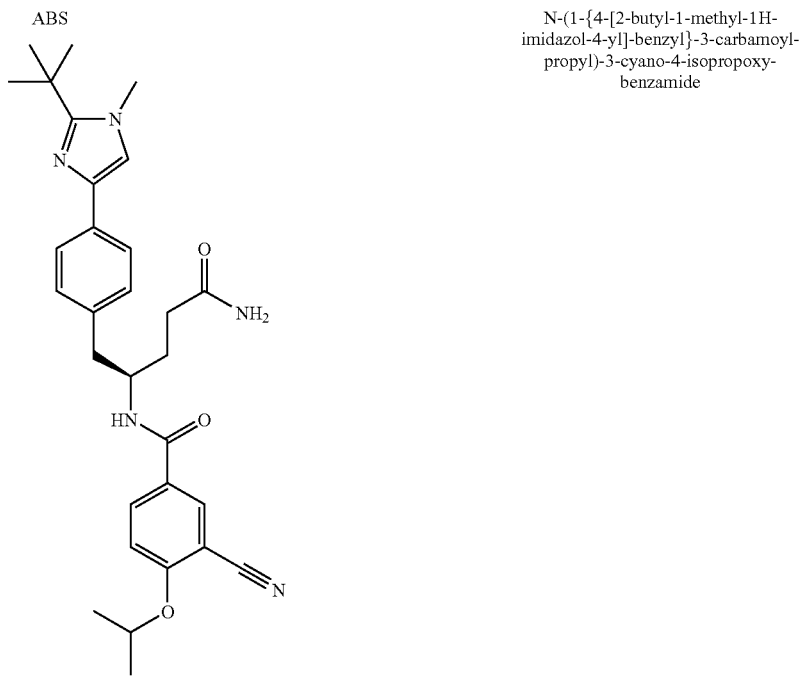
N-(1-{4-[2-butyl-1-methyl-1H-imidazol-4-yl]-benzyl}-3-carbamoyl-propyl)-3-cyano-4-isopropoxy-benzamide
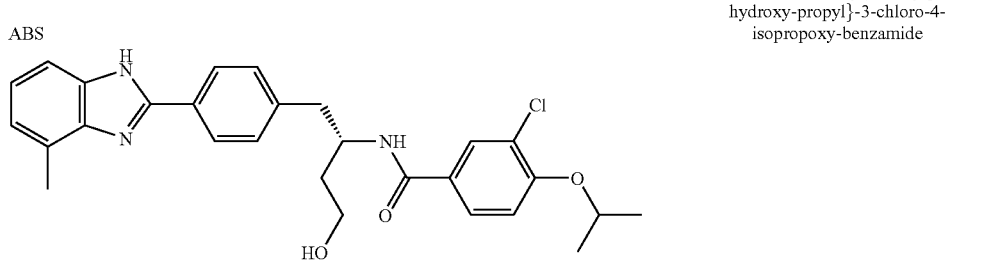
N-{1-[4-(4-methyl-3a,7a-dihydro-1H-benzoimidazol-2-yl)-benzyl]-3-hydroxy-propyl}-3-chloro-4-isopropoxy-benzamide
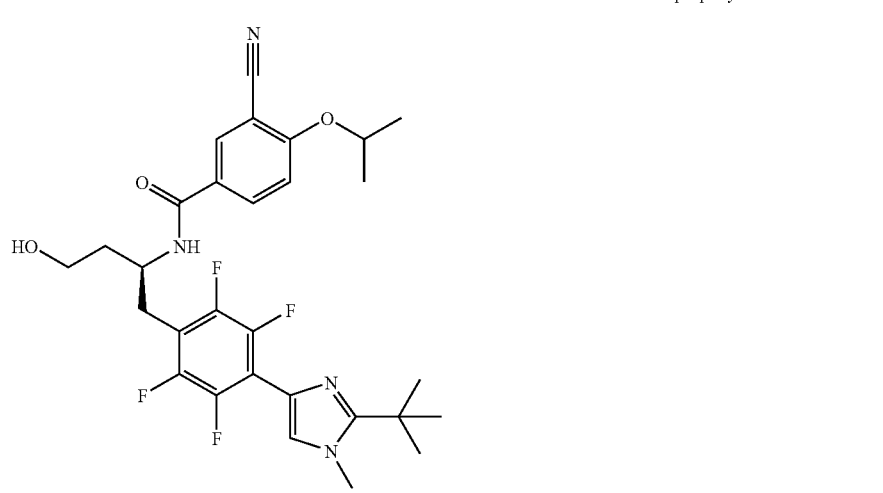
N-(1-{2,3,5,6-tetrafluoro-4-[2-t-butyl-1-methyl-1H-imidazol-4-yl]-benzyl}-3-hydroxy-propyl)-3-cyano-4-isopropoxy-benzamide TABLE 1-continued

| | |
|---|---|
| 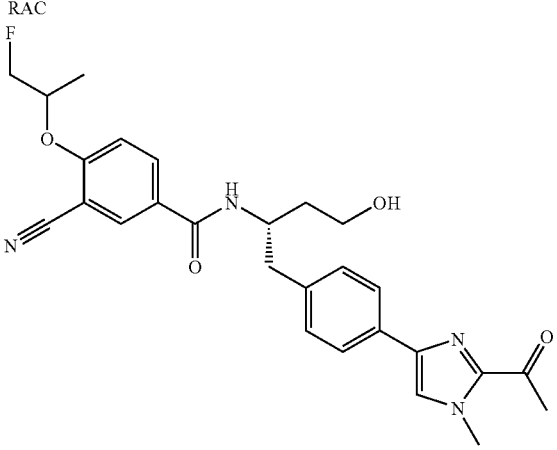 | N-(1-{4-[2-acetyl-1-methyl-1H-imidazol-4-yl]-benzyl}-3-hydroxy-propyl)-3-cyano-4-(1-fluoro-prop-2-yloxy)-benzamide |
| 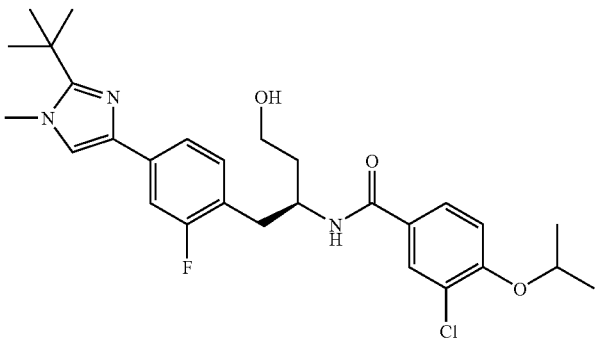 | N-(1-{4-[2-t-butyl-1-methyl-1H-imidazol-4-yl]-benzyl}-3-hydroxy-propyl)-3-chloro-4-isopropoxy-benzamide |
| 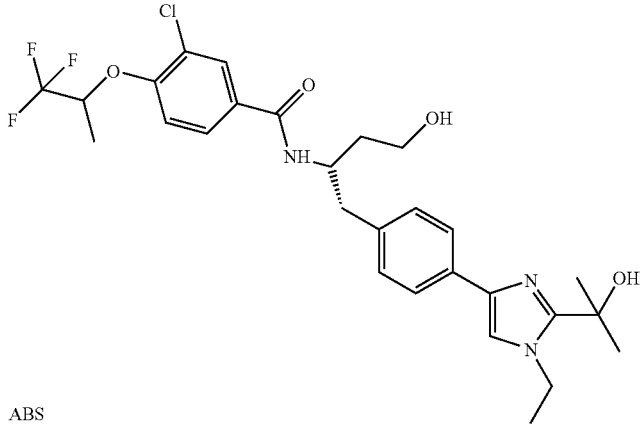 | N-(1-{4-[2-(1-hydroxy-1-methyl-ethyl)-1-ethyl-1H-imidazol-4-yl]-benzyl}-3-hydroxy-propyl)-3-chloro-4-(2,2,2-trifluoro-1-methyl-ethoxy)-benzamide |
| 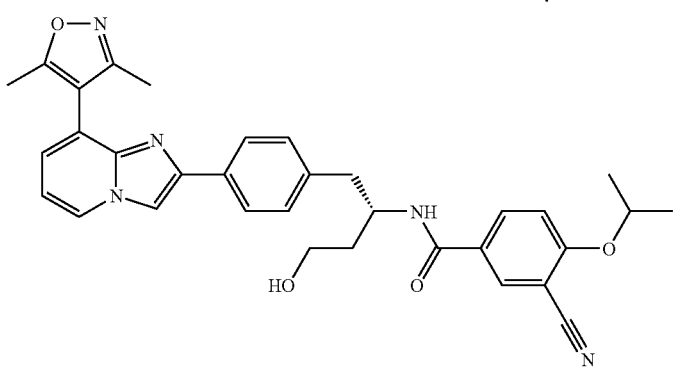 | N-{1-[4-(8-(3,5-dimethyl-isoxazol-4-yl)-imidazo[1,2-a]pyridin-2-yl)-benzyl]-3-hydroxy-propyl}-3-cyano-4-isopropoxy-benzamide |

TABLE 1-continued

| | | |
|---|---|---|
| ABS | 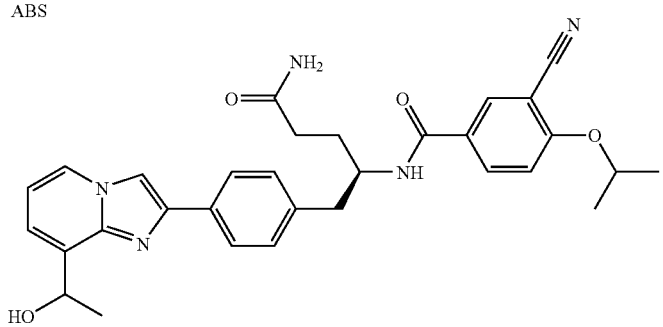 | N-{1-[4-(8-(1-hydroxy-ethyl)-imidazo[1,2-a]pyridin-2-yl)-benzyl]-3-carbamoyl-propyl}-3-cyano-4-isopropoxy-benzamide |
| RAC | 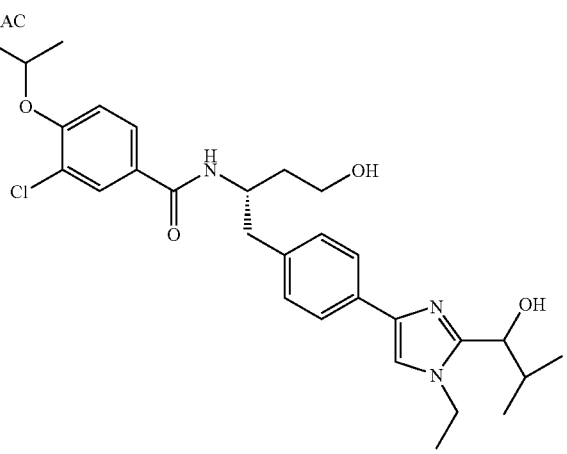 | N-(1-{4-[2-(1-hydroxy-2-methyl-propyl)-1-ethyl-1H-imidazol-4-yl]-benzyl}-3-hydroxy-propyl)-3-chloro-4-isopropoxy-benzamide |
| ABS | 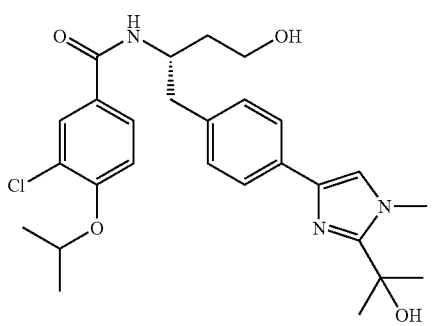 | N-(1-{4-[2-(1-hydroxy-1-methyl-ethyl)-1-methyl-1H-imidazol-4-yl]-benzyl}-3-hydroxy-propyl)-3-chloro-4-isopropoxy-benzamide |
| ABS | 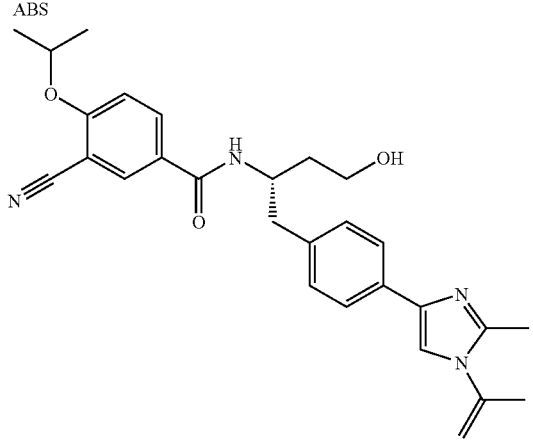 | N-(1-{4-[2-isopropenyl-1-methyl-1H-imidazol-4-yl]-benzyl}-3-hydroxy-propyl)-3-cyano-4-isopropoxy-benzamide |

TABLE 1-continued

| ABS 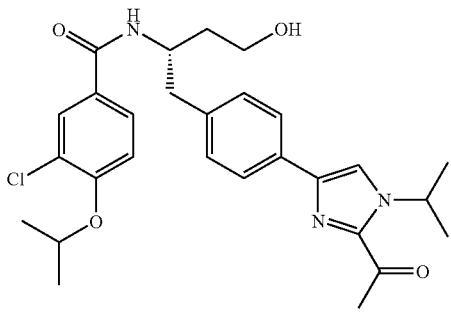 | N-(1-(4-[2-acetyl-1-isopropyl-1H-imidazol-4-yl]-benzyl}-3-hydroxy-propyl)-3-chloro-4-isopropoxy-benzamide |
| --- | --- |
| ABS 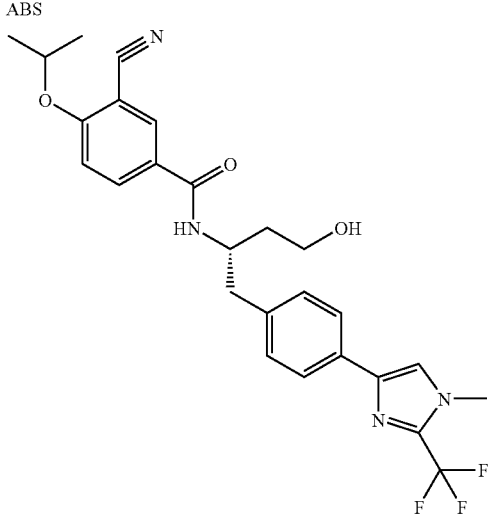 | N-(1-{4-[2-trifluoromethyl-1-methyl-1H-imidazol-4-yl]-benzyl}-3-hydroxy-propyl)-3-cyano-4-isopropoxy-benzamide |
| ABS 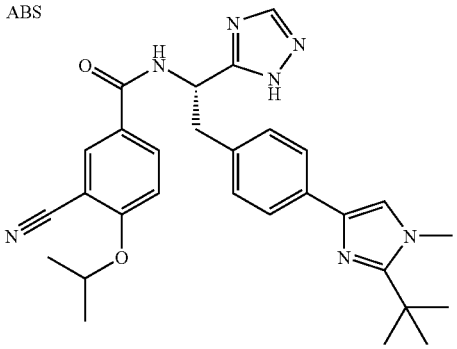 | N-(2-{4-[2-butyl-1-methyl-1H-imidazol-4-yl]-phenyl}-1-(1H-[1,2,4]triazol-5-yl)-ethyl)-3-cyano-4-isopropoxy-benzamide |
| ABS 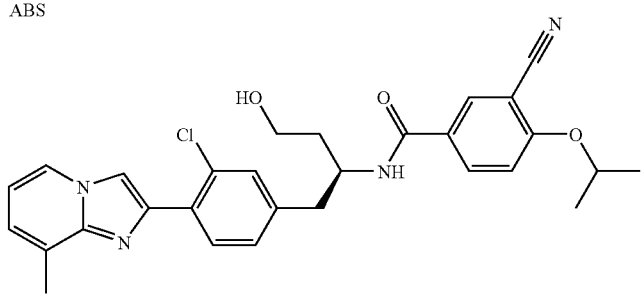 | N-{1-[3-chloro-4-(8-methyl-imidazo[1,2-a]pyridin-2-yl)-benzyl]-3-hydroxy-propyl}-3-cyano-4-isopropoxy-benzamide |

TABLE 1-continued

| ABS | 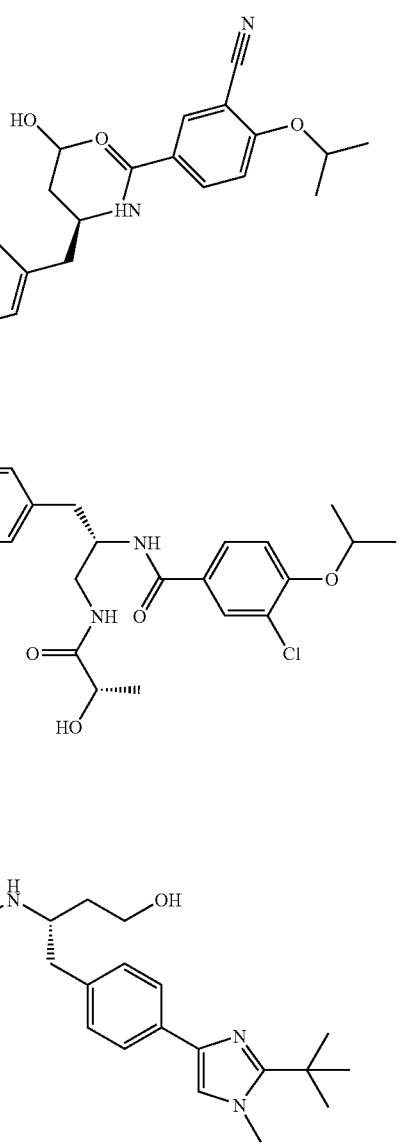 | N-{1-[4-(3-methyl-imidazo[2,1-b]oxazol-6-yl)-benzyl]-3-hydroxy-butyl}-3-cyano-4-isopropoxy-benzamide |
| --- | --- | --- |
| ABS | | N-(2-(2-hydroxy-propionylamino)-1-{4-[8-(1-hydroxy-ethyl)-imidazo[1,2-a]pyridin-2-yl]-benzyl}-ethyl)-3-chloro-4-isopropoxy-benzamide |
| | 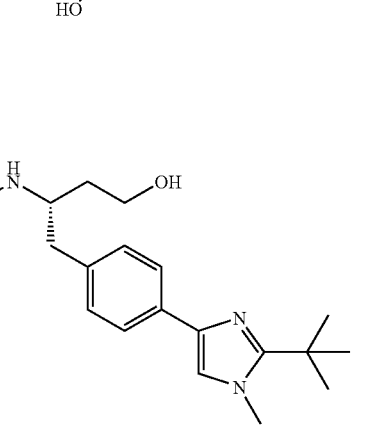 | N-(1-hydroxy-1-{4-[2-t-butyl-1-methyl-1H-imidazol-4-yl]-phenyl}-4-hydroxy-butyl)-3-chloro-4-isopropoxy-benzamide |
| ABS | 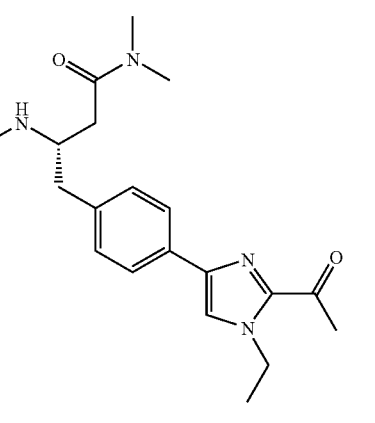 | N-(1-{4-[2-acetyl-1-ethyl-1H-imidazol-4-yl]-benzyl}-2-(N,N-dimethylcarbamoyl)-ethyl)-3-chloro-4-isopropoxy-benzamide |

TABLE 1-continued

| | | |
|---|---|---|
| ABS | 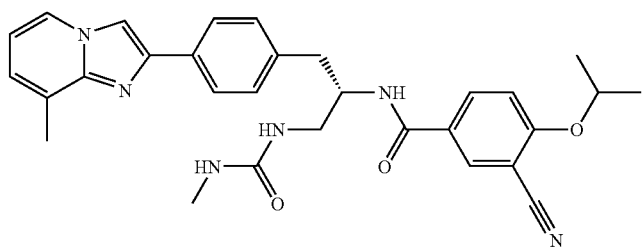 | N-(2-(2-hydroxy-propionylamino)-1-{4-[8-methyl-imidazo[1,2-a]pyridin-2-yl]-benzyl}-ethyl)-3-cyano-4-isopropoxy-benzamide |
| ABS | 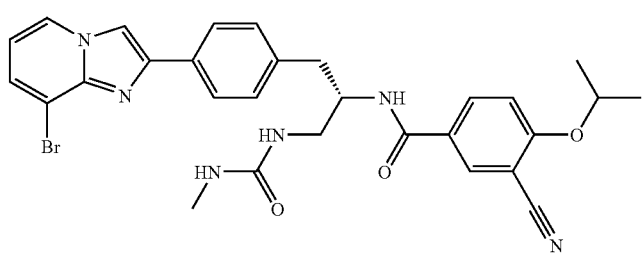 | N-[1-[4-(8-bromo-imidazo[1,2-a]pyridin-2-yl)-benzyl]-2-(3-methyl-ureido)-ethyl]-3-cyano-4-isopropoxy-benzamide |
| RAC | 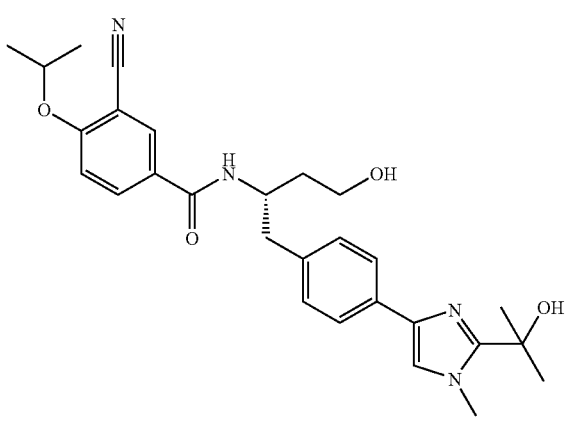 | N-(1-{4-[2-(1-hydroxy-1methyl-ethyl)-1-methyl-1H-imidazol-4-yl]-benzyl}-3-hydroxy-propyl)-3-cyano-4-isopropoxy-benzamide |
| ABS | 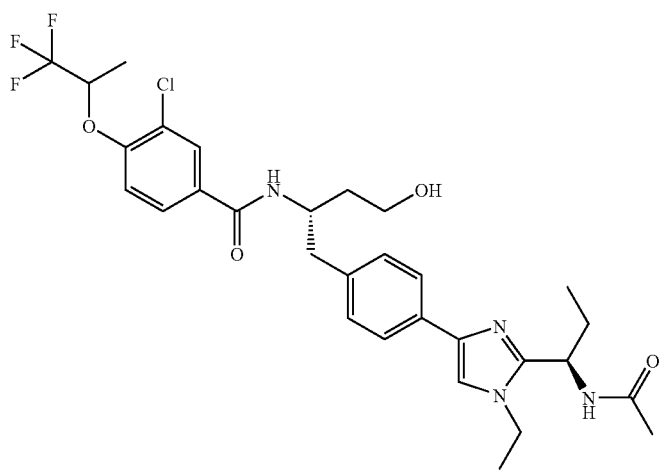 | N-(1-{4-[2-[1-(acetylamino)-propyl]-1-ethyl-1H-imidazol-4-yl]-benzyl}-3-hydroxy-propyl)-3-chloro-4-(2,2,2-trifluoro-1-methyl-ethoxy)-benzamide |

TABLE 1-continued
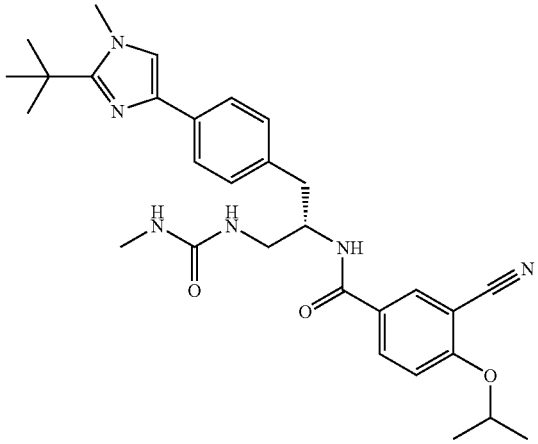
N-[1-[4-(2-t-butyl-1-methyl-1H-imidazol-4-yl)-benzyl]-2-(3-methyl-ureido)-ethyl]-3-cyano-4-isopropoxy-benzamide
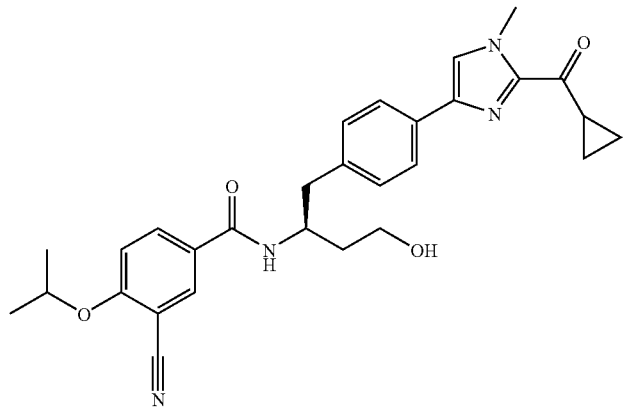
N-(1-{4-[2-(cyclopropylcarbonyl)-1-methyl-1H-imidazol-4-yl]-benzyl}-3-hydroxy-propyl)-3-cyano-4-isopropoxy-benzamide
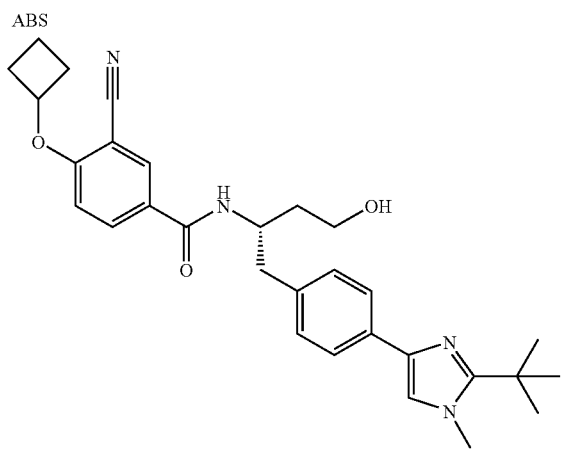
N-(1-{4-[2-t-butyl-1-methyl-1H-imidazol-4-yl]-benzyl}-3-hydroxy-propyl)-3-cyano-4-cyclobutoxy-benzamide TABLE 1-continued

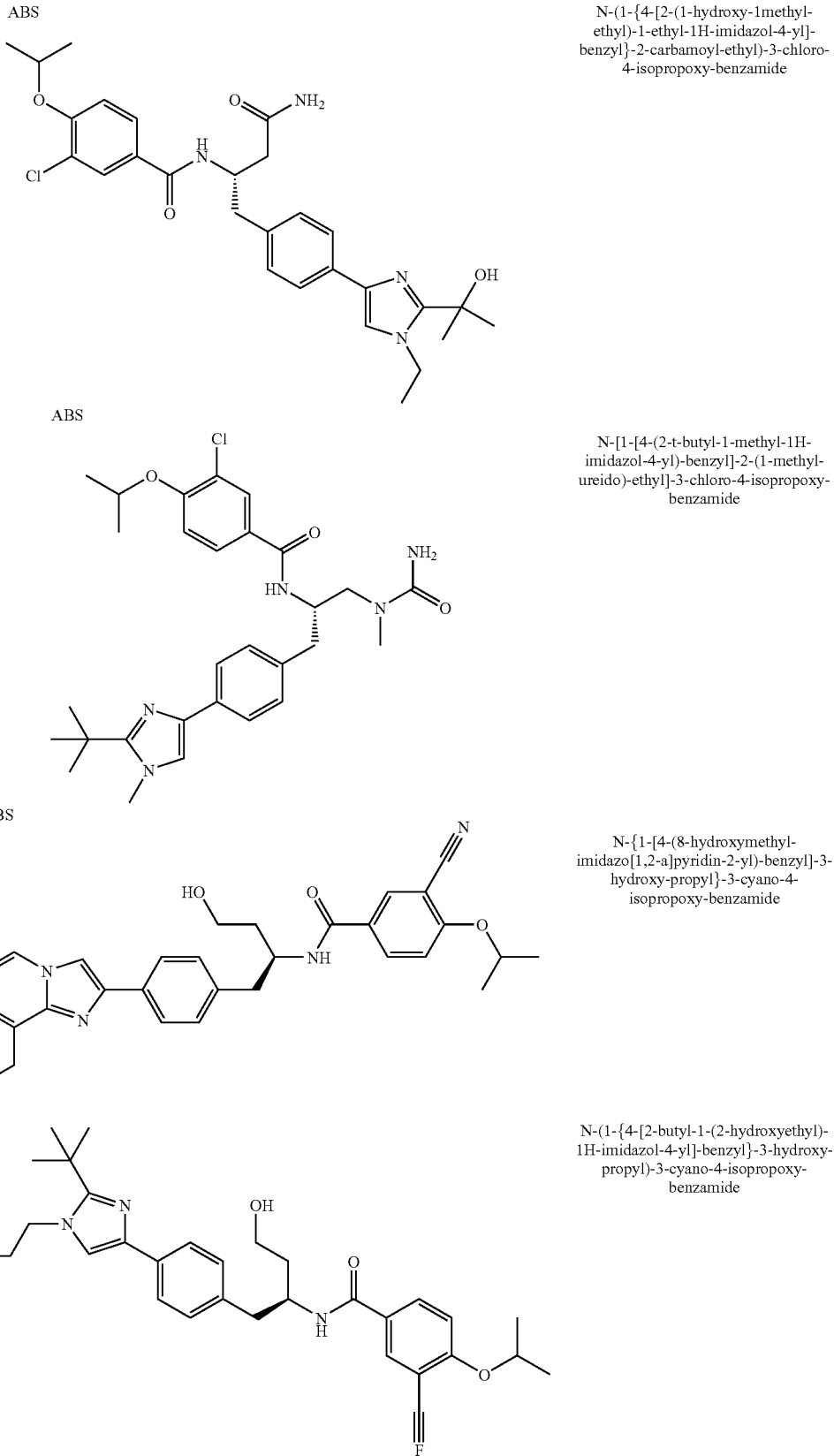

N-(1-{4-[2-(1-hydroxy-1methyl-ethyl)-1-ethyl-1H-imidazol-4-yl]-benzyl}-2-carbamoyl-ethyl)-3-chloro-4-isopropoxy-benzamide N-[1-[4-(2-t-butyl-1-methyl-1H-imidazol-4-yl)-benzyl]-2-(1-methyl-ureido)-ethyl]-3-chloro-4-isopropoxy-benzamide N-{1-[4-(8-hydroxymethyl-imidazo[1,2-a]pyridin-2-yl)-benzyl]-3-hydroxy-propyl}-3-cyano-4-isopropoxy-benzamide N-(1-{4-[2-butyl-1-(2-hydroxyethyl)-1H-imidazol-4-yl]-benzyl}-3-hydroxy-propyl)-3-cyano-4-isopropoxy-benzamide TABLE 1-continued

| | |
|---|---|
| ABS 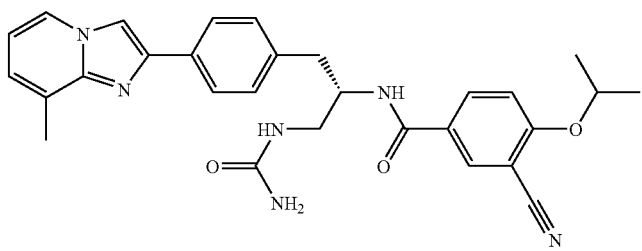 | N-[1-[4-(8-methyl-imidazo[1,2-a]pyridin-2-yl)-benzyl]-2-ureido-ethyl]-3-cyano-4-isopropoxy-benzamide |
| RAC 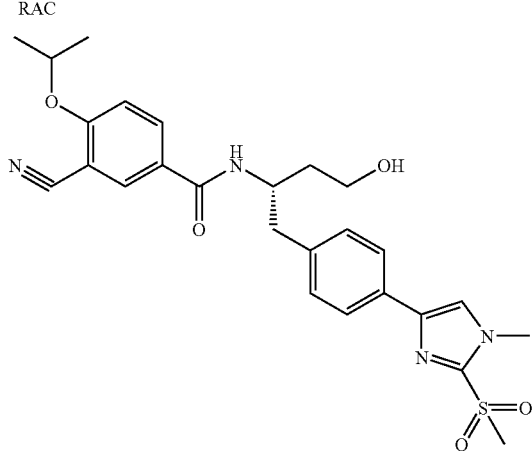 | N-(1-{4-[2-(methylsulfonyl)-1-methyl-1H-imidazol-4-yl]-benzyl}-3-hydroxy-propyl)-3-cyano-4-isopropoxy-benzamide |
| ABS 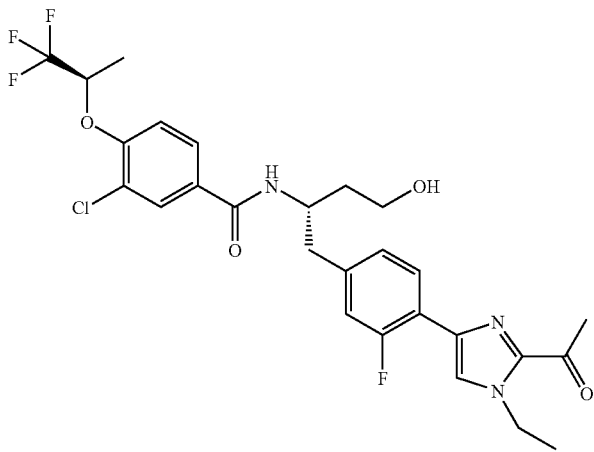 | N-(1-{3-fluoro-4-[2-acetyl-1-ethyl-1H-imidazol-4-yl]-benzyl}-3-hydroxy-propyl)-3-chloro-4-(2,2,2-trifluoro-1-methyl-ethoxy)-benzamide |
| ABS 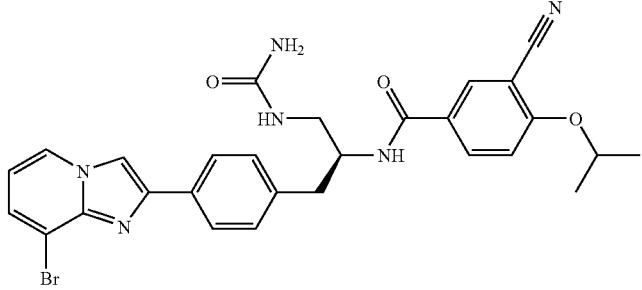 | N-[1-[4-(8-bromo-imidazo[1,2-a]pyridin-2-yl)-benzyl]-2-ureido-ethyl]-3-cyano-4-isopropoxy-benzamide |

TABLE 1-continued

| ABS | 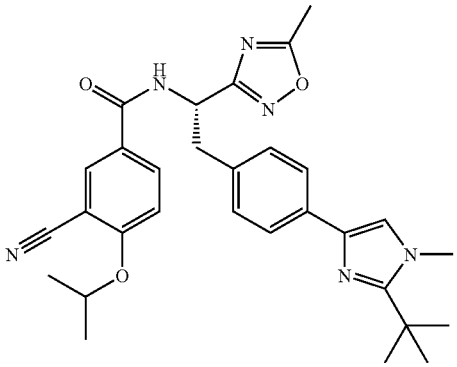 | N-(2-{4-[2-t-butyl-1-methyl-1H-imidazol-4-yl]-phenyl}-1-(5-methyl-[1,2,4]oxadiazol-3-yl)-ethyl)-3-cyano-4-isopropoxy-benzamide |
| ABS | 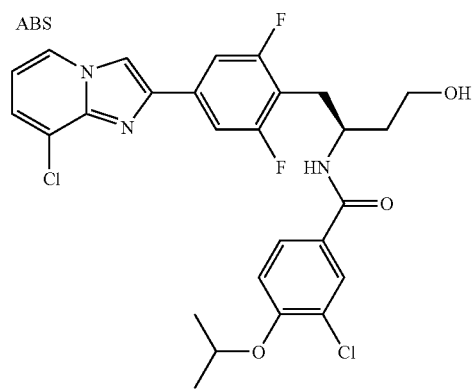 | N-{1-[2,6-difluoro-4-(8-chloro-imidazo[1,2-a]pyridin-2-yl)-benzyl]-3-hydroxy-propyl}-3-cyano-4-isopropoxy-benzamide |
| ABS | 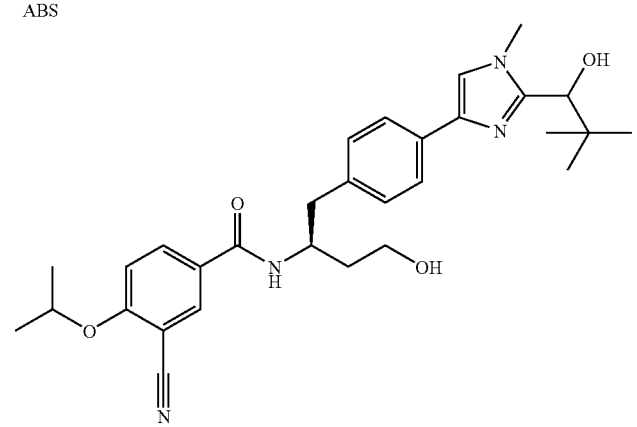 | N-(1-{4-[2-(1-hydroxy-2,2-dimethyl-propyl)-1-methyl-1H-imidazol-4-yl]-benzyl}-3-hydroxy-propyl)-3-cyano-4-isopropoxy-benzamide |
| ABS | 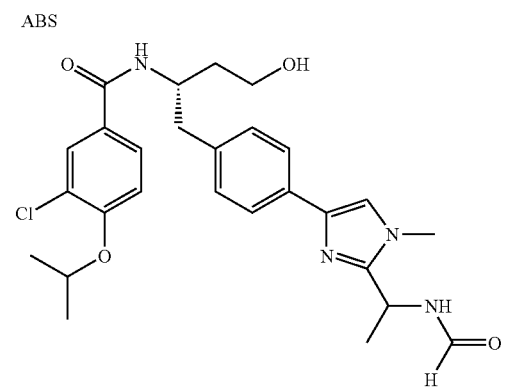 | N-(1-{4-[2-(1-formylamino-ethyl)-1-methyl-1H-imidazol-4-yl]-benzyl}-3-hydroxy-propyl)-3-chloro-4-isopropoxy-benzamide |

TABLE 1-continued

| | |
|---|---|
| ABS 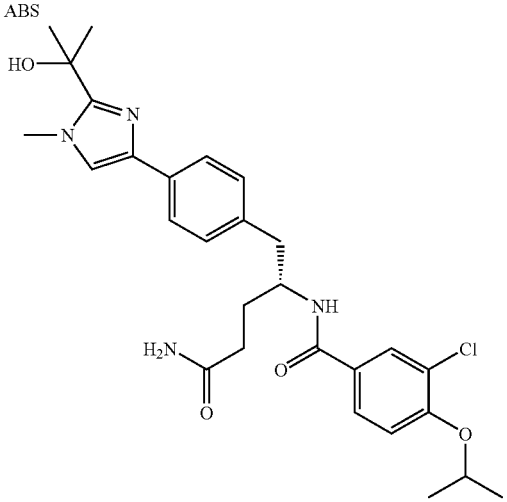 | N-(1-{4-[2-(1-hydroxy-1methyl-ethyl)-1-methyl-1H-imidazol-4-yl]-benzyl}-3-carbamoyl-propyl)-3-chloro-4-isopropoxy-benzamide |
| ABS 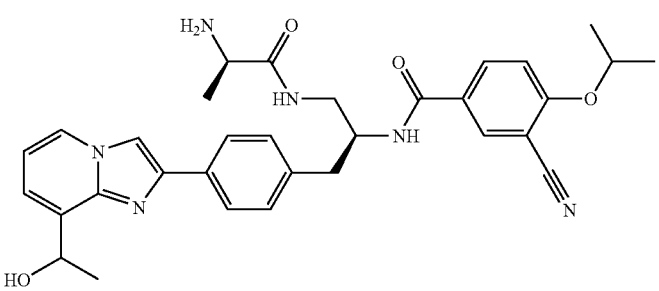 | N-(2-(2-amino-propionylamino)-1-{4-[8-(1-hydroxy-ethyl)-imidazo[1,2-a]pyridin-2-yl]-benzyl}-ethyl)-3-cyano-4-isopropoxy-benzamide |
| RAC 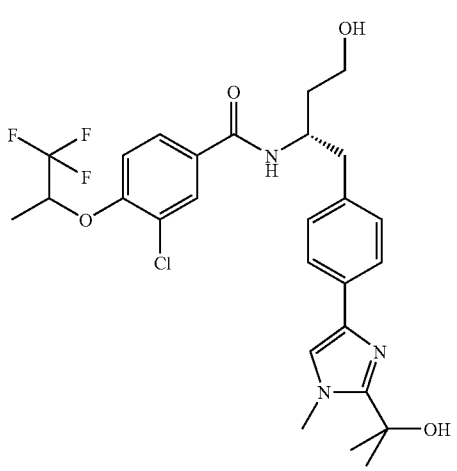 | N-(1-{4-[2-(1-hydroxy-1methyl-ethyl)-1-methyl-1H-imidazol-4-yl]-benzyl}-3-hydroxy-propyl)-3-chloro-4-(2,2,2-trifluoro-1-methyl-ethoxy)-benzamide |
| ABS 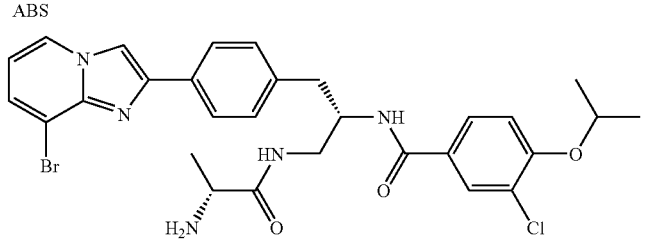 | N-(2-(2-amino-propionylamino)-1-{4-[8-bromo-imidazo[1,2-a]pyridin-2-yl]-benzyl}-ethyl)-3-chloro-4-isopropoxy-benzamide |

TABLE 1-continued

| ABS | | |
|---|---|---|
| | 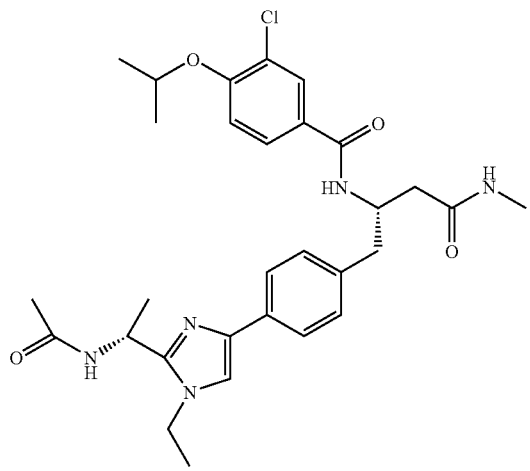 | N-(1-{4-[2-(1-acetylamino-ethyl)-1-ethyl-1H-imidazol-4-yl]-benzyl}-2-methylcarbamoyl-ethyl)-3-chloro-4-isopropoxy-benzamide |
| ABS | 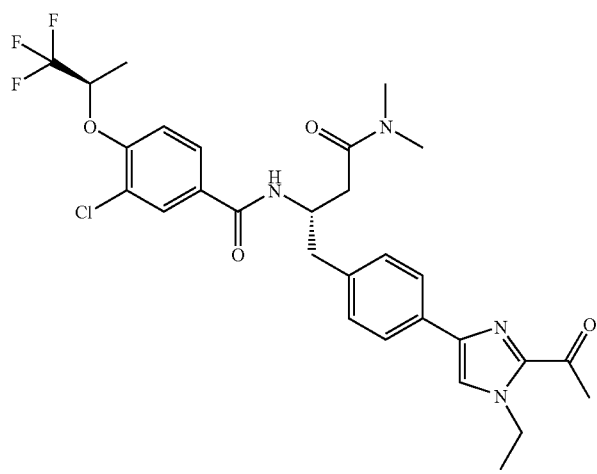 | N-(1-{4-[2-acetyl-1-ethyl-1H-imidazol-4-yl]-benzyl}-2-dimethylcarbamoyl-ethyl)-3-chloro-4-(2,2,2-trifluoro-1-methyl-ethoxy)-benzamide |
| ABS | 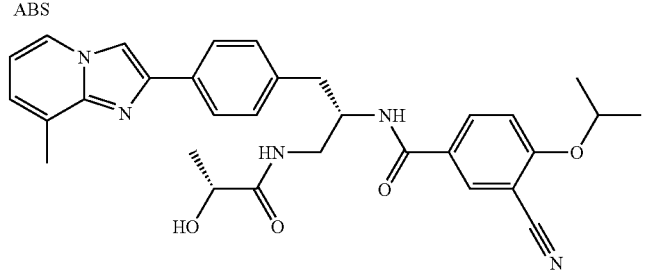 | N-(2-(2-hydroxy-propionylamino)-1-{4-[8-methyl-imidazo[1,2-a]pyridin-2-yl]-benzyl}-ethyl)-3-cyano-4-isopropoxy-benzamide |
| ABS | 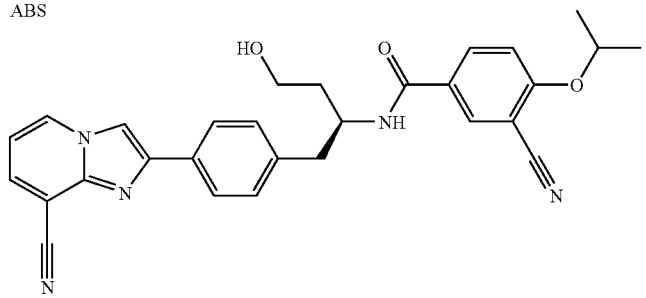 | N-{1-[4-(8-cyano-imidazo[1,2-a]pyridin-2-yl)-benzyl]-3-hydroxy-propyl}-3-cyano-4-isopropoxy-benzamide |

TABLE 1-continued

| | | |
|---|---|---|
| ABS | 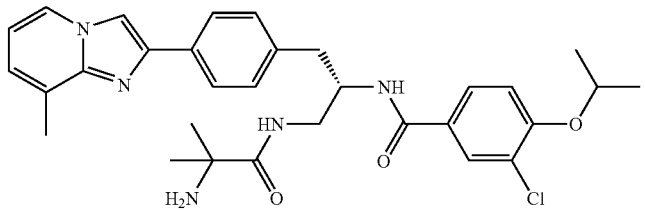 | N-(2-(2-amino-2-methyl-propionylamino)-1-{4-[8-methyl-imidazo[1,2-a]pyridin-2-yl]-benzyl}-ethyl)-3-chloro-4-isopropoxy-benzamide |
| ABS | 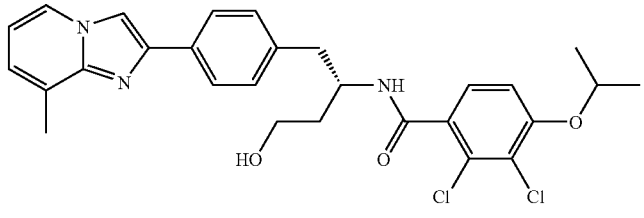 | N-{1-[4-(8-methyl-imidazo[1,2-a]pyridin-2-yl)-benzyl]-3-hydroxy-propyl}-2,3-dichloro-4-isopropoxy-benzamide |
| ABS | 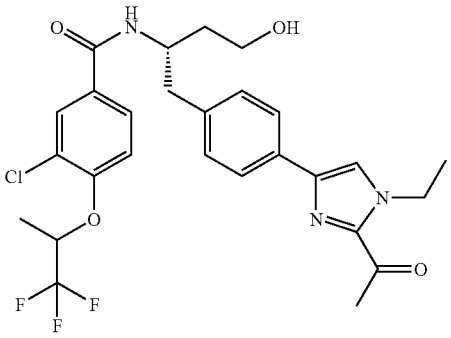 | N-(1-{4-[2-acetyl-1-ethyl-1H-imidazol-4-yl]-benzyl}-3-hydroxy-propyl)-3-chloro-4-(2,2,2-trifluoro-1-methyl-ethoxy)-benzamide |
| ABS | 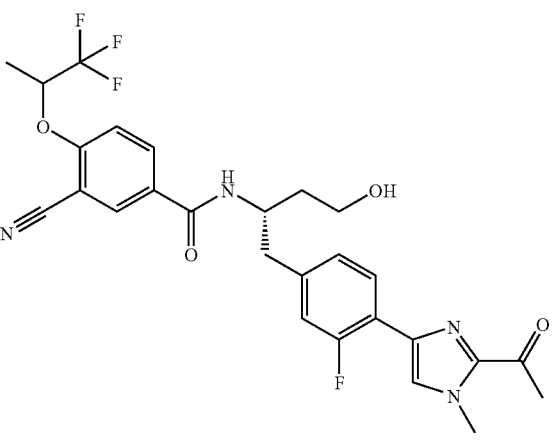 | N-(1-{3-fluoro-4-[2-acetyl-1-methyl-1H-imidazol-4-yl]-benzyl}-3-hydroxy-propyl)-3-cyano-4-(2,2,2-trifluoro-1-methyl-ethoxy)-benzamide |
| ABS | 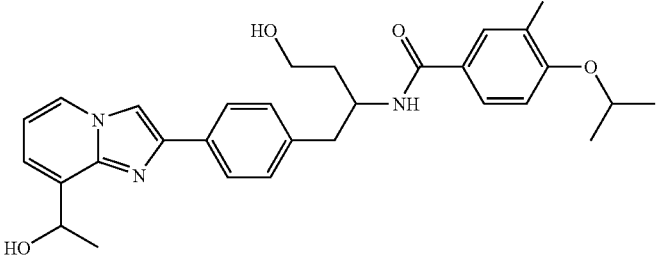 | N-{1-[4-(8-(1-hydroxy-ethyl)-imidazo[1,2-a]pyridin-2-yl)-benzyl]-3-hydroxy-propyl}-3-chloro-4-isopropoxy-benzamide |

TABLE 1-continued
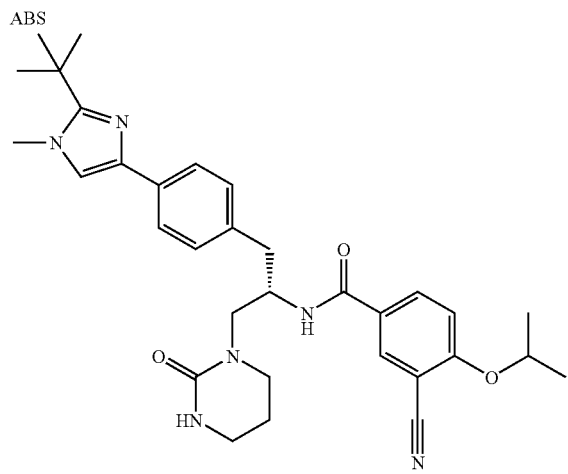
N-[1-[4-(2-t-butyl-1-methyl-1H-imidazol-4-yl)-benzyl]-2-(2-oxo-tetrahydro-pyrimidin-1-yl)-ethyl]-3-cyano-4-isopropoxy-benzamide
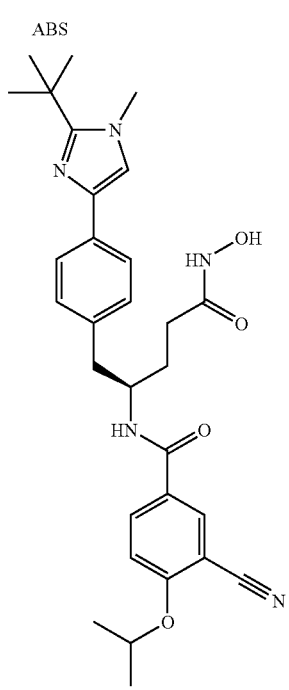
N-[1-[4-(2-t-butyl-1-methyl-1H-imidazol-4-yl)-benzyl]-3-hydroxycarbamoyl-propyl]-3-cyano-4-isopropoxy-benzamide
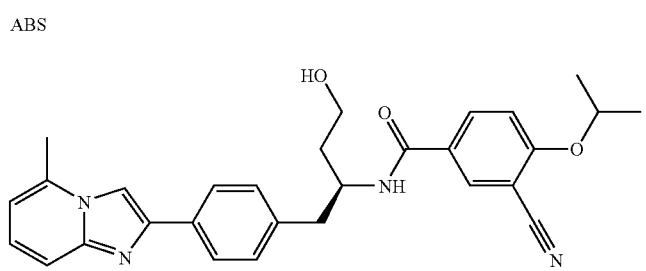
N-{1-[4-(5-methyl-imidazo[1,2-a]pyridin-2-yl)-benzyl]-3-hydroxy-propyl}-3-cyano-4-isopropoxy-benzamide

TABLE 1-continued
| | |
|---|---|
| ABS 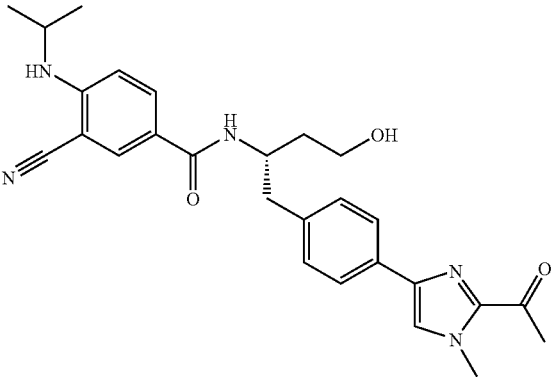 | N-(1-{4-[2-acetyl-1-methyl-1H-imidazol-4-yl]-benzyl}-3-hydroxy-propyl)-3-cyano-4-(isopropylamino)-benzamide |
| ABS 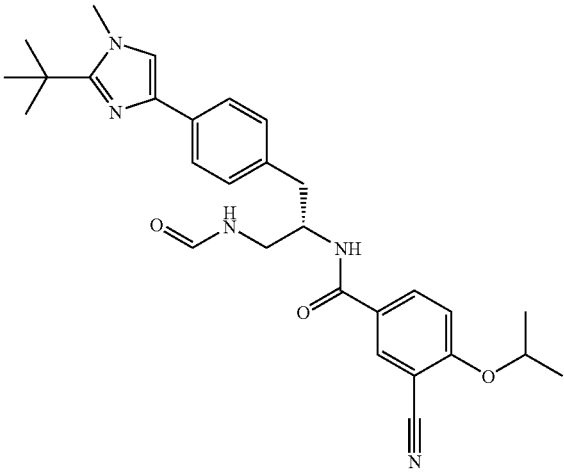 | N-[1-[4-(2-t-butyl-1-methyl-1H-imidazol-4-yl)-benzyl]-2-(formylamino)-ethyl]-3-cyano-4-ispropoxy-benzamide |
| ABS 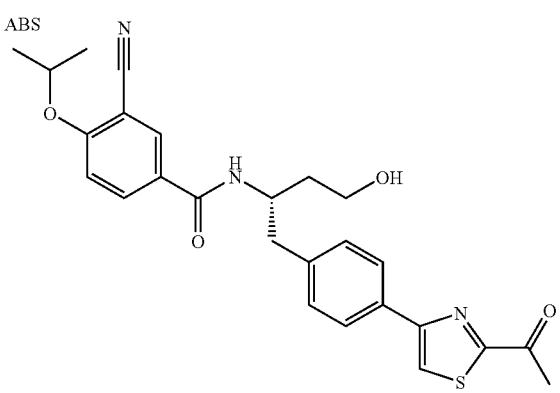 | N-(1-{4-(2-Acetyl-oxazol-4-yl)-benzyl}-3-hydroxy-propyl)-3-cyano-4-isopropoxy-benzamide |
| ABS 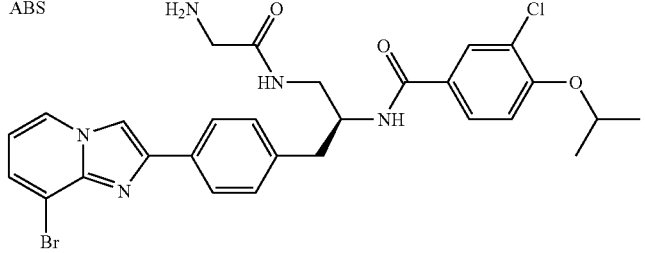 | N-(2-(2-amino-acetylamino)-1-{4-[8-bromo-imidazo[1,2-a]pyridin-2-yl]-benzyl}-ethyl)-3-chloro-4-isopropoxy-benzamide |

TABLE 1-continued

ABS 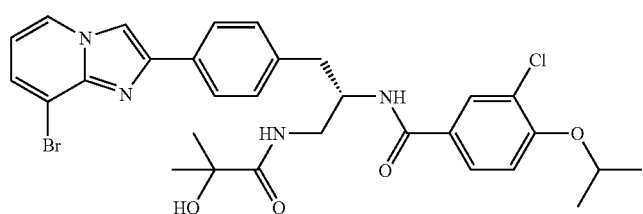

N-(2-(2-hydroxy-2-methyl-propionylamino)-1-{4-[8-bromo-imidazo[1,2-a]pyridin-2-yl]-benzyl}-ethyl)-3-chloro-4-isopropoxy-benzamide ABS 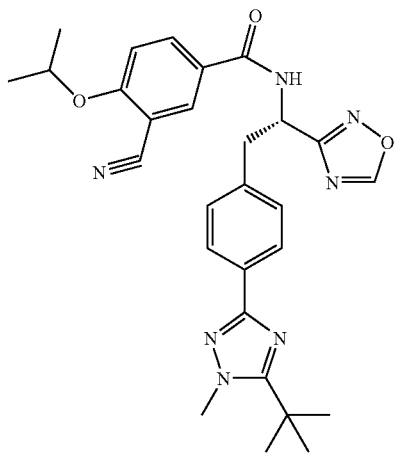

N-(2-{4-[5-t-butyl-1-methyl-1H-[1,2,4]triazol-3-yl]-phenyl}-1-([1,2,4]oxadiazol-3-yl)-ethyl)-3-cyano-4-isopropoxy-benzamide ABS 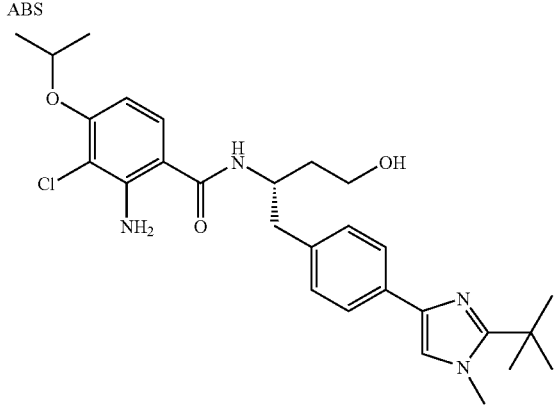

N-(1-{4-[2-t-butyl-1-methyl-1H-imidazol-4-yl]-benzyl}-3-hydroxy-propyl)-2-amino-3-chloro-4-isopropoxy-benzamide ABS 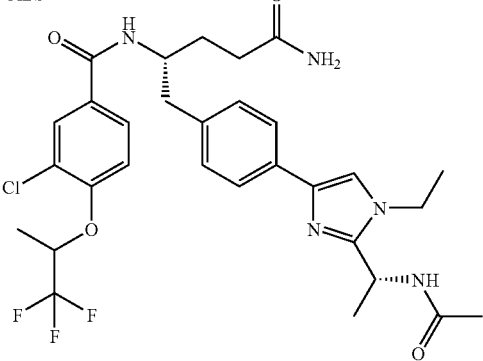

N-(1-{4-[2-(1-acetylamino-ethyl)-1-ethyl-1H-imidazol-4-yl]-benzyl}-3-carbamoyl-propyl)-3-chloro-4-(2,2,2-trifluoro-1-methyl-ethoxy)-benzamide TABLE 1-continued

| | | |
|---|---|---|
| ABS | 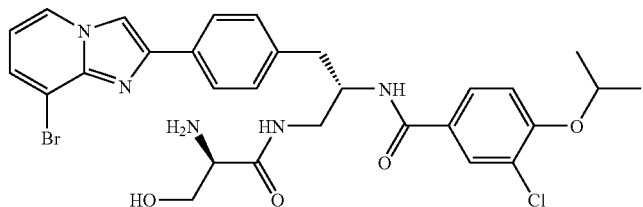 | N-(2-(2-amino-3-hydroxy-propionylamino)-1-{4-[8-bromo-imidazo[1,2-a]pyridin-2-yl]-benzyl}-ethyl)-3-chloro-4-isopropoxy-benzamide |
| ABS | 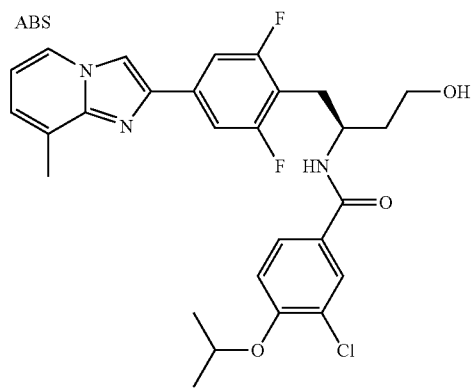 | N-{1-[2,6-difluoro-4-(8-methyl-imidazo[1,2-a]pyridin-2-yl)-benzyl]-3-hydroxy-propyl}-3-chloro-4-isopropoxy-benzamide |
| ABS | 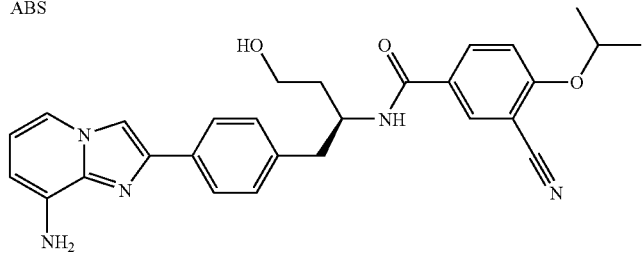 | N-{1-[4-(8-amino-imidazo[1,2-a]pyridin-2-yl)-benzyl]-3-hydroxy-propyl}-3-cyano-4-isopropoxy-benzamide |
| ABS | 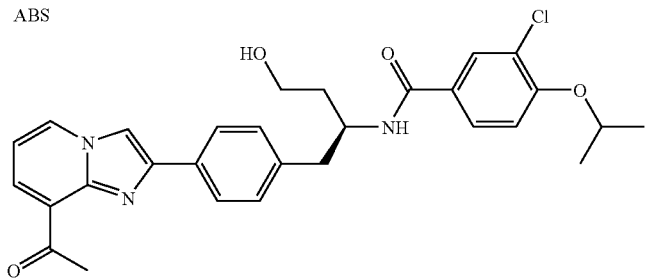 | N-{1-[4-(8-acetyl-imidazo[1,2-a]pyridin-2-yl)-benzyl]-3-hydroxy-propyl}-3-chloro-4-isopropoxy-benzamide |
| ABS | 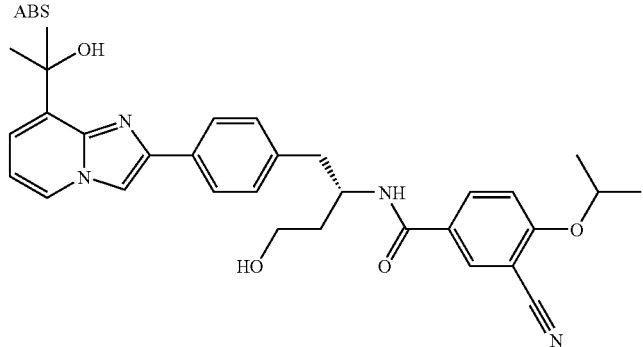 | N-{1-[4-(8-(1-methyl-1-hydroxy-ethyl)-imidazo[1,2-a]pyridin-2-yl)-benzyl]-3-hydroxy-propyl}-3-cyano-4-isopropoxy-benzamide |

TABLE 1-continued

| ABS | | Name |
|---|---|---|
| ABS | 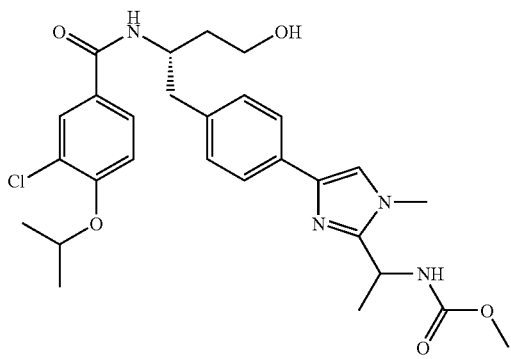 | N-(1-{4-[2-(1-(methoxycarbonylamino)-ethyl)-1-methyl-1H-imidazol-4-yl]-benzyl}-3-hydroxy-propyl)-3-chloro-4-isopropoxy-benzamide |
| ABS | 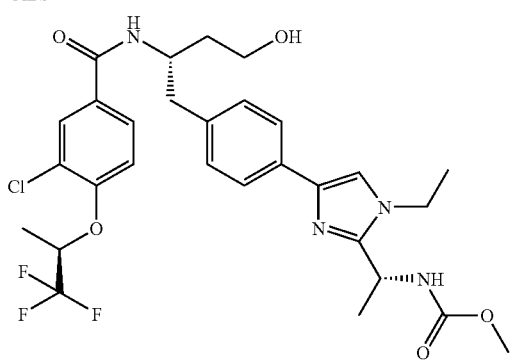 | N-(1-{4-[2-(1-(methoxycarbonylamino)-ethyl)-1-ethyl-1H-imidazol-4-yl]-benzyl}-3-hydroxy-propyl)-3-chloro-4-(2,2,2-trifluoro-1-methyl-ethoxy)-benzamide |
| ABS | 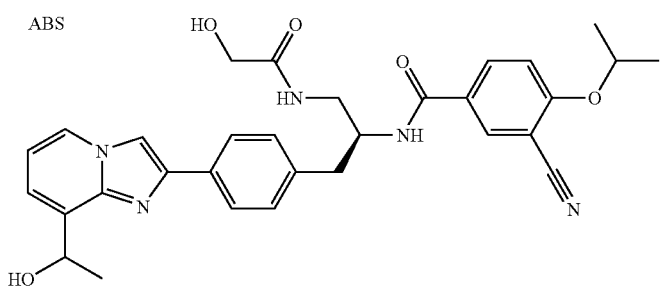 | N-(2-(2-hydroxy-acetylamino)-1-{4-[8-(1-hydroxy-ethyl)-imidazo[1,2-a]pyridin-2-yl]-benzyl}-ethyl)-3-cyano-4-isopropoxy-benzamide |
| ABS | 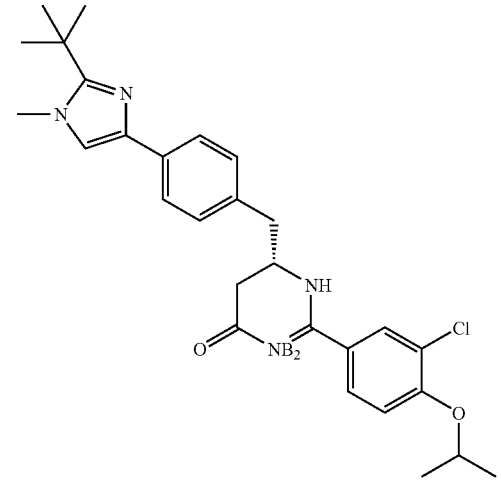 | N-[1-[4-(2-t-butyl-1-methyl-1H-imidazol-4-yl)-benzyl]-2-carbamoyl-ethyl]-3-chloro-4-ispropoxy-benzamide |

TABLE 1-continued

| ABS | | |
|---|---|---|
| | 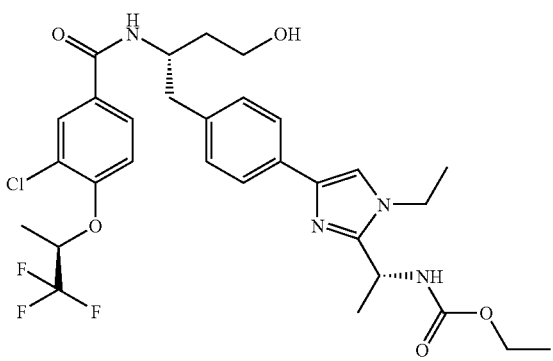 | N-(1-{4-[2-(1-(ethoxycarbonylamino)-ethyl)-1-ethyl-1H-imidazol-4-yl]-4-(2,2,2-trifluoro-1-methyl-ethoxy)-benzamide |
| ABS | 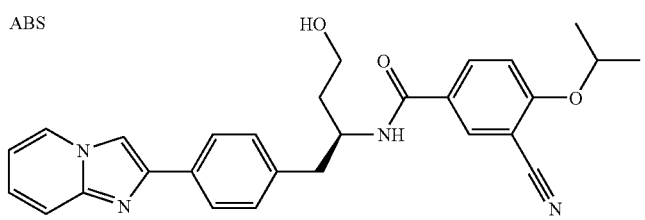 | N-{1-[4-(imidazo[1,2-a]pyridin-2-yl)-benzyl]-3-hydroxy-propyl}-3-cyano-4-isopropoxy-benzamide |
| ABS | 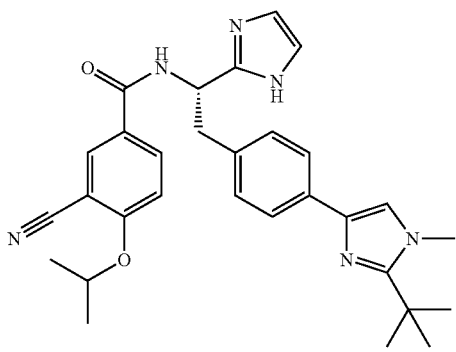 | N-(2-{4-[2-t-butyl-1-methyl-1H-imidazol-4-yl]-phenyl}-1-(1H-imidazol-2-yl)-ethyl)-3-cyano-4-isopropoxy-benzamide |
| ABS | 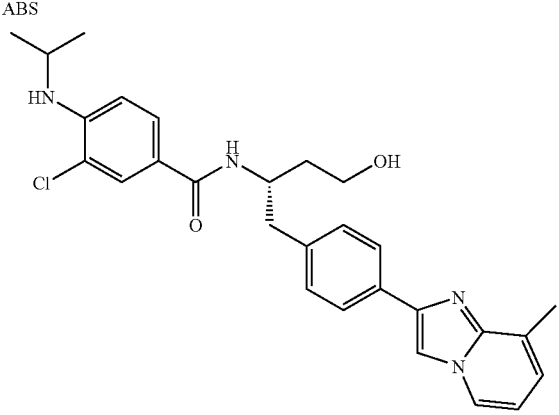 | N-{1-[4-(8-methyl-imidazo[1,2-a]pyridin-2-yl)-benzyl]-3-hydroxy-propyl}-3-chloro-4-(isopropylamino)-benzamide |

TABLE 1-continued

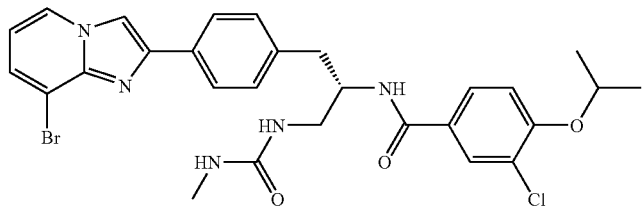

N-[1-[4-(8-bromo-imidazo[1,2-a]pyridin-2-yl)-benzyl]-2-(3-methyl-ureido)-ethyl]-3-chloro-4-isopropoxy-benzamide

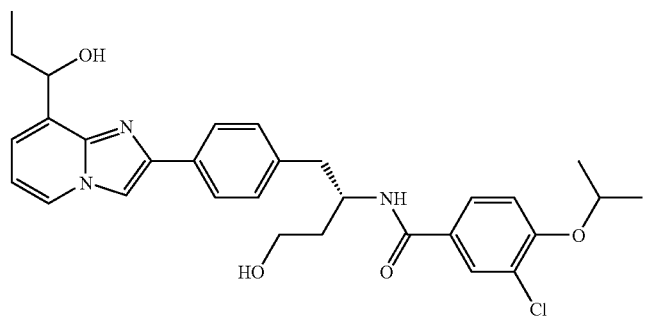

N-{1-[4-(8-(1-hydroxypropyl)-imidazo[1,2-a]pyridin-2-yl)-benzyl]-3-hydroxy-propyl}-3-chloro-4-isopropoxy-benzamide

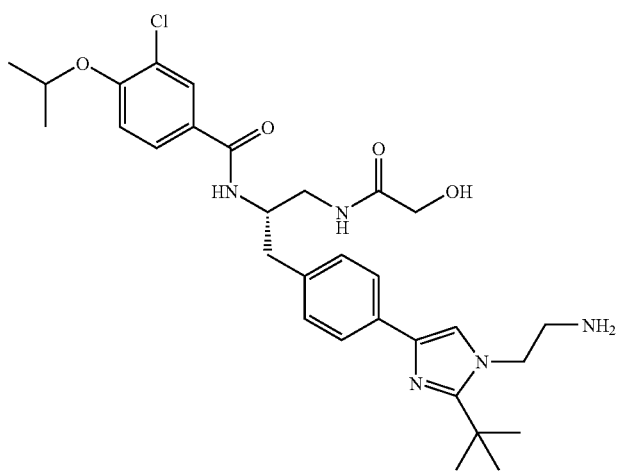

N-[1-[4-(2-t-butyl-1-(2-aminoethyl)-1H-imidazol-4-yl)-benzyl]-2-(2-hydroxy-acetylamino)-ethyl]-3-chloro-4-isopropoxy-benzamide

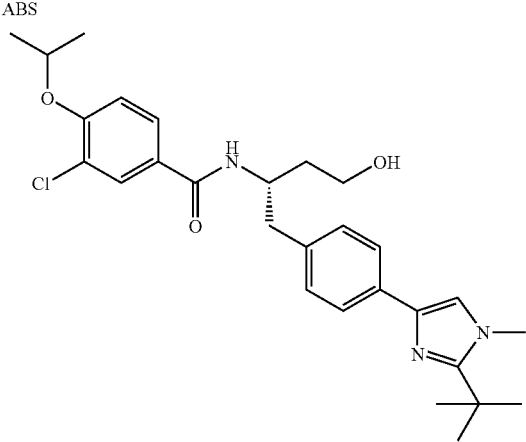

N-(1-{4-[2-t-butyl-1-methyl-1H-imidazol-4-yl]-benzyl}-3-hydroxy-propyl)-3-chloro-4-isopropoxy-benzamide TABLE 1-continued

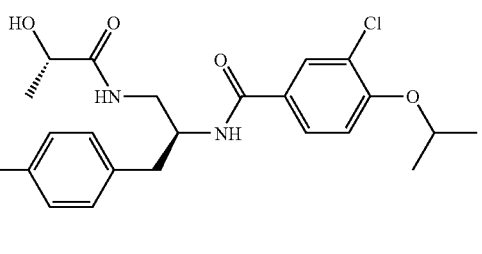
N-(2-(2-hydroxy-propionylamino)-1-{4-[8-methyl-imidazo[1,2-a]pyridin-2-yl]-benzyl}-ethyl)-3-chloro-4-isopropoxy-benzamide

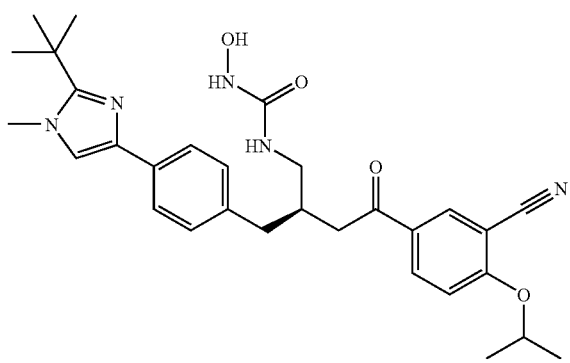
N-[1-[4-(2-t-butyl-1-methyl-1H-imidazol-4-yl)-benzyl]-2-(3-hydroxy-ureido)-ethyl]-3-cyano-4-isopropoxy-benzamide

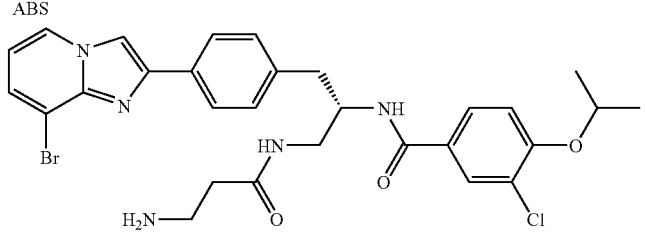
N-(2-(3-amino-propionylamino)-1-{4-[8-bromo-imidazo[1,2-a]pyridin-2-yl]-benzyl}-ethyl)-3-chloro-4-isopropoxy-benzamide

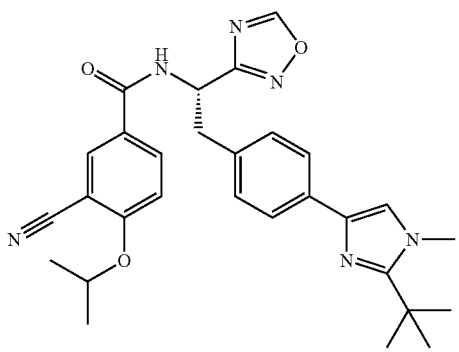
N-(2-{4-[2-t-butyl-1-methyl-1H-imidazol-4-yl]-phenyl}-1-([1,2,4]oxadiazol-3-yl)-ethyl)-3-cyano-4-isopropoxy-benzamide

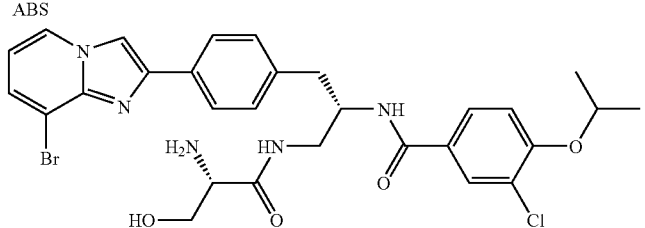
N-(2-(2-amino-3-hydroxy-propionylamino)-1-{4-[8-bromo-imidazo[1,2-a]pyridin-2-yl]-benzyl}-ethyl)-3-chloro-4-isopropoxy-benzamide TABLE 1-continued

| | |
|---|---|
| 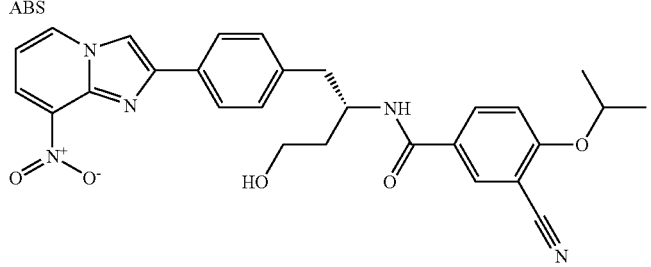 | N-{1-[4-(8-nitro-imidazo[1,2-a]pyridin-2-yl)-benzyl]-3-hydroxy-propyl}-3-cyano-4-isopropoxy-benzamide |
| 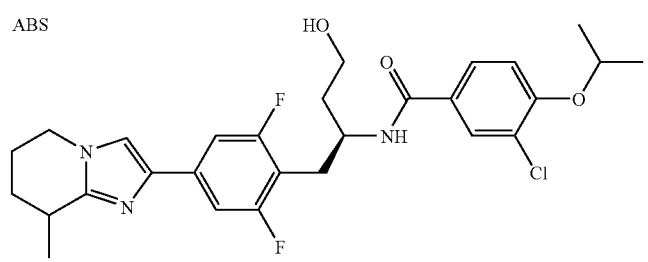 | N-{1-[2,6-difluoro-4-(8-methyl-5,6,7,8-tetrahydro-imidazo[1,2-a]pyridin-2-yl)-benzyl]-3-hydroxy-propyl}-3-chloro-4-isopropoxy-benzamide |
| 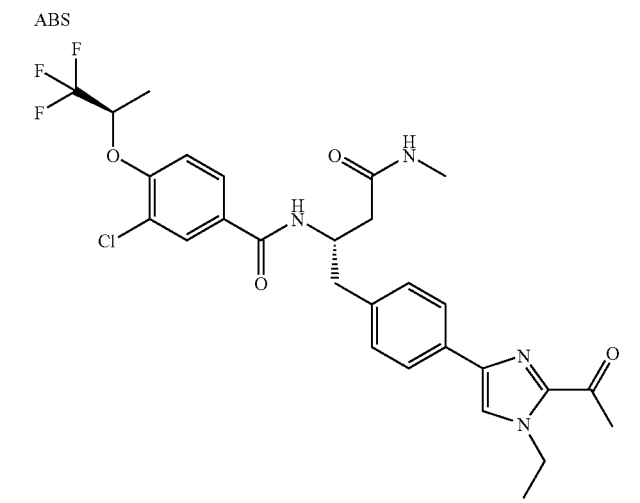 | N-(1-{4-[2-acetyl-1-ethyl-1H-imidazol-4-yl]-benzyl}-2-methylcarbamoyl-ethyl)-3-chloro-4-(2,2,2-trifluoro-1-methyl-ethoxy)-benzamide |
| 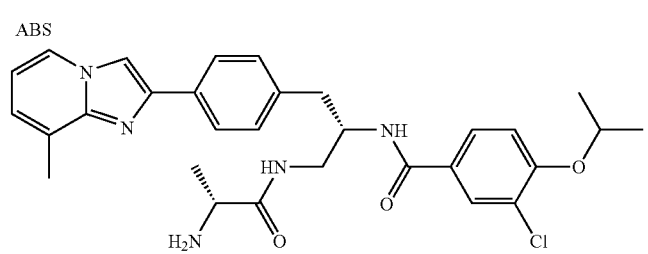 | N-(2-(2-amino-propionylamino)-1-{4-[8-methyl-imidazo[1,2-a]pyridin-2-yl]-benzyl}-ethyl)-3-chloro-4-isopropoxy-benzamide |

TABLE 1-continued

| | | |
|---|---|---|
| ABS | 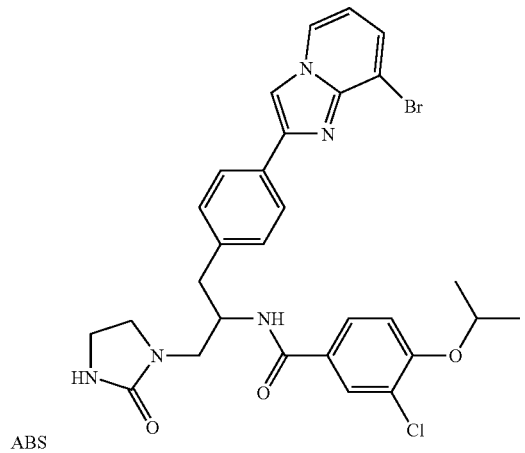 | N-[1-[4-(8-bromo-imidazo[1,2-a]pyridin-2-yl)-benzyl]-2-(2-oxo-imidazolidinyl)-ethyl]-3-chloro-4-isopropoxy-benzamide |
| ABS | 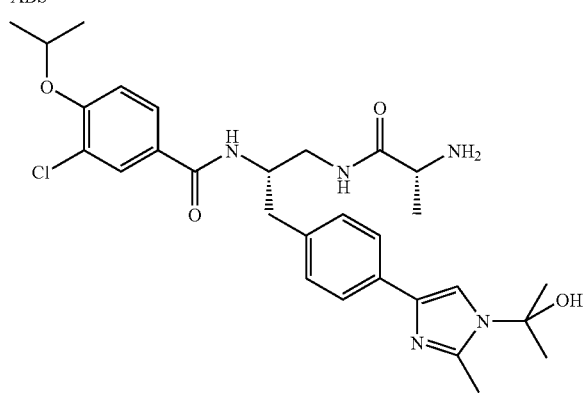 | N-[1-[4-(2-(1-hydroxy-1-methyl-ethyl)-1-methyl-1H-imidazol-4-yl)-benzyl]-2-(2-amino-propionylamino)-ethyl]-3-chloro-4-isopropoxy-benzamide |
| ABS | 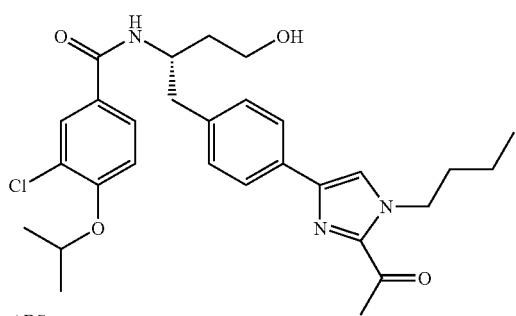 | N-(1-{4-[2-acetyl-1-butyl-1H-imidazol-4-yl]-benzyl}-3-hydroxy-propyl)-3-chloro-4-isopropoxy-benzamide |
| ABS | 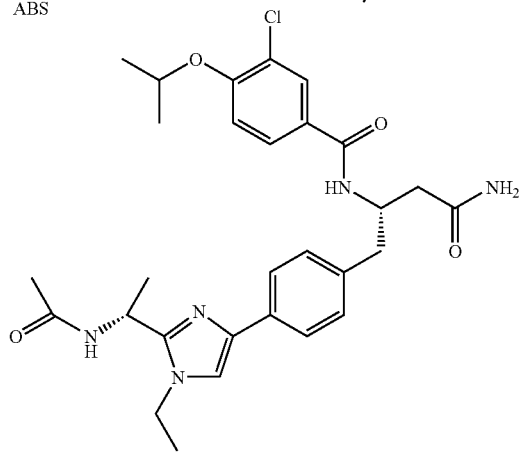 | N-(1-{4-[2-(1-acetylamino-ethyl)-1-ethyl-1H-imidazol-4-yl]-benzyl}-2-carbamoyl-ethyl)-3-chloro-4-isopropoxy-benzamide |

TABLE 1-continued

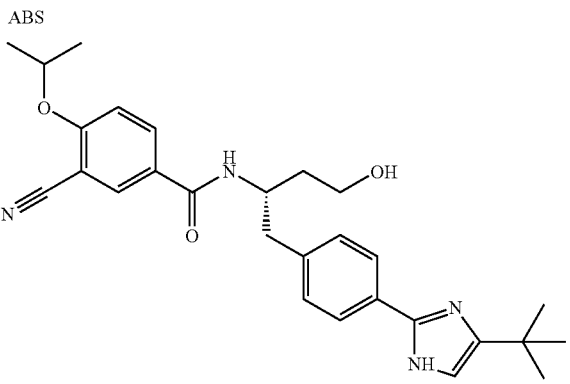

N-(1-{4-[4-t-butyl-1H-imidazol-2-yl]-benzyl}-3-hydroxy-propyl)-3-cyano-4-isopropoxy-benzamide

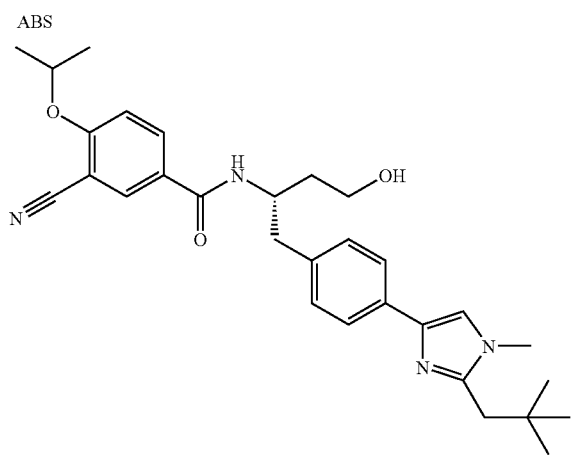

N-(1-{4-[2-(2,2-dimethyl-propyl)-1-methyl-1H-imidazol-4-yl]-benzyl}-3-hydroxy-propyl)-3-cyano-4-isopropoxy-benzamide

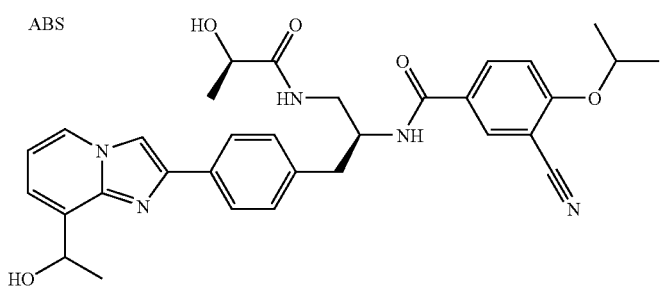

N-(2-(2-hydroxy-propionylamino)-1-{4-[8-(1-hydroxy-ethyl)-imidazo[1,2-a]pyridin-2-yl]-benzyl}-ethyl)-3-cyano-4-isopropoxy-benzamide

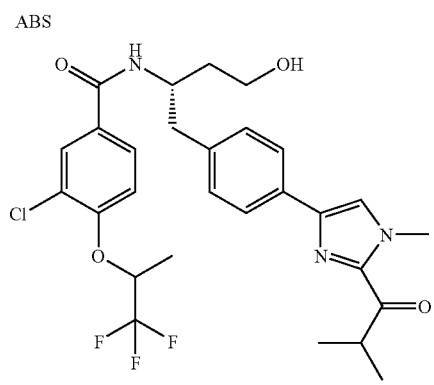

N-(1-{4-[2-isobutyryl-1-methyl-1H-imidazol-4-yl]-benzyl}-3-hydroxy-propyl)-3-chloro-4-(2,2,2-trifluoro-1-methyl-ethoxy)-benzamide TABLE 1-continued

| | | |
|---|---|---|
| ABS | 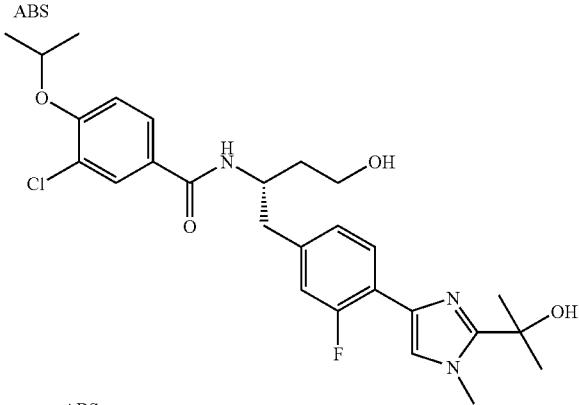 | N-(1-{3-fluoro-4-[2-(1-hydroxy-1-methyl-ethyl)-1-methyl-1H-imidazol-4-yl]-benzyl}-3-hydroxy-propyl)-3-chloro-4-isopropoxy-benzamide |
| ABS | 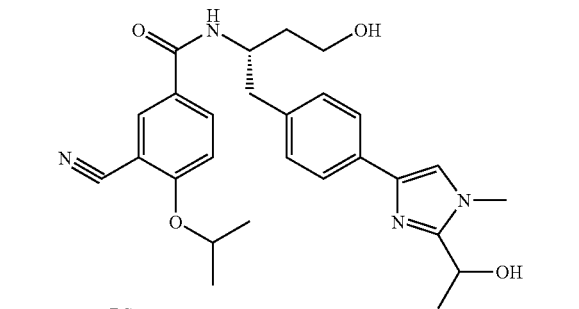 | N-(1-{4-[2-(1-hydroxy-ethyl)-1-methyl-1H-imidazol-4-yl]-benzyl}-3-hydroxy-propyl)-3-cyano-4-isopropoxy-benzamide |
| ABS | 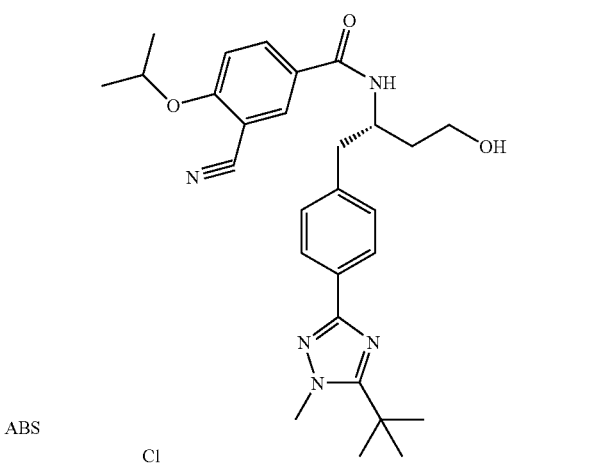 | N-(1-{4-[5-butyl-1-methyl-1H-[1,2,4]triazol-3-yl]-benzyl}-3-hydroxy-propyl)-3-cyano-4-isopropoxy-benzamide |
| ABS | 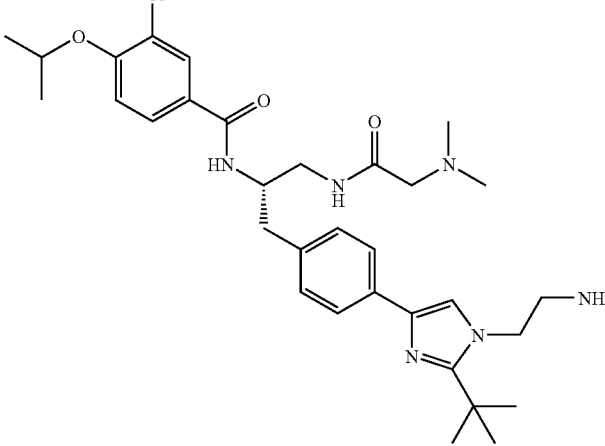 | N-[1-[4-(2-t-butyl-1-(2-amino-ethyl)-1H-imidazol-4-yl)-benzyl]-2-(2-dimethylamino-acetylamino)-ethyl]-3-chloro-4-isopropoxy-benzamide |

TABLE 1-continued

| Structure | Name |
|---|---|
| ABS (structure) | N-[1-{4-[1-(3-(t-butoxycarbonylamino)-propyl)-2-t-butyl-2,3-dihydro-imidazol-4-yl]-benzyl}-3-hydroxy-propyl]-3-chloro-4-isopropoxy-benzamide |
| ABS (structure) | N-(2-(2-hydroxy-propionylamino)-1-{4-[8-(1-hydroxy-ethyl)-imidazo[1,2-a]pyridin-2-yl]-benzyl}-ethyl)-3-cyano-4-isopropoxy-benzamide |
| ABS (structure) | N-(2-(acetylamino)-1-{4-[8-methyl-imidazo[1,2-a]pyridin-2-yl]-benzyl}-ethyl)-3-cyano-4-isopropoxy-benzamide |

TABLE 1-continued
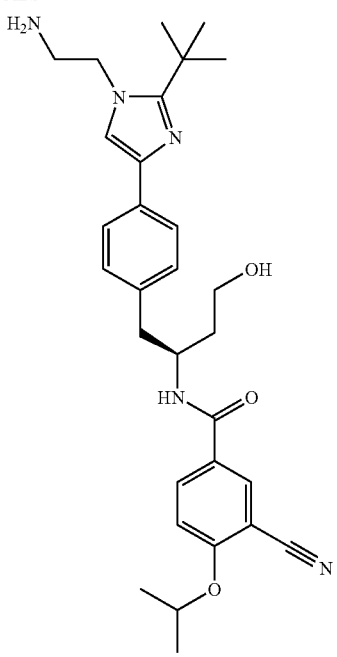
N-(1-{4-[2-butyl-1-(2-aminoethyl)-1H-imidazol-4-yl]-benzyl}-3-hydroxy-propyl)-3-cyano-4-isopropoxy-benzamide
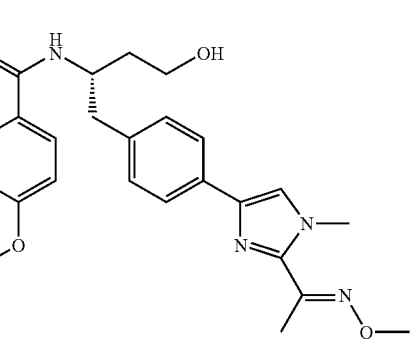
N-(1-{4-[2-(1-methoxyimino-ethyl)-1-metyl-1H-imidazol-4-yl]-benzyl}-3-hydroxy-propyl)-3-chloro-4-isopropoxy-benzamide
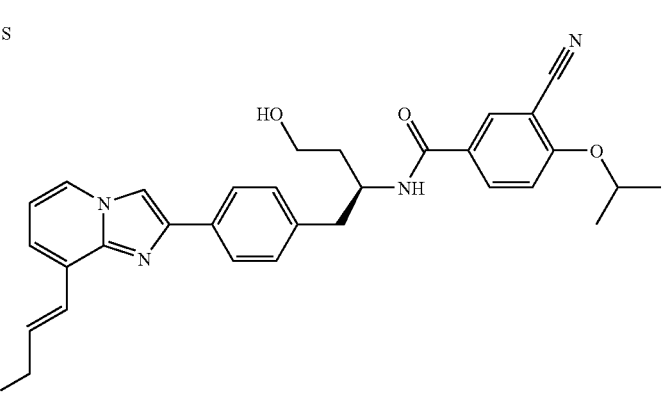
N-{1-[4-(8-(3-hydroxy-propenyl)-imidazo[1,2-a]pyridin-2-yl)-benzyl]-3-hydroxy-propyl}-3-cyano-4-isopropoxy-benzamide TABLE 1-continued

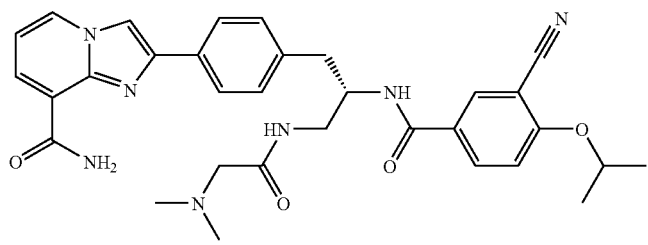

N-(2-(2-dimethylamino-acetylamino)-1-{4-[8-carbamoyl-imidazo[1,2-a]pyridin-2-yl]-benzyl}-ethyl)-3-cyano-4-isopropoxy-benzamide

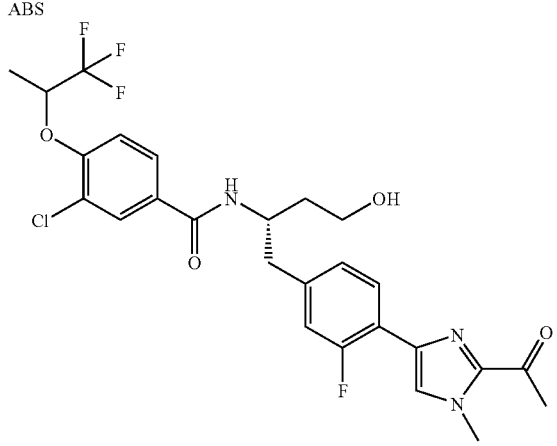

N-(1-{3-fluoro-4-[2-acetyl-1-methyl-1H-imidazol-4-yl]-benzyl}-3-hydroxy-propyl)-3-chloro-4-(2,2,2-trifluoro-1-methyl-ethoxy)-benzamide

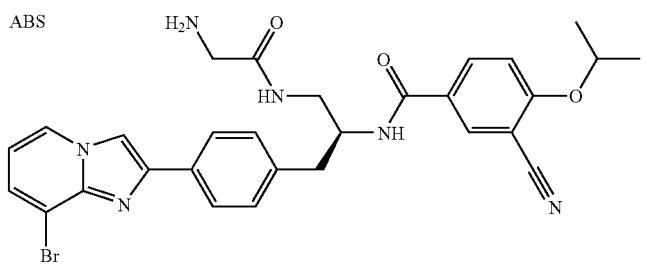

N-(2-(2-amino-acetylamino)-1-{4-[8-bromo-imidazo[1,2-a]pyridin-2-yl]-benzyl}-ethyl)-3-cyano-4-isopropoxy-benzamide

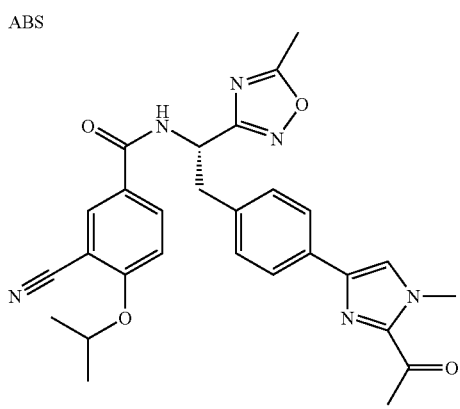

N-(2-{4-[2-acetyl-1-methyl-1H-imidazol-4-yl]-phenyl}-1-(5-methyl-[1,2,4]oxadiazol-3-yl)-ethyl)-3-cyano-4-isopropoxy-benzamide

TABLE 1-continued

| | | |
|---|---|---|
| RAC | 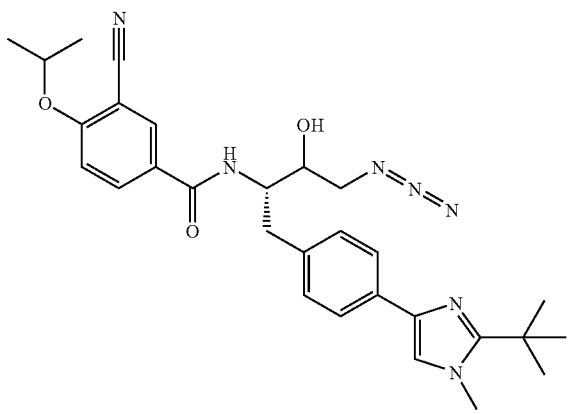 | N-[1-[4-(2-t-butyl-1-methyl-1H-imidazol-4-yl)-benzyl]-2-hydroxy-3-azido-propyl]-3-cyano-4-isopropoxy-benzamide |
| ABS | 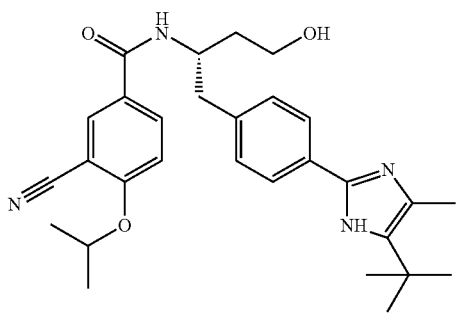 | N-(1-{4-[5-t-butyl-4-methyl-1H-imidazol-2-yl]-benzyl}-3-hydroxy-propyl)-3-cyano-4-isopropoxy-benzamide |
| ABS | 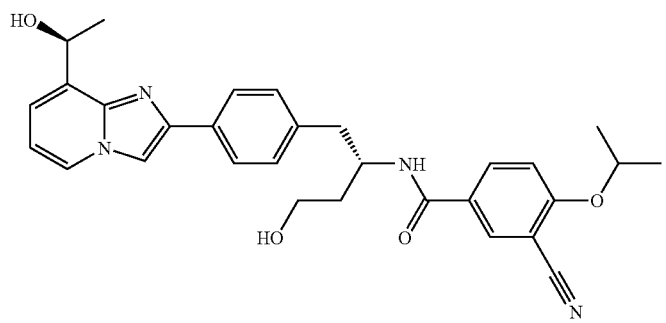 | N-(1-[4-(8-(1-hydroxy-ethyl)-imidazo[1,2-a]pyridin-2-yl)-benzyl]-3-hydroxy-propyl}-3-cyano-4-isopropoxy-benzamide |
| ABS | 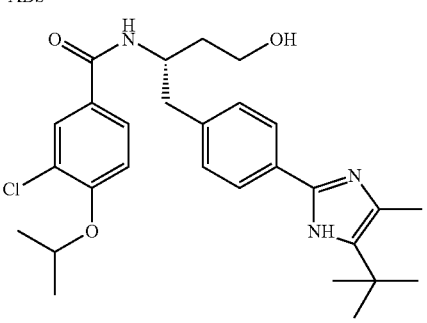 | N-(1-{4-[5-t-butyl-4-methyl-1H-imidazol-2-yl]-benzyl}-3-hydroxy-propyl)-3-chloro-4-isopropoxy-benzamide |

TABLE 1-continued

| ABS | N-(1-{4-[2-(1-acetylamino-ethyl)-1-methyl-1H-imidazol-4-yl]-benzyl}-3-hydroxy-propyl)-3-chloro-4-(2,2,2-trifluoro-1-methyl-ethoxy)-benzamide |
| ABS | N-(1-{4-[2-t-butyl-1-methyl-1H-imidazol-4-yl]-benzyl}-2-amino-butyl)-3-cyano-4-isopropoxy-benzamide |
| ABS | N-{1-[4-(8-methyl-imidazo[1,2-a]pyridin-2-yl)-benzyl]-3-hydroxy-butyl}-3-cyano-4-isopropoxy-benzamide |
| ABS | N-(1-{4-[2-t-butyl-1-methyl-1H-imidazol-4-yl]-benzyl}-2-hydroxy-propyl)-3-cyano-4-isopropoxy-benzamide |

TABLE 1-continued
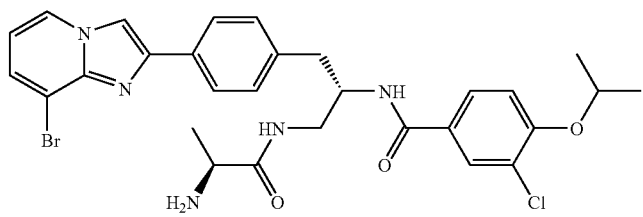
N-(2-(2-amino-propionylamino)-1-{4-[8-bromo-imidazo[1,2-a]pyridin-2-yl]-benzyl}-ethyl)-3-chloro-4-isopropoxy-benzamide
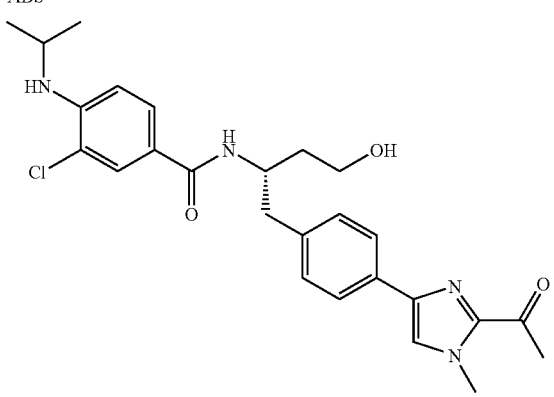
N-(1-{4-[2-acetyl-1-methyl-1H-imidazol-4-yl]-benzyl}-3-hydroxy-propyl)-3-chloro-4-isopropylamino-benzamide
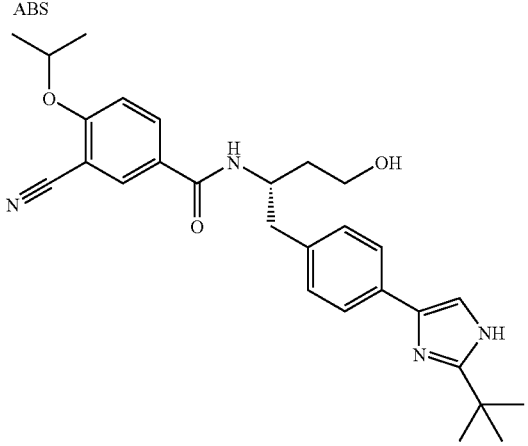
N-(1-{4-[2-t-butyl-1H-imidazol-4-yl]-benzyl}-3-hydroxy-propyl)-3-cyano-4-isopropoxy-benzamide
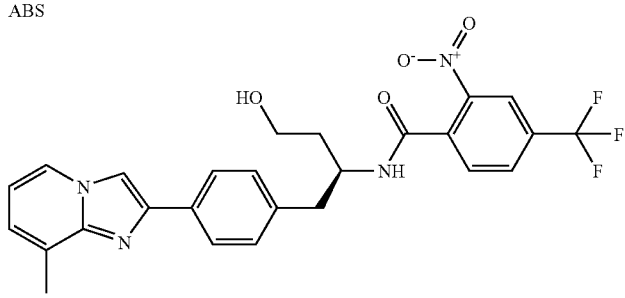
N-{1-[4-(8-methyl-imidazo[1,2-a]pyridin-2-yl)-benzyl]-3-hydroxy-propyl}-2-nitro-4-trifluoromethyl-benzamide

TABLE 1-continued

| | |
|---|---|
| RAC | N-(1-{4-[2-t-butyl-1-methyl-1H-imidazol-4-yl]-benzyl}-3-hydroxy-propyl)-3-iodo-4-isopropoxy-benzamide |

(S)-3-chloro-N-(1-(4-(1-ethyl-2-(2-hydroxypropan-2-yl)-1H-imidazol-4-yl)phenyl)-4-hydroxybutan-2-yl)-4-isopropoxybenzamide
(S)-N-(1-(4-(2-acetyl-1-ethyl-1H-imidazol-4-yl)phenyl)-4-hydroxybutan-2-yl)-3-chloro-4-isopropoxybenzamide
N-((S)-1-(4-(2-(1-acetamidoethyl)-1-ethyl-1H-imidazol-4-yl)phenyl)-4-hydroxybutan-2-yl)-3-chloro-4-isopropoxybenzamide
3-chloro-N-((S)-1-(4-(1-ethyl-2-(2-hydroxypropan-2-yl)-1H-imidazol-4-yl)phenyl)-4-hydroxybutan-2-yl)-4-(1,1,1-trifluoropropan-2-yloxy)benzamide
N-((S)-1-(4-(2-(1-acetamidoethyl)-1-ethyl-1H-imidazol-4-yl)phenyl)-4-hydroxybutan-2-yl)-3-chloro-4-(1,1,1-trifluoropropan-2-yloxy)benzamide
(S)-N-(1-(4-(2-acetyl-1-(2,2,2-trifluoroethyl)-1H-imidazol-4-yl)phenyl)-4-hydroxybutan-2-yl)-3-chloro-4-isopropoxybenzamide
3-chloro-N-((S)-4-hydroxy-1-(4-(8-(1-hydroxyethyl)imidazo[1,2-a]pyridin-2-yl)phenyl)butan-2-yl)-4-isopropoxybenzamide
(S)-3-chloro-N-(1-(2-(dimethylamino)acetamido)-3-(4-(8-methylimidazo[1,2-a]pyridin-2-yl)phenyl)propan-2-yl)-4-isopropoxybenzamide
3-chloro-N-((S)-1-(2-(dimethylamino)acetamido)-3-(4-(8-(1-hydroxyethyl)imidazo[1,2-a]pyridin-2-yl)phenyl)propan-2-yl)-4-isopropoxybenzamide
3-Cyano-N-((1S)-3-hydroxy-1-{[4-(8-methylimidazo[1,2-a]pyridin-2-yl)phenyl]methyl}propyl)-4-[(1-methylethyl)oxy]benzamide;
3-Chloro-N-[(1S)-3-hydroxy-1-({4-[8-(1-hydroxyethyl)imidazo[1,2-a]pyridin-2-yl]phenyl}methyl)propyl]-4-[(1-methylethyl)oxy]benzamide
3-Chloro-N-[(1S)-2-[(N,N-dimethylglycyl)amino]-1-({4-[8-(1-hydroxyethyl)imidazo[1,2-a]pyridin-2-yl]phenyl }methyl)ethyl]-4-[(1-methylethyl)oxy]benzamide
N-((1S)-2-(D-Alanylamino)-1-{[4-(8-bromoimidazo[1,2-a]pyridin-2-yl)phenyl]methyl}ethyl)-3-chloro-4-[(1-methylethyl)oxy]benzamide
3-Chloro-N-((1S)-2-[(2-methylalanyl)amino]-1-{[4-(8-methylimidazo[1,2-a]pyridin-2-yl)phenyl]methyl}ethyl)-4-[(1-methylethyl)oxy]benzamide
3-Chloro-N-((1S)-2-[(N,N-dimethylglycyl)amino]-1-{[4-(8-methylimidazo[1,2-a]pyridin-2-yl)phenyl]methyl}ethyl)-4-[(1-methylethyl)oxy]benzamide
N-((1R)-4-Amino-1-{[4-(8-methylimidazo[1,2-a]pyridin-2-yl)phenyl]methyl}-4-oxobutyl)-3-chloro-4-[(1-methylethyl)oxy]benzamide
N-((1R)-1-{[4-(2-acetyl-1-methyl-1H-imidazol-4-yl)phenyl]methyl}-4-amino-4-oxobutyl)-3-chloro-4-[(1-methylethyl)oxy]benzamide
3-Cyano-N-[(1S)-3-hydroxy-1-({4-[8-(1-hydroxyethyl)imidazo[1,2-a]pyridin-2-yl]phenyl}methyl)propyl]-4-[(1-methylethyl)oxy]benzamide
3-Chloro-N-((1S)-3-hydroxy-1-{[4-(8-methylimidazo[1,2-a]pyridin-2-yl)phenyl]methyl}propyl)-4-[(1-methylethyl)oxy]benzamide
3-Cyano-N-[(1S)-2-[(N,N-dimethylglycyl)amino]-1-({4-[8-(1-hydroxyethyl)imidazo[1,2-a]pyridin-2-yl]phenyl}methyl)ethyl]-4-[(1-methylethyl)oxy]benzamide
3-Cyano-N-((1S)-2-[(N,N-dimethylglycyl)amino]-1-{[4-(8-methylimidazo[1,2-a]pyridin-2-yl)phenyl]methyl}ethyl)-4-[(1-methylethyl)oxy]benzamide;
N-((1R)-1-{[4-(2-Acetyl-1-methyl-1H-imidazol-4-yl)phenyl]methyl}-4-amino-4-oxobutyl)-3-cyano-4-[(1-methylethyl)oxy]benzamide
N-[(1R)-4-Amino-1-({4-[2-(1-hydroxy-1-methylethyl)-1-methyl-1H-imidazol-4-yl]phenyl}methyl)-4-oxobutyl]-3-cyano-4-[(1-methylethyl)oxy]benzamide
N-[(1S)-2-(D-Alanylamino)-1-({4-[1-(2-aminoethyl)-2-(1,1-dimethylethyl)-1H-imidazol-4-yl]phenyl}methyl)ethyl]-3-chloro-4-[(1-methylethyl)oxy]benzamide
N-((1S)-2-{4-[1-(2-Aminoethyl)-2-(1,1-dimethylethyl)-1H-imidazol-4-yl]phenyl}-1-{[(2-methylalanyl)amino]methyl}ethyl)-3-chloro-4-[(1-methylethyl)oxy]benzamide
N-[(1S)-2-(D-Alanylamino)-1-({4-[1-(2-aminoethyl)-2-(1,1-dimethylethyl)-1H-imidazol-4-yl]phenyl}methyl)ethyl]-3-cyano-4-[(1-methylethyl)oxy]benzamide
N-((1S)-2-{4-[1-(2-Aminoethyl)-2-(1,1-dimethylethyl)-1H-imidazol-4-yl]phenyl}-1-{[(hydroxyacetyl)amino]methyl}ethyl)-3-cyano-4-[(1-methylethyl)oxy]benzamide
N-((1S)-2-{4-[1-(2-Aminoethyl)-2-(1,1-dimethylethyl)-1H-imidazol-4-yl]phenyl}-1-{[(2-methylalanyl)amino]methyl}ethyl)-3-cyano-4-[(1-methylethyl)oxy]benzamide
N-((1S)-2-{4-[1-(2-Aminoethyl)-2-(1,1-dimethylethyl)-1H-imidazol-4-yl]phenyl}-1-{[(N,N-dimethylglycyl)amino]methyl}ethyl)-3-cyano-4-[(1-methylethyl)oxy]benzamide
3-Chloro-N-[(1S)-2-{4-[8-(1-hydroxyethyl)imidazo[1,2-a]pyridin-2-yl]phenyl}-1-({[(2R)-2-hydroxypropanoyl]amino}methyl)ethyl]-4-[(1-methylethyl)oxy]benzamide TABLE 1-continued N-((1S)-2-[(Aminocarbonyl)amino]-1-{[4-(8-bromoimidazo[1,2-a]pyridin-2-yl)phenyl]methyl}ethyl)-3-chloro-4-[(1-methylethyl)oxy]benzamide
N-{(1S)-2-[4-(8-Bromoimidazo[1,2-a]pyridin-2-yl)phenyl]-1-[(2-oxotetrahydro-1(2H)-pyrimidinyl)methyl]ethyl}-3-chloro-4-[(1-methylethyl)oxy]benzamide
N-{(1S)-2-[4-(8-Bromoimidazo[1,2-a]pyridin-2-yl)phenyl]-1-[(2-oxohexahydro-1H-1,3-diazepin-1-yl)methyl]ethyl}-3-chloro-4-[(1-methylethyl)oxy]benzamide
N-((1S)-2-[(Aminocarbonothioyl)amino]-1-{[4-(8-bromoimidazo[1,2-a]pyridin-2-yl)phenyl]methyl}ethyl)-3-chloro-4-[(1-methylethyl)oxy]benzamide
2-(4-{(2S)-2-[({3-Cyano-4-[(1-methylethyl)oxy]phenyl}carbonyl)amino]-3-[(1,2,3-thiadiazol-4-ylcarbonyl)amino]propyl}phenyl)imidazo[1,2-a]pyridine-8-carboxamide
N-((1S)-2-[(Aminosulfonyl)amino]-1-{[4-(8-methylimidazo[1,2-a]pyridin-2-yl)phenyl]methyl}ethyl)-3-cyano-4-[(1-methylethyl)oxy]benzamide
(3S)-3-[({3-Chloro-4-[(1-methylethyl)oxy]phenyl}carbonyl)amino]-4-{4-[2-(1,1-dimethylethyl)-1-methyl-1H-imidazol-4-yl]phenyl}butanoic acid
N-[(1S)-2-[(Aminosulfonyl)amino]-1-({4-[2-(1,1-dimethylethyl)-1-methyl-1H-imidazol-4-yl]phenyl}methyl)ethyl]-3-cyano-4-[(1-methylethyl)oxy]benzamide
N-((1S)-1-{[4-(1H-Benzimidazol-2-yl)phenyl]methyl}-3-hydroxypropyl)-3-chloro-4-[(1-methylethyl)oxy]benzamide
3-Chloro-N-[(1S)-3-hydroxy-1-({4-[5-(trifluoromethyl)-1H-benzimidazol-2-yl]phenyl}methyl)propyl]-4-[(1-methylethyl)oxy]benzamide
3-Chloro-N-((1S)-1-{[4-(5,6-dimethyl-1H-benzimidazol-2-yl)phenyl]methyl}-3-hydroxypropyl)-4-[(1-methylethyl)oxy]benzamide
3-Chloro-N-[(1S)-3-hydroxy-1-({4-[5-(methyloxy)-1H-benzimidazol-2-yl]phenyl}methyl)propyl]-4-[(1-methylethyl)oxy]benzamide
3-Chloro-N-((1S)-1-{[4-(5-chloro-1H-benzimidazol-2-yl)phenyl]methyl}-3-hydroxypropyl)-4-[(1-methylethyl)oxy]benzamide
3-Chloro-N-((1S)-3-hydroxy-1-{[4-(4-methyl-1H-benzimidazol-2-yl)phenyl]methyl}propyl)-4-[(1-methylethyl)oxy]benzamide
3-Chloro-N-((1S)-1-{[4-(6-chloro-1H-imidazo[4,5-b]pyridin-2-yl)phenyl]methyl}-3-hydroxypropyl)-4-[(1-methylethyl)oxy]benzamide
Ethyl 2-(4-{(2S)-2-[({3-chloro-4-[(1-methylethyl)oxy]phenyl}carbonyl)amino]-4-hydroxybutyl}phenyl)-1H-benzimidazole-5-carboxylate
2-(4-{(2S)-2-[({3-Chloro-4-[(1-methylethyl)oxy]phenyl}carbonyl)amino]-4-hydroxybutyl}phenyl)-1H-benzimidazole-5-carboxylic acid
N-((1S)-3-Amino-1-{[4-(1H-benzimidazol-2-yl)phenyl]methyl}propyl)-3-chloro-4-[(1-methylethyl)oxy]benzamide
3-Cyano-N-((1S)-1-{[4-(8-cyanoimidazo[1,2-a]pyridin-2-yl)phenyl]methyl}-3-hydroxypropyl)-4-[(1-methylethyl)oxy]benzamide
N-((1S)-1-{[4-(8-Chloroimidazo[1,2-a]pyridin-2-yl)phenyl]methyl}-3-hydroxypropyl)-3-cyano-4-[(1-methylethyl)oxy]benzamide
3-Cyano-N-[(1S)-3-hydroxy-1-({4-[8-(trifluoromethyl)imidazo[1,2-a]pyridin-2-yl]phenyl}methyl)propyl]-4-[(1-methylethyl)oxy]benzamide
3-Cyano-N-((1S)-3-hydroxy-1-{[4-(8-hydroxylmidazo[1,2-a]pyridin-2-yl)phenyl]methyl}propyl)-4-[(1-methylethyl)oxy]benzamide
2-(4-{(2S)-2-[({3-Cyano-4-[(1-methylethyl)oxy]phenyl}carbonyl)amino]-4-hydroxybutyl}phenyl)imidazo[1,2-a]pyridine-7-carboxamide
Ethyl 2-(4-{(2S)-2-[({3-cyano-4-[(1-methylethyl)oxy]phenyl}carbonyl)amino]-4-hydroxybutyl}phenyl)imidazo[1,2-a]pyridine-7-carboxylate
3-Cyano-N-((1S)-3-hydroxy-1-{[4-(8-nitroimidazo[1,2-a]pyridin-2-yl)phenyl]methyl}propyl)-4-[(1-methylethyl)oxy]benzamide
N-((1S)-1-{[4-(8-Aminoimidazo[1,2-a]pyridin-2-yl)phenyl]methyl}-3-hydroxypropyl)-3-cyano-4-[(1-methylethyl)oxy]benzamide
2-(4-{(2S)-2-[({3-Cyano-4-[(1-methylethyl)oxy]phenyl}carbonyl)amino]-4-hydroxybutyl}phenyl)imidazo[1,2-a]pyridine-8-carboxamide
3-Cyano-N-[(1S)-3-hydroxy-1-({4-[8-(hydroxymethyl)imidazo[1,2-a]pyridin-2-yl]phenyl}methyl)propyl]-4-[(1-methylethyl)oxy]benzamide
N-[(1S)-1-({4-[8-(Aminomethyl)imidazo[1,2-a]pyridin-2-yl]phenyl}methyl)-3-hydroxypropyl]-3-cyano-4-[(1-methylethyl)oxy]benzamide
N-((1S)-1-{[4-(8-Acetylimidazo[1,2-a]pyridin-2-yl)phenyl]methyl}-3-hydroxypropyl)-3-cyano-4-[(1-methylethyl)oxy]benzamide
3-Cyano-N-[(1S)-3-hydroxy-1-({4-[8-(1-hydroxy-1-methylethyl)imidazo[1,2-a]pyridin-2-yl]phenyl}methyl)propyl]-4-[(1-methylethyl)oxy]benzamide
3-Cyano-N-[(1S)-3-hydroxy-1-({4-[8-(1-hydroxyethyl)imidazo[1,2-a]pyridin-2-yl]phenyl}methyl)propyl]-4-[(1-methylethyl)oxy]benzamide
3-Cyano-N-((1S)-3-hydroxy-1-{[4-(8-methyl-5,6,7,8-tetrahydroimidazo[1,2-a]pyridin-2-yl)phenyl]methyl}propyl)-4-[(1-methylethyl)oxy]benzamide
3-Cyano-N-[(1S)-1-({4-[2-(1,1-dimethylethyl)-1-(2-hydroxyethyl)-1H-imidazol-4-yl]phenyl}methyl)-3-hydroxypropyl]-4-[(1-methylethyl)oxy]benzamide
N-[(1S)-1-({4-[1-[2-(Acetylamino)ethyl]-2-(1,1-dimethylethyl)-1H-imidazol-4-yl]phenyl}methyl)-3-hydroxypropyl]-3-cyano-4-[(1-methylethyl)oxy]benzamide
3-Cyano-N-{(1S)-3-hydroxy-1-[(4-{8-[(1R)-1-hydroxyethyl]imidazo[1,2-a]pyridin-2-yl}phenyl)methyl]propyl}-4-[(1-methylethyl)oxy]benzamide
3-Cyano-N-{(1S)-3-hydroxy-1-[(4-{8-[(1S)-1-hydroxyethyl]imidazo[1,2-a]pyridin-2-yl}phenyl)methyl]propyl}-4-[(1-methylethyl)oxy]benzamide
3-Chloro-N-[(1S)-3-hydroxy-1-({4-[8-(1-hydroxypropyl)imidazo[1,2-a]pyridin-2-yl]phenyl}methyl)propyl]-4-[(1-methylethyl)oxy]benzamide
N-((1S)-1-{[4-(8-Bromoimidazo[1,2-a]pyridin-2-yl)phenyl]methyl}-3-hydroxypropyl)-3-chloro-4-[(1-methylethyl)oxy]benzamide
3-Chloro-N-((1S)-1-{[4-(8-chloroimidazo[1,2-a]pyridin-2-yl)phenyl]methyl}-3-

TABLE 1-continued hydroxypropyl)-4-[(1-methylethyl)oxy]benzamide
3-Chloro-N-[(1S)-3-hydroxy-1-({4-[8-(1-hydroxy-2-methylpropyl)imidazo[1,2-a]pyridin-2-yl]phenyl}methyl)propyl]-4-[(1-methylethyl)oxy]benzamide
N-[(1R)-4-Amino-1-({4-[8-(1-hydroxyethyl)imidazo[1,2-a]pyridin-2-yl]phenyl}methyl)-4-oxobutyl]-3-chloro-4-[(1-methylethyl)oxy]benzamide
N-[(1R)-4-Amino-1-({4-[8-(1-hydroxyethyl)imidazo[1,2-a]pyridin-2-yl]phenyl}methyl)-4-oxobutyl]-3-cyano-4-[(1-methylethyl)oxy]benzamide
3-Chloro-N-((1S)-1-{[4-(3-fluoro-8-methylimidazo[1,2-a]pyridin-2-yl)phenyl]methyl}-3-hydroxypropyl)-4-[(1-methylethyl)oxy]benzamide
3-Cyano-N-((1S)-1-{[4-(3-fluoro-8-methylimidazo[1,2-a]pyridin-2-yl)phenyl]methyl}-3-hydroxypropyl)-4-[(1-methylethyl)oxy]benzamide
3-Chloro-N-((1S)-2-hydroxy-1-{[4-(8-methylimidazo[1,2-a]pyridin-2-yl)phenyl]methyl}ethyl)-4-[(1-methylethyl)oxy]benzamide
3-Chloro-4-[(1-methylethyl)oxy]-N-[(1S)-2-[4-(8-methylimidazo[1,2-a]pyridin-2-yl)phenyl]-1-(4-morpholinylmethyl)ethyl]benzamide
3-Chloro-N-((1S)-2-(4-hydroxy-1-piperidinyl)-1-{[4-(8-methylimidazo[1,2-a]pyridin-2-yl)phenyl]methyl}ethyl)-4-[(1-methylethyl)oxy]benzamide
3-Chloro-N-((1S)-2-(3-hydroxy-1-pyrrolidinyl)-1-{[4-(8-methylimidazo[1,2-a]pyridin-2-yl)phenyl]methyl}ethyl)-4-[(1-methylethyl)oxy]benzamide
3-Chloro-N-((1S)-2-[(2S)-2-(hydroxymethyl)-1-pyrrolidinyl]-1-{[4-(8-methylimidazo[1,2-a]pyridin-2-yl)phenyl]methyl}ethyl)-4-[(1-methylethyl)oxy]benzamide
3-Chloro-N-((1S)-2-[(2R)-2-(hydroxymethyl)-1-pyrrolidinyl]-1-{[4-(8-methylimidazo[1,2-a]pyridin-2-yl)phenyl]methyl}ethyl)-4-[(1-methylethyl)oxy]benzamide
3-Chloro-4-[(1-methylethyl)oxy]-N-((1S)-2-[4-(8-methylimidazo[1,2-a]pyridin-2-yl)phenyl]-1-{[(2,2,2-trifluoroethyl)amino]methyl}ethyl)benzamide
3-Chloro-N-((1S)-2-[(2-hydroxyethyl)amino]-1-{[4-(8-methylimidazo[1,2-a]pyridin-2-yl)phenyl]methyl}ethyl)-4-[(1-methylethyl)oxy]benzamide
3-Cyano-N-((1S)-1-{[4-(8-ethyl-5-methylimidazo[1,2-a]pyridin-2-yl)phenyl]methyl}-3-hydroxypropyl)-4-[(1-methylethyl)oxy]benzamide
Methyl (3S)-3-[({-3-chloro-4-[(1-methylethyl)oxy]phenyl}carbonyl)amino]-4-{4-[(phenylcarbonyl)amino]phenyl}butanoate
3-Chloro-N-[(1S)-3-hydroxy-1-({4-[(phenylcarbonyl)amino]phenyl}methyl)propyl]-4-[(1-methylethyl)oxy]benzamide
3-Chloro-N-{(1S)-1-[(4-{[(4-chlorophenyl)carbonyl]amino}phenyl)methyl]-3-hydroxypropyl}-4-[(1-methylethyl)oxy]benzamide
Phenylmethyl (4-{(2S)-2-[({3-chloro-4-[(1-methylethyl)oxy]phenyl}carbonyl)amino]-4-hydroxybutyl}phenyl)carbamate
3-Chloro-N-((1S)-3-hydroxy-1-{[4-({[2-(methylamino)phenyl]carbonyl}amino)phenyl]methyl}propyl)-4-[(1-methylethyl)oxy]benzamide
N-(4-{(2S)-2-[({3-Chloro-4-[(1-methylethyl)oxy]phenyl}carbonyl)aminol-4-hydroxybutyl}phenyl)-4-pyridinecarboxamide
3-Chloro-N-[(1S)-1-({4-[(cyclohexylcarbonyl)amino]phenyl}methyl)-3-hydroxypropyl]-4-[(1-methylethyl)oxy]benzamide
3-Chloro-N-[(1S)-1-({4-[(3,3-dimethylbutanoyl)amino]phenyl}methyl)-3-hydroxypropyl]-4-[(1-methylethyl)oxy]benzamide
3-Chloro-N-[(1S)-3-hydroxy-1-({4-[(phenylacetyl)amino]phenyl}methyl)propyl]-4-[(1-methylethyl)oxy]benzamide
3-Chloro-N-{(1S)-3-hydroxy-1-[(4-{[(phenylamino)carbonyl]amino}phenyl)methyl]propyl}-4-[(1-methylethyl)oxy]benzamide
3-Cyano-N-((1S)-3-hydroxy-1-{[4-(8-methyl-5-oxo-5,6-dihydroimidazo[1,2-c]pyrimidin-2-yl)phenyl]methyl}propyl)-4-[(1-methylethyl)oxy]benzamide
3-Cyano-N-((1S)-3-hydroxy-1-{[4-(1-methyl-3-oxo-2,3-dihydro-1H-imidazo[1,2-a]imidazol-6-yl)phenyl]methyl}propyl)-4-[(1-methylethyl)oxy]benzamide
3-Cyano-N-((1S)-3-hydroxy-1-{[4-(8-oxo-7,8-dihydroimidazo[1,2-a]pyrazin-2-yl)phenyl]methyl}propyl)-4-[(1-methylethyl)oxy]benzamide
2,3-Dichloro-N-((1S)-3-hydroxy-1-{[4-(8-methylimidazo[1,2-a]pyridin-2-yl)phenyl]methyl}propyl)-4-[(1-methylethyl)oxy]benzamide
N-((1S)-3-Hydroxy-1-{[4-(8-methylimidazo[1,2-a]pyridin-2-yl)phenyl]methyl}propyl)-4-[(1-methylethyl)oxy]-3-nitrobenzamide
3-Chloro-N-[(1S)-2-[(hydroxyacetyl)amino]-1-({4-[8-(1-hydroxyethyl)imidazo[1,2-a]pyridin-2-yl]phenyl}methyl)ethyl]-4-[(1-methylethyl)oxy]benzamide
3-Chloro-N-[(1S)-2-{4-[8-(1-hydroxyethyl)imidazo[1,2-a]pyridin-2-yl]phenyl}-1-({[(2R)-2-hydroxypropanoyl]amino}methyl)ethyl]-4-[(1-methylethyl)oxy]benzamide
3-Chloro-N-[(1S)-2-{4-[8-(1-hydroxyethyl)imidazo[1,2-a]pyridin-2-yl]phenyl}-1-({[(2S)-2-hydroxypropanoyl]amino}methyl)ethyl]-4-[(1-methylethyl)oxy]benzamide
3-Chloro-N-[(1S)-2-[(N,N-dimethylglycyl)amino]-1-({4-[8-(1-hydroxyethyl)imidazo[1,2-a]pyridin-2-yl]phenyl}methyl)ethyl]-4-[(1-methylethyl)oxy]benzamide
N-[(1S)-2-(D-Alanylamino)-1-({4-[8-(1-hydroxyethyl)imidazo[1,2-a]pyridin-2-yl]phenyl}methyl)ethyl]-3-chloro-4-[(1-methylethyl)oxy]benzamide
3-Chloro-N-[(1S)-3-hydroxy-1-({4-[8-(1-hydroxyethyl)imidazo[1,2-a]pyridin-2-yl]phenyl}methyl)propyl]-4-[(1-methylethyl)oxy]benzamide
3-Chloro-N-((1S)-2-{4-[8-(1-hydroxyethyl)imidazo[1,2-a]pyridin-2-yl]phenyl}-1-{[(2-methylalanyl)amino]methyl}ethyl)-4-[(1-methylethyl)oxy]benzamide
(3S)-3-[({3-Chloro-4-[(1-methylethyl)oxy]phenyl}carbonyl)amino]-4-{4-[(phenylcarbonyl)amino]phenyl}butanoic acid
3-Chloro-N-{(1S)-3-hydroxy-1-[(4-imidazo[1,2-a]pyridin-6-ylphenyl)methyl]propyl}-4-[(1-methylethyl)oxy]benzamide
3-Chloro-N-[(1S)-1-({4-[2-(1,1-dimethylethyl)imidazo[1,2-a]pyridin-6-yl]phenyl}methyl)-3-

TABLE 1-continued hydroxypropyl)-4-[(1-methylethyl)oxy]benzamide
3-Chloro-N-{(1S)-3-hydroxy-1-[(4-imidazo[1,2-a]pyridin-2-ylphenyl)methyl]propyl}-4-[(1-methylethyl)oxy]benzamide
3-Chloro-N-{(1S)-3-hydroxy-1-[(4-imidazo[1,2-a]pyrimidin-2-ylphenyl)methyl]propyl}-4-[(1-methylethyl)oxy]benzamide
3-Chloro-N-((1S)-3-hydroxy-1-{[4-(5-methylimidazo[1,2-a]pyridin-2-yl)phenyl]methyl}propyl)-4-[(1-methylethyl)oxy]benzamide
3-Chloro-N-((1S)-3-hydroxy-1-{[4-(7-methylimidazo[1,2-a]pyrimidin-2-yl)phenyl]methyl}propyl)-4-[(1-methylethyl)oxy]benzamide
3-Cyano-N-{(1S)-3-hydroxy-1-[(4-imidazo[2,1-b][1,3]thiazol-6-ylphenyl)methyl]butyl}-4-[(1-methylethyl)oxy]benzamide
3-Cyano-N-((1S)-3-hydroxy-1-{[4-(3-methylimidazo[2,1-b][1,3]thiazol-6-yl)phenyl]methyl}butyl)-4-[(1-methylethyl)oxy]benzamide
3-Cyano-N-((1S)-1-{[4-(2,3-dihydroimidazo[2,1-b][1,3]thiazol-6-yl)phenyl]methyl}-3-hydroxybutyl)-4-[(1-methylethyl)oxy]benzamide
3-Cyano-N-((1S)-1-{[4-(1,1-dioxido-2,3-dihydroimidazo[2,1-b][1,3]thiazol-6-yl)phenyl]methyl}-3-hydroxybutyl)-4-[(1-methylethyl)oxy]benzamide
N-[(1S)-1-({4-[1-(3-Aminopropyl)-2-(1,1-dimethylethyl)-1H-imidazol-4-yl]phenyl}methyl)3-hydroxypropyl]-3-cyano-4-[(1-methylethyl)oxy]benzamide
3-Cyano-4-[(1-methylethyl)oxy]-N-[(1S)-2-[4-(8-methylimidazo[1,2-a]pyridin-2-yl)phenyl]-1-(5-methyl-1,2,4-oxadiazol-3-yl)ethyl]benzamide
3-Cyano-N-{(1S)-1-({4-[8-(3,5-dimethyl-4-isoxazolyl)imidazo[1,2-a]pyridin-2-yl]phenyl}methyl)-3-hydroxypropyl]-4-[(1-methylethyl)oxy]benzamide
3-Cyano-N-((1S)-3-hydroxy-1-{[4-(8-phenylimidazo[1,2-a]pyridin-2-yl)phenyl]methyl}propyl)-4-[(1-methylethyl)oxy]benzamide
3-Cyano-N-[(1S)-3-hydroxy-1-({4-[8-(1H-pyrazol-4-yl)imidazo[1,2-a]pyridin-2-yl]phenyl}methyl)propyl]-4-[(1-methylethyl)oxy]benzamide
3-Cyano-N-[(1S)-3-hydroxy-1-({4-[8-(4-isoxazolyl)imidazo[1,2-a]pyridin-2-yl]phenyl}methyl)propyl]-4-[(1-methylethyl)oxy]benzamide
N-((1S)-1-{[4-(8-Acetylimidazo[1,2-a]pyridin-2-yl)phenyl]methyl}-3-hydroxypropyl)-3-chloro-4-[(1-methylethyl)oxy]benzamide
Ethyl (2E)-3-[2-(4-{(2S)-2-[({3-cyano-4-[(1-methylethyl)oxy]phenyl}carbonyl)amino]-4-hydroxybutyl}phenyl)imidazo[1,2-a]pyridin-8-yl]-2-propenoate
(2E)-3-[2-(4-{(2S)-2-[({3-Cyano-4-[(1-methylethyl)oxy]phenyl}carbonyl)amino]-4-hydroxybutyl}phenyl)imidazo[1,2-a]pyridin-8-yl]-2-propenoic acid
N-{(1S)-1-[(4-{8-[(1E)-3-Amino-3-oxo-1-propen-1-yl]imidazo[1,2-a]pyridin-2-yl}phenyl)methyl]-3-hydroxypropyl}-3-cyano-4-[(1-methylethyl)oxy]benzamide
N-[(1S)-1-({4-[8-(3-Amino-3-oxopropyl)imidazo[1,2-a]pyridin-2-yl]phenyl}methyl)-3-hydroxypropyl]-3-cyano-4-[(1-methylethyl)oxy]benzamide
3-Chloro-N-((1S)-1-{[4-(3-chloro-8-methylimidazo[1,2-a]pyridin-2-yl)phenyl]methyl}-3-hydroxypropyl)-4-[(1-methylethyl)oxy]benzamide
N-((1S)-1-{[4-(3-Chloro-8-methylimidazo[1,2-a]pyridin-2-yl)phenyl]methyl}-3-hydroxypropyl)-3-cyano-4-[(1-methylethyl)oxy]benzamide
3-Cyano-N-[(1S)-1-({3-fluoro-4-[2-(1-hydroxy-1-methylethyl)-1-methyl-1H-imidazol-4-yl]phenyl}methyl)-3-hydroxypropyl]-4-[(1-methylethyl)oxy]benzamide
3-Chloro-N-((1S)-2-hydroxy-1-{[5-(8-methylimidazo[1,2-a]pyridin-2-yl)-2-pyridinylmethyl]ethyl)-4-[(1-methylethyl)oxy]benzamide
3-Chloro-N-((1S)-2-hydroxy-1-{[5-(8-methylimidazo[1,2-a]pyridin-2-yl)-2-thienyl]methyl}ethyl)-4-[(1-methylethyl)oxy]benzamide
3-Chloro-N-[(1S)-1-({4-[2-(1,1-dimethylethyl)-1-methyl-1H-imidazoi-4-yl]-2-fluorophenyl}methyl)-3-hydroxypropyl]-4-[(1-methylethyl)oxy]benzamide
3-Chloro-N-[(1S)-1-({4-[2-(1,1-dimethylethyl)-1-methyl-1H-imidazol-4-yl]-2,6-difluorophenyl}methyl)-3-hydroxypropyl]-4-[(1-methylethyl)oxy]benzamide
3-Chloro-N-[(1S)-1-({2-chloro-4-[2-(1,1-dimethylethyl)-1-methyl-1H-imidazol-4-yl]phenyl}methyl)-3-hydroxypropyl]-4-[(1-methylethyl)oxy]benzamide
3-Chloro-N-[(1S)-1-({5-[2-(1,1-dimethylethyl)-1-methyl-1H-imidazol-4-yl]-2-pyridinyl}methyl)-3-hydroxypropyl]-4-[(1-methylethyl)oxy]benzamide
3-Chloro-N-((1S)-1-{[2-chloro-4-(8-methylimidazo[1,2-a]pyridin-2-yl)phenyl]methyl}-3-hydroxypropyl)-4-[(1-methylethyl)oxy]benzamide
3-Chloro-N-((1S)-1-{[2-chloro-4-(8-chloroimidazo[1,2-a]pyridin-2-yl)phenyl]methyl}-3-hydroxypropyl)-4-[(1-methylethyl)oxy]benzamide
3-Chloro-N-((1S)-1-{[2,5-difluoro-4-(8-methylimidazo[1,2-a]pyridin-2-yl)phenyl]methyl}-3-hydroxypropyl)-4-[(1-methylethyl)oxy]benzamide
3-Chloro-N-((1S)-1-{[3-chloro-4-(8-methylimidazo[1,2-a]pyridin-2-yl)phenyl]methyl}-3-hydroxypropyl)-4-[(1-methylethyl)oxy]benzamide
3-Chloro-N-[(1S)-1-({4-[2-(1,1-dimethylethyl)-1-methyl-1H-imidazoi-4-yl]phenyl}methyl)-3-(methylamino)-3-oxopropyl]-4-[(1-methylethyl)oxy]benzamide
3-Cyano-N-[(1S)-2-{4-[2-(1,1-dimethylethyl)-1-methyl-1H-imidazol-4-yl]phenyl}-1-({[(phenylamino)carbonyl]amino}methyl)ethyl]-4-[(1-methylethyl)oxy]benzamide
3-Cyano-N-[(1S)-2-{4-[2-(1,1-dimethylethyl)-1-methyl-1H-imidazoi-4-yl]phenyl}-1-({[(ethylamino)carbonyl]amino}methyl)ethyl]-4-[(1-methylethyl)oxy]benzamide
N-[(1S)-2-(Aminosulfonyl)-1-({4-[2-(1,1-dimethylethyl)-1-methyl-1H-imidazol-4-yl]phenyl}methyl)ethyl]-3-chloro-4-[(1-methylethyl)oxy]benzamide
3-Cyano-N-((1S)-2-{4-[2-(1,1-dimethylethyl)-1-methyl-1H-imidazol-4-yl]phenyl}-1-{[(methylsulfonyl)amino]methyl}ethyl)-4-[(1-methylethyl)oxy]benzamide
3-Cyano-N-{(1S)-2-{4-[2-(1,1-dimethylethyl)-1-methyl-1H-imidazol-4-yl]phenyl}-1-[({[(2-hydroxyethyl)amino]carbonyl}amino)methyl]ethyl}-4-[(1-methylethyl)oxy]benzamide
N-[(S)-1-[4-(2-tert-Butyl-1-methyl-1H-imidazol-4-yl)-benzyl]-2-(2-methoxy-ethanoylamino)-ethyl]-3-cyano-4-isopropoxy-benzamide TABLE 1-continued (4R)-4-[({3-Cyano-4-[(1-methylethyl)oxy]phenyl}carbonyl)amino]-5-{4-[2-(1,1-dimethylethyl)-1-methyl-1H-imidazol-4-yl]phenyl}pentanoic acid
3-Cyano-N-{(1S)-2-{4-[2-(1,1-dimethylethyl)-1-methyl-1H-imidazol-4-yl]phenyl}-1-[(2-oxo-1-imidazolidinyl)methyl]ethyl}-4-[(1-methylethyl)oxy]benzamide
N-((1S)-2-Amino-1-{[4-(8-methylimidazo[1,2-a]pyridin-2-yl)phenyl]methyl}ethyl)-3-cyano-4-[(1-methylethyl)oxy]benzamide
N-((1S)-2-(Acetylamino)-1-{[4-(8-methylimidazo[1,2-a]pyridin-2-yl)phenyl]methyl}ethyl)-3-cyano-4-[(1-methylethyl)oxy]benzamide
3-Chloro-N-((1S)-2-{[(2R)-2-hydroxypropanoyl]amino}-1-{[4-(8-methylimidazo[1,2-a]pyridin-2-yl)phenyl]methyl}ethyl)-4-[(1-methylethyl)oxy]benzamide
3-Chloro-N-[(1S)-2-[(N,N-dimethylglycyl)amino]-1-({4-[2-(1-hydroxy-1-methylethyl)-1-methyl-1H-imidazol-4-yl]phenyl}methyl)ethyl]-4-[(1-methylethyl)oxy]benzamide
3-Cyano-N-[(1S)-2-[(N,N-dimethylglycyl)amino]-1-({4-[2-(1-hydroxy-1-methylethyl)-1-methyl-1H-imidazol-4-yl]phenyl}methyl)ethyl]-4-[(1-methylethyl)oxy]benzamide
3-chloro-N-((S)-4-hydroxy-1-(4-(1-methyl-2-((R)-1-(2-oxopyrrolidin-1-yl)ethyl)-1H-imidazol-4-yl)phenyl)butan-2-yl)-4-isopropoxybenzaxnide
3-chloro-N-((S)-4-hydroxy-1-(4-(1-methyl-2-((R)-1-(2-oxopyrrolidin-1-yl)ethyl)-1H-imidazol-4-yl)phenyl)butan-2-yl)-4-(1,1,1-trifluoropropan-2-yloxy)benzamide
3-chloro-N-((S)-4-hydroxy-1-(4-(1-methyl-2-((R)-1-(2-oxooxazolidin-3-yl)ethyl)-1H-imidazol-4-yl)phenyl)butan-2-yl)-4-isopropoxybenzamide
3-chloro-N-((S)-4-hydroxy-1-(4-(1-methyl-2-((R)-1-(2-oxooxazolidin-3-yl)ethyl)-1H-imidazol-4-yl)phenyl)butan-2-yl)-4-(1,1,1-trifluoropropan-2-yloxy)benzamide Particular compounds include those shown in the following tables:

TABLE 2

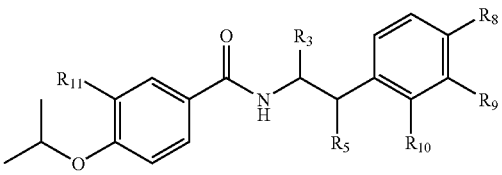

| $R_{11}$ | $R_3$ | $R_8$ | $R_9$ | $R_5$ | $R_{10}$ |
|---|---|---|---|---|---|
| Cl | Phenyl | H | H | 4-isopropoxy-3-chloro-benzoyl-amino- | H |
| Cl | Hydroxymethyl- | 2-tert-Butyl-3H-imidazol-4-yl | H | H | H |
| Cl | Hydroxymethyl- | Benzylamino- | H | H | H |
| Cl | H | 2-tert-Butyl-3H-imidazol-4-yl | H | H | H |
| Cl | Hydroxymethyl- | 4-tert-Butyl-5-methyl-1H-imidazol-2-yl | H | H | H |
| Cl | Hydroxymethyl- | 5-tert-Butyl-4H-[1,2,4]triazol-3-yl | H | H | H |
| Cl | Hydroxymethyl- | 1H-Benzoimidazol-2-yl | H | H | H |
| Cl | Hydroxymethyl- | 4-tert-Butyl-imidazol-1-yl | H | H | H |
| Cl | H | 1H-Benzoimidazol-2-yl | H | H | H |
| Cl | Methoxymethyl- | 2-tert-Butyl-3H-imidazol-4-yl | H | H | H |
| Cl | 3-Hydroxypropyl- | Benzoyloxy- | H | H | H |
| Cl | H | 2-Methylamino-benzylamino | H | H | H |
| Cl | Hydroxymethyl- | Benzoyloxy- | Cl | H | H |
| Cl | Hydroxymethyl- | Benzoyloxy- | Hydroxymethyl- | H | H |
| Cl | Hydroxymethyl- | 4-tert-Butyl-1H-imidazol-2-yl | H | H | H |
| Cl | 2-Hydroxymethyl | Benzyloxy- | H | H | H |
| Cl | H | Benzyloxy- | H | H | H |
| Cl | Hydroxymethyl- | Butoxycarbonyl-amino- | H | H | H |
| Cl | H | OH | H | H | H |
| Cyano | Hydroxymethyl- | Benzyloxy- | Cyano | H | H |
| Cl | Hydroxymethyl- | Benzyloxy- | Cyano | H | H |
| Cl | H | Amino | H | H | H |
| Cyano | 2-Hydroxyethyl- | 4-Cyano-benzyl- | H | H | H |
| Cl | Hydroxymethyl- | 4-tert-Butyl-1-methyl-1H-imidazol-2-yl | H | H | H |
| Cyano | Hydroxymethyl- | Benzyloxy- | Cl | H | H |
| Cl | Hydroxymethyl- | H | H | H | H |
| Cl | H | H | H | OH | H |

TABLE 2-continued

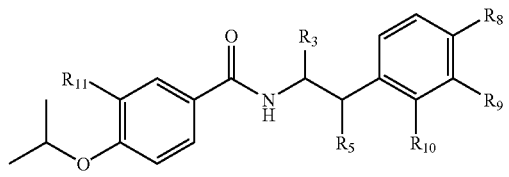

| $R_{11}$ | $R_3$ | $R_8$ | $R_9$ | $R_5$ | $R_{10}$ |
|---|---|---|---|---|---|
| Cl | H | H | Methoxy- | H | H |
| Cl | H | F | H | H | H |
| Cl | Pyridin-4-yl-methyl-amino-methyl- | Phenyl | H | H | H |
| Cl | Cyano | H | H | H | H |
| Cl | Hydroxymethyl- | Benzyloxy | Cl | H | H |
| Cl | Dimethylamino-methyl- | Phenyl | H | H | H |
| Cl | Pyridin-3-yl-methyl-amino-methyl- | Phenyl | H | H | H |
| Cl | Hydroxymethyl- | 2-Methylamino-benzylamino | H | H | H |
| Cl | Hydroxymethyl- | 2-tert-Butyl-2H-tetrazol-5-yl | H | H | H |
| Cl | (1,3-Dioxo-1,3-dihydro-isoindol-2-yl)-methyl- | 4-Isopropyl-4,5-dihydro-oxazol-2-yl | H | H | H |
| Cl | Aminomethyl- | Phenyl | H | H | H |
| Cl | (1,3-Dioxo-1,3-dihydro-isoindol-2-yl-methyl)- | Phenyl | H | H | H |
| Cl | Phenyl | H | Amino | H | H |
| Cl | Hydroxymethyl- | Hydroxy | H | H | H |
| Cl | Aminomethyl- | H | H | H | H |
| Cl | 1H-Tetrazol-5-yl | H | H | H | H |
| Cl | Dimethylamino- | H | H | H | H |
| Cl | H | Phenoxy- | H | H | H |
| Cl | H | Cl | H | H | H |
| Cl | H | H | H | Morpholino | H |
| Cl | H | Methoxy | H | H | H |
| Cl | Hydroxymethyl- | Cl | H | H | H |
| Cl | H | Methylenedioxy- | | H | H |
| Cl | H | H | Cl | H | H |
| Cl | Pyridin-2-ylmethyl-amino-methyl- | Phenyl | H | H | H |
| Cl | Cyano-(pyridin-2-ylmethylamino)-methyl- | Phenyl | H | H | H |
| Cl | 2-Hydroxyethyl-aminomethyl- | Phenyl | H | H | H |
| Cl | Hydroxymethyl- | H | H | OH | H |
| Cl | Aminoethyl-aminomethyl- | Phenyl | H | H | H |
| Cl | Methoxymethyl- | H | H | H | H |
| Cl | Chloromethyl- | Phenyl | H | H | H |
| Cl | Hydroxymethyl- | Phenyl | H | H | H |
| Cl | Hydroxymethyl- | Benzyloxy- | H | H | H |
| Cl | H | Aminosulfonyl- | H | H | H |
| Cl | Hydroxymethyl- | Cyano | H | H | H |
| Cl | Hydroxymethyl- | Carbamyl- | H | H | H |
| Cl | i-propylamino-methyl- | Cyclopropyl-methoxy- | H | H | H |
| Cl | Methylamino-methyl- | Phenyl | H | H | H |
| Cl | Methylamino-methyl- | Hydroxymethyl- | H | H | H |
| Cl | Aminomethyl- | Cyclopropyl-methoxy- | H | H | H |
| Cl | Ethylamino-methyl- | Phenyl- | H | H | H |
| Cl | Benzylamino-methyl- | Phenyl | H | H | H |
| Cl | N-(2-Hydroxypropyl)-aminomethyl- | Phenyl | H | H | H |
| Cl | 2-Hydroxyethyl- | 5-tert-Butyl-4-methyl-1H-imidazol-2-yl | H | H | H |

TABLE 2-continued

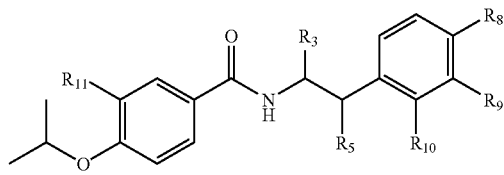

| $R_{11}$ | $R_3$ | $R_8$ | $R_9$ | $R_5$ | $R_{10}$ |
|---|---|---|---|---|---|
| Cl | Hydroxymethyl- | 2-tert-Butyl-1-methyl-1H-imidazol-4-yl | H | H | H |
| Cl | Methyl- | 2-tert-Butyl-1H-imidazol-4-yl | H | H | H |
| Cl | Hydroxymethyl- | 5-Methyl-4-trifluoromethyl-1H-imidazol-2-yl | H | H | H |
| Cl | Hydroxymethyl- | 1-tert-Butyl-2-methyl-1H-imidazol-4-yl | H | H | H |
| Cyano | 2-Hydroxyethyl- | 3-Hydroxy-2-methyl-propoxy- | H | H | H |
| Cl | 2-Aminoethyl- | 4-tert-Butyl-5-methyl-1H-imidazol-2-yl | H | H | H |
| Cyano | 2-Hydroxyethyl- | 5-tert-Butyl-isoxazol-3-yl | H | H | H |
| Cyano | Hydroxymethyl- | 1H-Benzoimidazole-2-yl | H | H | H |
| Cyano | Hydroxymethyl- | 1-Methoxymethyl-1H-benzoimidazole-2-yl | H | H | H |
| Cyano | Hydroxymethyl- | 4-tert-Butyl-5-methyl-1H-imidazol-2-yl | H | H | H |
| Cl | Hydroxymethyl- | Cyclopropylmethoxy- | H | H | H |
| Cl | H | Tert-Butoxycarbonyl- | H | H | H |
| Cl | Aminomethyl- | 2-tert-Butyl-1H-imidazol-4-yl | H | H | H |
| Cyano | Methylamino- | 5-tert-Butyl-4-methyl-1H-imidazol-2-yl | H | H | H |
| Cyano | H | Benzyloxy- | H | H | H |
| Cyano | 2-Hydroxyethyl- | 5-tert-Butyl-4-methyl-1H-imidazol-2-yl | H | H | H |
| Cyano | Hydroxymethyl- | Benzyloxy- | F | H | H |
| Cl | Hydroxymethyl- | Benzyloxy- | Dimethylcarbamoyl- | H | H |
| Cl | Hydroxymethyl- | Benzyloxy- | Carboxy- | H | H |
| Cl | Hydroxymethyl- | Benzyloxy- | F | H | H |
| Cyano | Hydroxymethyl- | Benzyloxy- | Cl | H | H |
| Cyano | Hydroxymethyl- | 2-tert-Butyl-1-methyl-1H-imidazol-4-yl | H | H | H |
| Cyano | Methyl- | 2-tert-Butyl-1H-imidazol-4-yl | H | H | H |
| Cyano | Hydroxymethyl- | 1-tert-Butyl-2-methyl-1H-imidazol-4-yl | H | H | H |
| Cyano | Hydroxymethyl- | Benzyloxy- | Carboxy | H | H |
| Cyano | 2-Hydroxyethyl- | 2-Cyano-benzyloxy- | H | H | H |
| Cyano | 2-Hydroxyethyl- | 3-Cyano-benzyloxy | H | H | H |
| Cyano | 2-Aminoethyl- | 4-tert-Butyl-5-methyl-1H-imidazol-2-yl | H | H | H |
| Cyano | Hydroxymethyl- | Benzyloxy- | Dimethylcarbamoyl- | H | H |
| Cyano | Hydroxymethyl- | Benzyloxy- | Methylcarbamoyl- | H | H |
| Cl | Amino- | Benzyloxy- | H | H | H |
| Cl | 2-(Acetylamino)-ethyl- | 4-tert-Butyl-5-methyl-1H-imidazol-2-yl | H | H | H |
| Cyano | 2-Hydroxyethyl- | Benzyloxy- | H | H | H |
| Cl | Aminomethyl- | 5-tert-Butyl-4-methyl-1H-imidazol-2-yl | H | H | H |
| Cyano | 2-(Methoxycarbonyl-amino)-ethyl- | 4-tert-Butyl-5-methyl-1H-imidazol-2-yl | H | H | H |
| Cyano | Hydroxymethyl- | Benzyloxy- | Acetylamino- | H | H |
| Cl | H | 2-Methylamino-benzoylamino- | H | H | H |
| Cl | H | Benzyloxy- | H | H | H |
| Cyano | 2-Aminoethyl- | 4-tert-Butyl-5-methyl-1H-imidazol-2-yl | H | H | H |
| Cyano | Hydroxymethyl- | Benzyloxy- | Hydroxy | H | H |
| Cl | Aminomethyl- | 1H-Benzoimidazol-2-yl | H | H | H |
| Cl | Hydroxymethyl- | Benzyloxy | H | H | H |
| Cl | Hydroxymethyl- | Hydroxy | H | H | H |
| Cl | H | Amino | H | H | H |
| Cl | H | Tert-Butoxycarbonyl- | H | H | H |
| Cl | H | Hydroxy | H | H | H |
| Cl | H | Nitro | H | H | H |

TABLE 2-continued

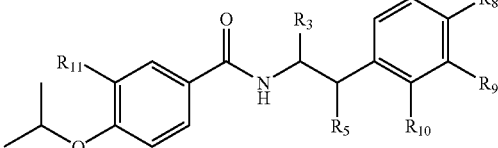

| R11 | R3 | R8 | R9 | R5 | R10 |
|---|---|---|---|---|---|
| Cl | Hydroxymethyl- | 4-tert-Butyl-1H-imidazol-2-yl | H | H | H |
| Cl | Hydroxymethyl- | Benzyoxy- | Dimethylcarbamoyl- | H | H |
| Cl | Hydroxymethyl- | 4-tert-Butyl-1-methyl-1H-imidazol-2-yl | H | H | H |
| Cyano | Hydroxymethyl- | Benzyloxy- | Carboxy- | H | H |
| Cyano | 2-Hydroxyethyl- | 4-Cyanobenzyloxy- | H | H | H |
| Cyano | 2-Hydroxyethyl- | 3-Cyanobenzyloxy- | H | H | H |
| Cyano | Hydroxymethyl- | Benzyloxy- | Cyano | H | H |
| Cl | Amino | Benzyloxy- | H | H | H |
| Cyano | 2-Hydroxymthyl- | 2-Cyanobenzyloxy- | H | H | H |
| Cyano | Hydroxymethyl- | 3-tert-Butyl-3H-imidazol-4-yl | H | H | H |
| Cyano | Hydroxymethyl- | Benzyloxy- | Acetylamino- | H | H |
| Cyano | H | Benzyloxy- | H | H | H |
| Cl | Hydroxymethyl- | Benzyloxy- | F | H | H |
| Cyano | 2-Hydroxyethyl- | 5-tert-Butyl-4-methyl-1H-imidazol-2-yl | H | H | H |
| Cl | Hydroxymethyl- | 2-tert-Butyl-3H-imidazol-4-yl | H | H | H |
| Cl | Hydroxymethyl- | Benzyloxy- | Dimethylaminomethyl- | H | H |
| Cyano | Hydroxymethyl- | Benzyloxy- | Cl | H | H |
| Cyano | Hydroxymethyl- | Benzyloxy- | Fluoro | H | H |
| Cl | Hydroxymethyl- | 4-tert-Butyl-imidazol-1-yl | H | H | H |
| Cl | Methoxymethyl- | 2-tert-Butyl-3H-imidazol-4-yl | H | H | H |
| Cl | H | 1H-Benzoimidazol-2-yl | H | H | H |
| Cl | Aminomethyl- | 5-tert-Butyl-4-methyl-1H-imidazol-2-yl | H | H | H |
| Cl | Hydroxymethyl- | Benzyloxy- | Cyano | H | H |
| Cl | Hydroxymethyl- | Benzyloxy- | Carboxy- | H | H |
| Cyano | Aminomethyl- | 5-tert-Butyl-4-methyl-1H-imidazol-2-yl | H | H | H |
| Cyano | Hydroxymethyl- | Benzyloxy- | Methylcarbamoyl- | H | H |
| Cyano | Hydroxymethyl- | Benzyloxy- | Dimethylcarbamoyl- | H | H |
| Iodo | 2-Hydroxyethyl- | 5-tert-Butyl-4-methyl-1H-imidazol-2-yl | H | H | H |
| Cl | 2-Hydroxyethyl- | 5-tert-Butyl-4-methyl-1H-imidazaol-2-yl | H | H | H |
| Cl | Hydroxymethyl- | 1-tert-Butyl-2-methyl-1H-imidazol-4-yl | H | H | H |
| Cyano | 2-Hydroxyethyl- | Hydroxy- | H | H | H |
| Cyano | 2-Hydroxyethyl- | 3-Hydroxy-2-methyl-propoxy- | H | H | H |
| Cyano | Hydroxymethyl- | 2-tert-Butyl-1-methyl-1H-imidazol-4-yl | H | H | H |
| Cl | Hydroxymethyl- | 5-Methyl-4-trifluoromethyl-1H-imidazol-2-yl | H | H | H |
| Cyano | Hydroxymethyl- | 5-Methyl-4-trifluoromethyl-1H-imidazol-2-yl | H | H | H |
| Cl | Methyl- | 2-tert-Butyl-1H-imidazol-4-yl | H | H | H |
| Cyano | Hydroxymethyl- | 1-tert-Butyl-2-methyl-1H-imidazol-4-yl | H | H | H |
| Cl | H | 2-tert-Butyl-3H-imidazol-4-yl | H | H | H |
| Cl | 2-Aminoethyl- | 4-tert-Butyl-5-methyl-1H-imidazol-2-yl | H | H | H |
| Cl | Aminomethyl- | Cyclopropyl-methoxy- | H | H | H |
| Cl | Isopropylamino-methyl- | Cyclopropyl-methoxy- | H | H | H |
| Cyano | Hydroxymethyl- | 4-tert-Butyl-5-methyl-1H-imidazol-2-yl | H | H | H |
| Cl | Hydroxymethyl- | 2-tert-Butyl-2H-tetrazol-5-yl | H | H | H |
| Cl | Hydroxymethyl- | Benzyloxy- | Hydroxymethyl- | H | H |
| Cl | Aminomethyl- | Carbamoyl- | H | H | H |

TABLE 2-continued

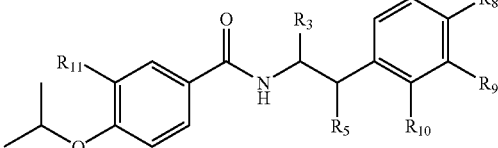

| $R_{11}$ | $R_3$ | $R_8$ | $R_9$ | $R_5$ | $R_{10}$ |
|---|---|---|---|---|---|
| Cl | Hydroxymethyl | Benzylamino- | H | H | H |
| Cl | Hydroxymethyl | 2-Methylamino-benzoylamino- | H | H | H |
| Cl | Aminomethyl- | 4-Isopropyl-4,5-dihydro-oxazol-2-yl | H | H | H |
| Cl | 2-Hydroxyethyl- | Benzyloxy- | H | H | H |
| Cl | Hydroxymethyl | 5-tert-Butyl-4H-[1,2,4]triazol-3-yl | H | H | H |
| Cl | Hydroxymethyl- | 4-tert-Butyl-5-methyl-1H-imidazol-2-yl | H | H | H |
| Cl | Hydroxymethyl- | Tert-Butoxycarbonylamino- | H | H | H |
| Cl | Hydroxymethyl- | Cyclopropylmethoxy- | H | H | H |
| Cl | (1,3-Dioxo-1,3-dihydro-isoindol-2-yl)-methyl- | Carbamoyl- | H | H | H |
| Cl | Hydroxymethyl- | Cyano | H | H | H |
| Cl | 3-Hydroxypropyl- | Benzyloxy- | H | H | H |
| Cyano | Hydroxymethyl- | 1-Methoxymethyl-1H-benzoimidazol-2-yl | H | H | H |
| Cl | (1,3-Dioxo-1,3-dihydro-isoindol-2-yl)-methyl- | 1H-benzoimidazole-2-yl | H | H | H |
| Cyano | Hydroxymethyl- | 2-tert-Butyl-3H-imidazol-4-yl | H | H | H |
| Cyano | 2-Hydroxyethyl- | Hydroxy- | H | H | H |
| Cyano | Hydroxymethyl- | 1H-benzoimidazole-2-yl | H | H | H |
| Cl | Hydroxymethyl- | 2H-Tetrazol-5-yl | H | H | H |
| Cl | Aminomethyl- | 2-tert-Butyl-1H-imidazol-4-yl | H | H | H |
| Cyano | 2-Hydroxyethyl- | Benzyloxy- | H | H | H |
| Cl | Hydroxymethyl- | Benzyloxy | H | H | H |
| Cl | Hydroxymethyl- | 2-tert-Butyl-1-methyl-1H-imidazol-4-yl | H | H | H |
| Cl | 2-Hydroxyethyl- | 5-tert-Butyl-[1,2,4]oxadiazol-3-ylmethoxy- | H | H | H |
| Cl | H | H | H | H | Cl |
| Cl | H | H | H | H | Methoxy- |
| Cl | 4-Methyl-piperazin-1-ylmethyl- | Phenyl | H | H | H |
| Cl | (2-Amino-ethylamino)-cyano-methyl- | Phenyl | H | H | H |
| Cl | (Piperazin-1-yl)-cyano-methyl- | Phenyl | H | H | H |
| Cl | Cyano-(2-hydroxy-2-phenyl-ethylamino)-methyl- | Phenyl | H | H | H |
| Cl | (2-Hydroxy-2-phenyl-ethylamino)-methyl- | Phenyl | H | H | H |
| Cl | Hydroxymethyl- | 4-Isopropyl-4,5-dihydro-oxazol-2-yl | H | H | H |
| Cl | Aminomethyl- | 1H-benzoimidazole-2-yl | H | H | H |
| Cl | 1H-Tetrazol-5-yl | Phenyl | H | H | H |
| Cl | Morpholin-4-ylmethyl- | Phenyl | H | H | H |
| Cl | [2-(2-Oxo-imidazolidin-1-yl)-ethylamino]-methyl- | Phenyl | H | H | H |

TABLE 3

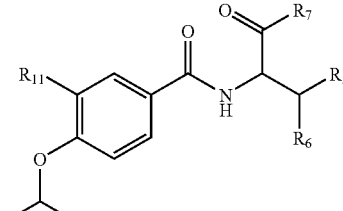

| R11 | R7 | R5 | R6 |
|---|---|---|---|
| Cl | Methylamino- | H | 4-(1H-Benzoimidazol-2-yl)-phenyl- |
| Cl | (Pyridin-4-yl)methyl-amino- | H | Phenyl |
| Cl | Methylamino- | H | Thiophen-3-yl |
| Cl | Amino | H | 4-Hydroxyphenyl- |
| Cl | Methylamino- | H | 3-Chlorophenyl- |
| Cl | Methylamino- | H | 4-(N=N=N)-phenyl- |
| Cl | Methylamino- | H | Benzo[b]thiophen-3-yl |
| Cl | Methylamino | H | Pyridin-2-yl |
| Cl | Methylamino | H | Pyridin-3-yl |
| Cl | Methylamino- | H | Cyclohexyl- |
| Cl | Methylamino- | H | Naphth-1-yl |
| Cl | Isopropylamino- | H | Phenyl |
| Cl | Methylamino- | H | 4-biphenyl- |
| Cl | Methylamino- | H | Thiazol-4-yl |
| Cl | Methylamino- | H | 4-biphenyl- |
| Cl | Amino | H | 4-biphenyl- |
| Cl | Methoxy- | H | 4-biphenyl- |
| Cl | Methylamino- | H | Phenyl |
| Cl | Methylamino | H | 4-Isobutylsulfamoyl-phenyl- |
| Cl | (1-Carbamoyl-2-methyl-propyl)-amino- | H | 4-biphenyl |
| Cl | Carbamoylmethyl-amino- | H | 4-tert-butoxyphenyl- |
| Cl | Methyl-amino- | H | 4-Isopropylsulfamoyl-phenyl- |
| Cl | Amino | H | 4-Cyclohexyloxy-phenyl- |
| Cl | Methyl-amino | H | 4-(1-Oxo-1H-phthalazin-2-yl)-phenyl- |
| Cl | Methyl-amino | H | 4-(2-Oxo-piperidin-1-yl)-phenyl- |
| Cl | Methyl-amino | H | 4-Dibenzylamino-phenyl- |
| Cl | Methylamino- | H | 4-Chlorophenyl |
| Cl | Methylamino- | H | Pyridin-4-yl |
| Cl | Methylamino- | H | 5-Methoxy-1H-indol-3-yl |
| Cl | Amino | H | Phenyl |
| Cl | OH | H | Phenyl |
| Cl | Methylamino- | H | Phenyl |
| Cl | Carbamoylmethyl-amino- | H | 4-Isobutylrylamino-phenyl- |
| Cl | Carbamoylmethyl-amino- | H | 4-(3-Methyl-butyrylamino)-phenyl- |
| Cl | Carbamoylmethyl-amino- | H | 4-(2,2-Dimthyl-propionylamino)-phenyl- |
| Cl | Carbamoylmethyl-amino- | H | 4-[(Morpholine-4-carbonyl)-amino]-phenyl- |
| Cl | Methylamino | H | 4-(Benzylamino)-phenyl- |
| Cl | Carbamoylmethyl-amino- | H | 4-(Cyclohexanecarbonyl-amino)-phenyl- |
| Cl | Methylamino- | H | 4-(Benzyloxy)-phenyl- |
| Cl | Carbamoylmethyl-amino- | H | 4-(4-Isopropyl-4,5-dihydro-oxazol-2-yl)-Phenyl- |
| Cl | Tert-Butoxy- | H | 4-(4-Morpholin-4-yl-[1,2,5]thiadiazol-3-yloxy)-phenyl- |
| Cl | Methoxy- | H | 4-(4-Isopropyl-4,5-dihydro-oxazol-2-yl)-phenyl- |
| Cl | Carbamoylmethyl-amino- | H | 4-(Cyclopropylmethoxy)-phenyl- |
| Cl | Amino- | H | 4-(2-Oxo-3-phenyl-cyclopentyloxy)-phenyl- |
| Cl | Amino- | H | 4-(3-Bromo-[1,2,4]thiadiazol-5-yloxy)-phenyl- |
| Cl | Methylamino | H | 2-Phenyl-1H-benzomidazole-5-yl |
| Cl | Ethoxy- | H | 4-(4-tert-Butyl-5-methyl-1H-imidazol-2-yl)-phenyl- |
| Cyano | Methylamino- | H | 4-Benzyloxy-phenyl- |
| Cl | Methylamino- | H | 4-[(3-Fluorophenyl)-carbonylamino]-cyclohexyl- |
| Cl | Methylamino- | H | 4-(1H-Benzoimidazol-2-yl)-phenyl- |
| Cl | Methylamino | H | 4-Benzyloxy-phenyl- |
| Cl | Methylamino | H | 4-(1H-Benzomidazol-2-yl)-phenyl- |
| Cl | Amino | H | 4-(1-Methoxymethyl-1H-benzoimidazol-2-yl)-phenyl- |
| Cl | Methylamino- | H | 4-(t-Butoxycarbonyl)-aminomethyl-phenyl- |
| Cl | Methylamino- | H | 4-(4-Aminomethyl-benzoylamino)-phenyl- |
| Cl | Methoxy- | H | 4-(Methoxycarbonyl)-phenyl- |
| Cl | Methylamino- | H | 4-(4-Allylcarbamoyl-1H-imidazol-2-yl)-phenyl- |
| Cl | Methylamino | H | 4-[(6-Morpholin-4-yl-pyridine-3-carbonyl)-amino]-phenyl- |
| Cl | Methylamino | H | 4-(4-Chloro-benzoylamino)-phenyl- |
| Cl | Methylamino | H | (3-tert-Butyl-ureido)-cyclohexan-4-yl |

TABLE 3-continued

| R$_{11}$ | R$_7$ | R$_5$ | R$_6$ |
|---|---|---|---|
| Cl | Methylamino | H | 4-(4-Dimethylcarbamoyl-1H-imidazol-2-yl)-phenyl- |
| Cl | Methylamino | H | (1H-Benzoimidazol-2-yl)-cyclohexan-4-yl |
| Cl | Methylamino | H | Carbamoyl-cyclohexan-4-yl |
| Cl | Methylamino | H | 4-(2-Chloro-benzoyl)-amino-phenyl- |
| Cl | Methylamino | H | 4-[4-(Morpholine-4-carbonyl)-1H-imidazol-2-yl]-phenyl- |
| Methoxy | Methylamino | H | 4-Benzyloxy-phenyl- |
| Cl | Methylamino | H | Carbamoyl-cyclohexan-4-yl |
| Cl | Methylamino | H | 4-(3-Chloro-benzoyl)-amino-phenyl- |
| Cl | Methylamino | H | tert-Butoxycarbonyl-amino-cyclohexan-4-yl |
| Cl | Methylamino | H | Benzylcarbamoyl-cyclohexan-4-yl |
| Cl | methylamino | H | 4-[4-(1-Hydroxy-1-methyl-ethyl)-thiazol-2-yl]-phenyl- |
| Cl | Methylamino | H | 4-[4-(2-Carboxy-1,1-dimethyl-ethyl)-1H-imidazol-2-yl]-phenyl |
| Cl | Methylamino- | H | 4-tert-Butoxycarbonylamino-phenyl- |
| Cl | Methylamino | H | tert-Butoxycarbonylamino-cyclohexan-4-yl |
| Cl | Methylamino | H | (4-tert-Butyl-1H-imidazol-2-yl)-cyclohexan-4-yl |
| Cl | Methylamino | H | 4-[4-(2-Ethoxycarbonyl-1,1-dimethyl-ethyl)-1H-imidazol-2-yl]-phenyl- |
| Cl | Methylamino- | H | 4-Aminocyclohexanyl- |
| Cl | Methylamino | H | 4-(Pyridin-3-ylcarbamoyl)-cyclohexanyl- |
| Cl | Methylamino | H | 4-(4-Oxo-1,4-dihydro-quinazolin-2-yl)-phenyl- |
| Cl | Methylamino | H | 4-[4-(1H-Pyrazol-3-ylcarbamoyl)-1H-imidazol-2-yl]-phenyl- |
| Cl | Methylamino | H | 4-(4-Propylcarbamoyl-1H-imidazol-2-yl)-phenyl- |
| Cl | Methylamino | H | 4-(4-Cyclopropylcarbamoyl-1H-imidazol-2-yl)-phenyl- |
| Fluoro | Methylamino | H | 4-Benzyloxyphenyl- |
| Cl | Methylamino | H | 4-(4-Trifluorometjhyl-1H-imidazol-2-yl)-phenyl- |
| Cl | Methylamino | H | 4-(4-Cyclopropylmethyl-carbamoyl-1H-imidazol-2-yl)-phenyl- |
| Cl | Methylamino | H | 4-Benzoimidazol-1-yl-phenyl- |
| Cl | Methylamino | H | 4-[4-(2-Methoxy-ethylcarbamoyl)-1H-imidazol-2-yl]-phenyl- |
| Cl | Methylamino | H | 4-(4-Isopropoxycarbamoyl-1H-imidazol-2-yl)-phenyl- |
| Cl | Methylamino | H | 4-[4-(2-Methoxy-phenyl)-1H-imidazol-2-yl]-phenyl- |
| Cl | Methylamino | H | 4-(Pyridin-4-ylcarbamoyl)-cyclohexanyl- |
| Cl | methylamino | H | 4-[4-(3-Methoxy-propylcarbamoyl)-1H-imidazol-2-yl]-phenyl- |
| Cl | Methylamino | H | 4-(4-Hydroxymethyl-thiazol-2-yl)-phenyl- |
| Cl | Methylamino | H | 4-[4-(4-Fluoro-phenyl)-1H-imidazol-2-yl]-phenyl- |
| Cl | Methylamino | H | 4-(Isopropylcarbonyl-amino)-cyclohexanyl- |
| Cl | Methylamino | H | 4-[4-(Pyridin-4-ylcarbaomyl)-1H-imidazol-2-yl]-phenyl- |
| Cl | Methylamino | H | 4-[4-(3-Methyl-butylcarbamoyl)-1H-imidazol-2-yl]-phenyl- |
| Cl | Methylamino | H | 4-[4-(3-Methoxy-phenylcarbamoyl)-1H-imidazol-2-yl]-phenyl- |
| Cl | Methylamino | H | 4-Isobutoxycarbonylamino-cyclohexanyl- |
| Cl | Methylamino | H | 4-(2-Fluoro-benzoylamino)-cyclohexanyl- |
| Cl | Methylamino | H | 4-[4-(2-Dimethylamino-ethylcarbamoyl)-1H-imidazol-2-yl]-phenyl- |
| Cl | Methylamino | H | 4-(6-Isopropyl-4-oxo-1,4-dihydro-pyrimidin-2-yl)-phenyl- |
| Cl | Methylamino | H | 4-(4-Morpholin-4-yl-benzoylamino)-phenyl- |
| Cl | Amino | H | 4-Hydroxycyclohexanyl- |
| Cl | Methylamino- | H | 4-(4-Ethoxycarbonyl-1H-imidazol-2-yl)-phenyl- |
| Cl | Methylamino | H | 4-(5-Benzyl[1,3,4]thiadiazol-2-yl)-phenyl- |
| Cl | Methylamino | H | 4-Cyanophenyl- |
| Cl | (Pyridin-3-yl-methyl)-amino- | H | Phenyl |
| Cl | Methylamino | H | p-tolyl- |

TABLE 3-continued

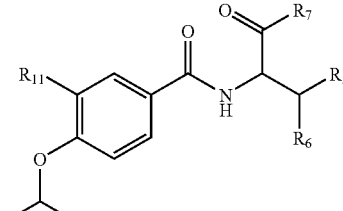

| R₁₁ | R₇ | R₅ | R₆ |
|---|---|---|---|
| Cl | Methylamino | H | 3-Hydroxyphenyl- |
| Cl | Methlamino | H | Thiophen-2-yl- |
| Cl | Methylamino | H | 2-Hydroxyphenyl- |
| Cl | Methylamino | H | 4-Biphenyl- |
| Cl | Methylamino | H | 1-Methyl-1H-imidazol-4-yl |
| Cl | Methylamino | H | 4-(4-Cyanophenyl)-phenyl- |
| Cl | Methylamino | H | 3-Methoxyphenyl- |
| Cl | (Furan-2-yl-methyl)-amino- | H | Phenyl |
| Cl | Methylamino | H | 4-(2-Hydroxyphenyl)-phenyl- |
| Cl | Methylamino | H | 2-Fluorophenyl- |
| Cl | Methylamino | H | 4-tert-butylphenyl- |
| H | Methylamino | H | 4-Biphenyl- |
| Cl | Methylamino | H | Naphth-2-yl |
| Cl | Methylamino | H | 4-Biphenyl- |
| Cl | Indan-2-yl-amino- | H | Phenyl |
| Cl | Methylamino | H | 4-(3-Fluorophenyl)-phenyl |
| Cl | Methylamino | H | 4-(4-Hydroxyphenoxy)-phenyl- |
| Cl | Methylamino | H | 4-(3-Methoxyphenyl)-phenyl- |
| Cl | Pyridin-2-yl-amino- | H | Phenyl |
| Cl | Methylamino | H | 1H-[1,2,4]triazol-1-yl |
| Cl | (2-Methyl-propyl)-amino- | H | Phenyl |
| Cl | Methylamino | H | 4-(2-Fluorophenyl)-phenyl- |
| Cl | Methylamino | H | Isoquinolin-3-yl |
| Cl | Methylamino | H | 3-Fluorophenyl- |
| Cl | Dimethylamino | H | 4-Biphenyl- |
| Cl | Methylamino | H | 4-(Phenylcarbonyl)-phenyl- |
| Cl | Methylamino | H | 4-Fluorophenyl- |
| Cl | OH | H | 4-Biphenyl- |
| Cl | Ethylamino | H | 4-Biphenyl- |
| Cl | Methylamino | H | 4-Hydroxybenzyl- |
| Cl | Methylamino | Methyl | Hydroxy |
| Cl | Methylamino | H | 1H-Indol-2-yl |
| Cl | Amino | H | Isopropyl |
| Cl | Methylamino | H | 1H-Pyrrolo[2,3-b]pyridin-2-yl |
| Cl | 2-(Dimethylamino)-ethyl-amino- | H | Phenyl |
| Cl | Methylamino | H | 2-Chlorophenyl |
| Cl | (3-Hydroxypropyl)-amino | H | Phenyl |
| Cl | Methylamino | Methyl | Phenyl |
| Cl | Amino | H | 4-(Pyrimidin-2-yloxy)-phenyl- |
| Cl | Methylamino | H | Benzyl- |
| Cl | Methylamino | H | 4-Carboxyphenyl- |
| Cl | Methylamino | H | 4-Bromophenyl- |
| Cl | Methylamino | H | Benzyl- |
| Cl | methylamino | H | 4-(tert-butoxycarbonylaminoethyl)-phenyl- |
| Cl | Methylamino | H | 4-Aminophenyl- |
| Cl | Pyridin-2-ylmethyl-amino- | H | Phenyl |
| Cl | Methylamino | H | 4-Aminomethyl-phenyl- |
| Cl | Methylamino | H | 4-Acetylamino-phenyl- |
| Cl | Methylamino | H | 4-(Thiophen-2-yl)-phenyl- |
| Cl | Methylamino | H | 4-(Hydroxy-phenyl-methyl)-phenyl- |
| Cl | Methylamino | H | 2-Bromophenyl- |
| Cl | Amino | H | 4-(5-Methyl-isoxazol-3-ylmethoxy)-phenyl- |
| Cl | Methylamino | H | 4-(4-Methylphenyl)-phenyl- |
| Cl | Methylamino | H | 4-(3-Hydroxyphenyl)-phenyl- |
| Cl | Methylamino | H | 4-Benzyloxy-phenyl- |
| Cl | Methylamino | H | 4-(5-Methyl-[1,2,4]oxadiazol-3-yl)-phenyl |
| Cl | Methylamino | H | 4-Hydroxyphenyl- |
| Cl | Cyclopropylamino- | H | Phenyl |
| Cl | Methoxy | H | 4-Hydroxyphenyl |
| Cl | (Tetrahydro-furan-2-yl-methyl)-amino | H | Phenyl |
| Cl | Methylamino | H | 4-Trifluoromethylphenyl- |
| Cl | Methylamino | H | 4-[(6-Morpholin-4-yl-pyridine-3-carbonyl)-amino]-phenyl- |

TABLE 3-continued

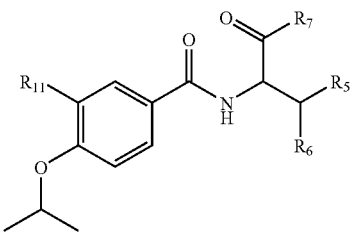

| R₁₁ | R₇ | R₅ | R₆ |
|---|---|---|---|
| Cl | Methylamino | H | 4-(3-Oxo-[1,2,4]triazolo[4,3-a]pyridin-2-yl)-phenyl- |
| Cl | Methylamino | H | 4-[4-(tert-Butoxycarbonylamino-methyl)-benzoylamino]-phenyl- |
| Cl | Methylamino | H | 4-(4-Aminomethyl-benzoylamino)-phenyl- |
| Cl | Methylamino | H | 4-(4-Carboxy-thiazol-2-yl)-benzoic acid |
| Cl | Methylamino | H | 4-(6-Oxo-1,6-dihydro-pyrimidin-2-yl)-phenyl |
| Cl | Methylamino | H | 4-Bromophenyl |
| Cl | Methylamino | H | 4-[4-(2-Methoxy-ethylcarbamoyl)-thiazol-2-yl]-phenyl |
| Cl | Methylamino | H | 4-[4-(Isopropylcarbamoyl)-thiazol-2-yl]-phenyl |
| Cl | Methylamino | H | 4-[4-(Dimethylcarbamoyl)-thiazol-2-yl]-phenyl |
| Cl | Methylamino | H | 4-[4-(4-Methyl-piperazine-1-carbonyl)-thiazol-2-yl]-phenyl |
| Cl | Methylamino | H | 4-[4-(Morpholine-4-carbonyl)-thiazol-2-yl]-phenyl |
| Cl | Methylamino | H | 4-Benzyloxy-3-methoxyphenyl |
| Cl | Methylamino | H | 4-(2-Furan-2-yl-thiazol-4-yl)-phenyl |
| Cl | 1-Carbamoyl-2-methyl-propylamino | H | 4-Biphenyl- |
| Cl | Methylamino | H | 4-(Dibenzylamino)-phenyl- |
| Cl | Methylamino | H | 4-(1-Oxo-1H-phthalazin-2-yl)-phenyl |
| Cl | Methylamino | H | 4-(Benzylamino)-phenyl- |
| Cl | Methylamino | H | 4-(2-Oxo-piperidin-1-yl)-phenyl |
| Cl | Carbamoyl-methylamino- | H | 4-[(Morpholine-4-carbonyl)-amino]-phenyl |
| Cl | Carbamoyl-methylamino- | H | 4-[(Cyclohexylcarbonyl)-amino]-phenyl |
| Cl | Carbamoyl-methylamino- | H | 4-(3-Methyl-butyrylamino)-phenyl |
| Cl | Amino | H | 4-(Piperidin-4-ylcarbamoylmethoxy)-phenyl |
| Cl | Amino | H | (4-(sec-Butylcarbamoyl-methoxy)-phenyl |
| Cl | Methylamino | H | 4-Isobutylsulfamoyl-phenyl |
| Cl | Methylamino | H | 4-Isopropylsulfamoyl-phenyl |
| Cl | Amino | H | 4-(4-Chloro-[1,2,5]thiadiazol-3-yloxy)-phenyl |
| Cl | Carbamoyl-methylamino | H | 4-(tert-Butoxycarbonyl)-phenyl |
| Cl | Carbamoyl-methylamino | H | 4-(4-Morpholin-4-yl-[1,2,5]thiadiazol-3-yloxy)-phenyl |
| Cl | Amino | H | 4-(Cyclohexyloxy)-phenyl |
| Cl | Methylamino | H | 4-(4-Oxo-4H-quinazolin-3-yl)-phenyl |
| Cl | Tert-Butoxy | H | 4-(4-Morpholin-4-yl-[1,2,5]thiadiazol-3-yloxy)-phenyl |
| Cl | Amino | H | 4-(3-Bromo-[1,2,4]thiadiazol-5-yloxy)-phenyl |
| Cl | Amino | H | 4-(2-Oxo-1-phenyl-pyrrolidin-3-yloxy)-phenyl |
| Cl | Methylamino | H | 4-(4-Fluoro-benzoylamino)-phenyl |
| Cl | Methylamino | H | 4-(3-Fluoro-benzoylamino)-phenyl |
| Cl | Carbamoyl-methylamino | H | 4-(1H-Benzoimidazol-2-yl)-phenyl |
| Cl | Hydroxy | H | 4-(1H-Benzoimidazol-2-yl)-phenyl |
| Cl | Methoxy | H | 4-(1H-Benzoimidazol-2-yl)-phenyl |
| Cl | Carbamoyl-methylamino | H | 4-(4-Isopropyl-4,5-dihydro-oxazol-2-yl)-phenyl |
| Cl | Hydroxy | H | 4-(4-Isopropyl-4,5-dihydro-oxazol-2-yl)-phenyl |
| Cl | Methoxy | H | 4-(4-Isopropyl-4,5-dihydro-oxazol-2-yl)-phenyl |
| Cl | Carbamoyl-methylamino | H | 4-(Cyclopropylmethoxy)-phenyl- |
| Cl | Tert-Butoxy | H | 4-(Pyridin-3-ylmethoxy)-phenyl |

TABLE 4

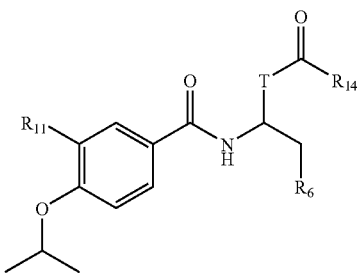

| R₁₁ | T | R₁₄ | R₆ |
|---|---|---|---|
| Cl | —CH₂NH— | Aminomethyl- | 4-(Cyclopropyl-methoxy)-phenyl- |
| Cl | —CH₂— | Methylamino- | 3-Chlorophenyl- |
| Cl | —CH₂NH— | 2-Hydrazinocarbonyl-phenyl- | 4-(4-Isopropyl-4,5-dihydro-oxazol-2-yl)-phenyl |
| Cl | —CH₂NH— | Aminomethyl- | 4-(1H-Benzomidazol-2-yl)-phenyl |
| Cl | —CH₂NH— | Aminomethyl- | 4-(Carbamoyl)-phenyl |
| Cl | —CH₂NH— | Aminomethyl- | 4-(4-Isopropyl-4,5-dihydro-oxazol-2-yl)-phenyl |
| Cl | —CH₂NH— | Aminomethyl- | 4-(cyclopropylmethoxy)-phenyl- |
| Cl | —CH₂O— | Methylamino | 4-(2-tert-Butyl-1H-imidazol-4-yl)-phenyl |
| Cl | —CH₂NH— | Methylamino | 4-(2-tert-Butyl-1H-imidazol-4-yl)-phenyl |
| Cyano | —CH₂NH— | Methylamino | 4-(4-tert-Butyl-5-methyl-1H-imidazol-2-yl)-phenyl |
| Cl | —CH₂O— | Methoxy- | 4-(2-tert-Butyl-1H-imidazol-4-yl)-phenyl |
| Cl | —CH₂NH— | Methyl | 4-Biphenyl |
| Cl | —CH₂NH— | Methyl | Phenyl |
| Cl | —CH₂CH₂— | Methylamino | 4-Benzyloxy-phenyl- |
| Cl | —CH₂— | Methylamino | 2-Chlorophenyl- |
| Cl | —CH₂— | Methylamino | Phenyl |
| Cl | —CH₂— | Methylamino | 4-Biphenyl- |
| Cl | —CH₂CH₂— | Methylamino | 4-Benzyloxy-phenyl- |
| Cl | Absent | Amino | Tert-butoxycarbonyl- |
| Cl | —CH₂NH— | Aminomethyl- | 4-Carbamoyl-phenyl- |
| Cl | —CH₂NH— | Aminomethyl- | 4-(1H-Benzoimidazol-2-yl)-phenyl- |
| Cl | —CH₂O— | 2-(Methyl-amino)-phenyl- | 4-[(2-Methylamino-benzoyl)-amino]-phenyl- |
| Cl | Absent | Amino | Benzyloxycarbonyl- |
| Cl | —CH₂— | OH | 4-Biphenyl- |

TABLE 5

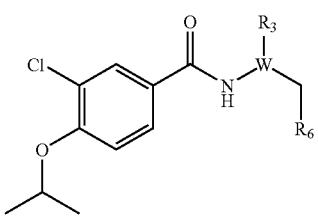

| W | R₃ | R₆ |
|---|---|---|
| CH | Hydrogen | Tert-butoxycarbonyl- |
| CH | 2-(Methylcarbamoyl)-ethyl- | Phenyl |
| CH | 2-(Carboxy)-ethyl- | Phenyl |
| —CH₂CH— | Carboxy | Phenyl |
| N | Methylamino-carbonyl- | 2-Phenyl-3H-benzoimidazol-5-yl |
| C | Hydroxymethyl- | Hydroxy |
| C | Hydrogen | Methylamino-carbonyl- |
| C | Hydrogen | (Dimethylamino)-carbonyl- |
| C | Amino-carbonyl- | (Methylsulfanyl)-methyl- |
| N | Methylamino-carbonyl- | 4-Benzyloxy-3-methyoxy-phenyl- |
| N | Methylamino-carbonyyl- | 3-Benzyloxy-phenyl- |
| N | Methylamino-carbonyl- | 4-(Benzoylamino)-phenyl- |

TABLE 5-continued

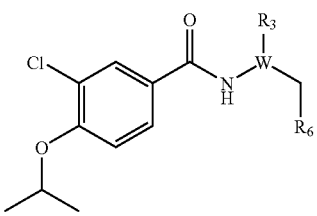

| W | R₃ | R₆ |
|---|---|---|
| N | Mehtylamino-carbonyl- | 4-Bromophenyl- |
| N | Methylamino-carbonyl- | 2-Phenyl-thiazole-4-yl |
| N | Methylamino-carbonyl- | Phenyl |
| N | Methylamino-carbonyl- | 5-Phenyl-[1,2,4]oxadiazol-3-yl |
| N | Methylamino-carbonyl- | 4-(1H-Benzoimidazol-2-yl)-phenyl- |
| CH | Methyl-sulfonylamino-methyl- | 4-Biphenyl- |

TABLE 6

N-[2-(4-Benzyloxy-phenyl)-1-methylcarbamoyl-ethyl]-2,3-dichloro-4-isopropoxy-benzamide
3-(3H-Imidazol-4-yl)-2-(4-trifluoromethyl-benzenesulfonylamino)-propionic acid
N-(2-Biphenyl-4-yl-1-methylcarbamoyl-ethyl)-benzamide
N-(1-Carbamoyl-2-phenyl-ethyl)-3-chloro-4-(2,2,2-trifluoro-1-methyl-ethoxy)-benzamide;
N-(1-Carbamoyl-2-phenyl-ethyl)-4-fluoro-benzamide
4-[2-(4-tert-Butoxy-3-chloro-benzoylamino)-2-methylcarbamoyl-ethyl]-benzoic acid tert-butyl ester
N-[2-(4-Benzyloxy-phenyl)-1-methylcarbamoyl-ethyl]-3-chloro-4-isopropylamino-benzamide
2-Benzyl-3-(3-chloro-4-isopropoxy-benzoylamino)-propionic acid
Naphthalene-2-carboxylic acid [2-(4-benzyloxy-phenyl)-1-methylcarbamoyl-ethyl]-amide
Quinoline-7-carboxylic acid [2-(4-benzyloxy-phenyl)-1-methylcarbamoyl-ethyl]-amide
1-Isopropyl-1H-benzoimidazole-5-carboxylic acid [2-(4-benzyloxy-phenyl)-1-methylcarbamoyl-ethyl]-amide
5-Biphenyl-4-ylmethyl-2-(3-chloro-4-isopropoxy-phenyl)-3,5-dihydro-imidazol-4-one
5-Biphenyl-4-ylmethyl-2-(3-chloro-4-isopropoxy-phenyl)-3H-imidazole-4-carboxylic acid methyl ester
5-Biphenyl-4-ylmethyl-2-(3-chloro-4-isopropoxy-phenyl)-3H-imidazole-4-carboxylic acid methylamide
4-(4-{4-[2-(3-Chloro-4-isopropoxy-phenyl)-4,5-dihydro-oxazol-4-ylmethyl]-phenoxy}-[1,2,5]thiadiazol-3-yl)-morpholine
4-(4-Benzyloxy-benzyl)-2-(3-chloro-4-isopropoxy-phenyl)-4,5-dihydro-oxazole
3-Biphenyl-4-ylmethyl-5-(3-chloro-4-isopropoxy-phenyl)-3H-[1,3,4]oxadiazol-2-one
1-(3-Chloro-4-isopropoxy-benzoyl)-3-(4-iodo-phenyl)-pyrrolidine-2-carboxylic acid methylamide
3-(4-Bromo-phenyl)-1-(3-chloro-4-isopropoxy-benzoyl)-pyrrolidine-2-carboxylic acid methyl ester
3-Biphenyl-4-yl-1-(3-chloro-4-isopropoxy-benzoyl)-pyrrolidine-2-carboxylic acid methylamide
1-(3-Chloro-4-isopropoxy-benzoyl)-3-phenyl-piperidine-2-carboxylic acid methylamide
1-(3-Chloro-4-isopropoxy-benzoyl)-4-phenyl-piperidine-2-carboxylic acid methylamide
1-(3-Chloro-4-isopropoxy-benzoyl)-4-phenyl-piperazine-2-carboxylic acid methylamide
(2-Biphenyl-4-ylmethyl-aziridin-1-yl)-(3-chloro-4-isopropoxy-phenyl)-methanone
3-Biphenyl-4-yl-N-carbamoylmethyl-2-(6-chloro-7-isopropoxy-2,4-dioxo-1,4-dihydro-2H-quinazolin-3-yl)-propionamide
3-Biphenyl-4-yl-N-carbamoylmethyl-2-(6-chloro-7-isopropoxy-4-oxo-4H-quinazolin-3-yl)-propionamide
3-Biphenyl-4-yl-N-carbamoylmethyl-2-(8-chloro-7-isopropoxy-4-oxo-4H-quinazolin-3-yl)-propionamide
3-Chloro-4-isopropoxy-N-(1,2,3,4-tetrahydro-quinolin-3-yl)-benzamide
3-Chloro-4-isopropoxy-N-(4-phenyl-pyrrolidin-3-yl)-benzamide
3-Chloro-4-isopropoxy-N-(5-methyl-3-phenyl-isoxazol-4-ylmethyl)-benzamide
3-Chloro-4-isopropoxy-N-(1-methyl-1H-imidazol-4-ylmethyl)-benzamide
3-Chloro-4-isopropoxy-N-(2-phenoxy-ethyl)-benzamide
N-[2-(4-Benzyl-piperazin-1-yl)-ethyl]-3-chloro-4-isopropoxy-benzamide
N-(1H-Benzoimidazol-2-ylmethyl)-3-chloro-4-isopropoxy-benzamide
3-Chloro-4-isopropoxy-N-(5-methyl-2-phenyl-2H-[1,2,3]triazol-4-ylmethyl)-benzamide In some embodiments, the chemical entity is a prodrug, such as a phosphate ester, of one of the compounds listed in Table 1, 2, 3, 4, 5, or 6. In some embodiments, the chemical entity is chosen from (3S)-4-[4-(2-acetyl-1-methyl-1H-imidazol-4-yl)phenyl]-3-[({3-chloro-4-[(1-methylethyl)oxy]phenyl}carbonyl)amino]butyl dihydrogen phosphate; and (3S)-3-[({3-chloro-4-[(1-methylethyl)oxy]phenyl}carbonyl)amino]-4-[4-(8-methylimidazo[1,2-a]pyridin-2-yl)phenyl]butyl dihydrogen phosphate.

The chemical entities described herein can be prepared by following the procedures set forth, for example, in PCT WO 99/13061, U.S. Pat. No. 6,420,561 and PCT WO 98/56756, each of which is incorporated herein by reference. The starting materials and other reactants are commercially available, e.g., from Aldrich Chemical Company, Milwaukee, Wis., or may be readily prepared by those skilled in the art using commonly employed synthetic methodology.

Unless specified otherwise, the terms "solvent", "inert organic solvent" or "inert solvent" mean a solvent inert under the conditions of the reaction being described in conjunction therewith, including, for example, benzene, toluene, acetonitrile, tetrahydrofuran ("THF"), dimethylformamide ("DMF"), chloroform, methylene chloride (or dichloromethane), diethyl ether, methanol, pyridine and the like. Unless specified to the contrary, the solvents used in the reactions of the present invention are inert organic solvents.

In general, esters of carboxylic acids may be prepared by conventional esterification procedures, for example alkyl esters may be prepared by treating the required carboxylic acid with the appropriate alkanol, generally under acidic conditions. Likewise, amides may be prepared using conventional amidation procedures, for example amides may be prepared by treating an activated carboxylic acid with the appropriate amine. Alternatively, a lower-alkyl ester such as a methyl ester of the acid may be treated with an amine to provide the required amide, optionally in presence of trimethylalluminium following the procedure described in Tetrahedron Lett. 48, 4171-4173, (1977). Carboxyl groups may be protected as alkyl esters, for example methyl esters, which esters may be prepared and removed using conventional procedures, one convenient method for converting carbomethoxy to carboxyl is to use aqueous lithium hydroxide.

The salts and solvates mentioned herein may as required be produced by methods conventional in the art. For example, if an inventive compound is an acid, a desired base addition salt can be prepared by treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; such as ethylenediamine, and cyclic amines, such as cyclohexylamine, piperidine, morpholine, and piperazine; as well as inorganic salts derived from sodium, calcium, potassium, magnesium, manganese, iron, copper, zinc, aluminum, and lithium.

If a compound is a base, a desired acid addition salt may be prepared by any suitable method known in the art, including treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, oxalic acid, glycolic acid, salicylic acid, pyranosidyl acid, such as glucuronic acid or galacturonic acid, alpha-hydroxy acid, such as citric acid or tartaric acid, amino acid, such as aspartic acid or glutamic acid, aromatic acid, such as benzoic acid or cinnamic acid, sulfonic acid, such as p-toluenesulfonic acid, methanesulfonic acid, ethanesulfonic acid, or the like.

Isolation and purification of the chemical entities and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures can, of course, also be used.

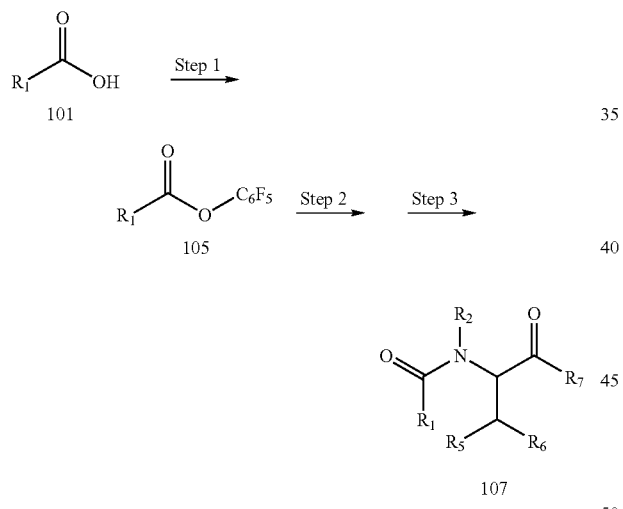

Referring to Reaction Scheme 1, Step 1, to a solution of a compound of Formula 103 in an inert solvent such as DCM are added an excess (such as about 1.2 equivalents) of pentafluorotrifluoroacetate and a base such as triethylamine at about 0° C. The reaction mixture is stirred for about 1 h. The product, a compound of Formula 105, is isolated and purified.

Referring to Reaction Scheme 1, Step 2, to a solution of a compound of Formula 105 in a polar, aprotic solvent are added an excess (such as about 1.2 equivalents) of a compound of formula $R_7(CO)$—$CH(NHR_2)$—$CH(R_5)(R_6)$ and a base such as N,N-diisopropylethylamine. The reaction is monitored by, for example, LC/MS, to yield a compound of Formula 107 wherein $R_7$ is $NH_2$, which is isolated and optionally purified.

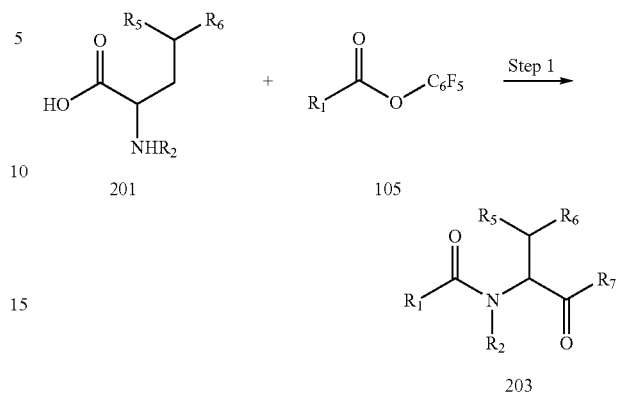

Referring to Reaction Scheme 2, to a solution of a compound of Formula 201 in a polar, aprotic solvent such as DMF are added an excess (such as about 1.2 equivalents) of a compound of Formula 105 and a base such as diisopropylethylamine at room temperature. The reaction mixture is monitored by, for example, LC/MS. After completion, a primary or secondary amine in an inert solvent such as THF and HBTU is added to the reaction solution. The reaction mixture is stirred for about 2 days. The product, a compound of Formula 203 wherein $R_7$ is optionally substituted amino, is isolated and purified.

In certain embodiments, $R_6$ in a compound of Formula 203 is a halide, alkyl halide, or aryl halide. This halide can be converted to various other substituents using a variety of reactions using techniques known in the art and further described in the examples below.

In other embodiments, $R_6$ in a compound of Formula 203 is an alkyl or aryl amine. Again, the amine moiety can be alkylated, acylated, converted to the sulfonamide, and the like using techniques known in the art and further described below.

In yet other embodiments, $R_6$ in a compound of Formula 203 is an alkyl alcohol or an aryl alcohol. The hydroxyl moiety can be converted to the corresponding ether or ester using techniques known in the art.

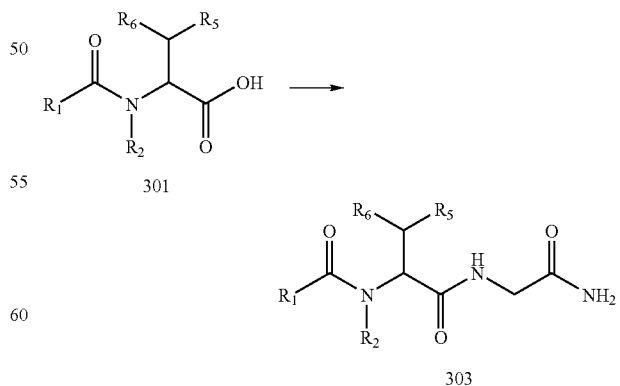

Referring to Reaction Scheme 3, to a solution of a compound of Formula 301 in a polar, aprotic solvent such as DMF added glycinamide hydrochloride, a base such as diisopropylethylamine, and HBTU. The reaction mixture is stirred for about 15 hours. The product, a compound of Formula 303, is isolated and purified.

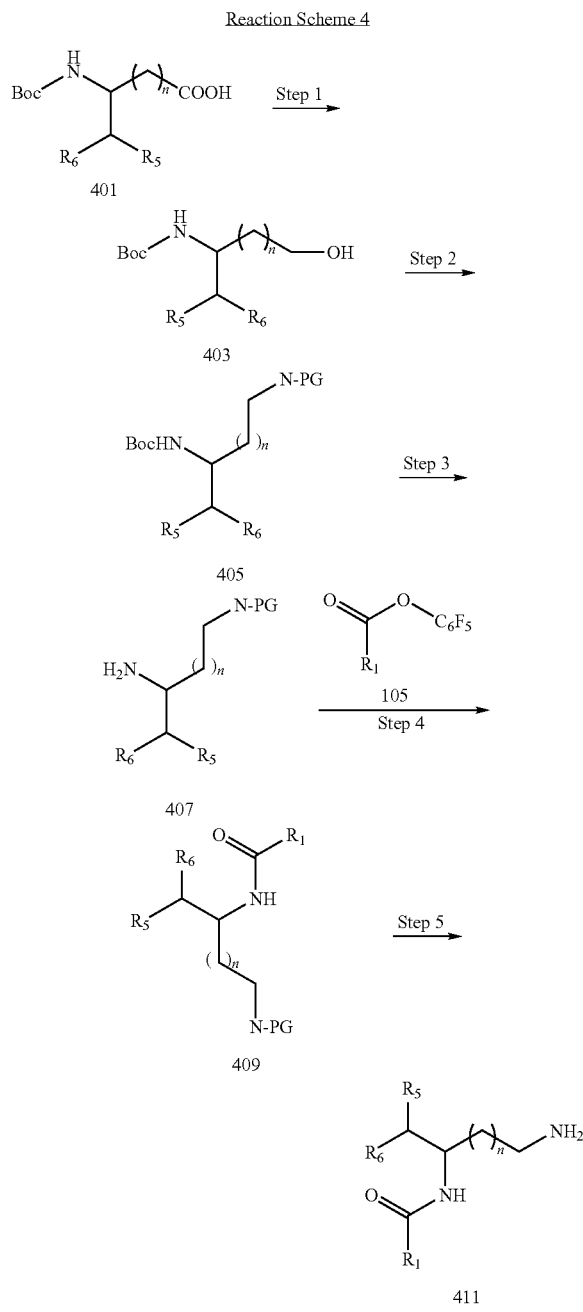

Referring to Reaction Scheme 4, Step 1, to a stirred solution of a compound of Formula 401 wherein n is 0, 1, or 2 in an inert solvent such as THF at about 0° C. is added an excess (such as about 2 equivalents) of LAH (such as a 1.0 M solution in THF). After stirring for about 2 hours, the product, a compound of Formula 403, is isolated and used without further purification.

Referring to Reaction Scheme 4, Step 2, the hydroxyl group is converted to a protected amino group. If the protecting group is phthamide, it can be made as follows. To a stirred solution of a compound of Formula 403 in an inert solvent such as THF are added an excess (such as about 1.1 equivalents) of isoindole-1,3-dione and triphenylphosphine. An excess (such as about 1.1 equivalents) of DEAD is then added dropwise and the reaction is stirred for about 30 min. The product, a compound of Formula 405, is isolated and purified.

Referring to Reaction Scheme 4, Step 3, the Boc protecting group is then removed to form the corresponding free amine. One of skill in the art will appreciate that this should be accomplished in such a manner as to leave the other protected amine intact. For example, to a solution of a compound of Formula 405 in a nonpolar, aprotic solvent such as DCM is added an acid, such as TFA, at room temperature. The reaction mixture is stirred for about 20 min. The product, a compound of Formula 407, is isolated and used without further purification.

Referring to Reaction Scheme 4, Step 4, to a solution of a compound of Formula 407 in an inert solvent such as DMF are added a compound of Formula 105 and a base such as diisopropylethylamine at room temperature. The reaction mixture is stirred overnight. The product, a compound of Formula 409, is isolated and purified.

Referring to Reaction Scheme 4, Step 5, the amine protecting group, PG, is then removed. If the amine protecting group, PG, is a phthalimide, it can be removed is follows. To a solution of a compound of Formula 409 in a polar, protic solvent such as methanol is added an excess (such as about 10 equivalents) of hydrazine hydrate. The reaction mixture is stirred at about 50° C. for about 5 h, and then cooled to room temperature. The product, a compound of Formula 411, is isolated and optionally, purified. Conditions for removing other protecting groups are known to those of skill in the art.

The free amine of a compound of Formula 411 can be acylated, alkylated, reductively alkylated, or sulfonylated using techniques known to those of skill in the art.

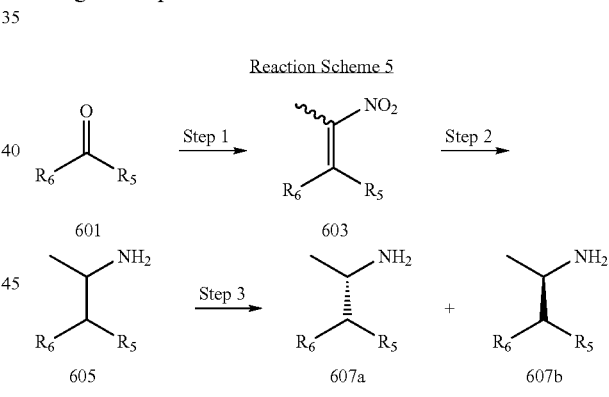

In certain compounds of the invention, particular stereo-configuration may be preferred for the compound of Formula I-XIII. For the sake of brevity in the remaining description of the synthesis of compounds of Formula I-XIII, it should be understood that either single isomer or a mixture of isomers can be employed to give the corresponding product.

Particular stereoisomers can be obtained from mixtures using techniques known in the art. For example, some embodiments, a free amine of Formula 605 is dissolved in an inert organic solvent (such as IPA) and warmed to 60° C. In a separate vessel, a resolving agent (such as dibenzoyl-D-tartaric acid) is dissolved, such as in the same warm solvent, and then quickly added (with agitation) to the warm amine solution. The reaction mixture is left to crystallize by cooling to room temperature over 16 hours under continuing agitation. The desired isomer is isolated and purified in the usual manner.

In some embodiments, an optically active amine of Formula 607 can be prepared from the corresponding aryl aldehyde as shown in Reaction Scheme 5.

Referring to Reaction Scheme 5, Step 1, a solution of a compound of Formula 601 and an excess of ammonium acetate in nitroethane is heated to about reflux for about 8 hours. The product, a compound of Formula 603, is isolated and optionally purified.

Referring to Reaction Scheme 5, Step 2, to an about 0° C. solution of a reducing agent such as sodium borohydride in an inert solvent such as tetrahydrofuran is added an excess (such as about 1.2 equivalents) of borane-tetrahydrofuran complex. The resulting solution is stirred at room temperature for about 15 minutes. A compound of Formula 603 in an inert solvent such as tetrahydrofuran is added dropwise, and the resulting solution is refluxed for about 4 hours. The product, a compound of Formula 605, is isolated and optionally purified.

The amine of Formula 605 can be then resolved using techniques known in the art. For example, a 0° C. solution of the amine of Formula 605 in an inert solvent such as ethyl acetate is saturated with hydrochloric acid (gas). The resulting salt is collected by filtrated and dried in vacuo. L-N-Acetylleucine sodium salt is added slowly to a stirred solution of the aforementioned salt in water. Crystals form overnight and are removed by filtration, washed with a small amount of cold water, and recrystallized from absolute methanol. The crystalline salt of Formula 607a is isolated and optionally purified.

The mother liquors, which were rich in a compound of Formula 607b, are combined, made strongly alkaline, and washed three times with diethyl ether. The combined organic layers are washed with water and dried over sodium sulfate. Hydrochloric acid is passed through the solution until the precipitation of hydrochloride salt is complete. The same procedure as above can be applied with D-N-acetylleucine salt. The crystalline compound of Formula 607b is isolated and optionally purified.

Referring to Reaction Scheme 6, Step 2, to a solution of a compound of Formula 703 in a polar, protic solvent such as ethanol is added an excess (such as about 5 equivalents) of $N_2H_4$—$H_2O$. The reaction mixture is heated to reflux and stirred for about 3 h. Upon cooling, the product, a compound of Formula 705, is isolated and purified.

Referring to Reaction Scheme 6, Step 3, to a solution of a compound of Formula 705 in an inert solvent such as THF is added an excess (such as about 1.1 equivalents) of carbonyldiimidazole. The reaction mixture is heated to reflux and stirred for 1.5 h. Upon cooling, the product, a compound of Formula 707, is isolated and purified.

Referring to Reaction Scheme 6, Step 4, to a solution of a compound of Formula 707 in an inert solvent such as acetonitrile is added an excess (such as about 1.1 equivalents) of $R_5R_6CH$—Z wherein Z is a leaving group and a base such as $K_2CO_3$. The reaction mixture is heated to about 80° C. under microwave irradiation for about 30 min followed by filtration and concentration in vacuo. The product, a compound of Formula 709, is isolated and optionally purified.

Referring to Reaction Scheme 6, Step 5, to a compound of Formula 709 is added an excess of a primary amine in an inert solvent such as THF. The reaction mixture is heated to about 100° C. under microwave irradiation for about 4 h. The product, a compound of Formula 711, is isolated and purified.

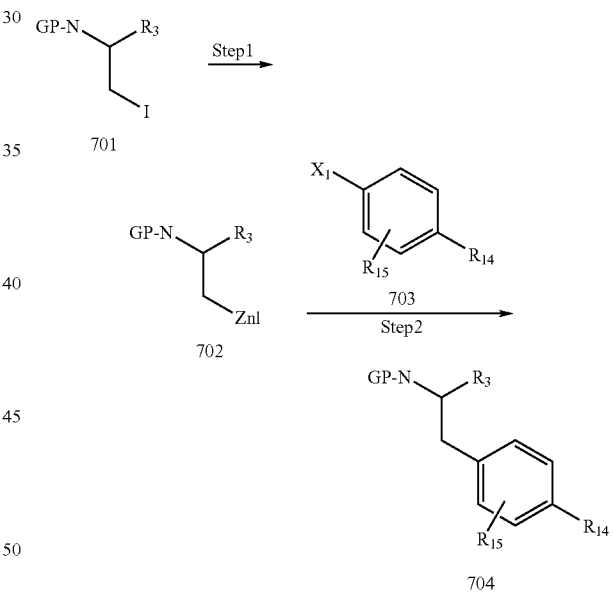

Reaction Scheme 7

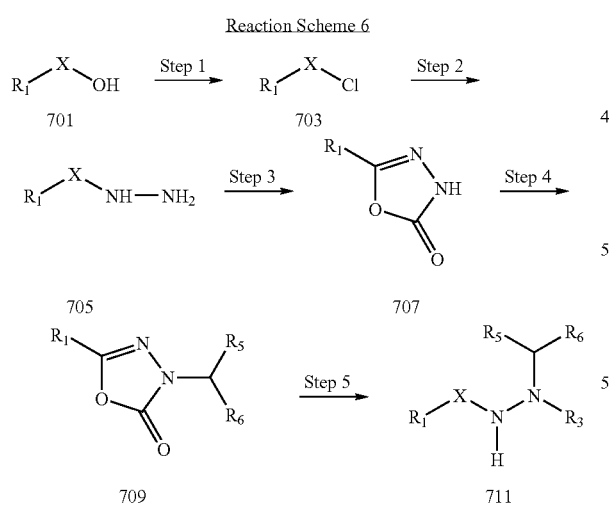

Reaction Scheme 6

Referring to Reaction Scheme 6, Step 1, to a solution of a compound of Formula 701 in a polar protic solvent such as methanol is added an excess (such as about 2 equivalents of $SOCl_2$. After stirring overnight at ambient temperature, the product, a compound of Formula 703, is isolated and used without further purification.

Referring to Reaction Scheme 7, Step 1, to a suspension of zinc powder in a dry degassed polar, aprotic solvent such as DMF was activated using techniques known in the art and further described in the example as follows. 1,2-Dibromoethane was added to the zinc solution under nitrogen. The mixture was heated using a heat gun for about 30 seconds until gas starts to evolve from the solution, indicating the activation of the zinc. The mixture was then allowed to cool to room temperature followed by the addition of TMSCl, and allowed to stir at room temperature for 30 min. A solution of a compound of Formula 701 in a dry degassed polar, aprotic solvent such as DMF was added to the zinc solution, and the reaction mixture was stirred for 1 hour at room temperature. The solution of 702 is used for the next step.

Referring to Reaction Scheme 7, Step 2, to a solution of 702 was added a solution of a compound of Formula 703 (where $X_1$ is Br or I) in a dry degassed polar, aprotic solvent such as DMF, and a palladium catalyst and a ligand such as $Pd_2(dba_3)$, and tri-o-tolylphospine. The reaction mixture was stirred for 3 hour. The product, a compound of Formula 704 is isolated and purified.

Once made, the chemical entities of the invention find use in a variety of applications involving alteration of mitosis. As will be appreciated by those skilled in the art, mitosis may be altered in a variety of ways; that is, one can affect mitosis either by increasing or decreasing the activity of a component in the mitotic pathway. Stated differently, mitosis may be affected (e.g., disrupted) by disturbing equilibrium, either by inhibiting or activating certain components. Similar approaches may be used to alter meiosis.

In some embodiments, the chemical entities of the invention are used to inhibit mitotic spindle formation, thus causing prolonged cell cycle arrest in mitosis. By "inhibit" in this context is meant decreasing or interfering with mitotic spindle formation or causing mitotic spindle dysfunction. By "mitotic spindle formation" herein is meant organization of microtubules into bipolar structures by mitotic kinesins. By "mitotic spindle dysfunction" herein is meant mitotic arrest.

The chemical entities of the invention bind to, and/or inhibit the activity of, one or more mitotic kinesin. In some embodiments, the mitotic kinesin is human, although the chemical entities may be used to bind to or inhibit the activity of mitotic kinesins from other organisms. In this context, "inhibit" means either increasing or decreasing spindle pole separation, causing malformation, i.e., splaying, of mitotic spindle poles, or otherwise causing morphological perturbation of the mitotic spindle. Also included within the definition of a mitotic kinesin for these purposes are variants and/or fragments of such protein and more particularly, the motor domain of such protein.

The chemical entities of the invention are used to treat cellular proliferation diseases. Such disease states which can be treated by the chemical entities provided herein include, but are not limited to, cancer (further discussed below), autoimmune disease, fungal disorders, arthritis, graft rejection, inflammatory bowel disease, cellular proliferation induced after medical procedures, including, but not limited to, surgery, angioplasty, and the like. Treatment includes inhibiting cellular proliferation. It is appreciated that in some cases the cells may not be in an abnormal state and still require treatment. Thus, in some embodiments, the invention herein includes application to cells or individuals afflicted or subject to impending affliction with any one of these disorders or states.

The chemical entities, pharmaceutical formulations and methods provided herein are particularly deemed useful for the treatment of cancer including solid tumors such as skin, breast, brain, cervical carcinomas, testicular carcinomas, etc. More particularly, cancers that can be treated include, but are not limited to:

Cardiac: sarcoma (angiosarcoma, fibrosarcoma, rhabdomyosarcoma, liposarcoma), myxoma, rhabdomyoma, fibroma, lipoma and teratoma;

Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma);

Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver: hepatoma (hepatocellular carcinoma), cholangiocarcinoma, hepatoblastoma, angiosarcoma, hepatocellular adenoma, hemangioma;

Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma);

Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma);

Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma];

Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

As used herein, treatment of cancer includes treatment of cancerous cells, including cells afflicted by any one of the above-identified conditions. Thus, the term "cancerous cell" as provided herein, includes a cell afflicted by any one of the above identified conditions.

Another useful aspect of the invention is a kit having at least one chemical entity described herein and a package insert or other labeling including directions treating a cellular proliferative disease by administering an effective amount of the at least one chemical entity. The chemical entity in the kits of the invention is particularly provided as one or more doses for a course of treatment for a cellular proliferative disease, each dose being a pharmaceutical formulation including a pharmaceutical excipient and at least one chemical entity described herein.

For assay of mitotic kinesin-modulating activity, generally either a mitotic kinesin or at least one chemical entity described herein is non-diffusably bound to an insoluble support having isolated sample receiving areas (e.g., a microtiter plate, an array, etc.). The insoluble support may be made of any composition to which the sample can be bound, is readily separated from soluble material, and is otherwise compatible with the overall method of screening. The surface of such supports may be solid or porous and of any convenient shape. Examples of suitable insoluble supports include microtiter plates, arrays, membranes and beads. These are typically made of glass, plastic (e.g., polystyrene), polysaccharides, nylon or nitrocellulose, Teflon™, etc. Microtiter plates and arrays are especially convenient because a large number of assays can be carried out simultaneously, using small amounts of reagents and samples. The particular manner of binding of the sample is not crucial so long as it is compatible with the reagents and overall methods of the invention, maintains the activity of the sample and is nondifflusable. Particular methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the sample, excess unbound material is removed by washing. The sample receiving areas may then be blocked through incubation with bovine serum albumin (BSA), casein or other innocuous protein or other moiety.

The chemical entities of the invention may be used on their own to inhibit the activity of a mitotic kinesin. In some embodiments, at least one chemical entity of the invention is combined with a mitotic kinesin and the activity of the mitotic kinesin is assayed. Kinesin activity is known in the art and includes one or more of the following: the ability to affect ATP hydrolysis; microtubule binding; gliding and polymerization/depolymerization (effects on microtubule dynamics); binding to other proteins of the spindle; binding to proteins involved in cell-cycle control; serving as a substrate to other enzymes, such as kinases or proteases; and specific kinesin cellular activities such as spindle pole separation.

Methods of performing motility assays are well known to those of skill in the art. (See e.g., Hall, et al. (1996), Biophys. J., 71: 3467-3476, Turner et al., 1996, AnaL Biochem. 242 (1):20-5; Gittes et al., 1996, Biophys. J. 70(1): 418-29; Shirakawa et al., 1995, J. Exp. BioL 198: 1809-15; Winkelmann et al., 1995, Biophys. J. 68: 2444-53; Winkelmann et al., 1995, Biophys. J. 68: 72S.)

Methods known in the art for determining ATPase hydrolysis activity also can be used. Suitably, solution based assays are utilized. U.S. Pat. No. 6,410,254, hereby incorporated by reference in its entirety, describes such assays. Alternatively, conventional methods are used. For example, $P_i$ release from kinesin (and more particularly, the motor domain of a mitotic kinesin) can be quantified. In some embodiments, the ATPase hydrolysis activity assay utilizes 0.3 M PCA (perchloric acid) and malachite green reagent (8.27 mM sodium molybdate II, 0.33 mM malachite green oxalate, and 0.8 mM Triton X-100). To perform the assay, 10 μL of the reaction mixture is quenched in 90 μL of cold 0.3 M PCA. Phosphate standards are used so data can be converted to mM inorganic phosphate released. When all reactions and standards have been quenched in PCA, 100 μL of malachite green reagent is added to the relevant wells in e.g., a microtiter plate. The mixture is developed for 10-15 minutes and the plate is read at an absorbance of 650 nm. If phosphate standards were used, absorbance readings can be converted to mM $P_i$ and plotted over time. Additionally, ATPase assays known in the art include the luciferase assay.

ATPase activity of kinesin motor domains also can be used to monitor the effects of agents and are well known to those skilled in the art. In some embodiments ATPase assays of kinesin are performed in the absence of microtubules. In some embodiments, the ATPase assays are performed in the presence of microtubules. Different types of agents can be detected in the above assays. In some embodiments, the effect of an agent is independent of the concentration of microtubules and ATP. In some embodiments, the effect of the agents on kinesin ATPase can be decreased by increasing the concentrations of ATP, microtubules or both. In some embodiments, the effect of the agent is increased by increasing concentrations of ATP, microtubules or both.

Chemical entities that inhibit the biochemical activity of a mitotic kinesin in vitro may then be screened in vivo. In vivo screening methods include assays of cell cycle distribution, cell viability, or the presence, morphology, activity, distribution, or number of mitotic spindles. Methods for monitoring cell cycle distribution of a cell population, for example, by flow cytometry, are well known to those skilled in the art, as are methods for determining cell viability. See for example, U.S. Pat. No. 6,437,115, hereby incorporated by reference in its entirety. Microscopic methods for monitoring spindle formation and malformation are well known to those of skill in the art (see, e.g., Whitehead and Rattner (1998), J. Cell Sci. 111:2551-61; Galgio et al, (1996) J. Cell Biol., 135:399-414), each incorporated herein by reference in its entirety.

The chemical entities of the invention inhibit one or more mitotic kinesins. One measure of inhibition is $IC_{50}$, defined as the concentration of the chemical entity at which the activity of the mitotic kinesin is decreased by fifty percent relative to a control. In some embodiments, the at least one chemical entity has an $IC_{50}$ of less than about 1 mM. In some embodiments, the at least one chemical entity has an $IC_{50}$ of less than about 100 μM. In some embodiments, the at least one chemical entity has an $IC_{50}$ of less than about 10 μM. In some embodiments, the at least one chemical entity has an $IC_{50}$ of less than about 1 μM. In some embodiments, the at least one chemical entity has an $IC_{50}$ of less than about 100 nM. In some embodiments, the at least one chemical entity has an $IC_{50}$ of less than about 10 nM. Measurement of $IC_{50}$ is done using an ATPase assay such as described herein.

Another measure of inhibition is $K_i$. For chemical entities with $IC_{50}$'s less than 1 μM, the $K_i$ or $K_d$ is defined as the dissociation rate constant for the interaction of the compounds described herein with a mitotic kinesin. In some embodiments, the at least one chemical entity has a $K_i$ of less than about 100 μM. In some embodiments, the at least one chemical entity has a $K_i$ of less than about 10 μM. In some embodiments, the at least one chemical entity has a $K_i$ of less than about 1 μM. In some embodiments, the at least one chemical entity has a $K_i$ of less than about 100 nM. In some embodiments, the at least one chemical entity has a $K_i$ of less than about 10 nM.

The $K_i$ for a chemical entity is determined from the $IC_{50}$ based on three assumptions and the Michaelis-Menten equation. First, only one compound molecule binds to the enzyme and there is no cooperativity. Second, the concentrations of active enzyme and the compound tested are known (i.e., there are no significant amounts of impurities or inactive forms in the preparations). Third, the enzymatic rate of the enzyme-inhibitor complex is zero. The rate (i.e., compound concentration) data are fitted to the equation:

$$V = V_{max}E_0\left[1 - \frac{(E_0 + I_0 + Kd) - \sqrt{(E_0 + I_0 + Kd)^2 - 4E_0I_0}}{2E_0}\right]$$

where V is the observed rate, $V_{max}$ is the rate of the free enzyme, $I_0$ is the inhibitor concentration, $E_0$ is the enzyme concentration, and $K_d$ is the dissociation constant of the enzyme-inhibitor complex.

Another measure of inhibition is $GI_{50}$, defined as the concentration of the chemical entity that results in a decrease in the rate of cell growth by fifty percent. In some embodiments, the at least one chemical entity has a $GI_{50}$ of less than about 1 mM. In some embodiments, the at least one chemical entity has a $GI_{50}$ of less than about 20 µM. In some embodiments, the at least one chemical entity has a $GI_{50}$ of less than about 10 µM. In some embodiments, the at least one chemical entity has a $GI_{50}$ of less than about 1 µM. In some embodiments, the at least one chemical entity has a $GI_{50}$ of less than about 100 nM. In some embodiments, the at least one chemical entity has a $GI_{50}$ of less than about 10 nM. Measurement of $GI_{50}$ is done using a cell proliferation assay such as described herein. Chemical entities of this class were found to inhibit cell proliferation.

In vitro potency of small molecule inhibitors is determined, for example, by assaying human ovarian cancer cells (SKOV3) for viability following a 72-hour exposure to a 9-point dilution series of compound. Cell viability is determined by measuring the absorbance of formazon, a product formed by the bioreduction of MTS/PMS, a commercially available reagent. Each point on the dose-response curve is calculated as a percent of untreated control cells at 72 hours minus background absorption (complete cell kill).

Anti-proliferative compounds that have been successfully applied in the clinic to treatment of cancer (cancer chemo-therapeutics) have $GI_{50}$'s that vary greatly. For example, in A549 cells, paclitaxel $GI_{50}$ is 4 nM, doxorubicin is 63 nM, 5-fluorouracil is 1 µM, and hydroxyurea is 500 µM (data provided by National Cancer Institute, Developmental Therapeutic Program. Therefore, compounds that inhibit cellular proliferation, irrespective of the concentration demonstrating inhibition, have potential clinical usefulness.

To employ the chemical entities of the invention in a method of screening for compounds that bind to a mitotic kinesin, the mitotic kinesin is bound to a support, and a compound of the invention is added to the assay. Alternatively, the chemical entity of the invention is bound to the support and a mitotic kinesin is added. Classes of compounds among which novel binding agents may be sought include specific antibodies, non-natural binding agents identified in screens of chemical libraries, peptide analogs, etc. Of particular interest are screening assays for candidate agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the chemical entities of the invention to a mitotic kinesin may be done in a number of ways. In some embodiments, the chemical entity is labeled, for example, with a fluorescent or radioactive moiety, and binding is determined directly. For example, this may be done by attaching all or a portion of a mitotic kinesin to a solid support, adding a labeled test compound (for example a chemical entity of the invention in which at least one atom has been replaced by a detectable isotope), washing off excess reagent, and determining whether the amount of the label is that present on the solid support.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

In some embodiments, only one of the components is labeled. For example, the kinesin proteins may be labeled at tyrosine positions using $^{125}I$, or with fluorophores. Alternatively, more than one component may be labeled with different labels; using $^{125}I$ for the proteins, for example, and a fluorophor for the antimitotic agents.

The chemical entities of the invention may also be used as competitors to screen for additional drug candidates. "Candidate agent" or "drug candidate" or grammatical equivalents as used herein describe any molecule, e.g., protein, oligopeptide, small organic molecule, polysaccharide, polynucleotide, etc., to be tested for bioactivity. They may be capable of directly or indirectly altering the cellular proliferation phenotype or the expression of a cellular proliferation sequence, including both nucleic acid sequences and protein sequences. In other cases, alteration of cellular proliferation protein binding and/or activity is screened. Screens of this sort may be performed either in the presence or absence of microtubules. In the case where protein binding or activity is screened, particular embodiments exclude molecules already known to bind to that particular protein, for example, polymer structures such as microtubules, and energy sources such as ATP. Particular embodiments of assays herein include candidate agents which do not bind the cellular proliferation protein in its endogenous native state termed herein as "exogenous" agents. In some embodiments, exogenous agents further exclude antibodies to the mitotic kinesin.

Candidate agents can encompass numerous chemical classes, though typically they are small organic compounds having a molecular weight of more than 100 and less than about 2,500 daltons. Candidate agents comprise functional groups necessary for structural interaction with proteins, particularly hydrogen bonding and lipophilic binding, and typically include at least an amine, carbonyl-, hydroxyl-, ether, or carboxyl group, generally at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, and/or amidification to produce structural analogs.

Competitive screening assays may be done by combining a mitotic kinesin and a drug candidate in a first sample. A second sample comprises at least one chemical entity of the present invention, a mitotic kinesin and a drug candidate. This may be performed in either the presence or absence of microtubules. The binding of the drug candidate is determined for both samples, and a change, or difference in binding between the two samples indicates the presence of a drug candidate capable of binding to a mitotic kinesin and potentially inhibiting its activity. That is, if the binding of the drug candidate is different in the second sample relative to the first sample, the drug candidate is capable of binding to a mitotic kinesin.

In some embodiments, the binding of the candidate agent to a mitotic kinesin is determined through the use of competitive binding assays. In some embodiments, the competitor is a binding moiety known to bind to the mitotic kinesin, such as an antibody, peptide, binding partner, ligand, etc. Under certain circumstances, there may be competitive binding as between the candidate agent and the binding moiety, with the binding moiety displacing the candidate agent.

In some embodiments, the candidate agent is labeled. Either the candidate agent, or the competitor, or both, is added first to the mitotic kinesin for a time sufficient to allow binding, if present. Incubations may be performed at any temperature which facilitates optimal activity, typically between 4 and 40° C.

Incubation periods are selected for optimum activity, but may also be optimized to facilitate rapid high throughput screening. Typically between 0.1 and 1 hour will be sufficient. Excess reagent is generally removed or washed away. The second component is then added, and the presence or absence of the labeled component is followed, to indicate binding.

In some embodiments, the competitor is added first, followed by the candidate agent. Displacement of the competitor is an indication the candidate agent is binding to the mitotic kinesin and thus is capable of binding to, and potentially inhibiting, the activity of the mitotic kinesin. In some embodiments, either component can be labeled. Thus, for example, if the competitor is labeled, the presence of label in the wash solution indicates displacement by the agent. Alternatively, if the candidate agent is labeled, the presence of the label on the support indicates displacement.

In some embodiments, the candidate agent is added first, with incubation and washing, followed by the competitor. The absence of binding by the competitor may indicate the candidate agent is bound to the mitotic kinesin with a higher affinity. Thus, if the candidate agent is labeled, the presence of the label on the support, coupled with a lack of competitor binding, may indicate the candidate agent is capable of binding to the mitotic kinesin.

Inhibition is tested by screening for candidate agents capable of inhibiting the activity of a mitotic kinesin comprising the steps of combining a candidate agent with a mitotic kinesin as above, and determining an alteration in the biological activity of the mitotic kinesin. Thus, in some embodiments, the candidate agent should both bind to the mitotic kinesin (although this may not be necessary), and alter its biological or biochemical activity as defined herein. The methods include both in vitro screening methods and in vivo screening of cells for alterations in cell cycle distribution, cell viability, or for the presence, morpohology, activity, distribution, or amount of mitotic spindles, as are generally outlined above.

Alternatively, differential screening may be used to identify drug candidates that bind to the native mitotic kinesin but cannot bind to a modified mitotic kinesin.

Positive controls and negative controls may be used in the assays. Suitably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g., albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

Accordingly, the chemical entities of the invention are administered to cells. By "administered" herein is meant administration of a therapeutically effective dose of at least one chemical entity of the invention to a cell either in cell culture or in a patient. By "therapeutically effective dose" herein is meant a dose that produces the effects for which it is administered. The exact dose will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art. By "cells" herein is meant any cell in which mitosis or meiosis can be altered.

A "patient" for the purposes of the present invention includes both humans and other animals, particularly mammals, and other organisms. Thus the methods are applicable to both human therapy and veterinary applications. In some embodiments, the patient is a mammal, and more particularly, the patient is human.

Chemical entities of the invention having the desired pharmacological activity may be administered, in some embodiments, as a pharmaceutically acceptable composition comprising an pharmaceutical excipient, to a patient, as described herein. Depending upon the manner of introduction, the chemical entities may be formulated in a variety of ways as discussed below. The concentration of the at least one chemical entity in the formulation may vary from about 0.1-100 wt. %.

The agents may be administered alone or in combination with other treatments, i.e., radiation, or other chemotherapeutic agents such as the taxane class of agents that appear to act on microtubule formation or the camptothecin class of topoisomerase I inhibitors. When used, other chemotherapeutic agents may be administered before, concurrently, or after administration of at least one chemical entity of the present invention. In one aspect of the invention, at least one chemical entity of the present invention is co-administered with one or more other chemotherapeutic agents. By "co-administer" it is meant that the at least one chemical entity is administered to a patient such that the at least one chemical entity as well as the co-administered compound may be found in the patient's bloodstream at the same time, regardless when the compounds are actually administered, including simultaneously.

The administration of the chemical entities of the present invention can be done in a variety of ways, including, but not limited to, orally, subcutaneously, intravenously, intranasally, transdermally, intraperitoneally, intramuscularly, intrapulmonary, vaginally, rectally, or intraocularly. In some instances, for example, in the treatment of wounds and inflammation, the compound or composition may be directly applied as a solution or spray.

Pharmaceutical dosage forms include at least one chemical entity described herein and one or more pharmaceutical excipients. As is known in the art, pharmaceutical excipients are secondary ingredients which function to enable or enhance the delivery of a drug or medicine in a variety of dosage forms (e.g.: oral forms such as tablets, capsules, and liquids; topical forms such as dermal, opthalmic, and otic forms; suppositories; injectables; respiratory forms and the like). Pharmaceutical excipients include inert or inactive ingredients, synergists or chemicals that substantively contribute to the medicinal effects of the active ingredient. For example, pharmaceutical excipients may function to improve flow characteristics, product uniformity, stability, taste, or appearance, to ease handling and administration of dose, for convenience of use, or to control bioavailability. While pharmaceutical excipients are commonly described as being inert or inactive, it is appreciated in the art that there is a relationship between the properties of the pharmaceutical excipients and the dosage forms containing them.

Pharmaceutical excipients suitable for use as carriers or diluents are well known in the art, and may be used in a variety of formulations. See, e.g., Remington's Pharmaceutical Sciences, 18th Edition, A. R. Gennaro, Editor, Mack Publishing Company (1990); Remington: The Science and Practice of Pharmacy, 20th Edition, A. R. Gennaro, Editor, Lippincott Williams & Wilkins (2000); Handbook of Pharmaceutical Excipients, 3rd Edition, A. H. Kibbe, Editor, American Pharmaceutical Association, and Pharmaceutical Press (2000); and Handbook of Pharmaceutical Additives, compiled by Michael and Irene Ash, Gower (1995), each of which is incorporated herein by reference for all purposes.

Oral solid dosage forms such as tablets will typically comprise one or more pharmaceutical excipients, which may for example help impart satisfactory processing and compression characteristics, or provide additional desirable physical characteristics to the tablet. Such pharmaceutical excipients may be selected from diluents, binders, glidants, lubricants, disintegrants, colors, flavors, sweetening agents, polymers, waxes or other solubility-retarding materials.

Compositions for intravenous administration will generally comprise intravenous fluids, i.e., sterile solutions of simple chemicals such as sugars, amino acids or electrolytes, which can be easily carried by the circulatory system and assimilated. Such fluids are prepared with water for injection USP.

Dosage forms for parenteral administration will generally comprise fluids, particularly intravenous fluids, i.e., sterile solutions of simple chemicals such as sugars, amino acids or electrolytes, which can be easily carried by the circulatory system and assimilated. Such fluids are typically prepared with water for injection USP. Fluids used commonly for intravenous (IV) use are disclosed in Remington, The Science and Practice of Pharmacy [full citation previously provided], and include:

alcohol, e.g., 5% alcohol (e.g., in dextrose and water ("D/W") or D/W in normal saline solution ("NSS"), including in 5% dextrose and water ("D5/W"), or D5/W in NSS);

synthetic amino acid such as Aminosyn, FreAmine, Travasol, e.g., 3.5 or 7; 8.5; 3.5, 5.5 or 8.5% respectively;

ammonium chloride e.g., 2.14%;

dextran 40, in NSS e.g., 10% or in D5/W e.g., 10%;

dextran 70, in NSS e.g., 6% or in D5/W e.g., 6%;

dextrose (glucose, D5/W) e.g., 2.5-50%;

dextrose and sodium chloride e.g., 5-20% dextrose and 0.22-0.9% NaCl;

lactated Ringer's (Hartmann's) e.g., NaCl 0.6%, KCl 0.03%, $CaCl_2$ 0.02%;

lactate 0.3%;

mannitol e.g., 5%, optionally in combination with dextrose e.g., 10% or NaCl e.g., 15 or 20%;

multiple electrolyte solutions with varying combinations of electrolytes, dextrose, fructose, invert sugar Ringer's e.g., NaCl 0.86%, KCl 0.03%, $CaCl_2$ 0.033%;

sodium bicarbonate e.g., 5%;

sodium chloride e.g., 0.45, 0.9, 3, or 5%;

sodium lactate e.g., ⅙ M; and sterile water for injection

The pH of such IV fluids may vary, and will typically be from 3.5 to 8 as known in the art.

The chemical entities of the invention can be administered alone or in combination with other treatments, i.e., radiation, or other therapeutic agents, such as the taxane class of agents that appear to act on microtubule formation or the camptothecin class of topoisomerase I inhibitors. When so-used, other therapeutic agents can be administered before, concurrently (whether in separate dosage forms or in a combined dosage form), or after administration of an active agent of the present invention.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All publications, including but not limited to patents and patent applications, cited in this specification are herein incorporated by reference as if each individual publication were specifically and individually indicated to be incorporated by reference herein as though fully set forth.

EXAMPLES

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

Example 1

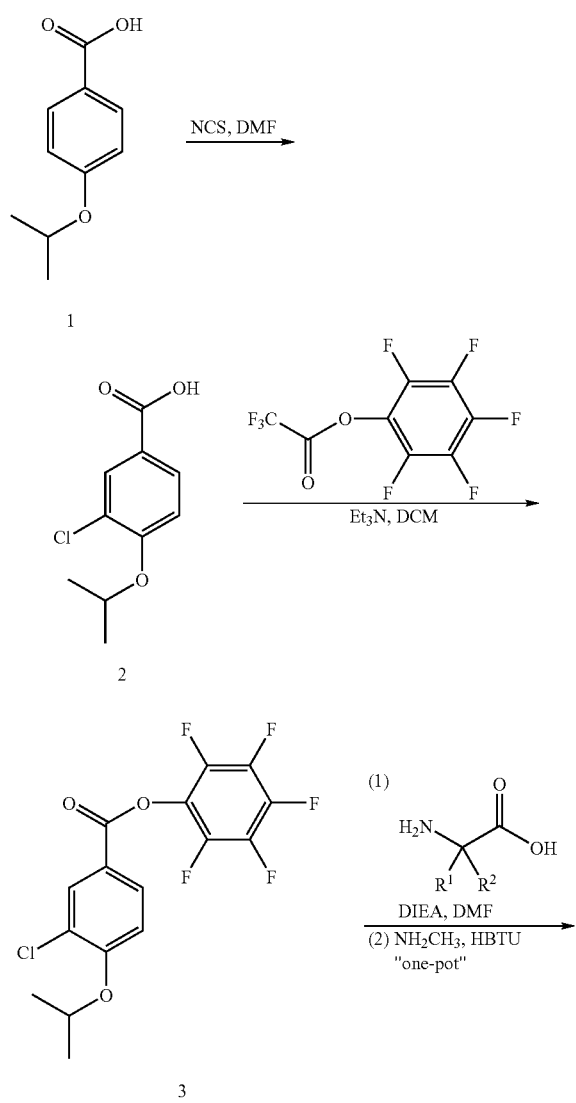

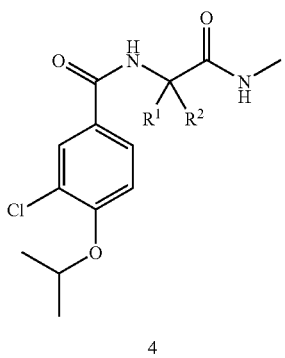

To a solution of 4-isopropoxylbenzoic acid 1 (25 g, 140 mmol) in DMF (150 mL) was added NCS (24 g, 182 mmol). The reaction mixture was stirred overnight. H$_2$O (500 mL) was added to the reaction mixture. The precipitate was collected and washed with water, and dried in vacuo to give 2 (26.4 g, 88%) as a white solid, which was used in the next step without further purification. LRMS (M+H$^+$) m/z 213.0.

To a solution of 2 (20 g, 93 mmol) in DCM were added pentafluorotrifluoroacetate (20 mL, 112 mmol) and triethylamine (17 mL, 112 mmol) at 0° C. The reaction mixture was stirred for 1 h. The solution was concentrated and the mixture purified by flash column chromatography (100% DCM) to give 3 (35 g, quant.) as a white solid.

To a solution of 3 in DMF (0.2 M) were added amino acid (1.2 equiv.) and N,N-diisopropylethylamine (3 equiv.). The reaction was monitored by LC/MS. After completion, methylamine (2 M in THF, 1.5 equiv.) and HBTU (1.5 equiv.) were added to the reaction solution. The reaction mixture was stirred for 4 h. The product was purified by either HPLC or flash column chromatography to give 4.

Example 2

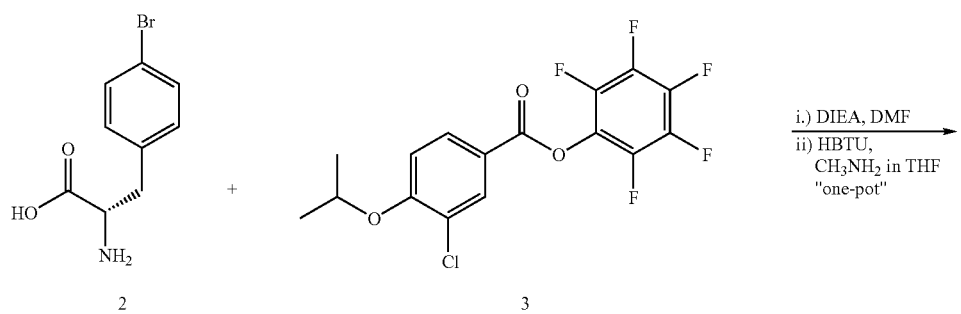

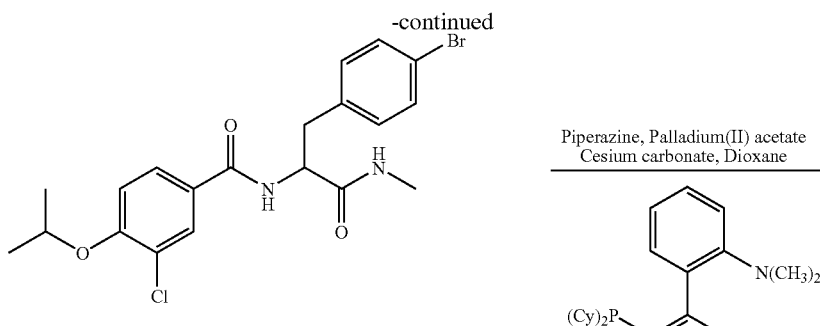

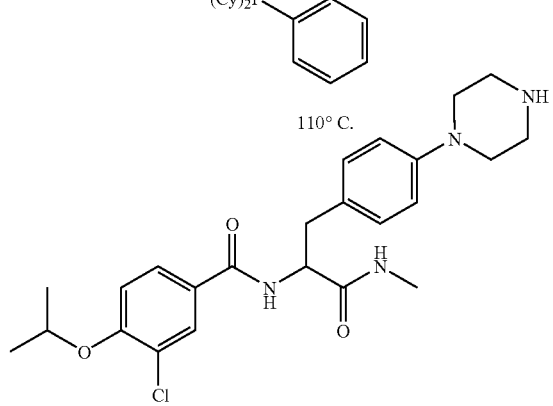

1a

To a solution of H-Phe(4-Br)—OH (2, 2.5 g, 10 mmol) in DMF (20 mL) were added 3 (4.7 g; 12 mmol) and diisopropylethylamine (5.4 mL, 30 mmol) at room temperature. The reaction mixture was monitored by LC/MS. After completion, methylamine (2M in THF, 7.7 mL, 15 mmol) and HBTU (5.8 g, 15 mmol) were added to the reaction solution. The reaction mixture was stirred for 2 days. The mixture was filtered, and the filtrate was purified on RP-HPLC using a mixture of acetonitrile and H$_2$O to give 4 (2.3 g, 50%). LRMS (M+H$^+$) m/z 455.0.

To a suspension of 4 (71 mg, 0.16 mmol) in dioxane (1 mL) were added piperazine (16 mg, 0.19 mmol), palladium (II) acetate (4 mg, 0.016 mmol), dicyclohexylphosphino-2'-(N, N'-dimethylamino)-biphenyl (6 mg, 0.016 mmol), and cesium carbonate (104 mg, 0.32 mmol). The resulting mixture was stirred for 36 hours at 110° C. The reaction mixture was diluted with EtOAc. The organic layer was washed with saturated NaHCO$_3$ (20 mL) and brine, dried over Na$_2$SO$_4$, and concentrated. The residue was purified on RP-HPLC using a mixture of acetonitrile and H$_2$O to give 1a (6 mg, 8%). LRMS (M+H$^+$) m/z 459.2.

Example 3

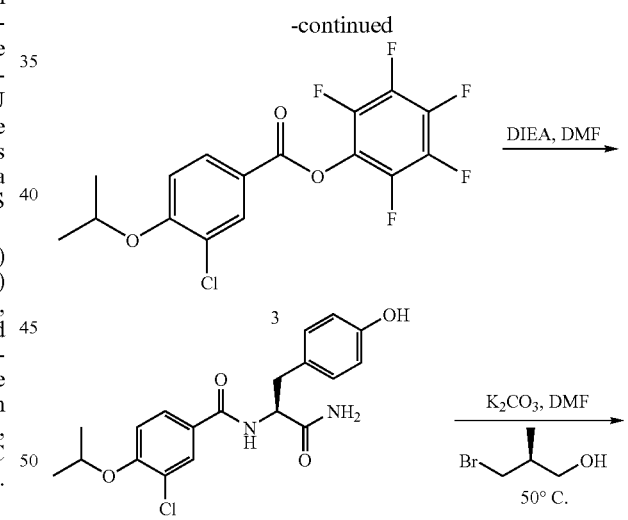

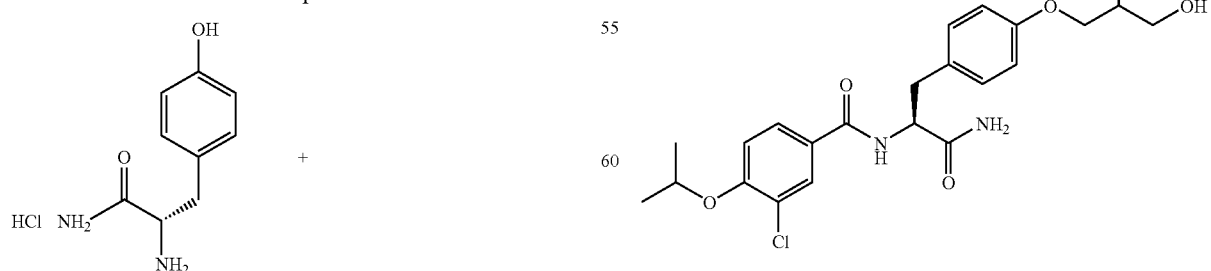

To a solution of H-Tyr-NH₂ HCl (2, 830 mg, 3.8 mmol) in DMF (5 mL) were added 3 (1.8 g, 4.5 mmol) and diisopropylethylamine (3.4 mL, 19 mmol) at room temperature. The reaction was stirred for 20 hours and filtered after adding water. The white precipitate was recrystallized in DCM and methanol to give 4 as white crystals (1.120 g, 78%). LRMS (M+H⁺) m/z 377.1.

To a solution of 4 (50 mg, 0.13 mmol) in DMF (1 mL) were added (s)-(+)-3-bromo-2-methyl-1-propanol (0.083 mL, 0.8 mmol) and potassium carbonate (110 mg, 0.8 mmol). The resulting mixture was stirred for 15 hours at 50° C. The mixture was filtered, and the filtrate was purified on RP-HPLC using a mixture of acetonitrile and H₂O to give 1b (30 mg, 51%). LRMS (M+H⁺) m/z 449.1.

Example 4

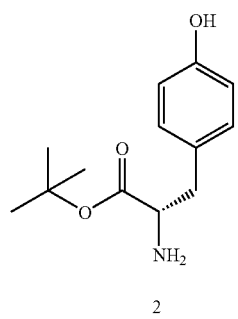

2

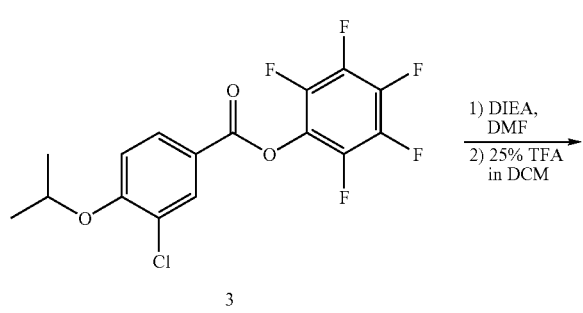

3

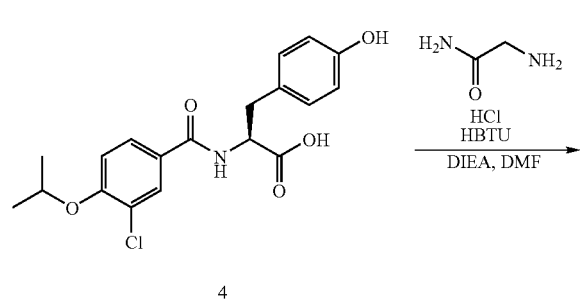

4

-continued

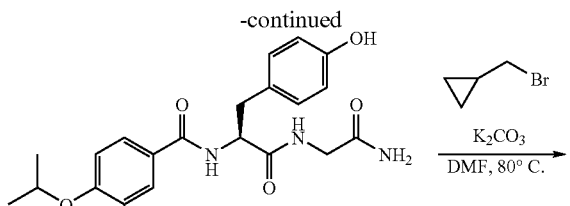

5

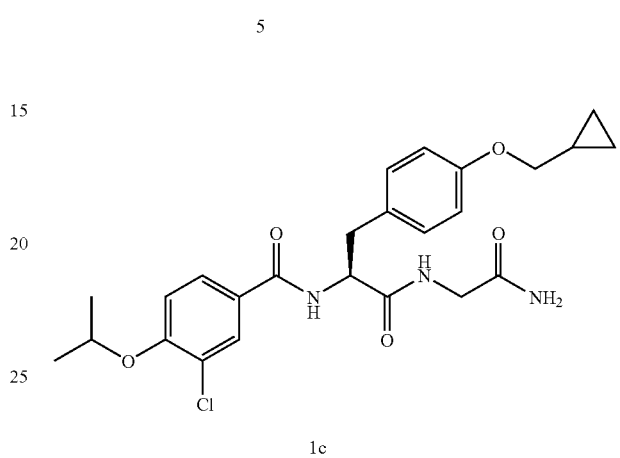

1c

To a solution of H-Tyr-OBut (2, 1.9 g, 8 mmol) in DMF (50 mL) were added 3 (2.4 g, 6.2 mmol) and diisopropylethylamine (3.3 mL, 19 mmol) at room temperature. The reaction was stirred for 2 hours. The resulting solution was diluted with EtOAc (200 mL) and washed with saturated NaHCO₃ (50 mL). The organic layer was separated, washed with brine, dried over Na₂SO₄, and concentrated to give a yellow solid. To a solution of the yellow solid in dichloromethane (10 mL) was added trifluoroacetic acid (30 mL). The mixture was stirred at room temperature for 12 hours and then concentrated under reduced pressure. The residue was dried in vacuo to give 4 (3.1 g), which was used in the next step without further purification. LRMS (M−H⁺) m/z 376.1.

To a solution of 4 (3.1 g, 8 mmol) in DMF (25 mL) was added glycinamide hydrochloride (1.1 g, 9.6 mmol), diisopropylethylamine (7 mL, 40 mmol), and HBTU (3.6 g, 9.6 mmol). The reaction mixture was stirred for 15 hours, after which solution was diluted with ethyl acetate and washed with saturated NaHCO₃. The organic layer was separated, washed with brine, dried over Na₂SO₄, and concentrated. The resulting crude was purified on RP-HPLC using a mixture of acetonitrile and H₂O to give 5 (38 mg, 35%). LRMS (M+H⁺) m/z 434.1.

To a solution of 5 (100 mg, 0.23 mmol) in DMF (1 mL) were added cyclopropylmethyl bromide (0.18 mL, 1.84 mmol) and potassium carbonate (317 mg; 2.3 mmol). The resulting mixture was stirred for 10 hours at 80° C. The mixture was filtered, and the filtrate was purified on RP-HPLC using a mixture of acetonitrile and H₂O to give 1c (36 mg, 34%). LRMS (M+H⁺) m/z 488.1.

Example 5

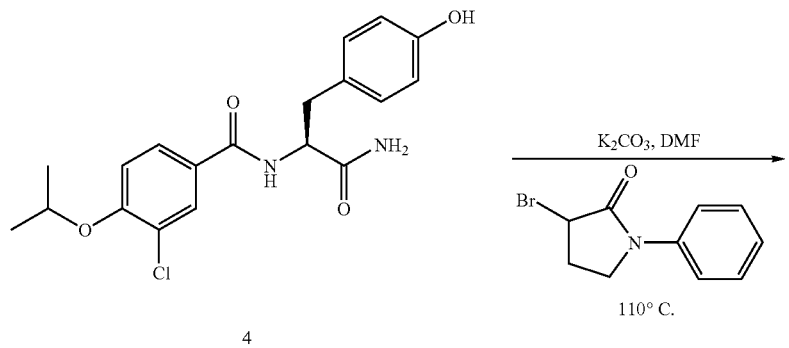

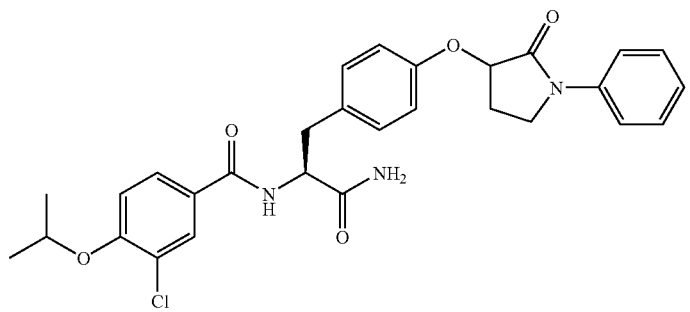

To a solution of 4 (80 mg, 0.2 mmol) in DMF (1 mL) were added (±)-3-bromo-1-phenyl-2-pyrrolidinone (250 mg, 1 mmol) and potassium carbonate (235 mg, 1.7 mmol). The resulting mixture was stirred for 10 hours at 110° C. The mixture was filtered, and the filtrate was purified on RP-HPLC using a mixture of acetonitrile and H$_2$O to give 5 (38 mg, 35%). LRMS (M+H$^+$) m/z 536.1.

Example 6

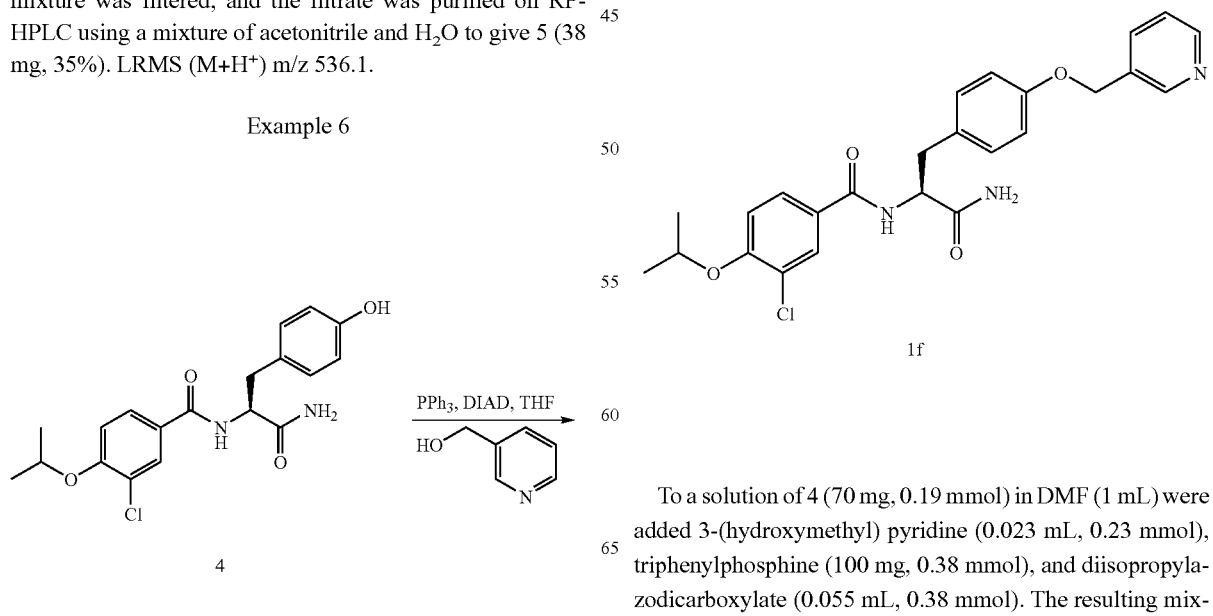

To a solution of 4 (70 mg, 0.19 mmol) in DMF (1 mL) were added 3-(hydroxymethyl) pyridine (0.023 mL, 0.23 mmol), triphenylphosphine (100 mg, 0.38 mmol), and diisopropylazodicarboxylate (0.055 mL, 0.38 mmol). The resulting mixture was stirred for 20 hours at room temperature. The reaction solution was concentrated and purified via flash column chromatography using a mixture of ethyl acetate and hexane as eluent to give 1f (22 mg, 25%). LRMS (M+H⁺) m/z 468.2.

Example 7

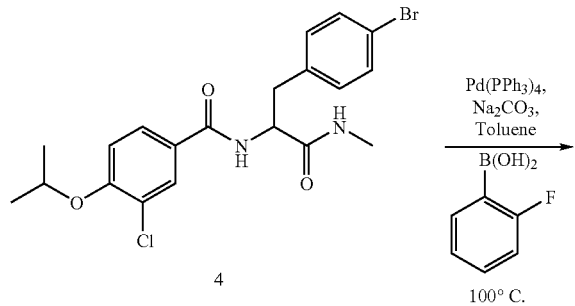

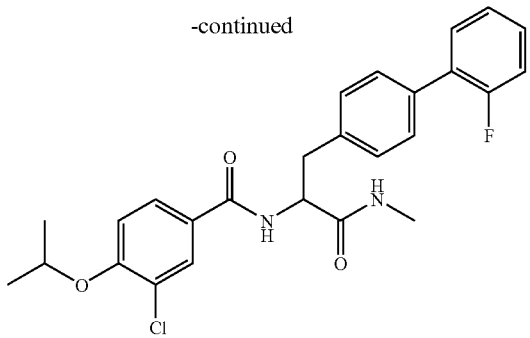

1g

To a solution of 4 (50 mg, 0.12 mmol) in toluene (2 mL) was added 2-(fluorophenyl)boronic acid (20 mg, 0.14 mmol), tetrakis(triphenylphosphine)palladium(0) (42 mg, 0.04 mmol), and 2M sodium carbonate (0.18 mL, 0.36 mmol). The reaction mixture was stirred for 90 min at 100° C. The resulting solution was purified on RP-HPLC using a mixture of acetonitrile and H₂O to give 5 (22 mg, 40%). LRMS (M+H⁺) m/z 469.2.

Example 8

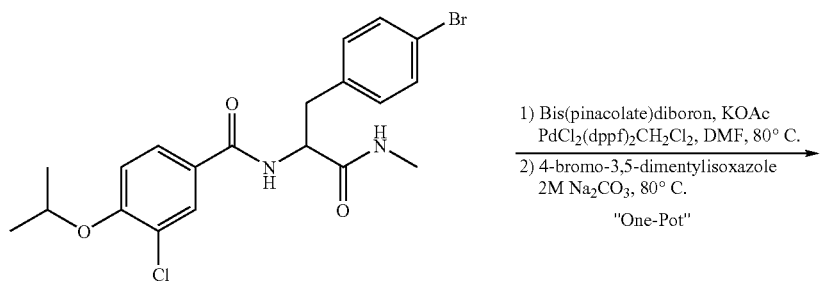

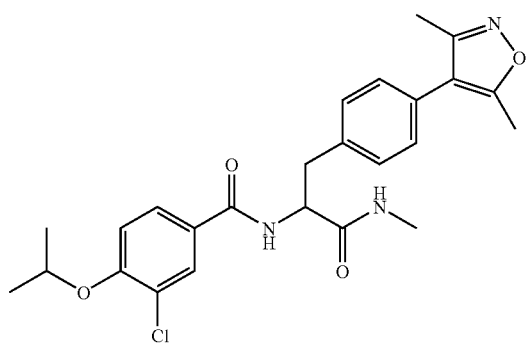

1h

To a solution of 4 (45 mg, 0.1 mmol) in DMF (1 mL) were added bis(pinacolate) diboron (30 mg, 0.12 mmol), 1,1'-bis(diphenylphosphino)ferrocene-palladium(II) dichloride dichloromethane complex (17 mg, 0.02 mmol), and potassium acetate (39 mg, 0.4 mmol). The reaction mixture was stirred for 1 hour at 80° C. The resulting mixture was added 4-bromo-3,5-dimethylisoxazole (35 mg, 0.2 mmol) and 2M sodium carbonate (0.4 mL, 0.8 mmol). The mixture was stirred at 80° C. for 90 min. The resulting residue was filtered, and the filtrate was purified on RP-HPLC using a mixture of acetonitrile and H$_2$O to give 1 h (23 mg, 49%). LRMS (M+H$^+$) m/z 470.1.

Example 9

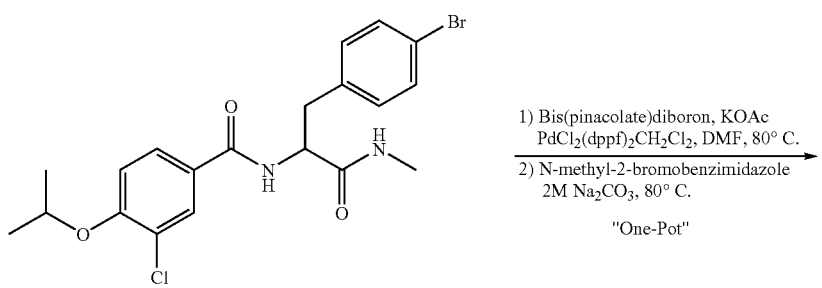

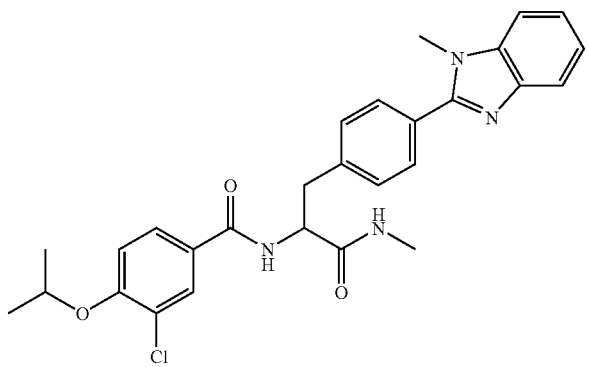

To a solution of 4 (62 mg, 0.14 mmol) in DMF (1 mL) was added bis(pinacolate)diboron (42 mg, 0.16 mmol), 1,1'-bis(diphenylphosphino)ferrocene-palladium(II) dichloride dichloromethane complex (34 mg, 0.04 mmol), and potassium acetate (54 mg, 0.55 mmol). The reaction mixture was stirred for 1 hour at 80° C. The resulting mixture was added N-methyl-2-bromobenzimidazole (58 mg, 0.27 mmol) and 2M sodium carbonate (0.54 mL, 1.08 mmol). The mixture was stirred at 80° C. for 60 min. The resulting solution was diluted with ethylacetate (20 mL), and washed with saturated NaHCO$_3$ (20 mL). The organic layer was separated, washed with brine, dried over Na$_2$SO$_4$, and concentrated. The resulting residue was purified on RP-HPLC using a mixture of acetonitrile and H$_2$O to give 1i (44 mg, 64%). LRMS (M+H$^+$) m/z 505.1.

Example 10

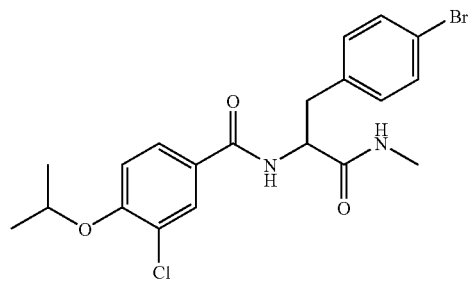

4

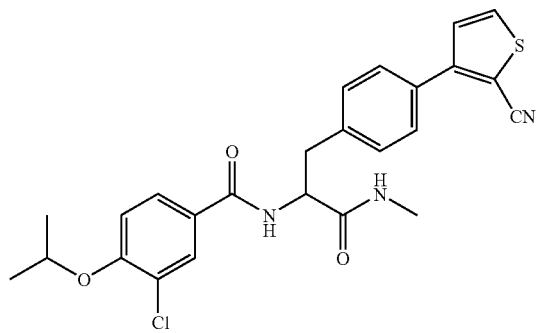

1j

To a solution of 4 (50 mg, 0.13 mmol) in DMF (1 mL) were added bis(pinacolate) diboron (34 mg, 0.13 mmol), 1,1'-bis(diphenylphosphino)ferrocene-palladium(II) dichloride dichloromethane complex (27 mg, 0.03 mmol), and potassium acetate (43 mg, 0.44 mmol). The reaction mixture was stirred for 1 hour at 80° C. To the resulting mixture was added 3-bromothiophene-2-carbonitrile (41 mg, 0.22 mmol) and 2M sodium carbonate (0.44 mL, 0.88 mmol). The mixture was stirred at 80° C. for 90 min. The resulting residue was filtered, and the filtrate was purified on RP-HPLC using a mixture of acetonitrile and H$_2$O to give 5 (20 mg, 37%). LRMS (M+H$^+$) m/z 482.1.

Example 11

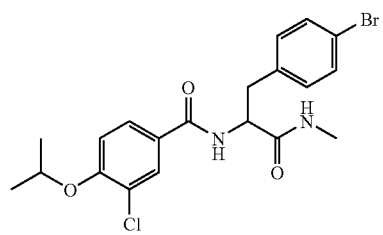

4

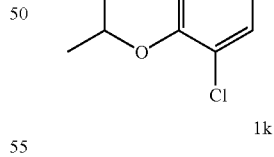

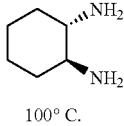

100° C.

-continued

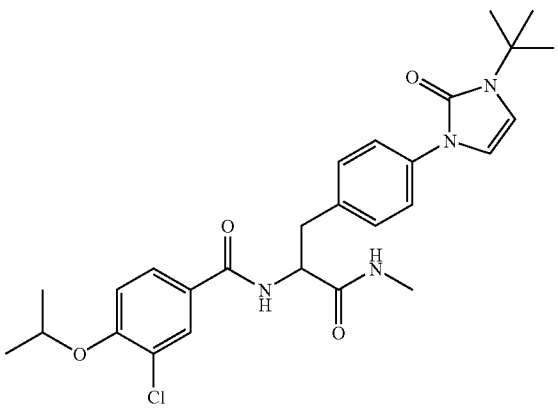

1k

To a solution of 4 (85 mg, 0.2 mmol) in toluene (2 mL) was added 1-t-butyl-1,3-dihydro-imidazol-2-one (53 mg, 0.4 mmol), copper(I) iodide (18 mg; 0.1 mmol), trans-1,2-diamino-cyclohexane (11 mg, 0.1 mmol), and cesium carbonate (124 mg, 0.4 mmol). The reaction mixture was stirred for 4 hours at 100° C. The mixture was filtered, and the filtrate was concentrated. The resulting residue was filtered, and the filtrate was purified on RP-HPLC using a mixture of acetonitrile and H$_2$O to give 1k (27 mg, 28%). LRMS (M+H$^+$) m/z 513.1.

Example 12

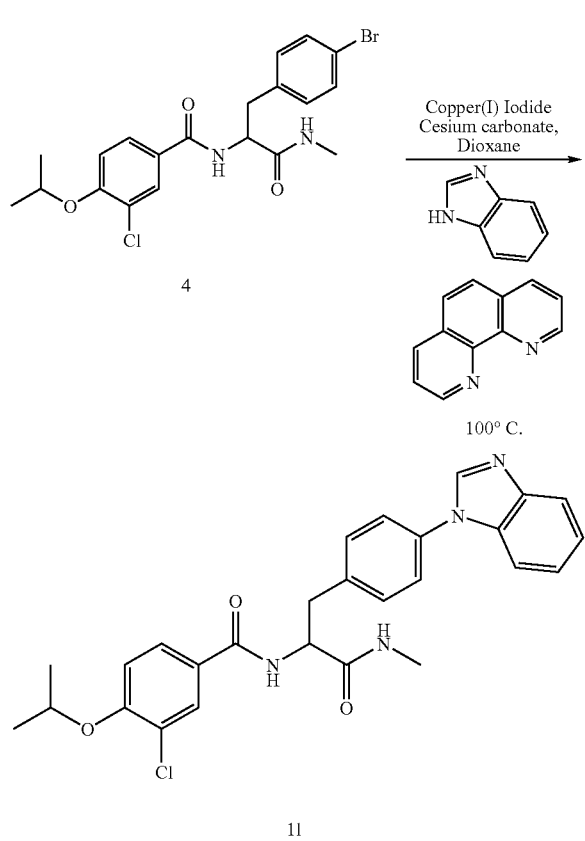

To a solution of 4 (100 mg, 0.2 mmol) in dioxane (2 mL) was added benzimidazole (39 mg, 0.33 mmol), copper (I) iodide (8.4 mg, 0.04 mmol), 1,10-phenanthroline (16 mg, 0.1 mmol), and cesium carbonate (144 mg, 0.44 mmol). The reaction mixture was stirred for 15 hours at 100° C. The mixture was filtered, and the filtrate was concentrated. The resulting residue was filtered, and the filtrate was purified on RP-HPLC using a mixture of acetonitrile and H$_2$O to give 1l (5.7 mg, 6%). LRMS (M+H$^+$) m/z 491.1.

Example 13

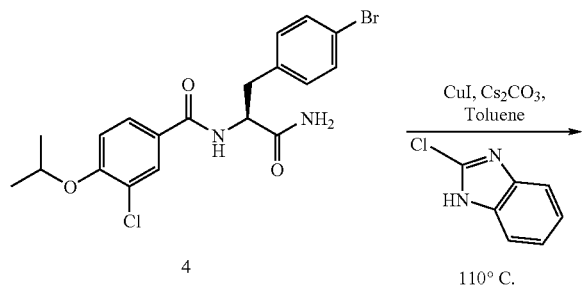

To a solution of 4 (60 mg, 0.16 mmol) in toluene (1 mL) was added 2-chlorobenzimidazole (50 mg, 0.32 mmol), copper(I) iodide (9 mg, 0.05), and cesium carbonate (105 mg, 0.32 mmol). The reaction mixture was stirred for 28 hours at 110° C. The mixture was filtered, and the filtrate was purified on RP-HPLC using a mixture of acetonitrile and H$_2$O to give 1m (8 mg, 10%). LRMS (M+H$^+$) m/z 493.0.

Example 14

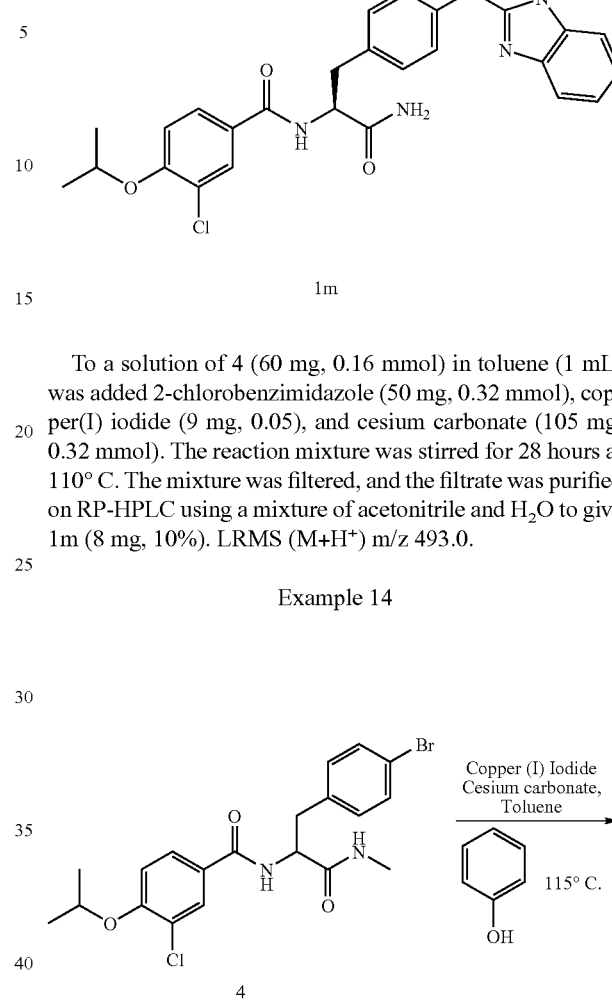

To a solution of 4 (50 mg, 0.1 mmol) in toluene (1 mL) was added phenol (21 mg, 0.2 mmol), copper(I) iodide (6 mg, 0.03 mmol), and cesium carbonate (72 mg, 0.2 mmol). The reaction mixture was stirred for 5 hours at 115° C. The mixture was filtered, and the filtrate was concentrated. The resulting residue was purified via flash column chromatography using a mixture of ethyl acetate and hexane as eluent to give 1n (23 mg, 45%). LRMS (M+H$^+$) m/z 467.1.

Examples 15

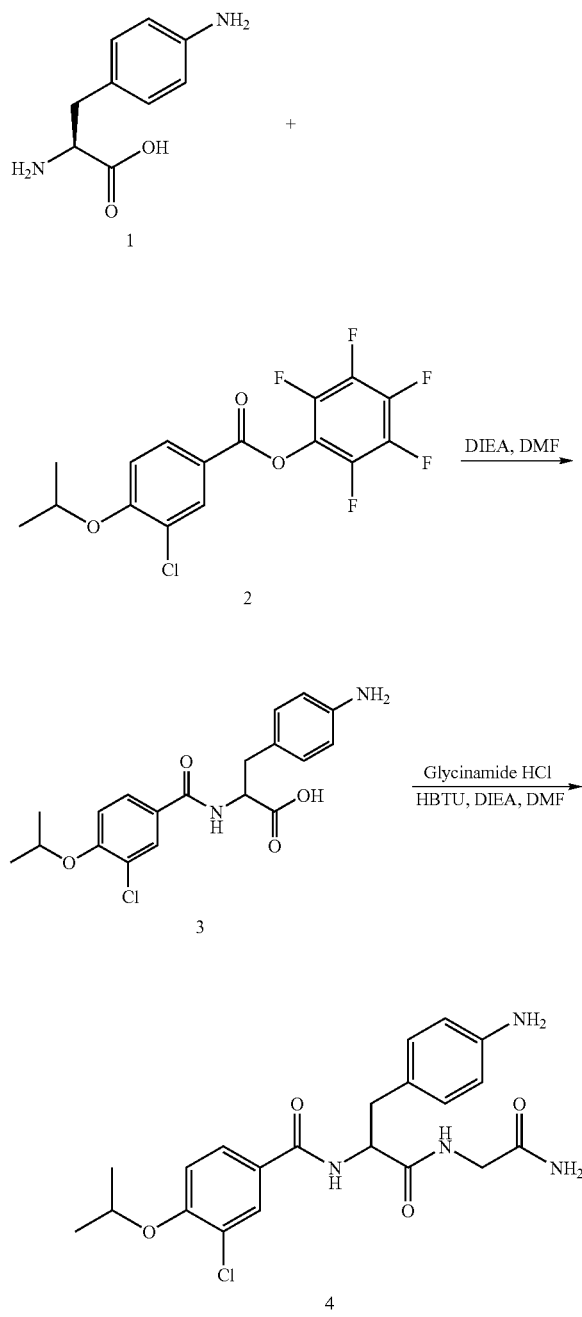

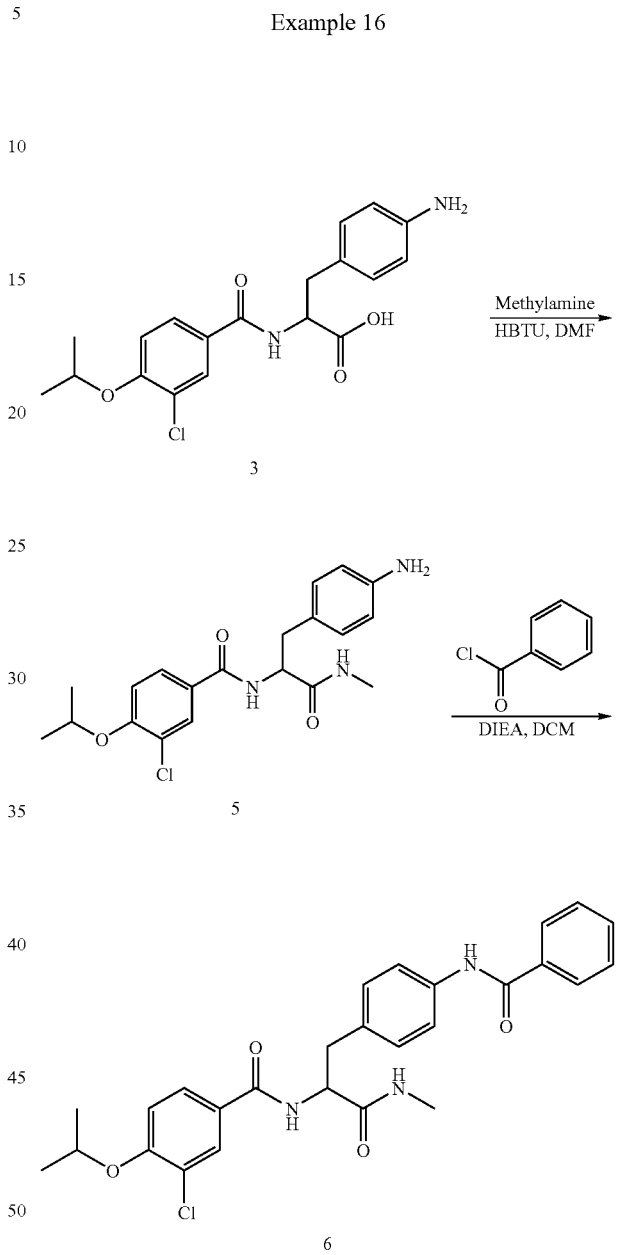

Example 16

To a solution of 1 (2.3 g, 12.6 mmol) in DMF (30 mL) were added 2 (4.0 g, 10.5 mmol) and N,N-diisopropylethylamine (5.2 mL, 30 mmol). The reaction was monitored by LC/MS. The resulting solution was used in the next step without further purification. LRMS (M+H$^+$) m/z 377.1.

To a solution of crude 3 in DMF (6 mL, ~2 mmol) were added glycinamide HCl (330 mg, 3 mmol), HBTU (1.14 g, 3 mmol) and N,N-diisopropylethylamine (522 μL, 3 mmol). The reaction was stirred overnight. The resulting crude product was purified via RP-HPLC using a mixture of acetonitrile and H$_2$O to give 4 (600 mg, 69% from 2). LRMS (M+H$^+$) m/z 433.1.

To a solution of crude 3 in DMF (15 mL, ~5.25 mmol) were added methylamine (2 M in THF, 4 mL, 8 mmol), and HBTU (3 g, 7.9 mmol). The reaction was stirred overnight. The mixture was diluted with ethyl acetate (200 mL). The organic layer was washed with H$_2$O, brine, dried over sodium sulfate, and concentrated. The resulting crude 5 was used in the next step without further purification. LRMS (M+H$^+$) m/z 390.1.

To a solution of crude 5 (75 mg, ~0.2 mmol) in DCM (2 mL) were added benzoyl chloride (23 μL, 0.2 mmol) and N,N-diisopropylethylamine (35 μL, 0.2 mmol). The reaction mixture was stirred overnight. The solution was concentrated and purified on RP-HPLC using a mixture of acetonitrile and H₂O to give 6 (36 mg, 40% from 2). LRMS (M+H⁺) m/z 494.1.

Example 17

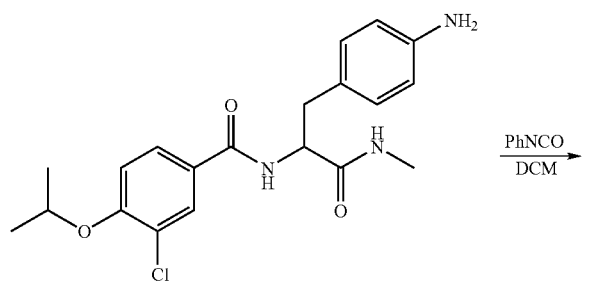

To a solution of 5 (75 mg, ~0.2 mmol) in DCM (2 mL) was added phenyl isocyanate (26 μL, 0.24 mmol). The reaction mixture was stirred overnight. The resulting solution was concentrated and purified on RP-HPLC using a mixture of acetonitrile and H₂O to give 7 (40 mg, 39% from 2). LRMS (M+H⁺) m/z 509.1.

Example 18

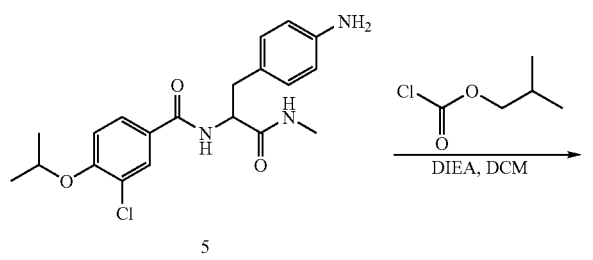

To a solution of 5 (75 mg, 0.19 mmol) in DCM (3 mL) were added isobutyl chloroformate (38 μL, 0.29 mmol) and N,N-diisopropylethylamine (50 μL, 0.29 mmol). The reaction mixture was stirred overnight. The resulting solution was concentrated and purified on RP-HPLC using a mixture of acetonitrile and H₂O to give 8 (45 mg, 48%). LRMS (M+H⁺) m/z 490.1.

Example 19

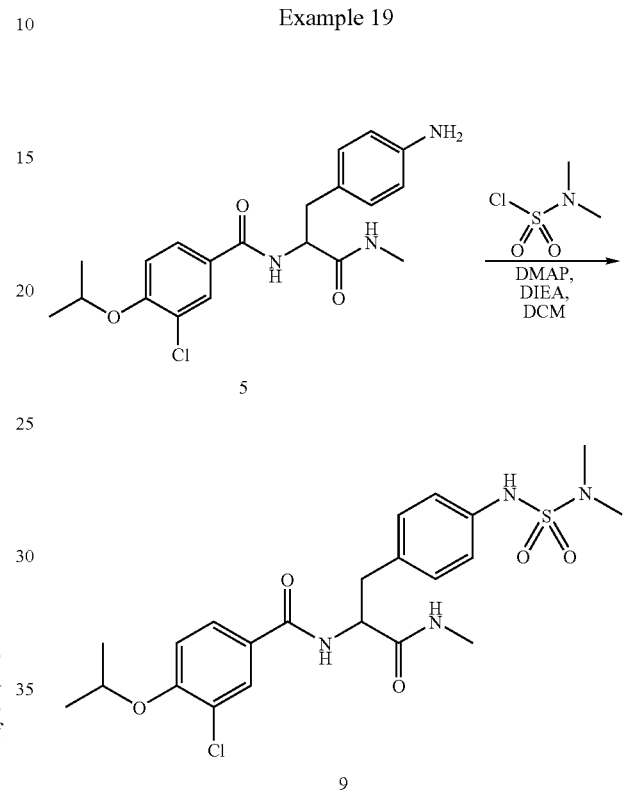

To a solution of 5 (75 mg, 0.19 mmol) in DCM (5 mL) were added dimethylsulfamoyl chloride (30 μL, 0.29 mmol), N,N-diisopropylethylamine (50 μL, 0.29 mmol) and DMAP (50 mg, 0.4 mmol). The reaction mixture was stirred overnight. The reaction mixture was then heated to 30° C. and stirring continued for 8 h. The resulting solution was concentrated and purified on RP-HPLC using a mixture of acetonitrile and H₂O to give 9 (30 mg, 32%). LRMS (M+H⁺) m/z 497.1.

Example 20

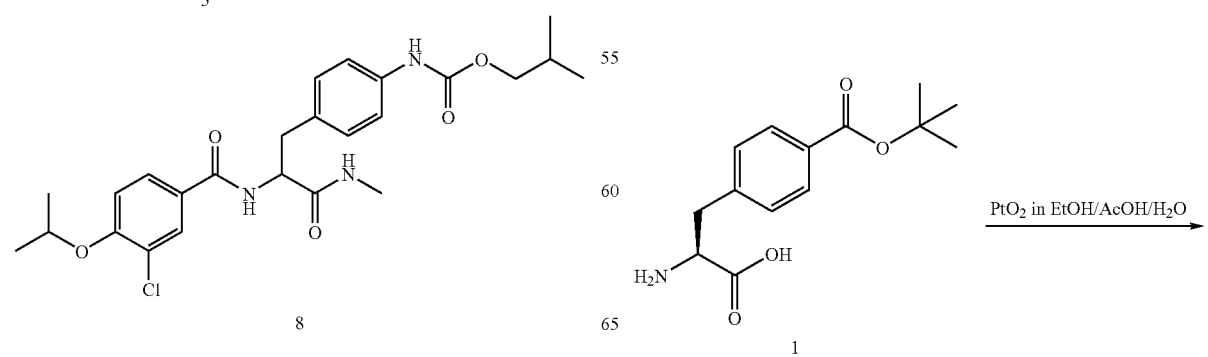

-continued

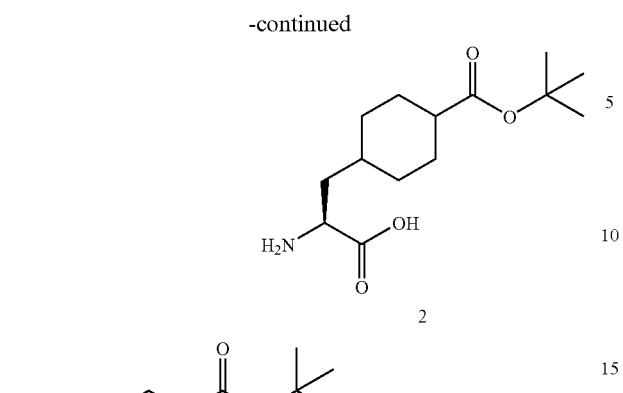

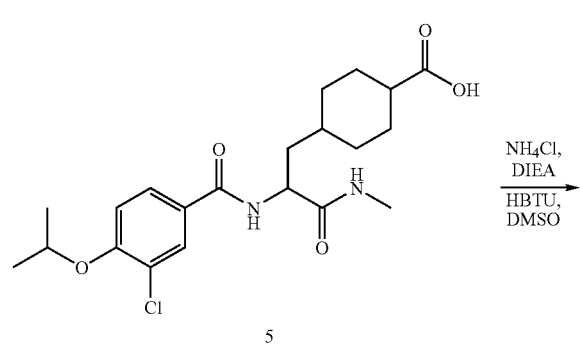

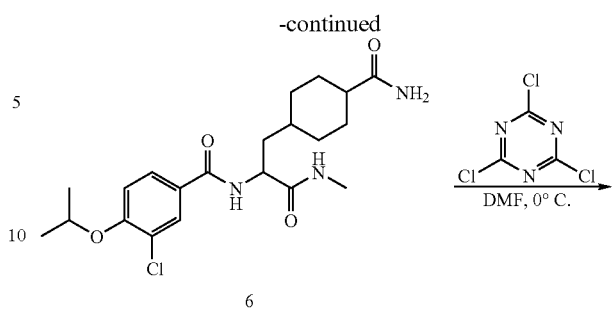

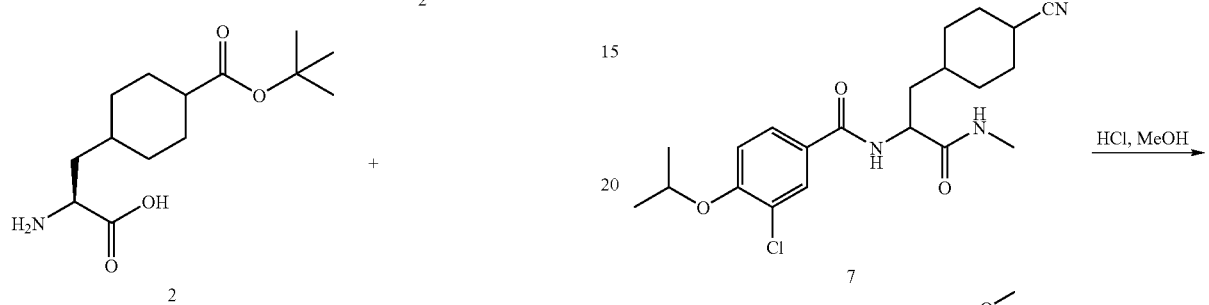

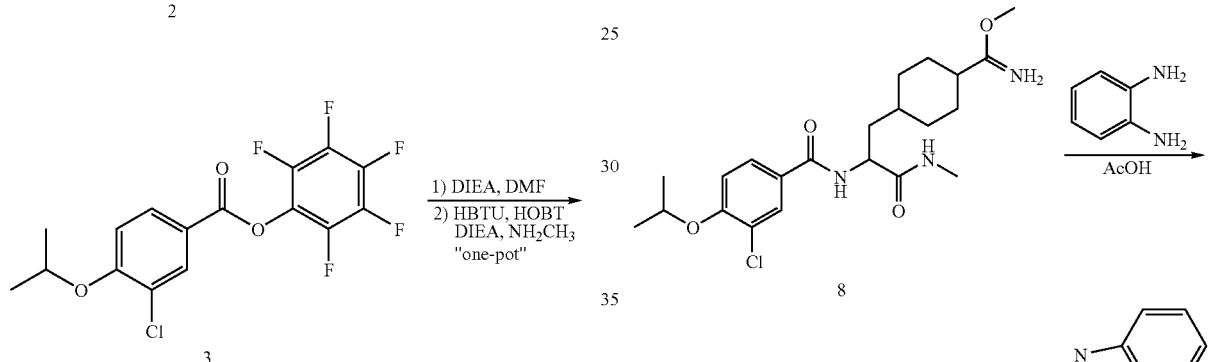

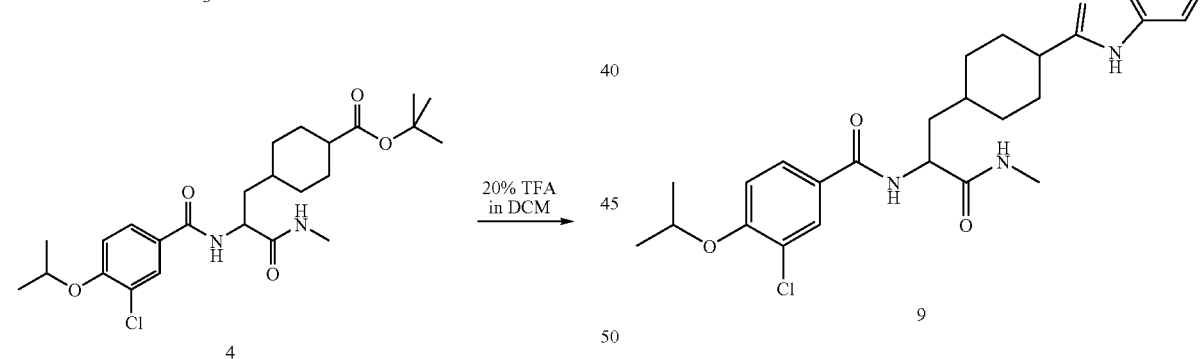

To a solution of H-Phe(4-COOtBu)—OH (5.8 g, 22 mmol) in ethyl acetate (60 mL) and water (20 mL) were added platinum (IV) oxide (400 mg, 1.8 mmol) and acetic acid (50 mL). The reaction mixture was stirred under a stream of $H_2$ (60 psi) for 20 hrs. The catalyst was removed by filtration through a PTFE (0.45 μm) filter and the solvent evaporated to give 2 (5.9 g), which was used in the next step without further purification. LRMS (M+H⁺) m/z 272.1.

To a solution of 2 (6.9 g, 18 mmol) in DMF (30 mL) were added 3 (5.9 g, 21.8 mmol) and N,N-diisopropylethylamine (9.5 mL, 54.3 mmol). The reaction was monitored by LC/MS. After completion, 2M methylamine in THF (13.6 mL, 27 mmol), HOBt (4 g, 27 mmol), and HBTU (10 g, 27 mmol) were added to the reaction solution. The reaction was stirred for 4 hours. The mixture was diluted with ethyl acetate (60 mL) and washed with saturated $NaHCO_3$ (20 mL). The organic layer was separated, and the aqueous phase was extracted with ethyl acetate (2×50 mL). The combined organic layers were washed with brine, dried over sodium sulfate, and concentrated. The resulting crude product was purified via flash column chromatography using a mixture of ethyl acetate and hexane as eluent to give 4 (cis isomer 808 mg, 1.68 mmol, trans isomer 300 mg, 0.63 mmol). LRMS (M+H$^+$) m/z 481.1.

To a solution of 4 (290 mg, 0.6 mmol) in dichloromethane (20 mL) was added trifluoroacetic acid (5 mL). The resulting solution was stirred at room temperature for 1 hour and then concentrated under reduced pressure. The residue was purified via flash column chromatography using a mixture of 99% ethyl acetate and 1% acetic acid as eluent to give 5 as a white solid (140 mg, 55%). LRMS (M+H$^+$) m/z 425.1.

To a solution of 5 (330 mg, 0.7 mmol) in DMSO (5 mL) were added ammonium chloride (83 mg, 1.5 mmol), diisopropylethylamine (0.27 mL, 1.5 mmol), and HBTU (580 mg, 1.5 mmol). The resulting solution was stirred at room temperature for 15 hours. Additional ammonium chloride (37 mg, 0.7 mmol), diisopropylethylamine (0.12 mL, 0.7 mmol), and HBTU (266 mg, 0.7 mmol) were added. Stirring was continued for additional 5 hours, and the mixture was diluted with ethyl acetate (50 mL) and washed with saturated NaHCO$_3$ (20 mL). The organic layer was separated, and the aqueous phase was extracted with ethyl acetate (2×50 mL). The combined organic layers were washed with brine, dried over sodium sulfate, and concentrated to yield slightly yellow crude. The residue was purified on RP-HPLC using a mixture of acetonitrile and H$_2$O to give 6 (128 mg, 30%). LRMS (M+H$^+$) m/z 424.1.

To a solution of 6 (94 mg, 0.2 mmol) in DMF (2 mL) was added cyanuric chloride (45 mg, 0.2 mmol) at 0° C., and the reaction mixture was stirred under nitrogen. After 1 hour, the reaction solution was concentrated to give 7 (79 mg), which was used in the next step without further purification. LRMS (M+H$^+$) m/z 406.1.

To a solution of 7 (17 mg, 0.04 mmol) in methanol (2 mL) was stirred under a stream of HCl for 15 min. A stream of nitrogen was then bubbled through the reaction mixture. After 1 hour, the reaction solution was concentrated to give 8, which was used in the next step without further purification. LRMS (M+H$^+$) m/z 438.1.

To a solution of crude 8 (17 mg, 0.04 mmol) in acetic acid (2 mL) was added o-phenylenediamine (50 mg, 0.46 mmol), and the resulting solution was stirred at 80° C. for 1 h. The reaction mixture was concentrated and purified via preparative thin layer chromatography using 5% methanol in dichloromethane as eluent to give a white solid. The solid was purified on RP-HPLC using a mixture of acetonitrile and H$_2$O to give 9 (9 mg, 45%). LRMS (M+H$^+$) m/z 497.1.

Example 21

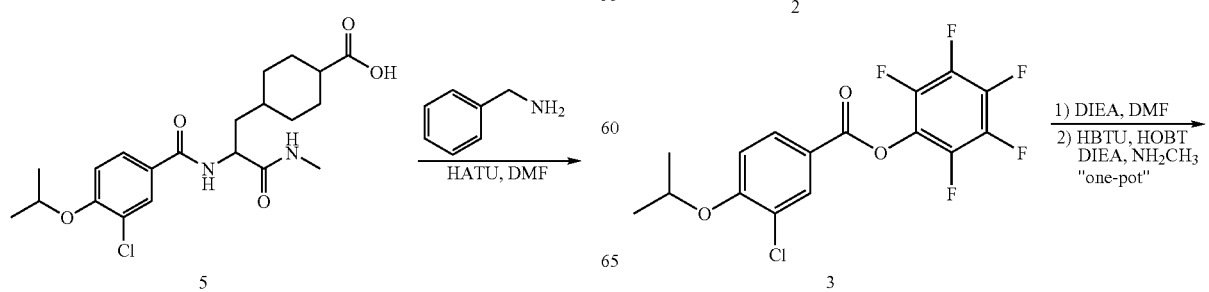

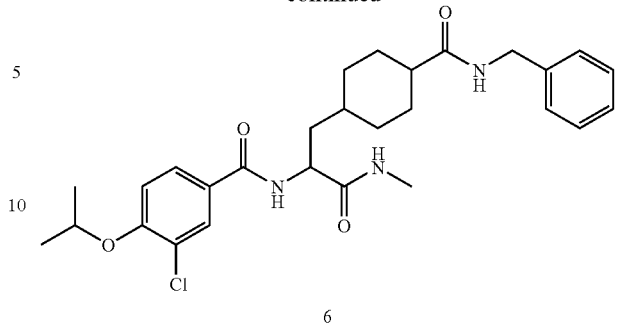

To a solution of 5 (50 mg, 0.12 mmol) in DMF (1 mL) were added benzylamine (16 mg, 0.14 mmol) and HATU (57 mg, 0.14 mmol). The reaction mixture was stirred at room temperature for 3 hours. The resulting solution was filtered and the filtrate was purified on RP-HPLC using a mixture of acetonitrile and H$_2$O to give 6 (16 mg, 26%). LRMS (M+H$^+$) m/z 514.1.

Examples 22-24

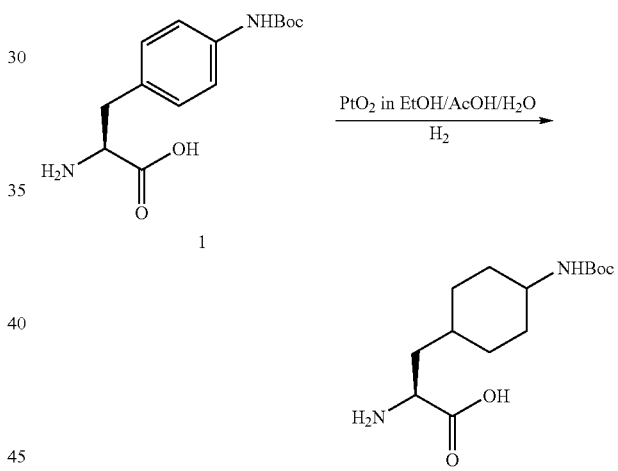

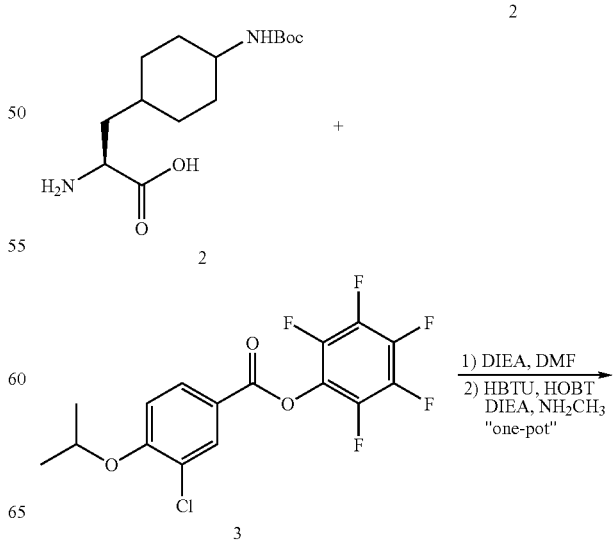

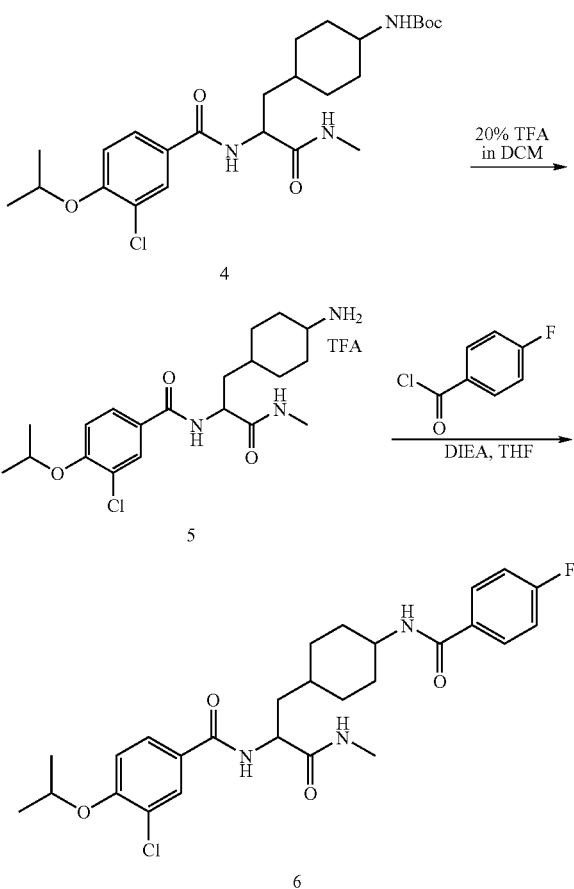

To a solution of H-Phe(4-NHBoc)-OH (4.8 g, 17.1 mmol) in ethanol (60 mL), methanol (20 mL), acetic acid (60 mL), and water (30 mL) was added platinum (IV) oxide (360 mg, 1.6 mmol). The reaction mixture was stirred under a stream of $H_2$ (45 psi) for 20 hrs. The catalyst was removed by filtration through a PTFE (0.45 μm) filter and the solvent evaporated to give 2 (5 g), which was used in the next step without further purification. LRMS (M+H$^+$) m/z 287.1.

To a solution of crude 2 (3.2 g, 11.2 mmol) in DMF (20 mL) were added 3 (3.8 g, 10 mmol) and N,N-diisopropylethylamine (5.2 mL, 30 mmol). The reaction was monitored by LC/MS. After completion, methylamine (2 M in THF, 7.5 mL, 15 mmol), and HBTU (5.7 g, 15 mmol) were added to the reaction solution. The reaction was stirred overnight. The mixture was diluted with ethyl acetate (60 mL) and washed with saturated NaHCO$_3$ (20 mL). The organic layer was separated, and the aqueous phase was extracted with ethyl acetate (2×50 mL). The combined organic layers were washed with brine, dried over sodium sulfate, and concentrated. The resulting crude was purified via RP-HPLC using a mixture of acetonitrile and H$_2$O to give 4 (1.0 g, 18% from 1). LRMS (M+H$^+$) m/z 496.1.

To a solution of 4 (1.0 g, 2.0 mmol) in dichloromethane (25 mL) was added trifluoroacetic acid (8 mL). The resulting solution was stirred at room temperature for 4 hours and then concentrated under reduced pressure. The residue was purified via RP-HPLC using a mixture of acetonitrile and H$_2$O to give 5 (820 mg, 79%). LRMS (M+H$^+$) m/z 396.1.

To a solution of 5 (75 mg, 0.16 mmol) in THF (3 mL) were added 4-fluorobenzoyl chloride (28 μL, 0.23 mmol) and N,N-diisopropylethylamine (100 μL, 0.57 mmol). The reaction mixture was stirred overnight. The resulting solution was concentrated and purified on RP-HPLC using a mixture of acetonitrile and H$_2$O to give 6 (65 mg, 78%). LRMS (M+H$^+$) m/z 518.1.

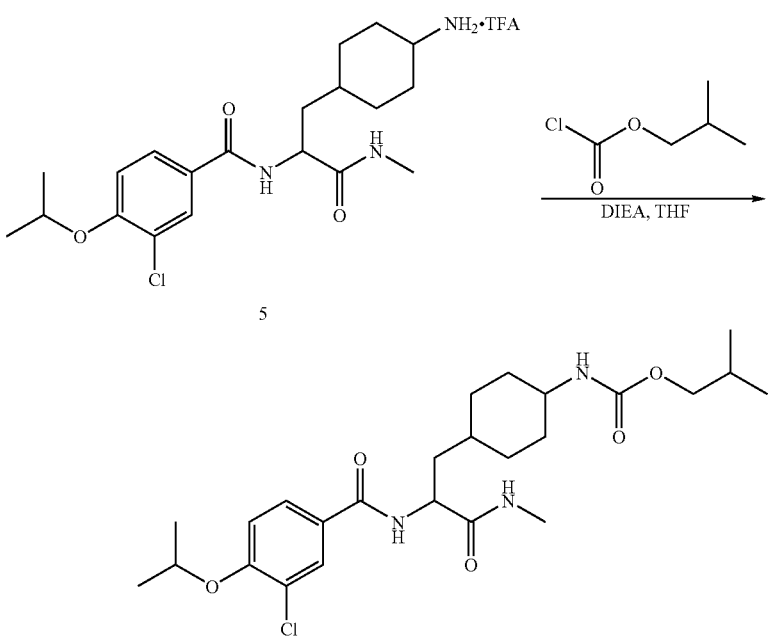

To a solution of 5 (75 mg, 0.16 mmol) in THF (3 mL) were added isobutyl chloroformate (30 μL, 0.23 mmol) and N,N-diisopropylethylamine (100 μL, 0.57 mmol). The reaction mixture was stirred overnight. The resulting solution was concentrated and purified on RP-HPLC using a mixture of acetonitrile and H₂O to give 7 (62 mg, 78%). LRMS (M+H⁺) m/z 496.1.

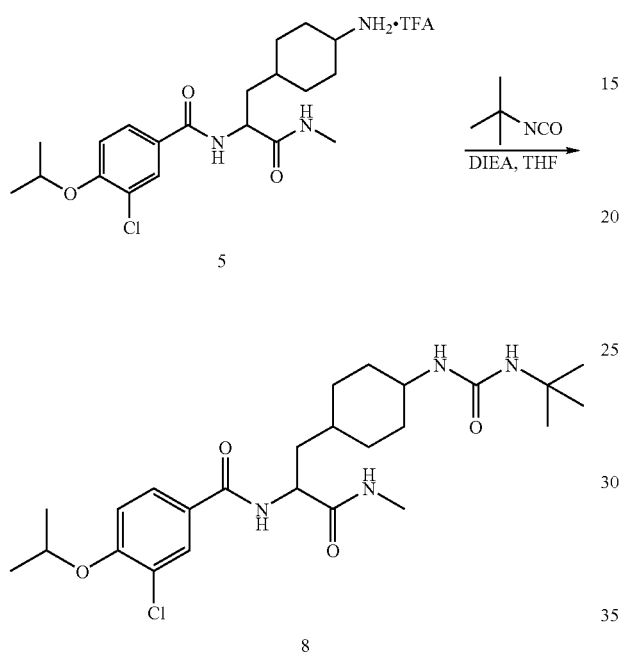

To a solution of 5 (75 mg, 0.16 mmol) in THF (3 mL) was added tert-butyl isocyanate (26 μL, 0.23 mmol) and N,N-diisopropylethylamine (100 μL, 0.57 mmol). The reaction mixture was stirred overnight. The resulting solution was concentrated and purified on RP-HPLC using a mixture of acetonitrile and H₂O to give 7 (55 mg, 69%). LRMS (M+H⁺) m/z 495.1.

Example 25

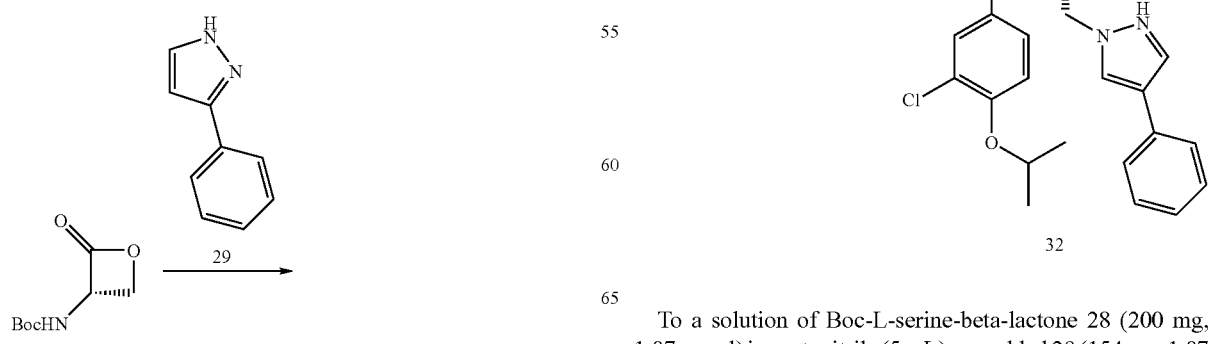

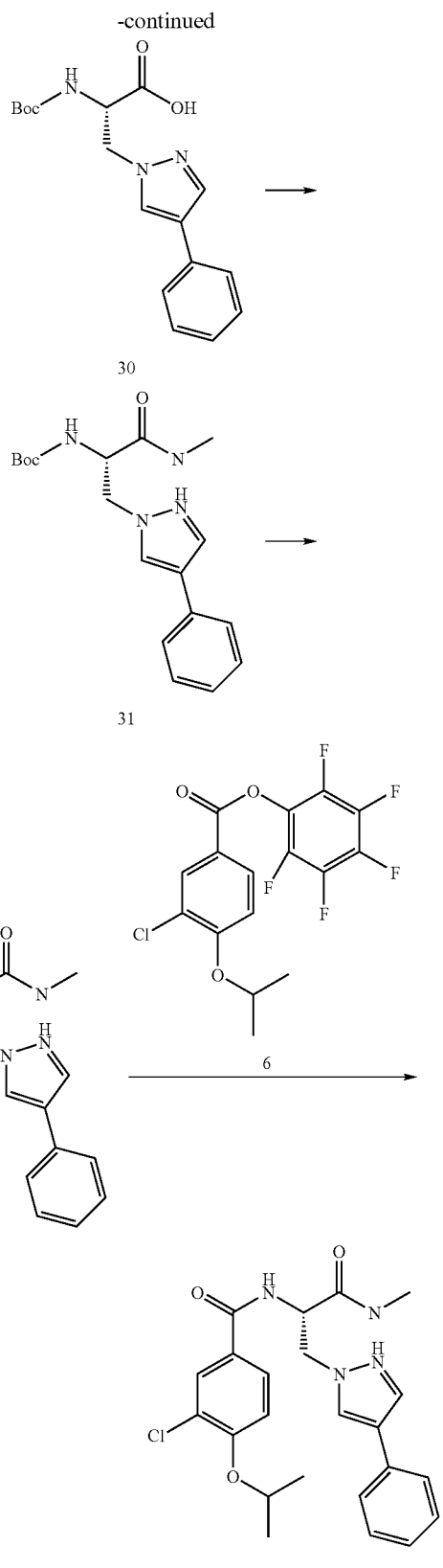

To a solution of Boc-L-serine-beta-lactone 28 (200 mg, 1.07 mmol) in acetonitrile (5 mL) was added 29 (154 mg, 1.07 mmol). The mixture was stirred at 56° C. overnight. Concentrated under reduced pressure to give 30.

Crude 30 was redissolved in DMF (1 mL) treated with methylamine (2 M in THF) (0.54 mL, 1.08 mmol) and HBTU (404 mg, 1.07 mmol). The mixture was stirred for 1 hour, after which it was filtered, and the filtrate purified on reverse phase HPLC (C18) using a mixture of acetonitrile and $H_2O$ to give 31 (50.0 g, 14%).

To a solution of 31 (50.0 g, 0.145 mmol) in DCM (5 mL) was added TFA (5 mL) at room temperature. The reaction mixture was stirred for 20 min. The solvents were evaporated under reduced pressure and the residue re-suspended in DMF (100 mL) followed by the addition of 6 (66.3 mg, 0.174 mmol) and diisopropylethylamine (51 µL, 0.290 mmol) at room temperature. The reaction mixture was stirred for 1 hour, then concentrated under reduced pressure, and the residue purified on a flash silica gel soumn (hexane:EtOAc, 1:1) to give 32 (50.0 mg, 78.2%). LCMS (M+H$^+$) m/z 441.1.

Example 26

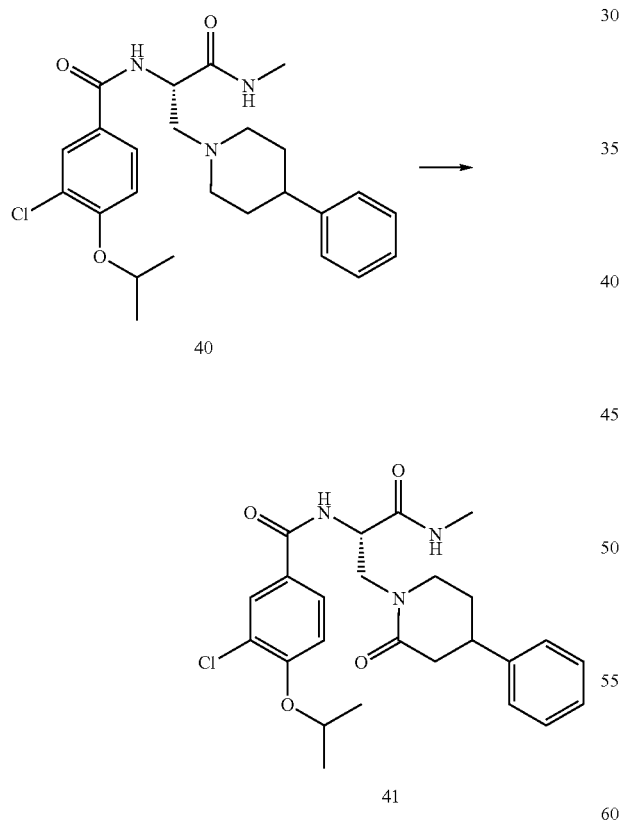

To a solution of 40 (50.0 g, 0.0874 mmol) in water (1 mL) and methanol (1 mL) were added sodium EDTA (88.1 mg, 0.262 mmol) and Hg(OAc)$_2$ (83.7 mg, 0.262 mmol). The reaction mixture was stirred at 100° C. for 1 h and then concentrated under reduced pressure. The residue was purified on a flash silica gel column (DCM:MeOH, 10:1) to give 41 (29.6 mg, 71%). LCMS (M+H$^+$) m/z 472.4.

Example 27

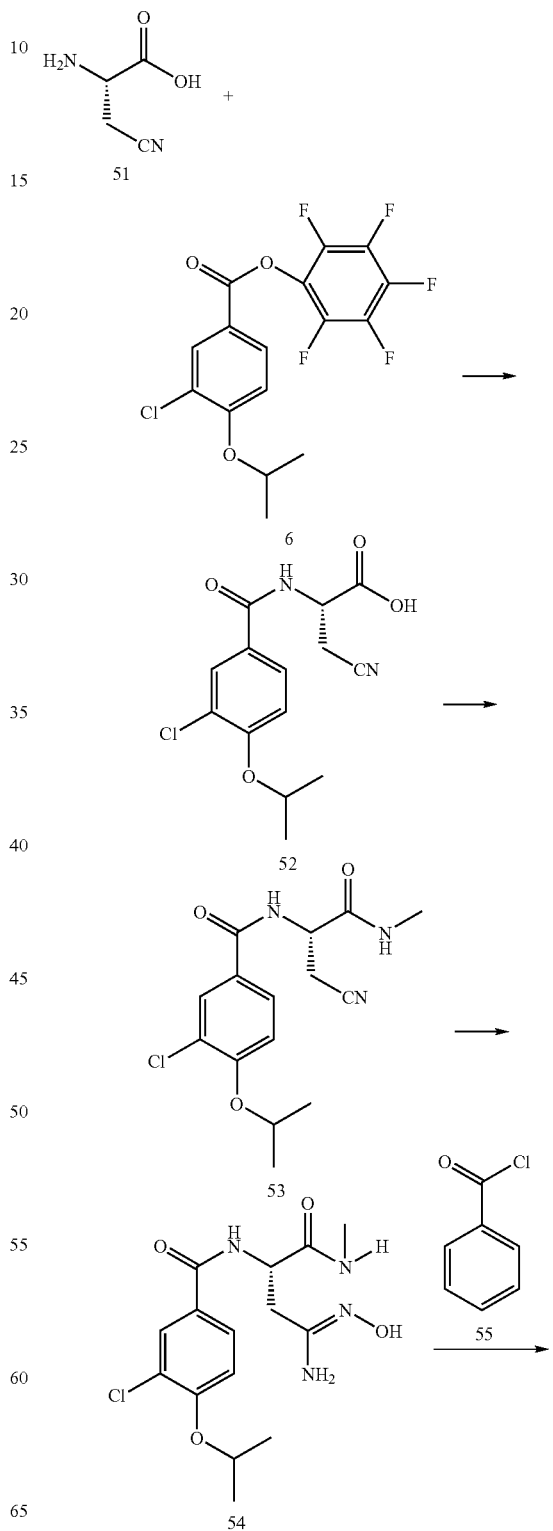

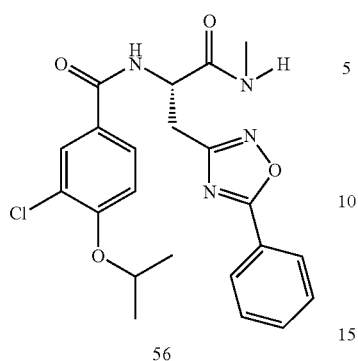

56

To a stirring solution of 51 (1.0 g, 8.76 mmol) in DMF (20 mL) were added 6 (3.34 g, 8.76 mmol) and diisopropylethylamine (2.30 mL, 13.1 mmol) at room temperature. The reaction mixture was monitored by reverse phase HPLC/MS. After completion, 2 M methylamine in THF (8.80 mL, 17.5 mmol) and HBTU (4.97 g, 13.1 mmol) were added to the reaction solution. After stirring for 1 hour, the reaction mixture was concentrated and purified on a flash silica gel column (hexane:EtOAc, 1:1) to give 53 (1.0 g, 35.3%).

To a solution of 53 (1.0 g, 3.09 mmol) in ethanol (20 mL) were added triethylamine (0.517 mL, 3.71 mmol) and hydroxyamine hydrochloride (258 mg, 3.71 mmol). After stirring at reflux for 24 hours, the solvents were evaporated under reduced pressure. The residue was purified on reverse phase HPLC (C18) using a mixture of acetonitrile and H₂O to give 54 (280 mg, 25%).

To a stirred solution of 54 (280 mg, 0.785 mmol) in THF (50 mL) were added diisopropylethylamine (164 uL, 0.942 mmol) and benzoyl chloride (100 uL, 0.864 mmol) at room temperature. After stirring for 30 min, the reaction mixture was concentrated, the residue was dissolved in HOAc (100 mL), and the mixture was stirred at reflux for 5 hours. The solvents were removed under reduced pressure, and the residue was purified on a flash silica gel column (hexane:EtOAc, 1:1) to give 56 (49 mg, 14.1%). LCMS (M+H⁺) m/z 443.1.

Example 28

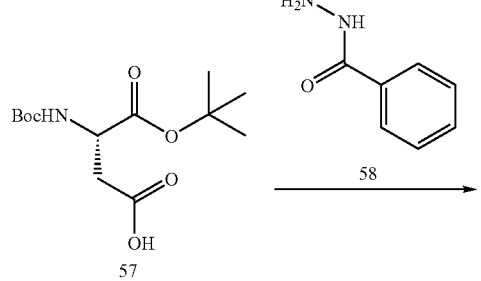

57  58

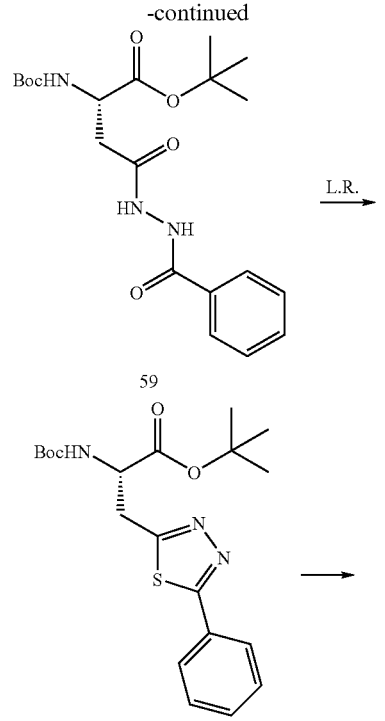

59

60

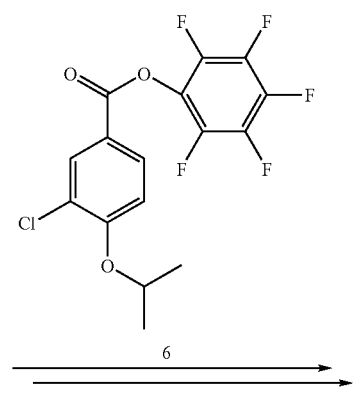

61  6

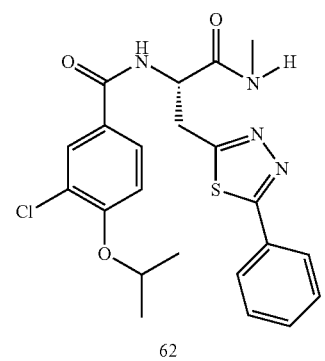

62

To a solution of 57 (3.0 g, 10.4 mmol) in DMF (50 mL) were added 58 (1.69 g, 12.4 mmol) and HBTU (5.92 g, 15.6 mmol). The reaction mixture was monitored by reverse phase HPLC/MS. After stirring 5 hours, the solvents were evaporated under reduced pressure and the residue purified on a flash silica gel column (hexane:EtOAc, 1:1) to give 59 (3.50 g, 82%).

To a solution of 59 (200 mg, 0.491 mmol) in toluene (5 mL) was added Lawesson's Reagent (109 mg, 0.270 mmol). After stirring at 100° C. for 30 min, the solvents were evaporated under reduced pressure. The residue was purified on a flash silica gel column (hexane:EtOAc, 1:1) to give 60 (160 mg, 80%).

To a solution of 60 (150 mg, 0.431 mmol) in DCM (5 mL) was added TFA (5 mL) at room temperature. The reaction mixture was stirred for 2 hours. The solvents were evaporated under reduced pressure, and the residue 61 (121 mg, 100%) was dried under vacuum overnight.

To a stirred solution of 61 (0.395 mmol) in DMF (5 mL) were added 6 (180 mg, 0.473 mmol) and diisopropylethylamine (138 uL, 0.790 mmol) at room temperature. The reaction mixture was monitored by HPLC/MS. After completion, 2 M methylamine in THF (395 uL, 0.790 mmol) and HBTU (225 mg, 0.593 mmol) were added to the reaction solution. The reaction mixture was stirred for 30 min, after which the mixture was filtered, and the filtrate purified by reverse phase HPLC (C18) using a mixture of acetonitrile and $H_2O$ to give 62 (70.0 mg, 38.6%). LCMS (M+H$^+$) m/z 459.0.

Example 29

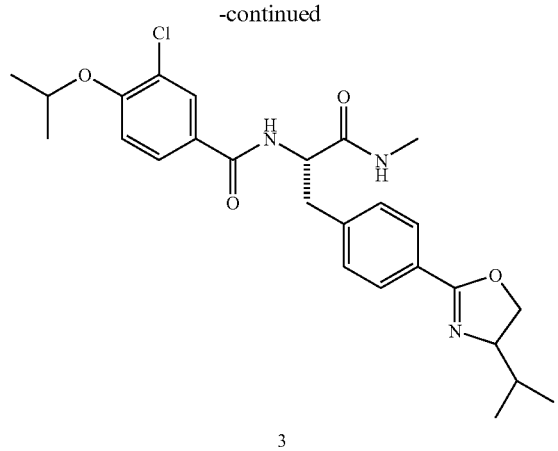

3

A solution of the nitrile 1 (640 mg, 1.6 mmol) and MeOH (25 mL) at 0° C. was saturated with HCl gas. The reaction vessel was allowed to warm to 23° C. After 2 h at 23° C. the reaction solution was concentrated in vacuo and the resulting residue 2 was used without further purification.

A solution of crude imidate 2 (50 mg, 0.12 mmol), 2-amino-3-methyl-propanol (36 mg, 0.35 mmol), and THF (1 mL) was stirred at 80° C. for 30 min. The reaction mixture was then concentrated in vacuo and the resulting residue was dissolved in EtOAc (10 mL) and washed with 1 N NaOH (5 mL) and brine (5 mL). The organic layer was dried (MgSO$_4$), filtered, and concentrated in vacuo. The resulting residue was purified by flash column chromatography (silica gel, 100% EtOAc) to yield 25 mg (43%) of the oxazole 3. LRMS (M+H$^+$) m/z 486.3.

Example 30

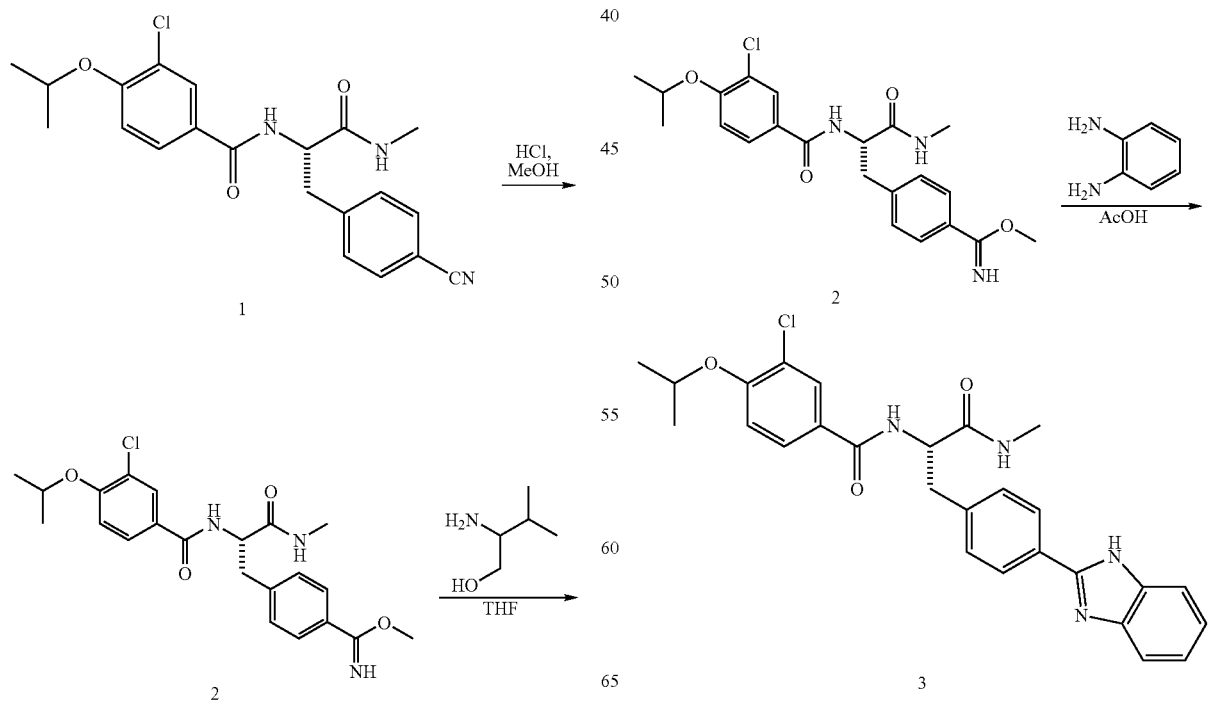

A solution of crude imidate 2 (50 mg, 0.12 mmol), phenylene diamine (36 mg, 0.32 mmol), and acetic acid (1 mL) was stirred at 80° C. for 30 min. The reaction mixture was then concentrated in vacuo, and the resulting residue was dissolved in EtOAc (10 mL) and washed with 1 N NaOH (5 mL) and brine (5 mL). The organic layer was dried (MgSO$_4$), filtered, and concentrated in vacuo. The resulting residue was purified by flash column chromatography (silica gel, 1:3 hexanes:EtOAc) to yield 20 mg (34%) of the benzimidazole 3. LRMS (M+H$^+$) m/z 491.2.

Example 31

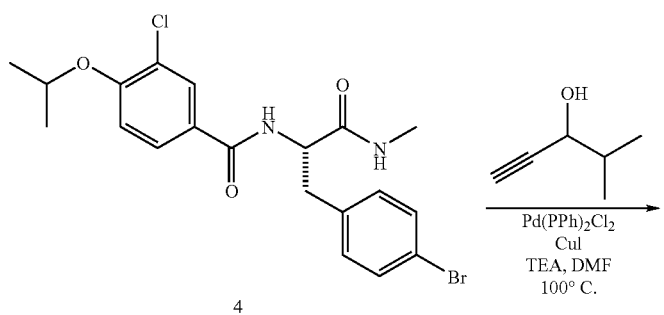

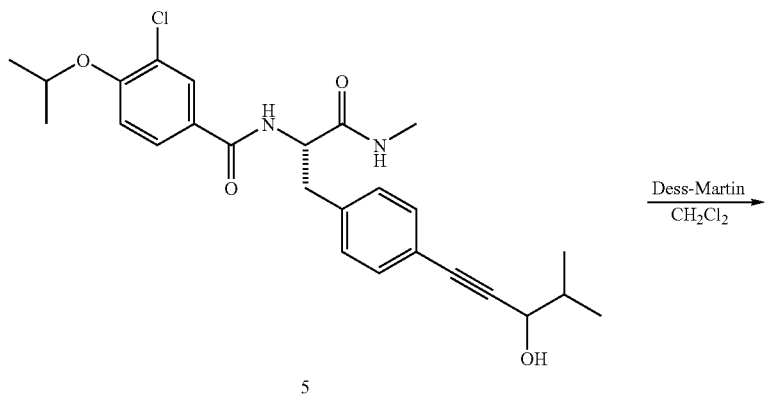

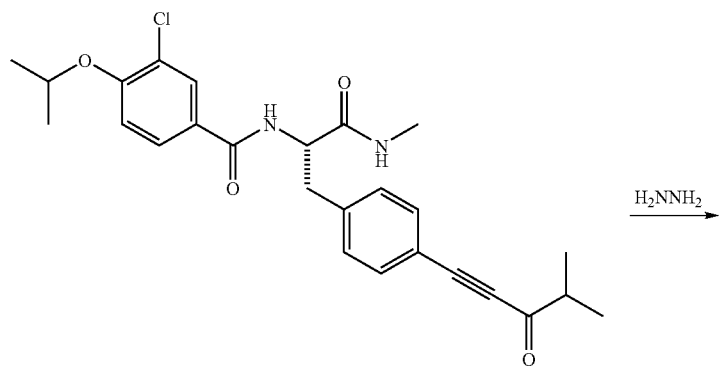

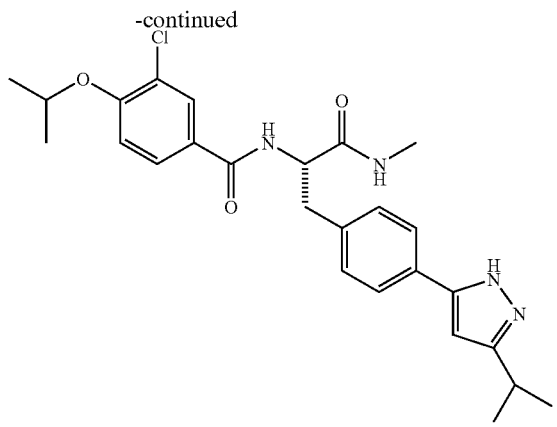

7

A solution of bromide 4 (500 mg, 1.1 mmol), 4-methyl-1-pentyn-3-ol (0.15 mL, 1.32 mmol), bis(triphenylphosphine)palladium(II) chloride (390 mg, 0.55 mmol), copper iodide (52 mg, 0.28 mmol), triethylamine (5 mL), and DMF (10 mL) was stirred at 100° C. for 3 hours. The reaction mixture then concentrated in vacuo and the resulting residue was dissolved in EtOAc (50 mL) and washed with 0.1 N HCl (3×20 mL) and brine (20 mL). The organic layer was dried (MgSO$_4$), filtered, and concentrated in vacuo. The resulting residue was purified by flash column chromatography (silica gel, 1:1 hexanes:EtOAc) to yield 200 mg (42%) of the acetylene 5. LRMS (M+H$^+$) m/z 471.2.

A solution of alcohol 5 (50 mg, 0.12 mmol), Dess-Martin periodinane (90 mg, 0.21 mmol), and CH$_2$Cl$_2$ (3 mL) was stirred at 23° C. for 2 hours. The reaction mixture was diluted in EtOAc (20 mL), and washed with saturated aqueous NaHCO$_3$ (10 mL) and brine (20 mL). The organic layer was dried (MgSO$_4$), filtered, and concentrated in vacuo. The resulting residue was used directly.

A solution of crude ketone 6 (30 mg, 0.06 mmol), hydrazine (0.13 mL, 1.0 M in THF), and DMF (1 mL) was stirred at 23° C. for 12 hours. The reaction mixture was then diluted in EtOAc (10 mL), and washed with 0.1 N HCl (5 mL) and brine (5 mL). The organic layer was dried (MgSO$_4$), filtered, and concentrated in vacuo. The resulting residue was purified by reverse phase HPLC (C18, acetonitrile/water) to yield 5 mg (18%) of the pyrazine 7. LRMS (M+H$^+$) m/z 483.2

Example 32

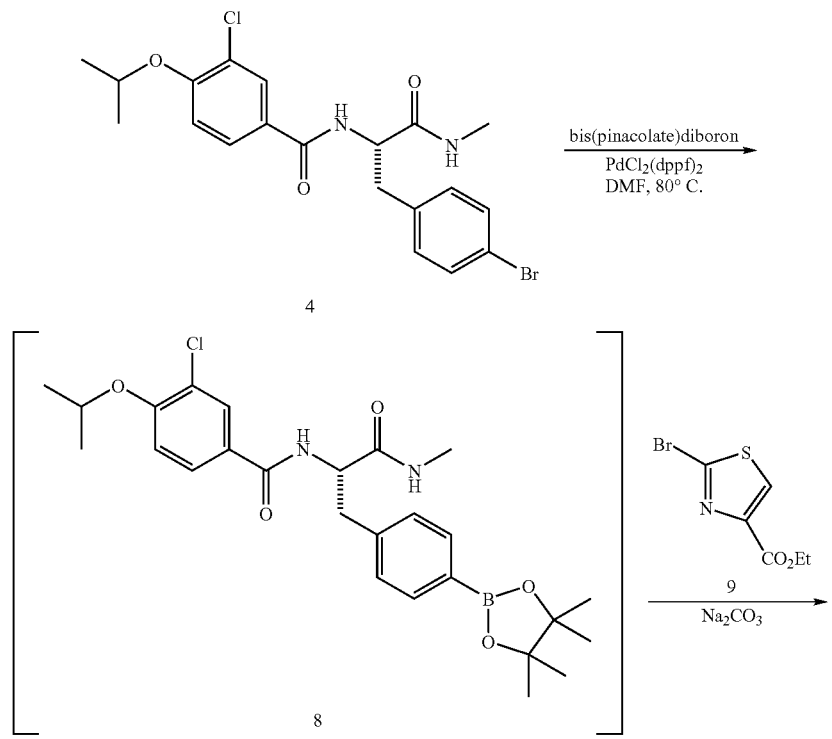

-continued
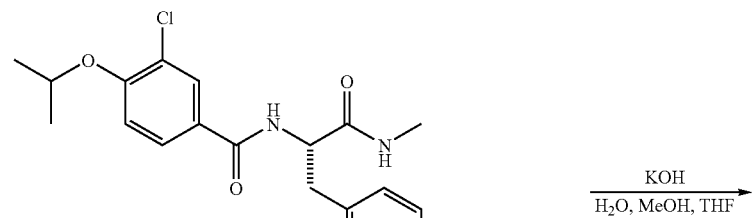
10
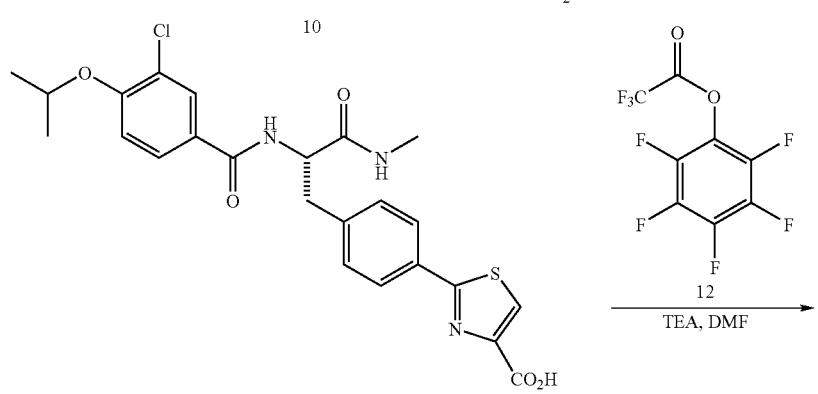
11
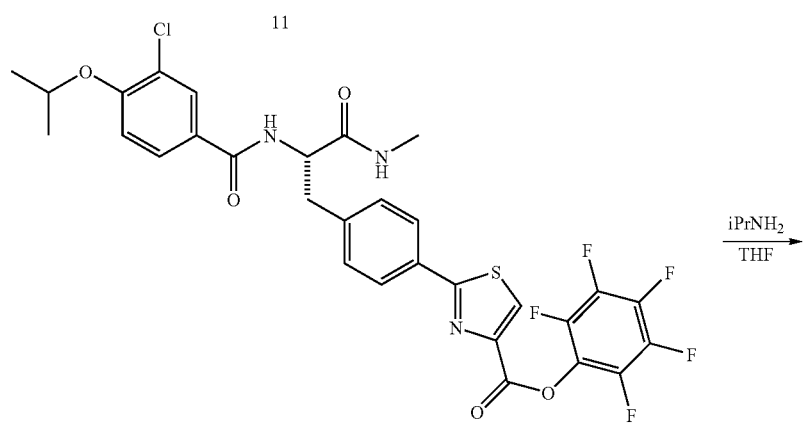
13
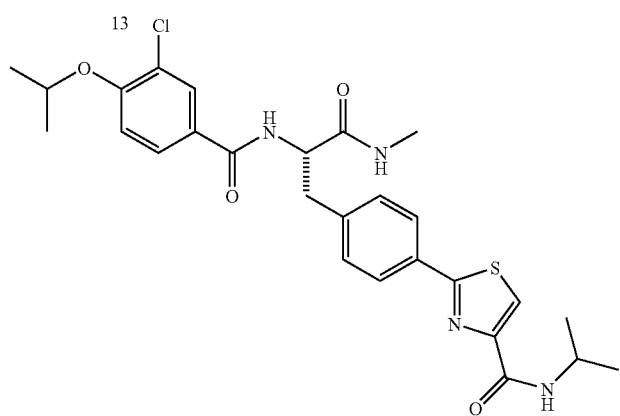
14

A solution of bromide 4 (500 mg, 1.1 mmol), bis(pinacolote)diboron (420 mg, 1.65 mmol), potassium acetate (433 mg, 4.4 mmol), [1,1'-bis(diphenylphosphino) ferrocene]-dichloropalladium(II) (180 mg, 0.22 mmol), and DMF (5 mL) was stirred at 80° C. for 3 min. Bromide 9 (366 mg, 4.65 mmol) and $Na_2CO_3$ (4.4 mL, 2.0 M in $H_2O$) were then added and the mixture stirred at 80° C. for 2 hours. The reaction mixture was then diluted in EtOAc (50 mL), the layers were separated, and the organic layer was washed with 0.1 N HCl (10 mL) and brine (10 mL). The organic layer was dried ($MgSO_4$), filtered, and concentrated in vacuo. The resulting residue was purified by reverse phase HPLC (C18, acetonitrile/water) to yield 165 mg (28%) of the thiazole 10. LRMS ($M+H^+$) m/z 531.2.

A solution of ester 10 (165 mg, 0.31 mmol), potassium hydroxide (35 mg, 0.62 mmol), $H_2O$ (1 mL), MeOH (1 mL), and THF (2 mL) was stirred at 50° C. for 2 hours. The reaction mixture then diluted with EtOAc (20 mL), and washed with 1 N HCl (5 mL) and brine (10 mL). The organic layer was dried ($MgSO_4$), filtered, and concentrated in vacuo, and the resulting residue was used directly.

A solution of acid 11 (140 mg, 0.28 mmol), pentafluorophenol trifluoroacetate 12 (96 μL, 0.56 mmol), triethylamine (77 μL, 0.56 mmol), and DMF (4 mL) was stirred at 23° C. for 2 hours. The reaction mixture was then diluted with EtOAc (20 mL), and washed with 1 N HCl (5 mL), saturated aqueous $NaHCO_3$ (5 mL) and brine (10 mL). The organic layer was dried ($MgSO_4$), filtered, and concentrated in vacuo. The resulting residue was purified by flash column chromatography (silica gel, 1:1 hexanes:EtOAc) to yield 80 mg of the ester 13.

A solution of ester 13 (20 mg, 0.03 mmol), isopropyl amine (5 μL, 0.06 mmol), and THF (1 mL) was stirred at 23° C. for 12 hours. The reaction mixture was then diluted with EtOAc (20 mL), and washed with 1 N HCl (5 mL), saturated aqueous $NaHCO_3$ (5 mL) and brine (10 mL). The organic layer was dried ($MgSO_4$), filtered, and concentrated in vacuo. The resulting residue was purified by flash column chromatography (silica gel, 1:3 hexanes:EtOAc) to yield 9 mg (55%) of the amide 14. LRMS ($M+H^+$) m/z 543.2.

Example 33

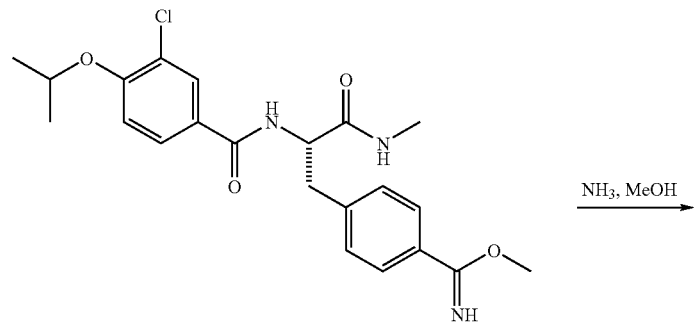

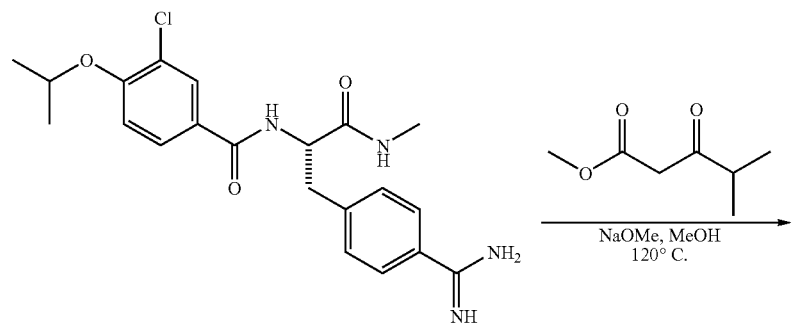

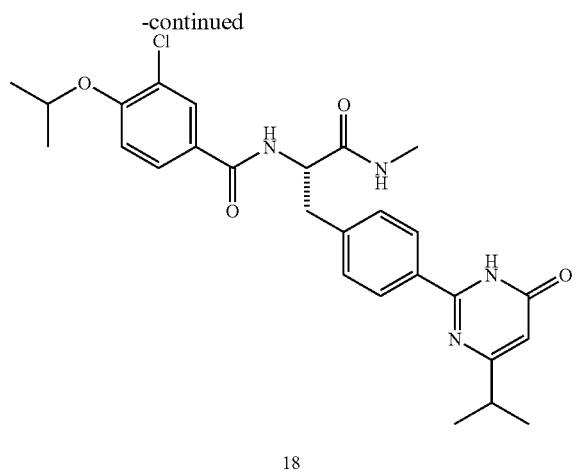

18

A solution of imidate 2 (1.6 g, 4.0 mmol) and 2.0 M NH₃ in MeOH (10 mL) was stirred at 23° C. for 12 hr. The reaction mixture was then concentrated in vacuo and the resulting residue was purified by flash column chromatography (silica gel, 1:10 CH₂Cl₂:MeOH) to yield 1.3 g (78%) of the amidine 17. LRMS (M+H⁺) m/z 417.2

A solution of amidine 17 (50 mg, 0.12 mmol), methyl isobutyrylacetate (17 µL, 0.12 mmol), and NaOMe (0.5 M in MeOH, 0.72 mL) was stirred at 120° C. for 1 hr. The reaction mixture was then concentrated in vacuo and the resulting residue purified by reverse phase HPLC (C18, acetonitrile/water) to yield 10 mg (16%) of the pyrimidine 18. LRMS (M+H⁺) m/z 511.2.

Example 34

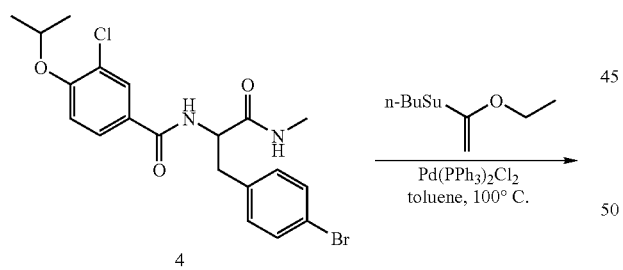

4

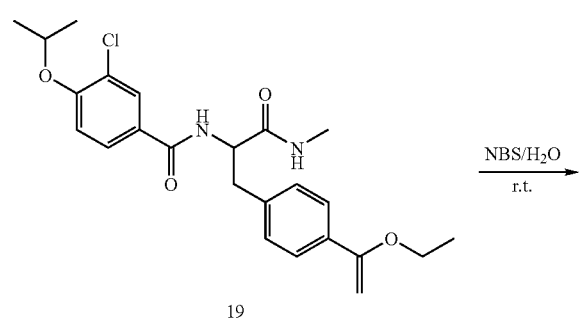

19

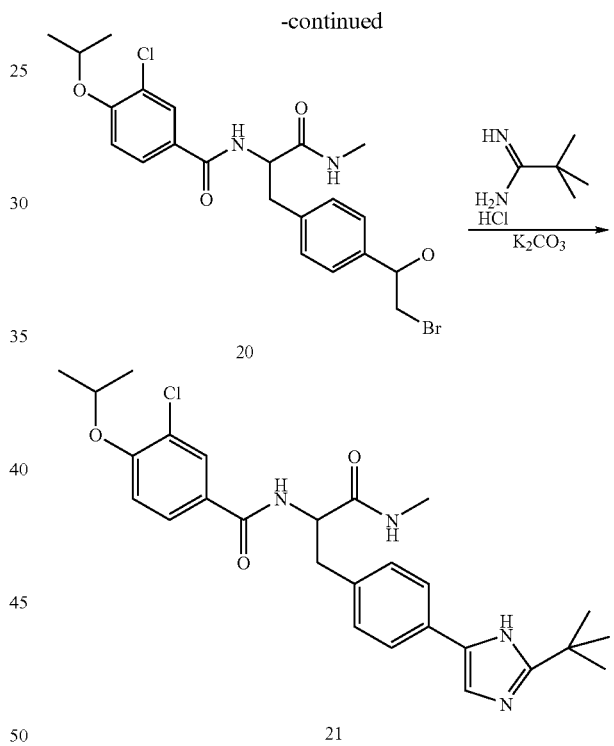

A solution of bromide 4 (1.0 g, 2.20 mol), dichlorobis(triphenylphosphine)palladium(II) (154 mg, 0.220 mol), tributyl(1-ethoxyvinyl)tin (1.49 ml, 4.41 mmol), and toluene (15 mL) under N₂ was stirred at 100° C. for 6 hours. Upon completion, as monitored by LCMS, the reaction mixture was cooled, filtered through Celite, and concentrated in vacuo. The resulting residue was purified by flash column chromatography (silica gel, 2:1:0.1 EtOAc:hexanes:triethylamine) to give 540 mg (55%) of styrene 19. LRMS (M+H⁺) m/z 445.2.

A solution of compound 19 (540 mg, 1.21 mmol), THF:H₂O (3:1, 12 mL), and N-bromo-succinimide (216 mg, 1.21 mmol) was stirred at 23° C. for 1.5 min. The reaction mixture was then concentrated in vacuo and the crude residue diluted with EtOAc (30 mL), washed with brine (10 mL), and concentrated in vacuo. The resulting residue was purified by flash column chromatography (silica gel, 1:1 EtOAc:hexanes) to give 210 mg (35%) of bromoketone 20. LRMS (M+H⁺) m/z 495.1.

A solution of bromoketone 20 (210 mg, 0.42 mmol), K₂CO₃ (174 mg 1.26 mmol), tert-butylcarbamidine hydrochloride (115 mg, 0.84 mmol), and DMF (4 mL) was stirred at 23° C. under N₂ for 18 hours. The reaction mixture was concentrated under high vacuum (0.1 mm Hg), and the resulting residue was purified by column chromatography (silica gel, 4:1 EtOAc:hexanes) to give 50 mg (24%) of imidazole 21. LRMS (M+H⁺) m/z 497.2.

Example 35

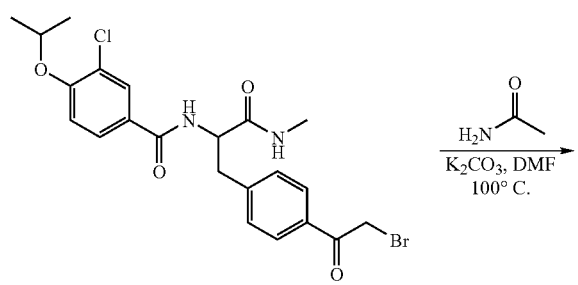

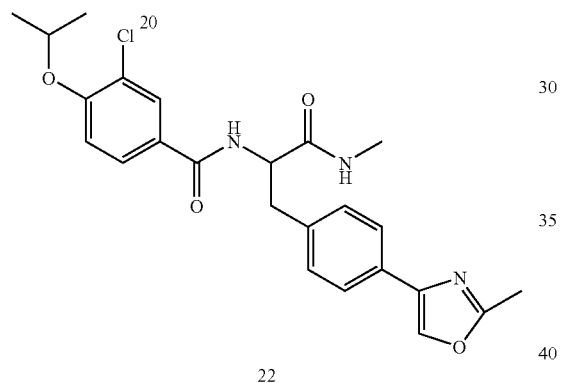

A solution of bromoketone 20 (25 mg, 0.05 mmol), K₂CO₃ (14 mg 0.1 mmol), acetamide (6 mg, 0.1 mmol), and DMF (1 mL) was stirred at 100° C. for 4 hours. The reaction mixture was diluted with EtOAc (15 mL), washed with brine (3×10 mL), and concentrated in vacuo. The resulting residue was purified by column chromatography (silica gel, 2:1 EtOAc:hexanes) to give 5 mg (22%) of oxazole 22. LRMS (M+H⁺) m/z 446.2.

Example 36

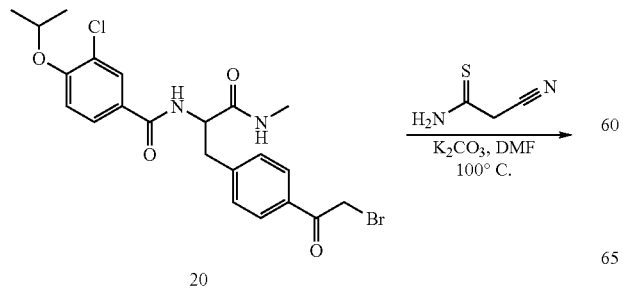

-continued

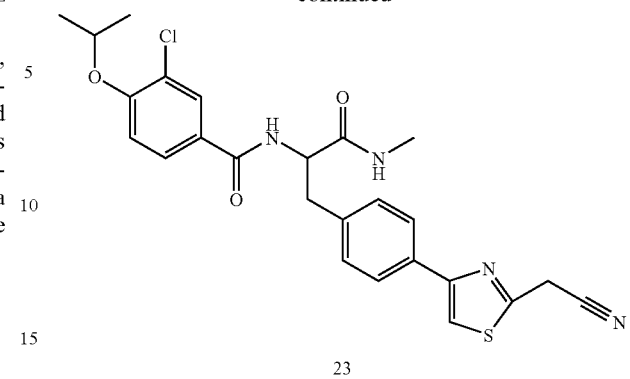

A solution of bromoketone 20 (25 mg, 0.05 mmol), K₂CO₃ (14 mg 0.1 mmol), cyanothioacetamide (10 mg, 0.1 mmol), and DMF (1 mL) was stirred at 100° C. for 4 hours. The reaction mixture was diluted with EtOAc (15 mL), washed with brine (3×10 mL), and concentrated in vacuo. The resulting residue was purified by reverse phase HPLC (C18, acetonitrile/water) to give 5 mg (20%) of thiazole 23. LRMS (M+H⁺) m/z 497.2.

Example 37

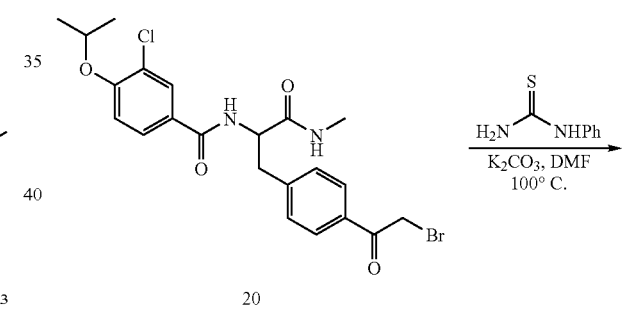

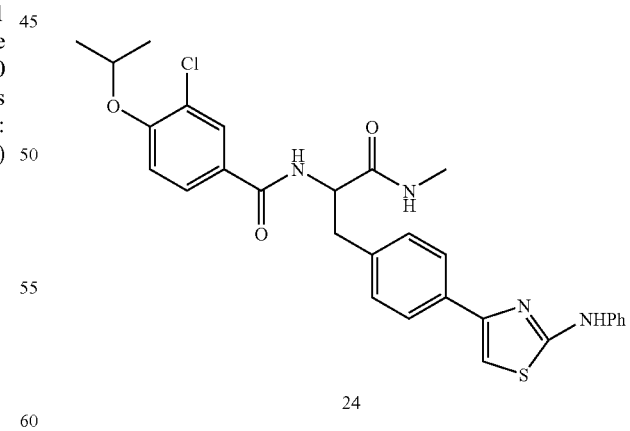

A solution of bromoketone 20 (30 mg, 0.06 mmol), K₂CO₃ (25 mg 0.18 mmol), phenylthiourea (18 mg, 0.12 mmol), and DMF (1 mL) was stirred at 100° C. for 4 hours. The reaction mixture was diluted with EtOAc (15 mL), washed with brine (3×10 mL), and concentrated in vacuo. The resulting residue was purified by reverse phase HPLC (C18, acetonitrile/water) to give 10 mg (30%) of aminothiazole 24. LRMS (M+H⁺) m/z 549.2.

Example 38

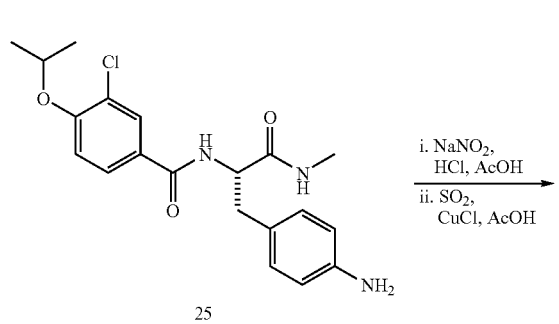

25

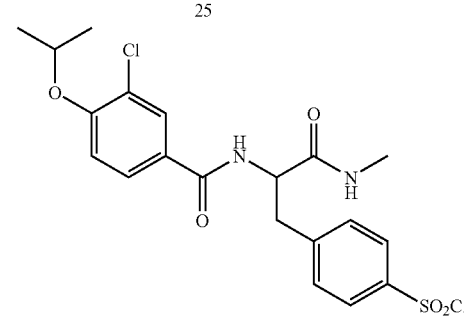

26

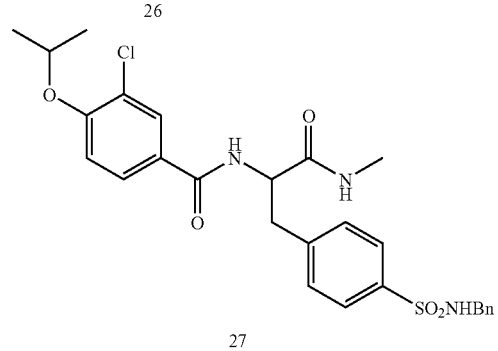

27

A solution of aniline 25 (100 mg, 0.25 mmol), concentrated HCl (1 mL), and AcOH (1 mL) was cooled to −5° C. NaNO₂ (20 mg, 0.29 mmol) was then added slowly to the solution over 1 min. The reaction solution was stirred at −5° C. for 45 min to provide a solution of the diazonium salt.

In another reaction vessel, SO₂ was bubbled through a solution of AcOH (1 mL) and copper(I)chloride (6 mg, 0.06 mmol) until a blue-green color persisted. The diazonium solution was then added slowly over 1 min to the SO₂/CuCl solution. The internal temperature of the reaction solution was stirred below 30° C. The resulting reaction mixture was then poured into cold H₂O (10 mL), extracted with diethyl ether (3×10 mL), and the organic layer was dried (MgSO₄), filtered, and concentrated in vacuo. The crude sulfonyl chloride 26 was used without further purification.

A solution of sulfonyl chloride 26 (74 mg, 0.16 mmol), diisopropyl ethylamine (81 mL, 0.16 mmol), benzyl amine (17 mL, 0.16 mmol) and THF (1 mL) was stirred at 23° C. for 18 hours. The reaction mixture was diluted with EtOAc (15 mL), washed with brine (3×10 mL), and concentrated in vacuo. The resulting residue was purified by column chromatography (silica gel, 1:1 EtOAc:hexanes) to give 25 mg (29%) of sulfonamide 27. LRMS (M+H⁺) m/z 544.2

Example 39

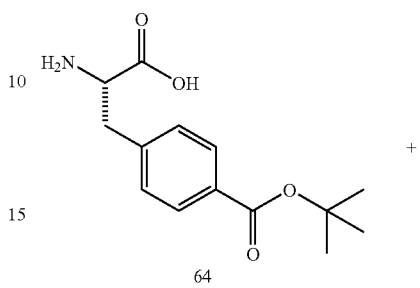

64

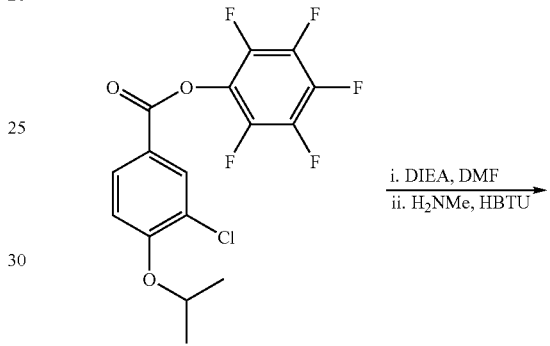

28

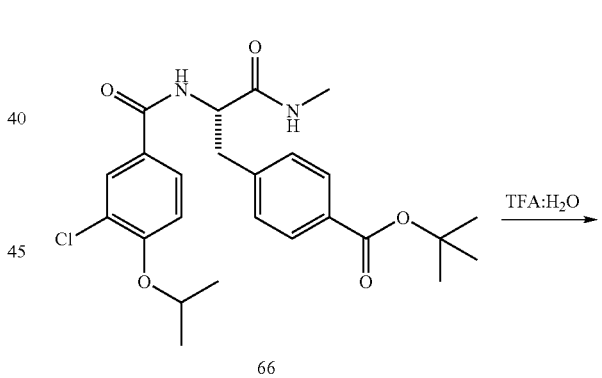

66

67

-continued

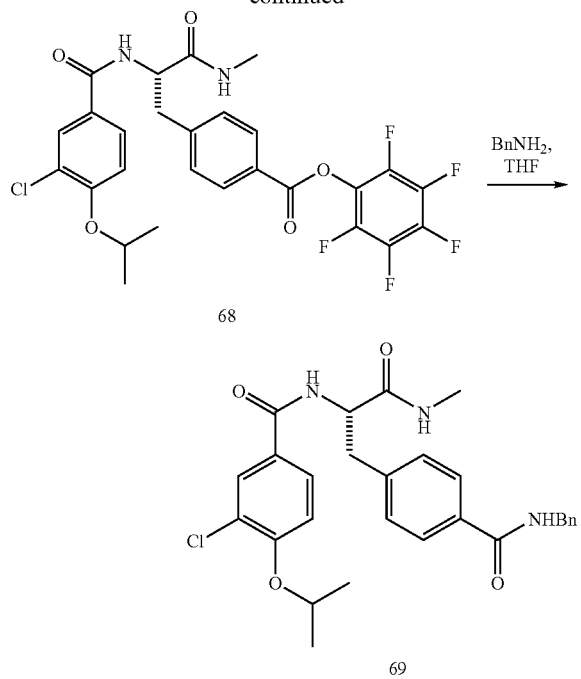

68

69

A solution of amino acid 64 (2.20 g, 8.27 mmol), pentafluorophenyl ester 28 (3.0 g, 7.88 mmol), diisopropylethylamine (5.5 mL, 31.5 mmol), and DMF (30 mL) was stirred at 23° C. After 18 hours, $H_2NMe$ (2.0 M in THF, 3.94 mL), O-benzotriazole-N,N,N',N'-tetramethyl-uronium-hexafluoro-phosphate (HBTU, 6.0 g, 15.76 mmol) was added. After 4 hours, the reaction solution was dissolved in EtOAc (200 mL), washed with brine (3×200 mL), and concentrated in vacuo. The resulting residue was purified by column chromatography (silica gel, 2:1 EtOAc:hexanes) to give 3.5 g (93%) of amide 30. LRMS (M+H$^+$) m/z 475.2.

A solution of ester 66 (3.5 g, 7.36 mmol), TFA:H$_2$O (97.5:2.5, 10 mL), and CH$_2$Cl$_2$ (10 mL) was stirred at 23° C. for 3 hrs. The reaction solution was concentrated in vacuo, and the resulting residue was placed under high vacuum for 2 hours and then used without farther purification.

A solution of acid 67 (4.7 g, 11.2 mmol), pentafluorophenol trifluoroacetate 12 (3.86 mL, 22.4 mmol), triethylamine (4.7 mL, 33.6 mmol), and DMF (25 mL) was stirred at 23° C. for 18 hours. The reaction mixture was then diluted with EtOAc (200 mL), and washed with 1 N HCl (50 mL), saturated aqueous NaHCO$_3$ (50 mL) and brine (100 mL). The organic layer was dried (MgSO$_4$), filtered, and concentrated in vacuo. The resulting residue was purified by flash column chromatography (silica gel, 2:1 hexanes:EtOAc) to yield 1.1 g (17%) of the ester 68.

A solution of ester 68 (20 mg, 0.03 mmol), benzyl amine (6 μL, 0.05 mmol), and THF (0.5 mL) was stirred at 23° C. for 18 hours. The reaction mixture was then diluted with EtOAc (10 mL), and washed with 1 N HCl (5 mL), saturated aqueous NaHCO$_3$ (5 mL) and brine (5 mL). The organic layer was dried (MgSO$_4$), filtered, and the filtrate was concentrated in vacuo. The resulting residue was purified by reverse phase HPLC (C18, acetonitrile/water) to yield 13 mg (85%) of the amide 14. LRMS (M+H$^+$) m/z 508.2.

Example 40

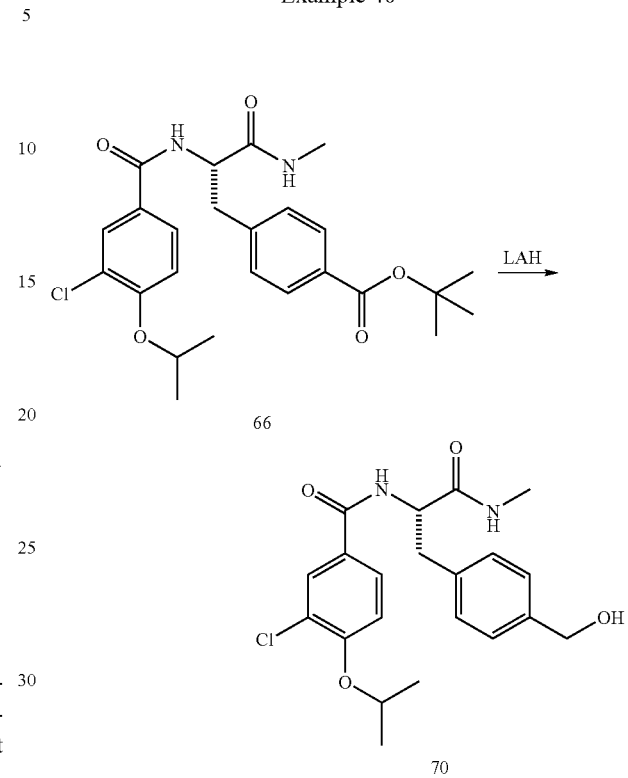

66

70

A solution of ester 66 (50 mg, 0.1 mmol), LiAlH$_4$ (1.0 M in THF, 0.21 mL), and THF (1 mL) was stirred at 23° C. for 2 hours. The reaction mixture was quenched with MeOH (1 mL), then diluted with EtOAc (10 mL), washed with 1 N HCl (5 mL), and brine (5 mL). The organic layer was dried (MgSO$_4$), filtered, and the filtrate was concentrated in vacuo. The resulting residue was purified by reverse phase HPLC (C18, acetonitrile/water) to yield 2 mg (5%) of the alcohol 70. LRMS (M+H$^+$) m/z 405.2.

Example 41

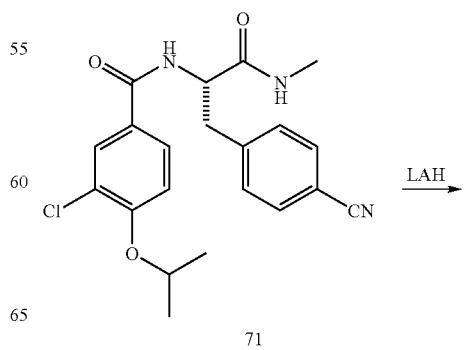

71

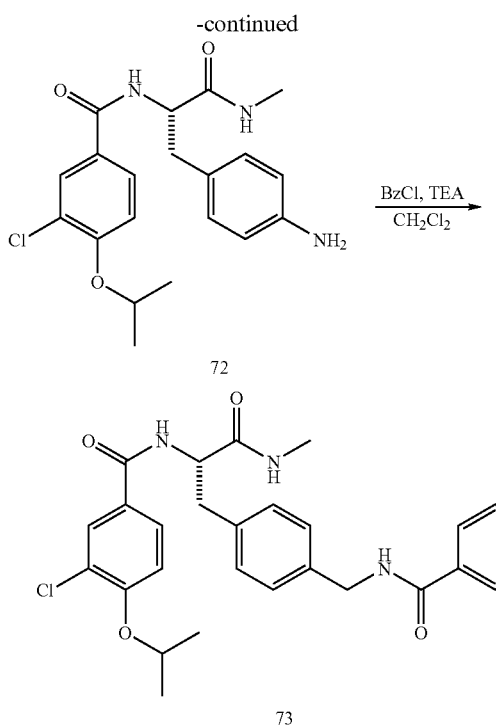

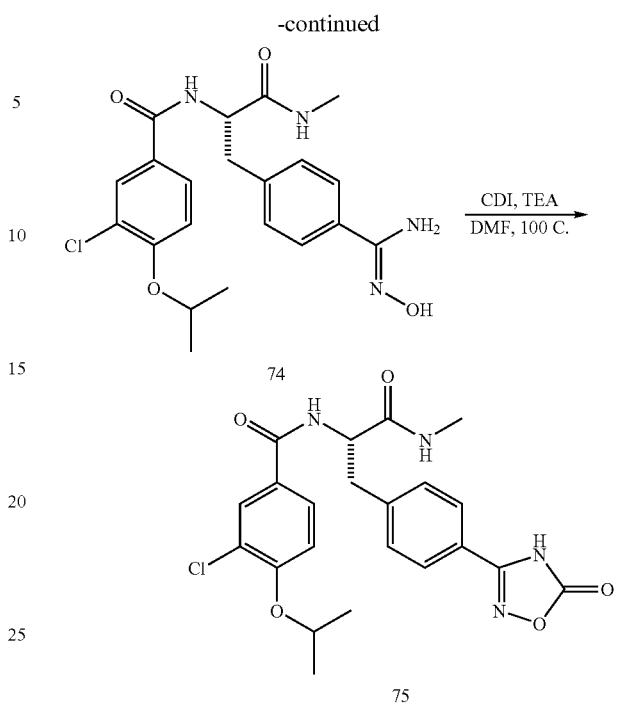

A solution of nitrile 71 (108 mg, 0.27 mmol), LiAlH$_4$ (1.0 M in THF, 0.1 mL), and THF (2 mL) was stirred at 23° C. for 2 hours. The reaction mixture was quenched with MeOH (1 mL), then diluted with EtOAc (10 mL), washed with 1 N HCl (5 mL), and brine (5 mL). The organic layer was dried (MgSO$_4$), filtered, and the filtrate was concentrated in vacuo. The resulting residue was purified by reverse phase HPLC (C18, acetonitrile/water) to yield 30 mg (28%) of the amine 72. LRMS (M+H$^+$) m/z 404.2.

A solution of amine 72 (10 mg, 0.02 mmol), benzoyl chloride (3.2 μL, 0.03 mmol), triethylamine (50 μL, 0.36 mmol), and CH$_2$Cl$_2$ (0.5 mL) was stirred at 23° C. for 2 hours. The reaction mixture was then diluted with EtOAc (15 mL), and washed with 1 N HCl (2 mL), saturated aqueous NaHCO$_3$ (2 mL) and brine (5 mL). The organic layer was dried (MgSO$_4$), filtered, and concentrated in vacuo. The resulting residue was purified by flash column chromatography (silica gel, 2:1 hexanes:EtOAc) to yield 5 mg (49%) of the amide 73. LRMS (M+H$^+$) m/z 508.2.

A solution of nitrile 71 (300 mg, 0.75 mmol), hydroxylamine hydrochloride (156 mg, 2.25 mmol), K$_2$CO$_3$ (726 mg, 5.25 mmol), and EtOH (10 mL) was stirred at 80° C. for 18 hours. The reaction mixture was concentrated in vacuo. The resulting residue was diluted with EtOAc (15 mL) and washed with brine (5 mL). The organic layer was dried (MgSO$_4$), filtered, and the filtrate was concentrated in vacuo. The resulting residue was purified by flash column chromatography (silica gel, 1:20 MeOH:EtOAc) to yield 80 mg (25%) of the hydroxyamidine 74. LRMS (M+H$^+$) m/z 433.2.

A solution of hydroxyamidine 74 (20 mg, 0.05 mmol), carbonyldiimidazole (CDI, 15 mg, 0.09 mmol), triethylamine (13 μL, 0.09 mmol), and DMF (1 mL) was stirred at 100° C. for 2 hours. The resulting residue was diluted with EtOAc (15 mL) and washed with brine (3×5 mL). The organic layer was dried (MgSO$_4$), filtered, and the filtrate was concentrated in vacuo. The resulting residue was purified by flash column chromatography (silica gel, 1:20 MeOH:EtOAc) to yield 10 mg (44%) of the oxadiazolone 75. LRMS (M+H$^+$) m/z 459.2.

Example 42

Example 43

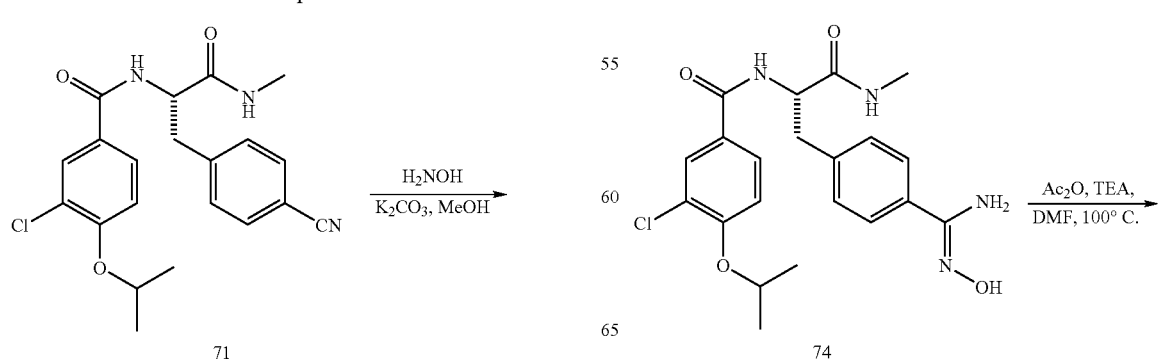

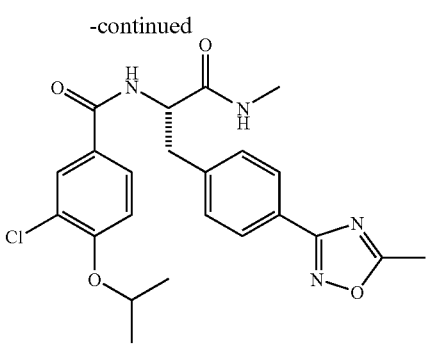

76

A solution of hydroxyamidine 74 (20 mg, 0.05 mmol), triethylamine (13 μL, 0.09 mmol), acetic anhydride (0.5 mL), and DMF (0.5 mL) was stirred at 100° C. for 2 hours. The resulting residue was diluted with EtOAc (15 mL) and washed with brine (3×5 mL). The organic layer was dried (MgSO$_4$), filtered, and the filtrate was concentrated in vacuo. The resulting residue was purified by flash column chromatography (silica gel, 1:20 MeOH:EtOAc) to yield 13 mg (57%) of the oxadiazole 75. LRMS (M+H$^+$) m/z 457.2.

Example 44

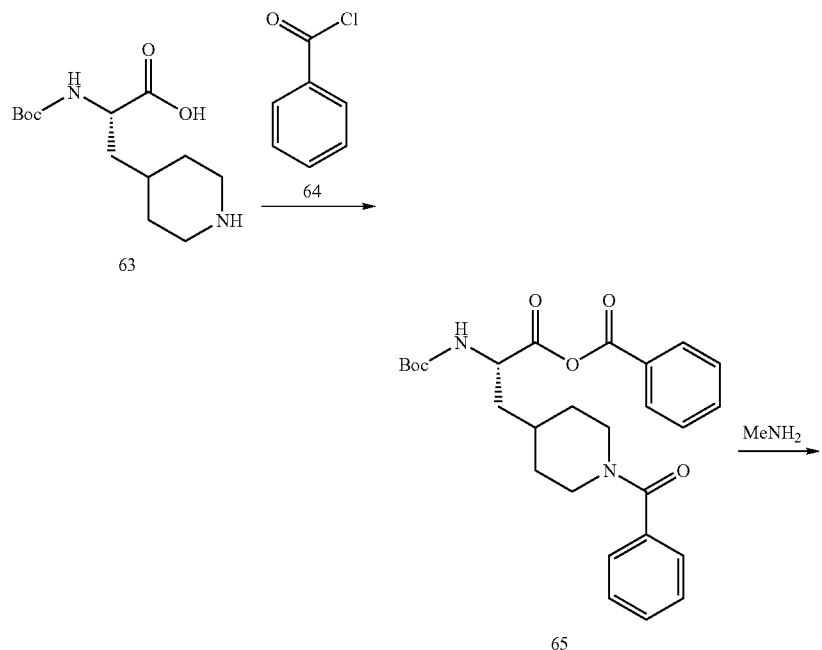

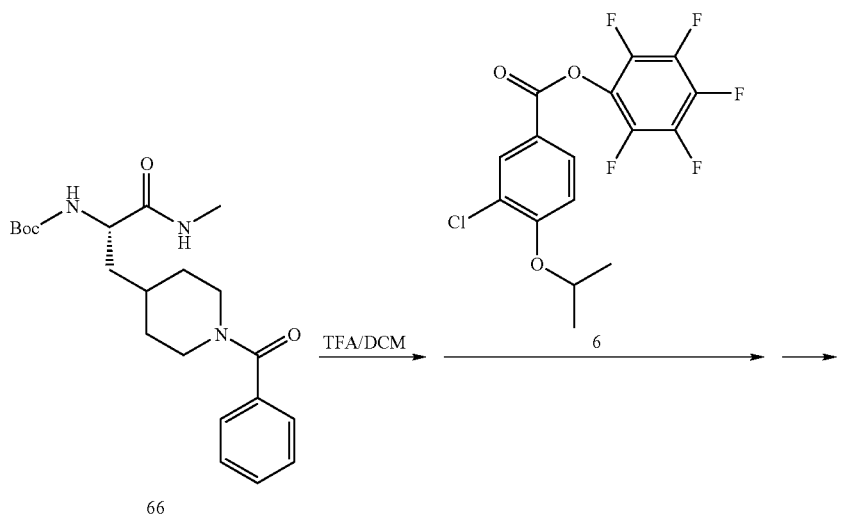

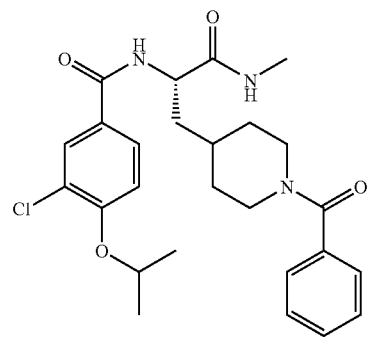

67

To a solution of 63 (100 mg, 0.367 mmol) in DCM (10 mL) were added benzoic chloride 64 (93.8 uL, 0.808 mmol) and diisopropylethylamine (192 uL, 1.10 mmol). After stirring for 10 min, 2 M methylamine in THF (550 uL, 1.10 mmol) was added to the reaction solution. The reaction mixture was stirred for 30 min and concentrated. The residue was purified on a flash silica gel column (hexane:EtOAc, 1:1) to give 66 (100 mg, 70%).

To a solution of 66 (100 mg, 0.257 mmol) in DCM (5 mL) was added TFA (5 mL) at room temperature. The reaction mixture was stirred for 100 min. The solvents were evaporated under reduced pressure, and the residue dried under high vacuum overnight. The residue was dissolved in DMF (2 mL) and then stirred with 6 (117 mg, 0.308 mmol) and diisopropylethylamine (90.0 uL, 0.515 mmol) at room temperature. The reaction mixture was monitored by reverse phase HPLC/MS. The reaction mixture was stirred for 30 min, after which it was filtered, and the filtrate purified by reverse phase HPLC (C18) using a mixture of acetonitrile and H$_2$O to give 67 (100 mg, 52.9%). LCMS (M+H$^+$) m/z 486.2.

Example 45

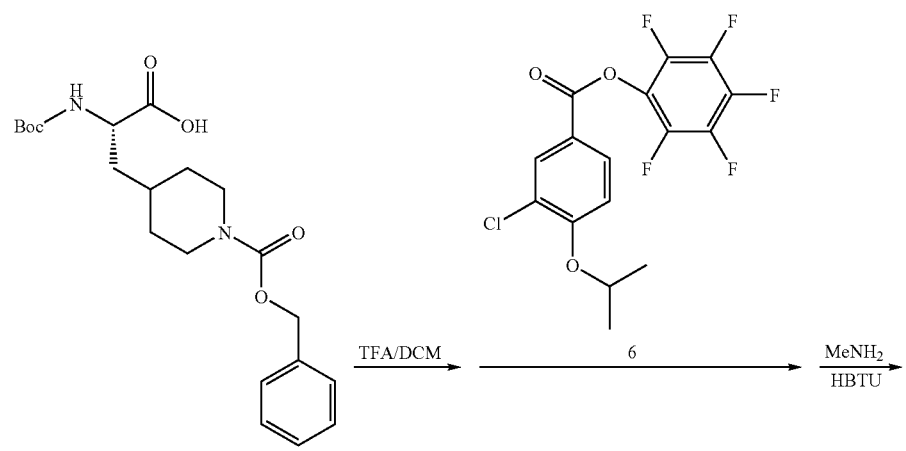

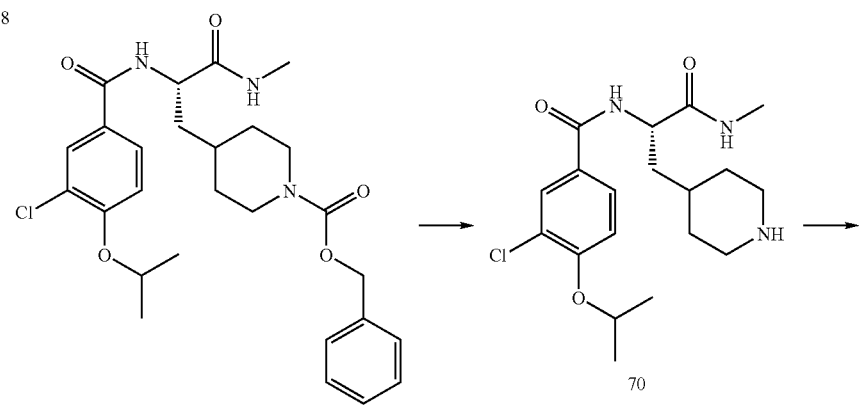

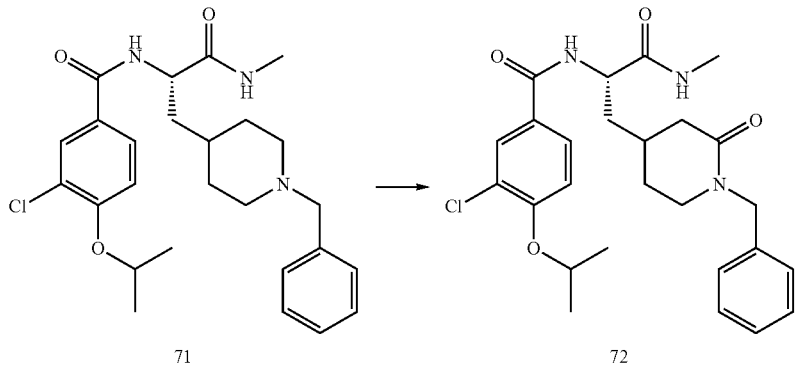

71 → 72

To a solution of 68 (500 mg, 1.23 mmol) in DCM (10 mL) was added TFA (10 mL) at room temperature. The reaction mixture was stirred for 10 min, and then the solvents were evaporated under reduced pressure. The resulting residue (~1.23 mmol) was resuspended in DMF (50 mL) to which was added 6 (562 mg, 1.48 mmol) and diisopropylethylamine (429 uL, 2.46 mmol) at room temperature. The reaction mixture was monitored by reverse phase HPLC/MS. After starting material was no longer observed, 2 M methylamine in THF (1.23 mL, 2.46 mmol) and HBTU (702 mg, 1.85 mmol) were added to the solution. After stirring for 30 min, the solvents were evaporated under reduced pressure and the residue purified on a flash silica gel column (hexane:EtOAc, 1:1) to give 69 (450 g, 71%). LCMS (M+H$^+$) m/z 516.2.

69 (400 mg, 0.775 mmol) was dissolved in HBr/HOAc solution (10 mL). After stirring for 10 min, the solvents were removed. The residue was dissolved in sodium bicarbonate solution (50 mL), and extracted with DCM (50 mL) three times. The combined DCM layers were dried over sodium sulfate and filtered, and the filtrate concentrated under reduced pressure to give 70 (285 mg, 96%).

To a solution of 70 (82.5 g, 0.216 mmol) in DMF (2 mL) were added benzyl bromide (30.8 uL, 0.259 mmol) and diisopropylethylamine (75.3 uL, 0.432 mmol). The reaction mixture was monitored by reverse phase HPLC/MS. After stirring for 2 hours, the mixture was filtered and the filtrate purified by reverse phase HPLC (C18) using a mixture of acetonitrile and H$_2$O to give 71 (183 mg, 90%). LCMS (M+H$^+$) m/z 472.1.

To a solution of 71 (128 mg, 0.271 mmol) in water (1 mL) and methanol (1 mL) were added sodium EDTA (273 mg, 0.814 mmol), HOAc (20 uL) and Hg(OAc)$_2$ (259 mg, 0.814 mmol). The reaction mixture was stirred at 100° C. for 8 h, after which the solvents were evaporated under reduced pressure. The residue was re-dissolved in DMF (2 mL) and filtered, and the filtrate was purified by reverse phase HPLC (C18) using a mixture of acetonitrile and H$_2$O to give 72 (37.6 mg, 28.5%). LCMS (M+H$^+$) m/z 486.1.

Example 46

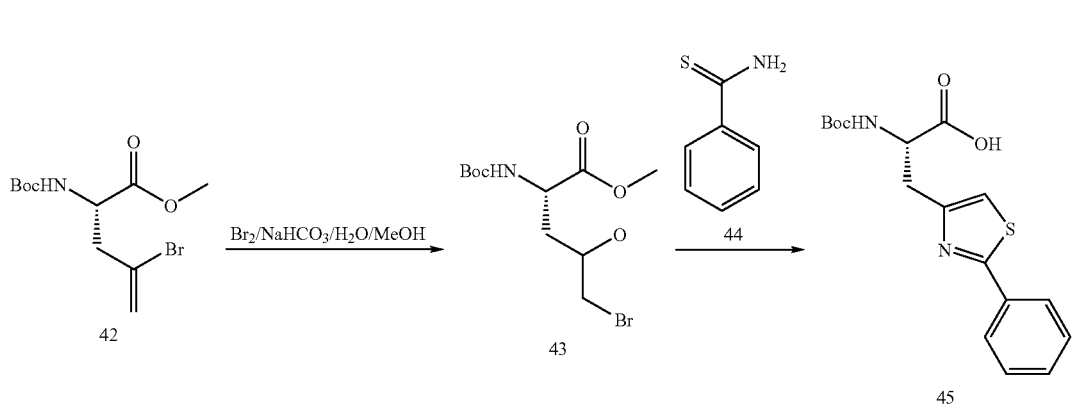

-continued
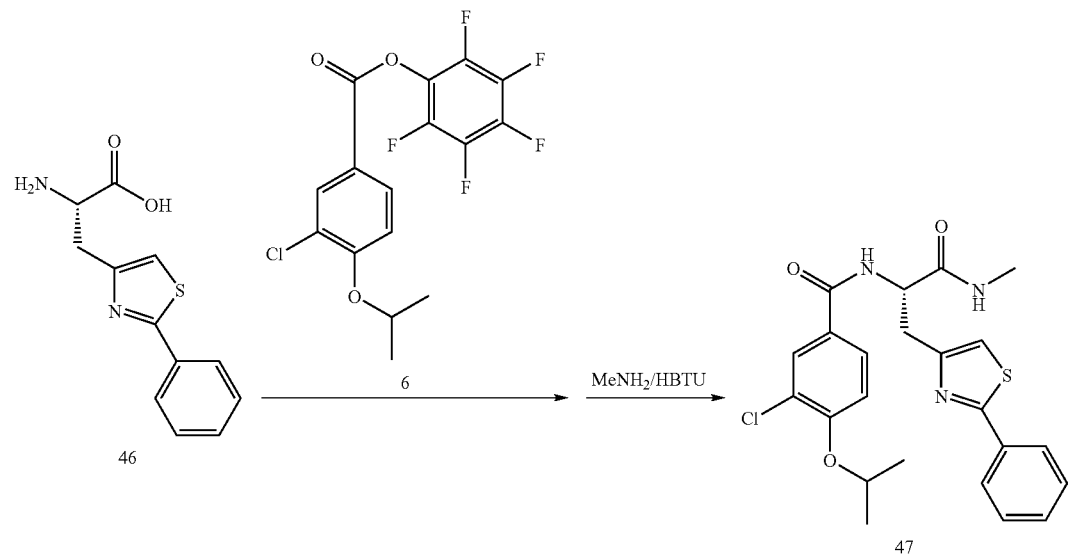
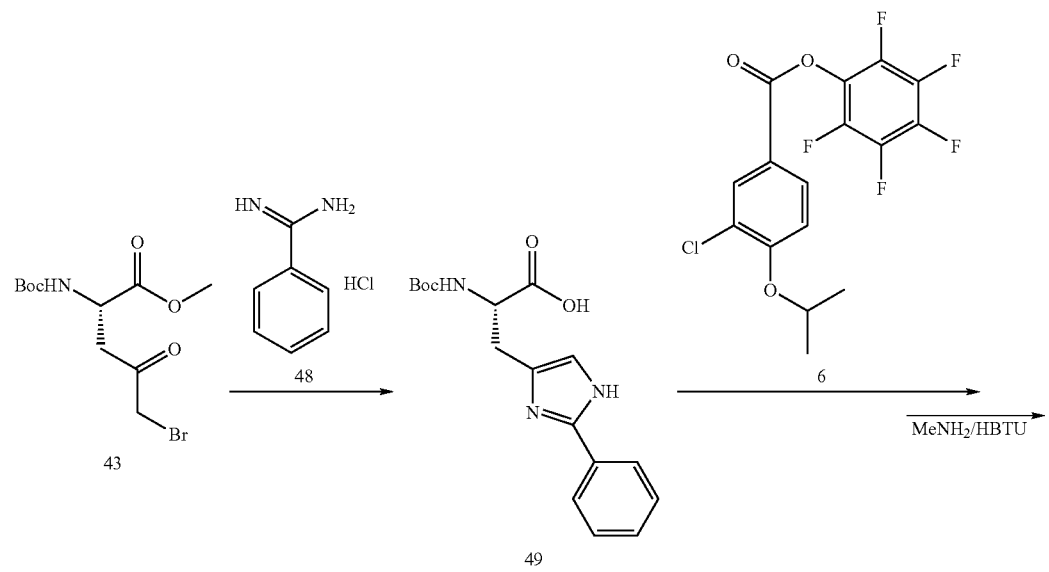
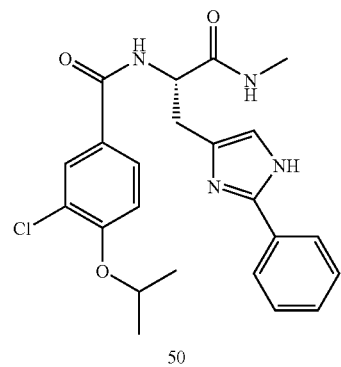

To a solution of 42 (1.0 g, 3.24 mmol) in methanol/water (2/1, 20 mL) was added sodium bicarbonate (327 mg, 3.24 mmol). While stirring over an ice-bath, bromine (200 uL, 3.89 mmol) was added dropwise into the reaction mixture. The reaction mixture was monitored by reverse phase HPLC/MS. After starting material was no longer observed, the solvents were evaporated under reduced pressure. The residue was dissolved in water (100 mL), and extracted with DCM (50 mL) three times. The combined DCM layers were dried over sodium sulfate, the mixture was filtered, and the filtrate was concentrated to give 43.

To a solution of crude 43 (3.24 mmol) in methanol (50 mL) were added diisopropylethylamine (1.14 mL, 6.48 mmol) and benzyl thioamide 44 (445 mg, 3.24 mmol). After stirring at reflux for 24 hours, the solvents were evaporated under reduced pressure. The residue was purified by reversed phase HPLC (C18) using a mixture of acetonitrile and $H_2O$ to give 45 (200 mg, 18%).

To a solution of 45 (150 mg, 0.431 mmol) in DCM (5 mL) was added TFA (5 mL) at room temperature. The reaction mixture was stirred for 10 min. Then the solvents were evaporated under reduced pressure, and the residue 46 (107 mg, 100%) was dried under high vacuum overnight.

To a stirred solution of 46 (0.431 mmol) in DMF (20 mL) were added 6 (197 mg, 0.517 mmol) and diisopropylethylamine (150 uL, 0.862 mmol) at room temperature. The reaction mixture was monitored by reverse phase. HPLC/MS. After starting material was no longer observed, 2 M methylamine in THF (0.431 mL, 0.862 mmol) and HBTU (245 mg, 0.647 mmol) were added to the solution. The reaction mixture was stirred for 30 min, after which the mixture was filtered, and the filtrate purified by reversed phase HPLC (C18) using a mixture of acetonitrile and $H_2O$ to give 47 (80.0 mg, 40.5%). LCMS (M+H$^+$) m/z 458.1.

The same procedures applied to 47 were used for making 50 (58.3 mg). LCMS (M+H$^+$) m/z 441.4.

Example 47

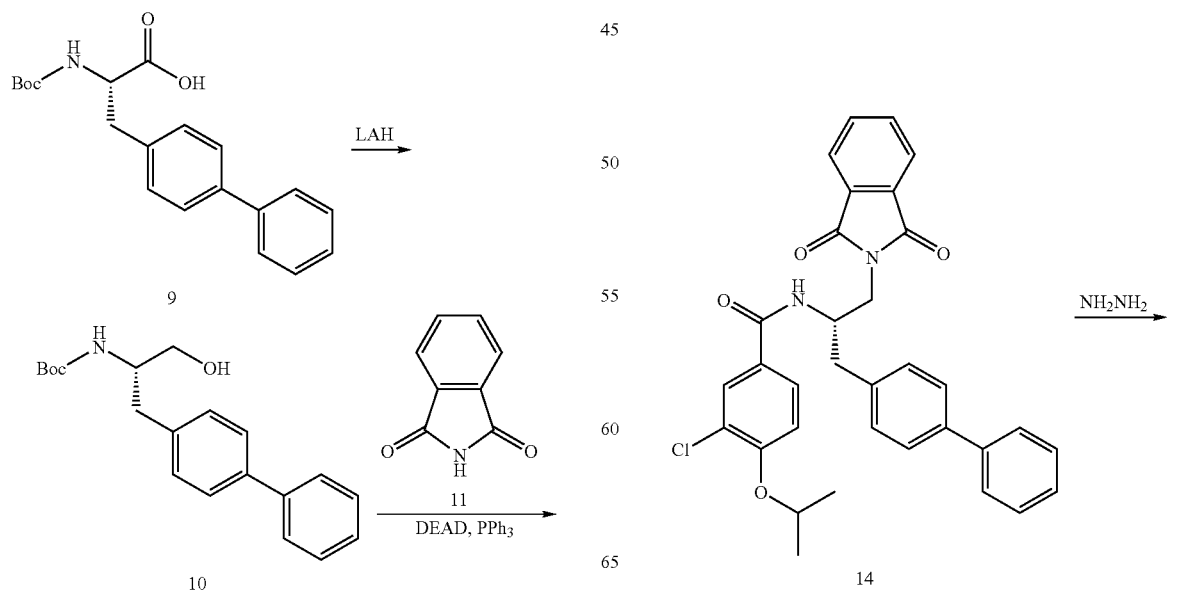

-continued

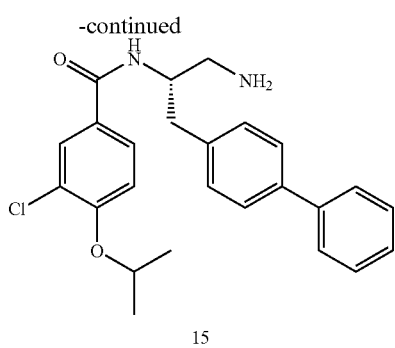

15

To a stirred solution of Boc-p-biphenylalanine 9 (3.0 g; 8.79 mmol) in THF (200 mL) over ice bath was added LAH (1.0 M in THF, 17.6 mL, 17.6 mmol). After stirring for 2 hours, the reaction was quenched with MeOH (10 mL) followed by NaOH solution (17.6 mL, 35.1 mmol). The mixture was filtered through Celite and the filtrate concentrated under reduced pressure. The residue was dissolved in water (200 mL) and extracted by DCM (200 mL) three times. The combined DCM layers were dried (Na₂SO₄), filtered, and concentrated under reduced pressure to give 10 (2.85 g, 98%).

To a stirred solution of 10 (2.85 g, 8.70 mmol) in THF (250 mL) were added 11 (1.54 g, 10.4 mmol) and triphenylphosphine (2.51 g, 9.57 mmol). DEAD (1.49 mL, 9.57 mmol) was then added dropwise and the reaction stirred for 30 min. concentrated in vacuo, and the residue was purified on a flash silica gel column (hexane:EtOAc, 6:1) to obtain the product 12 (2.0 g, 50%).

To a solution of 12 (2.0 g, 4.38 mmol) in DCM (50 mL) was added TFA (50 mL) at room temperature. The reaction mixture was stirred for 20 mm and then concentrated in vacuo to give 13 (1.56 g 100%).

To a solution of 13 in DMF (100 mL) were added 6 (2.0 g, 5.26 mmol) and diisopropylethylamine (1.53 mL, 8.76 mmol) at room temperature. The reaction mixture was stirred overnight. The solvents were evaporated under reduced pressure and the residue purified over silica gel (hexane: EtOAc=2:1) to give 14 (1.5 g, 61.9%). LRMS (M+H⁺) m/z 553.1.

To a solution of 14 (1.5 g, 2.71 mmol) in methanol (20 mL) was added hydrazine hydrate (0.845 mL, 27.1 mmol). The reaction mixture was stirred at 50° C. for 5 h, and then cooled to room temperature. The solid was filtered off, and the filtrate was concentrated under reduced pressure to give 15 (1.0 g, 87.2%). LCMS (M+H⁺) m/z 423.1.

Example 48

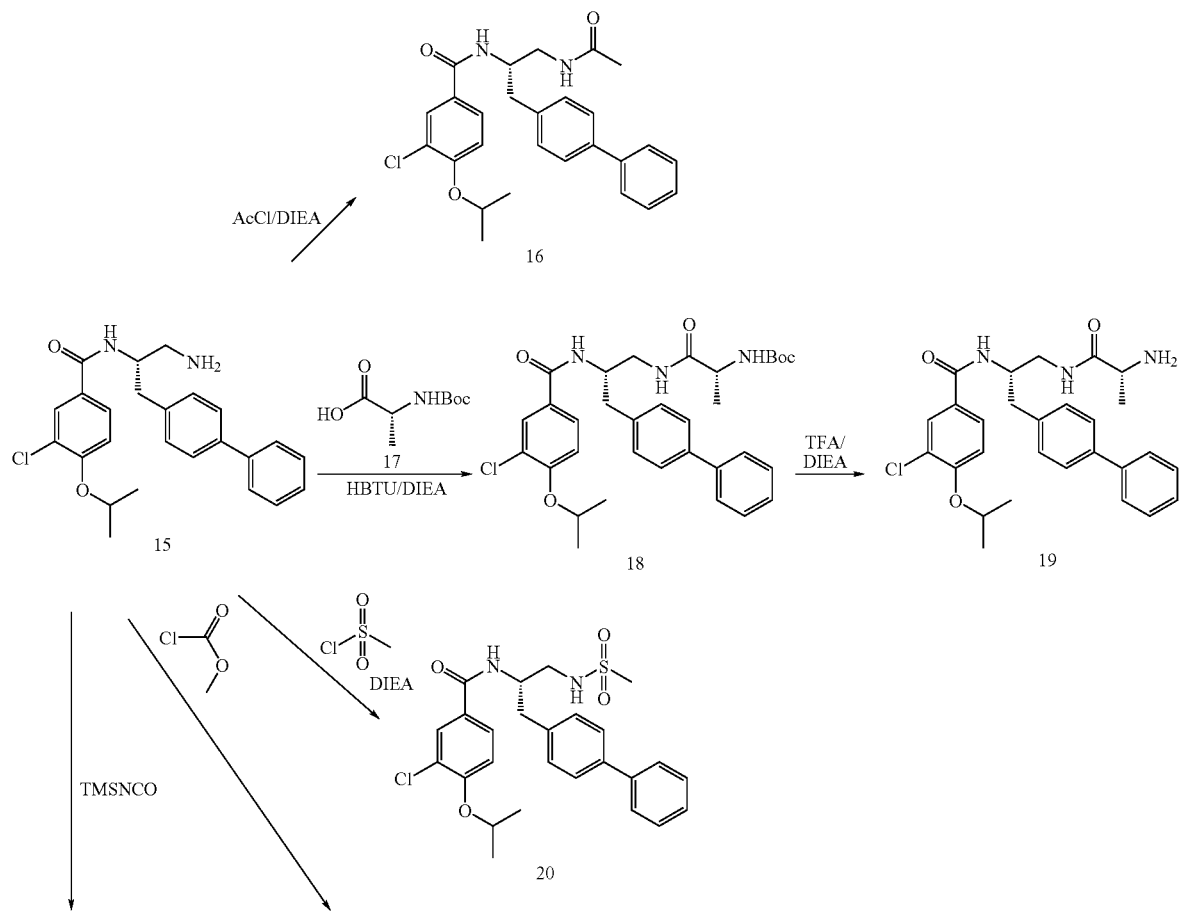

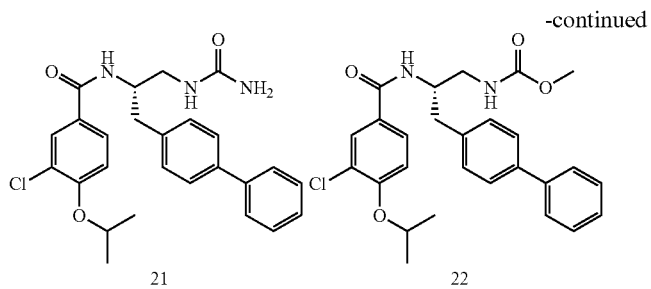

To a solution of 15 (20.0 mg, 0.0473 mmol) in DCM (10 mL) were added diisopropylethylamine (24.7 uL, 0.142 mmol) and acetyl chloride (5.0 uL, 0.0709 mmol). The reaction mixture was stirred for 10 min, then concentrated under reduced pressure and purified on reverse phase HPLC (C18) using a mixture of acetonitrile and H$_2$O to give 16 (8.0 mg, 36.4%). LCMS (M+H$^+$) m/z 465.2.

To a solution of 15 (60.0 mg, 0.142 mmol) in DCM (2 mL) were added diisopropylethylamine (49.5 uL, 0.282 mmol), 17 (32.2 mg, 0.170 mmol) and HBTU (80.8 mg, 0.213 mmol). The reaction mixture was stirred for 10 min and then concentrated under reduced pressure. The resulting residue was dissolved in DCM (1 mL) and TFA (1 mL) and stirred for 10 min. concentrated under reduced pressure and the product purified on reverse phase HPLC (C18) using a mixture of acetonitrile and H$_2$O to give 19 (25.0 mg, 35.6%). LCMS (M+H$^+$) m/z 494.2.

To a solution of 15 (35.0 mg, 0.0828 mmol) in DCM (2 mL) were added diisopropylethylamine (28.8 uL, 0.166 mmol) and methanesulfonyl chloride (9.64 uL, 0.124 mmol). The reaction mixture was stirred for 10 min, then concentrated under reduced pressure and product purified on reverse phase HPLC (C18) using a mixture of acetonitrile and H$_2$O to give 20 (25.0 mg, 60.3%). LCMS (M+H$^+$) m/z 501.2.

To a solution of 15 (60.0 mg, 0.142 mmol) in DCM (2 mL) were added diisopropylethylamine (49.5 uL, 0.282 mmol) and trimethylsiliylisocyanide (19.6 mg, 0.170 mmol). The reaction mixture was stirred for 10 min, then concentrated under reduced pressure and the product purified on reverse phase HPLC (C18) using a mixture of acetonitrile and H$_2$O to give 21 (20.6 mg, 31.1%). LCMS (M+H$^+$) m/z 466.1.

To a solution of 15 (60.0 mg, 0.142 mmol) in DCM (2 mL) were added diisopropylethylamine (49.5 uL, 0.282 mmol) and methyl chloroformate (13.1 uL, 0.170 mmol). The reaction mixture was stirred for 10 min, then concentrated under reduced pressure and the residue purified on reverse phase HPLC (C18) using a mixture of acetonitrile and H$_2$O to give 22 (19.9 mg, 29.1%). LCMS (M+H$^+$) m/z 481.1.

Example 49

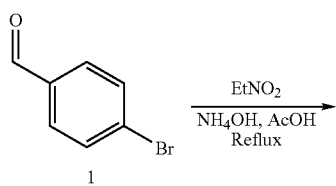

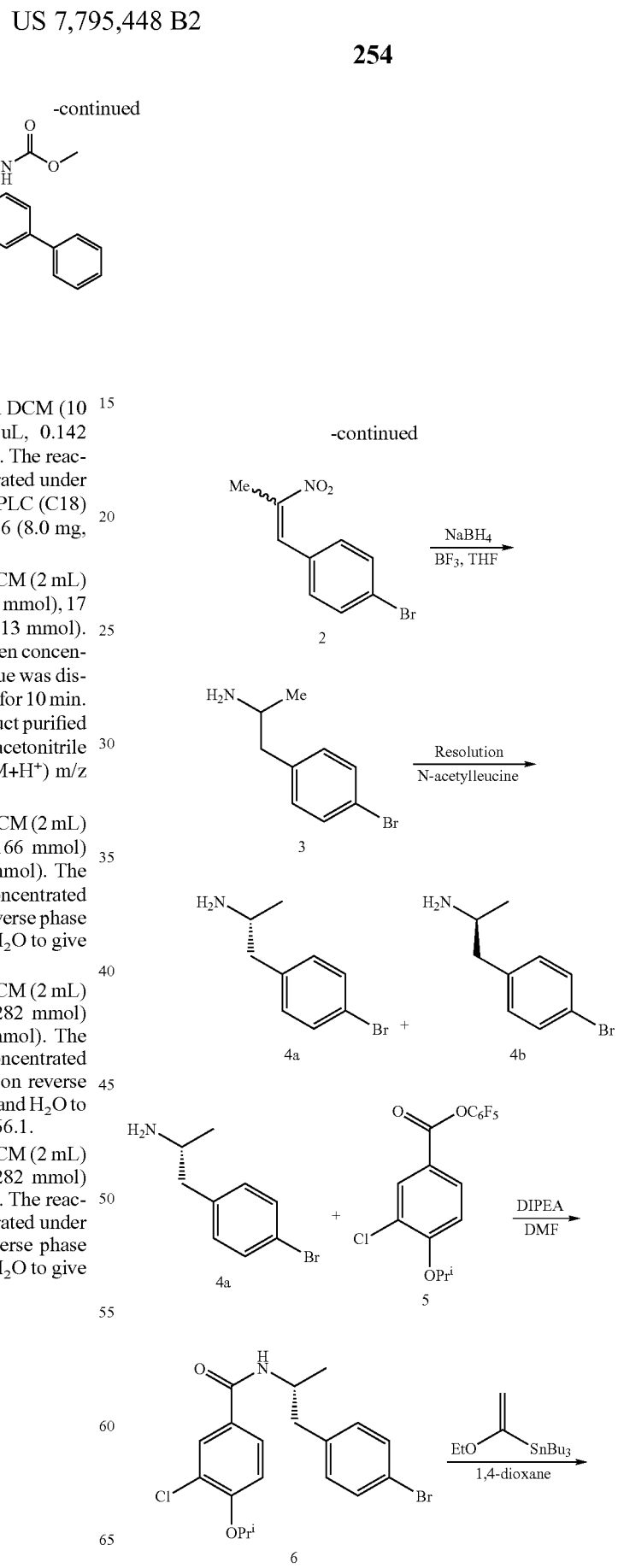

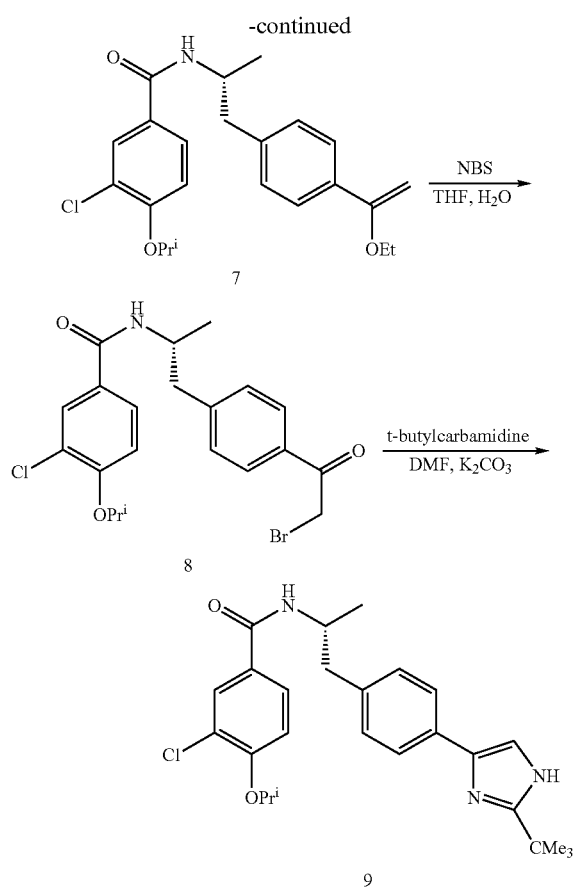

A solution of 4-bromobenzaldehyde (14.8 g, 80 mmol) and ammonium acetate (14.0 g, 180 mmol) in nitroethane (50.0 g) was heated to reflux for 8 hours. It was then cooled to room temperature, partitioned between dichloromethane (150 mL) and water (30 mL). The phases were separated; after which the organic layer was dried over sodium sulfate and concentrated in vacuo. The residue was passed down a plug silica gel column (ethyl acetate/hexane as eluent) followed by recrystallization from methanol to yield intermediate 2 (9.8 g, 51%), which was determined to be pure enough for use in subsequent transformations (LC/MS (LRMS (M+H$^+$) m/z: 240.97).

To a 0° C. solution of sodium borohydride (4.6 g, 124 mmol) in tetrahydrofuran (100 mL) was added borane-tetrahydrofuran complex (150 mL, 150 mmol, 1.0 M). The resulting solution was then stirred at room temperature for an additional 15 minutes. Intermediate 2 (6.5 g, 27 mmol) in tetrahydrofuran (30 mL) was added dropwise, and the resulting solution was refluxed for 4 hours. It was cooled to room temperature and the reaction quenched with water and extracted with dichloromethane (3×80 mL). The combined organic layers were dried over sodium sulfate and concentrated in vacuo, and the residue was purified by flash chromatography (silica gel, hexane/ethyl acetate) to provide intermediate 3 (5.2 g, 90%), which was characterized by LC/MS (LRMS (M+H$^+$) m/z: 213.02).

A 0° C. solution of amine 3 (4.0 g, 16 mmol) in ethyl acetate (30 mL) was saturated with hydrochloric acid (gas). The resulting salt was collected by filtration and dried in vacuo.

L-N-Acetylleucine sodium salt (8.0 mmol) (prepared by addition of 1 N sodium hydroxide solution to a suspension of L-N-acetylleucine (1.39 g, 8.0 mmol) in 5 mL of water until pH=7) was added slowly to a stirred solution of the aforementioned 3 hydrochloride salt in water (10 mL). Crystals formed overnight and were removed by filtration, washed with a small amount of cold water, and recrystallized from absolute methanol. The crystalline 4a salt was collected and dried in vacuo.

The mother liquors, which were rich in (S)-3, were combined, made strongly alkaline with 5 N sodium hydroxide solution, and washed three times with diethyl ether. The combined organic layers were washed with water and dried over sodium sulfate. After removal of sodium sulfate, hydrochloric acid was passed through the solution until the precipitation of hydrochloride salt was complete. The same procedure as above was applied with D-N-acetylleucine salt. The crystalline 4b salt was collected and dried in vacuo.

The diastereomeric salt of each enantiomer was partitioned between 20 mL of water, made strongly alkaline with 5 N sodium hydroxide solutions, and extracted with diethyl ether. The combined organic layers were washed with water and dried over sodium sulfate. The solvents were removed, and both products were determined to be pure enough for use in subsequent transformations (4a: 1.3 g, 32%; 4b: 0.9 g, 22%) ($^1$H-NMR and LC/MS (LRMS (M+H$^+$) m/z: 213.02)). Capillary electrophoresis indicated >98% ee.

To a room temperature solution of amine 4a (111 mg, 0.52 mmol) in dimethylformamide (5 mL) was added diisopropylethylamine (99 µl, 0.57 mmol). The resulting solution was stirred for 5 minutes and intermediate 5 (217 mg, 0.57 mmol) was added. The reaction mixture was stirred under an atmosphere of nitrogen for 30 minutes and the solvents were removed in vacuo. The residue was partitioned between ethyl acetate (20 mL) and aqueous citric acid solution (20 mL, 10%). The layers were separated, and the organic phase was washed with aqueous citric acid solution (20 mL, 10%) and aqueous potassium hydroxide solution (2×20 mL, 0.1 M). It was then dried over sodium sulfate and concentration in vacuo to yield 6 (212 mg, 100%), which was determined to be pure enough for use in subsequent transformations (LRMS (M+H$^+$) m/z: 410.1).

To a room temperature solution of bromide 6 (212 mg, 0.53 mmol) in dioxane (10 mL) were added trans-dichlorobis (triphenylphosphine)palladium(II) (37 mg, 10 mol %) and 1-ethoxyvinyltri-n-butyltin (481 mg, 1.33 mmol), successively. The resulting solution was heated to 100° C. for 4 hours. It was cooled to room temperature and the solvents were removed in vacuo. The residue was then purified by flash chromatography (silica gel, ethyl acetate plus 5% triethylamine) to provide intermediate 7 (250 mg) which was unstable and determined to be pure enough for use in subsequent transformations LC/MS (LRMS (M+H$^+$) m/z: 402.8).

Intermediate 7 in tetrahydrofuran (10 mL) and water (3 mL) was stirred with N-bromosuccinimide (190 mg, 1.1 mmol) at 50° C. for 2 hours. The solvents were removed in vacuo, and the resulting residue was partitioned between water (10 mL) and extracted with ethyl acetate (3×50 mL). The combined organic layers were dried over sodium sulfate and concentrated in vacuo. The residue was then purified by flash chromatography (silica gel, hexane/ethyl acetate) to provide intermediate 8 (55 mg, 23%), which was characterized by LC/MS (LRMS (M+H$^+$) m/z: 452.1).

To a room temperature solution of intermediate 9 (55 mg, 0.12 mmol) in dimethylformamide (3 mL) was added potassium carbonate (34 mg, 0.24 mmol) and tert-butylcarbamidine (31 mg, 0.30 mmol). The reaction mixture was stirred under an atmosphere of nitrogen at 50° C. for 1.5 hours. It was cooled to room temperature and the solvents were removed in vacuo. The residue was partitioned between ethyl acetate (15 mL) and water (15 mL). The layers were separated and the aqueous phase was extracted with ethyl acetate (2×20 mL). The combined organic layers were dried over sodium sulfate and concentrated in vacuo. The residue was then purified by flash chromatography (silica gel, hexane/ethyl acetate) to provide 9 (35 mg, 67%), which was characterized by $^1$H NMR and LC/MS (LRMS (M+H$^+$) m/z: 452.1).

Example 50

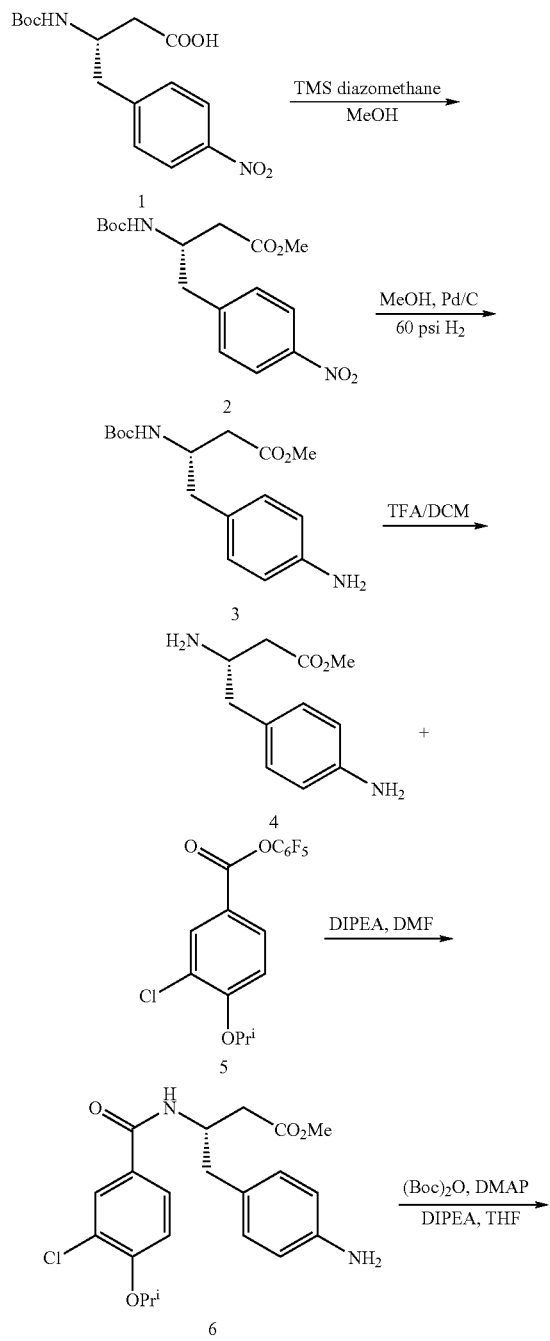

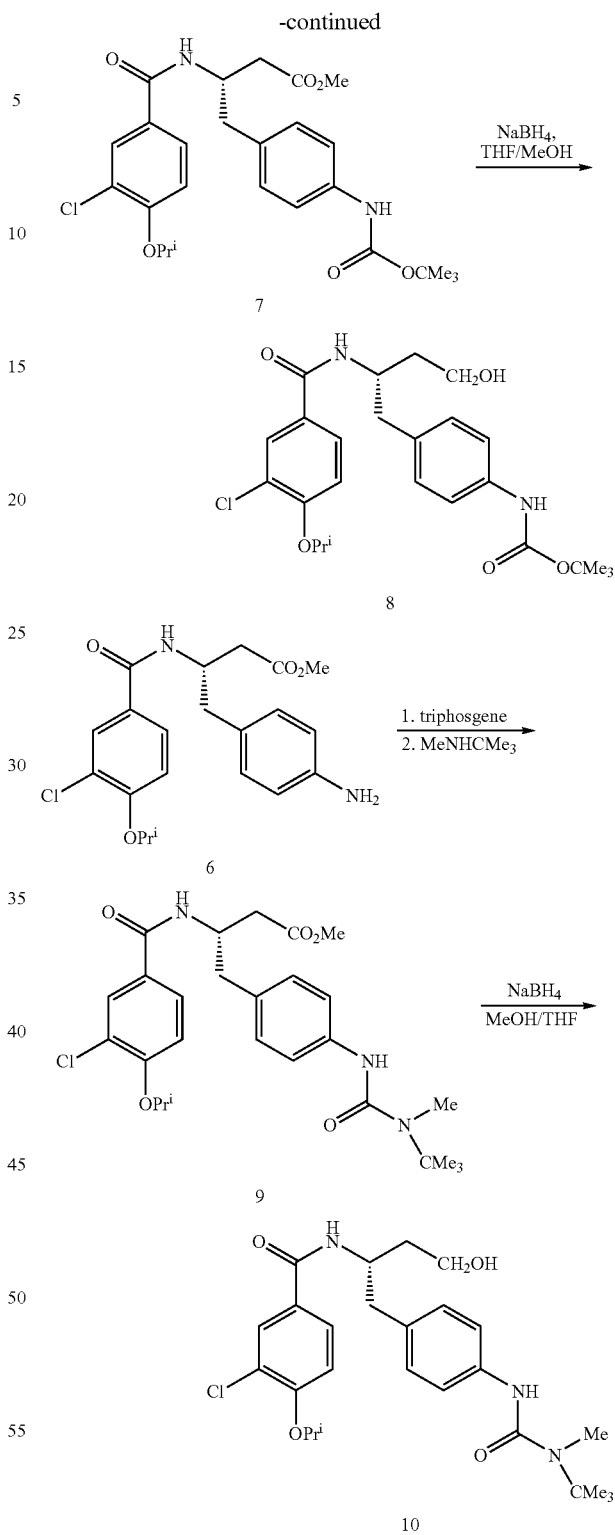

To a room temperature solution of acid 1 (2.98 g, 9.2 mmol) in methanol (15 mL) was added dropwise a solution of TMS diazomethane in hexanes (9.2 mL, 18.4 mmol, 2.0 M). The resulting yellow solution was stirred at ambient temperature for 30 minutes, and the solvents were removed in vacuo. The residual viscous oil 2 (3.10 g, 9.2 mmol) was dried and determined to be pure enough for use in subsequent transformations (LC/MS (LRMS (M+H$^+$) m/z: 339.10)).

A mixture of intermediate 2 (3.10 g, 9.2 mmol) and palladium on carbon (310 mg) in methanol (30 mL) was stirred under hydrogen at room temperature for 2 hours. It was then filtered through Celite and concentrated to provide aniline 3 (2.47 g, 8.0 mmol) as a viscous oil, which was dried and determined to be pure enough for use in subsequent transformations (LC/MS (LRMS (M+H$^+$) m/z: 309.20)).

To a room temperature solution of aniline 3 (2.47 g, 8.0 mmol) in dichloromethane (20 mL) was added trifluoroacetic acid (20 mL). The resulting solution was stirred for 45 minutes, and the solvents were removed in vacuo. The residue was partitioned between dichloromethane (75 mL) and saturated aqueous sodium bicarbonate solution (25 mL), and the layers were separated. The aqueous phase was saturated with sodium chloride and extracted with dichloromethane (3×75 mL) and tetrahydrofuran (2×50 mL). The combined organic layers were dried over sodium sulfate and concentrated in vacuo to provide 4 (1.30 g, 6.3 mmol) as a viscous oil, which was characterized by LC/MS (LRMS (MH) m/z: 209.30).

A solution of amine 4 (1.30 g, 6.25 mmol) in dimethylformamide (20 mL) was stirred with diisopropylethylamine (3.27 ml, 18.80 mmol) at room temperature for 5 minutes, followed by the addition of intermediate 5 (2.38 g, 6.25 mmol). The reaction mixture was stirred for additional 30 minutes, and the solvents were removed in vacuo. The residue was partitioned between ethyl acetate (50 mL) and water (50 mL). The layers were separated, and the aqueous phase was extracted with ethyl acetate (3×50 mL). The combined organic layers were dried over sodium sulfate and concentrated in vacuo. The residue was purified by flash chromatography (silica gel, hexane/ethyl acetate) to provide 6 (1.47 g, 58%) as a foamy white solid, which was characterized by (LC/MS (LRMS (M+H$^+$) m/z: 405.15).

To a room temperature solution of aniline 6 (131 mg, 0.32 mmol) in tetrahydrofuran (5 mL) were added diisopropylethylamine (85 µL, 0.48 mmol), 4-(dimethylamino)pyridine (15 mg, 0.12 mmol), and di-tert-butyldicarbonate (85 mg, 0.39 mmol). The resulting solution was stirred overnight and then diluted with ethyl acetate (20 mL), washed with aqueous hydrochloric acid solution (2×15 mL, 0.1 M) and dried over sodium sulfate. Removal of solvents yielded carbamate 7 (139 mg, 88%) as a glassy solid, which was determined to be pure enough for use in subsequent transformations (LC/MS (LRMS (M+H$^+$) m/z: 505.10).

To a room temperature solution of carbamate 7 (139 mg, 0.28 mmol) in methanol (2 mL) and tetrahydrofuran (2 mL) was added sodium borohydride (261 mg, 6.9 mmol). The resulting mixture was stirred for 2 hours, after which the solvents were removed in vacuo. The residue was partitioned between ethyl acetate (15 mL) and water (15 mL), the layers were separated, and the aqueous phase was extracted with ethyl acetate (3×15 mL). The combined organic layers were dried over sodium sulfate and concentrated in vacuo. The residue was purified by reverse-phase HPLC using a mobile phase gradient consisting of acetonitrile and water. The pure product 8 (47 mg, 36%) was isolated and characterized by $^1$H-NMR and LC/MS (LRMS (M+H$^+$) m/z: 477.20).

To a 0° C. solution of triphosgene (37 mg, 0.13 mmol) in tetrahydrofuran (15 mL) was added dropwise a solution of 6 (145 mg, 0.36 mmol) and diisopropylethylamine (130 µL, 0.75 mmol) in tetrahydrofuran (5 mL). The resulting mixture was kept under an atmosphere of nitrogen at the same temperature for 30 minutes and quenched with methyl-tert-butylamine (215 µL, 1.80 mmol). The reaction mixture was stirred for an additional 30 minutes followed by removal of the solvents in vacuo. The residue was partitioned between ethyl acetate (15 mL) and aqueous hydrochloric acid solution (15 mL, 0.1 M), the layers were separated, and the aqueous phase was extracted with ethyl acetate (2×15 mL). The combined organic layers were dried over sodium sulfate and concentrated in vacuo to yield urea 9 (152 mg, 0.29 mmol) as a glassy solid, which was determined to be pure enough for use in subsequent transformations (LC/MS (LRMS (M+H$^+$) m/z: 518.2).

To a room temperature solution of urea 9 (150 mg, 0.29 mmol) in methanol (2 mL) and tetrahydrofuran (2 mL) was added sodium borohydride (260 mg, 6.90 mmol). The resulting mixture was stirred under an atmosphere of nitrogen at room temperature for 2 hours. The solvents were removed and the residue was partitioned between ethyl acetate (15 mL) and water (15 mL). The layers were separated and the aqueous phase was extracted with ethyl acetate (3×15 mL). The combined organic layers were dried over sodium sulfate and concentrated in vacuo. The residue was purified by reverse-phase HPLC using a mobile phase gradient consisting of acetonitrile and water. The pure product 10 (4 mg, 28%) was isolated and characterized by $^1$H-NMR and LC/MS (LRMS (M+H$^+$) m/z: 490.1).

Example 51

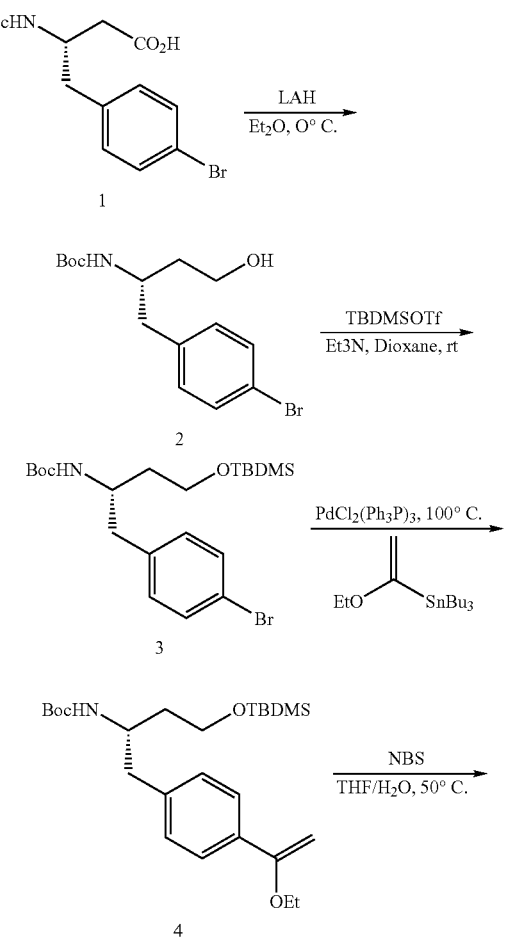

-continued

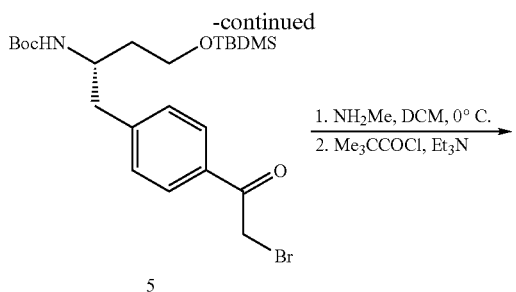
5

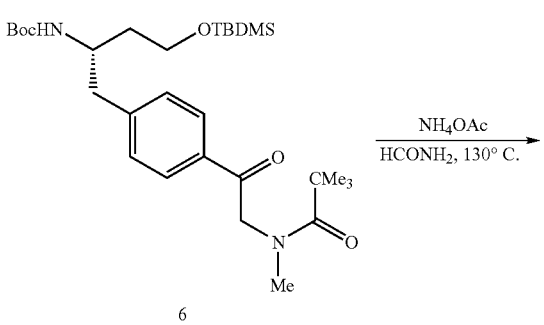
6

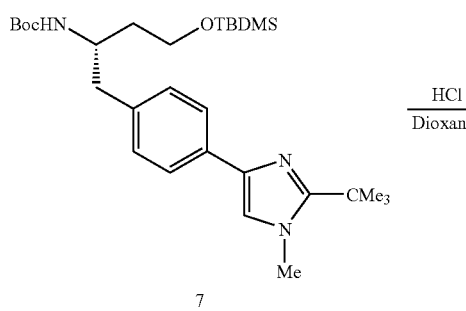
7

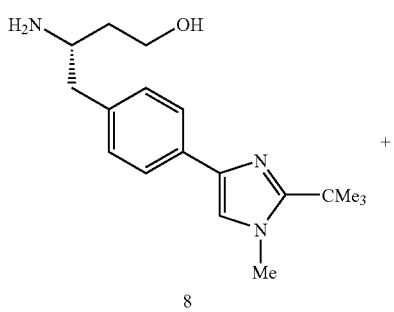
8

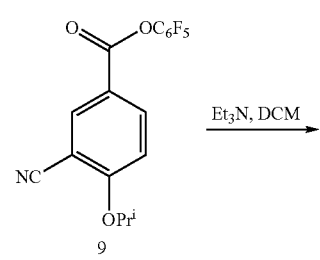
9

-continued

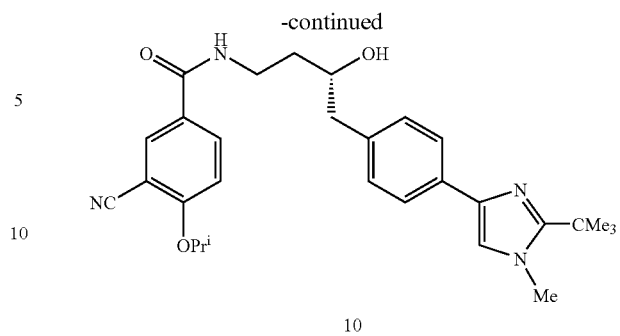
10

To a solution of carboxylic acid 1 (10.0 g, 28 mmol) in anhydrous diethyl ether (200 mL) at 0° C. was added dropwise a solution of lithium aluminum hydride in tetrahydrofuran (40 mL, 40 mmol, 1 M). The resulting solution was then stirred for an additional 2 hours at the same temperature. It was carefully quenched with water (2.5 mL), aqueous sodium hydroxide (2.5 mL, 1M) and water (3.0 mL). The solution was then dried over sodium sulfate and removal of the solvents yielded intermediate 2 (9.2 g, 96%), which was determined to be pure enough for use in subsequent transformations ($^1$H-NMR and LC/MS (LRMS (M+H$^+$) m/z: 344.08)).

To a room temperature solution of intermediate 2 in anhydrous dioxane (200 mL) were added triethylamine (6 mL, 40 mmol) and tert-butyldimethylsilyltrifluoro methanesulfonate (8.6 g, 32 mmol). The resulting solution was then stirred overnight and quenched with saturated aqueous sodium bicarbonate solution. It was extracted with dichloromethane (3×100 mL), and the combined organic layers were dried over sodium sulfate and concentrate in vacuo. The residue was purified by flash chromatography (silica gel, hexane/ethyl acetate) to provide intermediate 3 (9.2 g, 72% overall), which was characterized by LC/MS (LRMS (M+H$^+$) m/z: 458.16).

To a room temperature solution of bromide 3 (6.0 g, 13 mmol) in dioxane (100 mL) were added trans-dichlorobis(triphenylphosphine)palladium(II) (500 mg) and 1-ethoxyvinyltri-n-butyltin (12.3 g, 34 mmol), successively. The resulting solution was heated to 100° C. for 4 hours. Removal of the solvents in vacuo was followed by purification by flash chromatography (silica gel, hexane/ethyl acetate plus 5% triethylamine) to provide intermediate 4 (5.4 g) which was characterized by LC/MS (LRMS (M+H$^+$) m/z: 450.30). The product was found to be unstable and used immediately in subsequent transformations.

Intermediate 4 in methanol (100 mL) and water (50 mL) was stirred with N-bromosuccinimide (5.9 g, 33 mmol) at 50° C. for 4 hours. The solvents were removed in vacuo, and the resulting residue extracted with ethyl acetate (3×50 mL). The combined organic layers were dried over sodium sulfate and concentrate in vacuo. The residue was then purified by flash chromatography (silica gel, hexane/ethyl acetate) to provide intermediate 5 (4.5 g, 69% overall), which was characterized by LC/MS (LRMS (M+H$^+$) m/z: 500.54).

Under a nitrogen atmosphere, a pressure-equalizing dropping funnel charged with the bromomethyl ketone 5 (2.5 g, 5.0 mmol) in dichloromethane (40 mL) was attached to a 150-mL flask which contains a solution of methylamine (15 mL, 30 mmol, 1 M in THF). The flask was cooled to 0° C., and the bromide solution was added dropwise over 2 hours. The resulting solution was stirred for one more hour, after which triethylamine (1 mL) and a solution of trimethylacetyl chloride (4.8 mL, 40 mmol) in dichloromethane (10 mL) were added. The resulting mixture was stirred for another 2 hours and then quenched with saturated sodium bicarbonate solution. The mixture was extracted with ethyl acetate (3×50 mL), and the combined organic layers were dried over sodium sulfate and concentrated in vacuo. Purification of the residue by flash chromatography (silica gel, ethyl acetate/hexane) provided ester 6 (1.3 g, 49% overall), which was characterized by $^1$H-NMR and LC/MS analysis (LRMS (M+H$^+$) m/z: 535.35).

A solution of 6 (1.3 g, 2.6 mmol) in an excess of ammonium acetate in formamide (10 mL) was heated to 130° C. under a nitrogen atmosphere for 3 hours. The resulting mixture was cooled to room temperature, partitioned between water and extracted with dichloromethane (3×50 mL). The combined organic layers were dried over sodium sulfate and concentrated in vacuo. The residue was purified by flash chromatography (silica gel, ethyl acetate/hexane) providing imidazole 7 (0.8 g, 60%), which was characterized by $^1$H-NMR and LC/MS analysis (LRMS (M+H$^+$) m/z: 516.35).

A solution of 7 (800 mg, 1.55 mmol) in tetrahydrofuran (10 mL) was stirred with hydrogen chloride in 1,4-dioxane (10 mL, 4.0 M) at room temperature for one hour. The solvents were removed in vacuo, and the residue was dried under high vacuum overnight to yield intermediate 8 (600 mg), which was determined to be pure enough for the next transformation ($^1$H-NMR and LC/MS (LRMS (M+H$^+$) m/z 302.22)).

To a room temperature solution of amine 8 (60 mg, 0.02 mmol) in dimethylformamide (3 mL) was added diisopropylethylamine (53 µl, 0.30 mmol) and the resulting solution stirred at room temperature for 5 minutes. Intermediate 9 (23 mg, 0.06 mmol) was then added, and the reaction mixture was stirred under an atmosphere of nitrogen for 30 minutes. The solvents were removed in vacuo, and the residue purified by flash chromatography (silica gel, methanol/dichloromethane) to provide 10 (25 mg, 26%) as a glassy solid, which was characterized by $^1$H NMR and LC/MS (LRMS (M+H$^+$) m/z: 489.28).

Example 52

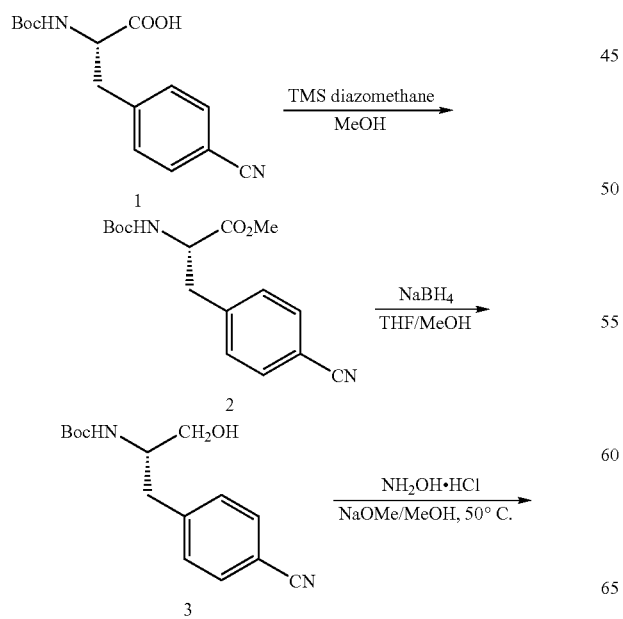

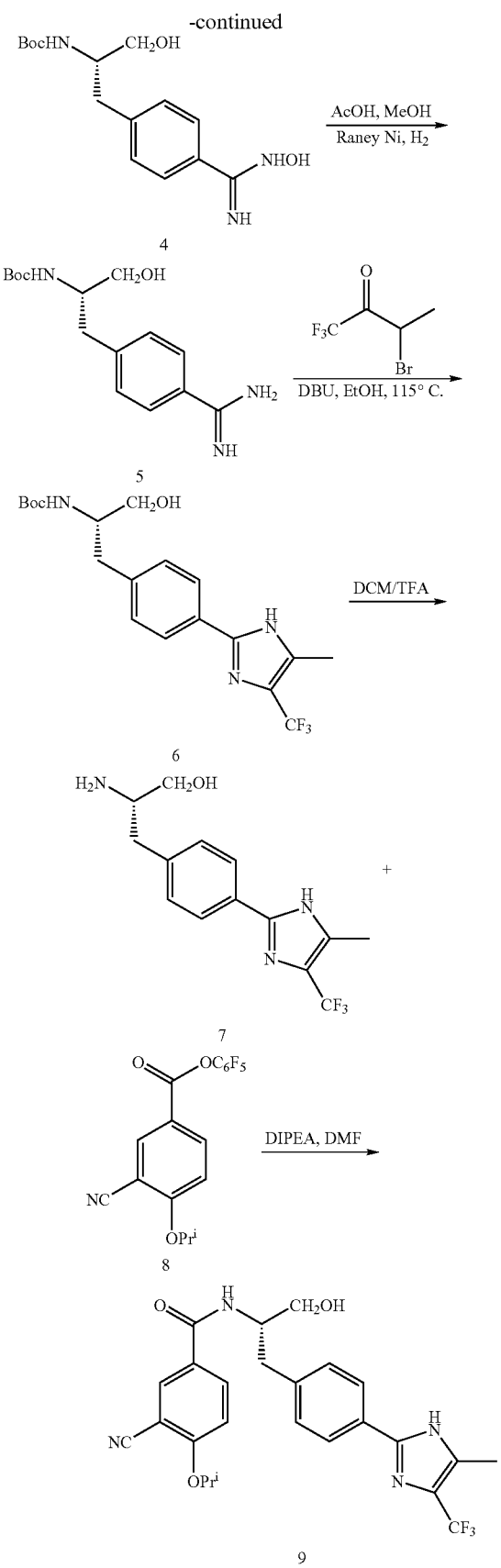

To a room temperature solution of 1 (4.96 g, 17 mmol) in methanol (15 mL) was added dropwise a solution of TMS diazomethane in hexanes (17.0 mL, 34 mmol, 2 M). The resulting yellow solution was stirred at ambient temperature for 30 minutes. The solvents were removed in vacuo, and the viscous oil 2 (5.19 g, 17 mmol) was dried under high vacuum and determined to be pure enough for use in subsequent transformations (LC/MS (LRMS (M+H$^+$) m/z: 305.3)).

Intermediate 2 (5.19 g, 17 mmol) was stirred with sodium borohydride (3.23 g, 85 mmol) in methanol (50 mL) and tetrahydrofuran (50 mL) at room temperature for 2 hours. The solvents were removed in vacuo, and the residue was partitioned between ethyl acetate (50 mL) and water (50 mL). The layers were separated and the aqueous phase was extracted with ethyl acetate (3×50 mL), and the combined organic layers were dried over sodium sulfate and concentrated in vacuo to yield 3 (4.71 g, 17 mmol) as a white solid, which was determined to be pure enough for use in subsequent transformations LC/MS (LRMS (M+H$^+$) m/z: 277.3). Nitrile 3 (1.92 g, 6.9 mmol) was stirred with sodium methoxide in methanol (27.7 mL, 13.9 mmol, 0.5 M) and hydroxylamine hydrochloride (964 mg, 13.9 mmol) under an atmosphere of nitrogen at 50° C. for 2 hours. It was then cooled to room temperature and the solvents were removed in vacuo. The residue was partitioned between saturated aqueous ammonium chloride solution (30 mL) and ethyl acetate (30 mL). The layers were separated and the aqueous phase was extracted with ethyl acetate (2×30 mL). The combined organic extracts were dried over sodium sulfate and concentrated in vacuo, and the residue was purified by flash chromatography (silica gel, hexane/ethyl acetate) to yield intermediate 4 (1.08 g, 51%), which was characterized by $^1$H NMR and LC/MS (LRMS (M+H$^+$) m/z: 310.2).

To a room temperature solution of 4 (1.08 g, 3.5 mmol) in methanol (30 mL) was added Raney nickel (200 mg) and acetic acid (1 mL). The resulting mixture was stirred under an atmosphere of hydrogen at room temperature for 2 hours. It was filtered through Celite and concentrated in vacuo to provide 5 (1.02 g, 100%) as a white solid, which was determined to be pure enough for use in subsequent transformations (LC/MS (LRMS (M+H$^+$) m/z: 294.3)).

To a room temperature solution of amidine 5 (304 mg, 1.0 mmol) in anhydrous ethanol (15 mL) was added 1,8-diazabicyclo[5.4.0]undec-7-ene (622 μL, 4.2 mmol) and 3-bromo-1,1,1-trifluoro-2-butanone (424 mg, 2.1 mmol). The resulting mixture was stirred under an atmosphere of nitrogen at 115° C. for 30 minutes. It was then cooled to room temperature and the solvents removed in vacuo. The residue was purified by reverse-phase HPLC using a mobile phase gradient consisting of acetonitrile and water. Compound 6 (76 mg, 20%) was isolated and characterized by $^1$H NMR and LC/MS (LRMS (M+H$^+$) m/z: 400.1).

A solution of 6 (76 mg, 0.2 mmol) in dichloromethane (2 mL) was stirred with trifluoroacetic acid (2 mL) at room temperature for 45 minutes. The solvents were removed in vacuo to provide 7 (57 mg, 100%), which was determined to be pure enough for use in subsequent transformations (LC/MS (LRMS (M+H$^+$) m/z: 300.3)).

To a room temperature solution of amine 7 (25 mg, 0.08 mmol) in dimethylformamide (3 mL) was added diisopropylethylamine (87 μl, 0.50 mmol). The resulting solution was stirred at room temperature for 5 minutes and intermediate 8 (32 mg, 0.08 mmol) was added. The reaction mixture was stirred under an atmosphere of nitrogen at room temperature for 30 minutes, and the solvents were removed in vacuo. The residue was partitioned between ethyl acetate (5 mL) and water (5 mL), after which the layers were separated and the aqueous phase was extracted with ethyl acetate (3×10 mL). The combined organic layers were dried over sodium sulfate and concentrated in vacuo. The residue was purified by flash chromatography (silica gel, ethyl acetate) to provide 9 (7 mg, 18%) as a glassy solid, which was characterized by $^1$H NMR and LC/MS (LRMS (M+H$^+$) m/z: 496.4).

Example 53

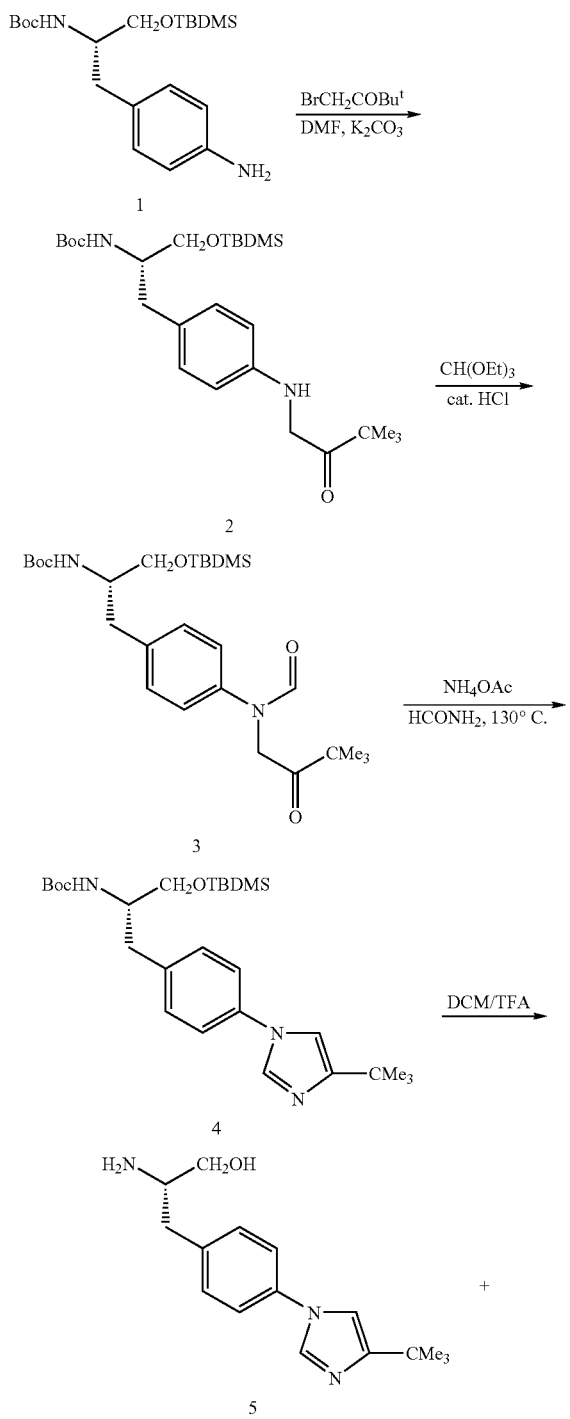

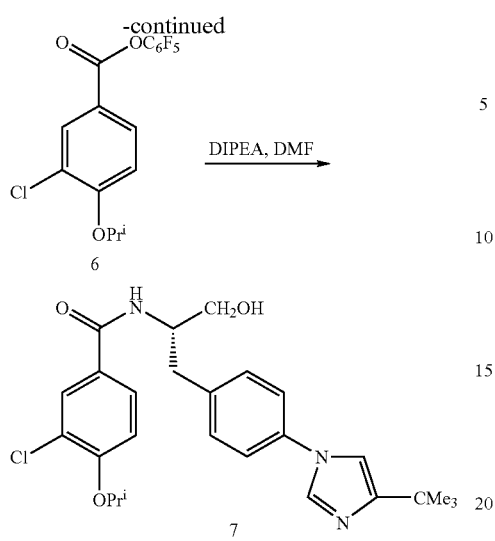

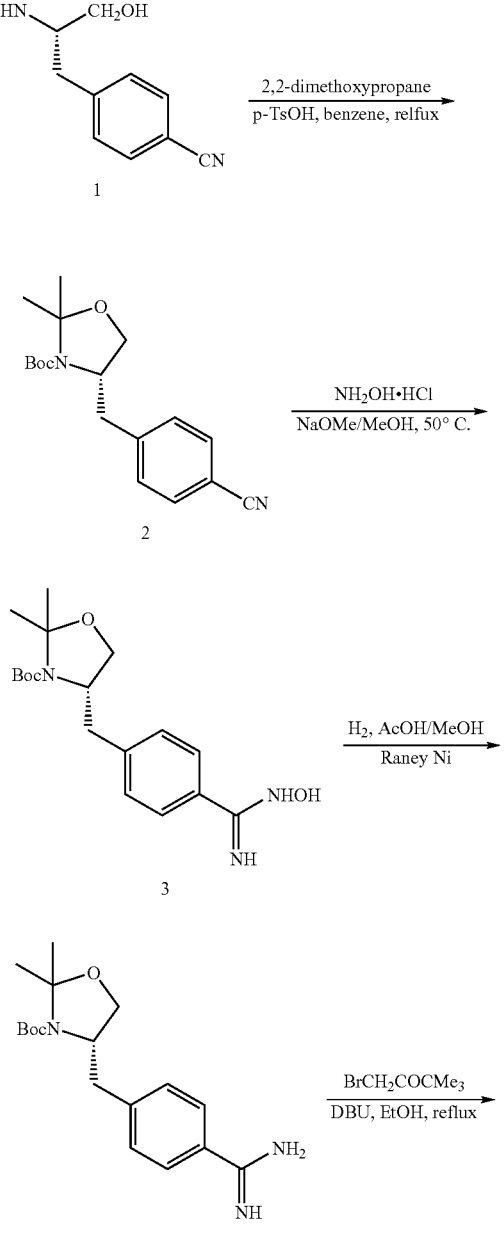

Crude amine 5 (72 mg, 0.26 mmol) was stirred with diisopropylethylamine (197 µl, 1.1 mmol) in dimethylformamide (3 mL) at room temperature for 5 minutes, after which intermediate 6 (100 mg, 0.26 mmol) was added. The resulting mixture was stirred for another 30 minutes and the solvents removed in vacuo. The crude residue was purified by reverse-phase HPLC using a mobile phase gradient consisting of acetonitrile and water to give compound 7 (10 mg, 8%) as a glassy solid, which was characterized by $^1$H NMR and LC/MS (LRMS (M+H$^+$) m/z: 470.2).

Example 54

To a room temperature solution of aniline 1 (500 mg, 1.3 mmol) in dimethylformamide (3 mL) were added potassium carbonate (1.5 g) and 1-bromopinacolone (500 mg, 2.8 mmol). The reaction mixture was stirred at 50° C. for 4 hours, and the solvents were removed in vacuo. The residue was partitioned between ethyl acetate (50 mL) and water (15 mL), the layers were separated, and the aqueous phase was extracted with ethyl acetate (3×50 mL). The combined organic layers were dried over sodium sulfate and concentrated in vacuo. The residue was purified by flash chromatography (silica gel, ethyl acetate) to provide 2 (320 mg, 51%), which was characterized by $^1$H NMR and LC/MS (LRMS (M+H$^+$) m/z: 479.74).

To a room temperature solution of 2 (307 mg, 0.64 mmol) in triethyl orthoformate (20 mL) was added concentrated aqueous HCl (25 µL). The resulting mixture was stirred at 90° C. for 3 hours and then cooled to room temperature. The solvents were removed in vacuo and the residue partitioned between water (15 mL) and ethyl acetate (50 mL). The layers were separated and the organic layer washed with water (3×20 mL) and brine (3×20 mL), and dried over sodium sulfate. Removal of the solvents yielded intermediate 3 (326 mg, 100%) as a viscous oil, which was characterized by LC/MS (LRMS (M+H$^+$) m/z: 507.1).

Intermediate 3 (207 mg, 0.41 mmol) was stirred with ammonium acetate (1.57 g, 20.40 mmol) in formamide under an atmosphere of nitrogen at 130° C. for 4.5 hours. The resulting solution was cooled to room temperature and partitioned between ethyl acetate (50 mL) and water (10 mL). The layers were separated, the organic layer was washed with water (4×10 mL) and brine (20 mL) and dried over sodium sulfate. The solvents were removed in vacuo, and the residue was purified by reverse-phase HPLC using a mobile phase gradient consisting of acetonitrile and water to yield imidazole 4 (159 mg, 80%), which wag isolated and characterized by $^1$H NMR and LC/MS (LRMS (M+H$^+$) m/z: 488.2).

To a room temperature solution of 4 (159 mg, 0.33 mmol) in dichloromethane (4 mL) was added trifluoroacetic acid (4 mL), and the resulting solution stirred at room temperature overnight. The solvents were removed in vacuo provide amine 5 (89 mg) as a glassy solid, which was determined to be pure enough for use in subsequent transformations LC/MS (LRMS (M+H$^+$) m/z: 274.1).

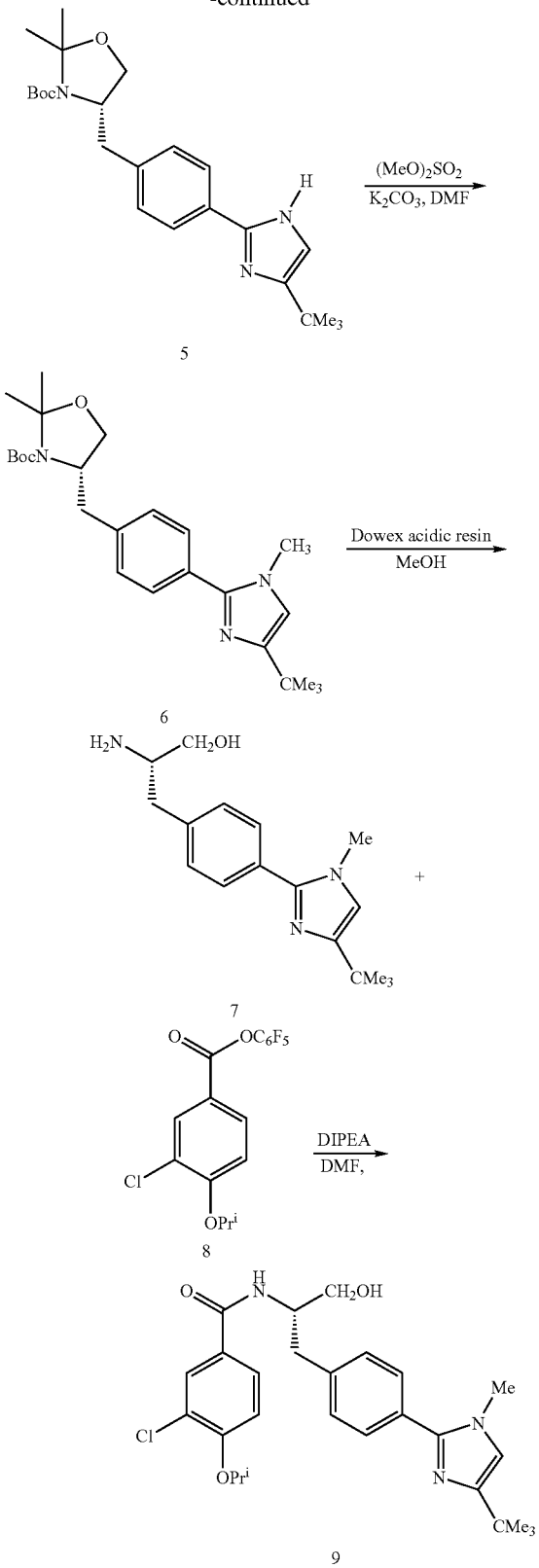

To a room temperature solution of alcohol 1 (2.59 g, 9.4 mmol) in benzene (50 mL) was added 2,2-dimethoxypropane (1.75 mL, 14.1 mmol) and p-toluenesulfonic acid (179 mg, 0.94 mmol). The resulting solution was stirred under an atmosphere of nitrogen at 110° C. for 1.5 hours. The solvents were removed in vacuo, and the residue purified using flash chromatography (silica gel, ethyl acetate/hexanes) to provide 2 (765 mg, 27%), which was characterized using LC/MS (LRMS (M+H$^+$) m/z: 317.4).

Nitrile 2 (765 mg, 2.4 mmol) was stirred with sodium methoxide in methanol (10.0 mL, 5.0 mmol, 0.5 M) and hydroxylamine hydrochloride (336 mg, 4.8 mmol) under an atmosphere of nitrogen at 50° C. for 2 hours. It was then cooled to room temperature and the solvents removed in vacuo. The residue was partitioned between saturated aqueous ammonium chloride solution (30 mL) and ethyl acetate (30 mL), the layers were separated, and the aqueous phase extracted with ethyl acetate (2×30 mL). The combined organic extracts were dried over sodium sulfate and concentrated in vacuo. The residue was purified by flash chromatography (silica gel, hexane/ethyl acetate) to yield intermediate 3 (314 mg, 38%), which was characterized by $^1$H NMR and LC/MS (LRMS (M+H$^+$) m/z: 350.1).

To a room temperature solution of 3 (314 mg, 0.9 mmol) in methanol (15 mL) was added Raney nickel (50 mg) and acetic acid (300 μL). The resulting mixture was stirred under an atmosphere of hydrogen at room temperature for 2 hours. It was filtered through Celite and concentrated in vacuo to provide 4 (275 mg, 0.83 mmol) as a white solid, which was determined to be pure enough for use in subsequent transformations (LC/MS (LRMS (M+H$^+$) m/z: 414.1)).

To a room temperature solution of amidine 4 (138 mg, 0.4 mmol) in anhydrous ethanol (15 mL) was added 1,8-diazabicyclo[5.4.0]undec-7-ene (622 μL, 4.2 mmol) and 1-bromopinacolone (84 μL, 0.6 mmol). The resulting mixture was stirred under an atmosphere of nitrogen at 115° C. for 30 minutes. It was then cooled to room temperature and the solvents removed in vacuo. The residue was purified by reverse-phase HPLC using a mobile phase gradient consisting of acetonitrile and water to give compound 5 (29 mg, 17%), which was characterized using $^1$H NMR and LC/MS (LRMS (M+H$^+$) m/z: 414.1).

To a room temperature solution of imidazole 5 (29 mg, 0.07 mmol) in anhydrous dimethylformamide (5 mL) were added potassium carbonate (39 mg, 0.28 mmol) and dimethylsulfate (133 μL, 1.40 mmol). The resulting mixture was stirred under an atmosphere of nitrogen at 50° C. for 24 hours, after which the solvents were removed in vacuo. The residue was purified using flash chromatography (silica gel, ethyl acetate/hexanes) to provide 6 (15 mg, 43%) as a glassy solid, which was characterized by $^1$H NMR and LC/MS (LRMS (M+H$^+$) m/z: 428.3).

A solution of 6 (15 mg, 0.04 mmol) in anhydrous methanol (3 mL) and water (300 μL) was stirred with DOWEX 50WX8-400 ion-exchange resin (100 mg) at room temperature for 16 hours. The resin was removed by filtration and rinsed with triethylamine (3 mL). The solvents were removed under high vacuum to provide 7 (12 mg, 0.04 mmol), which was determined to be sufficiently pure for the next transformation (LRMS (M+H$^+$) m/z: 288.2).

To a room temperature solution of amine 7 (12 mg, 0.04 mmol) in dimethylformamide (3 mL) was added diisopropylethylamine (20 μl, 0.10 mmol). The resulting solution was stirred at room temperature for 5 minutes, after which intermediate 8 (16 mg, 0.04 mmol) was added. The reaction mixture was stirred for another 30 minutes. The solvents were removed in vacuo and the residue purified by flash chromatography (silica gel, methanol/dichloromethane) to provide 9

(10 mg, 50%) as a glassy solid, which was characterized by $^1$H NMR and LC/MS (LRMS (M+H$^+$) m/z: 484.2).

Example 55

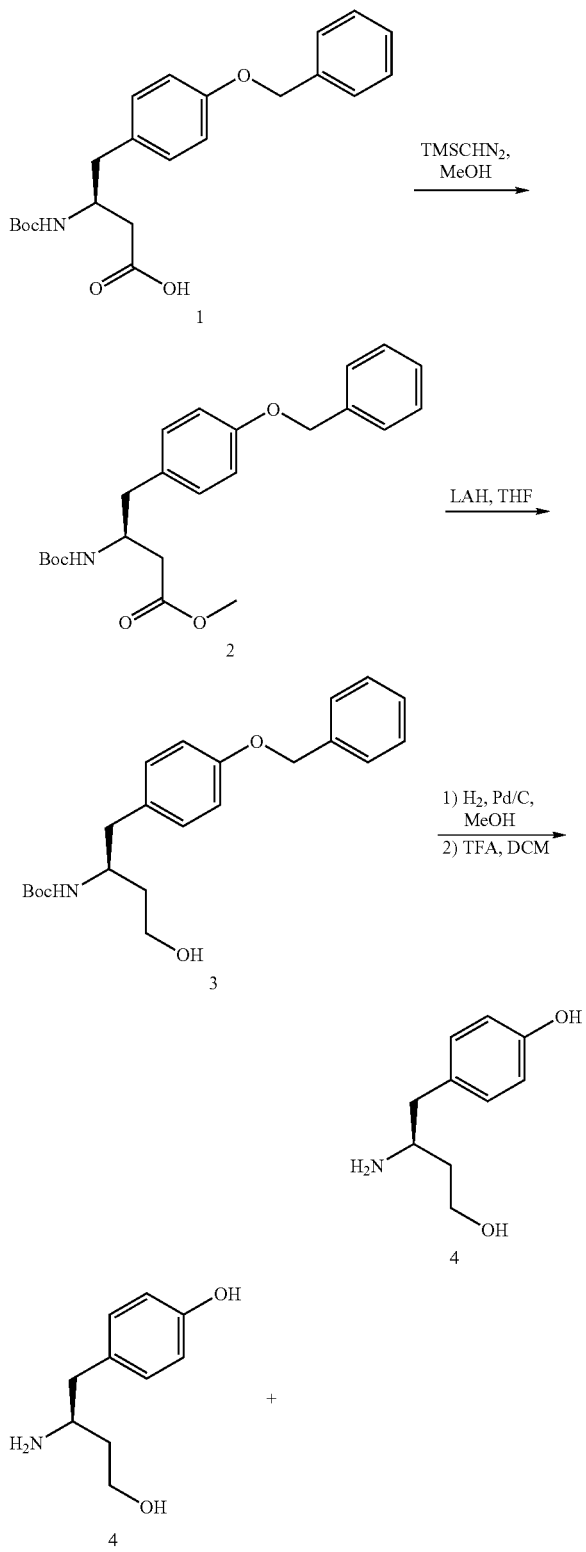

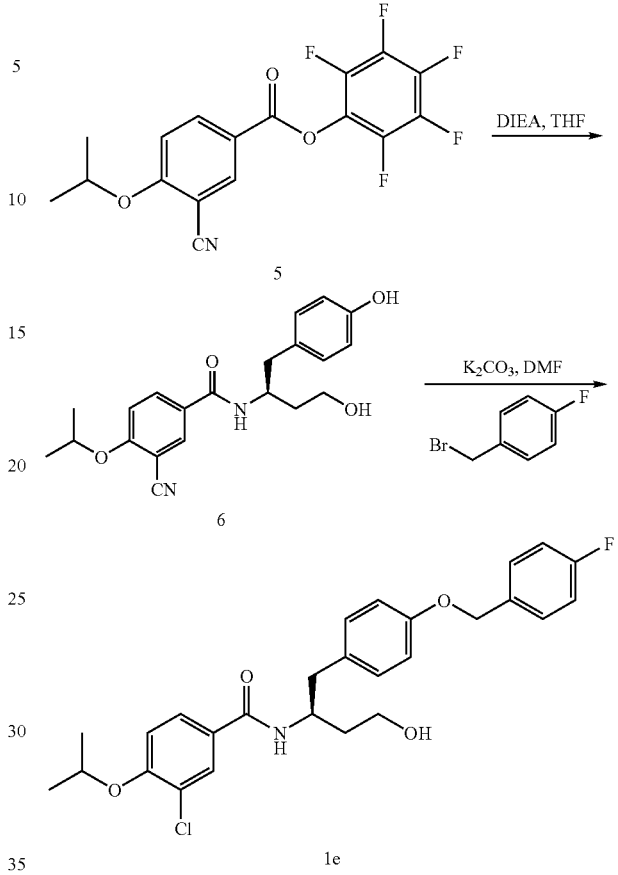

To a solution of Boc-L-β-homotyrosine (OBzl) (5 g, 13 mmol) in methanol (200 mL) was added trimethylsilyldiazomethane (2 M in hexanes, 40 mL, 78 mmol) dropwisely. The reagent was continuously added if necessary until bubbling ceased. The mixture was concentrated to give 2 (5.5 g), which was used in the next step without further purification. LRMS (M+H$^+$) m/z 300.3.

To a solution of 2 (5.5 g, 13.76 mmol) in THF (100 mL) was added LAH (1 M in THF, 13.7 mL, 13.7 mmol) at 0° C. The resulting solution was stirred for 2 hours, and methanol (~20 mL) was added to quench the reaction. The solvents were then evaporated to obtain the yellowish solid which was diluted in ethyl acetate and washed in saturated NaHCO$_3$. The organic layer was washed with brine, dried over Na$_2$SO$_4$ and concentrated under reduced pressure. The residue was purified via flush column chromatography using a mixture of ethyl acetate and hexanes as eluent to give 3 as a white solid (3.5 g, 70%). LRMS (M+H$^+$) m/z 394.4.

A solution of 3 (1.9 g, 5 mmol) in MeOH (40 mL) was stirred under a stream of H$_2$ (50 psi) in the presence of 10% Pd/C (200 mg) for 30 h. The catalyst was removed by filtration through a PTFE (0.45 μm) filter and the solvent evaporated to give a white solid (1.5 g), which was stirred in the mixture of TFA (1 mL) and DCM (9 mL) for 2 hours. The resulting solution was concentrated and used in the next step without further purification. LRMS (M+H$^+$) m/z 182.3.

To a solution of 4 (926 mg, 5 mmol) in THF (10 mL) were added 5 (950 mg, 2.6 mmol) and N,N-diisopropylethylamine (4.5 mL, 25.5 mmol). The reaction was stirred at room temperature for 10 hours. The mixture was concentrated and dried on high vacuum. The resulting crude product was purified via flash column chromatography using ethyl acetate as eluent to give 6 (710 mg, 74%). LRMS (M+H⁺) m/z 370.4.

To a solution of 6 (70 mg, 0.2 mmol) in DMF (1 mL) was added 4-fluorobenzyl bromide (0.15 mL, 1.2 mmol) and potassium carbonate (166 mg, 1.2 mmol). The resulting mixture was stirred for 12 hours at room temperature. The mixture was filtered, and the filtrate was purified on RP-HPLC using a mixture of acetonitrile and H₂O to give 1e (35 mg, 37%). LRMS (M+H⁺) m/z 477.5.

Example 56

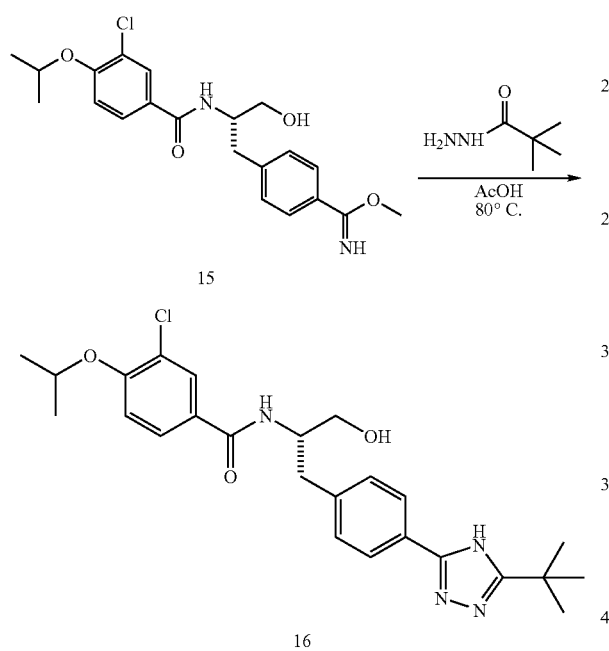

A solution of imidate 15 (20 mg, 0.05 mmol), pivalic acid hydrazide (9 mg, 0.08 mmol), and acetic acid (1 mL) was stirred at 80° C. for 1 hr. The reaction mixture was then concentrated in vacuo and the resulting residue purified by reverse phase HPLC (C18, acetonitrile/water) to yield 10 mg (43%) of the tetrazole 16. LRMS (M+H⁺) m/z 471.2.

Example 57

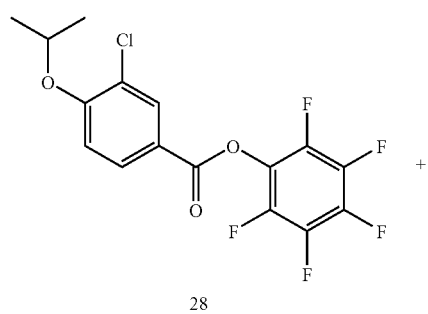

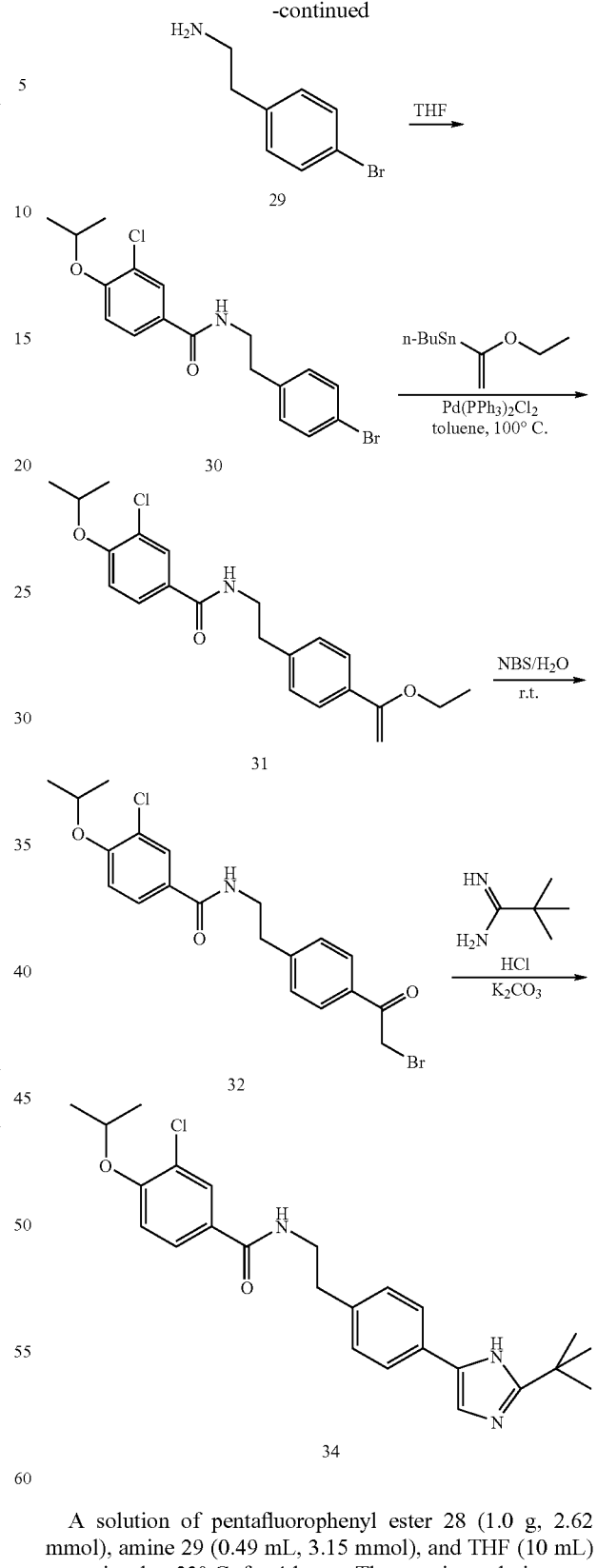

A solution of pentafluorophenyl ester 28 (1.0 g, 2.62 mmol), amine 29 (0.49 mL, 3.15 mmol), and THF (10 mL) was stirred at 23° C. for 4 hours. The reaction solution was concentrated in vacuo, and the resulting residue was purified by column chromatography (silica gel, 1:1 EtOAc:hexanes) to give 1.1 g (88%) of amide 30. LRMS (M+H⁺) m/z 396.1.

A solution of bromide 30 (200 mg, 0.51 mol), dichlorobis(triphenylphosphine)palladium(II) (35 mg, 0.05 mol), tributyl(1-ethoxyvinyl)tin (0.34 ml, 1.0 mmol), and toluene (2 mL) under $N_2$ was stirred at 100° C. for 4 hours. Upon completion, as monitored by LCMS, the reaction mixture was cooled, filtered through cotton, and concentrated in vacuo. The resulting residue was purified by flash column chromatography (silica gel, 1:4:0.1 EtOAc:hexanes:triethylamine) to give 100 mg (52%) of styrene 31. LRMS (M+H$^+$) m/z 388.2.

A solution of compound 31 (100 mg, 0.25 mmol), THF:$H_2O$ (3:1, 4 mL), and N-bromo-succinimide (46 mg, 0.25 mmol) was stirred at 23° C. for 15 min. The reaction mixture was then concentrated in vacuo, and the crude residue was diluted with EtOAc (30 mL), washed with brine (10 mL), and concentrated in vacuo. The resulting residue was purified by flash column chromatography (silica gel, 4:1 EtOAc:hexanes) to give 50 mg (46%) of bromoketone 32. LRMS (M+H$^+$) m/z 438.1.

A solution of bromoketone 32 (50 mg, 0.11 mmol), $K_2CO_3$ (47 mg 0.34 mmol), tert-butylcarbamidine hydrochloride (21 mg, 0.23 mmol), and DMF (2 mL) was stirred at 23° C. under $N_2$ for 18 hours. The reaction mixture was concentrated in vacuo under high vacuum (0.1 mm Hg), and the resulting residue was purified by column chromatography (silica gel, 2:1 EtOAc:hexanes) to give 35 mg (72%) of imidazole 34. LRMS (M+H$^+$) m/z 440.2.

Example 58

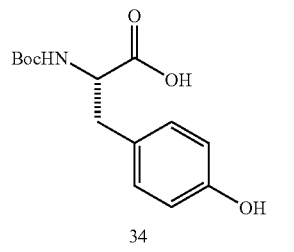

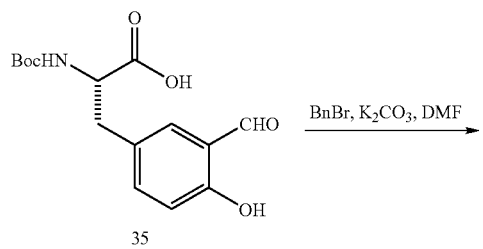

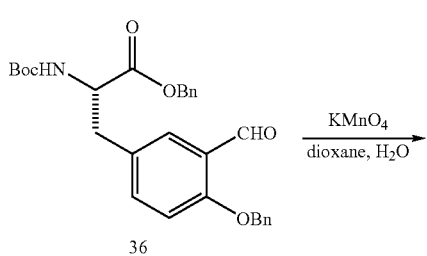

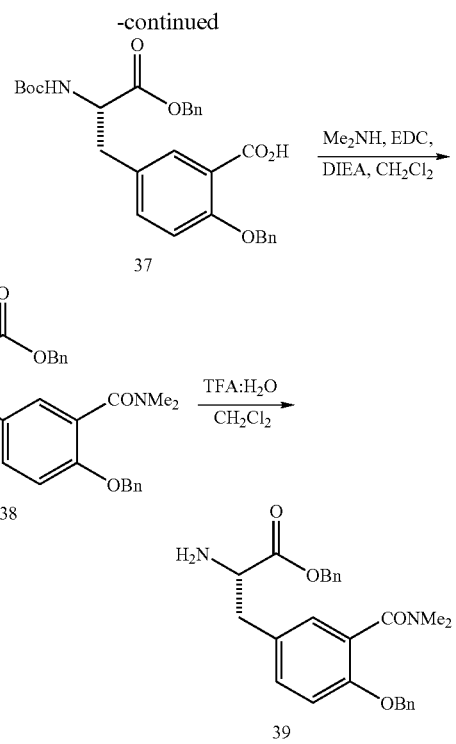

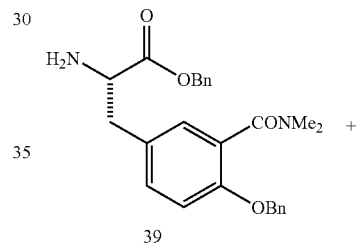

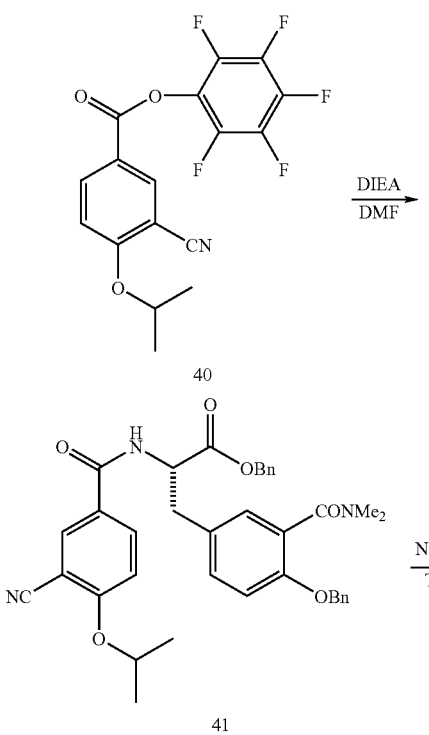

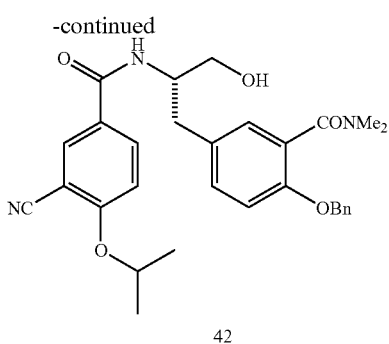

42

Chloroform (20 mL) was added slowly over 2 hours to a solution of Boc-tyrosine (20 g, 71 mmol) and 10% NaOH in H₂O (400 mL) at 85° C. After a total of 4 hours, the reaction solution was acidified with 3 N HCl (200 mL) and extracted with EtOAc (3×150 mL). The organic layer was dried (MgSO₄), filtered, and concentrated in vacuo. The resulting residue was purified by flash column chromatography (silica gel, 1:1:0.1 hexanes:EtOAc:AcOH) to yield 6.3 g of a mixture of aldehyde 35 and some recovered 34.

A solution of aldehyde 35 (contaminated with 34, 6.3 g, 20 mmol), K₂CO₃ (5.8 g, 42 mmol), benzyl bromide (5.0 mL, 42 mmol), and DMF (100 mL) was stirred at 23° C. for 18 hours. The reaction mixture was diluted with EtOAc (200 mL), and washed with 1 N HCL (3×200 mL) and brine (3×200 mL). The organic layer was dried (MgSO₄), filtered, and concentrated in vacuo. The resulting residue was purified by column chromatography (silica gel, 1:4 EtOAc:hexanes) to give 2.2 g (22%) of ester 36. LRMS (M+H⁺) m/z 490.2.

A solution of aldyhyde 36 (570 mg, 1.16 mmol), KMnO₄ (368 mg, 2.32 mmol), dioxane (3 mL), and H₂O (1 mL) was stirred at 23° C. for 3 hours. The reaction mixture was concentrated in vacuo and the resulting residue was purified by column chromatography (silica gel, 1:1 EtOAc:hexanes) to give 350 mg (60%) of acid 37. LRMS (M+H⁺) m/z 506.2.

A solution of acid 37 (115 mg, 0.23 mmol), dimethyl amine (0.23 mL, 2.0 M in THF), 1-ethyl-3-(3-dimethylaminopropyl)carbodiimide hydrochloride (65 mg, 0.34 mmol), diisopropyl ethyl amine (0.12 mL, 0.68 mmol), and CH₂Cl₂ (1 mL) was stirred at 23° C. for 4 hours. The reaction mixture was then diluted with EtOAc (10 mL), and washed with 1 N HCl (5 mL) and brine (5 mL). The organic layer was dried (MgSO₄), filtered, and concentrated in vacuo. The resulting residue was purified by flash column chromatography (silica gel, 1:1 hexanes:EtOAc) to yield 60 mg (49%) of the amide 38. LRMS (M+H⁺) m/z 533.3.

A solution of amide 38 (60 mg, 0.11 mmol), TFA:H₂O (97.5:2.5, 1 mL) and CH₂Cl₂ (1 mL) was stirred at 23° C. for 30 min. The reaction solution was concentrated in vacuo, and the resulting residue was placed under high vacuum for 2 hours and then used without further purification.

A solution of amine 39 (69 mg, 0.16 mmol), pentafluorophenol ester 40 (71 mg, 0.19 mmol), diisopropylethylamine (83 μL, 0.68 mmol), and DMF (1 mL) was stirred at 23° C. for 4 hours. The reaction mixture was then diluted with EtOAc (10 mL), and washed with 1 N HCl (5 mL) and brine (5 mL). The organic layer was dried (MgSO₄), filtered, and concentrated in vacuo. The resulting residue was purified by flash column chromatography (silica gel, 1:1 hexanes: EtOAc) to yield 60 mg (60%) of the ester amide 41. LRMS (M+H⁺) m/z 620.3.

A solution of ester 41 (50 mg, 0.08 mmol), NaBH₄ (30 mg, 0.81 mmol), THF (0.5 mL), and MeOH (0.5 mL) was stirred at 23° C. for 2 hours. The reaction mixture was then diluted with EtOAc (10 mL), and washed with 1 N HCl (5 mL) and brine (5 mL). The organic layer was dried (MgSO₄), filtered, and concentrated in vacuo. The resulting residue was purified by flash column chromatography (silica gel, 1:50 MeOH: EtOAc) to yield 31 mg (75%) of the alcohol 42. LRMS (M+H⁺) m/z 516.3.

Example 59

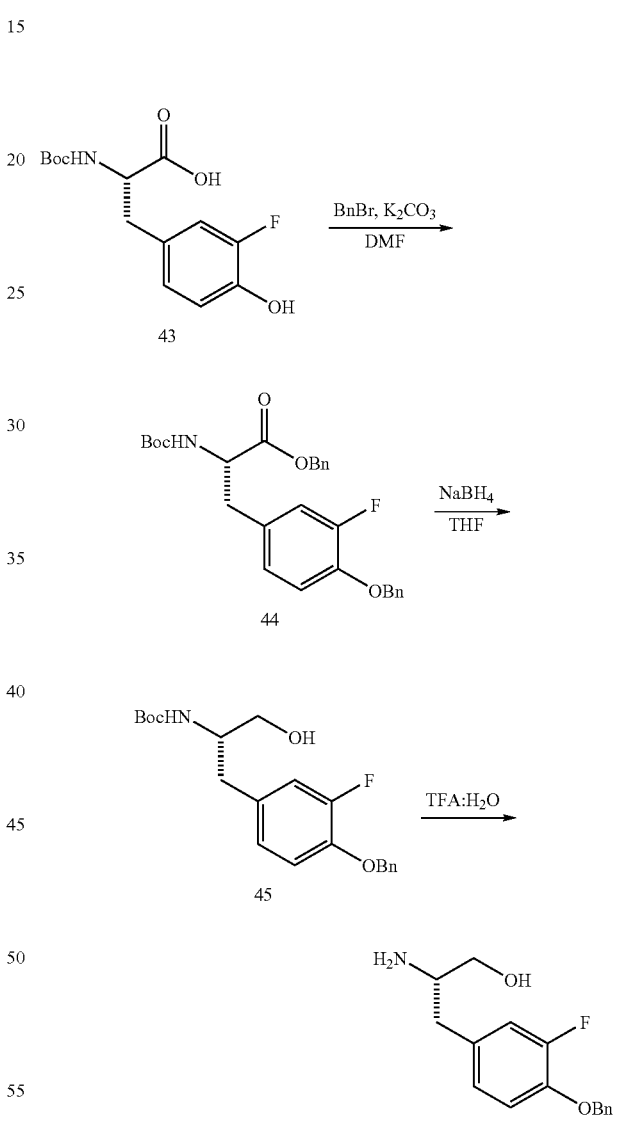

Example 60

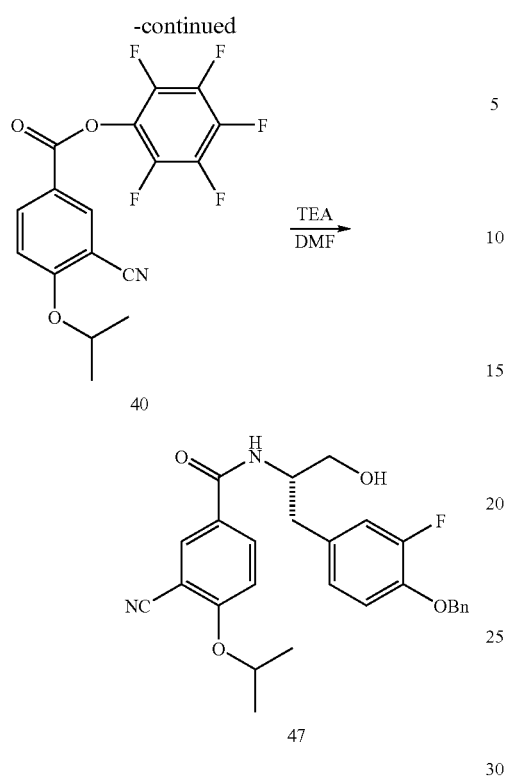

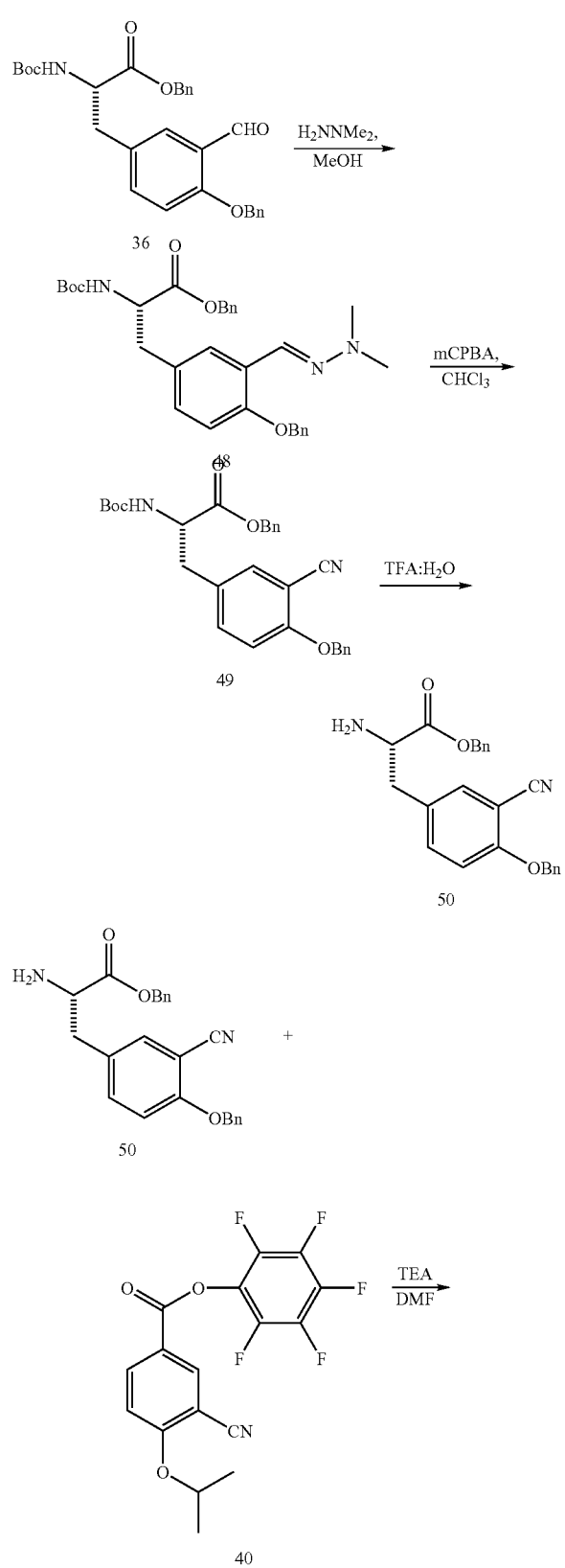

A solution of acid 43 (300 mg, 1.0 mmol), K₂CO₃ (276 mg, 2.0 mmol), benzyl bromide (0.24 mL, 2.0 mmol), and DMF (4 mL) was stirred at 23° C. for 18 hours. The reaction mixture was diluted with EtOAc (30 mL), and washed with 1 N HCl (10 mL) and brine (3×15 mL). The organic layer was dried (MgSO₄), filtered, and concentrated in vacuo. The resulting residue was purified by column chromatography (silica gel, 1:3 EtOAc:hexanes) to give 400 mg (83%) of ester 44. LRMS (M+H⁺) m/z 480.2.

A solution of ester 44 (100 mg, 0.21 mmol), NaBH₄ (24 mg, 0.63 mmol), THF (1 mL), and MeOH (1 mL) was stirred at 23° C. for 18 hours. The reaction mixture was then diluted with EtOAc (10 mL), washed with 1 N HCl (5 mL), and brine (5 mL). The organic layer was dried (MgSO₄), filtered, and concentrated in vacuo. The resulting residue was used without further purification.

A solution of alcohol 45 (100 mg, 0.27 mmol) and TFA:H₂O (97.5:2.5, 1 mL) was stirred at 23° C. for 30 min. The reaction solution was concentrated in vacuo, and the resulting residue was placed under high vacuum for 2 hours and then used without further purification.

A solution of amine 46 (40 mg, 0.15 mmol), pentafluorophenyl ester 40 (43 mg, 0.12 mmol), triethylamine (51 µL, 0.29 mmol), and DMF (0.6 mL) was stirred at 23° C. for 4 hours. The reaction mixture was then diluted with EtOAc (10 mL), and washed with 1 N HCl (5 mL) and brine (5 mL). The organic layer was dried (MgSO₄), filtered, and concentrated in vacuo. The resulting residue was purified by flash column chromatography (silica gel, 1:2 hexanes:EtOAc) to yield 30 mg (43%) of the ester amide 47. LRMS (M+H⁺) m/z 463.2.

-continued

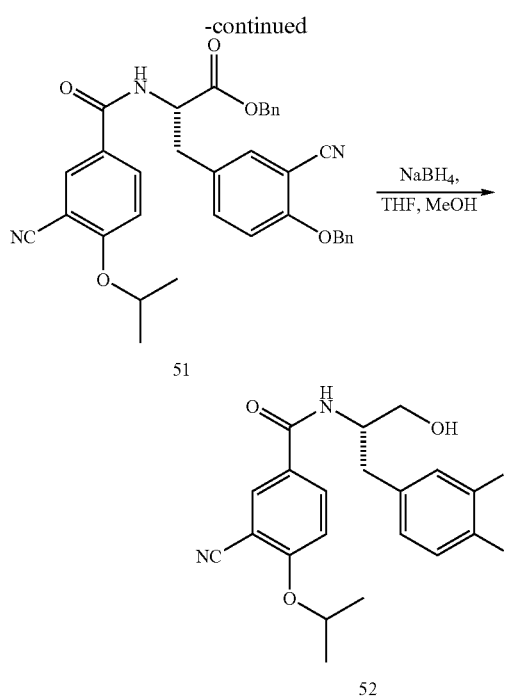

51

52

A solution of aldehyde 36 (300 mg, 0.6 mmol), dimethyl hydrazine (47 μL, 0.6 mmol), and MeOH (2.5 mL) was stirred at 0° C. for 2 hours, then allowed to warm to 23° C. and stirred for an additional 15 hours. The reaction solution was concentrated in vacuo and the resulting residue was used without further purification.

To a −5° C. solution of crude hydrazone 48 (325 mg, 0.6 mmol) and CHCl$_3$ (2 mL) was added dropwise a solution of m-chloroperoxybenzoic acid (212 mg, 1.23 mmol) and CHCl$_3$ (2 mL). The reaction solution was allowed to warm to 23° C. and was stirred for 2 days. The reaction mixture was then diluted with EtOAc (10 mL), and washed with saturated aqueous NaHCO$_3$ (5 mL) and brine (5 mL). The organic layer was dried (MgSO$_4$), filtered, and concentrated in vacuo. The resulting residue was purified by flash column chromatography (silica gel, 1:2 hexanes:EtOAc) to yield 100 mg (34%) of the nitrile 49. LRMS (M+H$^+$) m/z 487.2.

A solution of nitrile 49 (60 mg, 0.27 mmol) and TFA:H$_2$O (97.5:2.5, 2 mL) was stirred at 23° C. for 30 min. The reaction solution was concentrated in vacuo, and the resulting residue was placed under high vacuum for 2 hours and then used without further purification.

A solution of amine 50 (100 mg, 0.25 mmol), pentafluorophenyl ester 40 (85 mg, 0.22 mmol), triethylamine (96 μL, 0.74 mmol), and DMF (1 mL) was stirred at 23° C. for 4 hours. The reaction mixture then diluted with EtOAc (10 mL), and washed with 1 N HCl (5 mL) and brine (5 mL). The organic layer was dried (MgSO$_4$), filtered, and concentrated in vacuo. The resulting residue was purified by flash column chromatography (silica gel, 1:1 hexanes:EtOAc) to yield 60 mg (42%) of 51. LRMS (M+H$^+$) m/z 574.2.

A solution of ester 51 (60 mg, 0.1 mmol), NaBH$_4$ (12 mg, 0.3 mmol), THF (1 mL), and MeOH (1 mL) was maintained at 23° C. for 18 hrs. The reaction mixture then diluted with EtOAc (10 mL), washed with 1 N HCl (5 mL), and brine (5 mL). The organic layer was dried (MgSO$_4$), filtered, and concentrated in vacuo. The resulting residue was purified by flash column chromatography (silica gel, 1:2 hexanes:EtOAc) to yield 30 mg (64%) of the alcohol 52. LRMS (M+H$^+$) m/z 470.2.

Example 61

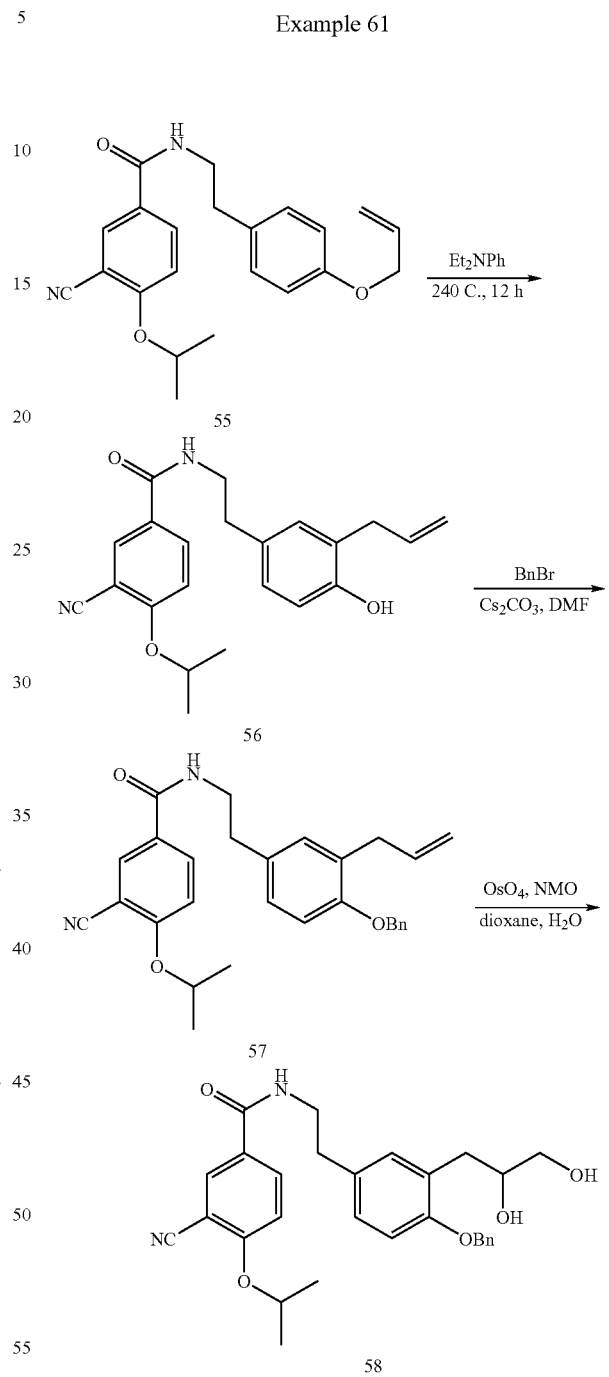

55

56

57

58

A solution of amide 55 (1.6 g, 4.38 mmol) and diethylaniline 56 (5 mL) was maintained at 240 C for 18 hrs. The reaction solution was cooled to 23° C., diluted with EtOAc (30 mL), and washed with 1 N HCl (3×50 mL) and brine (2×50 mL). The organic layer was dried (MgSO$_4$), filtered, and the filtrate was concentrated in vacuo. The resulting residue was purified by flash column chromatography (silica gel, 2:1 hexanes:EtOAc) to yield 1 g (63%) of the phenol 56. LRMS (M+H$^+$) m/z 365.2.

A solution of phenol 56 (700 mg, 1.92 mmol), Cs$_2$CO$_3$ (1.25 mg, 3.84 mmol), benzyl bromide (0.46 mL, 3.84 mmol), and DMF (10 mL) was maintained at 50° C. for 2 hrs. The reaction mixture was diluted with EtOAc (30 mL), washed with 1 N HCL (20 mL) and brine (3×30 mL). The organic layer was dried (MgSO$_4$), filtered, and the filtrate was concentrated in vacuo. The resulting residue was purified by flash column chromatography (silica gel, 1:3 EtOAc:hexanes) to give 500 mg (57%) of amide 57. LRMS (M+H$^+$) m/z 455.2.

A solution of amide 57 (150 mg, 0.33 mmol), osmium tetroxide (8 mg, 0.03 mmol), N-methylmorpholine-N-oxide (182 mg, 1.55 mmol), pyridine (2.4 µL, 0.03 mmol), THF (2 mL) and H$_2$O (2 mL) was maintained at 23° C. After 2 hrs, Celite (1 g), NaHSO$_3$ (1 g) and EtOAc (20 mL) were added and the resulting mixture was stirred. After 30 mins, the reaction mixture was filtered and the resulting filtrate was concentrated in vacuo. The resulting residue was purified by flash column chromatography (silica gel, 3:1 EtOAc:hexanes) to give 100 mg (62%) of diol 58. LRMS (M+H$^+$) m/z 489.2.

A solution of diol 58 (52 mg, 0.11 mmol), Pb(OAc)$_4$, and CH$_2$Cl$_2$ (2 mL) was maintained at 23 C for 30 mins. The reaction mixture was then filtered through a plug of Celite and the filtrate was concentrated to provide the aldehyde as a colorless oil.

A solution of the crude aldehyde (~50 mg, ~0.11 mmol), NaBH$_4$ (24 mg, 0.63 mmol), THF (1 mL), and MeOH (1 mL) was maintained at 23° C. for 30 mins. The reaction mixture then diluted with EtOAc (10 mL), washed with 1 N HCl (5 mL), and brine (5 mL). The organic layer was dried (MgSO$_4$), filtered, and the filtrate was concentrated in vacuo. The resulting residue was purified by flash column chromatography (silica gel, 2:1 EtOAc:hexanes) to give 20 mg (40%) of alcohol 59. LRMS (M+H$^+$) m/z 459.2.

Example 62

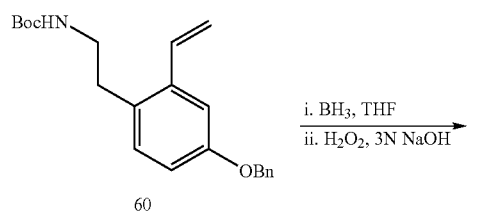

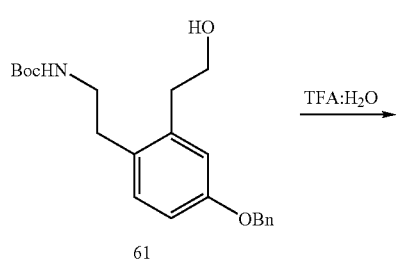

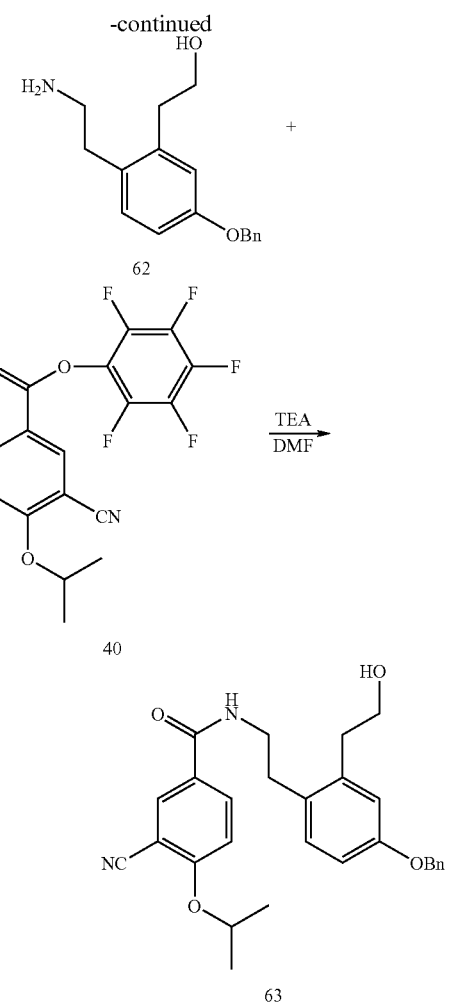

A solution of styrene 60 (190 mg, 0.54 mmol), borane-THF (1.0 M, 0.54 mL) was maintained at 23° C. for 2 hrs. An additional amount of borane-THF (0.54 mL) was then added. After another 2 hrs, an third portion (0.54 mL) was added. The reaction solution was maintained for 18 hrs, cooled to 0° C., then 3 N NaOH (0.5 mL) and H$_2$O$_2$ (0.5 mL) was added. After 2 hrs at 23° C., the reaction mixture was diluted with EtOAc (20 mL) and washed with brine (20 mL). The organic layer was dried (MgSO$_4$), filtered, and the filtrate was concentrated in vacuo. The resulting residue was purified by flash column chromatography (silica gel, 2:1 EtOAc:hexanes) to give 150 mg (75%) of alcohol 61. LRMS (M+H$^+$) m/z 372.2.

A solution of alcohol 61 (120 mg, 0.32 mmol), TFA:H$_2$O (97.5:2.5, 4 mL) was maintained at 23° C. for 30 mins. The reaction solution was concentrated in vacuo, and the resulting residue was placed under high vacuum for 2 hours and then used without further purification.

A solution of the above amine 62 (50 mg, 0.18 mmol), pentafluorophenol ester 40 (82 mg, 0.22 mmol), triethylamine (96 µL, 0.55 mmol), and DMF (1 mL) was maintained at 23° C. for 2 hrs. The reaction mixture then diluted with EtOAc (10 mL), washed with 1 N HCl (5 mL), and brine (5 mL). The organic layer was dried (MgSO$_4$), filtered, and the filtrate was concentrated in vacuo. The resulting residue was purified by reverse phase HPLC (C18, acetonitrile/water) to yield 6 mg (7%) of the amide 63. LRMS (M+H) m/z 459.2.

Example 63

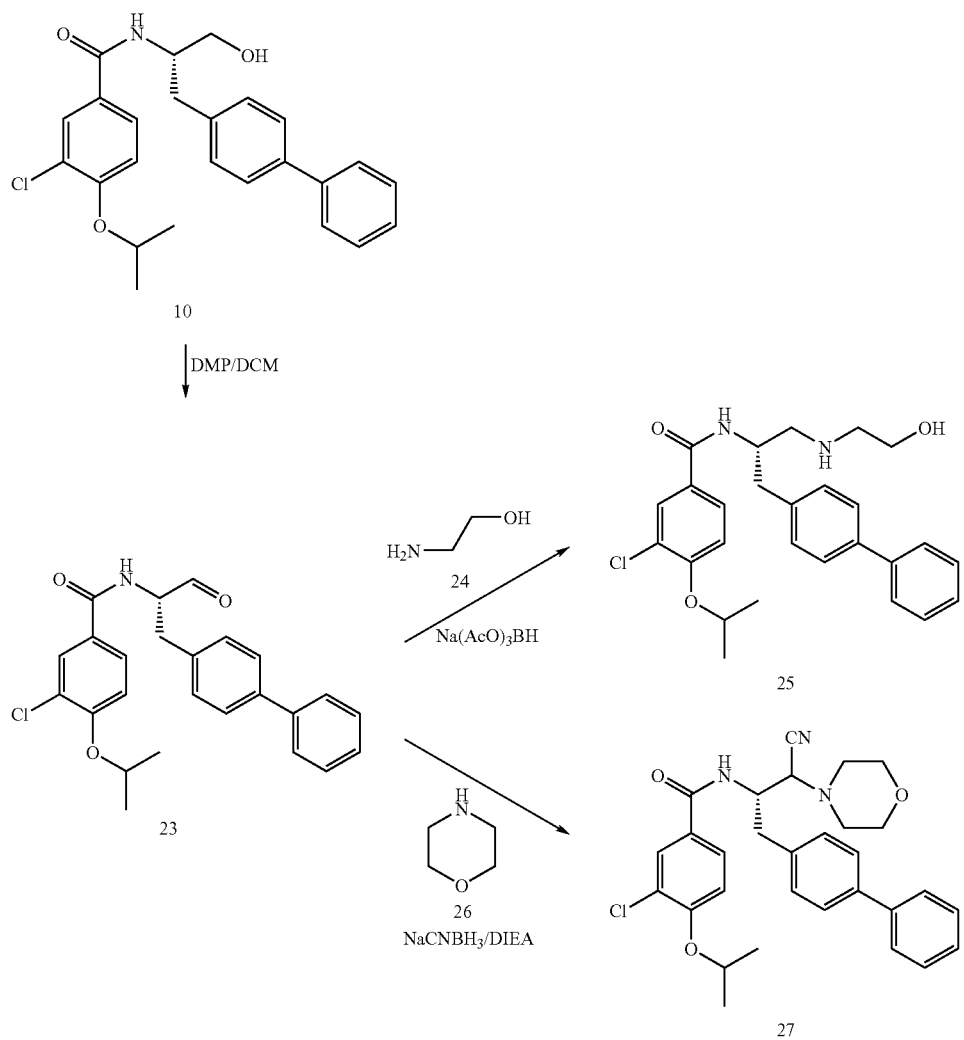

To a solution of 10 (1.15 g, 2.71 mmol) in DCM (100 mL) was added Dess-Martin periodinane (2.30 g, 5.42 mmol). The reaction mixture was stirred for 1 h, after which the DCM solution was washed by sodium thiosulfate solution and sodium bicarbonate solution, and dried over sodium sulfate. The mixture was filtered and the filtrate concentrated under reduced pressure to give 23 (1.0 g, 87%).

To a solution of 23 (30.0 mg, 0.0711 mmol) in DCM (2 mL) were added diisopropylethylamine (37.0 uL, 0.213 mmol), 24 (12.9 uL, 0.213 mmol) and sodium triacetoxyborohydride (20.0 mg, 0.142 mmol). The reaction mixture was stirred overnight, and then concentrated under reduced pressure. The residue was purified on reverse phase HPLC (C18) using a mixture of acetonitrile and H$_2$O to give 25 (5.6 mg, 16.9%). LRMS (M+H$^+$) m/z 467.4.

To a solution of 23 (50.0 mg, 0.119 mmol) in methanol (2 mL) were added diisopropylethylamine (62.0 uL, 0.356 mmol), 26 (31.1 uL, 0.356 mmol) and sodium cyanoborohydride (22.4 mg, 0.356 mmol). The reaction mixture was stirred for overnight, then concentrated under reduced pressure and the residue purified on reverse phase HPLC (C18) using a mixture of acetonitrile and H$_2$O to give 27 (31.0 mg, 22.9%). LRMS (M+H$^+$) m/z 518.5.

Example 64

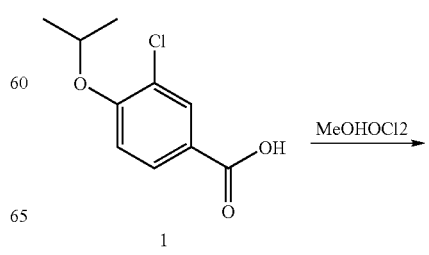

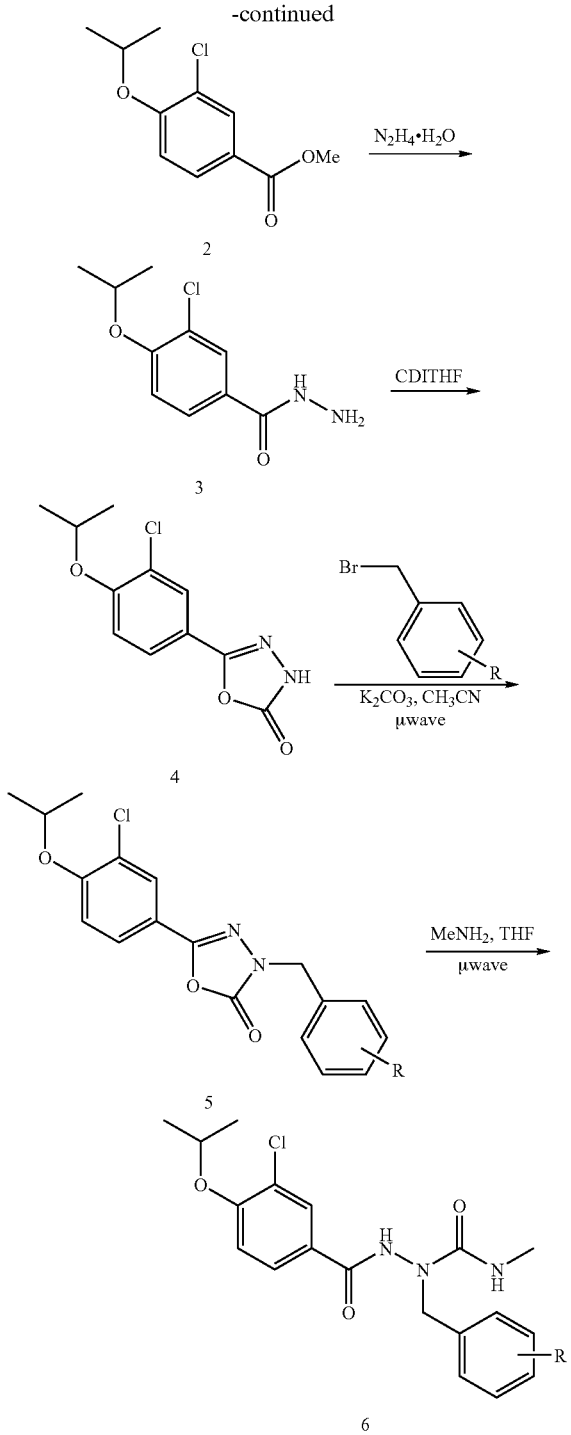

trated. Recrystallization from CH₂Cl₂ yielded 1.01 g 3 as white crystals; 95% yield, 2 steps.

To a solution of 3 (0.477 g, 2.09 mmol) in THF (8.0 mL) was added carbonyldiimidazole (0.379 g, 2.29 mmol). The reaction mixture was heated to reflux and stirred for 1.5 h. Upon cooling, the solution was concentrated in vacuo and purified via flash column chromatography (10-40% EtOAc/Hex) to yield 0.515 g 4 as a white solid; 97% yield.

To a solution of 4 (1.0 equiv.; typically 0.3-1.0 mmol) in CH₃CN (2.0 mL) was added the electrophile (1.1 equiv.) and K₂CO₃ (1.1 equiv.). The reaction mixture was heated to 80° C. under microwave irradiation for 30 min followed by filtration and concentration in vacuo. The product can be taken on without purification or purified via flash column chromatography (typically 10-40% EtOAc/Hex) to afford 5 in generally >90% yield.

To 5 (1.0 equiv.; typically 0.3-1.0 mmol) was added methylamine (2.0 M solution in THF, 10.0 equiv.). The reaction mixture was heated to 100° C. under microwave irradiation for 4 h followed by concentration in vacuo. The product was purified via flash column chromatography (typically 40-80% EtOAc/Hex) to afford 6 in generally 70-85% yield.

Example 65

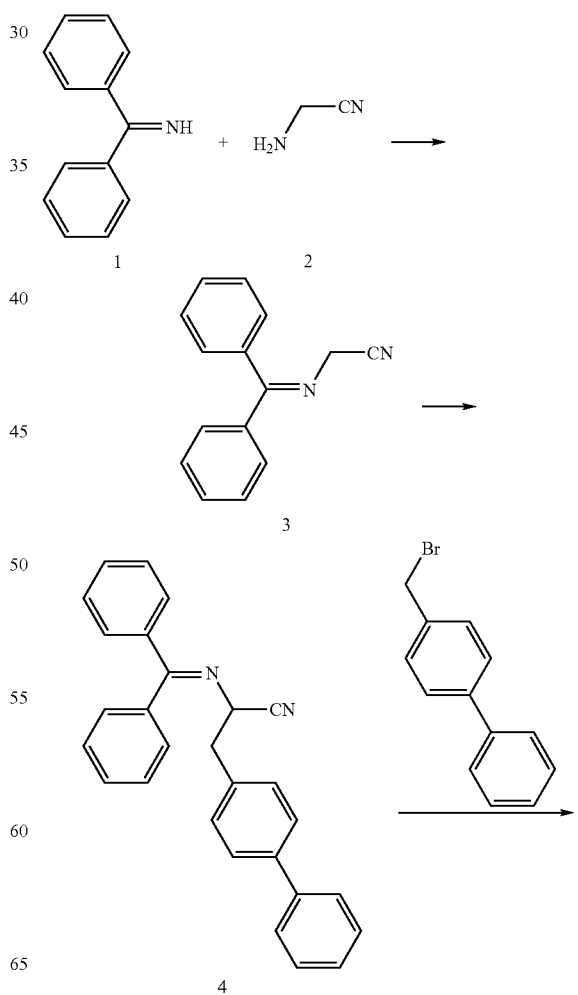

To a solution of 1 (1.0 g, 4.66 mmol) in MeOH (10.0 mL) was added SOCl₂ (0.68 mL, 9.32 mmol). After stirring overnight at ambient temperature, the solution was concentrated in vacuo and taken on without purification.

To a solution of 2 (~1.065 g crude, 4.66 mmol) in EtOH (1.5 mL) was added N₂H₄·H₂O (1.13 mL, 23.3 mmol). The reaction mixture was heated to reflux and stirred for 3 h. Upon cooling, the solution was treated with H₂O, extracted with trice with EtOAc, dried over MgSO₄, filtered, and concen-

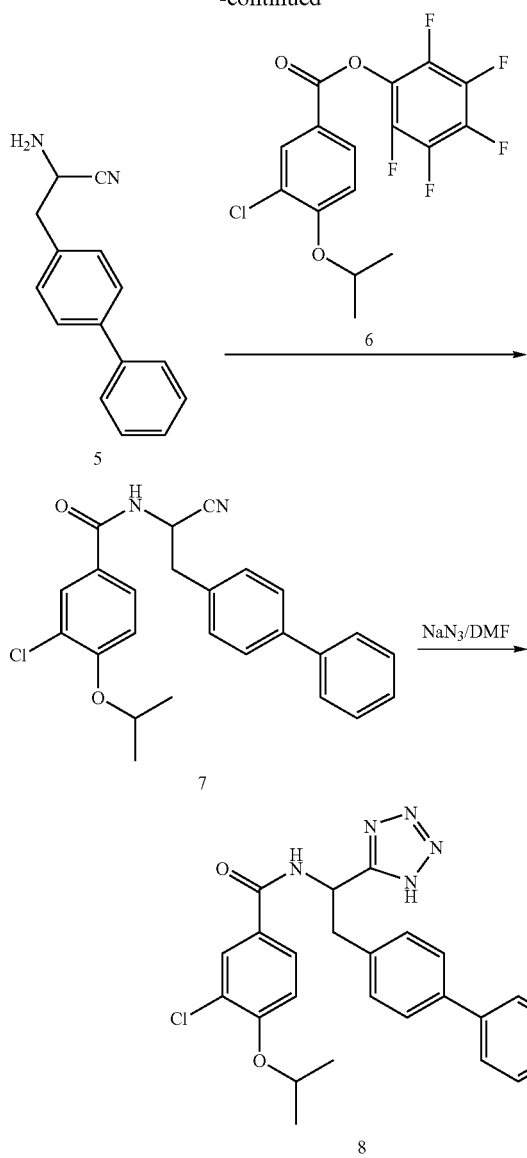

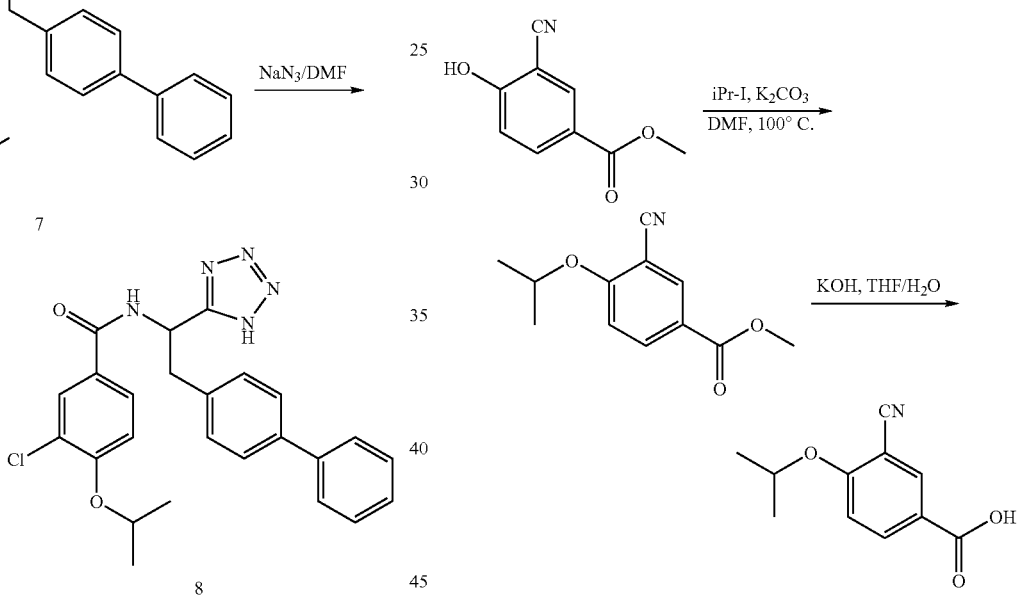

reduced pressure, and the resulting solid 5 was washed with ethyl ether (50 mL) three times and dried under vacuum (0.39 g, 32.1%).

To a solution of 5 (0.39 g, 1.75 mmol) in DMF (10 mL) were added 6 (0.801 g, 2.11 mmol) and diisopropylethylamine (0.61 mL, 3.50 mmol) at room temperature. The reaction mixture was stirred overnight. The solvents were then evaporated under reduced pressure, and the residue purified on a flash silica gel column (hexane:EtOAc, 3:1) to give 7 (0.40 g, 54.5%). LCMS (M+H$^+$) m/z 419.1.

To a solution of 7 (50 mg, 0.119 mmol) in DMF (2 mL) were added sodium azide (15.5 mg, 0.239 mmol) and ammonium chloride (12.8 mg, 0.238 mmol). The mixture was stirred at 80° C. overnight and then filtered. The filtrate was purified on reverse phase HPLC (C18) using a mixture of acetonitrile and H$_2$O to give 8 (6.40 mg, 11.6%). LCMS (M+H$^+$) m/z 462.4.

Example 66

To a stirred solution of 2-aminoacetonitrile bisulfate (2.9 g, 0.013 mmol) in DCM (50 mL) was added benzophenone (3.48 mL, 0.0208 mmol) followed by DIEA (4.53 mL, 0.026 mmol). After stirring 18 h, the DCM solution was washed with water (50 mL), dried over sodium sulfate, filtered, and the filtrate concentrated under reduced pressure. The residue was purified on a flash silica gel column (hexanes:EtOAc, 1:1) to give 3 (2.40 g, 82%).

Lithium bis(trimethylsilyl)amide (1 M solution in THF) was slowly added to a stirred solution of 3 (1.2 g, 0.00545 mol) and p-phenylbenzyl bromide (1.08 g, 0.00436 mol) in THF (50 mL) over an acetone-dry ice bath under a nitrogen atmosphere. After 1 hour, the reaction was quenched by adding methanol, and the solvent was evaporated under reduced pressure. The residue was purified on a flash silica gel column (hexanes:EtOAc, 1:1) to obtain 4. 4 was re-suspended in EtOAc (100 mL) and treated with concentrated HCl (5 mL). After stirring for 1 hour, the solvents were evaporated under Methyl 3-cyano-4-[(1-methylethyl)oxy]benzoate

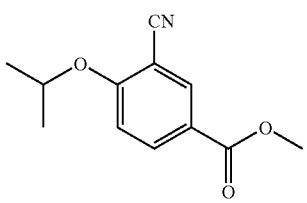

To a solution of methyl 3-cyano-4-hydroxybenzoate (82 g, 463 mmol; *J. Med. Chem,* 2002, 45, 5769) in dimethylformamide (800 mL) was added 2-iodopropane (93 mL, 926 mmol) and potassium carbonate (190 g, 1.4 mol). The resulting mixture was heated at 50° C. for 16 h, at which time it was allowed to cool to room temperature. The reaction was filtered and the mother liquor diluted with 0.5 N sodium hydroxide (1 L). The resulting mixture was extracted with ether (2×1 L) and the organics washed with 1 N HCl (1 L) and brine (700 mL), dried (MgSO$_4$) and concentrated to give 100 g (~100%) of methyl 3-cyano-4-[(1-methylethyl)oxy]benzoate as a yellow solid.

3-Cyano-4-[(1-methylethyl)oxy]benzoic acid

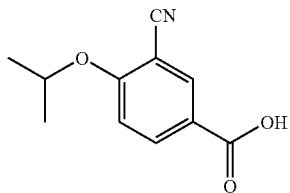

To a cooled (0° C.) solution of methyl 3-cyano-4-[(1-methylethyl)oxy]benzoate (100 g, 463 mmol) in tetrahydrofuran (500 mL) was added 10% potassium hydroxide (500 mL). The resulting solution was allowed to warm to room temperature and maintained for 16 h, at which time it was concentrated to remove the tetrahydrofuran. The residue was diluted with water (500 mL) and washed with ether (2×500 mL). The aqueous layer was then acidified with 3 N HCl and stood for 2 h. The solids were collected by filtration and washed several times with water, then dissolved in methylene chloride (1 L). The mostly homogeneous mixture was filtered through Celite and concentrated to a minimal volume of methylene chloride. Collection of the solids by filtration gave 82 g (87%) of 3-cyano-4-[(1-methylethyl)oxy]benzoic acid as a white solid.

Scheme B:
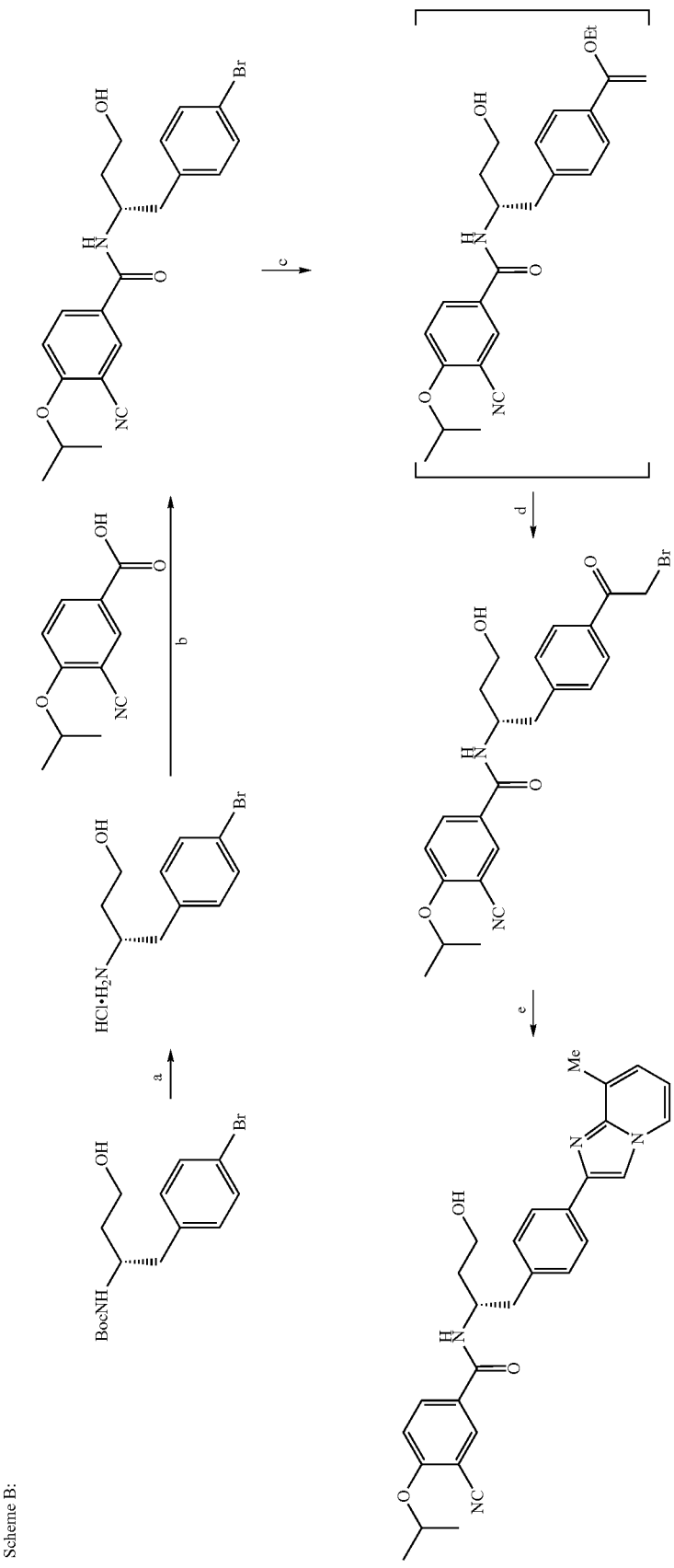

Reagents and Conditions: a) 4N HCl/dioxane, rt; b) HBTU, i-Pr₂NEt, DMF, rt; c) 1-ethoxyvinyltri-n-butyltin, PdCl₂(PPh₃)₂, dioxane, 100° C.; d) NBS, THF/H₂O (3:1), rt; e) 2-amino-3-picoline, NaHCO₃, i-PrOH, 80° C.

(3S)-3-Amino-4-(4-bromophenyl)-1-butanol hydrochloride

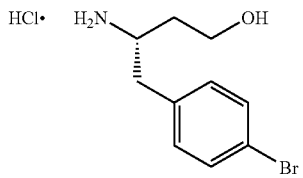

1,1-Dimethyl ethyl {(1S)-1-[(4-bromophenyl)methyl]-3-hydroxypropyl}carbamate (4.4 g, 12.8 mmol) was dissolved in 4N HCl/dioxane (20 mL). After 2 h, the reaction mixture was concentrated in vacuo to give 3.69 g (94%) of the title compound as a white solid. LC/MS (ES) m/e 244.0 (M+H)⁺.

N-{(1S)-1-[(4-Bromophenyl)methyl]-3-hydroxypropyl}-3-cyano-4-[(1-methylethyl)oxy]benzamide

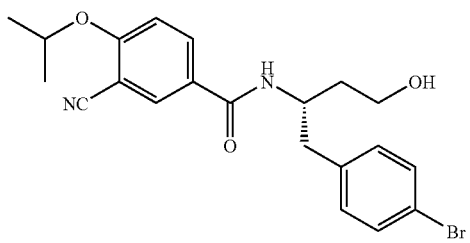

To a suspension of (3S)-3-Amino-4-(4-bromophenyl)-1-butanol hydrochloride (1.80 g, 6.42 mmol) in dry DMF (32 mL) was added N,N-diisopropylethyl amine (2.49 g, 19.3 mmol) and the resultant clear solution was stirred for 3 min. 3-Cyano-4-[(1-methylethyl)oxy]benzoic acid (1.45 g, 7.06 mmol) and HBTU (2.68 g, 7.06 mmol) were added and the reaction was stirred at rt under nitrogen. After 1.5 h, the reaction mixture was quenched with water (50 mL) and extracted with EtOAc (3×30 mL). The extracts were dried (Na₂SO₄), filtered and concentrated under reduced pressure. The residue was purified by silica gel chromatography (75% EtOAc/hexanes) to give 2.18 g (78%) of the title compound as a white solid. LC/MS (ES) m/e 431.2 (M+H)⁺.

N-((1S)-1-{[4-(Bromoacetyl)phenyl]methyl}-3-hydroxypropyl)-3-cyano-4-[(1-methylethyl)oxy]benzamide

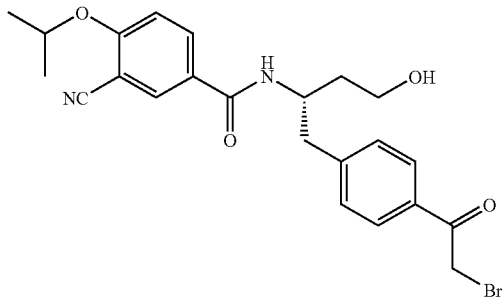

A flask, dried with a heat gun under argon purge, was charged with N-{(1S)-1-[(4-bromophenyl)methyl]-3-hydroxypropyl}-3-cyano-4-[(1-methylethyl)oxy]benzamide (1.0 g, 2.32 mol), dichlorobis(triphenylphosphine)-palladium(II) (81 mg, 0.116 mol), tributyl(1-ethoxyvinyl)tin (1.68 g, 4.64 mmol), and 1,4-dioxane (15 mL). The mixture was stirred at 100° C. for 2 hours under argon. Upon completion, as monitored by LCMS, the reaction was concentrated under reduced pressure and the residue was purified immediately on deactivated silica gel (65% EtOAc/hexanes with 5% triethylamine) to give 720 mg (1.70 mmol) of enol ether intermediate as a colorless foam which was immediately dissolved in THF:H₂O (3:1, 18 mL) and treated with N-bromosuccinimide (318 mg, 1.79 mmol). After 15 min at rt, the reaction mixture was concentrated under reduced pressure and the crude residue was diluted with EtOAc (30 mL), washed with brine (10 mL) and water (10 mL) and concentrated under reduced pressure. The residue was purified by silica gel chromatography (80% EtOAc/hexanes) to give 651 mg (59%) of N-((1S)-1-{[4-(bromoacetyl)phenyl]methyl}-3-hydroxypropyl)-3-cyano-4-[(1-methylethyl)oxy]benzamide as a white tacky solid. LC/MS (ES) m/e 473.2 (M+H)⁺.

3-Cyano-N-((1S)-3-hydroxy-1-{[4-(8-methylimidazo[1,2-a]pyridin-2-yl)phenyl]methyl}propyl)-4-[(1-methylethyl)oxy]benzamide

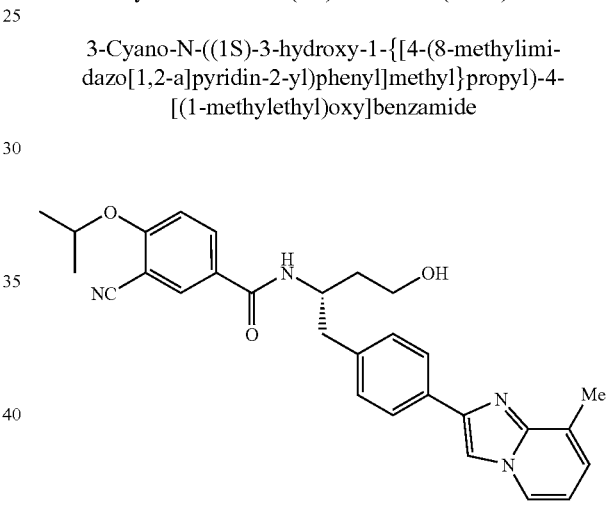

To a solution of N-((1S)-1-{[4-(bromoacetyl)phenyl]methyl}-3-hydroxypropyl)-3-cyano-4-[(1-methylethyl)oxy]benzamide (300 mg, 0.634 mmol) in i-PrOH (6 mL) was added 2-amino-3-picoline (Aldrich, 69 mg, 0.634 mmol) followed by solid NaHCO₃ (64 mg, 0.761 mmol). The resultant suspension was heated to 80° C. After 7 h, a majority of the i-PrOH was removed under reduced pressure and the residue was dissolved in 3% MeOH/EtOAc (30 mL) and washed with water (10 mL) and brine (10 mL). The combined aqueous layers were extracted with 3% MeOH/EtOAc (30 mL) and the combined extracts were dried (Na₂SO₄), filtered and concentrated under reduced pressure. The residue was purified by reverse phase HPLC (MeCN/H₂O with 0.1% TFA) and the clean fractions were adjusted to pH ~8 with saturated aqueous NaHCO₃ and extracted with 3% MeOH/EtOAc (3×30 mL). The extracts were dried (Na₂SO₄), filtered and concentrated under reduced pressure to give 215 mg (70%) of the title compound as a pale yellow solid. LC/MS (ES) m/e 483.2 (M+H)⁺.

1-(2-amino-3-pyridinyl)ethanol

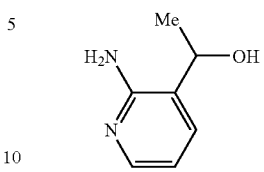

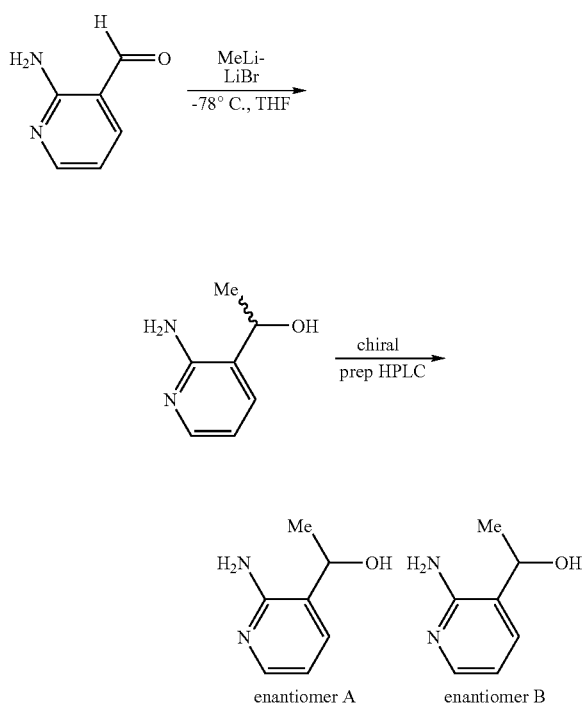

To a dry flask (dried with a heat gun under argon purge) was added dry THF (400 mL) and MeLi—LiBr (137 mL of a 1.5M solution in Et$_2$O, 204.9 mmol) via cannula. This solution was cooled to −78° C. when a solution of 2-aminopyridine-3-carboxaldehyde (10.0 g, 82.0 mmol) in THF (150 mL) was added dropwise via a pressure equalizing addition funnel over ~45 with vigorous stirring (exotherm observed, orange color persisted). Upon complete addition, the solution was allowed to stir for 1 hour at −78° C., at which time TLC (KMnO$_4$ stain with heat) indicated that most of the starting material had been converted to product. The reaction was quenched very carefully with water (200 mL; dropwise initially), diluted with EtOAc (200 mL) and allowed to warm to rt. The layers were separated and the aqueous layer was extracted with 3% MeOH in EtOAc. The combined extracts were dried over sodium sulfate, filtered and concentrated under reduced pressure. The residue was purified by silica gel chromatography (Analogix; 0 to 5% MeOH in EtOAc) to give 7.78 g (68%) of the desired racemic product as a yellow oil that solidified under high vac over several days. This material was separated into its respective enantiomers (>98% ee) by SFC with a chiralcel OD-H (20×250 mm) column (10% EtOH/0.1% isopropylamine in heptane/0.1% isopropylamine).

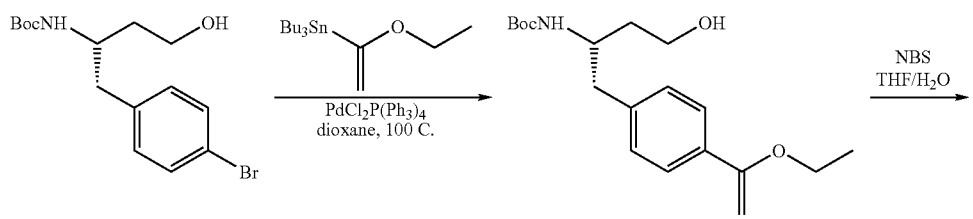

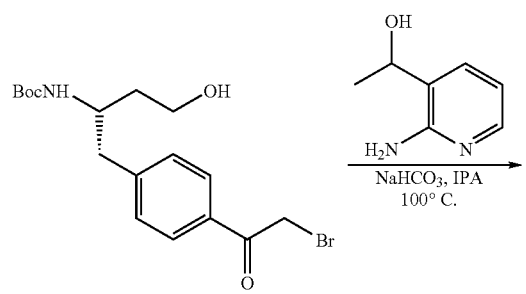

-continued

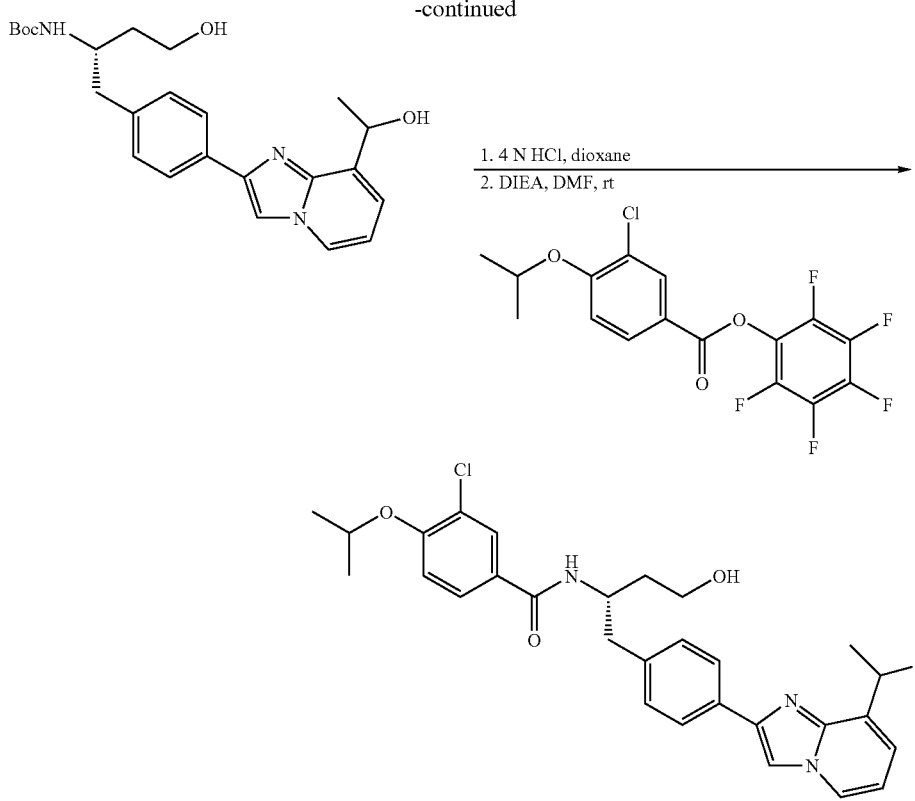

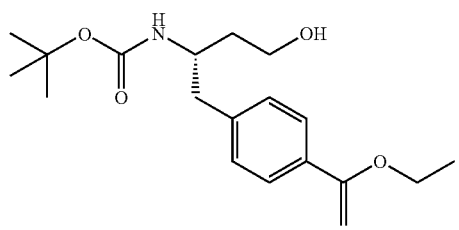

1,1-Dimethylethyl [(1S)-1-({4-[1-(ethyloxy)ethenyl]phenyl}methyl)-3-hydroxypropyl]carbamate To a solution of 1,1-dimethylethyl {(1S)-1-[(4-bromophenyl)methyl]-3-hydroxypropyl}carbamate (20 g, 58 mmol) in dioxane (500 mL) was added tributyl[1-(ethyloxy)ethenyl]stannane (39 mL, 116 mmol) and PdCl$_2$(PPh$_3$)$_2$. The resulting solution was heated at 100° C. for 5 h. The reaction was then concentrated and the residue purified by flash chromatography (47.5% EtOAc, 47.5% hexanes, 5% triethylamine) to give 15 g (77%) of 1,1-dimethylethyl [(1S)-1-({4-[1-(ethyloxy)ethenyl]phenyl}methyl)-3-hydroxypropyl]carbamate as a brown solid.

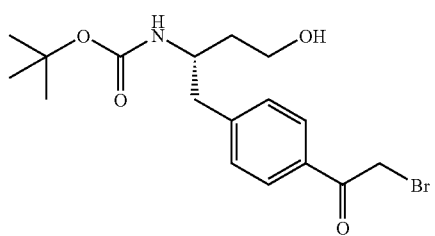

1,1-Dimethylethyl ((1S)-1-{[4-(bromoacetyl)phenyl]methyl}-3-hydroxypropyl)carbamate To a cooled (0° C.) solution of 1,1-dimethylethyl [(1S)-1-({4-[1-(ethyloxy)ethenyl]phenyl}methyl)-3-hydroxypropyl]carbamate (15 g, 44 mmol) in tetrahydrofuran (450 mL) and water (150 mL) was added N-bromosuccinimide. The resulting solution was allowed to warm to room temperature and maintained for 90 minutes. The reaction was then concentrated and diluted with ethyl acetate (1 L). The resulting solution was washed with water (1 L) and brine (500 mL), dried (MgSO$_4$) and concentrated to give 19.5 g (~100%) of 1,1-dimethylethyl ((1S)-1-{[4-(bromoacetyl)phenyl]methyl}-3-hydroxypropyl)carbamate as a slightly yellow solid. ESMS [M+H]$^+$: 386.2.

301

1,1-Dimethylethyl [(1S)-3-hydroxy-1-({4-[8-(1-hydroxyethyl)imidazo[1,2-a]pyridin-2-yl]phenyl}methyl)propyl]carbamate

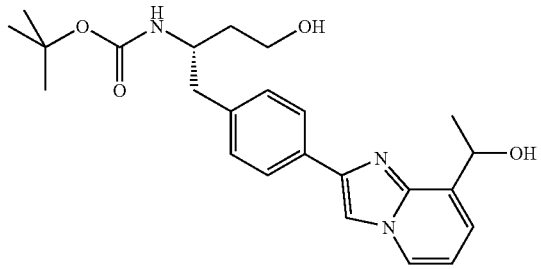

A mixture of 1,1-dimethylethyl ((1S)-1-{[4-(bromoacetyl)phenyl]methyl}-3-hydroxypropyl)carbamate (1.00 g, 2.59 mmol), 1-(2-amino-3-pyridinyl)ethanol (0.358 g, 2.59 mmol), and solid sodium bicarbonate (0.272 g, 3.24 mmol) in isopropanol (25 mL) was heated at reflux for 3.5 h. and concentrated in vacuo. The residue was dissolved in ethyl acetate, washed with water and brine, dried (Na$_2$SO$_4$), and concentrated. The resulting pale yellow solid was used in the next reaction without further purification. MS (ES+) m/e 426 [M+H]$^+$.

302

3-Chloro-N-[(1S)-3-hydroxy-1-({4-[8-(1-hydroxyethyl)imidazo[1,2-a]pyridin-2-yl]phenyl}methyl)propyl]-4-[(1-methylethyl)oxy]benzamide

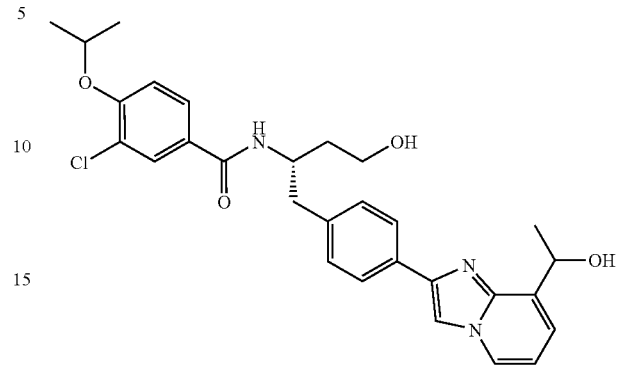

A mixture of 1,1-dimethylethyl [(1S)-3-hydroxy-1-({4-[8-(1-hydroxyethyl)imidazo[1,2-a]pyridin-2-yl]phenyl}methyl)propyl]carbamate (1.08 g, 2.54 mmol) and 4M HCl in 1,4-dioxane (8.0 mL, 32 mmol) was stirred at room temperature for 30 minutes. The reaction was concentrated to dryness redissolved in DMF (25 mL), and to this solution was added N,N-diisopropylethylamine (1.64 g, 12.7 mmol) and pentafluorophenyl 3-chloro-4-[(1-methylethyl)oxy]benzoate (0.963 g, 2.54 mmol). The mixture was stirred for 3.0 h at room temperature, diluted with water, and extracted into ethyl acetate. The extracts were washed with water and saturated sodium chloride, dried (Na$_2$SO$_4$), and concentrated in vacuo. The residue was purified by flash chromatography on silica gel (2% MeOH:EtOAc) to give the title compound (0.7 g, 53%) as a pale yellow powder. MS (ES+) m/e 522 [M+H]$^+$.

Scheme E:

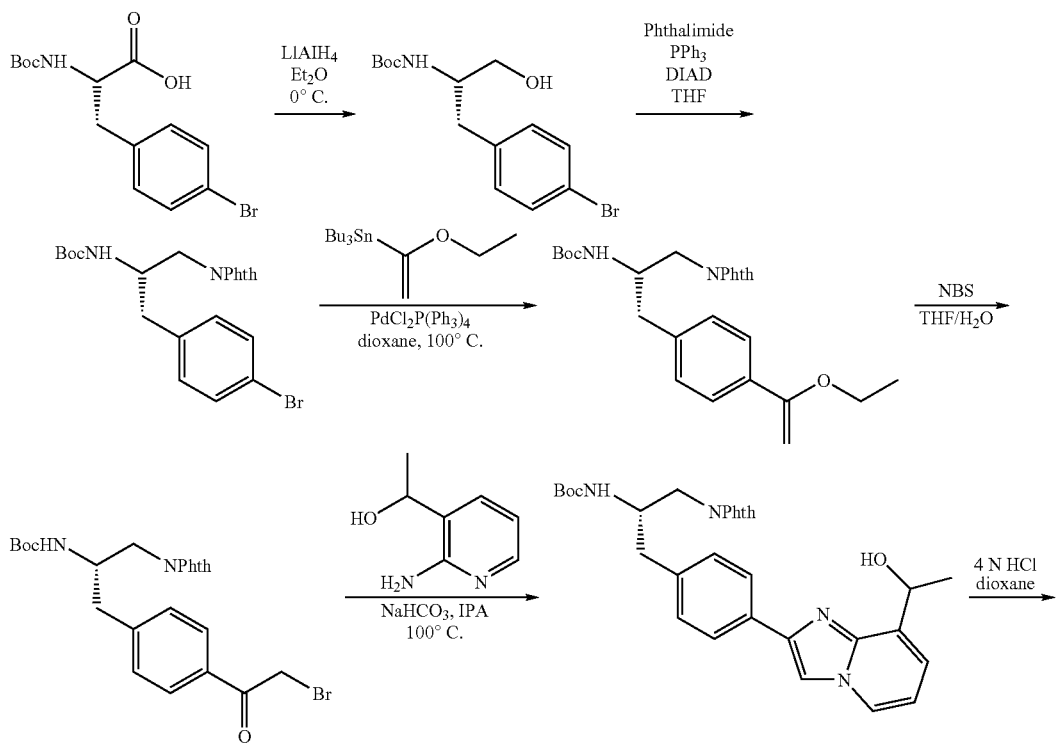

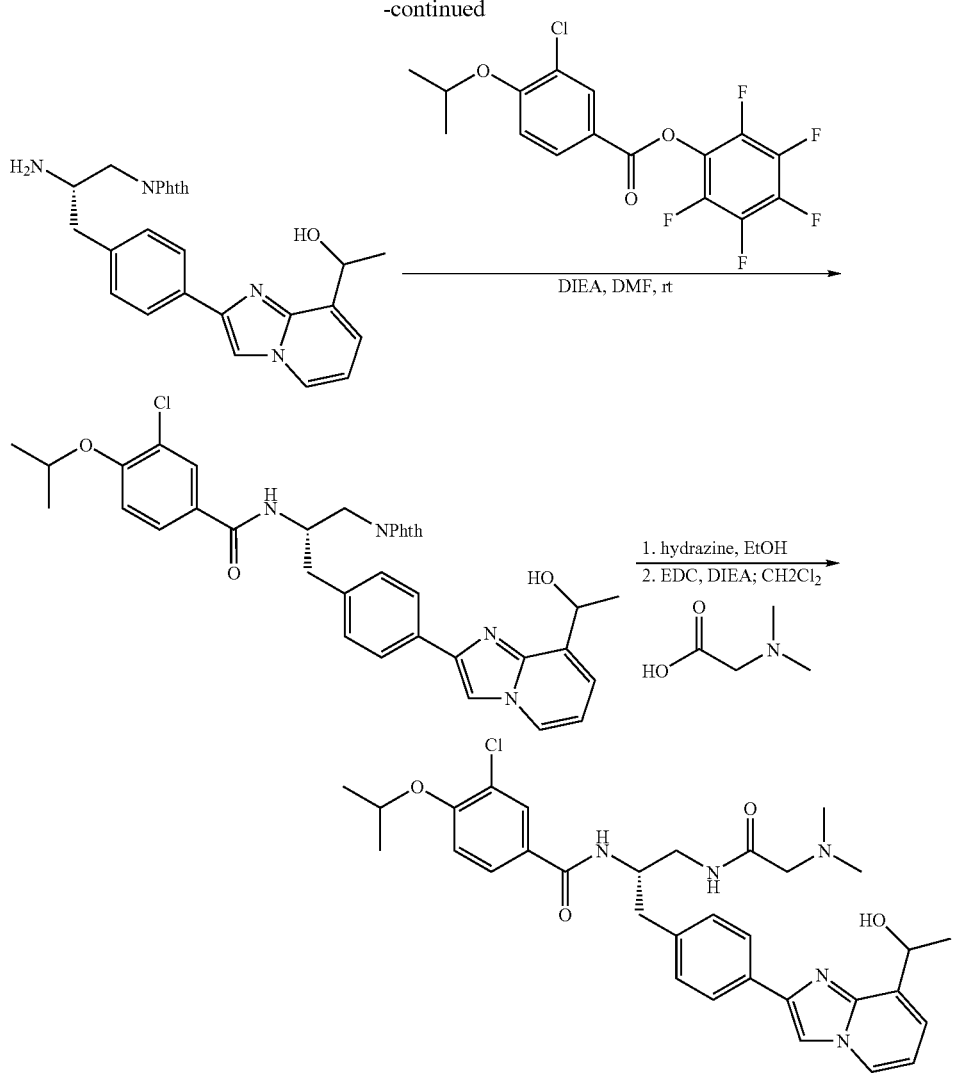

1,1-Dimethylethyl [(1S)-2-(4-bromophenyl)-1-(hydroxymethyl)ethyl]carbamate

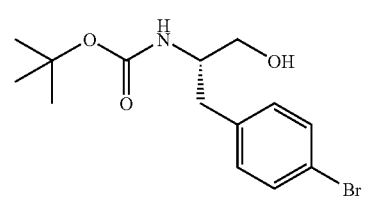

To a solution of 4-bromo-N-{[(1,1-dimethylethyl)oxy]carbonyl}-L-phenylalanine (72.6 mmol), in anhydrous diethyl ether (550 mL) at 0° C. was added slowly lithium aluminum hydride, 95% (108.9 mmol). The resulting solution was stirred for an additional 2 h at 0° C. The reaction was then carefully quenched with a saturated aqueous solution of sodium bicarbonate (73 mL) which stirred at RT for half an hour. Lithium aluminium salts crashed out of solution which were removed by filtration. The filtrate was concentrated and vacuum pumped for 24 h to afford the title product as a white solid (97%). ESMS [M+H]$^+$: 331.2.

1,1-Dimethylethyl {(1S)-2-(4-bromophenyl)-1-[(1,3-dioxo-1,3-dihydro-2H-isoindol-2-yl)methyl]ethyl}carbamate

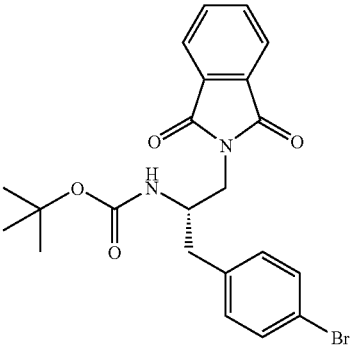

To a solution of 1,1-dimethylethyl [(1S)-2-(4-bromophenyl)-1-(hydroxymethyl)ethyl]carbamate (70.6 mmol), triphenylphosphine (84.7 mmol), and phthalimide (84.7 mmol) in anhydrous tetrahydrofuran (550 mL) at 0° C. was added dropwise diisopropyl azodicarboxylate (84.7 mmol) over 10 minutes. The reaction continued to stir allowing to warm to RT over 5 h. The reaction was then concentrated in vacuo and product was tritarated out of solution using 1 acetate (500 mL). The precipitate was filtered, washed with ethyl acetate (3×100 mL), and dried to afford the title product as a white solid (57%). ESMS [M+H]$^+$: 460.4.

1,1-Dimethylethyl {(1S)-2-[4-(bromoacetyl)phenyl]-1-[(1,3-dioxo-1,3-dihydro-2H-isoindol-2-yl)methyl]ethyl}carbamate

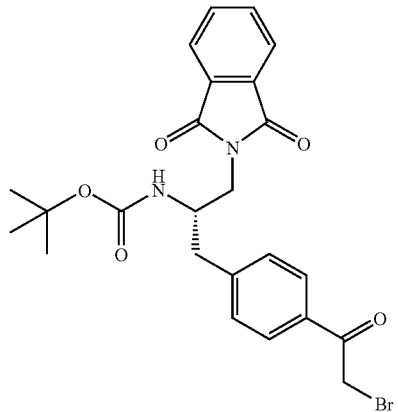

A solution of 1,1-dimethylethyl {(1S)-2-(4-bromophenyl)-1-[(1,3-dioxo-1,3-dihydro-2H-isoindol-2-yl)methyl]ethyl}carbamate (21.7 mmol), 1-ethoxyvinyltri-n-butylin (43.5 mmol), and trans-dichlorobis(triphenylphosphine)palladium(II) (5 mol %) were stirred in anhydrous dioxane (300 mL) at 100° C. for 3 h. The reaction was then concentrated in vacuo and redissolved in a solution of tetrahydrofuran and water (3:1, 400 mL) and treated with N-bromosuccinimide (108.8 mmol) and stirred at RT for half an hour. The reaction solution was then concentrated to dryness and redissolved in ethyl acetate (150 mL) and precipate formed upon addition of hexanes (350 mL). The precipitate was filtered and dried to afford the title product as yellow solid (71%). ESMS [M+H]$^+$: 502.4.

1,1-Dimethylethyl [(1S)-2-(1,3-dioxo-1,3-dihydro-2H-isoindol-2-yl)-1-({4-[8-(1-hydroxyethyl)imidazo[1,2-a]pyridin-2-yl]phenyl}methyl)ethyl]carbamate

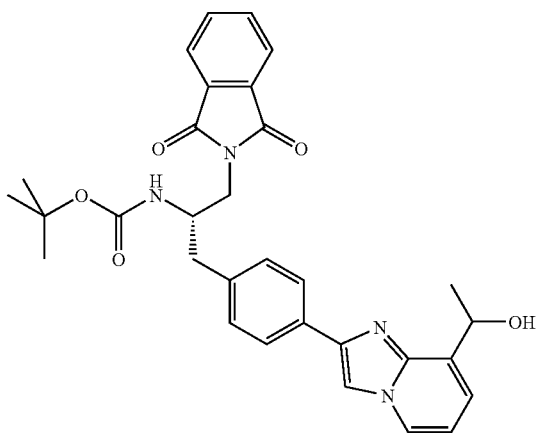

A mixture of 1,1-dimethylethyl {(1S)-2-{4-(bromoacetyl)phenyl]-1-[(1,3-dioxo-1,3-dihydro-2H-isoindol-2-yl)methyl]ethyl}carbamate (1.90 g, 3.79 mmol), 1-(2-amino-3-pyridinyl)ethanol (0.523 g, 3.79 mmol), and solid sodium bicarbonate (0.398 g, 4.72 mmol) in isopropanol (24 mL) was refluxed for 3.0 h. and concentrated in vacuo. The residue was dissolved in ethyl acetate, washed with water and saturated sodium chloride, dried (Na$_2$SO$_4$), and concentrated to give the title compound (1.79 g, 87%) as a light pink solid. MS (ES+) m/e 541 [M+H]$^+$.

3-Chloro-N-[(1S)-2-(1,3-dioxo-1,3-dihydro-2H-isoindol-2-yl)-1-({4-[8-(1-hydroxyethyl)imidazo[1,2-a]pyridin-2-yl]phenyl}methyl)ethyl]-4-[(1-methylethyl)oxy]benzamide:

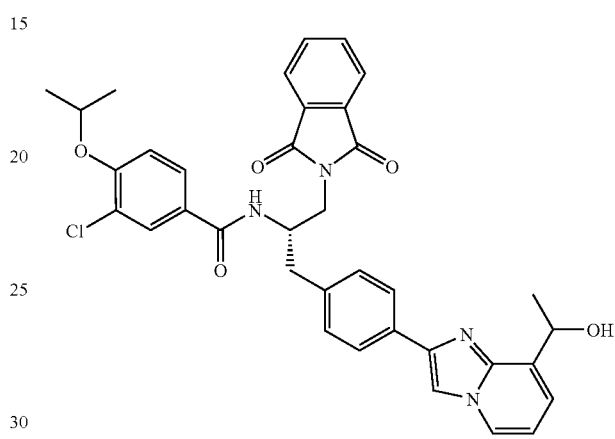

A mixture of 1,1-dimethylethyl [(1S)-2-(1,3-dioxo-1,3-dihydro-2H-isoindol-2-yl)-1-({4-[8-(1-hydroxyethyl)imidazo[1,2-a]pyridin-2-yl]phenyl}methyl)ethyl]carbamate (1.79 g, 3.31 mmol) and 4M HCl in 1,4-dioxane (20 mL, 80 mmol) was stirred at room temperature for 45 minutes. The reaction was concentrated to dryness, redissolved in DMF (30 mL), and to this solution was added N,N-diisopropylethylamine (2.14 g, 16.55 mmol) and pentafluorophenyl 3-chloro-4[(1-methylethyl)oxy]benzoate (1.36 g, 3.31 mmol). The mixture was stirred overnight at room temperature, diluted with water, and extracted into ethyl acetate. The extracts were washed with water, dried (Na$_2$SO$_4$), and concentrated in vacuo to give the title compound (2.10 g, 100%) as a tan solid. MS (ES+) m/e 637 [M+H]$^+$.

N-[(1S)-2-Amino-1-({4-[8-(1-hydroxyethyl)imidazo[1,2-a]pyridin-2-yl]phenyl}methyl)ethyl]-3-chloro-4-[(1-methylethyl)oxy]benzamide

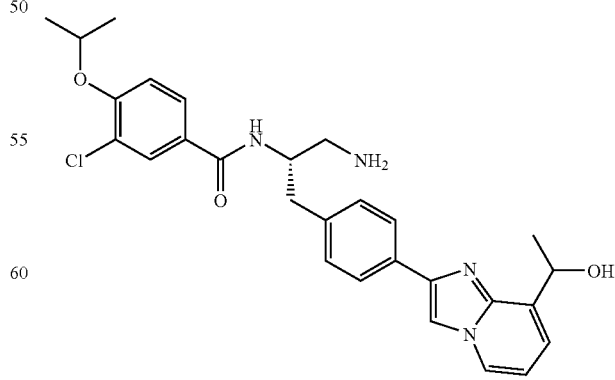

A mixture of 3-chloro-N-[(1S)-2-(1,3-dioxo-1,3-dihydro-2H-isoindol-2-yl)-1-({4-[8-(1-hydroxyethyl)imidazo[1,2-a]

pyridin-2-yl]phenyl}methyl)ethyl]-4-[(1-methylethyl)oxy]benzamide (2.10 g, 3.30 mmol) and hydrazine monohydrate (0.83 g, 16.5 mmol) in ethanol (30 mL) was heated at 57° C. overnight. The reaction was cooled, diluted with ethanol, filtered, and concentrated to give the title compound (1.67 g, 100%) as a pale yellow powder. MS (ES+) m/e 507 [M+H]$^+$.

3-Chloro-N-[(1S)-2-[(N,N-dimethylglycyl)amino]-1-({4-[8-(1-hydroxyethyl)imidazo[1,2-a]pyridin-2-yl]phenyl}methyl)ethyl]-4-[(1-methylethyl)oxy]benzamide

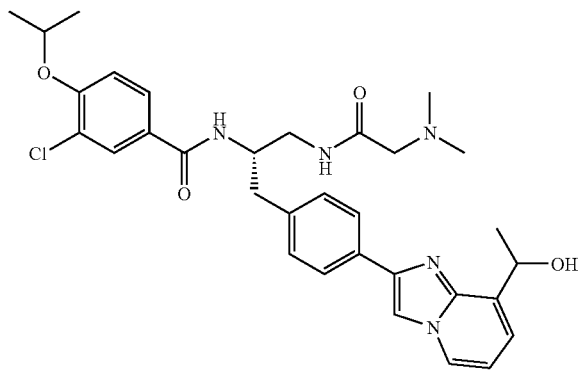

A mixture of N-[(1S)-2-amino-1-({4-[8-(1-hydroxyethyl)imidazo[1,2-a]pyridin-2-yl]phenyl}methyl)ethyl]-3-chloro-4-[(1-methylethyl)oxy]benzamide (0.912 g, 1.80 mmol), EDCI (0.69 g, 3.6 mmol), N,N-diisopropylethylamine (0.466 g, 3.6 mmol), and N,N-dimethylglycine (0.372 g, 3.6 mmol) in methylene chloride (17 mL) was stirred overnight at room temperature. The reaction was diluted with water, washed with brine, dried (Na$_2$SO$_4$), and concentrated. The residue was purified by flash chromatography on silica gel (8%-10% MeOH:CH$_2$Cl$_2$) to give the title compound (0.515 g, 48%) as a pale yellow solid. MS (ES+) m/e 592 [M+H]$^+$.

1,1-Dimethylethyl {(1S)-2-[4-(8-bromoimidazo[1,2-a]pyridin-2-yl)phenyl]-1-[(1,3-dioxo-1,3-dihydro-2H-isoindol-2-yl)methyl]ethyl}carbamate

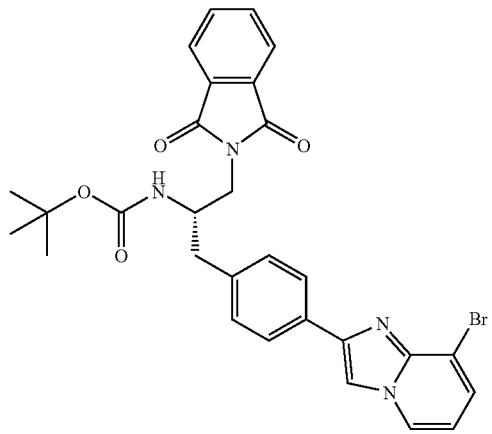

A solution of 1,1-dimethylethyl {(1S)-2-[4-(bromoacetyl)phenyl]-1-[(1,3-dioxo-1,3-dihydro-2H-isoindol-2-yl)me-thyl]ethyl}carbamate (6.9 mmol), 3-bromo-2-pyridinamine (8.4 mmol), and sodium bicarbonate (10.4 mmol) in isopropanol (70 mL) were stirred at 80° C. for 18 h. The reaction was then cooled to RT and a precipitate formed which was filtered, washed with cold hexanes (3×100 mL), and dried to afford the title compound as light gray solid (72%). ESMS [M+H]$^+$: 576.2.

1,1-Dimethylethyl ((1S)-2-(1,3-dioxo-1,3-dihydro-2H-isoindol-2-yl)-1-{[4-(8-methylimidazo[1,2-a]pyridin-2-yl)phenyl]methyl}ethyl)carbamate

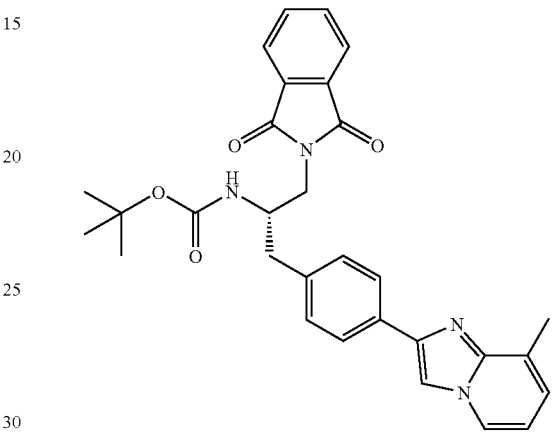

Following the procedure described above with 3-methyl-2-pyridinamine, instead of 3-bromo-2-pyridinamine, provided the title product as a light pink solid. ESMS [M+H]$^+$: 511.0.

N-{(1S)-2-[4-(8-Bromoimidazo[1,2-a]pyridin-2-yl)phenyl]-1-[(1,3-dioxo-1,3-dihydro-2H-isoindol-2-yl)methyl]ethyl}-3-chloro-4-[(1-methylethyl)oxy]benzamide

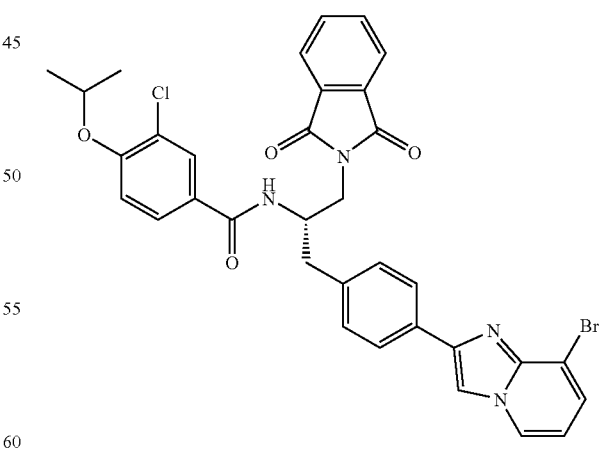

A solution of 1,1-dimethylethyl {(1S)-2-[4-(8-bromoimidazo[1,2-a]pyridin-2-yl)phenyl]-1-[(1,3-dioxo-1,3-dihydro-2H-isoindol-2-yl)methyl]ethyl}carbamate (3.5 mmol) and hydrogen chloride in 1,4-dioxane (20 mL, 4.0M) stirred for 1 h at RT. The reaction was concentrated to dryness and redissolved in N,N-dimethylformamide (35 mL). Added to the solution was diisopropylethylamine (10.5 mmol) and pentafluorophenyl 3-chloro-4-[(1-methylethyl)oxy]benzoate (3.8 mmol), which was stirred at RT for half an hour. The reaction was dissolved in ethyl acetate (80 mL) and washed with water (3×50 mL) and brine (1×50 mL). To the separated organic layer was added hexanes (150 mL) upon which a precipitate was formed, filtered, and dried to afford the title compound as an off white solid (65%). ESMS [M+H]$^+$: 672.2.

3-Chloro-N-((1S)-2-(1,3-dioxo-1,3-dihydro-2H-isoindol-2-yl)-1-{[4-(8-methylimidazo[1,2-a]pyridin-2-yl)phenyl]methyl}ethyl)-4-[(1-methylethyl)oxy]benzamide

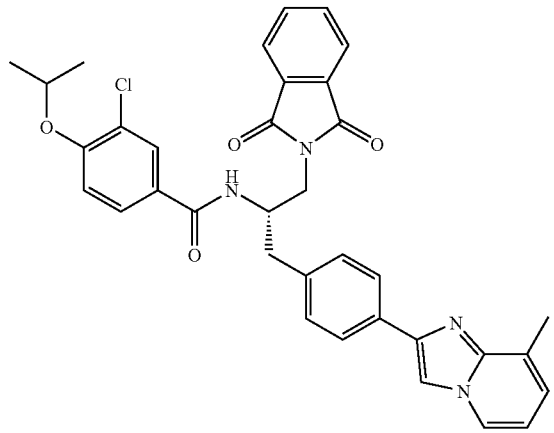

Following the procedure described above with 1,1-dimethylethyl ((1S)-2-(1,3-dioxo-1,3-dihydro-2H-isoindol-2-yl)-1-{[4-(8-methylimidazo[1,2-a]pyridin-2-yl)phenyl]methyl}ethyl)carbamate provided the title product as an off white solid. ESMS [M+H]$^+$: 608.2.

N-((1S)-2-Amino-1-{[4-(8-bromoimidazo[1,2-a]pyridin-2-yl)phenyl]methyl}ethyl)-3-chloro-4-[(1-methylethyl)oxy]benzamide

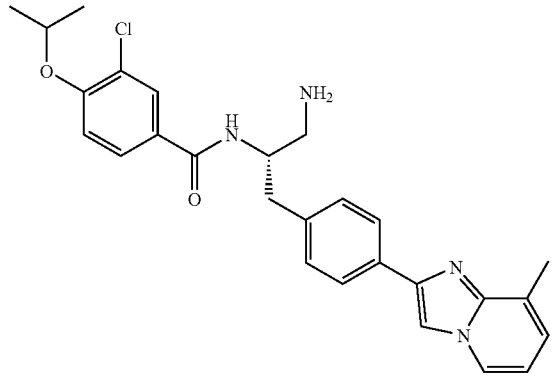

To a solution, of N-{(1S)-2-[4-(8-bromoimidazo[1,2-a]pyridin-2-yl)phenyl]-1-[(1,3-dioxo-1,3-dihydro-2H-isoindol-2-yl)methyl]ethyl}-3-chloro-4-[(1-methylethyl)oxy]benzamide (1.5 mmol) in ethanol (10 mL) was added hydrazine monohydrate (7.6 mmol). The reaction stirred for 18 h at 50° C. upon which a white precipitate formed and filtered. The filtrate was concentrated in vacuo. The resultant light yellow solid was used directly in the next reaction without further purification. ESMS [M+H]$^+$: 533.2

N-((1S)-2-Amino-1-{[4-(8-methylimidazo[1,2-a]pyridin-2-yl)phenyl]methyl}ethyl)-3-chloro-4-[(1-methylethyl)oxy]benzamide

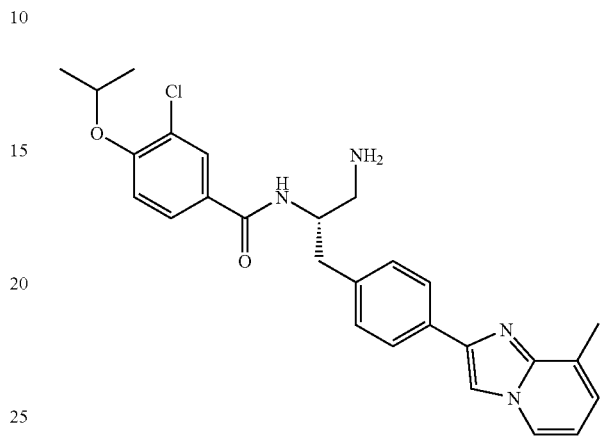

Following the procedure described above with 3-chloro-N-((1S)-2-(1,3-dioxo-1,3-dihydro-2H-isoindol-2-yl)-1-{[4-(8-methylimidazo[1,2-a]pyridin-2-yl)phenyl]methyl}ethyl)-4-[(1-methylethyl)oxy]benzamide provided the title product as an off white solid. ESMS [M+H]$^+$: 478.2.

N-((1S)-2-(D-Alanylamino)-1-{[4-(8-bromoimidazo[1,2-a]pyridin-2-yl)phenyl]methyl}ethyl)-3-chloro-4-[(1-methylethyl)oxy]benzamide

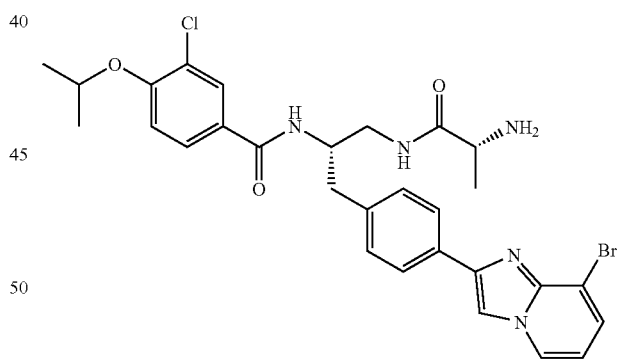

A solution of N-((1S)-2-amino-1-{[4-(8-bromoimidazo[1,2-a]pyridin-2-yl)phenyl]methyl}ethyl)-3-chloro-4-[(1-methylethyl)oxy]benzamide (0.28 mmol), N-{[(1,1-dimethylethyl)oxy]carbonyl}-D-alanine (0.56 mmol), EDCI (0.56 mmol), and TEA (1.12 mmol) stirred in methylene chloride (2 mL) at RT for 18 h. The reaction was then treated with 4 M HCl in 1,4-dioxane (2 mL) and stirred at RT for 1 h and concentrated in vacuo, redissolved in ethyl acetate (25 mL) and washed with saturated aqueous sodium bicarbonate solution (1×10 mL). The organic layer was concentrated in vacuo. Purification of the residue by Gilson reverse phase HPLC afforded the title product as a white solid (25%). ESMS [M+H]$^+$: 613.2.

311

3-Chloro-N-((1S)-2-[(2-methylalanyl)amino]-1-{[4-(8-methylimidazo[1,2-a]pyridin-2-yl)phenyl]methyl}ethyl)-4-[(1-methylethyl)oxy]benzamide

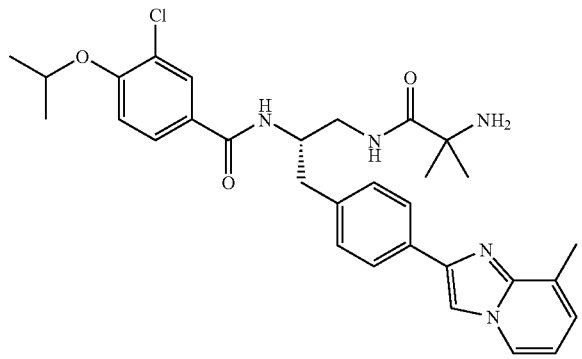

Following the procedure described above with N-((1S)-2-amino-1-{[4-(8-methylimidazo[1,2-a]pyridin-2-yl)phenyl]methyl}ethyl)-3-chloro-4-[(1-methylethyl)oxy]benzamide and N-{[(1,1-dimethylethyl)oxy]carbonyl}-2-methylalanine provided the title product as a white solid. ESMS [M+H]$^+$: 563.2.

3-Chloro-N-((1S)-2-[(N,N-dimethylglycyl)amino]-1-{[4-(8-methylimidazo[1,2-a]pyridin-2-yl)phenyl]methyl}ethyl)-4-[(1-methylethyl)oxy]benzamide

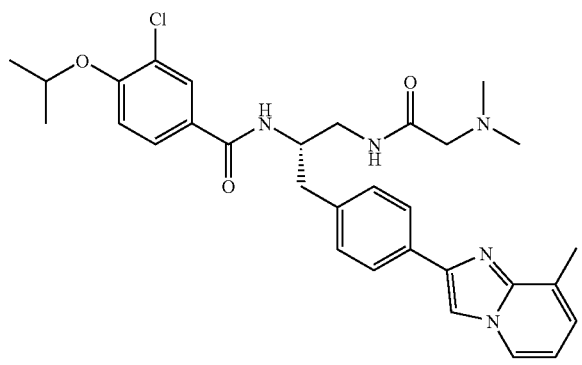

Following the procedure described above with N-((1S)-2-amino-1-{[4-(8-methylimidazo[1,2-a]pyridin-2-yl)phenyl]methyl}ethyl)-3-chloro-4-[(1-methylethyl)oxy]benzamide and N,N-dimethylglycine provided the title product as a white solid. ESMS [M+H]$^+$: 563.2.

Scheme F:

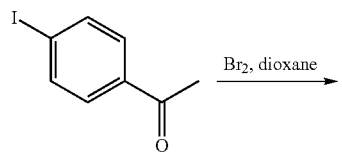

-continued

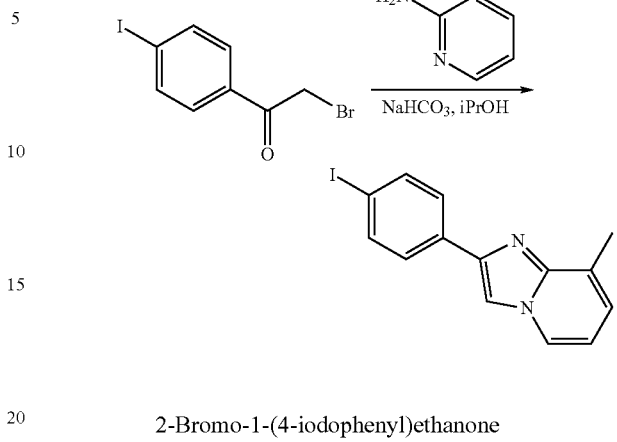

2-Bromo-1-(4-iodophenyl)ethanone

A solution of 1-(4-iodophenyl)ethanone (55.9 mmol) in dioxane (160 mL) was cooled to 10° C. Bromine (1.1 equiv, 61.6 mmol) was added dropwise to the reaction mixture. After 10 min, the cooling bath was removed and the reaction mixture was stirred at room temperature. After 1.5 h, the reaction mixture was concentrated in vacuo, poured into water (100 mL), and extracted with (3×100 mL) ethyl acetate. The combined organic layers were dried over sodium sulfate and concentrated in vacuo to a tan solid (18.2 g) which was used directly in the next step.

2-(4-Iodophenyl)-8-methylimidazo[1,2-a]pyridine

A mixture of crude 2-bromo-1-(4-iodophenyl)ethanone (18.2 g), 2-amino-3-picoline (1.1 equiv, 61.6 mmol), and sodium bicarbonate (1.3 equiv, 72.8 mmol) in isopropanol (160 mL) was heated at 80° C. for 16 h. After concentrating the reaction mixture in vacuo, water (100 mL) was added and the resultant tan slurry was filtered, rinsing with water (2×50 mL). The brown solid was recrystallized from hot isopropanol and further dried in vacuo to provide the title product as a brown solid (13.2 g, 71%). ESMS [M+H]$^+$: 335.0.

Scheme G:

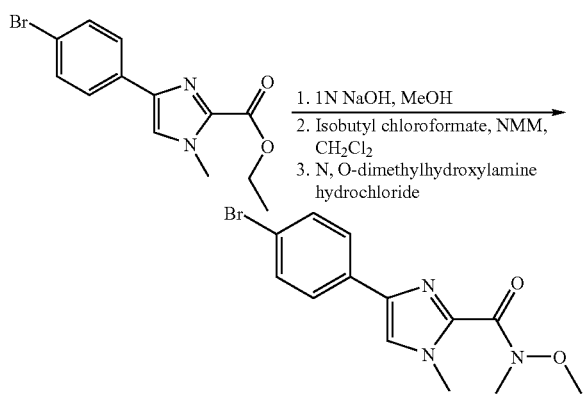

4-(4-Bromophenyl)-N,1-dimethyl-N-(methyloxy)-1H-imidazole-2-carboxamide

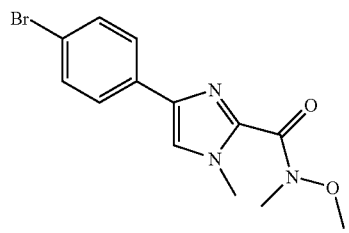

To a solution of ethyl 4-(4-bromophenyl)-1-methyl-1H-imidazole-2-carboxylate (1.66 g, 5.37 mmol) in MeOH (38 mL) was added 1N NaOH solution (19 mL). The reaction turned cloudy white and was stirred at room temperature for 30 minutes. The reaction mixture was concentrated in vacuo and pumped under high vacuum overnight to give the sodium salt of 4-(4-bromophenyl)-1-methyl-1H-imidazole-2-carboxylic acid as a white solid. The sodium salt of 4-(4-bromophenyl)-1-methyl-1H-imidazole-2-carboxylic acid was dissolved in anhydrous $CH_2Cl_2$ (40 mL) under nitrogen at −15° C. (ice/methanol bath) and N-methylmorpholine (1.1 equiv, 5.91 mmol) was added followed by isobutyl chloroformate (1.1 equiv, 5.91 mmol). The reaction mixture was stirred at −15° C. for 15 minutes and then N,O-dimethylhydroxylamine hydrochloride (1.0 equiv, 5.37 mmol) was added. The reaction was allowed to warm to room temperature and was stirred for 17 hours. The reaction was quenched with $H_2O$ (10 mL). The product was extracted using EtOAc (3×30 mL) and the combined organic layers were washed with brine (20 mL), dried over $MgSO_4$, and concentrated in vacuo. Purification by silica gel chromatography (Analogix IF280, 20-100% EtOAc/hexanes) afforded the title compound as a tan solid (32%). ESMS $[M+H]^+$: 324.2.

Scheme H:

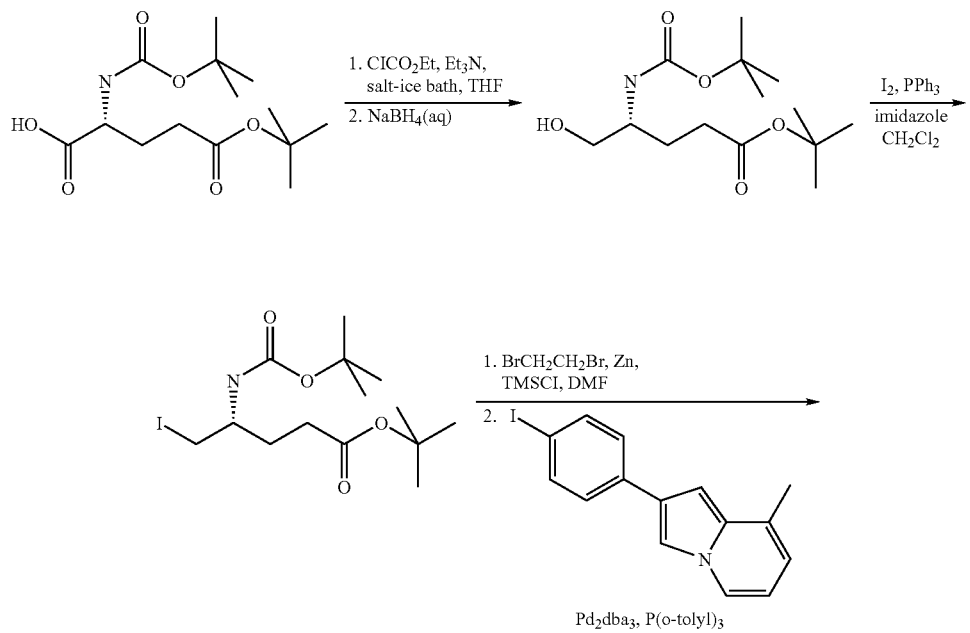

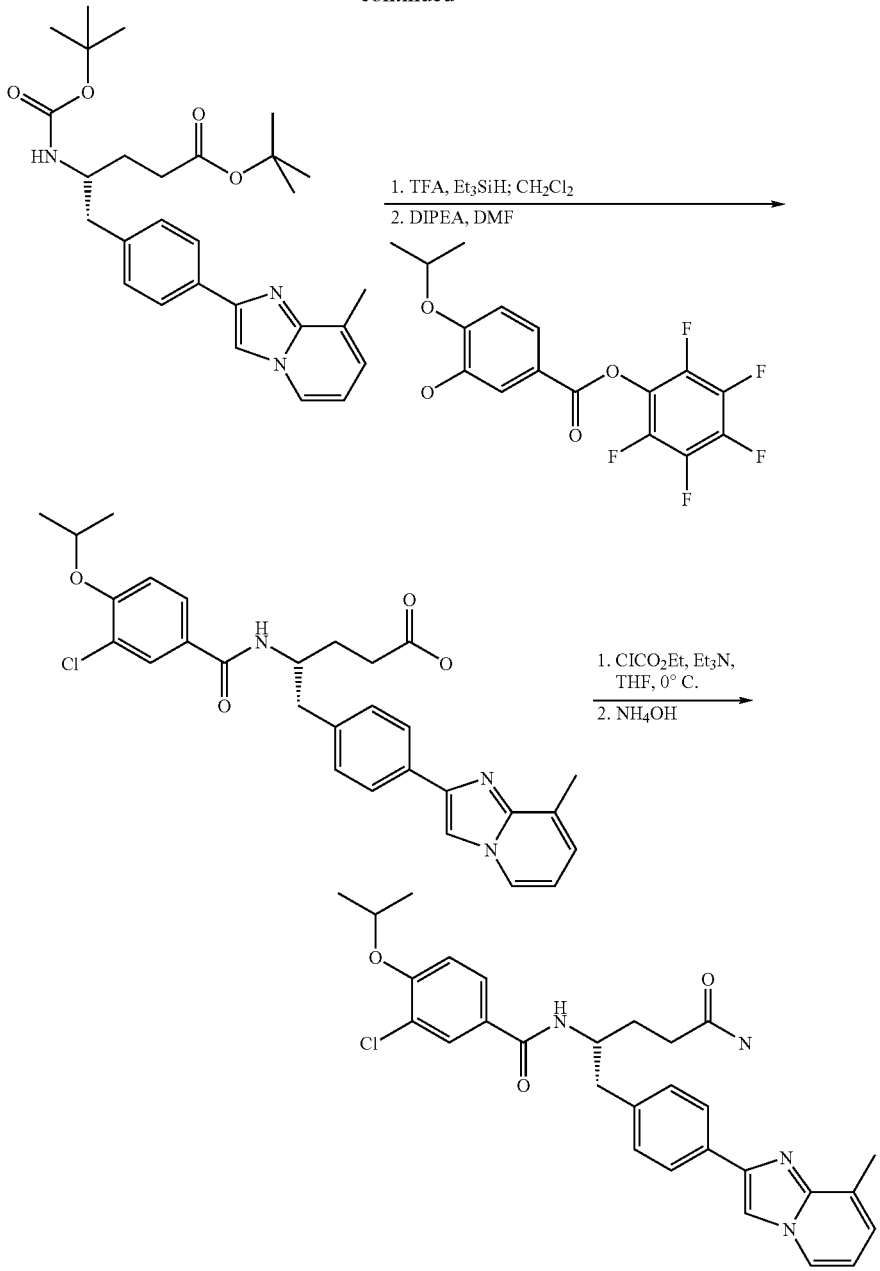

1,1-Dimethylethyl (4R)-4-({[(1,1-dimethylethyl)oxy]carbonyl}amino)-5-hydroxypentanoate

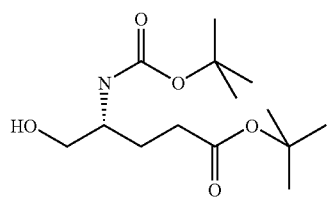

Triethylamine (11.49 mL, 82.4 mmol) and ethyl chloroformate (8.27 mL, 86.5 mmol) were added successively by syringe to N-t-BOC-D-glutamic acid 5-tert-butyl ester (25 g, 82.4 mmol) in THF (588 mL) at <0° C. (ice-salt bath). After stirring in the cold bath for 40 min, solids were filtered and were washed with THF (150 mL). The filtrate was transferred to a 250-mL addition funnel and added to a solution of sodium borohydride (8.42 g, 222.5 mmol) in H₂O (114 mL) at 0° C. over 1 hour. The reaction mixture was maintained at 0° C. for 1.5 h and then stirred for 16 h (0° C. to room temperature). After the bulk of solvents were removed by rotary evaporation, the concentrate was quenched with ice water (50 mL) and 1 N HCl (50 mL). After extraction with EtOAc (4×100 mL), the extracts were washed with 100 mL: 0.5 M citric acid, saturated NaHCO₃, H₂O, and brine and concentrated in vacuo to give the title compound, which was used directly in the next step. ESMS [M+H]$^+$=290.4, [2M+H]$^+$=579.4. (Literature prep: *J. Med. Chem,* 1999, 42(1), 95-108 for other isomer).

1,1-dimethylethyl (4R)-4-({[(1,1-dimethylethyl)oxy]carbonyl}amino)-5-iodopentanoate

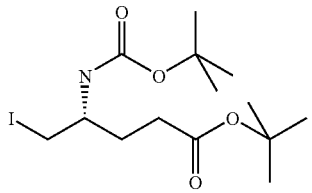

To a solution of crude 1,1-dimethylethyl (4R)-4-({[(1,1-dimethylethyl)oxy]carbonyl}amino)-5-hydroxypentanoate (23.8 g, 82.4 mmol), triphenylphosphine (32.42 g, 123.6 mmol) and imidazole (8.41 g, 123.6 mmol) in 515 mL anhydrous $CH_2Cl_2$ under $N_2$ at 0° C. was added iodine over 15 min portionwise. The ice bath was removed and the reaction was allowed to warm to room temperature and stirred over 30 minutes. The reaction was quenched with 200 mL $H_2O$. The aqueous layer was extracted with diethyl ether (2×150 mL). The combined organic layers were washed with sat. aq. $Na_2SO_3$ solution (2×25 mL) and brine (25 mL), dried over $MgSO_4$, and concentrated, in vacuo. Purification of the residue by silica gel chromatography (Analogix IF280, 5%-50% EtOAc/Hex) afforded the title compound as a white solid (25.34 g, 77%). ESMS [M+H]$^+$=400.4.

1,1-dimethylethyl (4R)-4-({[(1,1-dimethylethyl)oxy]carbonyl}amino)-5-[4-(8-methylimidazo[1,2-a]pyridin-2-yl)phenyl]pentanoate

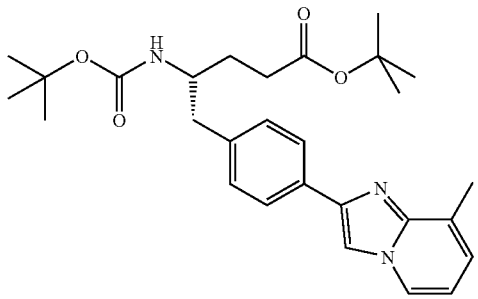

A flask containing zinc dust (6.0 equiv, 325 mesh, Strem) was heated with a heat gun while evacuating and filling with nitrogen (3 times). Under nitrogen, degassed DMF (14 mL) was added via syringe followed by 1,2-dibromoethane (0.35 equiv). The grey reaction mixture was stirred in an oil bath at 100° C. for 15 minutes and then cooled to room temperature. Chlorotrimethylsilane (0.25 equiv) was added to the mixture via syringe and the reaction was stirred at room temperature for 30 minutes. A solution of 1,1-dimethylethyl (4R)-4-({[(1,1-dimethylethyl)oxy]carbonyl}amino)-5-iodopentanoate (2.0 g, 1.2 equiv) in degassed DMF (14 mL) was added to the reaction mixture via cannula. The flask containing the solution was rinsed with degassed DMF (4 mL) and cannulated into the reaction mixture. The reaction was stirred at room temperature for 1 hour. Then, tris(dibenzylideneacetone)dipalladium (0) (2.5 mol %), tri-o-tolylphosphine (10 mol %) and 2-(4-iodophenyl)-8-methylimidazo[1,2-a]pyridine (1.4 g, 1.0 equiv) were added through the top all at once. The reaction mixture was stirred at room temperature for 17 hours. The reaction was diluted with EtOAc (40 mL) and filtered through Celite®. The filtrate was washed with $H_2O$ (20 mL) and brine (20 mL), and the organic layer was dried over $MgSO_4$ and concentrated in vacuo. Purification by silica gel chromatography (Analogix IF280, 5-90% EtOAc/hexanes) afforded the title compound as a white solid (90%). ESMS [M+H]$^+$=480.4.

1,1-dimethylethyl (4R)-4-({[(1,1-dimethylethyl)oxy]carbonyl}amino)-5-[4-(1-methyl-2-{[methyl(methyloxy)amino]carbonyl}-1H-imidazol-4-yl)phenyl]pentanoate

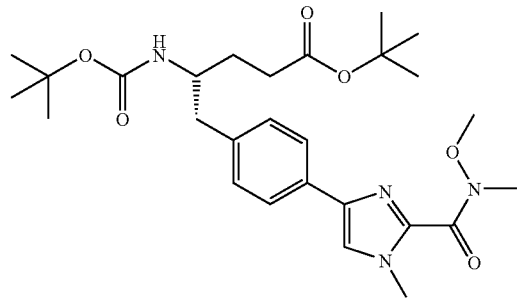

Following the procedure described above using 4-(4-bromophenyl)-N,1-dimethyl-N-(methyloxy)-1H-imidazole-2-carboxamide provided the title compound as a solid (82%). ESMS [M+H]$^+$=517.2.

(4R)-4-[({3-chloro-4-[(1-methylethyl)oxy]phenyl}carbonyl)amino]-5-[4-(8-methylimidazo[1,2-a]pyridin-2-yl)phenyl]pentanoic acid

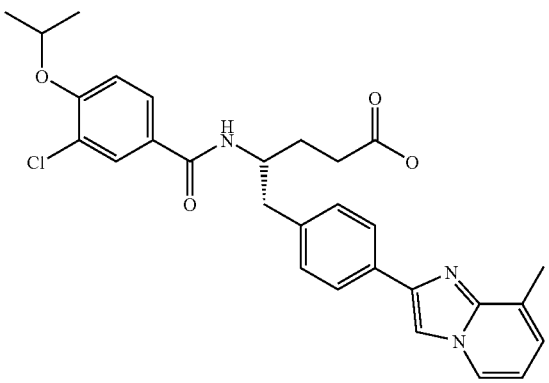

To a solution of 1,1-dimethylethyl (4R)-4-({[(1,1-dimethylethyl)oxy]carbonyl}amino)-5-[4-(8-methylimidazo[1,2-a]pyridin-2-yl)phenyl]pentanoate (1.35 g, 2.82 mmol) in $CH_2Cl_2$ (14 mL) was added trifluoroacetic acid (10 mL) followed by triethylsilane (2.5 equiv, 7.04 mmol). The reaction was stirred for 45 minutes at room temperature and then concentrated in vacuo. DMF (35 mL) was added to the residue followed by diisopropylamine (14.7 mL, 84.51 mmol) under nitrogen. The reaction was stirred for 5 minutes and pentafluorophenyl 3-chloro-4-[(1-methylethyl)oxy]benzoate (1.1 equiv, 3.10 mmol) was added. The reaction was stirred for 45 minutes and then concentrated in vacuo. Ethyl acetate (50 mL) was added to the residue and it was washed with $H_2O$ (30 mL). The aqueous layer was extracted with EtOAc (20 mL) and the combined organic layers were dried over $MgSO_4$ and concentrated in vacuo. Purification by silica gel chromatography (Analogix IF280, 25-100% EtOAc/hexanes) provided the title compound as a white foamy solid (61%). ESMS $[M+H]^+=520.2$.

(4R)-4-[({3-chloro-4-[(1-methylethyl)oxy]phenyl}carbonyl)amino]-5-[4-(1-methyl-2-{[methyl(methyloxy)amino]carbonyl}-H-imidazol-4-yl)phenyl]pentanoic acid

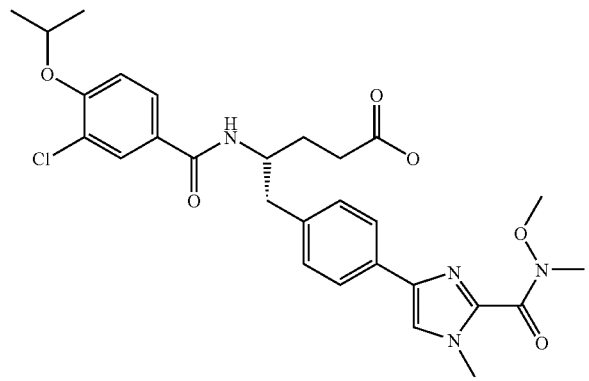

Following the procedure described above with 1,1-dimethylethyl (4R)-4-({[(1,1-dimethylethyl)oxy]carbonyl}amino)-5-[4-(1-methyl-2-{[methyl(methyloxy)amino]carbonyl}-1H-imidazol-4-yl)phenyl]pentanoate and foregoing purification provided the title compound as a solid. ESMS $[M+H]^+=557.2$.

(4R)-5-[4-(2-acetyl-1-methyl-1H-imidazol-4-yl)phenyl]-4-[({3-chloro-4-[(1-methylethyl)oxy]phenyl}carbonyl)amino]pentanoic acid

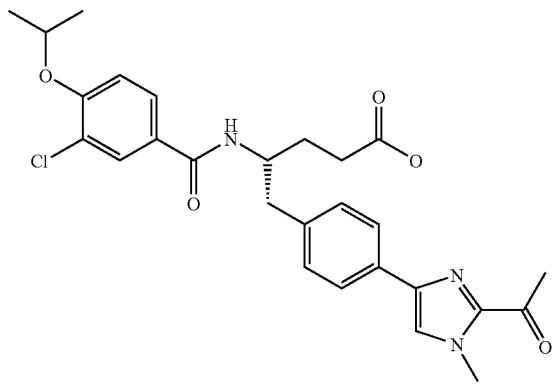

To a solution of crude (4R)-4-[({3-chloro-4-[(1-methylethyl)oxy]phenyl}carbonyl)amino]-5-[4-(1-methyl-2-{[methyl(methyloxy)amino]carbonyl}-1H-imidazol-4-yl)phenyl]pentanoic acid (3.18 mmol) in anhydrous THF (16 mL) under nitrogen at 0° C. was added methylmagnesium bromide (10.6 mL, 10 equiv, 3.0 M in ether) dropwise by syringe. The reaction was stirred for 30 minutes at 0° C. and then carefully quenched with sat. aq. $NH_4Cl$ solution (10 mL), followed by 1N HCl solution (60 mL) such that the pH of the aqueous layer 5.5. The product was extracted with EtOAc (4×40 mL) and the combined organic layers were dried over $MgSO_4$ and concentrated in vacuo to give the title compound, which was used directly in the next reaction. ESMS $[M+H]^+=512.4$.

N-((1R)-4-Amino-1-{[4-(8-methylimidazo[1,2-a]pyridin-2-yl)phenyl]methyl}-4-oxobutyl)-3-chloro-4-[(1-methylethyl)oxy]benzamide

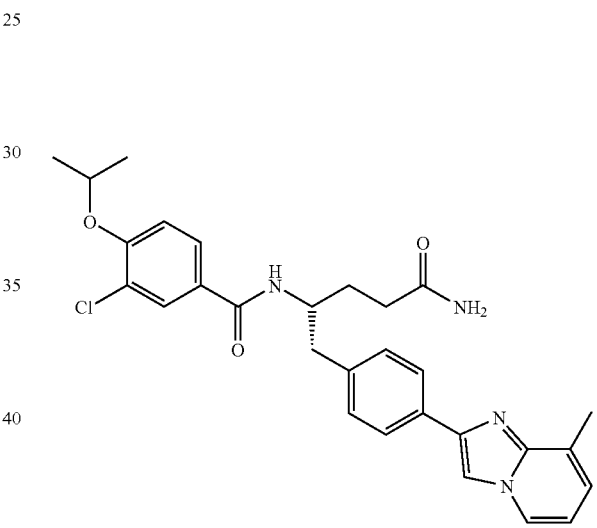

To a solution of (4R)-4-[({3-chloro-4-[(1-methylethyl)oxy]phenyl}carbonyl)amino]-5-[4-(8-methylimidazo[1,2-a]pyridin-2-yl)phenyl]pentanoic acid (900 mg, 1.73 mmol) in anhydrous THF (12.4 mL) at 0° C. under nitrogen was added triethylamine (242 uL, 1.73 mmol) followed by ethyl chloroformate (174 uL, 1.82 mmol). The reaction was stirred for 40 mins at 0° C. and then the solids were filtered and washed with 5 mL THF. The filtrate was added to a flask containing $NH_4OH$ (5 mL) at room temperature and the reaction mixture was stirred for 1 hour. The product was extracted from the reaction mixture with EtOAc (50 mL). The aqueous layer was extracted with EtOAc (20 mL) and then acidified with 1N HCl solution (30 mL) and re-extracted with EtOAc (10 mL). The combined organic layers were dried over $MgSO_4$ and concentrated in vacuo to give a white solid. Purification by recrystallization from hot isopropanol afforded the title compound as a white solid (90%). ESMS $[M+H]^+=519.4$.

N-((1R)-1-{[4-(2-acetyl-1-methyl-1H-imidazol-4-yl)phenyl]methyl}-4-amino-4-oxobutyl)-3-chloro-4-[(1-methylethyl)oxy]benzamide
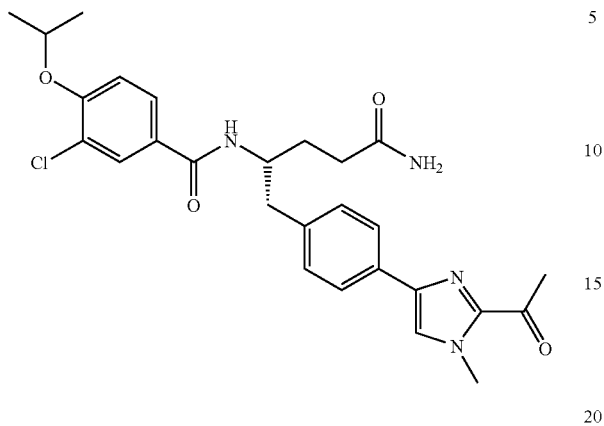
Following the procedure described in above with (4R)-5-[4-(2-acetyl-1-methyl-1H-imidazol-4-yl)phenyl]-4-[({3-chloro-4-[(1-methylethyl)oxy]phenyl}carbonyl)amino]pentanoic acid and purification by Gilsin reverse phase HPLC provided the title compound as a white solid. ESMS $[M+H]^+=511.2$.
Scheme I:
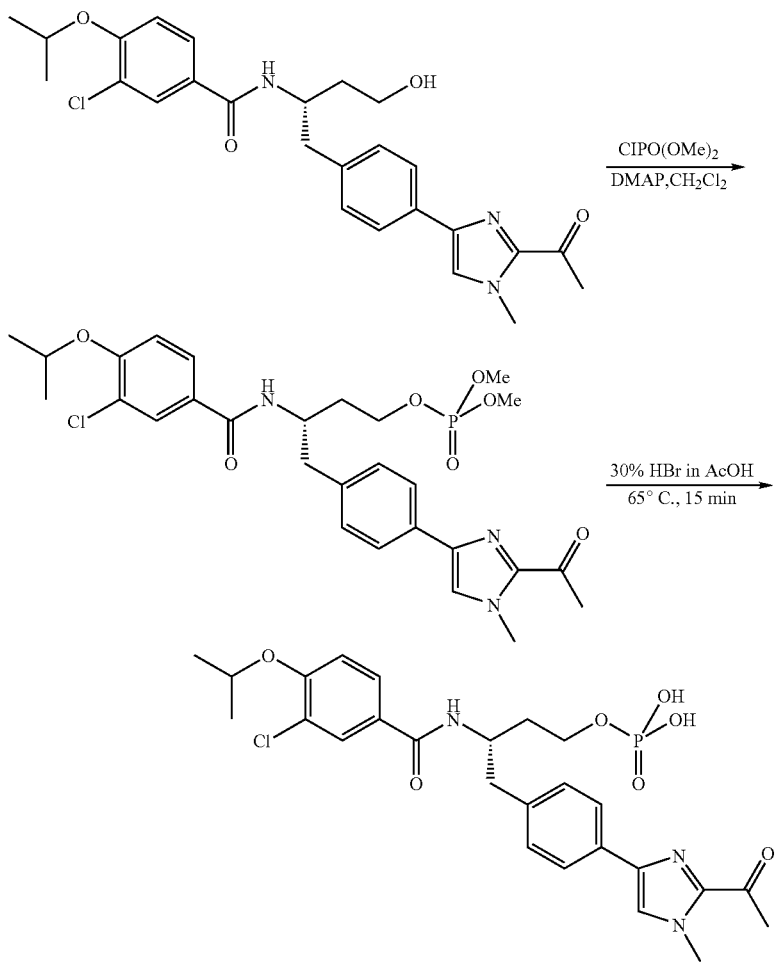

(3S)-4-[4-(2-acetyl-1-methyl-1H-imidazol-4-yl)phenyl]-3-[({3-chloro-4-[(1-methylethyl)oxy]phenyl}carbonyl)amino]butyl dimethyl phosphate

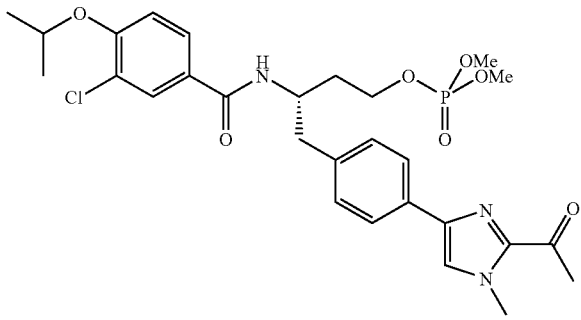

To a solution of N-((1S)-1-{[4-(2-acetyl-1-methyl-1H-imidazol-4-yl)phenyl]methyl}-3-hydroxypropyl)-3-chloro-4-[(1-methylethyl)oxy]benzamide (500 mg, 1.04 mmol) in dry CH₂Cl₂ (10 mL) under N₂, was added dimethyl chlorophosphate (748 mg, 5.18 mmol) followed by DMAP (660 mg, 5.41 mmol) at rt. After 30 min, TLC (95:5 EtOAc/MeOH) showed ~50% conversion, so an additional portion of dimethyl chlorophosphate (748 mg, 5.18 mmol) and DMAP (660 mg, 5.41 mmol) were added. After an additional 30 min, the reaction was quenched with saturated aqueous NH₄Cl and diluted with CH₂Cl₂. The aqueous layer was back-extracted with CH₂Cl₂ and the combined organics were dried (Na₂SO₄), filtered and concentrated under reduced pressure. The residue was purified by silica gel chromatography (100% EtOAc; isocratic on Analogix) to give 475 mg (77%) of the title compound as a pale yellow oil. LC/MS (ES) m/e 592.4 (M+H)⁺. Note that the product was contaminated with ~1 eq of the starting dimethyl chlorophosphate/dimethyl hydrogenphosphate reagent and carried on as is.

(3S)-4-[4-(2-acetyl-1-methyl-1H-imidazol-4-yl)phenyl]-3-[({3-chloro-4-[(1-methylethyl)oxy]phenyl}carbonyl)amino]butyl dihydrogen phosphate

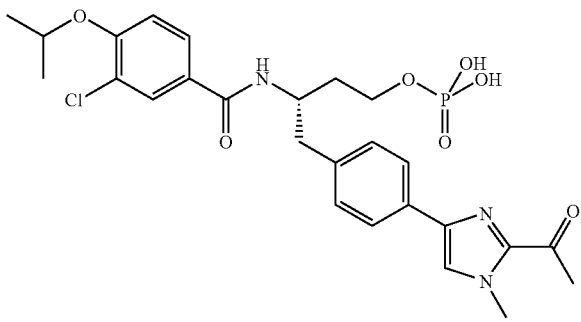

A yellow solution of (3S)-4-[4-(2-acetyl-1-methyl-1H-imidazol-4-yl)phenyl]-3-[({3-chloro-4-[(1-methylethyl)oxy]phenyl}carbonyl)amino]butyl dimethyl phosphate (475 mg, 0.804 mmol) in 30% HBr in AcOH was placed in a pre-heated (60° C.) bath for 10 min, then immediately allowed to cool to rt. The reaction mixture was concentrated under reduced pressure and the residue was dissolved in DMSO (6 mL), filtered and purified by Gilson reverse phase HPLC (MeCN/H₂O with 0.1% TFA). The MeCN of the clean fractions was removed under reduced pressure and the remaining aqueous solution was frozen and lyophilized overnight to give 84 mg (19%) of the title compound as a yellow powder. LC/MS (ES) m/e 564.2 (M+H)⁺.

(3S)-3-[({3-chloro-4-[(1-methylethyl)oxy]phenyl}carbonyl)amino]-4-[4-(8-methylimidazo[1,2-a]pyridin-2-yl)phenyl]butyl dihydrogen phosphate

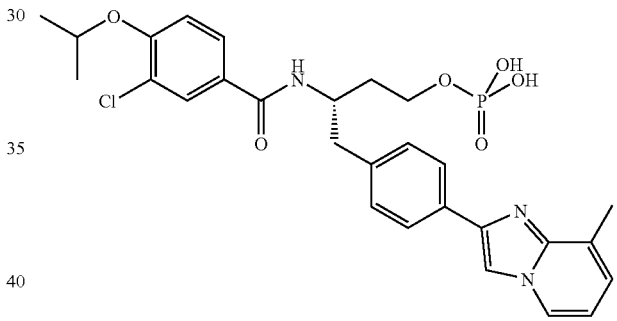

Following the procedures described above, except substituting 3-chloro-N-((1S)-3-hydroxy-1-{[4-(8-methylimidazo[1,2-a]pyridin-2-yl)phenyl]methyl}propyl)-4-[(1-methylethyl)oxy]benzamide for N-((1S)-1-{[4-(2-acetyl-1-methyl-1H-imidazol-4-yl)phenyl]methyl}-3-hydroxypropyl)-3-chloro-4-[(1-methylethyl)oxy]benzamide and potassium tert-butoxide for DMAP, the title compound was prepared as a white powder (35% yield). LC/MS (ES) m/e 563 (M+H)⁺.

Scheme J:

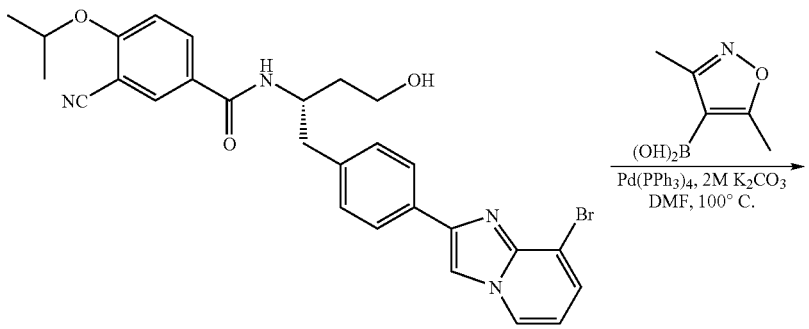

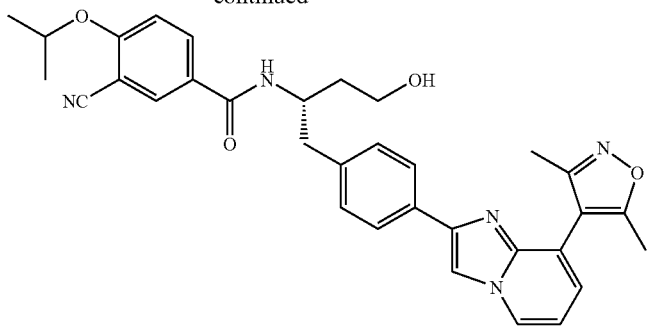

3-Cyano-N-[(1S)-1-({4-[8-(3,5-dimethyl-4-isox-azolyl)imidazo[1,2-a]pyridin-2-yl]phenyl}methyl)-3-hydroxypropyl]-4-[(1-methylethyl)oxy]benzamide

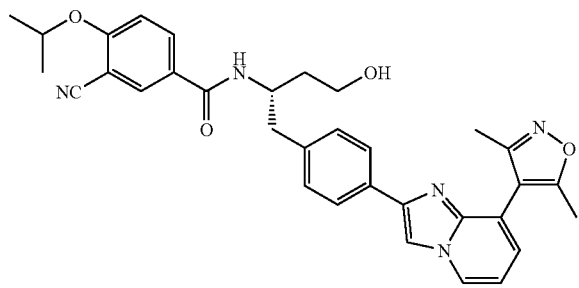

To a solution of N-((1S)-1-{[4-(8-bromoimidazo[1,2-a]pyridin-2-yl)phenyl]methyl}-3-hydroxypropyl)-3-cyano-4-[(1-methylethyl)oxy]benzamide (200 mg, 0.366 mmol) in dry DMF (2 mL) were added 3,5-dimethyl-isoxazole-4-boronic acid (63 mg, 0.439 mmol), tetrakistriphenylphosphine palladium(0) (21 mg, 0.018 mmol) and 2.0M aqueous $K_2CO_3$ (0.46 mL) successively at rt. The reaction mixture was purged with argon and heated to 100° C., stirred for 22 h, cooled to rt, filtered and purified directly by reverse phase HPLC (MeCN/$H_2O$ with 0.1% TFA). The clean fractions were adjusted to pH ~8 with saturated aqueous $NaHCO_3$ and extracted with 3% MeOH/EtOAc (3×30 mL). The extracts were dried ($Na_2SO_4$), filtered and concentrated under reduced pressure to give 45 mg (22%) of the title compound as an off-white solid. LC/MS (ES) m/e 564.2 $(M+H)^+$.

Scheme K:

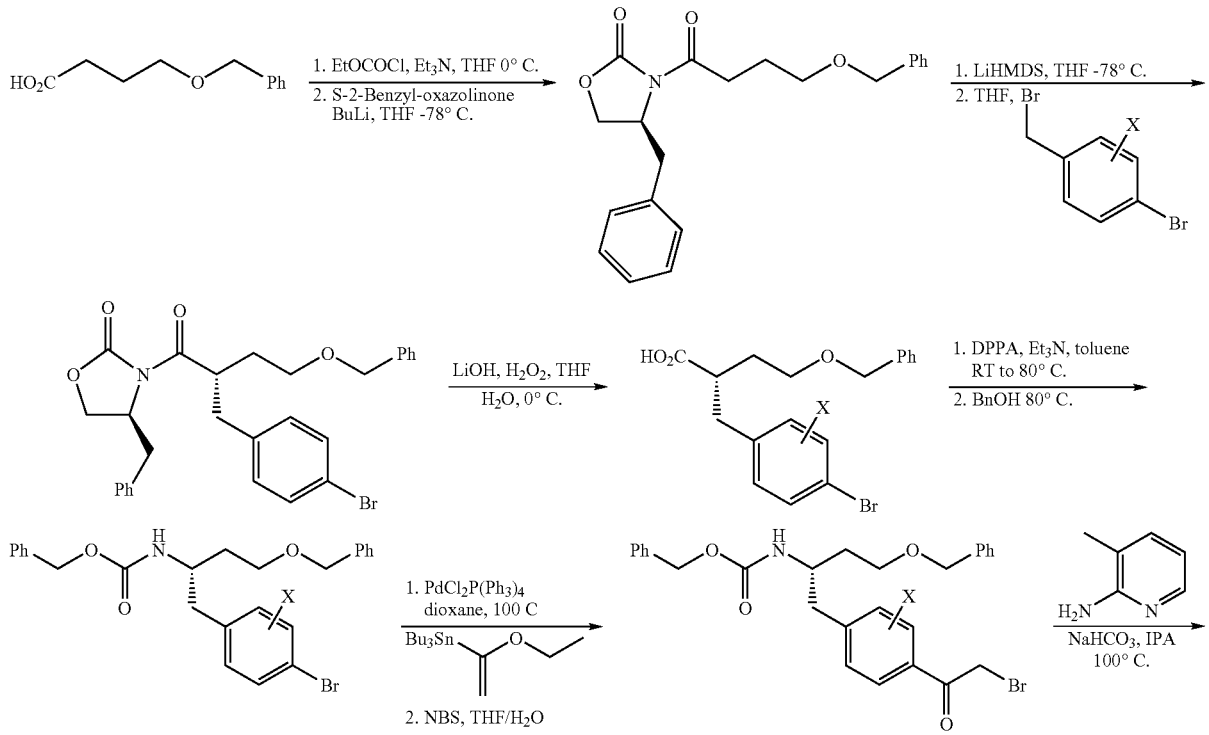

-continued

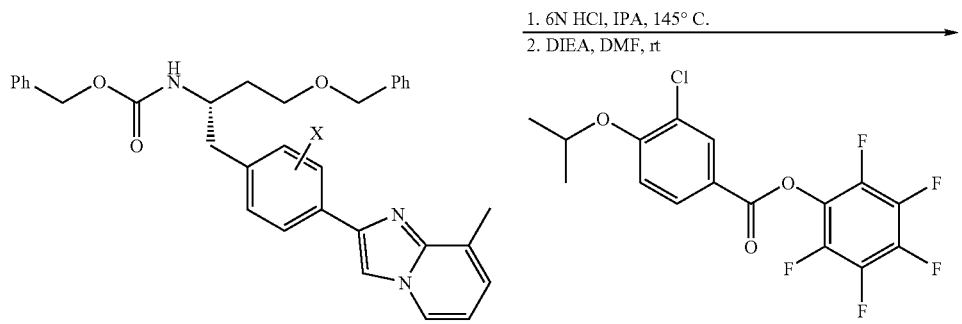

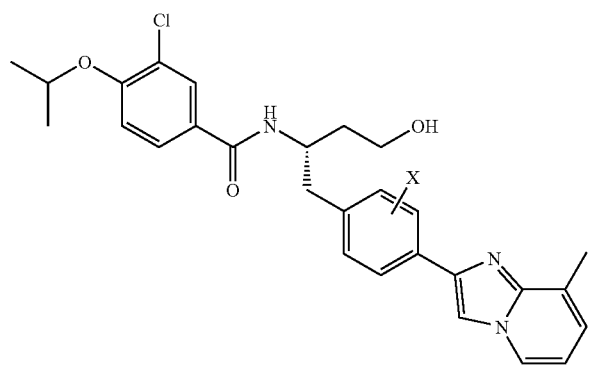

3-chloro-N-((1S)-1-{[3-chloro-4-(8-methylimidazo[1,2-a]pyridin-2-yl)phenyl]methyl}-3-hydroxypropyl)-4-[(1-methylethyl)oxy]benzamide The following compounds were prepared using the procedures described above:

Structure

Name (M+H)$^+$

Following the procedures described in the literature (*J. Org. Chem.* 2003, 68, 4215; *J. Org. Chem.* 2002, 67, 1738; *J. Am. Chem. Soc.* 1972, 94, 6203), as well as the procedures above, the title compound was prepared as a white solid. LC/MS (ES) m/e 526 (M+H)$^+$.

| 329 | 330 |
|---|---|
| N-((1R)-1-{[4-(2-Acetyl-1-methyl-1H-imidazol-4-yl)phenyl]methyl}-4-amino-4-oxobutyl)-3-cyano-4-[(1-methylethyl)oxy]benzamide | N-[(1S)-2-(D-Alanylamino)-1-({4-[1-(2-aminoethyl)-2-(1,1-dimethylethyl)-1H-imidazol-4-yl]phenyl}methyl)ethyl]-3-chloro-4-[(1-methylethyl)oxy]benzamide |
| 502.4 | 583.6 |

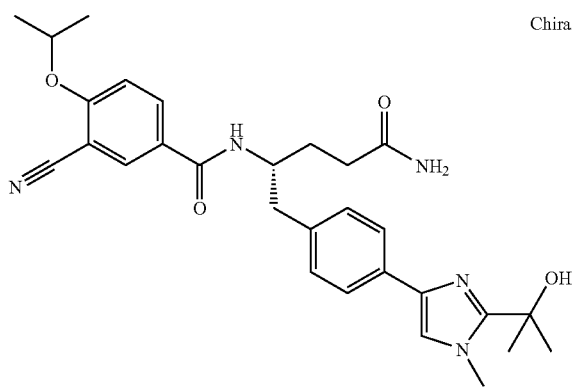

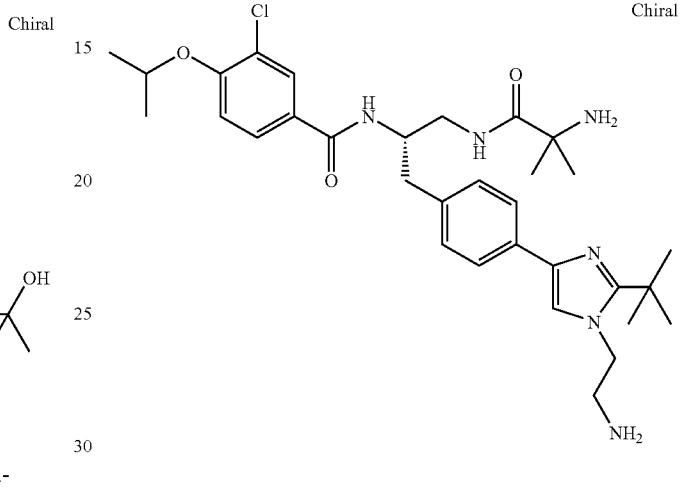

N-[(1R)-4-Amino-1-({4-[2-(1-hydroxy-1-methyl-ethyl)-1-methyl-1H-imidazol-4-yl]phenyl}methyl)-4-oxobutyl]-3-cyano-4-[(1-methylethyl)oxy]benzamide 518.4

N-((1S)-2-{4-[1-(2-Aminoethyl)-2-(1,1-dimethyl-ethyl)-1H-imidazol-4-yl]phenyl}-1-{[(2-methylala-nyl)amino]methyl}ethyl)-3-chloro-4-[(1-methyl-ethyl)oxy]benzamide 597.6

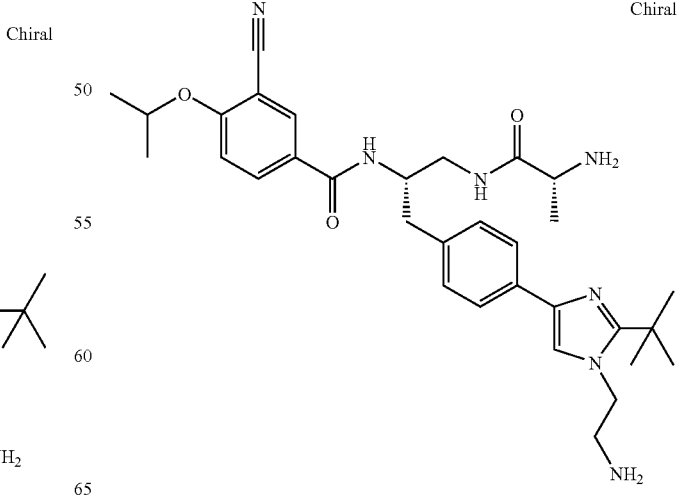

331

N-[(1S)-2-(D-Alanylamino)-1-({4-[1-(2-aminoethyl)-2-(1,1-dimethylethyl)-1H-imidazol-4-yl]phenyl}methyl)ethyl]-3-cyano-4-[(1-methylethyl)oxy]benzamide 574.4

332

N-((1S)-2-{4-[1-(2-Aminoethyl)-2-(1,1-dimethylethyl)-1H-imidazol-4-yl]phenyl}-1-{[(2-methylalanyl)amino]methyl}ethyl)-3-cyano-4-[(1-methylethyl)oxy]benzamide 588.2

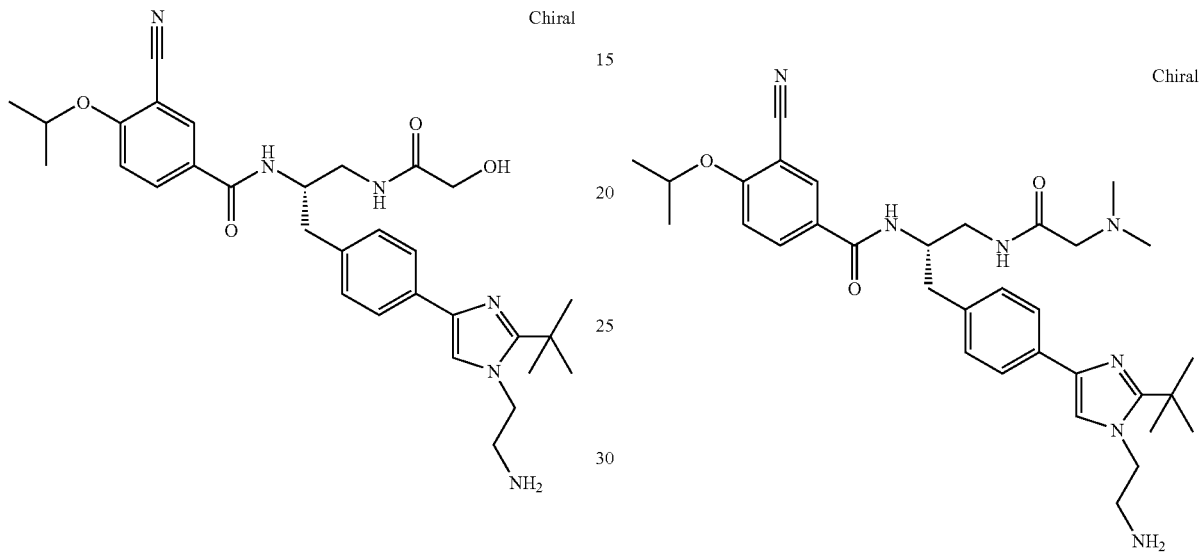

N-((1S)-2-{4-[1-(2-Aminoethyl)-2-(1,1-dimethylethyl)-1H-imidazol-4-yl]phenyl}-1-{[(hydroxyacetyl)amino]methyl}ethyl)-3-cyano-4-[(1-methylethyl)oxy]benzamide 561.4

N-((1S)-2-{4-[1-(2-Aminoethyl)-2-(1,1-dimethylethyl)-1H-imidazol-4-yl]phenyl}-1-{[(N,N-dimethylglycyl)amino]methyl}ethyl)-3-cyano-4-[(1-methylethyl)oxy]benzamide 588.4

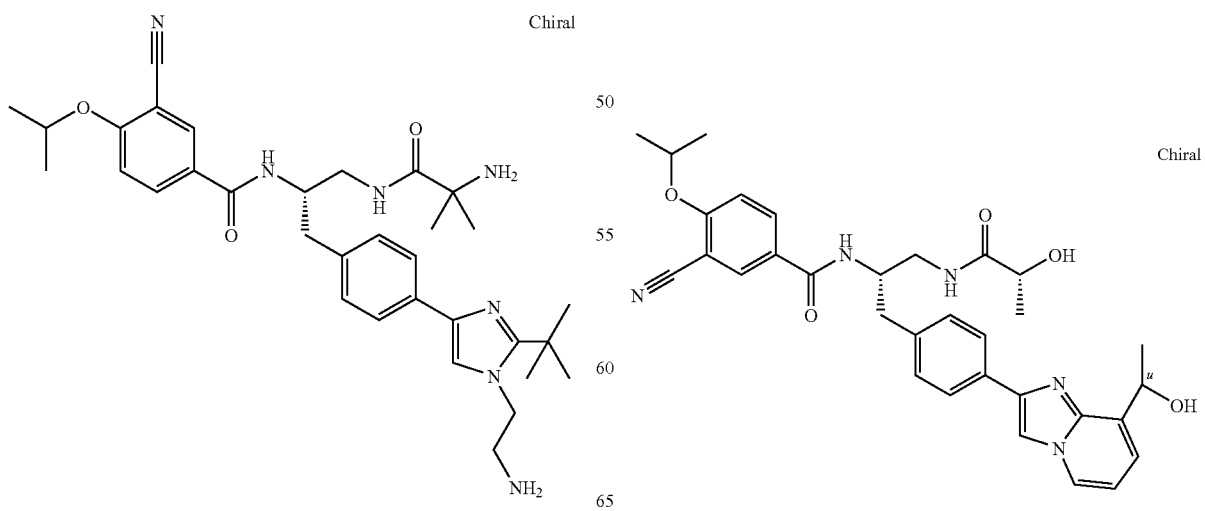

333

3-Cyano-N-[(1S)-2-{4-[8-(1-hydroxyethyl)imidazo[1,2-a]pyridin-2-yl]phenyl}-1-({[(2R)-2-hydroxypropanoyl]amino}methyl)ethyl]-4-[(1-methylethyl)oxy]benzamide 569.4

334

N-{(1S)-2-[4-(8-Bromoimidazo[1,2-a]pyridin-2-yl)phenyl]-1-[(2-oxohexahydro-1H-1,3-diazepin-1-yl)methyl]ethyl}-3-chloro-4-[(1-methylethyl)oxy]benzamide 639.2

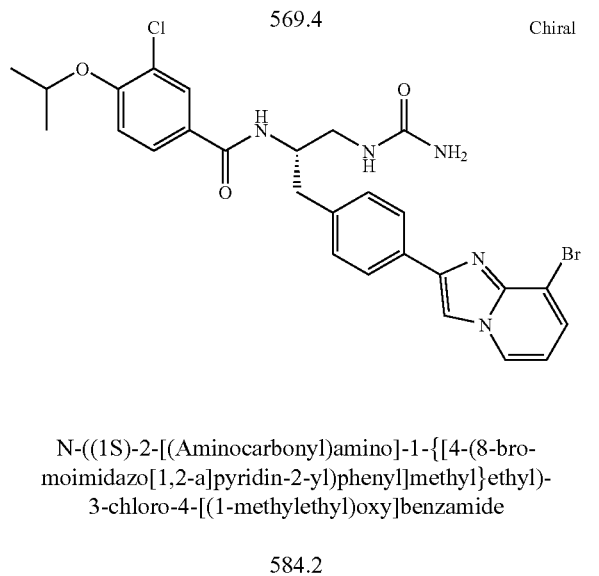

N-((1S)-2-[(Aminocarbonyl)amino]-1-{[4-(8-bromoimidazo[1,2-a]pyridin-2-yl)phenyl]methyl}ethyl)-3-chloro-4-[(1-methylethyl)oxy]benzamide 584.2

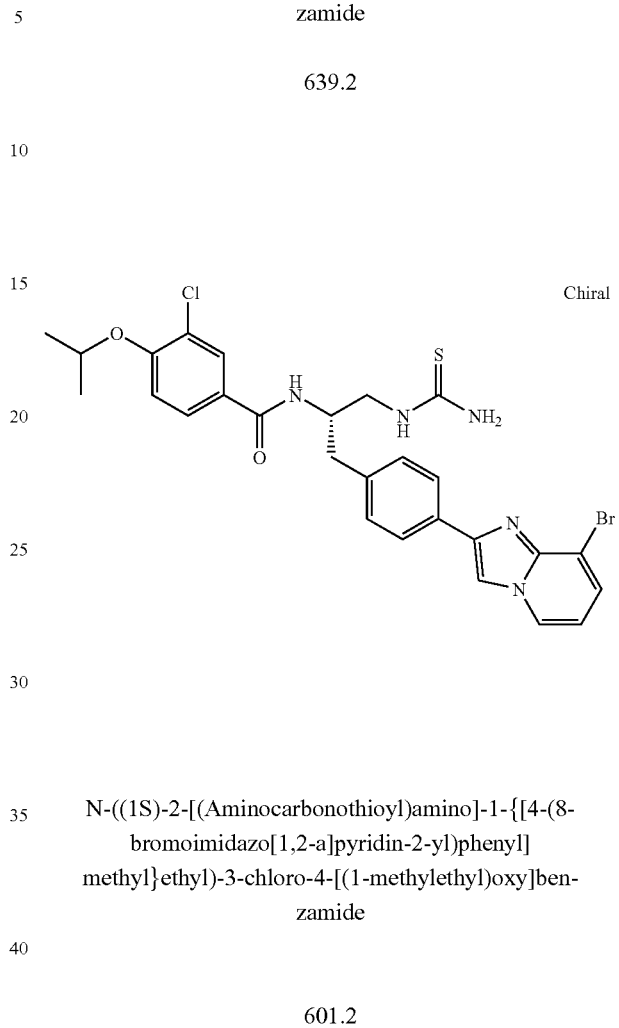

N-((1S)-2-[(Aminocarbonothioyl)amino]-1-{[4-(8-bromoimidazo[1,2-a]pyridin-2-yl)phenyl]methyl}ethyl)-3-chloro-4-[(1-methylethyl)oxy]benzamide 601.2

N-{(1S)-2-[4-(8-Bromoimidazo[1,2-a]pyridin-2-yl)phenyl]-1-[(2-oxotetrahydro-1(2H)-pyrimidinyl)methyl]ethyl}-3-chloro-4-[(1-methylethyl)oxy]benzamide 625.1

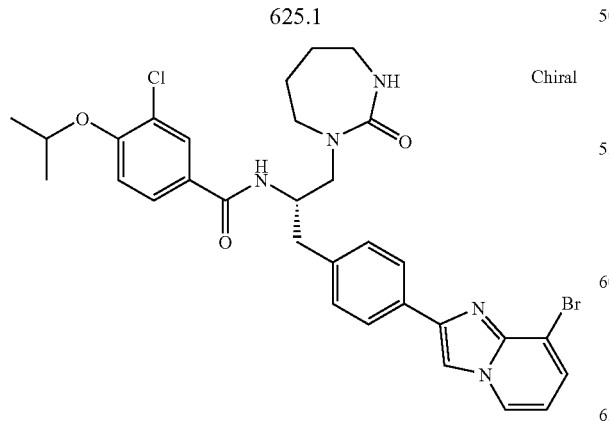

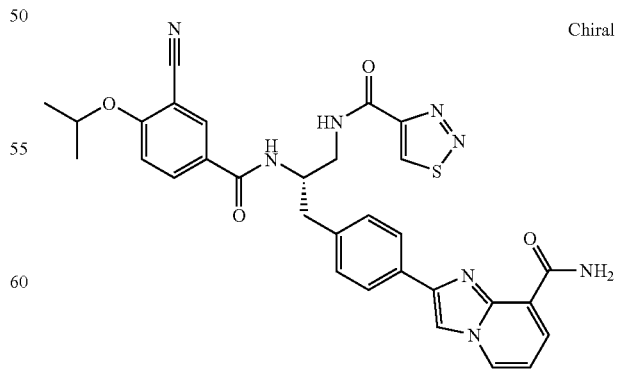

335

2-(4-{(2S)-2-[({3-Cyano-4-[(1-methylethyl)oxy]phenyl}carbonyl)amino]-3-[(1,2,3-thiadiazol-4-yl-carbonyl)amino]propyl}phenyl)imidazo[1,2-a]pyridine-8-carboxamide

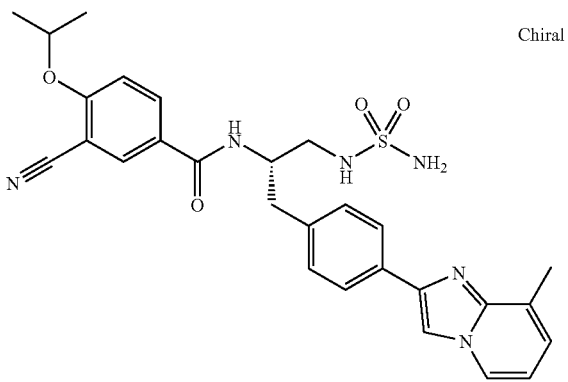

N-((1S)-2-[(Aminosulfonyl)amino]-1-{[4-(8-methylimidazo[1,2-a]pyridin-2-yl)phenyl]methyl}ethyl)-3-cyano-4-[(1-methylethyl)oxy]benzamide 547.2

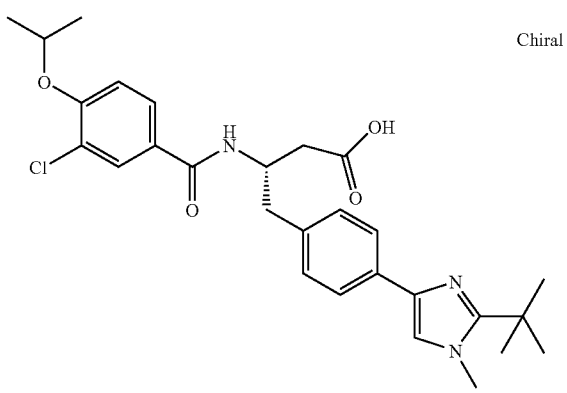

(3S)-3-[({3-Chloro-4-[(1-methylethyl)oxy]phenyl}carbonyl)amino]-4-{4-[2-(1,1-dimethylethyl)-1-methyl-1H-imidazol-4-yl]phenyl}butanoic acid 512.4

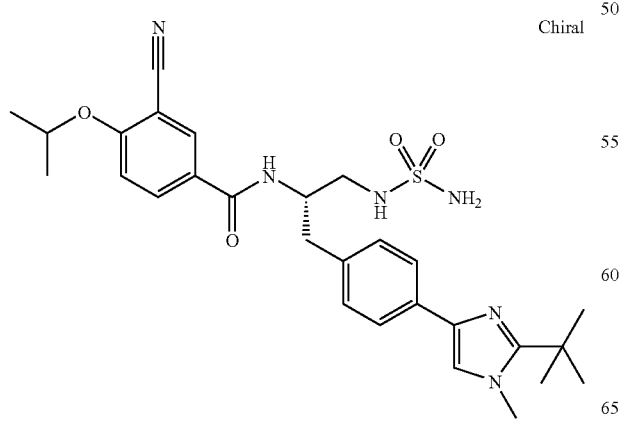

336

N-[(1S)-2-[(Aminosulfonyl)amino]-1-({4-[2-(1,1-dimethylethyl)-1-methyl-1H-imidazol-4-yl]phenyl}methyl)ethyl]-3-cyano-4-[(1-methylethyl)oxy]benzamide 553.2

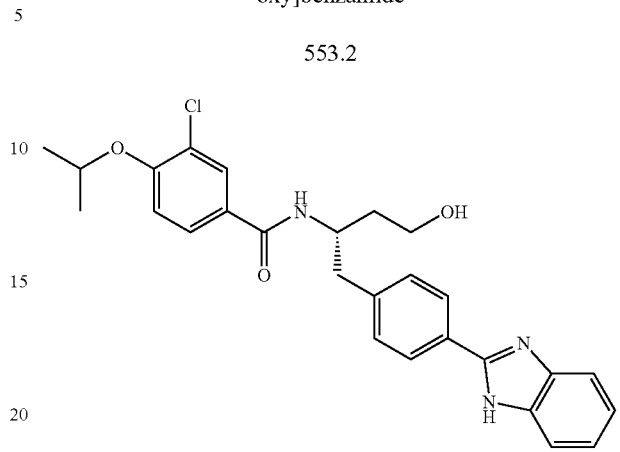

N-((1S)-1-{[4-(1H-Benzimidazol-2-yl)phenyl]methyl}-3-hydroxypropyl)-3-chloro-4-[(1-methylethyl)oxy]benzamide 477.8

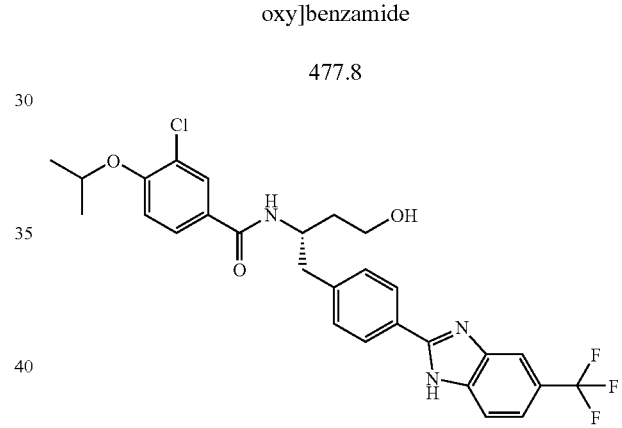

3-Chloro-N-[(1S)-3-hydroxy-1-({4-[5-(trifluoromethyl)-1H-benzimidazol-2-yl]phenyl}methyl)propyl]-4-[(1-methylethyl)oxy]benzamide 546.2

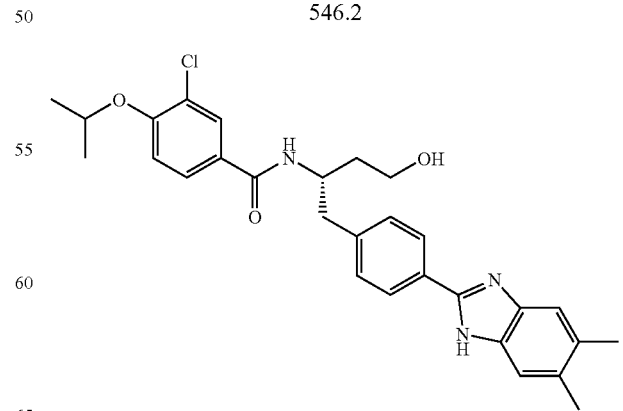

337

3-Chloro-N-((1S)-1-{[4-(5,6-dimethyl-1H-benzimi-dazol-2-yl)phenyl]methyl}-3-hydroxypropyl)-4-[(1-methylethyl)oxy]benzamide 506.2

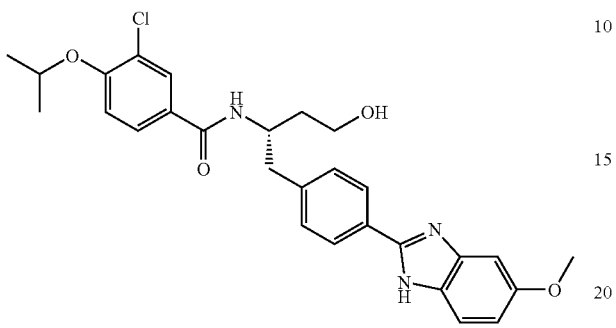

3-Chloro-N-[(1S)-3-hydroxy-1-({4-[5-(methyloxy)-1H-benzimidazol-2-yl]phenyl}methyl)propyl]-4-[(1-methylethyl)oxy]benzamide 508.2

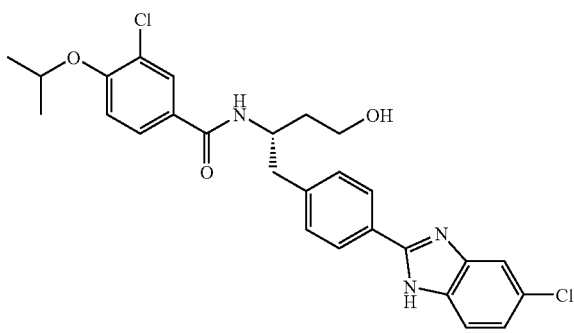

3-Chloro-N-((1S)-1-{[4-(5-chloro-1H-benzimidazol-2-yl)phenyl]methyl}-3-hydroxypropyl)-4-[(1-methylethyl)oxy]benzamide 512.0

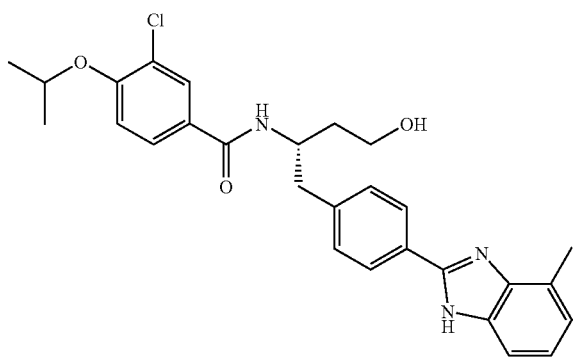

338

3-Chloro-N-((1S)-3-hydroxy-1-{[4-(4-methyl-1H-benzimidazol-2-yl)phenyl]methyl}propyl)-4-[(1-methylethyl)oxy]benzamide 492.2

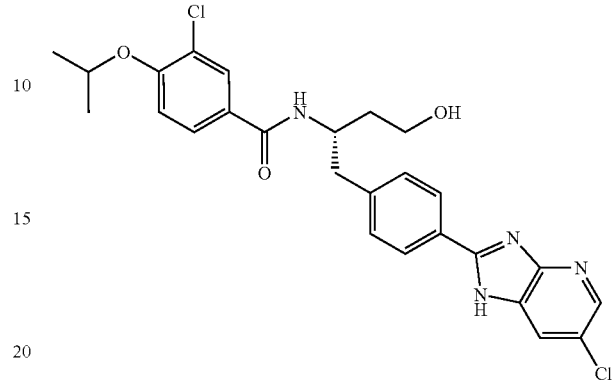

3-Chloro-N-((1S)-1-{[4-(6-chloro-1H-imidazo[4,5-b]pyridin-2-yl)phenyl]methyl}-3-hydroxypropyl)-4-[(1-methylethyl)oxy]benzamide 513.2

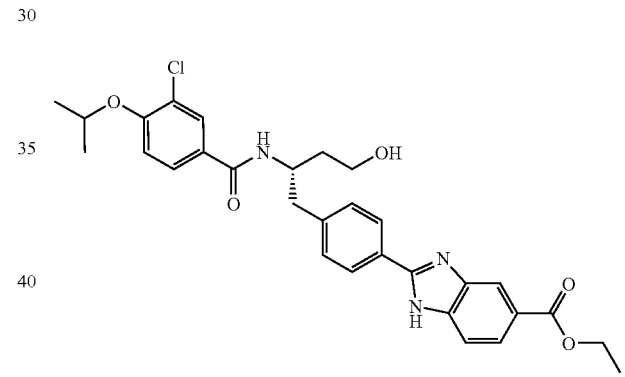

Ethyl 2-(4-{(2S)-2-[({3-chloro-4-[(1-methylethyl)oxy]phenyl}carbonyl)amino]-4-hydroxybutyl}phenyl)-1H-benzimidazole-5-carboxylate 550.2

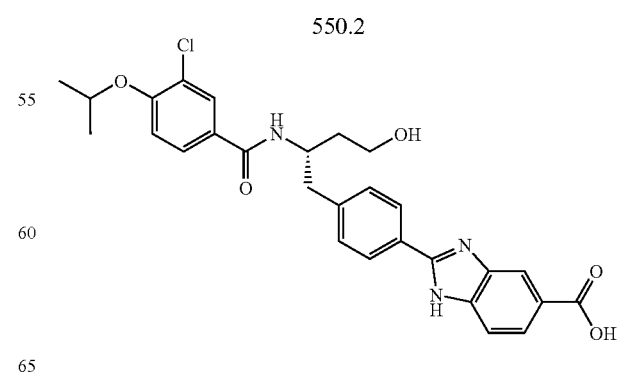

| 339 | 340 |
|---|---|
| 2-(4-{(2S)-2-[({3-Chloro-4-[(1-methylethyl)oxy]phenyl}carbonyl)amino]-4-hydroxybutyl}phenyl)-1H-benzimidazole-5-carboxylic acid | N-((1S)-1-{[4-(8-Chloroimidazo[1,2-a]pyridin-2-yl)phenyl]methyl}-3-hydroxypropyl)-3-cyano-4-[(1-methylethyl)oxy]benzamide |
| 522.2 | 504.2 |

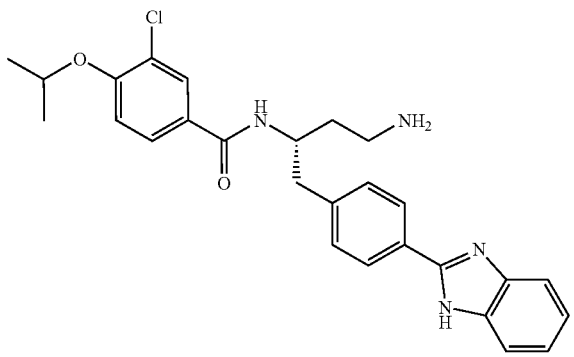

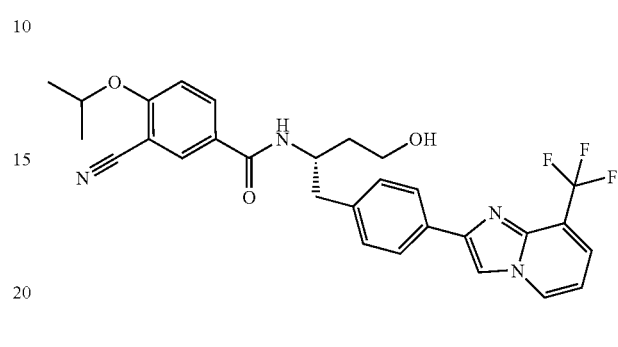

N-((1S)-3-Amino-1-{[4-(1H-benzimidazol-2-yl)phenyl]methyl}propyl)-3-chloro-4-[(1-methylethyl)oxy]benzamide 477.0

3-Cyano-N-[(1S)-3-hydroxy-1-({4-[8-(trifluoromethyl)imidazo[1,2-a]pyridin-2-yl]phenyl}methyl)propyl]-4-[(1-methylethyl)oxy]benzamide 537.2

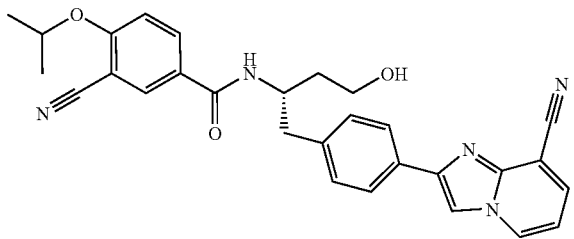

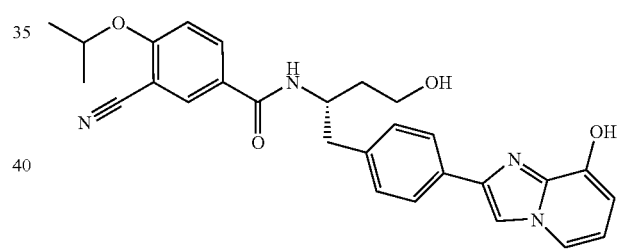

3-Cyano-N-((1S)-1-{[4-(8-cyanoimidazo[1,2-a]pyridin-2-yl)phenyl]methyl}-3-hydroxypropyl)-4-[(1-methylethyl)oxy]benzamide 494.4

3-Cyano-N-((1S)-3-hydroxy-1-{[4-(8-hydroxyimidazo[1,2-a]pyridin-2-yl)phenyl]methyl}propyl)-4-[(1-methylethyl)oxy]benzamide 485.2

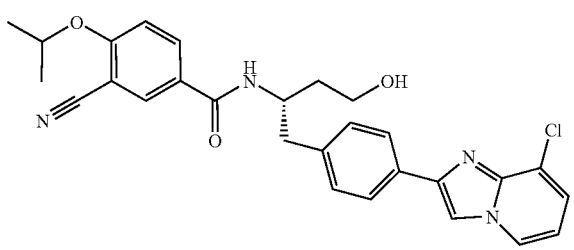

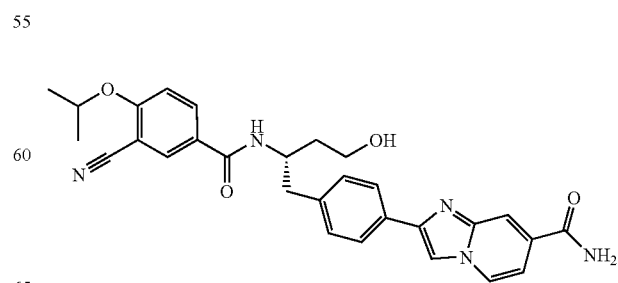

| 341 | 342 |
|---|---|
| 2-(4-{(2S)-2-[({3-Cyano-4-[(1-methylethyl)oxy]phenyl}carbonyl)amino]-4-hydroxybutyl}phenyl)imidazo[1,2-a]pyridine-7-carboxamide | N-((1S)-1-{[4-(8-Aminoimidazo[1,2-a]pyridin-2-yl)phenyl]methyl}-3-hydroxypropyl)-3-cyano-4-[(1-methylethyl)oxy]benzamide |
| 512.2 | 484.2 |

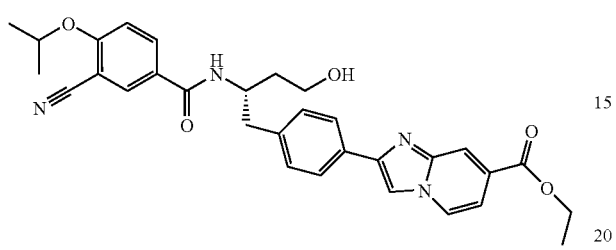

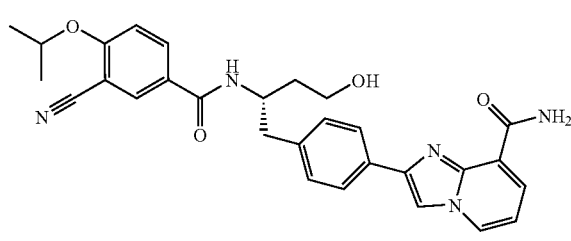

Ethyl 2-(4-{(2S)-2-[({3-cyano-4-[(1-methylethyl)oxy]phenyl}carbonyl)amino]-4-hydroxybutyl}phenyl)imidazo[1,2-a]pyridine-7-carboxylate 2-(4-{(2S)-2-[({3-Cyano-4-[(1-methylethyl)oxy]phenyl}carbonyl)amino]-4-hydroxybutyl}phenyl)imidazo[1,2-a]pyridine-8-carboxamide 512.2

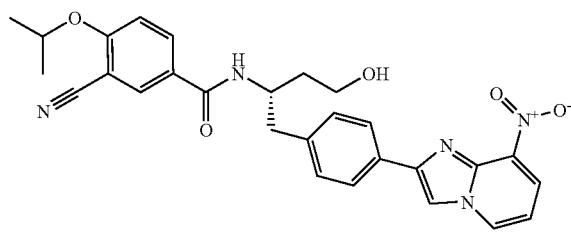

3-Cyano-N-((1S)-3-hydroxy-1-{[4-(8-nitroimidazo[1,2-a]pyridin-2-yl)phenyl]methyl}propyl)-4-[(1-methylethyl)oxy]benzamide 3-Cyano-N-[(1S)-3-hydroxy-1-({4-[8-(hydroxymethyl)imidazo[1,2-a]pyridin-2-yl]phenyl}methyl)propyl]-4-[(1-methylethyl)oxy]benzamide 514.4

499.4

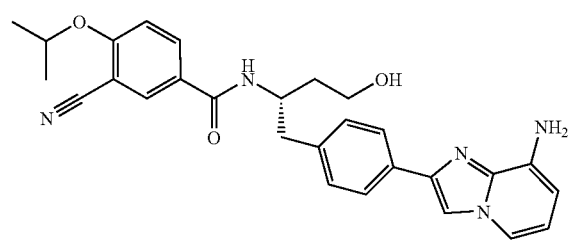

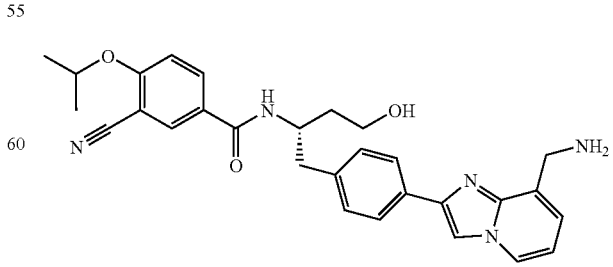

343

N-[(1S)-1-({4-[8-(Aminomethyl)imidazo[1,2-a]pyridin-2-yl]phenyl}methyl)-3-hydroxypropyl]-3-cyano-4-[(1-methylethyl)oxy]benzamide 498.4

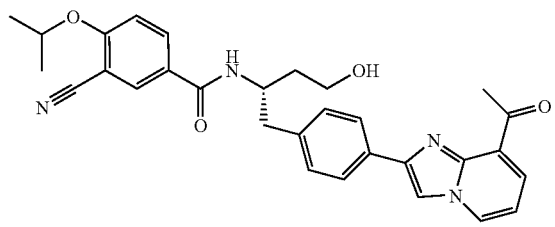

N-((1S)-1-{[4-(8-Acetylimidazo[1,2-a]pyridin-2-yl)phenyl]methyl}-3-hydroxypropyl)-3-cyano-4-[(1-methylethyl)oxy]benzamide 511.2

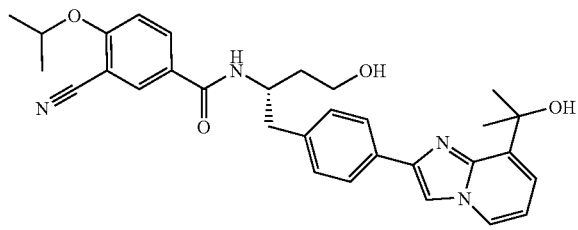

3-Cyano-N-[(1S)-3-hydroxy-1-({4-[8-(hydroxy-1-methylethyl)imidazo[1,2-a]pyridin-2-yl]phenyl}methyl)propyl]-4-[(1-methylethyl)oxy]benzamide 527.4

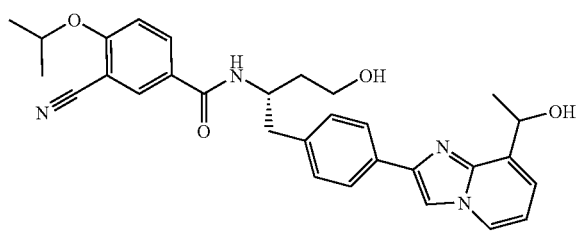

344

3-Cyano-N-[(1S)-3-hydroxy-1-({4-[8-(1-hydroxyethyl)imidazo[1,2-a]pyridin-2-yl]phenyl}methyl)propyl]-4-[(1-methylethyl)oxy]benzamide 513.4

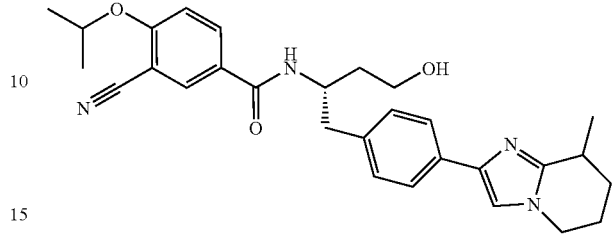

3-Cyano-N-((1S)-3-hydroxy-1-{[4-(8-methyl-5,6,7,8-tetrahydroimidazo[1,2-a]pyridin-2-yl)phenyl]methyl}propyl)-4-[(1-methylethyl)oxy]benzamide 487.2

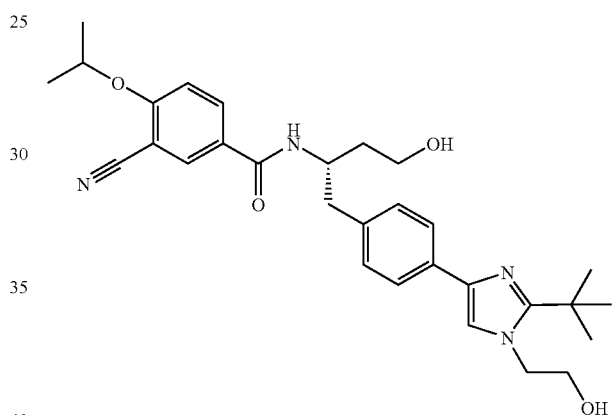

3-Cyano-N-[(1S)-1-({4-[2-(1,1-dimethylethyl)-1-(2-hydroxyethyl)-1H-imidazol-4-yl]phenyl}methyl)-3-hydroxypropyl]-4-[(1-methyl ethyl)oxy]benzamide 519.4

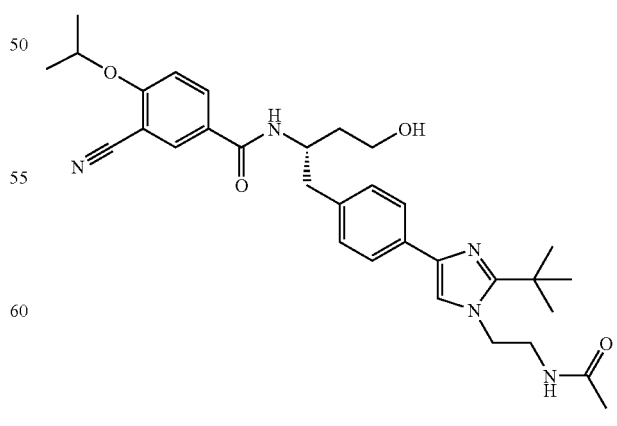

345

N-[(1S)-1-({4-[1-[2-(Acetylamino)ethyl]-2-(1,1-dimethylethyl)-1H-imidazol-4-yl]phenyl}methyl)-3-hydroxypropyl]-3-cyano-4-[(1-methylethyl)oxy]benzamide 560.4

346

3-Chloro-N-[(1S)-3-hydroxy-1-({4-[8-(1-hydroxypropyl)imidazo[1,2-a]pyridin-2-yl]phenyl}methyl)propyl]-4-[(1-methylethyl)oxy]benzamide 536.2

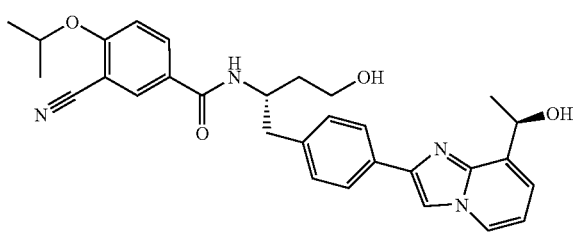

3-Cyano-N-{(1S)-3-hydroxy-1-[(4-{8-[(1R)-1-hydroxyethyl]imidazo[1,2-a]pyridin-2-yl}phenyl)methyl]propyl}-4-[(1-methylethyl)oxy]benzamide 513.4

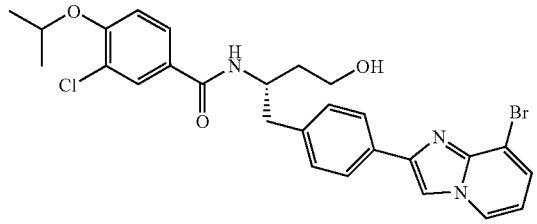

N-((1S)-1-{[4-(8-Bromoimidazo[1,2-a]pyridin-2-yl)phenyl]methyl}-3-hydroxypropyl)-3-chloro-4-[(1-methyethyl)oxy]benzamide 556.2

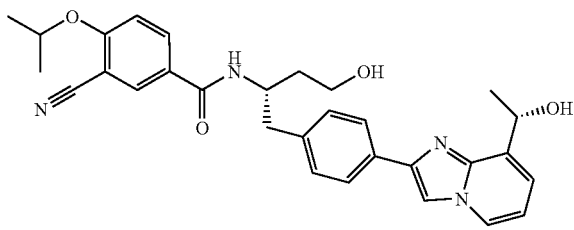

3-Cyano-N-{(1S)-3-hydroxy-1-[(4-{8-[(1S)-1-hydroxyethyl]imidazo[1,2-a]pyridin-2-yl}phenyl)methyl]propyl}-4-[(1-methylethyl)oxy]benzamide 513.4

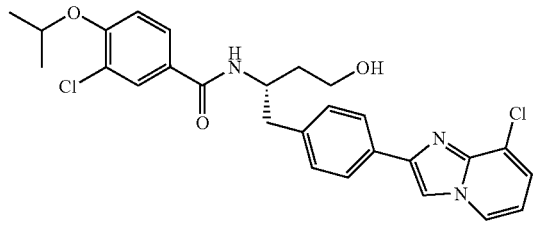

3-Chloro-N-((S)-1-{[4-(8-chloroimidazo[1,2-a]pyridin-2-yl)phenyl]methyl}-3-hydroxypropyl)-4-[(1-methylethyl)oxy]benzamide 512.4

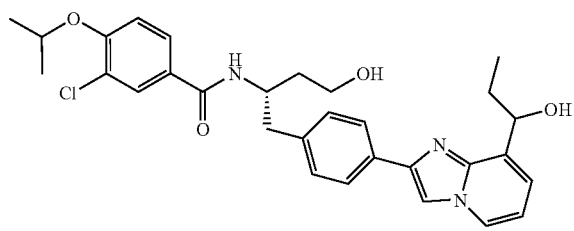

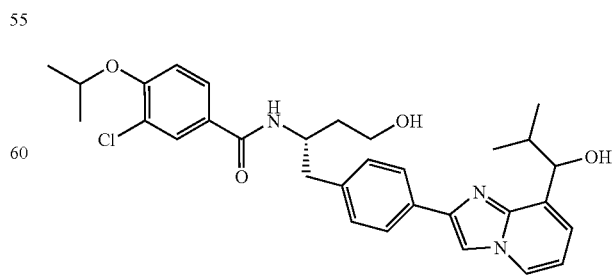

347

3-Chloro-N-[(1S)-3-hydroxy-1-({4-[8-(1-hydroxy-2-methylpropyl)imidazo[1,2-a]pyridin-2-yl]phenyl}methyl)propyl]-4-[(1-methylethyl)oxy]benzamide 550.4

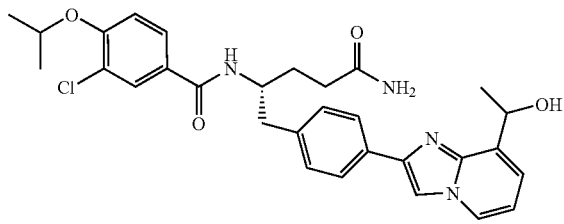

N-[(1R)-4-Amino-1-({4-[8-(1-hydroxyethyl)imidazo[1,2-a]pyridin-2-yl]phenyl}methyl)-4-oxobutyl]-3-chloro-4-[(1-methylethyl)oxy]benzamide 549.2

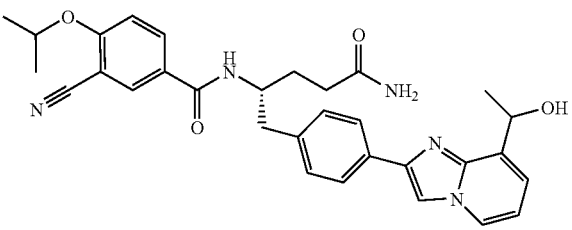

N-[(1R)-4-Amino-1-({4-[8-(1-hydroxyethyl)imidazo[1,2-a]pyridin-2-yl]phenyl}methyl)-4-oxobutyl]-3-cyano-4-[(1-methylethyl)oxy]benzamide 540.6

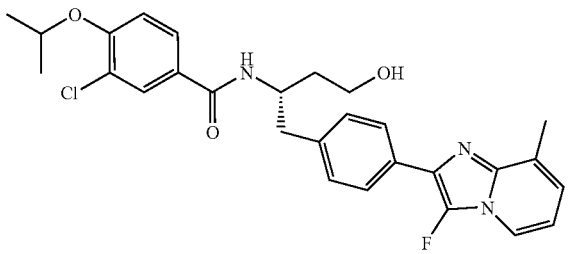

348

3-Chloro-N-((1S)-1-{[4-(3-fluoro-8-methylimidazo[1,2-a]pyridin-2-yl)phenyl]methyl}-3-hydroxypropyl)-4-[(1-methylethyl)oxy]benzamide 510.2

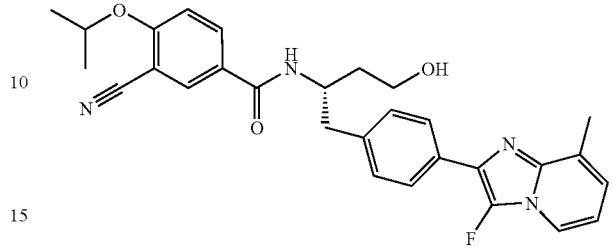

3-Cyano-N-((1S)-1-{[4-(3-fluoro-8-methylimidazo[1,2-a]pyridin-2-yl)phenyl]methyl}-3-hydroxypropyl)-4-[(1-methylethyl)oxy]benzamide 501.2

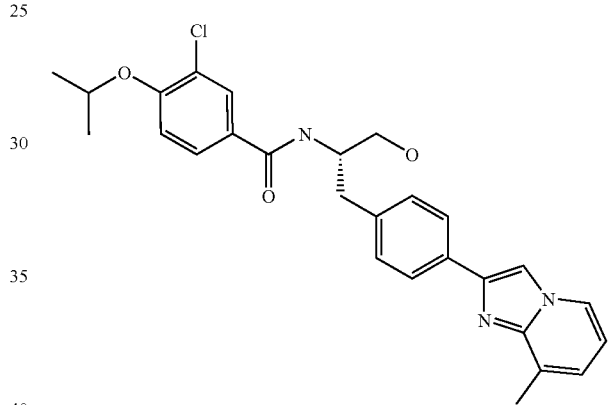

3-Chloro-N-((1S)-2-hydroxy-1-{[4-(8-methylimidazo[1,2-a]pyridin-2-yl)phenyl]methyl}ethyl)-4-[(1-methylethyl)oxy]benzamide 478.2

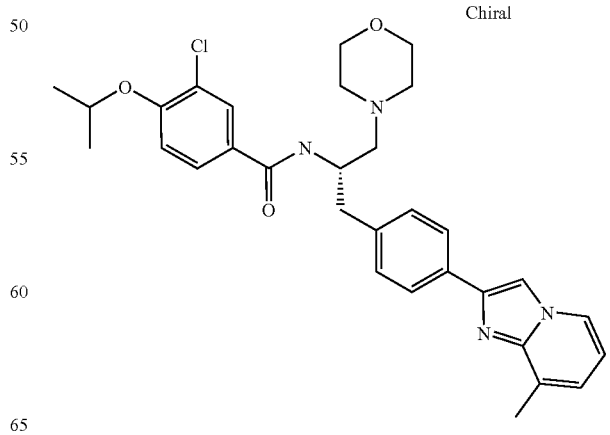

349

3-Chloro-4-[(1-methylethyl)oxy]-N-[(1S)-2-[4-(8-methylimidazo[1,2-a]pyridin-2-yl)phenyl]-1-(4-morpholinylmethyl)ethyl]benzamide 547.2

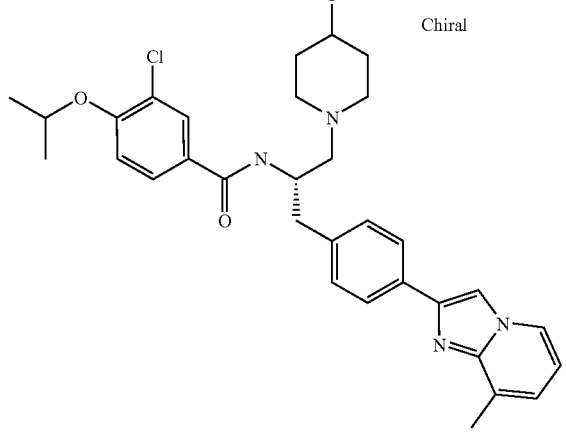

3-Chloro-N-((1S)-2-(4-hydroxy-1-piperidinyl)-1-{[4-(8-methylimidazo[1,2-a]pyridin-2-yl)phenyl]methyl}ethyl)-4-[(1-methylethyl)oxy]benzamide 561.2

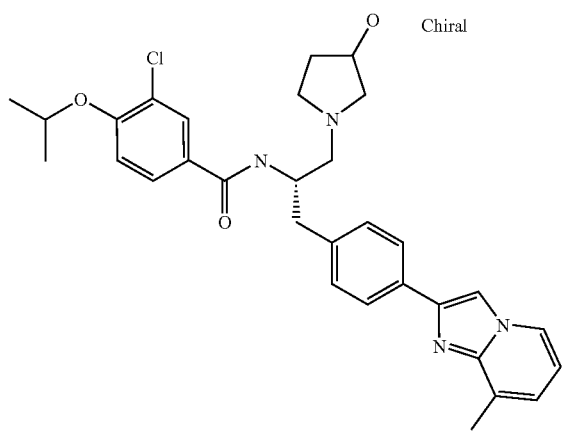

3-Chloro-N-((1S)-2-(3-hydroxy-1-pyrrolidinyl)-1-{[4-(8-methylimidazo[1,2-a]pyridin-2-yl)phenyl]methyl}ethyl)-4-[(1-methylethyl)oxy]benzamide 547.2

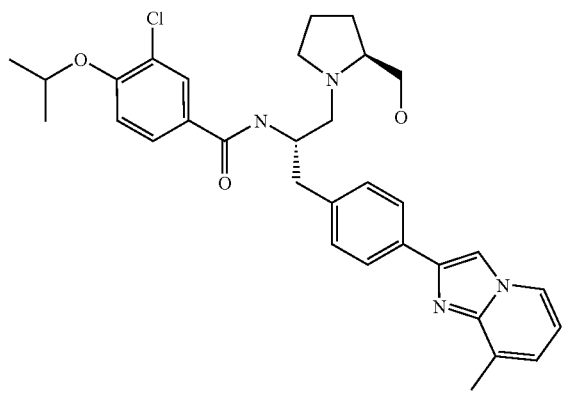

350

3-Chloro-N-((1S)-2-[(2S)-2-(hydroxymethyl)-1-pyrrolidinyl]-1-{[4-(8-methylimidazo[1,2-a]pyridin-2-yl)phenyl]methyl}ethyl)-4-[(1-methylethyl)oxy]benzamide 561.2

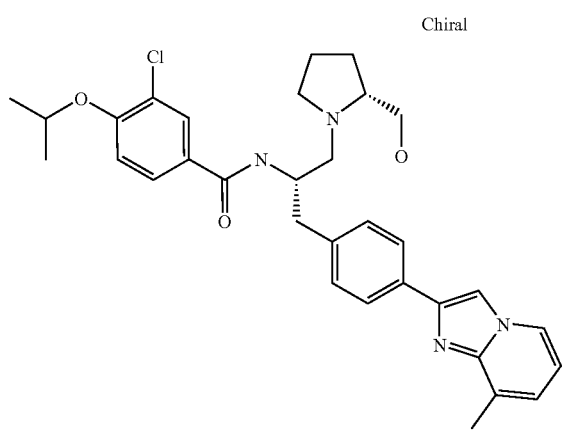

3-Chloro-N-((1S)-2-[(2R)-2-(hydroxymethyl)-1-pyrrolidinyl]-1-{[4-(8-methylimidazo[1,2-a]pyridin-2-yl)phenyl]methyl}ethyl)-4-[(1-methylethyl)oxy]benzamide 561.2

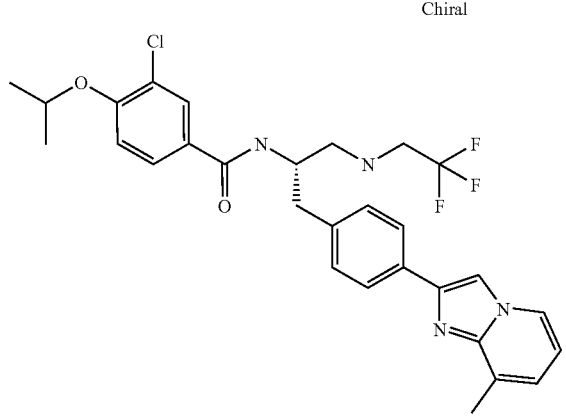

351

3-Chloro-4-[(1-methylethyl)oxy]-N-((1S)-2-[4-(8-methylimidazo[1,2-a]pyridin-2-yl)phenyl]-1-{[(2,2,2-trifluoroethyl)amino]methyl}ethyl)benzamide 559.2

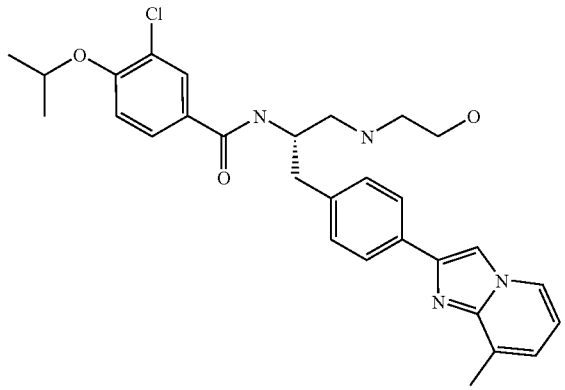

3-Chloro-N-((1S)-2-[(2-hydroxyethyl)amino]-1-{[4-(8-methylimidazo[1,2-a]pyridin-2-yl)phenyl]methyl}ethyl)-4-[(1-methylethyl)oxy]benzamide 521.2

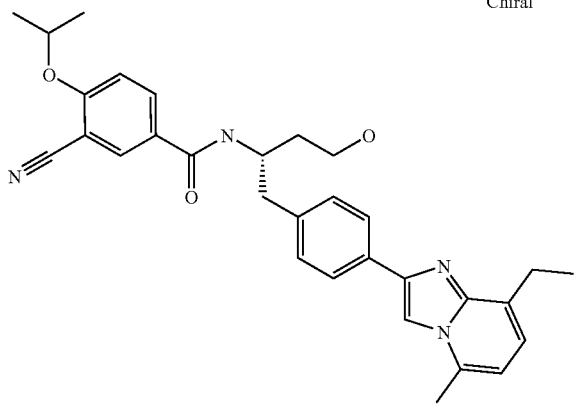

3-Cyano-N-((1S)-1-{[4-(8-ethyl-5-methylimidazo[1,2-a]pyridin-2-yl)phenyl]methyl}-3-hydroxypropyl)-4-[(1-methylethyl)oxy]benzamide 511.2

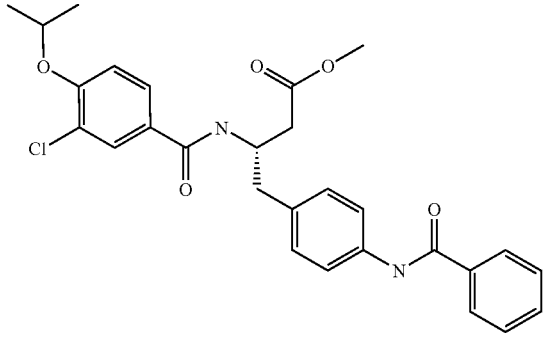

352

Methyl (3S)-3-[({3-chloro-4-[(1-methylethyl)oxy]phenyl}carbonyl)amino]-4-{4-[(phenylcarbonyl)amino]phenyl}butanoate

509

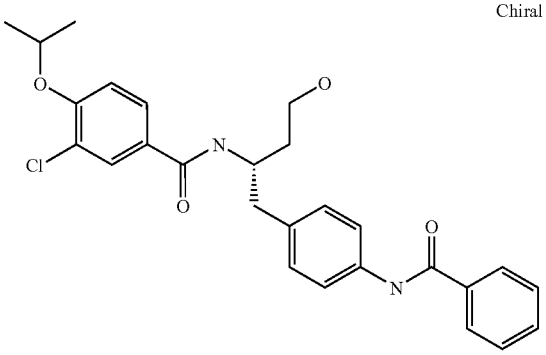

3-Chloro-N-[(1S)-3-hydroxy-1-({4-[(phenylcarbonyl)amino]phenyl}methyl)propyl]-4-[(1-methylethyl)oxy]benzamide

481

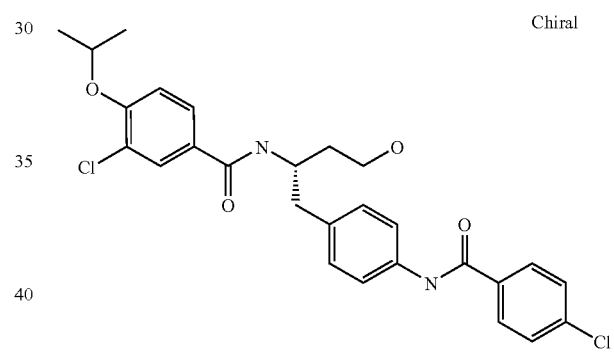

3-Chloro-N-{(1S)-1-[(4-{[(4-chlorophenyl)carbonyl]amino}phenyl)methyl]-3-hydroxypropyl}-4-[(1-methylethyl)oxy]benzamide

515

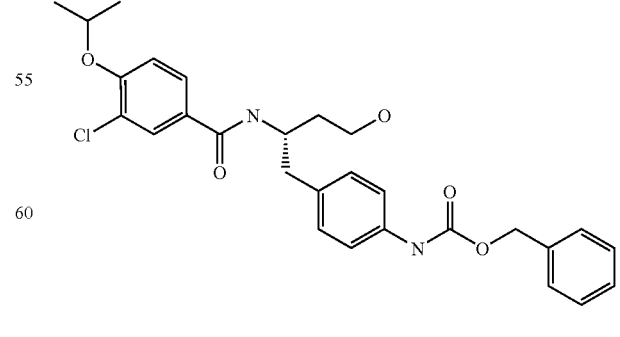

| 353 | 354 |
|---|---|
| Phenylmethyl(4-{(2S)-2-[({3-chloro-4-[(1-methyl-ethyl)oxy]phenyl}carbonyl)amino]-4-hydroxybutyl}phenyl)carbamate | 3-Chloro-N-[(1S)-1-({4-[(cyclohexylcarbonyl)amino]phenyl}methyl)-3-hydroxypropyl]-4-[(1-methylethyl)oxy]benzamide |
| 511 | 487 |

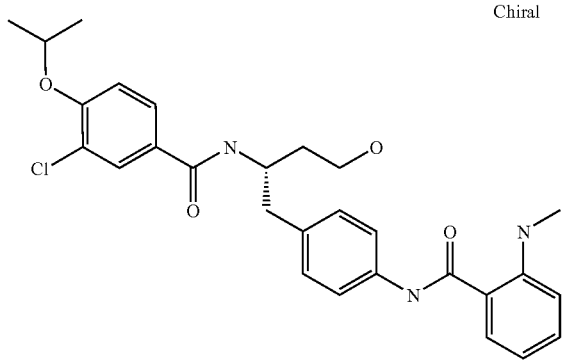

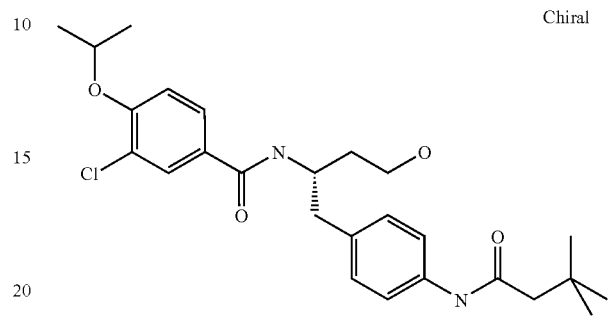

3-Chloro-N-((1S)-3-hydroxy-1-{[4-({[2-(methylamino)phenyl]carbonyl}amino)phenyl]methyl}propyl)-4-[(1-methylethyl)oxy]benzamide 3-Chloro-N-[(1S)-1-({4-[(3,3-dimethylbutanoyl)amino]phenyl}methyl)-3-hydroxypropyl]-4-[(1-methylethyl)oxy]benzamide

510

475

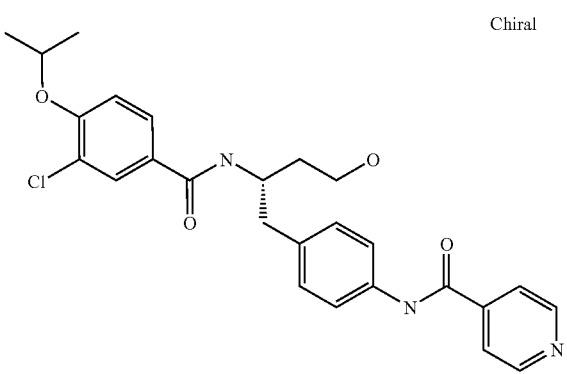

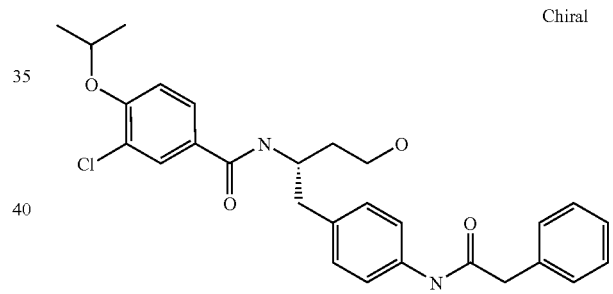

N-(4-{(2S)-2-[({3-Chloro-4-[(1-methylethyl)oxy]phenyl}carbonyl)amino]-4-hydroxybutyl}phenyl)-4-pyridinecarboxamide 3-Chloro-N-[(1S)-3-hydroxy-1-({4-[(phenylacetyl)amino]phenyl}methyl)propyl]-4-[(1-methylethyl)oxy]benzamide

482

495

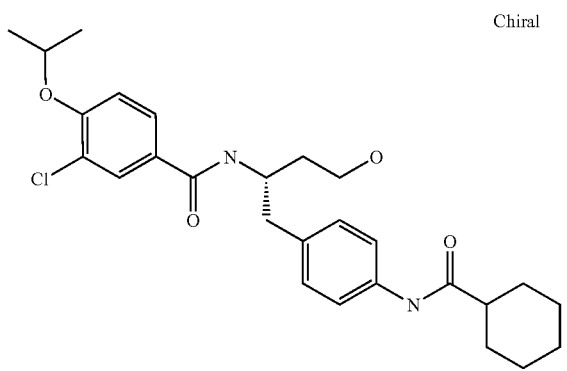

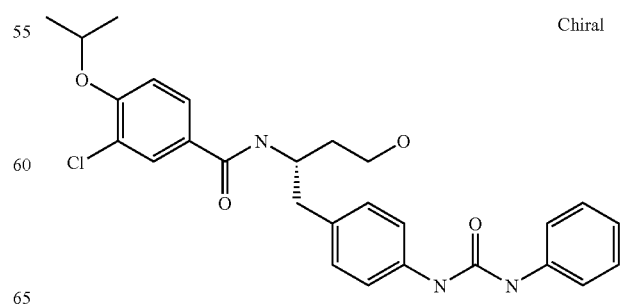

355
3-Chloro-N-{(1S)-3-hydroxy-1-[(4-{[(phenylamino)carbonyl]amino}phenyl)methyl]propyl}-4-[(1-methylethyl)oxy]benzamide

496

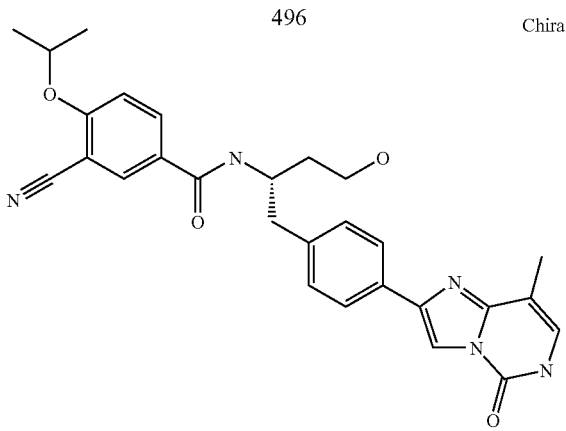

3-Cyano-N-((1S)-3-hydroxy-1-{[4-(8-methyl-5-oxo-5,6-dihydroimidazo[1,2-c]pyrimidin-2-yl)phenyl]methyl}propyl)-4-[(1-methylethyl)oxy]benzamide

500

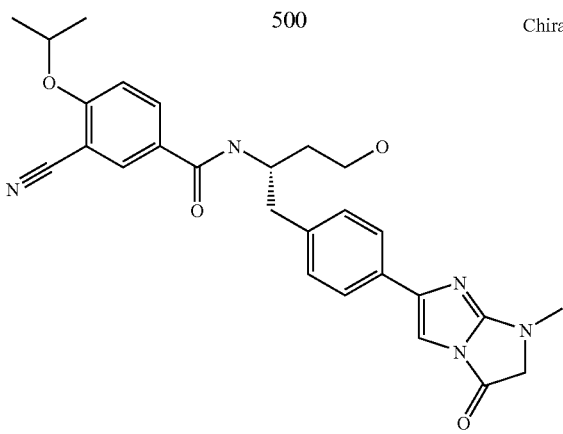

3-Cyano-N-((1S)-3-hydroxy-1-{[4-(1-methyl-3-oxo-2,3-dihydro-1H-imidazo[1,2-a]imidazol-6-yl)phenyl]methyl}propyl)-4-[(1-methylethyl)oxy]benzamide

488

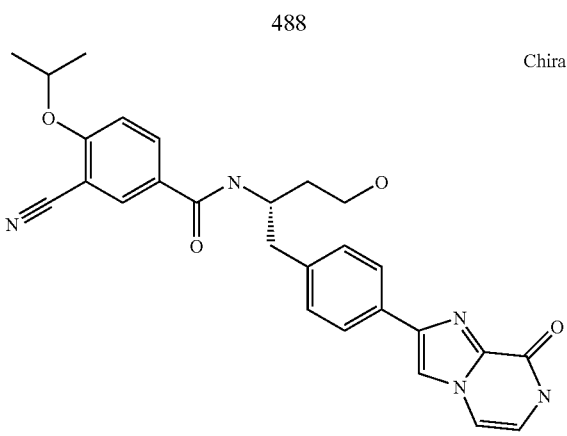

356
3-Cyano-N-((1S)-3-hydroxy-1-{[4-(8-oxo-7,8-dihydroimidazo[1,2-a]pyrazin-2-yl)phenyl]methyl}propyl)-4-[(1-methylethyl)oxy]benzamide

486

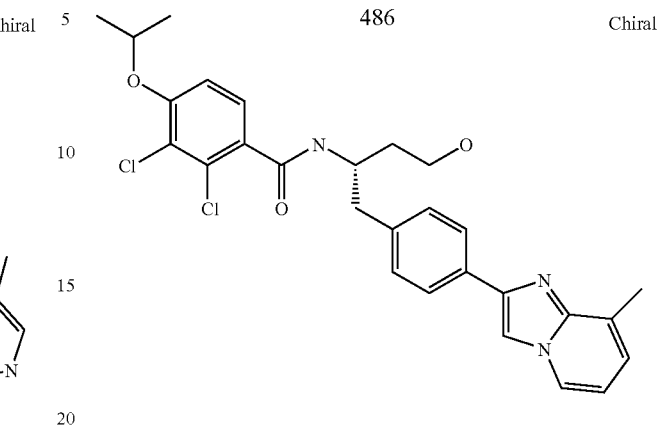

2,3-Dichloro-N-((1S)-3-hydroxy-1-{[4-(8-methylimidazo[1,2-a]pyridin-2-yl)phenyl]methyl}propyl)-4-[(1-methylethyl)oxy]benzamide

526

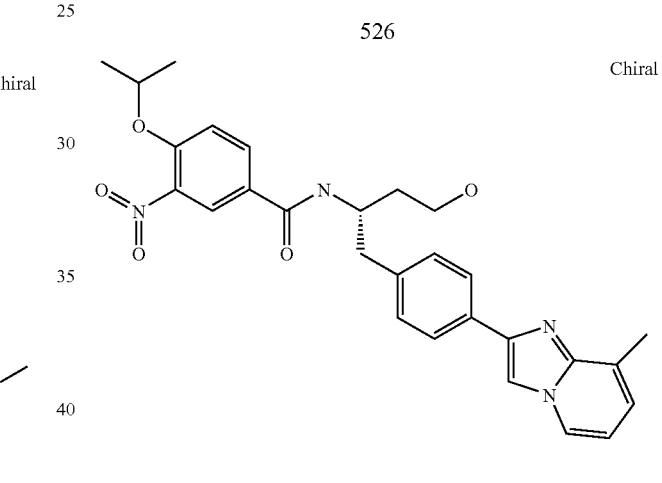

N-((1S)-3-Hydroxy-1-{[4-(8-methylimidazo[1,2-a]pyridin-2-yl)phenyl]methyl}propyl)-4-[(1-methylethyl)oxy]-3-nitrobenzamide

503

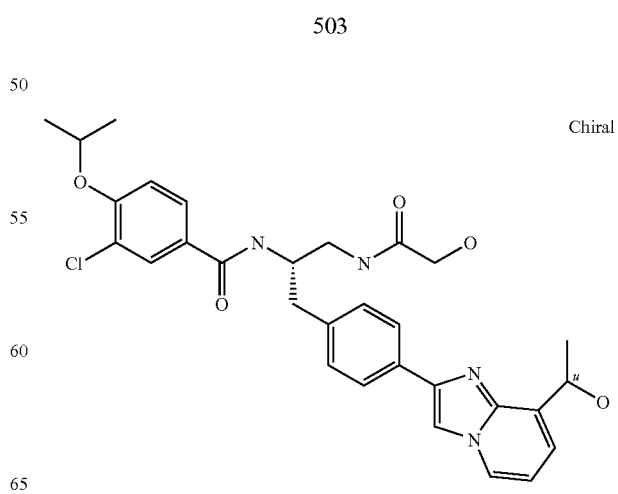

357

3-Chloro-N-[(1S)-2-[(hydroxyacetyl)amino]-1-({4-[8-(1-hydroxyethyl)imidazo[1,2-a]pyridin-2-yl]phenyl}methyl)ethyl]-4-[(1-methylethyl)oxy]benzamide

565

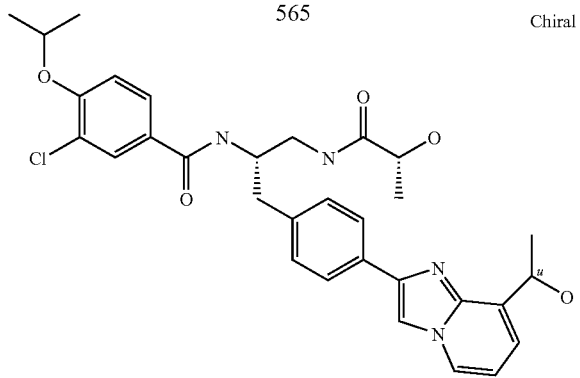

3-Chloro-N-[(1S)-2-{4-[8-(1-hydroxyethyl)imidazo[1,2-a]pyridin-2-yl]phenyl}-1-({[(2R)-2-hydroxypropanoyl]amino}methyl)ethyl]-4-[(1-methylethyl)oxy]benzamide

579

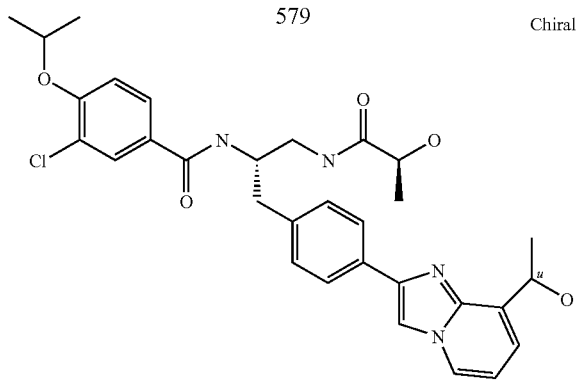

3-Chloro-N-[(1S)-2-{4-[8-(1-hydroxyethyl)imidazo[1,2-a]pyridin-2-yl]phenyl}-1-({[(2S)-2-hydroxypropanoyl]amino}methyl)ethyl]-4-[(1-methylethyl)oxy]benzamide

579

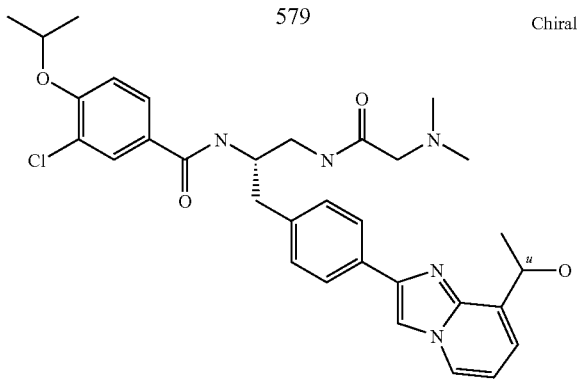

358

3-Chloro-N-[(1S)-2-[(N,N-dimethylglycyl)amino]-1-({4-[8-(1-hydroxyethyl)imidazo[1,2-a]pyridin-2-yl]phenyl}methyl)ethyl]-4-[(1-methylethyl)oxy]benzamide

592

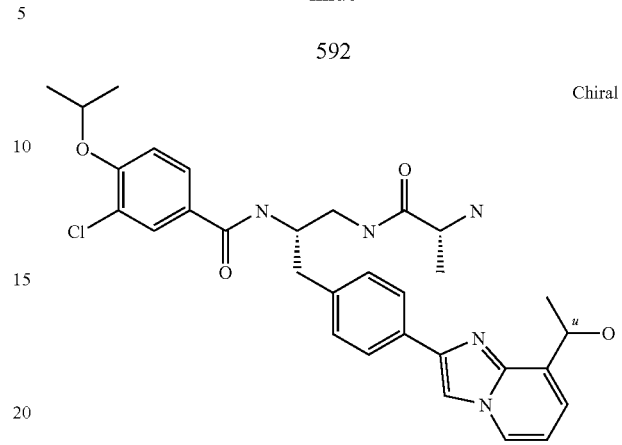

N-[(1S)-2-(D-Alanylamino)-1-({4-[8-(1-hydroxyethyl)imidazo[1,2-a]pyridin-2-yl]phenyl}methyl)ethyl]-3-chloro-4-[(1-methylethyl)oxy]benzamide

578

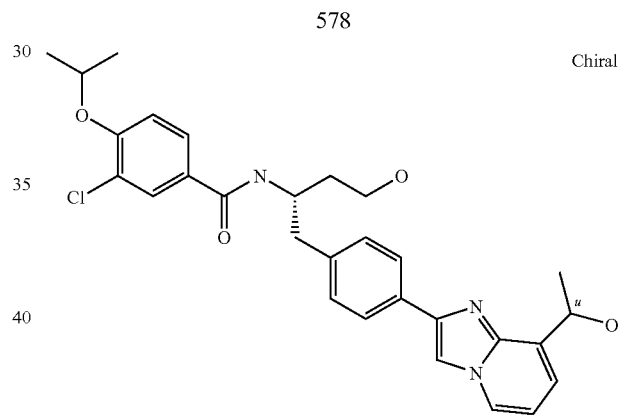

3-Chloro-N-[(1S)-3-hydroxy-1-({4-[8-(1-hydroxyethyl)imidazo[1,2-a]pyridin-2-yl]phenyl}methyl)propyl]-4-[(1-methylethyl)oxy]benzamide

522

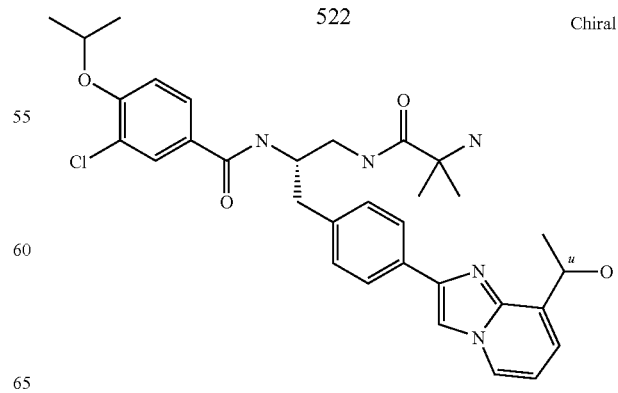

359

3-Chloro-N-((1S)-2-{4-[8-(1-hydroxyethyl)imidazo[1,2-a]pyridin-2-yl]phenyl}-1-{[(2-methylalanyl)amino]methyl}ethyl)-4-[(1-methylethyl)oxy]benzamide

592

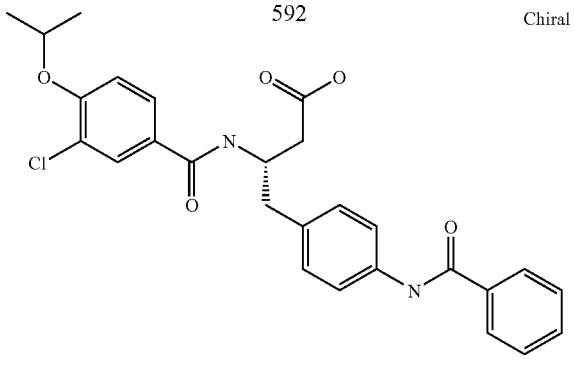

(3S)-3-[({3-Chloro-4-[(1-methylethyl)oxy]phenyl}carbonyl)amino]-4-{4-[(phenylcarbonyl)amino]phenyl}butanoic acid

495

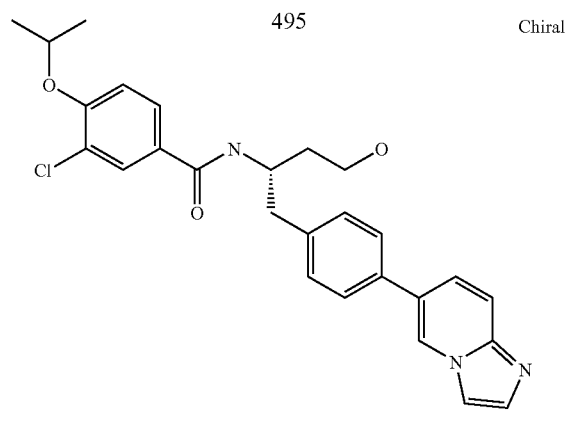

3-Chloro-N-{(1S)-3-hydroxy-1-[(4-imidazo[1,2-a]pyridin-6-ylphenyl)methyl]propyl}-4-[(1-methylethyl)oxy]benzamide 477.8

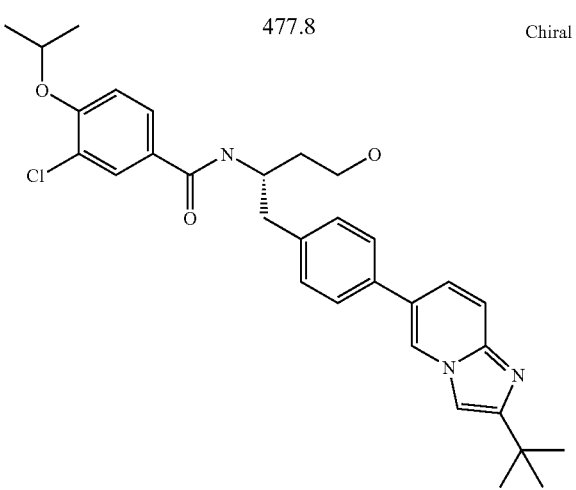

360

3-Chloro-N-[(1S)-1-({4-[2-(1,1-dimethylethyl)imidazo[1,2-a]pyridin-6-yl]phenyl}methyl)-3-hydroxypropyl]-4-[(1-methylethyl)oxy]benzamide 534.2

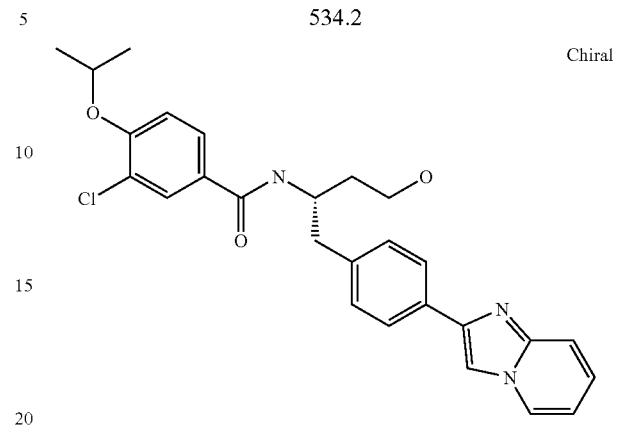

3-Chloro-N-{(1S)-3-hydroxy-1-[(4-imidazo[1,2-a]pyridin-2-ylphenyl)methyl]propyl}-4-[(1-methylethyl)oxy]benzamide 478.2

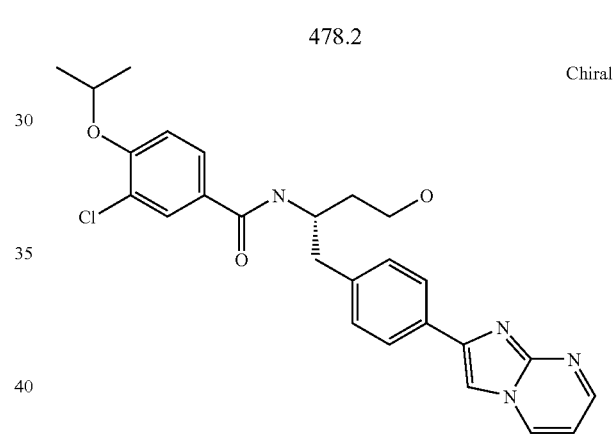

3-Chloro-N-{(1S)-3-hydroxy-1-[(4-imidazo[1,2-a]pyrimidin-2-ylphenyl)methyl]propyl}-4-[(1-methylethyl)oxy]benzamide 479.2

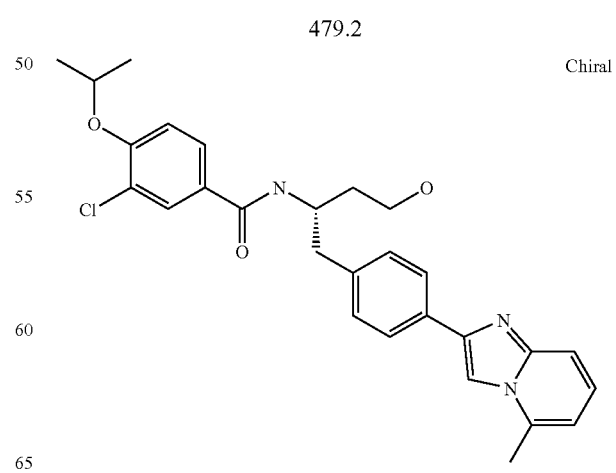

361

3-Chloro-N-((1S)-3-hydroxy-1-{[4-(5-methylimidazo[1,2-a]pyridin-2-yl)phenyl]methyl}propyl)-4-[(1-methylethyl)oxy]benzamide 492.2

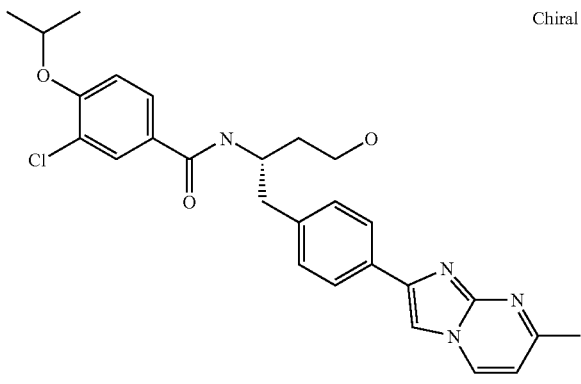

3-Chloro-N-((1S)-3-hydroxy-1-{[4-(7-methylimidazo[1,2-a]pyrimidin-2-yl)phenyl]methyl}propyl)-4-[(1-methylethyl)oxy]benzamide 494.2

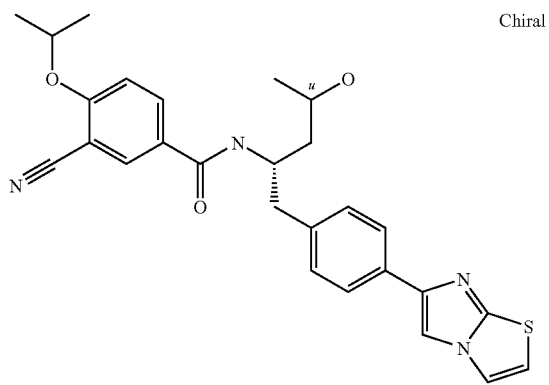

3-Cyano-N-{(1S)-3-hydroxy-1-[(4-imidazo[2,1-b][1,3]thiazol-6-ylphenyl)methyl]butyl}-4-[(1-methylethyl)oxy]benzamide 489.0

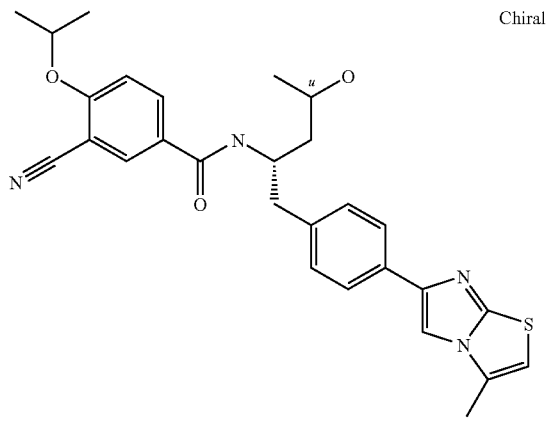

362

3-Cyano-N-((1S)-3-hydroxy-1-{[4-(3-methylimidazo[2,1-b][1,3]thiazol-6-yl)phenyl]methyl}butyl)-4-[(1-methylethyl)oxy]benzamide 503.2

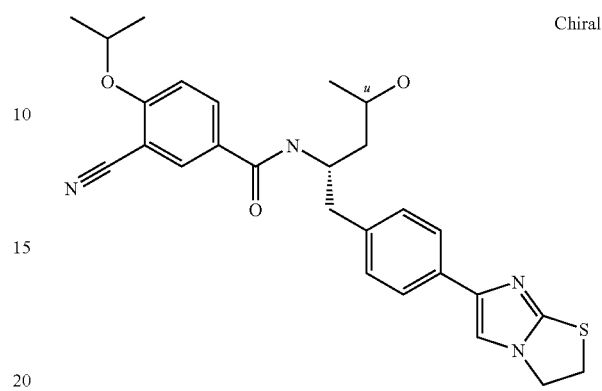

3-Cyano-N-((1S)-1-{[4-(2,3-dihydroimidazo[2,1-b][1,3]thiazol-6-yl)phenyl]methyl}-3-hydroxybutyl)-4-[(1-methylethyl)oxy]benzamide 491.2

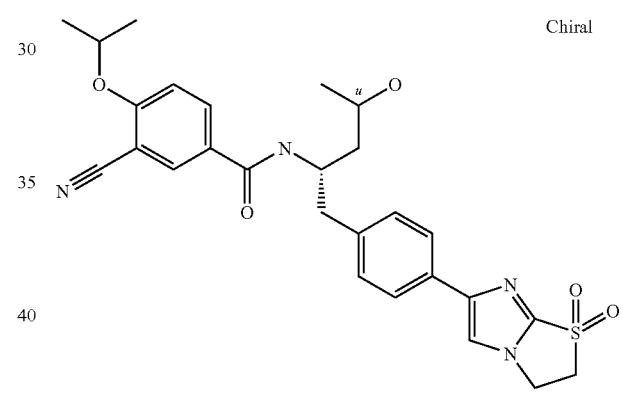

3-Cyano-N-((S)-1-{[4-(1,1-dioxido-2,3-dihydroimidazo[2,1-b][1,3]thiazol-6-yl)phenyl]methyl}-3-hydroxybutyl)-4-[(1-methylethyl)oxy]benzamide 523.2

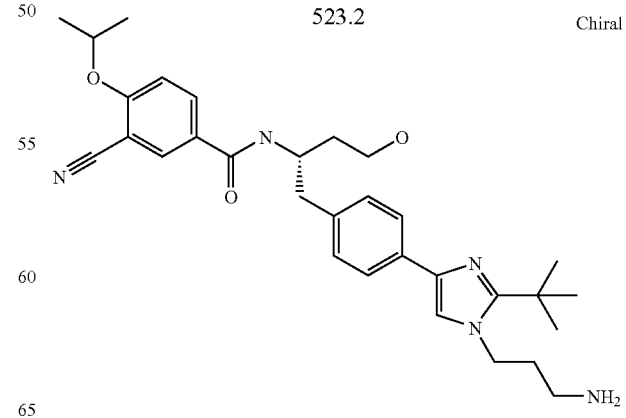

363
N—[(S)-1-({4-[1-(3-Aminopropyl)-2-(1,1-dimethylethyl)-1H-imidazol-4-yl]phenyl}methyl)-3-hydroxypropyl]-3-cyano-4-[(1-methylethyl)oxy]benzamide 532.4

364
3-Cyano-N-((1S)-3-hydroxy-1-{[4-(8-phenylimidazo[1,2-a]pyridin-2-yl)phenyl]methyl}propyl)-4-[(1-methylethyl)oxy]benzamide 545.4

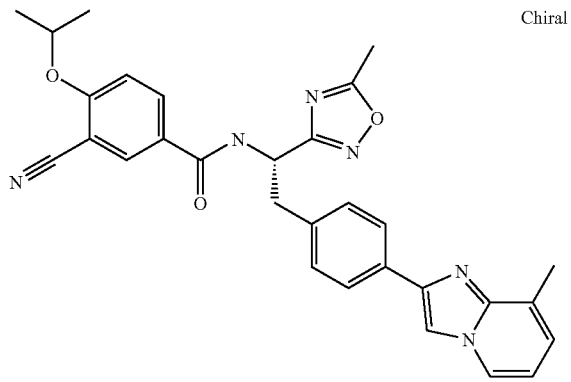
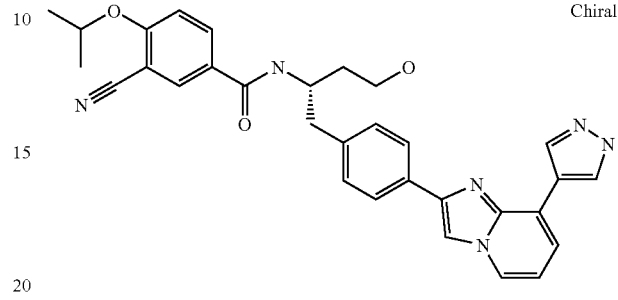

3-Cyano-4-[(1-methylethyl)oxy]-N-[(1S)-2-[4-(8-methylimidazo[1,2-a]pyridin-2-yl)phenyl]-1-(5-methyl-1,2,4-oxadiazol-3-yl)ethyl]benzamide 521.4

3-Cyano-N-[(1S)-3-hydroxy-1-({4-[8-(1H-pyrazol-4-yl)imidazo[1,2-a]pyridin-2-yl]phenyl}methyl)propyl]-4-[(1-methylethyl)oxy]benzamide 535.4

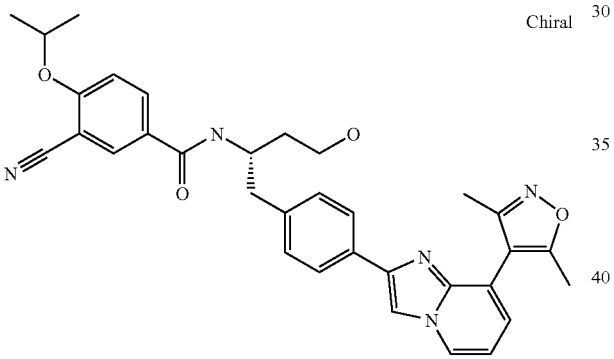
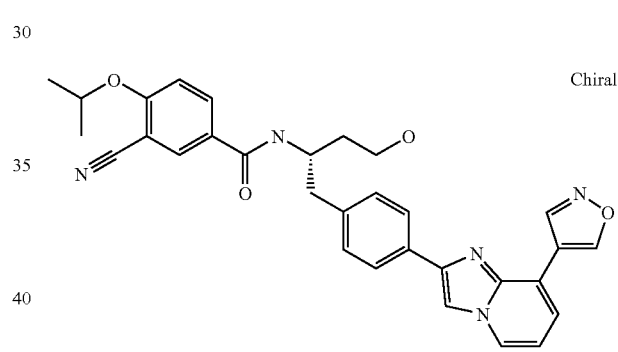

3-Cyano-N-[(1S)-1-({4-[8-(3,5-dimethyl-4-isoxazolyl)imidazo[1,2-a]pyridin-2-yl]phenyl}methyl)-3-hydroxypropyl]-4-[(1-methylethyl)oxy]benzamide 564.2

3-Cyano-N-[(1S)-3-hydroxy-1-({4-[8-(4-isoxazolyl)imidazo[1,2-a]pyridin-2-yl]phenyl}methyl)propyl]-4-[(1-methylethyl)oxy]benzamide 536.2

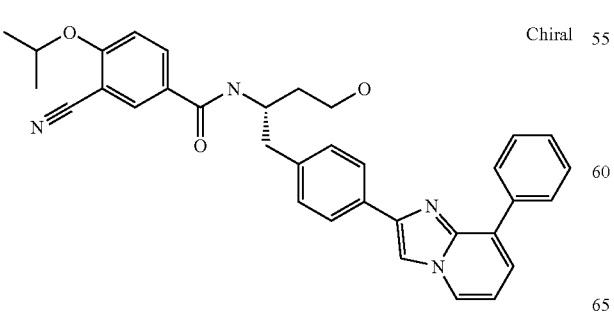
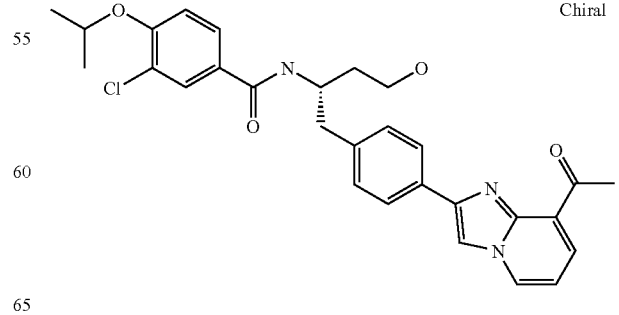

| 365 | 366 |
|---|---|
| N-((1S)-1-{[4-(8-Acetylimidazo[1,2-a]pyridin-2-yl)phenyl]methyl}-3-hydroxypropyl)-3-chloro-4-[(1-methylethyl)oxy]benzamide | N-{(1S)-1-[(4-{8-[(1E)-3-Amino-3-oxo-1-propen-1-yl]imidazo[1,2-a]pyridin-2-yl}phenyl)methyl]-3-hydroxypropyl}-3-cyano-4-[(1-methylethyl)oxy]benzamide |
| 520.2 | 538.4 |

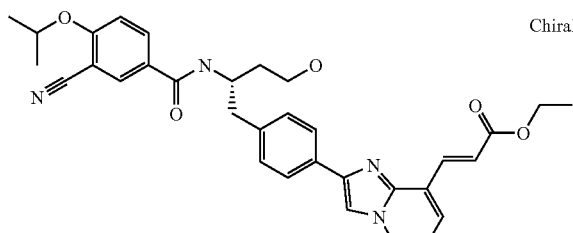

| Ethyl (2E)-3-[2-(4-{(2S)-2-[({3-cyano-4-[(1-methylethyl)oxy]phenyl}carbonyl)amino]-4-hydroxybutyl}phenyl)imidazo[1,2-a]pyridin-8-yl]-2-propenoate | N-[(1S)-1-({4-[8-(3-Amino-3-oxopropyl)imidazo[1,2-a]pyridin-2-yl]phenyl}methyl)-3-hydroxypropyl]-3-cyano-4-[(1-methylethyl)oxy]benzamide |
|---|---|
| 567.6 | 540.4 |

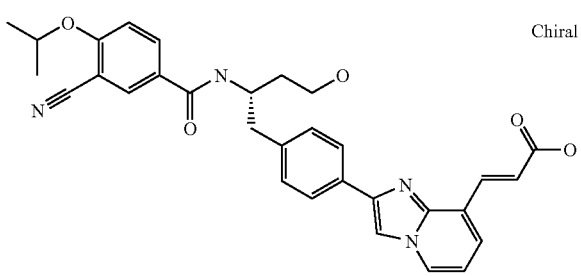

| (2E)-3-[2-(4-{(2S)-2-[({3-Cyano-4-[(1-methylethyl)oxy]phenyl}carbonyl)amino]-4-hydroxybutyl}phenyl)imidazo[1,2-a]pyridin-8-yl]-2-propenoic acid | 3-Chloro-N-((1S)-1-{[4-(3-chloro-8-methylimidazo[1,2-a]pyridin-2-yl)phenyl]methyl}-3-hydroxypropyl)-4-[(1-methylethyl)oxy]benzamide |
|---|---|
| 539.4 | 526.2 |

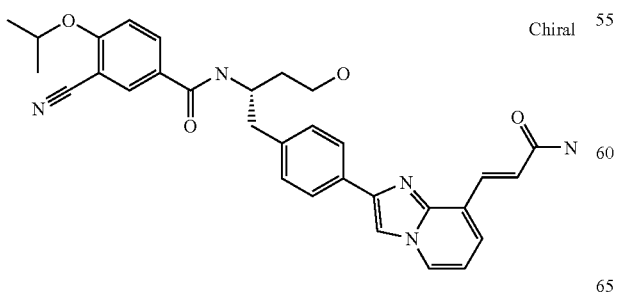
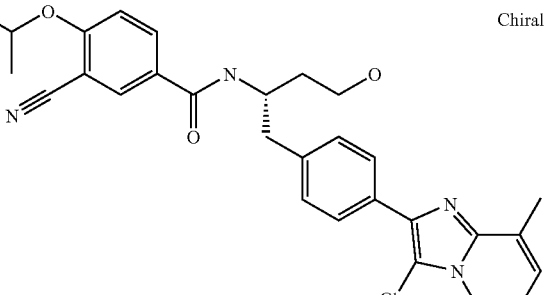

367

N-((1S)-1-{[4-(3-Chloro-8-methylimidazo[1,2-a]pyridin-2-yl)phenyl]methyl}-3-hydroxypropyl)-3-cyano-4-[(1-methylethyl)oxy]benzamide 517.2

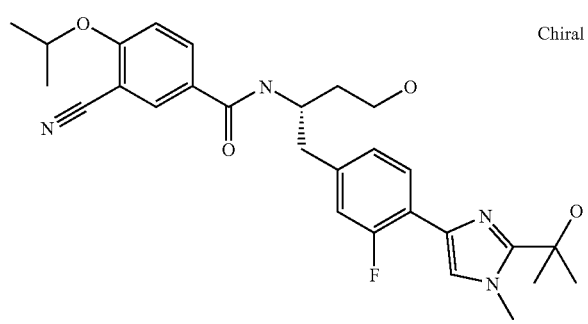

3-Cyano-N-[(1S)-1-({3-fluoro-4-[2-(1-hydroxy-1-methylethyl)-1-methyl-1H-imidazol-4-yl]phenyl}methyl)-3-hydroxypropyl]-4-[(1-methylethyl)oxy]benzamide 509.2

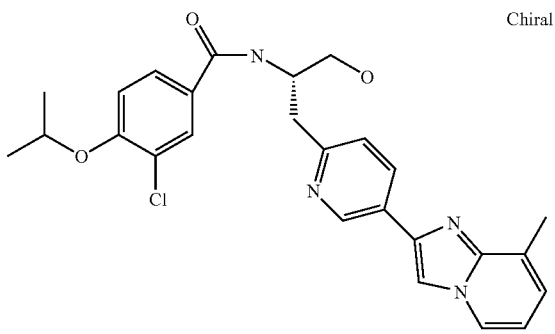

3-Chloro-N-((1S)-2-hydroxy-1-{[5-(8-methylimidazo[1,2-a]pyridin-2-yl)-2-pyridinyl]methyl}ethyl)-4-[(1-methylethyl)oxy]benzamide

479

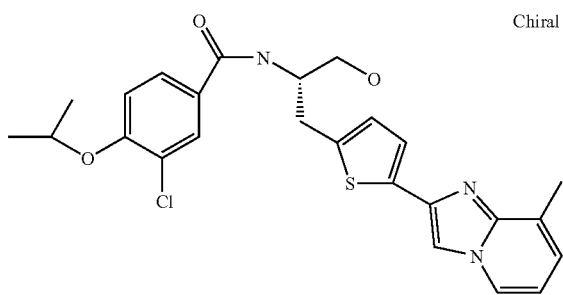

368

3-Chloro-N-((1S)-2-hydroxy-1-{[5-(8-methylimidazo[1,2-a]pyridin-2-yl)-2-thienyl]methyl}ethyl)-4-[(1-methylethyl)oxy]benzamide

484

3-Chloro-N-[(1S)-1-({4-[2-(1,1-dimethylethyl)-1-methyl-1H-imidazol-4-yl]-2-fluorophenyl}methyl)-3-hydroxypropyl]-4-[(1-methylethyl)oxy]benzamide

516

3-Chloro-N-[(1S)-1-({4-[2-(1,1-dimethylethyl)-1-methyl-1H-imidazol-4-yl]-2,6-difluorophenyl}methyl)-3-hydroxypropyl]-4-[(1-methylethyl)oxy]benzamide

534

369

3-Chloro-N-[(1S)-1-({2-chloro-4-[2-(1,1-dimethyl-ethyl)-1-methyl-1H-imidazol-4-yl]phenyl}methyl)-3-hydroxypropyl]-4-[(1-methylethyl)oxy]benzamide

532

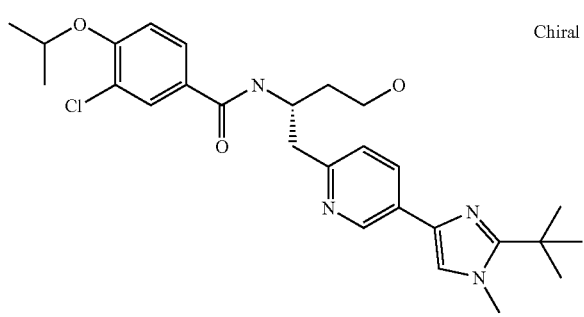

3-Chloro-N-[(1S)-1-({5-[2-(1,1-dimethylethyl)-1-methyl-1H-imidazol-4-yl]-2-pyridinyl}methyl)-3-hydroxypropyl]-4-[(1-methylethyl)oxy]benzamide

499

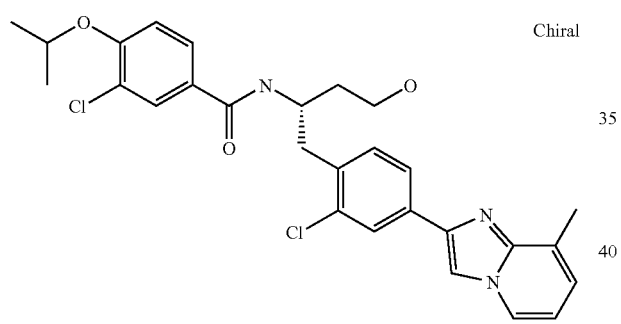

3-Chloro-N-((1S)-1-{[2-chloro-4-(8-methylimidazo[1,2-a]pyridin-2-yl)phenyl]methyl}-3-hydroxypropyl)-4-[(1-methyl ethyl)oxy]benzamide

526

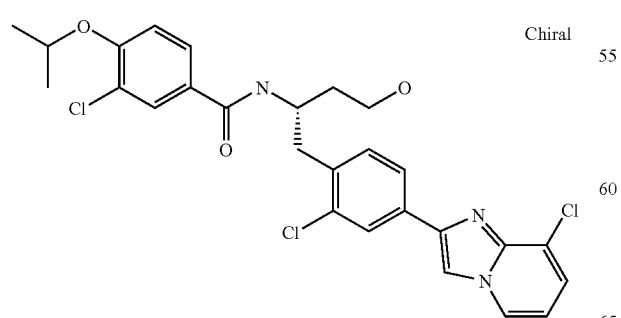

370

3-Chloro-N-((1S)-1-{[2-chloro-4-(8-chloroimidazo[1,2-a]pyridin-2-yl)phenyl]methyl}-3-hydroxypropyl)-4-[(1-methylethyl)oxy]benzamide

546

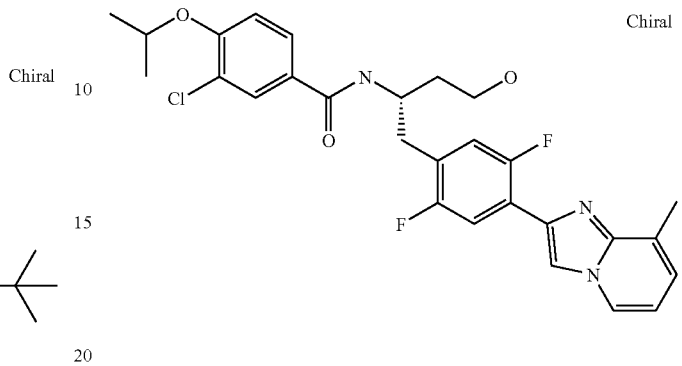

3-Chloro-N-((1S)-1-{[2,5-difluoro-4-(8-methylimidazo[1,2-a]pyridin-2-yl)phenyl]methyl}-3-hydroxypropyl)-4-[(1-methylethyl)oxy]benzamide

528

3-Chloro-N-[(1S)-1-({4-[2-(1,1-dimethylethyl)-1-methyl-1H-imidazol-4-yl]phenyl}methyl)-3-(methylamino)-3-oxopropyl]-4-[(1-methylethyl)oxy]benzamide 525.4

371

3-Cyano-N-[(1S)-2-{4-[2-(1,1-dimethylethyl)-1-methyl-1H-imidazol-4-yl]phenyl}-1-({[(phenylamino)carbonyl]amino}methyl)ethyl]-4-[(1-methylethyl)oxy]benzamide 593.2

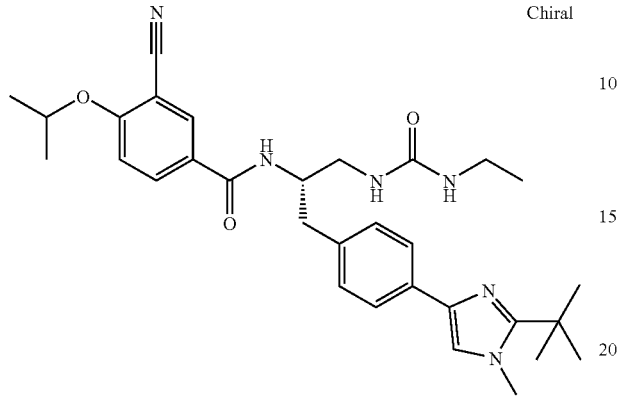

3-Cyano-N-[(1S)-2-{4-[2-(1,1-dimethylethyl)-1-methyl-1H-imidazol-4-yl]phenyl}-1-({[(ethylamino)carbonyl]amino}methyl)ethyl]-4-[(1-methylethyl)oxy]benzamide 545.2

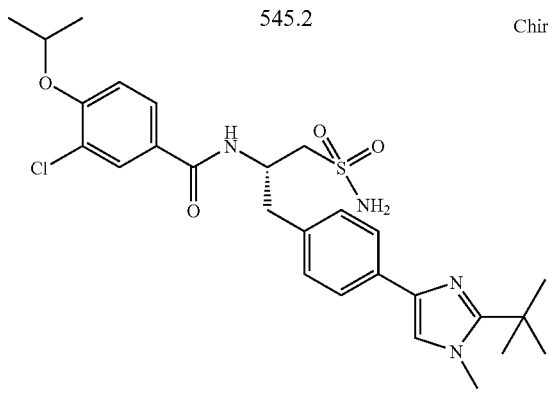

N-[(1S)-2-(Aminosulfonyl)-1-({4-[2-(1,1-dimethylethyl)-1-methyl-1H-imidazol-4-yl]phenyl}methyl)ethyl]-3-chloro-4-[(1-methylethyl)oxy]benzamide 548.2

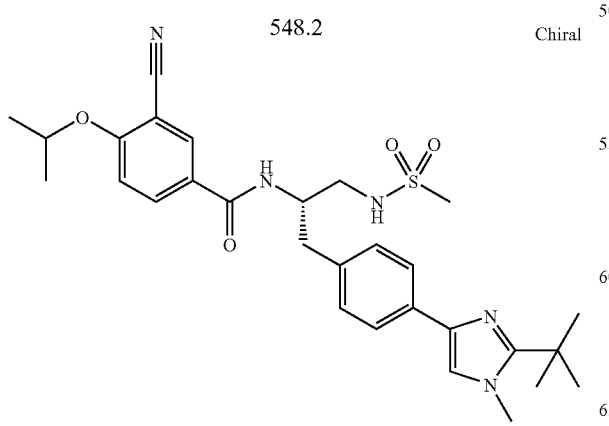

372

3-Cyano-N-((1S)-2-{4-[2-(1,1-dimethylethyl)-1-methyl-1H-imidazol-4-yl]phenyl}-1-{[(methylsulfonyl)amino]methyl}ethyl)-4-[(1-methylethyl)oxy]benzamide 552.4

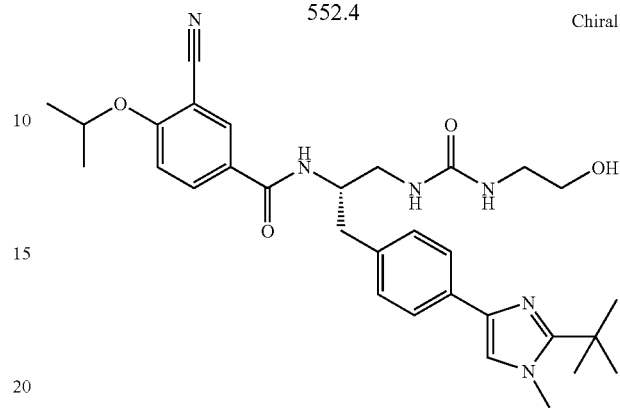

3-Cyano-N-{(1S)-2-{4-[2-(1,1-dimethylethyl)-1-methyl-1H-imidazol-4-yl]phenyl}-1-[({[(2-hydroxyethyl)amino]carbonyl}amino)methyl]ethyl}-4-[(1-methylethyl)oxy]benzamide 561.2

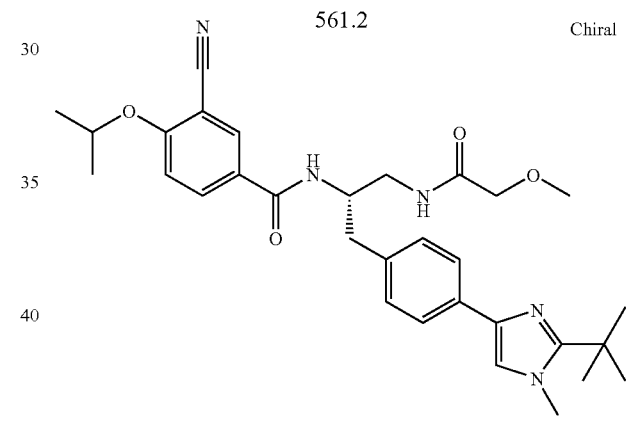

N—[(S)-1-[4-(2-tert-Butyl-1-methyl-1H-imidazol-4-yl)-benzyl]-2-(2-methoxy-ethanoylamino)-ethyl]-3-cyano-4-isopropoxy-benzamide 546.2

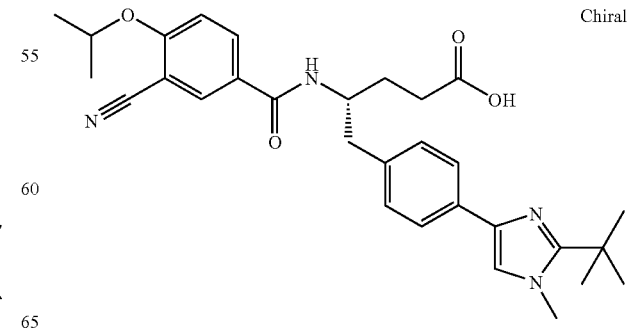

373

(4R)-4-[({3-Cyano-4-[(1-methylethyl)oxy]phenyl}carbonyl)amino]-5-{4-[2-(1,1-dimethylethyl)-1-methyl-1H-imidazol-4-yl]phenyl}pentanoic acid 517.4

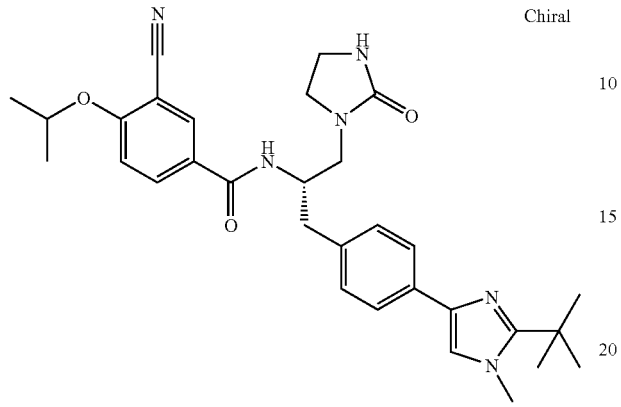

3-Cyano-N-{(1S)-2-{4-[2-(1,1-dimethylethyl)-1-methyl-1H-imidazol-4-yl]phenyl}-1-[(2-oxo-1-imidazolidinyl)methyl]ethyl}-4-[(1-methylethyl)oxy]benzamide 543.4

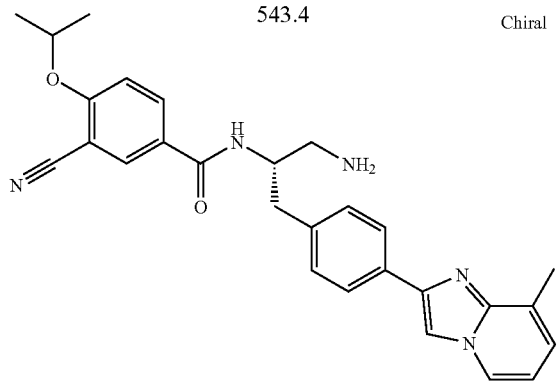

N-((1S)-2-Amino-1-{[4-(8-methylimidazo[1,2-a]pyridin-2-yl)phenyl]methyl}ethyl)-3-cyano-4-[(1-methylethyl)oxy]benzamide 468.2

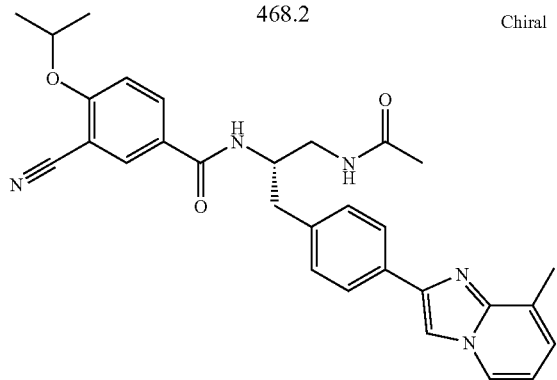

374

N-((1S)-2-(Acetylamino)-1-{[4-(8-methylimidazo[1,2-a]pyridin-2-yl)phenyl]methyl}ethyl)-3-cyano-4-[(1-methylethyl)oxy]benzamide 510.4

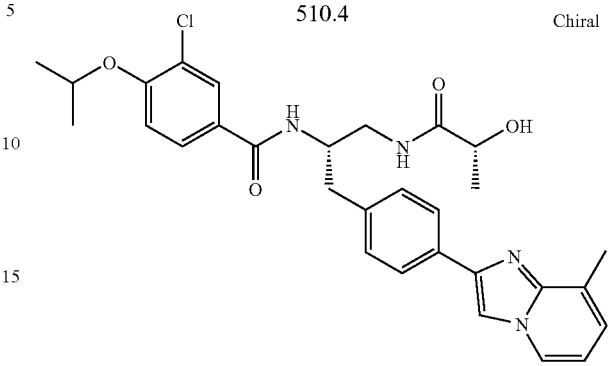

3-Chloro-N-((1S)-2-{[(2R)-2-hydroxypropanoyl]amino}-1-{[4-(8-methylimidazo[1,2-a]pyridin-2-yl)phenyl]methyl}ethyl)-4-[(1-methylethyl)oxy]benzamide 549.2

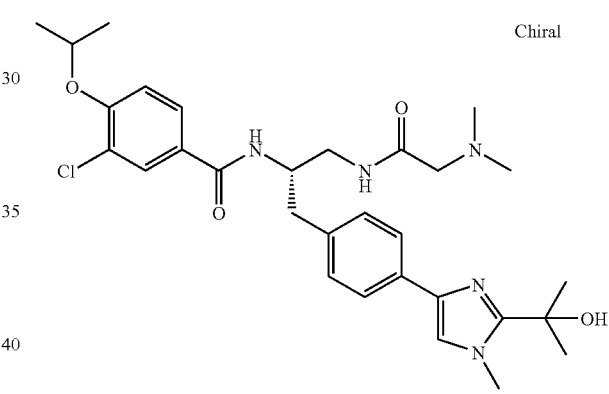

3-Chloro-N-[(1S)-2-[(N,N-dimethylglycyl)amino]-1-({4-[2-(1-hydroxy-1-methylethyl)-1-methyl-1H-imidazol-4-yl]phenyl}methyl)ethyl]-4-[(1-methylethyl)oxy]benzamide 570.4

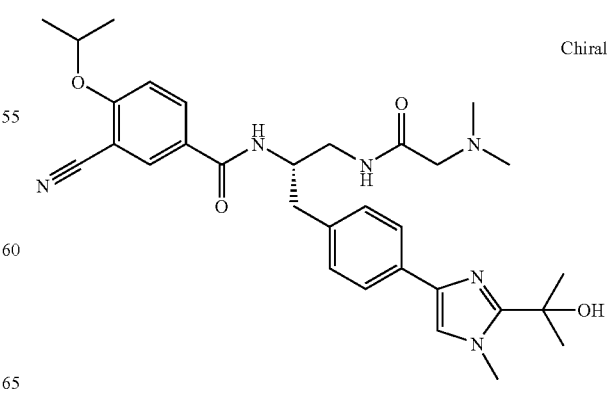

3-Cyano-N-[(1S)-2-[(N,N-dimethylglycyl)amino]-1-({4-[2-(1-hydroxy-1-methylethyl)-1-methyl-1H-imidazol-4-yl]phenyl}methyl)ethyl]-4-[(1-methylethyl)oxy]benzamide 561.4

Example 67

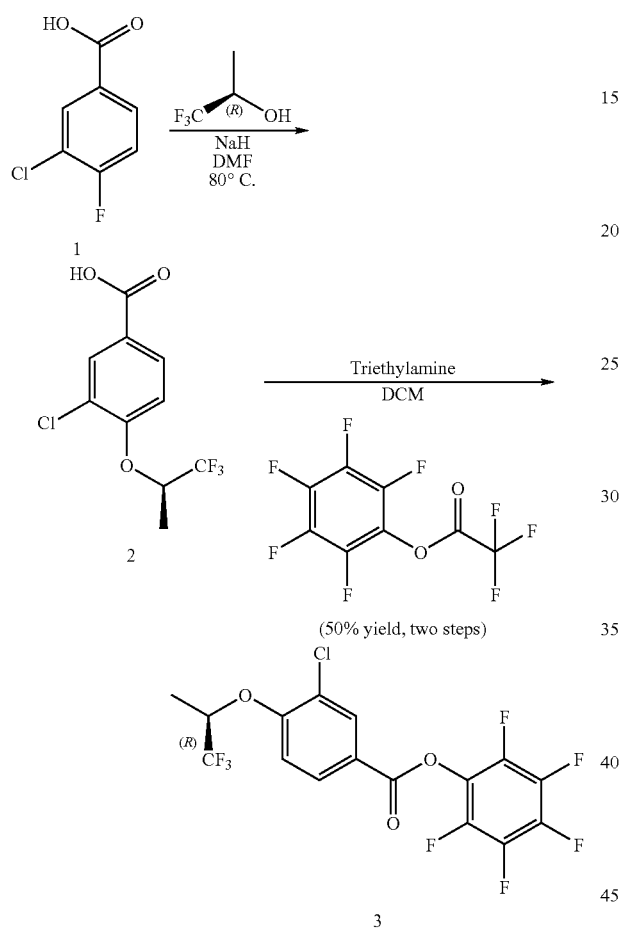

To a 0° C. solution of compound 1 (10.7 g, 61.37 mmol), (R)-1,1,1-trifluoropropanol (3.5 g, 30.68 mmol) in dimethylformamide (200 mL) was added sodium hydride (3.7 g, 92.05 mmol) portion wise over 5 minutes. After 10 min, the ice bath was removed and the reaction mixture was stirred while warming to room temperature. The reaction mixture was heated to 80° C. and stirred overnight. The reaction was monitored by LC/MS. After the reaction was done it was cooled to room temperature. The reaction mixture was quenched with HCl (0.5N, 200 mL) and extracted with ethyl acetate (3×250 mL). The organic layer was dried over sodium sulfate, filtered, and the filtrate was concentrated in vacuo giving crude compound 2 (8.2 g) which was used directly in the next step without further purification.

To a 0° C. crude solution of compound 2 (4.1 g, 15.34 mmol), triethylamine (6.4 mL, 46.02 mmol) in dichloromethane (200 ml) was added pentafluorophenyl trifluoroacetate (6.35 mL, 36.82 mmol) via syringe over 3 mins. After 5 mins the ice bath was removed and the reaction mixture was stirred while warming to room temperature for another 2 hours. The reaction mixture was concentrated in vacuo. The resulting residue was purified by flash chromatography (silica gel, hexanes/ethyl acetate=1:0, 50:1) to give compound 3 (3.5 g, 50% yield).

Example 68

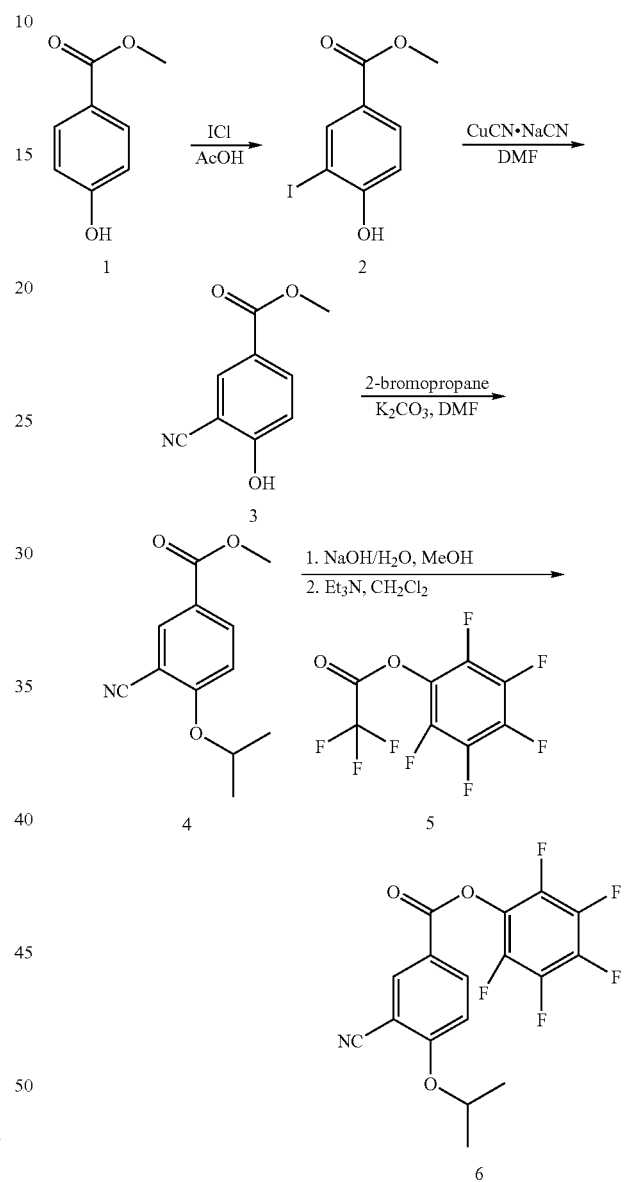

Methyl 4-hydroxy-3-iodobenzoate 2: Methyl 4-hydroxybenzoate (35.5 g, 0.233 mol) was dissolved in 200 mL of acetic acid, and the stirred mixture was warmed to 65° C. A solution of ICl (37.8 g, 0.233 mol) in 50 mL of AcOH was added dropwise over 40 min. The mixture was stirred at 65° C. for 5 h and then stirred an additional 16 h at room temperature. The precipitated product was isolated via filtration, washed with water and dried under vacuum to give 27.5 g (99% pure by LCMS and HNMR)) of desired product. The mother liquors were evaporated and resulting residue was washed with water and dried under vacuum to give another 31 g (95% pure by LCMS and NMR) of desired product. The combined yield of methyl 4-hydroxy-3-iodobenzoate was 58.5 g (90.3% yield). LCMS m/z=.

Methyl 3-cyano-4-hydroxybenzoate 3: 28 g (0.1 mol) of methyl 4-hydroxy-3-iodobenzoate 2 dissolved in 100 mL of DMF was treated with 9.92 g (0.11 mol) of CuCN and 0.49 g (0.11 mol) of NaCN. The system was flushed with nitrogen after which the mixture warmed to 105° C. and stirred to 18 h. The mixture was allowed to cool to room temperature, and any precipitates were removed via filtration and washed with EtOAc. The combined organics were diluted with 200 mL of water and then extracted with EtOAc (2×200 mL). The combined layers were dried over sodium sulfate, filtered and evaporated to dryness. After drying under vacuum, the resulting 18 g (100% yield) of 3 was characterized by LCMS and HNMR.

Methyl 3-cyano-4-isopropoxybenzoate 4: Methyl 3-cyano-4-hydroxybenzoate 3 (18 g, 0.1 mol) was dissolved in 100 mL of DMF and treated with 14.2 mL (0.15 mol) of 2-bromopropane and 41.9 g (0.3 mol) of anhydrous potassium carbonate. The system was flushed with nitrogen, and the mixture was heated to 90° C. and stirred overnight. After cooling to room temperature, the mixture was diluted with 200 mL of water and extracted with CH$_2$Cl$_2$ (2×200 mL). The combined organic layers were dried over sodium sulfate, filtered and evaporated to dryness to give 20.5 g (99% yield) of 4 as an oil that was characterized by LCMS and HNMR.

Perfluorophenyl 3-cyano-4-isopropoxybenzoate 6: 20.5 g (0.093 mol) of methyl 3-cyano-4-isopropoxybenzoate 4 was dissolved in 200 mL of a 6:4 mixture of methanol and water. To this was added 5.61 g (0.14 mol) of NaOH, and the mixture was stirred for 2 hours at room temperature. The solution was then filtered through a silica gel plug and the solvents removed under vacuum. The resulting solid was re-dissolved in 200 mL of CH$_2$Cl$_2$ and treated with 19.3 mL (0.11 mol) of perfluorophenyl 2,2,2-trifluoroacetate 5 and 19.5 mL (0.14 mol) of triethylamine. After stirring overnight, the solution was filtered and any solids rinsed with CH$_2$Cl$_2$ The combined organic mixtures were run through a short silica gel column and then evaporated to dryness to give 29 g (83.5% yield) of 6 which was characterized by LCMS and HNMR.

Example 69

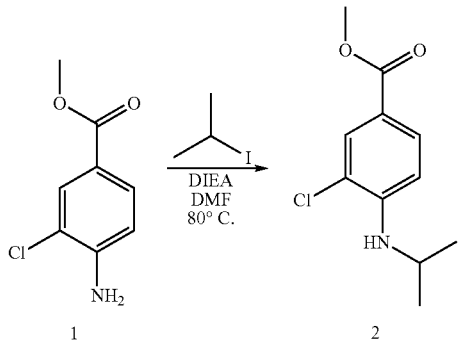

To a solution of compound 1 (200 mg, 1.077 mmol) and 2-iodopropane, (322 uL, 3.23 mmol) in DMF (10 mL) was added DIEA (750 uL, 4.31 mmol). The reaction mixture was heated to 80° C. and stirred overnight. The reaction was monitored by LC/MS. After the reaction was done it was cooled to room temperature. The reaction mixture was quenched with HCl (0.5N, 30 mL) and extracted with ethyl acetate (50 mL×3). The organic layer was dried over sodium sulfate and concentrated and dried under high vacuum. The resulting residue was purified by reverse phase chromatography (using a mixture of acetonitrile and water) to give compound 2 (50 mg, 20%).

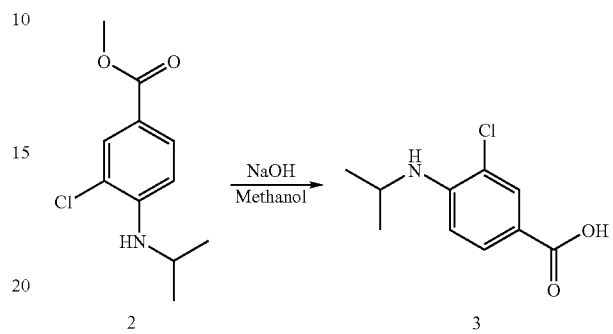

To a solution of compound 2 (50 mg, 0.22 mmol), in MEOH (1.0 mL) was added NaOH in water (1.0 M, 330 uL, 0.330 mmol). The reaction mixture was stirred at ambient temperature for 2 hours. The reaction was monitored by LC/MS. The reaction mixture was quenched with HCl (0.5N, 5 mL) and extracted with ethyl acetate (10 mL×3). The organic layer was dried over sodium sulfate, and concentrated to give 2 (45 mg). LRMS (M−H$^+$) m/z 212.0

Example 70

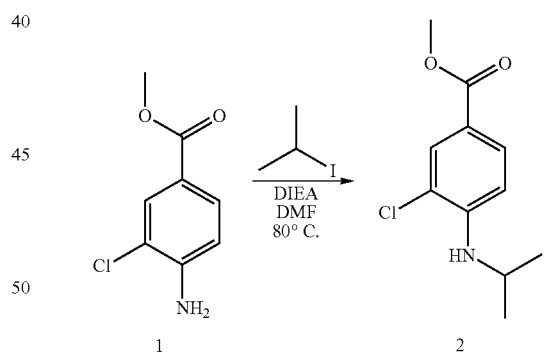

To a solution of compound 1 (200 mg, 1.077 mmol) and 2-iodopropane, (322 uL, 3.23 mmol) in DMF (10 mL) was added DIEA (750 uL, 4.31 mmol). The reaction mixture was heated to 80° C. and stirred overnight. The reaction was monitored by LC/MS. After the reaction was done it was cooled to room temperature. The reaction mixture was quenched with HCl (0.5 N, 30 mL) and extracted with ethyl acetate (50 mL×3). The organic layer was dried over sodium sulfate and concentrated and dried under high vacuum. The resulting residue was purified by reverse phase chromatography using a mixture of acetonitrile and water to give compound 2 (50 mg, 20%).

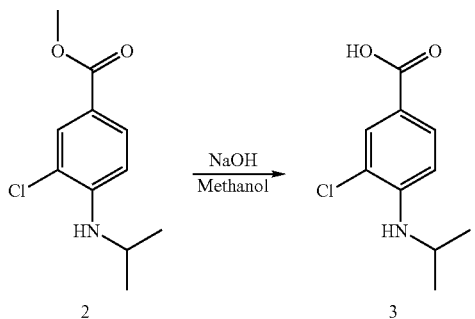

To a solution of compound 2 (50 mg, 0.22 mmol), in MEOH (1.0 mL) was added NaOH in water (1.0 M, 330 uL, 0.330 mmol). The reaction mixture was stirred at ambient temperature for 2 hours. The reaction was monitored by LC/MS. The reaction mixture was quenched with HCl (0.5 N, 5 mL) and extracted with ethyl acetate (10 mL×3). The organic layer was dried over sodium sulfate, and concentrated to give 2 (45 mg). LRMS (M−H$^+$) m/z 212.0

Example 71

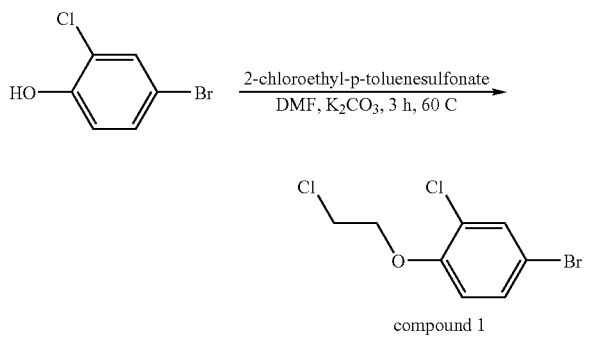

4-bromo-2-chlorophenol (5.04 g, 24.3 mmol) was dissolved in DMF (30 mL) and $K_2CO_3$ (10.10 g, 72.9 mmol) was added, followed by 2-chloroethyl-p-toluenesulfonate (4.86 mL, 26.7 mmol). The resulting mixture was heated to 60° C. for 3 hours and then cooled to room temperature. The reaction was diluted with EtOAc (350 mL) and washed with water (5×150 mL). The organic phase was dried ($Na_2SO_4$) and concentrated to a viscous oil which solidified to a white solid while under high vacuum. Compound 1 (6.46 g, 24.1 mmol, quantitative yield) was characterized using $^1$H NMR and used in the following step without further purification.

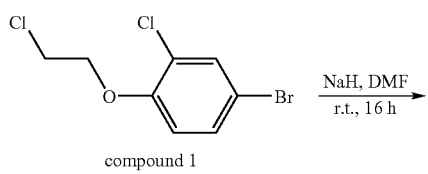

-continued

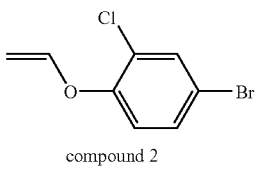

Compound 1 (6.46 g, 24.1 mmol) was dissolved in DMF (30 mL) and sodium hydride (1.94 g of 60% dispersion in mineral oil, 48.6 mmol) was added. The resulting mixture was stirred at room temperature for 16 hours. The reaction was diluted with water (100 mL) and EtOAc (350 mL). The layers were separated, and the organic layer was washed with water (4×150 mL). The organic phase was dried ($Na_2SO_4$) and concentrated to a white solid. Compound 2 (5.56 g, 24.0 mmol, quantitative yield) was dried under high vacuum and characterized using $^1$H NMR. It was used in the following step without further purification.

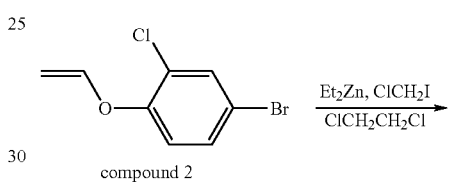

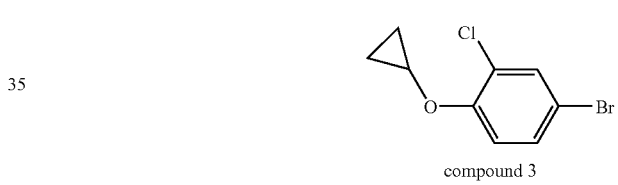

Compound 2 (5.56 g, 24.0 mmol) was combined with chloroiodomethane (5.59 mL, 76.8 mmol) and dissolved in 1,2-dichloroethane (35 mL) under an atmosphere of nitrogen. The solution was cooled to 0° C. with an ice bath and diethyl zinc (38.4 mL, 1.0 M in hexanes, 38.4 mmol) was added over 10 minutes. The resulting mixture was stirred for 30 minutes and allowed to warm to room temperature. It was cooled to 0° C. with an ice bath, and saturated aqueous $NH_4Cl$ (150 mL) was added, followed by concentrated aqueous $NH_4OH$ (25 mL) and EtOAc (200 mL). The layers were separated and the aqueous phase was extracted with additional EtOAc (2×100 mL). The organic phases were combined, dried ($Na_2SO_4$) and concentrated to a crude oil which was purified using silica gel (100% hexanes). Compound 3 (1.76 g, 7.2 mmol, 30% yield) was a colorless oil which was characterized using $^1$H NMR.

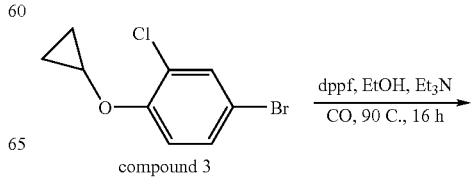

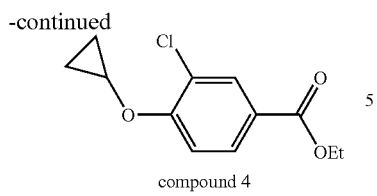

compound 4

In a high-pressure reactor, compound 3 (1.76 g, 7.2 mmol) was dissolved in EtOH (40 mL). Triethylamine (5.0 mL 35.8 mmol) was added, followed by [1,1-bis(diphenylphosphino)ferrocene]dichloropalladium (II) (188 mg, 0.36 mmol). The reaction vessel was pressurized with carbon monoxide (100 psi), evacuated and repressurized with carbon monoxide (100 psi). The vessel was evacuated and then pressurized again with carbon monoxide (350 psi). The reaction was heated to 90° C. and stirred for 16 h. It was cooled to room temperature, depressurized and filtered through celite. The solvents were evaporated, and the remaining residue was partitioned between dichloromethane (150 mL) and 1 M aqueous KHSO$_4$ (75 mL). The layers were separated and the organic phase was washed with additional 1 M aqueous KHSO$_4$ (1×75 mL). The organic phase was dried (Na$_2$SO$_4$) and concentrated to an oil which was purified using silica gel (EtOAc/Hexanes), providing compound 4 (648 mg, 2.70 mmol, 38% yield) as a white solid, characterized using $^1$H NMR.

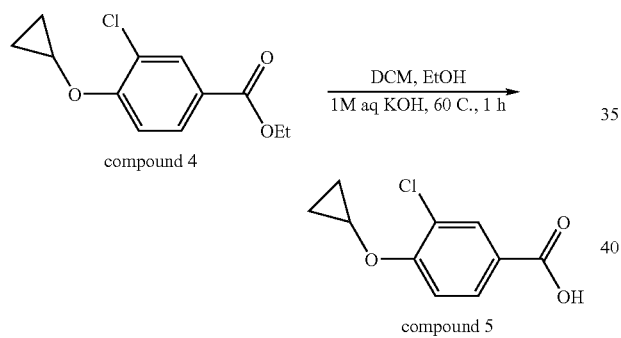

To a solution of compound 4 (648 mg, 2.70 mmol) in dichloromethane (3 mL) and EtOH (15 mL) was added 1 M aqueous KOH (7 mL, 7 mmol). The resulting cloudy mixture was heated to 60° C. for 1 h. The dichloromethane and EtOH were evaporated under reduced pressure, and the remaining aqueous solution was acidified using concentrated HCl. The resulting precipitate was filtered. The filtered, white solid was pure compound 5 (506 mg, 2.39 mmol, 88% yield), characterized using LC/MS (LRMS (M−H) 211.1 m/z).

Example 72

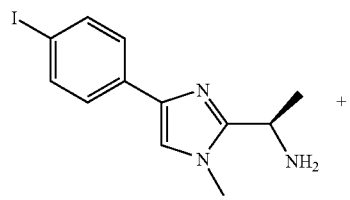

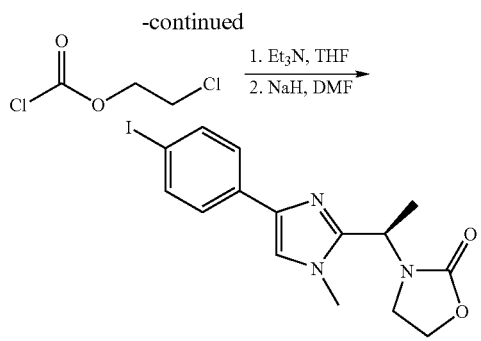

To a solution of the amine (580 mg, 1.7 mmol) and triethylamine (449 µl, 3.4 mmol, 2 eq.) in THF (8.5 ml, 0.2 M), was added chloroethyl chloroformate (278 µl, 2.6 mmol, 1.5 eq). The mixture was stirred for 30 min. at room temperature. Then, it was diluted in ethyl acetate, washed with 1 N HCl and brine. The organic layer was dried, filtered, and concentrated in vacuo to yield a crude material as a yellow oil (900 mg). To a solution of the crude material in DMF (10 ml), NaH (272 mg, 6.8 mmol, 4 eq) was added and stirred at room temperature for 16 hrs. The mixture was diluted in ethyl acetate (100 ml) and washed with brine (5×50 ml). The organic layer was dried, filtered, and concentrated in vacuo to yield a crude material as an oil. Purification by column chromatography (1:1 Ethyl acetate:Hexanes) gave 800 mg (24%) of the desired product. m/z (+1)=398.0.

Example 73

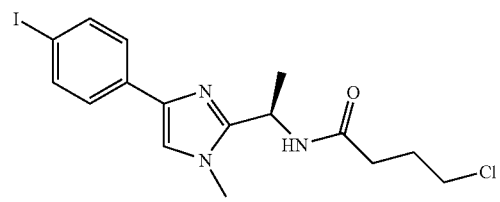

(R)-4-chloro-N-(1-(4-(4-iodophenyl)-1-methyl-1H-imidazol-2-yl)ethyl)butanamide. To a 100 mL round bottom flask was added (R)-benzyl 1-(4-(4-iodophenyl)-1-methyl-1H-imidazol-2-yl)ethylcarbamate (1.50 g, 3.27 mmol, 1.0 equiv), CH$_3$CN (20 mL), and TMSI (900 µL, 6.3 mmol, 1.9 equiv). The reaction mixture was capped and stirred for 2 hours. Methanol (40 mL) was then added to the flask and the mixture was concentrated, dissolved in EtOAc (100 mL), and washed with water. The organic layer was dried over Na$_2$SO$_4$, filtered, and concentrated. The residue was dissolved in DCM and purified by silica gel chromatography (35-60% CH$_3$CN/CH$_2$Cl$_2$, then 20% MeOH/CH$_2$Cl$_2$) to afford 950 mg (90%) of the desired primary amine as an oil (M+H (m/z)=328). To this amine was added CH$_2$Cl$_2$ (20 mL) and pyridine (260 µL, 1.1 equiv), followed by 4-chlorobutyryl chloride (344 µL, 1.05 equiv) in a dropwise fashion. The reaction was stirred for 15 min, followed by the addition of EtOAc (50 mL) and water (10 mL). The organic layer was separated, dried over Na$_2$SO$_4$, filtered, and concentrated. The residue was dissolved in DCM and purified by silica gel chromatography (5-35% CH$_3$CN/CH$_2$Cl$_2$) to afford 747 mg (60%) of (R)-4- chloro-N-(1-(4-(4-iodophenyl)-1-methyl-1H-imidazol-2-yl)ethyl)butanamide as an off-white solid (M+H (m/z)=432).

Example 74

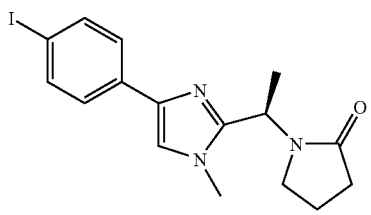

(R)-1-(1-(4-(4-iodophenyl)-1-methyl-1H-imidazol-2-yl)ethyl)pyrrolidin-2-one. To a 20-dram vial was added (R)-4-chloro-N-(1-(4-(4-iodophenyl)-1-methyl-1H-imidazol-2-yl)ethyl)butanamide and THF (10 mL). The vial was then cooled to 0° C. under a nitrogen atmosphere and potassium t-butoxide (214 mg, 1.91 mmol) was added. The reaction was stirred for 1.5 h. To the reaction mixture was added EtOAc (50 mL) and water (10 mL). The organic layer was separated, dried over Na$_2$SO$_4$, filtered, and concentrated. The residue was then dissolved in DCM and purified by silica gel chromatography (5-50% CH$_3$CN/CH$_2$Cl$_2$) to afford 593 mg (86%) of (R)-1-(1-(4-(4-iodophenyl)-1-methyl-1H-imidazol-2-yl)ethyl)pyrrolidin-2-one as a white solid (M+H (m/z)=396).

Example 75

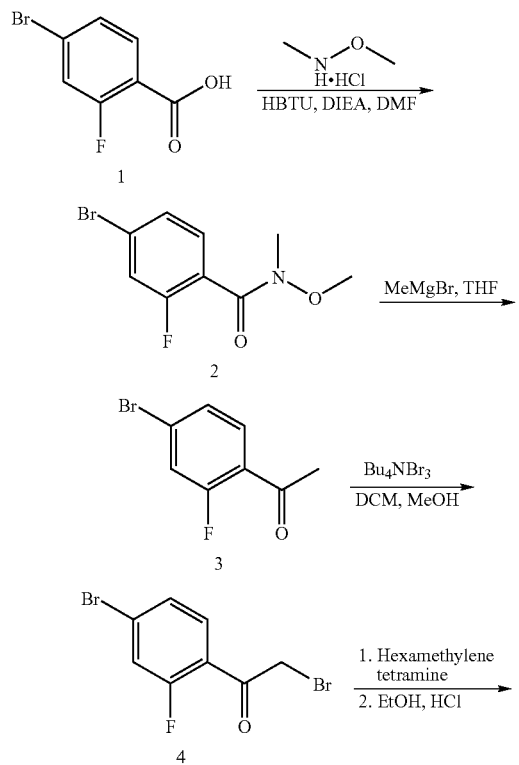

-continued

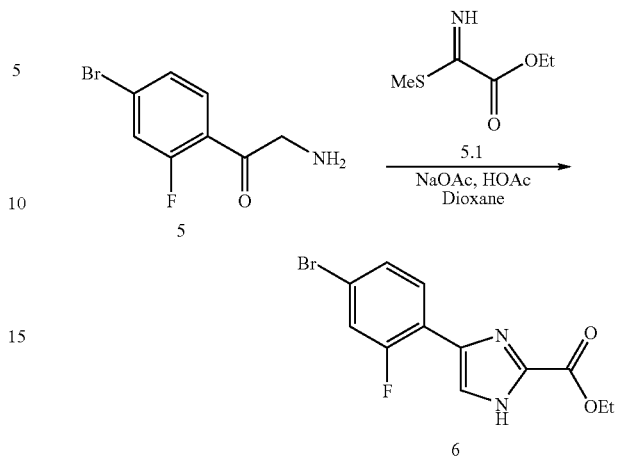

To a solution of 1 (10 g, 45.7 mmol) in DMF (150 mL) were added HBTU (26 g, 68.5 mmol), dimethylhydroxylamine HCl salt (5.35 g, 54.8 mmol) and DIEA (9.6 mL, 55.0 mmol) at 0° C. After stirring for 2 h, the mixture was allowed to warm up to room temperature. Stirring continued for 2 days. The reaction mixture was partitioned between EtOAc (500 mL) and H$_2$O (200 mL). The organic layer was washed with NaOH (2N, 200 mL), HCl (2N, 200 mL), H$_2$O, brine, dried over Na$_2$SO$_4$, and concentrated to give 2 (9.6 g), which was used without further purification. LRMS (M+H$^+$) m/z 262.0.

To a solution of 2 (9.6 g, ~36.8 mmol) in Et$_2$O (100 mL) was added member (3 M in Et$_2$O, 27 ml) at 0° C. The resulting mixture was stirred for 4 h while it was allowed to warm up to room temperature. The reaction mixture was quenched with saturated NH$_4$Cl (100 mL). The organic layer was washed with H$_2$O, brine, dried over Na$_2$SO$_4$, and concentrated to give 3 (7 g, 71% from 1), which was characterized by NMR.

To a solution of 3 (6.5 g, 30 mmol) in DCM (200 mL) and MeOH (100 mL) was added tetrabutylammonium tribromide (14.5 g, 30 mmol). The reaction mixture was stirred for 14 h. The mixture was concentrated, and dried under high vacuum to give 5 (characterized by NMR), which was used in the next step without further purification.

To a solution of 4 (5 g, ~16.9 mmol) in DCM (50 mL) was added hexamethylenetetramine (2.6 g, 18.5 mmol). The reaction mixture was stirred for 2 h. The mixture was diluted with DCM (500 mL). The precipitate was collected, washed with DCM (500 mL×2), and dried under high vacuum. To the resulting residue was added EtOH (60 mL) and concentrated HCl (30 mL). The reaction mixture was stirred for 2 h. The mixture was concentrated, dried to give 5, which was used without further purification. LRMS (M+H$^+$) m/z 231.9.

To a solution of crude 5 (~16.9 mmol) in dioxane (50 mL) were added NaOAc (6.93 g, 84.5 mmol), HOAc (4.8 mL, 84.5 mmol), and 5.1. (5.93 g, 84.5 mmol). After 1 h, the reaction mixture was warmed up to 80° C. and stirred for 3 h. The reaction mixture was partitioned between EtOAc (500 mL) and saturated NaHCO$_3$ (200 mL). The aqueous layer was extracted with EtOAc (300 mL×2). The combined organic layers were washed with brine, dried over Na$_2$SO$_4$, and concentrated. The resulting residue was purified on silica gel (hexane/EtOAc, 1:0, 1:2, 1:1, 0:1) to give 6 (1.2 g, 23% from 4). LRMS (M+H⁺) m/z 312.9.

Example 76

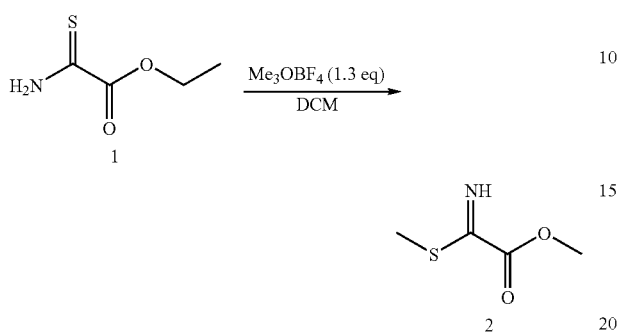

To a solution of ethyl thiooxamate (10.0 g, 75 mmol) in dichloromethane (400 mL) was slowly added trimethyloxonium tetrafluoroborate (13.1 g, 89 mmol) at 0° C. After 10 min the ice bath was removed, and the reaction mixture was stirred overnight. The solvent was removed to give 18.0 g of product 2 as white solid, which was used without further purification.

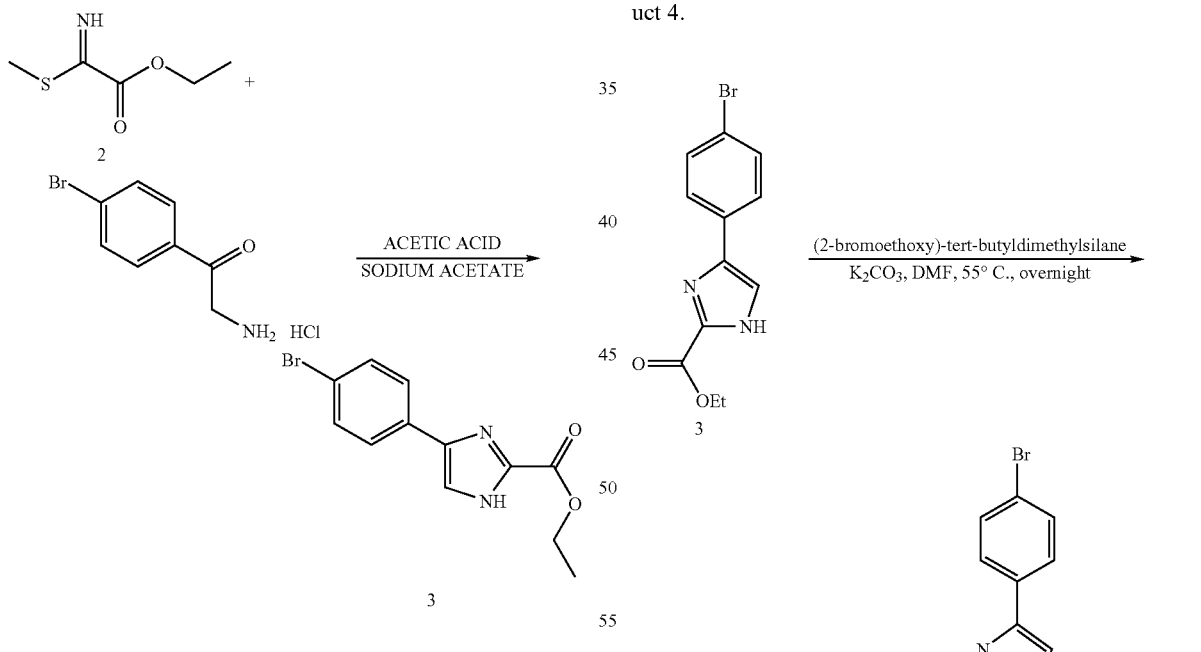

A mixture of 2-amino-4'-bromoacetophene hydrochloride (10.0 g, 40 mmol), sodium acetate (16.4 g, 200 mmol), acetic acid (11.5 mL, 200 mmol) and compound 2 (19.2 g, 80 mmol) in dioxane (70 mL) was stirred at 65° C. until TLC showed no compound 2 left (about 2 h). The reaction mixture was carefully neutralized with saturated NaHCO₃ solution and extracted with ethyl acetate. The organic solution was dried over Na₂SO₄ and concentrated. Purification with flash column chromatography (EtOAc:Hexs 1:1) gave product 3 (9.11 g, 79%) as a white solid.

In a round-bottom flask, product 3 (2.00 g, 6.8 mmol) was dissolved in DMF (20 mL), followed by the addition of Iodomethane (5.1 mL, 10.1 mmol), and K₂CO₃ (1.4 g, 10.1 mmol). The mixture was allowed to stir at 60° C. for 3 hours until complete by TLC. The solution was quenched with brine, extracted three times with EtOAc, dried over sodium sulfate and concentrated. Purification via column chromatography using EtAc:Hex 1:1. gave 1.381 g (66% yield) of product 4.

To a solution of compound 3 (3.174 g, 10.8 mmol) in DMF (15 mL) was added K₂CO₃ (4.478 g, 32.4 mmol) and (2-bromoethoxy)-tert-butyldimethylsilane (2.780 mL, 13.0 mmol). The resulting mixture was stirred at 55° C. overnight. The solution was concentrated, diluted with water and extracted with EtOAc (3×50 mL). The organic layers were combined and dried over Na$_2$SO$_4$. The solvent was removed to give a viscous oil (4.805 g, 10.6 mmol, 98.4%), which was used in the subsequent step without further purification.

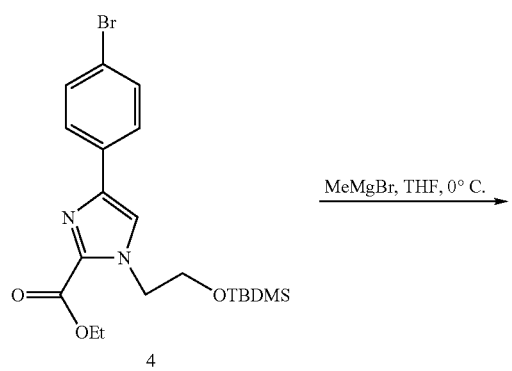

4

To a solution of compound 4 (2.174 g, 4.8 mmol) in anhydrous THF (25 mL) was added dropwise methylmagnesium bromide (4.8 mL, 3 M in diethyl ether, 14.4 mmol) under nitrogen at 0° C. The reaction was stirred at 0° C. for 15 minutes. The reaction was carefully quenched with saturated ammonium chloride solution (5 mL) and water (30 mL) and extracted with EtOAc (3×50 mL). The organic layers were combined, dried over Na$_2$SO$_4$ and concentrated to a crude oil. Purification with flash column chromatography (15% EtOAc/Hexanes) gave the desired product 5 (1.371 g, 65%) as a white amorphous solid.

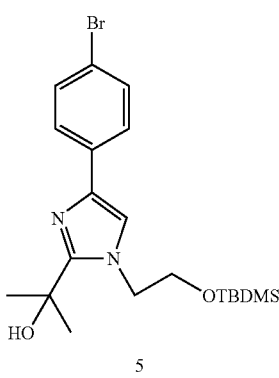

5

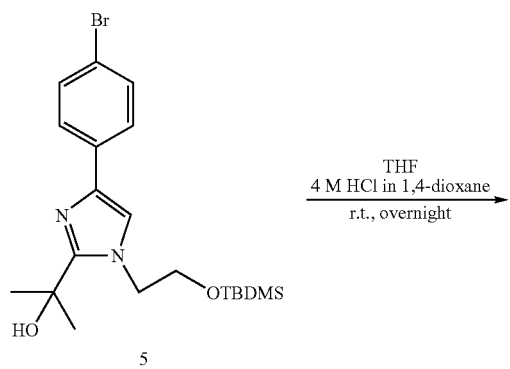

5

-continued

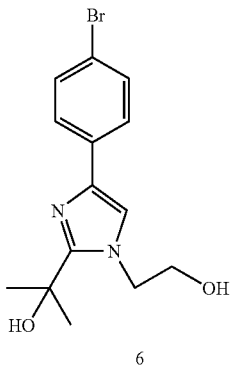

6

To a solution of compound 5 (1.371 g, 3.1 mmol) in THF (5 mL) was added 35 mL of HCl (4 M in 1,4-dioxane). The resulting solution was stirred at room temperature overnight. The solvents were removed to give the product 6 (1.0 g, 99%) as white solid.

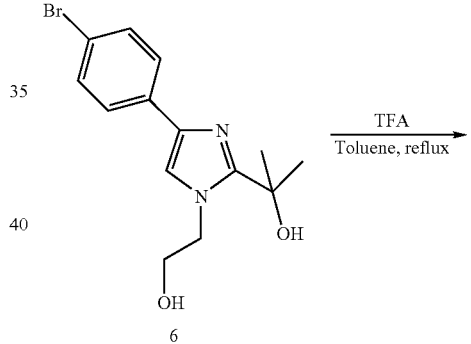

6

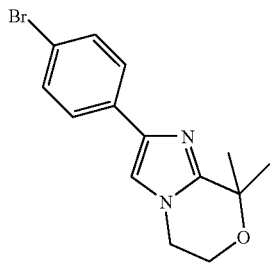

7

A mixture of compound 6 (0.5 g, 1.54 mmol) and 1 mL of TFA in toluene (60 mL) was refluxed overnight. The solid 6 did not dissolve until around the boiling point of toluene. The solvent was removed. The residue was diluted with EtOAc, washed with NaHCO$_3$ aqueous solution, dried over Na$_2$SO$_4$,

Example 77

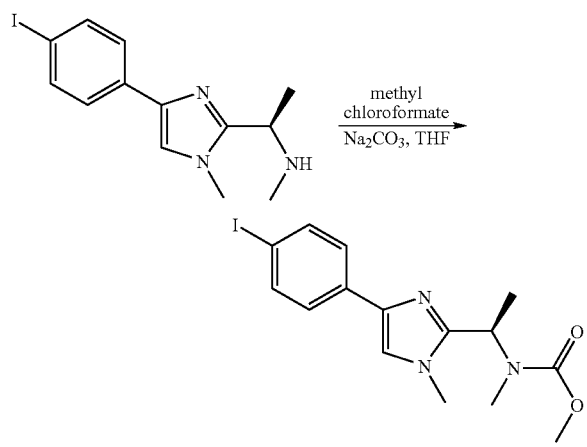

(R)-methyl 1-(4-(4-iodophenyl)-1-methyl-1H-imidazol-2-yl)ethyl(methyl)carbamate. To a 250 mL round bottom flask was added (R)-1-(4-(4-iodophenyl)-1-methyl-1H-imidazol-2-yl)-N-methylethanamine (3.1 g, 9.1 mmol), methyl chloroformate (0.84 mL, 10.9 mmol), $Na_2CO_3$ (1.15 g, 10.9 mmol), and THF (100 mL). The reaction was stirred for 2 hours, followed by the addition of EtOAc (50 mL) and water (10 mL). The organic layer was dried over $Na_2SO_4$, filtered, and concentrated to give 1.50 g (41%) of (R)-methyl 1-(4-(4-iodophenyl)-1-methyl-1H-imidazol-2-yl)ethyl(methyl)carbamate as an off-white solid (M+H (m/z)=400).

Example 78

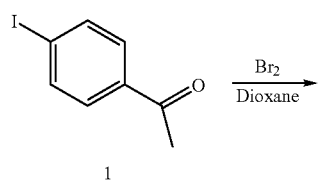

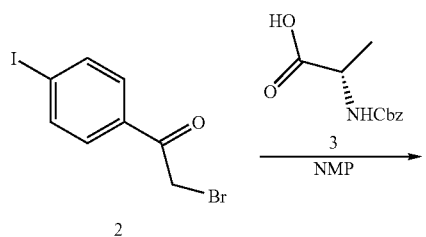

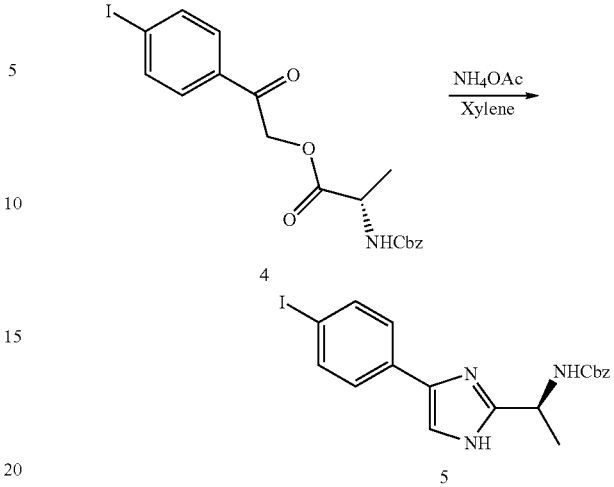

Ref: *J. Med. Chem.* 2001, 44, 2990-3000

To a stirring solution of p-iodoacetophenone 1 (30.0 g, 122 mmol) in dioxane (200 mL) over an ice-bath was added bromine (6.56 mL, 128 mmol) dropwise. The reaction mixture was stirred at room temperature and monitored by LC/MS. After completion (about 1 hour), the solvent was evaporated by rotovap, and the residue was dried under vacuum to give solid 2 (40 g, 100%).

(Based on *J. Med. Chem.* 2001, 44, 2990-3000) To a solution of Cbz-D-Ala-OH 3 (5.0 g, 22.4 mmol) in NMP (100 mL) was added cesium carbonate (3.72 g, 11.4 mmol). After stirring at RT for 1 h, 2 (7.60 g, 22.4 mmol) was added. The reaction mixture was stirred at room temperature and monitored by LC/MS to form 4. The reaction solution was diluted with xylene (100 mL) and ammonium acetate (9.25 g, 120 mmol) and then stirred at 120° C. for 4 hours. Up to 50 eq of additional ammonium acetate may be needed depending on the reaction progress. The key is to see solid in the flask at all times. After cooling to room temperature, the reaction mixture was diluted with ethyl acetate (200 mL). The EtOAc solution was washed with saturated sodium bicarbonate solution (200 mL) twice, and dried by sodium sulfate, then filtered, and the filtrate was concentrated under reduced pressure. The residue was dissolved in DCM (100 mL) and stirred for 1 h to give a precipitate, and the solid 5 (4.0 g) was filtered off and dried under vacuum. The mother solution was concentrated by rotovap, the residue was purified on Bio-tage to give 5 (Hexane:EtOAc=1:1 to EtOAc 100%). The two products were combined and dried under vacuum to give 5 (5.8 g, 58%).

Example 79

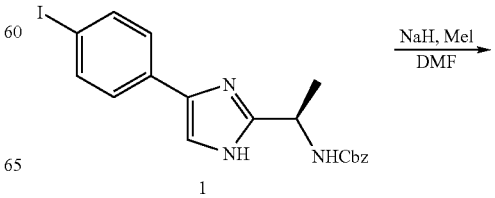

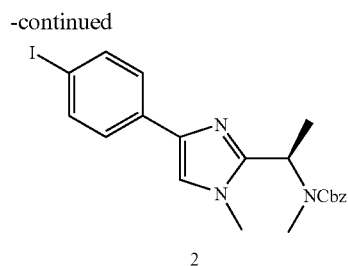

(R)-Benzyl 1-(4-(4-iodophenyl)-1-methyl-1H-imidazol-2-yl)ethyl(methyl)carbamate 2: A stirred mixture of (R)-benzyl 1-(4-(4-iodophenyl)-1H-imidazol-2-yl)ethylcarbamate 1 (5 g, 11 mmol) in 55 mL of DMF was cooled to 0° C. and treated with NaH (1.33 g, 60% dispersion in oil, 33 mmol) in small portions to avoid foaming. When bubbling from the last portion ceased, MeI (2.1 mL, 34 mmol) was added all at once and the mixture stirred an additional 30 min. The solvents were removed under vacuum and the residue dissolved in 200 mL of EtOAc. The solution was washed with saturated NH$_4$Cl (4×100 mL) and saturated NaCl (4×100 mL), and then filtered and evaporated to dryness. The crude residue was purified via flash column chromatography over silica gel (60:40, EtOAc/hexanes) to give 5.13 g (97% yield) of 2 which was characterized by LCMS.

Example 80

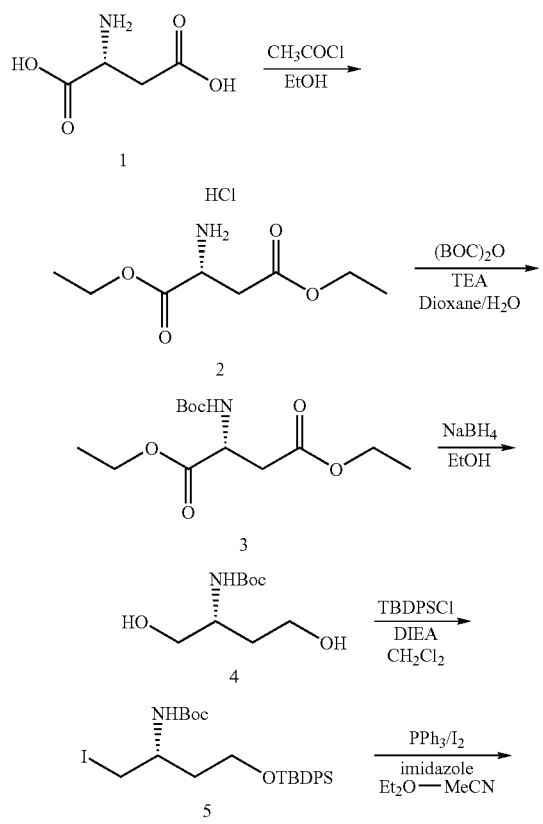

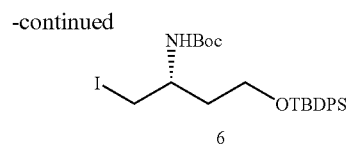

Acetyl chloride (54.6 mL, 0.75 mol) was added drop-wise into ethanol (316 mL) at 0-5 C. When the addition was completed, the ice bath was removed and the solution was allowed to stir while warming to room temperature for another 30 mins. D-aspartic acid 1 (25 g, 0.188 mol) was then added. The reaction mixture was refluxed for 2 hours. The reaction solution was then concentrated in vacuo and placed under high vacuum (0.4 mm Hg) overnight. Compound 2 was obtained as a white solid (42 g, 99%) and used directly in the next step.

(BOC)$_2$O (44.7 g, 0.21 mol) was added portion-wise over 10 mins to a 0 C solution of compound 1 (42 g, 0.19 mol), trimethyl amine (51.9 ml, 0.37 mol), dioxane (140 mL) and water (56 mL). After another 10 min, the ice bath was removed and the reaction mixture was stirred while warming to room temperature for another 2 hours. The reaction mixture was diluted in ethyl acetate (150 mL) and washed with 0.5 N HCl (200 mL×3). The organic layer was dried over magnesium sulfate, filtered, and the filtrate was concentrated in vacuo giving compound 3 (52 g, yield 97%) which was used directly in the next step.

NaBH$_4$ (54.4 g, 1.44 mol) was added portion-wise over 30 mins to a 0 C solution of compound 3 (52 g, 86.4 mmol) and ethanol (600 mL). The reaction mixture was extremely exothermic and great care was exercised during the addition of reducing agent. After the addition was complete, the reaction mixture was heated to reflux for 1 hour. The solution was cooled to ambient temperature and the reaction mixture solidified. The solid was broken-up to a slurry, which was then poured into brine (250 mL). The resulting mixture was filtered and the filtrate was concentrated in vacuo. The resulting residue was vigorously stirred with ether (200 mL×5). The ether layers were successively decanted from the residue. The combined ether extracts were dried over magnesium sulfate, filtered, and the filtrate was concentrated in vacuo giving compound 4 as white solid (25.2 g, yield 68%). [Note: Yield was 89% when performed on a 25 g (compound 3) scale.]

t-Butyldiphenylchlorosilane (31.9 mL, 0.123 mol) was added to a solution of compound 4 (25.2 g, 0.123 mol), diisopropylethylamine (42.8 mL, 0.245 mol), and CH$_2$Cl$_2$ (500 mL). The reaction solution was stirred at ambient temperature for 24 hrs. The reaction solution was then washed with 0.5 N HCl (150 mL×3) and brine (150 mL). The organic layer was dried over magnesium sulfate, filtered, and the filtrate was concentrated in vacuo. The resulting residue was purified by flash chromatography (silica gel, 4:1 hexanes:EtOAc) to give compound 5 (42 g, yield 77%). [Note: Yield was 85% when performed on 15 g (compound 4) scale.]

Iodine (24 g, 94.7 mmol) was added portion-wise over 15 mins to a 0 C solution of compound 5 (28 g, 63.1 mmol), Ph$_3$P (24.8 g, 94.7 mmol), imidazole (6.4 g, 94.7 mmol), diethyl ether (450 mL) and acetonitrile (150 mL). The ice bath was removed and the reaction solution was allowed to warm to ambient temperature over 30 mins. The reaction was judged complete by TLC analysis (4:1 hexanes:EtOAc). The reaction was quenched with water (400 mL). The layers were separated and the aqueous layer was extracted by diethyl ether (100 mL). The combined organic layers were washed with saturated aqueous Na$_2$SO$_3$ (100×2) and brine (100 mL). The organic layer was dried over magnesium sulfate, filtered, and the filtrate was concentrated in vacuo. The resulting residue was purified by flash column chromatography (silica gel, 4:1 hexanes:EtOAc) to give compound 6 (32 g, 92%).

Example 81

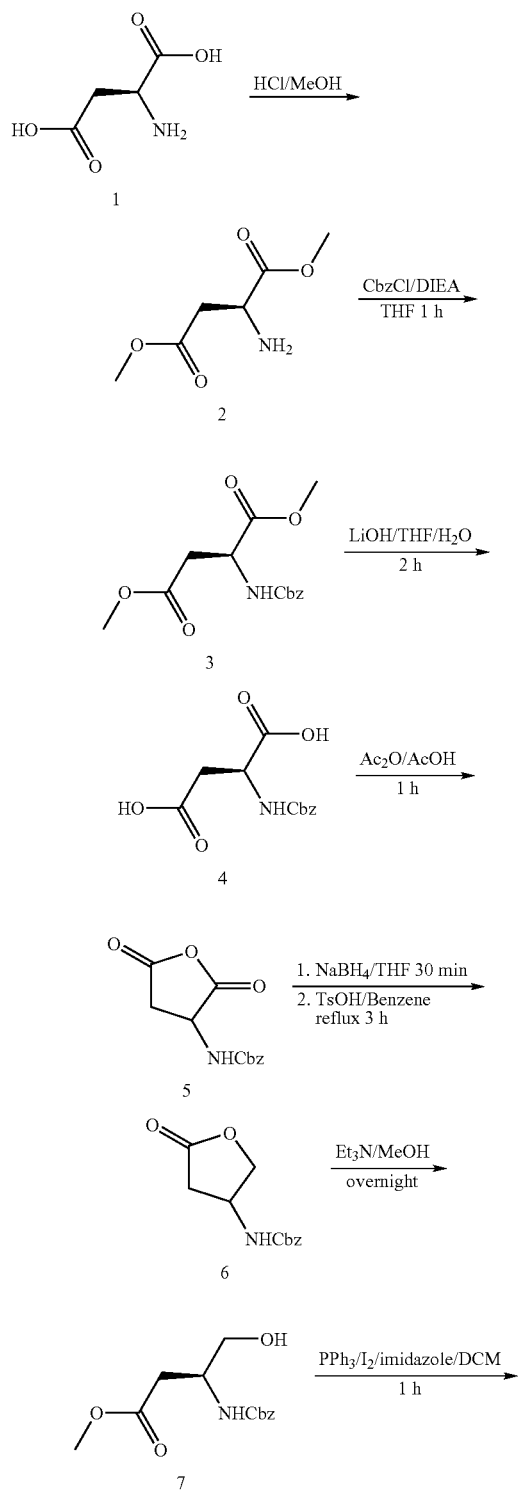

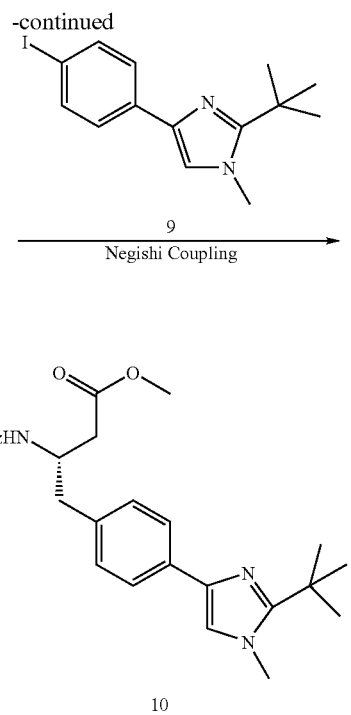

Under ice-bath, to a solution of D-Aspartic acid 1 (59 g, 0.376 mol) in methanol (200 mL) was bubbled HCl gas for 10 minutes. After the reacting solution was stirred at RT overnight, the solvent was evaporated. The resulting residue was dried under Vacuum to have product 2 as HCl salt (0.376 mol).

To a stirred solution of 2 (0.376 mol), DIEA (196 mL, 1.13 mol) and THF (200 mL), benzyl chloroformate (59.0 mL, 0.414 mol) was dropped in. After the reaction solution was stirred at room temperature for 1 hr, the solution was concentrated on rot-vap. Then the residue was dissolved in NaHCO3 solution (300 mL) and extracted with DCM (100 mL×3). The combined DCM solution was dried over sodium sulfate, filtered, and the filtrate was concentrated in vacuum to have the product 3 (0.376 mol).

To a solution of 3 (0.376 mol), THF (200 mL) and Water (100 mL) was added Lithium hydroxide (31.6 g, 0.752 mol) and stirred for 2 hours. The reaction mixture was filtered through a silic gel plug (the pH of the filtrate was about 7) and concentrated. The residue was dried under Vacuum to give 4 (0.376 mol).

After a solution of 4 (0.376 mol) and acetic anhydrate (200 mL) was stirred for 1 hour, the reaction mixture was concentrated. The residue was dried under Vacuum to give 5 (0.376 mol).

Under ice-bath, to a solution of 5 (0.376 mol) and THF (1000 mL) was added Sodium borohydride (14.2 g, 0.376 mol) during 30 minutes and stirred for 3 hrs. Then HCl solution (4N) was dropped into the reaction solution until the pH was about 2. The solution was concentrated to about a quarter left, diluted with water (300 mL) and extracted by ethyl ether (200 mL×3). The combined ether solution was dried over sodium sulfate, filtered, and the filtrate was concentrated in vacuum. The resulting residue was dissolved in benzene (300 mL) and TsOH (500 mg) was added. Then the reaction mixture was stirred at reflux 3 hrs. The solution was concentrated to about 100 ml and ether (200 mL) was added to form precipitate. The white solid 6 (57.5 g, 65% from 1) was filtered out, washed with some ether and dried under Vacuum.

To a solution of 6 (30.0 g, 0.128 mol) and methanol (200 mL) was added triethylamine (142 mL, 1.02 mol) and stirred overnight. The reaction mixture was concentrated. The residue was dried under Vacuum to give 7 (LC-MS showed about 20% mol 6 was left) which was directly used in the next step.

Under ice-bath, to a solution of compound 7 (0.128 mol), Ph$_3$P (50.4 g, 0.192 mol), imidazole (13.1 g, 0.192 mol) and DCM (300 mL) was stirred for 10 min. Iodine (48.7 g, 0.192 mol) was added portion-wise over 15 minutes. The ice bath was removed and the reaction solution was stirred at room temperature over 1 hour. The solid was filtered out. The filtrate was washed with saturated aqueous Na$_2$SO$_3$ (200 mL×2) and brine (200 mL). The organic layer was dried over sodium sulfate, filtered, and the filtrate was concentrated. The resulting residue was purified by flash silica gel column chromatography (hexanes:EtOAc 4:1 to 1:1) to give compound 8 (27.5 g, 59.2% from 6) as a white solid.

To a mixture of zinc powder (Strem, 10.1 g, 0.154 mol) and DMF (15 mL) was purged under Nitrogen for 10 minutes and added 1,2 dibromoethane (0.758 mL, 8.80 mmol). The mixture was heated with a heat gun for ~2 minutes, cooled down for 5 minutes and heated with a heat gun again, then cooled to room temperature. TMSCl (281 µL, 2.20 mmol) was added to the mixture. After the mixture was stirred for 30 minutes, 8 (9.98 g, 26.5 mmol) was added. After 1 hour, LCMS showed complete consumption of 8. To above reaction solution was added aryl iodide 9 (7.50 g, 22.0 mmol), Pd$_2$(dba)$_3$ (50.4 mg, 0.55 mmol) and tri-o-tolylphosphine (670 mg, 2.20 mmol). The reaction mixture was maintained at 50 C for 1 hour (monitored on LC-MS analysis). The reaction mixture was directly loaded to a silica gel plug and washed with hexanes: EtOAc (3:1 to 1:1) to give compound 10 (5.0 g, 49%).

To an oven dried round-bottom flask, zinc powder (1753 mg, 27 mmol) was added followed by DMF (15 mL). The flask was capped and purged with nitrogen for 10 min. To the solution was added 1,2 dibromoethane (0.139 mL, 1.6 mmol). The mixture was then heated using a heat gun for about 30 seconds until gas began to evolve indicating the activation of the zinc. The mixture was allowed to cool while stirring for 1 min before it was heated again using a heat gun until gas evolved. The mixture was then allowed to cool to room temperature, followed by the addition of TMSCl (0.042 mL, 0.33 mmol) and stirring for 30 min. Reagent A was then dissolved in DMF, bubbled with nitrogen, added to the zinc solution, and allowed to stir for 1 hour at room temperature. Bromide 4 (1.381 g, 4.5 mmol) was dissolved in DMF, bubbled with nitrogen and then injected into the solution, followed by the addition of Pd$_2$(dba)$_3$ (102 mg, 0.11 mmol) and Tri-o-tolylphosphine (136 mg, 0.44 mmol). The solution mixture was bubbled with nitrogen and held under nitrogen while stirring for one hour at room temperature. After 1 hour, the stirring solution was heated to 40° C. for 2 hours until complete by TLC and LC/MS. The solution was quenched using brine and extracted five times using EtOAc. The combined organic layers were dried over sodium sulfate and concentrated. The crude product 5 was purified via column chromatography using EtOAc:Hex 1:1 to obtain 2.0 g (70% yield) of pure product 5.

Example 83

Example 82

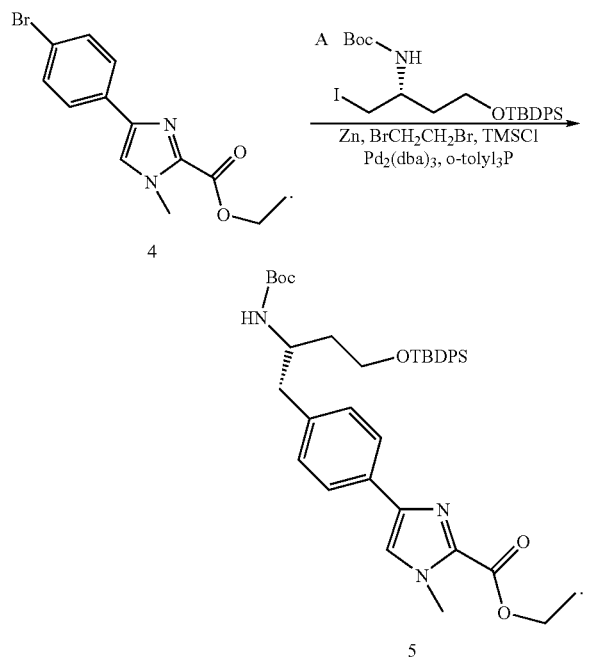

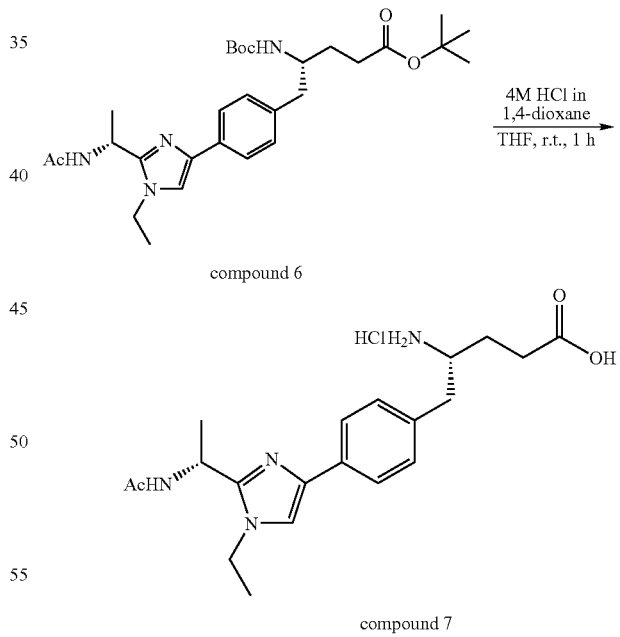

To a solution of compound 6 (940 mg, 1.78 mmol) in THF (5 mL) was added 4 M HCl in 1,4-dioxane (20 mL, 80 mmol). The resulting mixture was stirred at room temperature for 1 hour. The solvents were evaporated, and the remaining compound 7 (726 mg, 1.78 mmol, quantitative yield) was thoroughly dried under high vacuum. Compound 7 was characterized using LCMS (LRMS (MH) 373 m/z) and used in the following step without further purification.

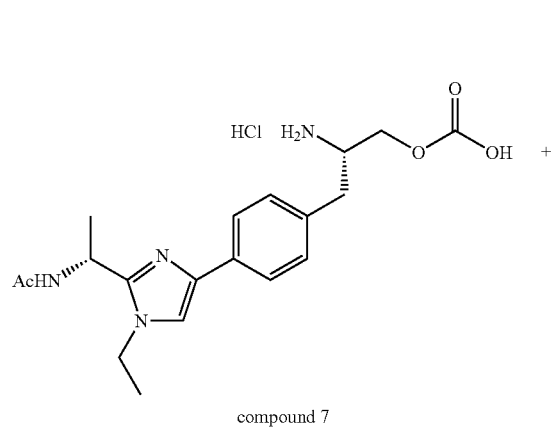

compound 7

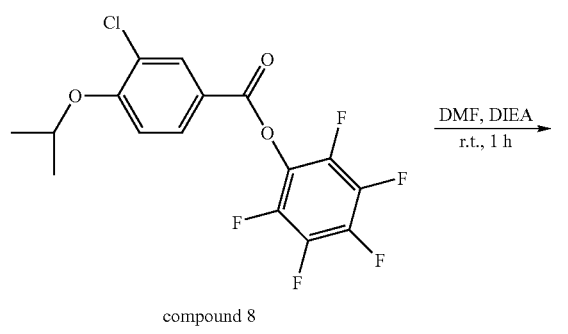

compound 8

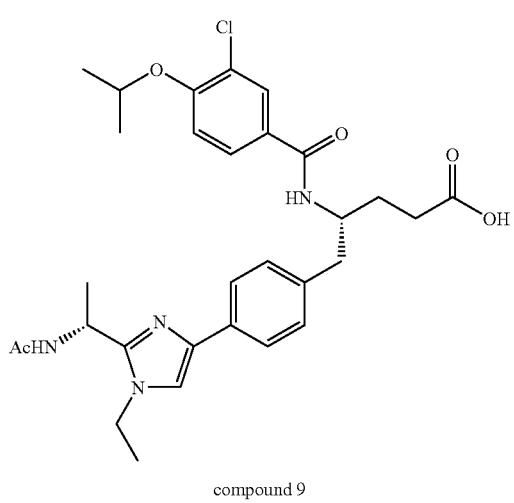

compound 9

To a solution of compound 7 (662 mg, 1.62 mmol) in DMF (5 mL) was added DIEA (930 μL, 5.34 mmol) and compound 8 (678 mg, 1.78 mmol). The resulting solution was stirred at room temperature for 1 hour. The DMF was evaporated and the crude residue was directly purified using preparative HPLC to provide compound 9 (435 mg, 0.77 mmol, 48% yield), which was characterized by $^1$H NMR and LC/MS (LRMS (MH) 569 m/z.)

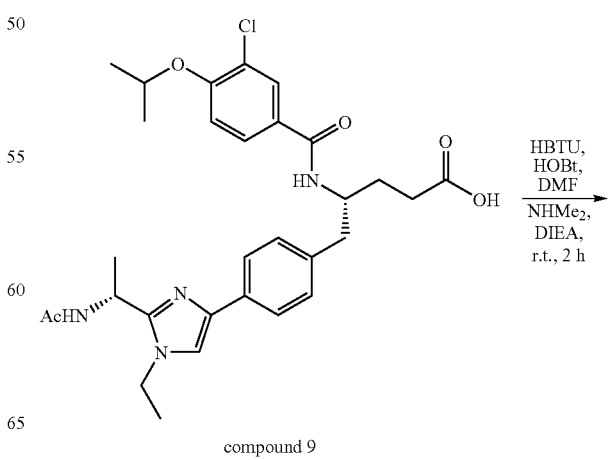

compound 9 compound 10

Compound 9 (100 mg, 0.176 mmol) was combined with HATU (134 mg, 0.352 mmol), HOAT (48 mg, 0.352 mmol) and NH$_4$Cl (50 mg, 0.944 mmol). The solids were dissolved in N-methylpyrrolidinone (5 mL) and DIEA was added (93 μL, 0.528 mmol). The resulting mixture was stirred at room temperature for 2 hours and then directly purified with preparative HPLC to provide compound 10 (16 mg, 0.028 mmol, 16% yield) as a glassy solid which was characterized by $^1$H NMR and LC/MS (LRMS (MH) 568 m/z.)

compound 9

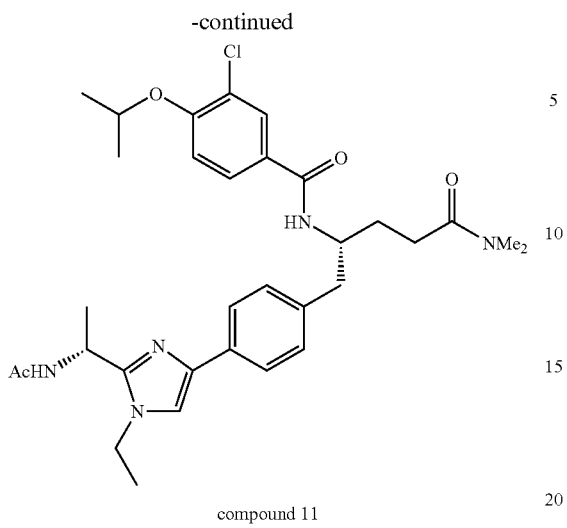

compound 11

Compound 9 (91 mg, 0.160 mmol) was combined with HBTU (121 mg, 0.320 mmol) and HOBt (43 mg, 0.320 mmol). The solids were dissolved in DMF (3 mL), and dimethylamine (400 µL, 0.800 mmol, 2 M in THF) and DIEA (93 µL, 0.528 mmol) were added. The resulting solution was stirred at room temperature for 2 hours. The crude product was directly purified using preparative HPLC to provide compound 11 (25 mg, 0.042 mmol, 26% yield) as a glassy solid which was characterized by $^1$H NMR and LC/MS (LRMS (MH) 596 m/z.)

Example 84

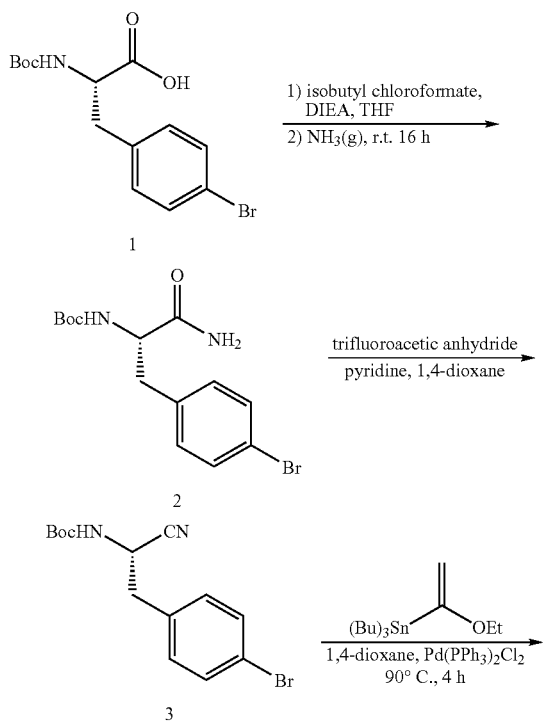

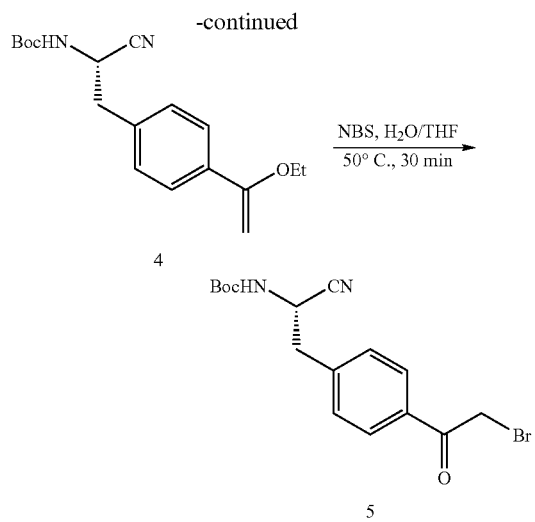

To a 0° C. solution of 1 (40.2 g, 117 mmol) in THF (250 mL) and DIEA (11.4 mL, 175 mmol) was added isobutyl chloroformate (21.2 mL, 163 mmol). The resulting mixture was stirred at room temperature for 3 hours. The reaction was purged with gaseous ammonia for 1 hour and then stirred at room temperature for 16 hours. It was diluted with water (200 mL), ethyl acetate (200 mL) and filtered. The white, filtered solid was the desired product. Additional product was obtained by transferring the biphasic filtrate to a separatory funnel and separating the layers. The aqueous phase was extracted with additional ethyl acetate (3×150 mL). The organic phases were combined, dried ($Na_2SO_4$) and concentrated to a white solid, which was recrystallized from ethyl acetate to afford the desired product. The pure product 2 (20.6 g, 60 mmol) was characterized by $^1$H-NMR and LC/MS (LRMS (MH) m/z: 343.1).

Amide 2 (18.1 g, 53 mmol) was suspended in 1,4-dioxane (200 mL) and pyridine (10.7 mL, 132 mmol). Trifluoroacetic anhydride (22.0 mL, 158 mmol) was added, and the white, suspended solid immediately dissolved. The homogeneous solution was stirred at room temperature for 30 minutes. The solvents were removed under reduced pressure, and the remaining residue was dissolved in ethyl acetate (200 mL) and washed with 1 M aqueous $KHSO_4$ (2×100 mL) and saturated aqueous $NaHCO_3$ (2×100 mL). The organic phase was dried over $Na_2SO_4$ and concentrated in vacuo. The remaining, desired product 3 (14.9 g, 46 mmol) was determined to be sufficiently pure for the next transformation (LC/MS (LRMS (MH) m/z: 198.0)).

Nitrile 3 (14.9 g, 46 mmol) was dissolved in 1,4-dioxane (100 mL) and tributyl (1-ethoxyvinyl)tin (23.3 mL, 69 mmol) was added, followed by $Pd(PPh_3)_2Cl_2$ (1.6 g, 5 mol %). The resulting mixture was heated to 90° C. and stirred for 4 hours. It was cooled to room temperature and the solvent was removed under reduced pressure. The remaining residue was directly purified using silica gel, prepared in a slurry using 95% hexane/triethylamine. Elution was stepwise, beginning with 95% hexane/triethylamine and changing to 50% ethyl acetate/hexane/5% triethylamine. The desired product 4 eluted with the latter mobile phase and was a viscous yellow oil, characterized by LC/MS (LRMS (MH) m/z: 317.1). The product was used immediately in the next transformation.

To a solution of vinyl ether 4 (14.5 g, 46 mmol) in THF (60 mL) and water (20 mL) was added N-bromosuccinimide (12.3 g, 69 mmol). The resulting mixture was stirred at 50° C. for 30 minutes. It was cooled to room temperature and diluted with 2 M aqueous Na₂CO₃. The mixture was extracted with ethyl acetate (2×150 mL), the organic extracts were combined, dried over Na₂SO₄ and concentrated to an amorphous solid which was purified using silica gel (dichloromethane/ethyl acetate). The desired product 5 (10.6 g, 29 mmol) was a yellow solid, characterized by $^1$H-NMR and LC/MS (LRMS (MH) m/z: 239.9).

Example 85

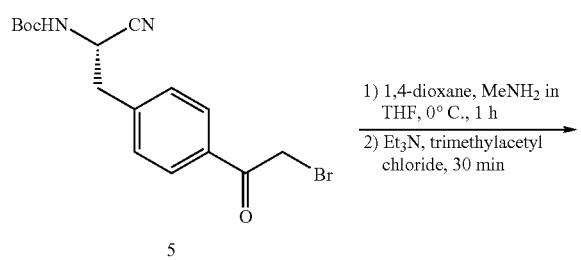

5

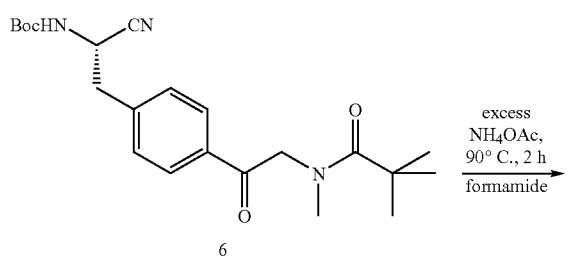

6

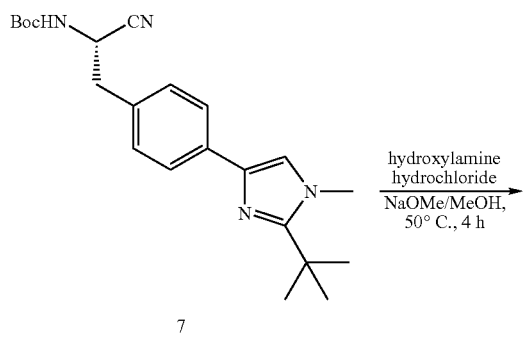

7

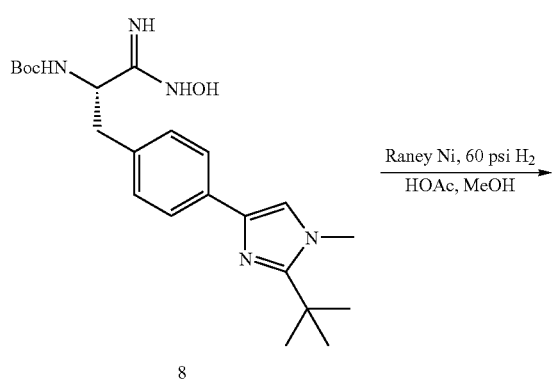

8

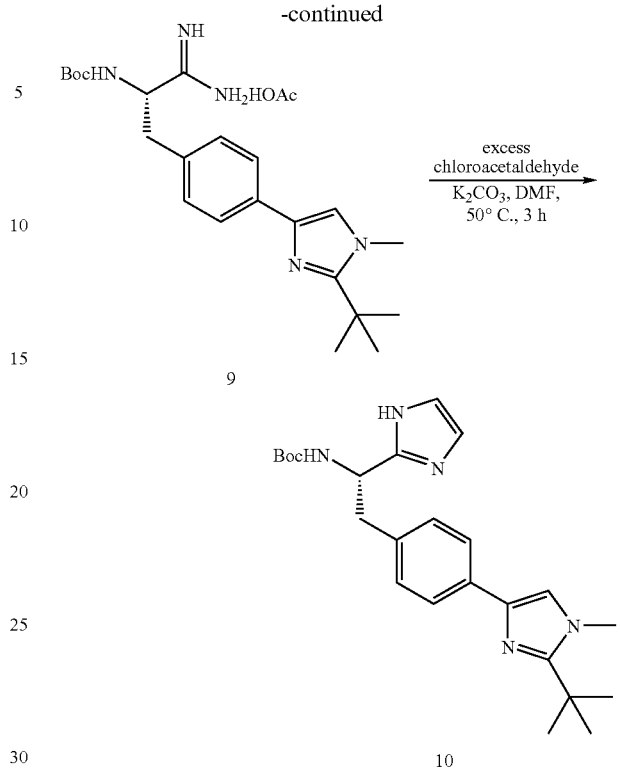

A solution of ketone 5 (10.6 g, 29 mmol) in 1,4-dioxane (50 mL) was dripped into a solution of methylamine (72 mL, 144 mmol, 2 M in THF) over 45 minutes at 0° C. The resulting cloudy solution was stirred for an additional 15 minutes at room temperature. The THF and methylamine were evaporated under reduced pressure, and care was taken not to evaporate 1,4-dioxane. To the resulting mixture at room temperature was added triethylamine (12 mL, 87 mmol), followed by trimethylacetyl chloride (15 mL, 144 mmol). The resulting suspension was stirred at room temperature for 30 minutes. It was diluted with water (125 mL) and extracted with ethyl acetate (3×100 mL). The organic phases were combined, dried over Na₂SO₄ and concentrated in vacuo. The crude product 6 was characterized by LC/MS (LRMS (MH) m/z: 402.1) and carried forward without further purification.

Amide 6 (11.6 g, 29 mmol) was combined with ammonium acetate (55 g, 723 mmol) and formamide (150 mL). The resulting mixture was heated to 100° C. and stirred for 3 hours. It was cooled to room temperature, diluted with ethyl acetate (500 mL) and washed with water (3×200 mL). The organic phase was dried over Na₂SO₄ and concentrated under reduced pressure. The remaining crude residue was purified using silica gel (diethyl ether/hexane) to provide pure 7 (6.1 g, 16 mmol) as a foamy yellow solid, characterized by $^1$H-NMR and LC/MS (LRMS (MH) m/z: 383.2).

Imidazole 7 (1.316 g, 3.4 mmol) was combined with hydroxylamine hydrochloride (478 mg, 6.9 mmol) and dissolved in a solution of sodium methoxide in methanol (14 mL, 6.9 mmol, 0.5 M). The resulting solution was stirred at 50° C. for 4 hours. It was concentrated under reduced pressure and directly purified using silica gel (5% methanol/dichloromethane) to provide the desired amidoxime 8 (913 mg, 2.2 mmol) as a White solid, characterized by LC/MS (LRMS (MH) m/z: 416.1).

To a solution of amidoxime 8 (652 mg, 1.6 mmol) in methanol (10 mL) was added Raney nickel (50 mg) and acetic acid (250 µL). The mixture was stirred at room temperature under 60 psi $H_2$ for 3 hours and then filtered through a bed of celite. Concentration under reduced pressure provided pure amidine 9 as a white solid (638 mg, 1.6 mmol), characterized using LC/MS (LRMS (MH) m/z: 400.2).

Chloroacetaldehyde (360 mL, 5.7 mmol) was added to a solution of amidine 9 (283 mg, 0.71 mmol) in DMF (4 mL) and $K_2CO_3$ (195 mg, 1.4 mmol). The mixture was heated to 50° C. and stirred for 4 hours. The reaction was filtered and directly purified by reverse-phase HPLC using a mobile phase gradient consisting of acetonitrile and water. The pure product 10 (25 mg, 0.06 mmol)* was a glassy solid characterized by $^1$H-NMR and LC/MS (LRMS (MH) m/z: 424.1).

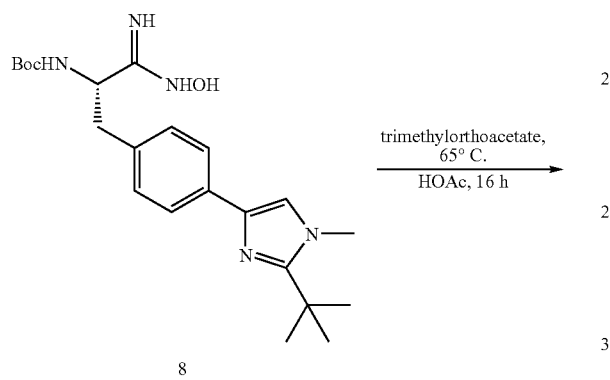

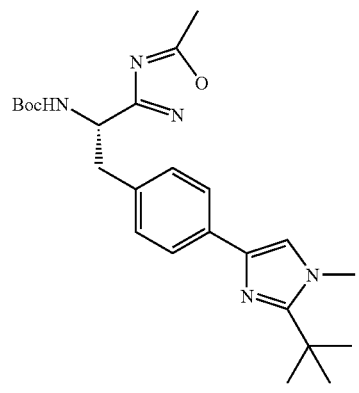

To a solution of amidoxime 8 (148 mg, 0.35 mmol) in trimethylorthoacetate (5 mL) was added glacial acetic acid (100 µL). The resulting solution was stirred at 65° C. for 16 hours. The solvents were evaporated and the residue was directly purified through silica gel (5% methanol/dichloromethane) to provide the desired product 9 as a glassy solid, characterized by LC/MS (LRMS (MH) m/z: 440.1.

Example 86

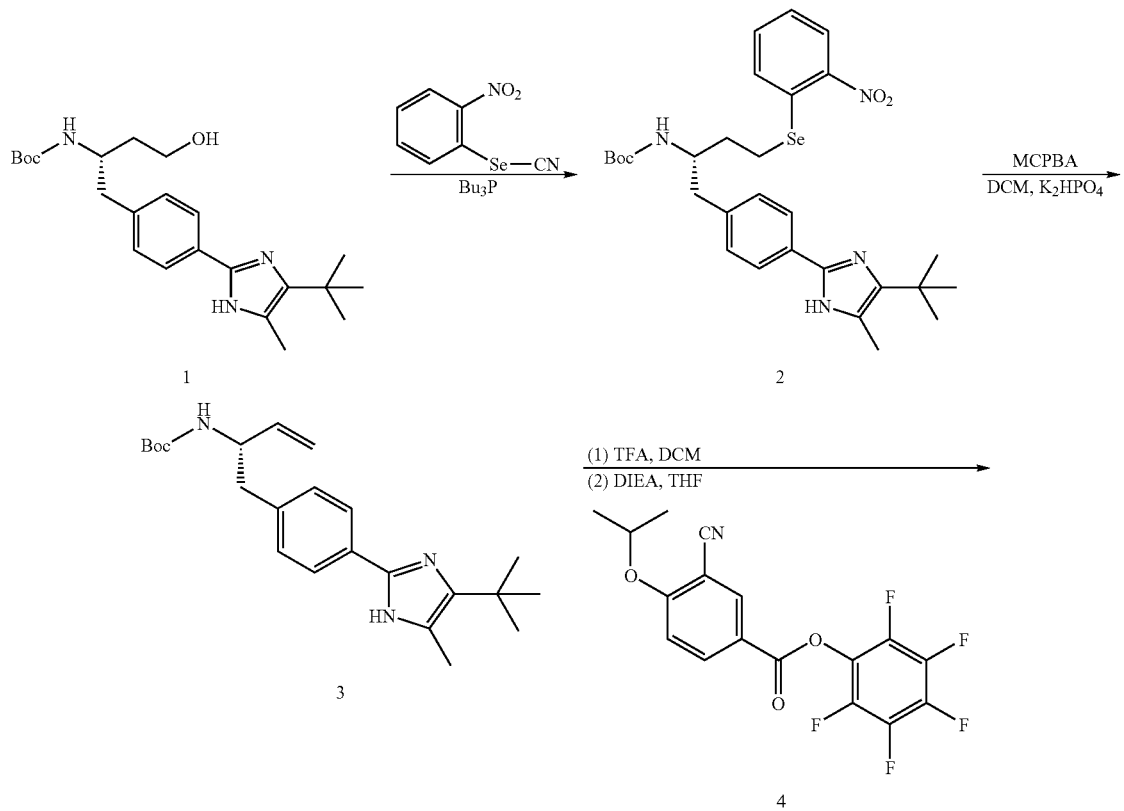

-continued

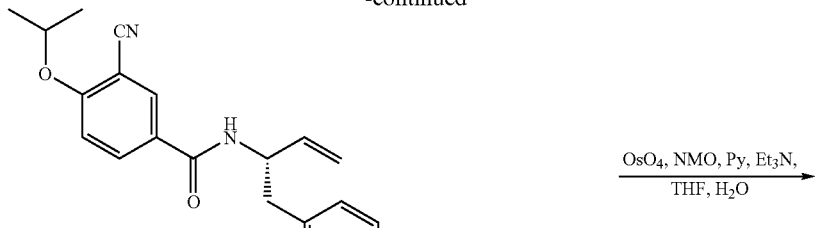

5

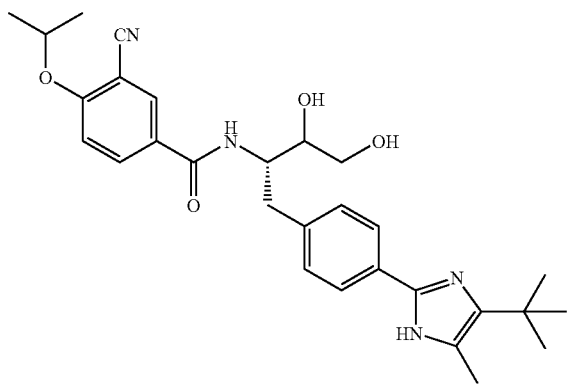

6a/6b

To a solution of 1 (200 mg, 0.5 mmol) in THF (3 mL) were added Bu$_3$P (150 uL, 0.6 mmol) and 2-nitrophenylselenocyanate (136 mg, 0.6 mmol) at room temperature. The reaction mixture was stirred for 14 h. The mixture was partitioned between EtOAc (200 mL) and H$_2$O (50 mL). The organic layer was washed with brine, dried over Na$_2$SO$_4$, and concentrated. The resulting residue was used without further purification. LRMS (M+H$^+$) m/z 587.1.

To a solution of 2 (~0.5 mmol) in DCM (5 mL) were added aqueous KH$_2$PO$_4$ (2 M, 1 ml) and MCPBA (77%, 135 mg, 0.6 mmol). The resulting mixture was stirred for 6 h. The reaction mixture was quenched with saturated Na$_2$S$_2$O$_3$ (10 mL). The organic layer was washed with saturated NaHCO$_3$, H$_2$O, brine, dried over Na$_2$SO$_4$, and concentrated. The residue was purified on RP-HPLC using a mixture of acetonitrile and H$_2$O to give 3 (150 mg, 65% from 1). LRMS (M+H$^+$) m/z 384.2.

To a solution of 3 (150 mg, 0.39 mmol) in DCM (8 mL) was added TFA (1 mL). The reaction mixture was stirred for 4 h. The mixture was concentrated, and dried under high vacuum. To the resulting residue (90 mg, 0.32 mmol) in THF (4 mL) were added DIEA (165 uL, 0.95 mmol) and 4 (140 mg, 0.38 mmol). The resulting mixture was stirred for 14 h. The reaction mixture was concentrated. The residue was purified on RP-HPLC using a mixture of acetonitrile and H$_2$O to give 5 (120 mg, 65%). LRMS (M+H$^+$) m/z 471.2.

To a solution of 5 (90 mg, 0.19 mmol) in THF/H$_2$O (2 mL/2 mL) were added OsO$_4$ (4.8 mg, 0.019 mmol), NMO (117 mg, 0.95 mmol) and pyridine (1.5 uL, 0.019 mmol). The resulting mixture was stirred for 6 h. NaHSO$_3$ (300 mg) was added. The reaction mixture was concentrated. The resulting solid was washed with EtOAc (100 mL×3). The filtrate was concentrated. The resulting residue was purified on preparative TLC plate (silica gel, 5:1 EtOAc/MeOH) to give diastereoisomers 6a (23 mg, 24%) and 6b (2 mg, 2%). LRMS (M+H$^+$) m/z 505.2.

Example 87

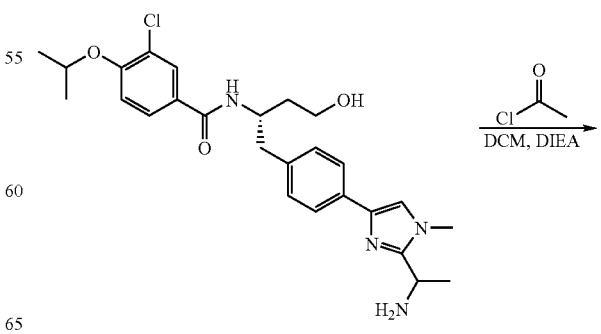

1

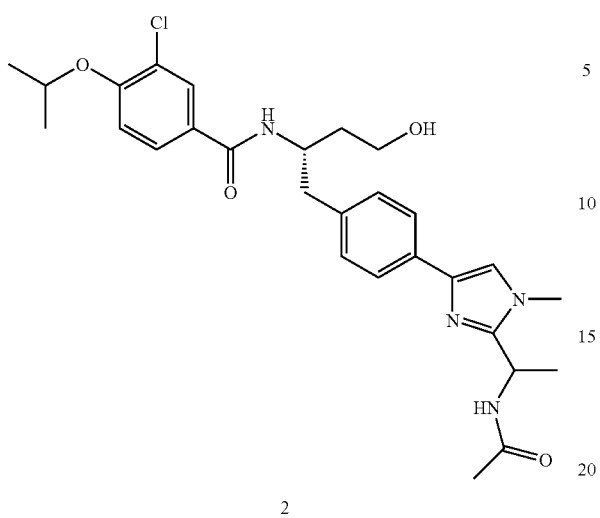

2

To a solution of amine 1 (150 mg, 0.309 mmol), DCM (2 mL) and DIEA (53.8 uL, 0.309 mmol) was added acetyl chloride (53.8 uL, 0.309 mmol). The resulting solution was stirred at room temperature for 10 minutes. The solvent was evaporated, and the remaining residue was purified on reverse phase Prep-HPLC (Acetonitrile/Water) to provide 2 (43.7 mg, 26.8%). MS (MW+1): 527.2

Example 88

To a solution of amine 1 (150 mg, 0.309 mmol), DCM (2 mL) and DIEA (53.8 uL, 0.309 mmol) was added trimethylsilyl isocyanate (35.6 uL, 0.309 mmol). The resulting solution was stirred at room temperature overnight. The solvent was evaporated, and the remaining residue was purified on reverse phase Prep-HPLC (Acetonitrile/Water) to provide 3 (30.3 mg, 18.6%). MS (MW+1): 528.2

Example 89

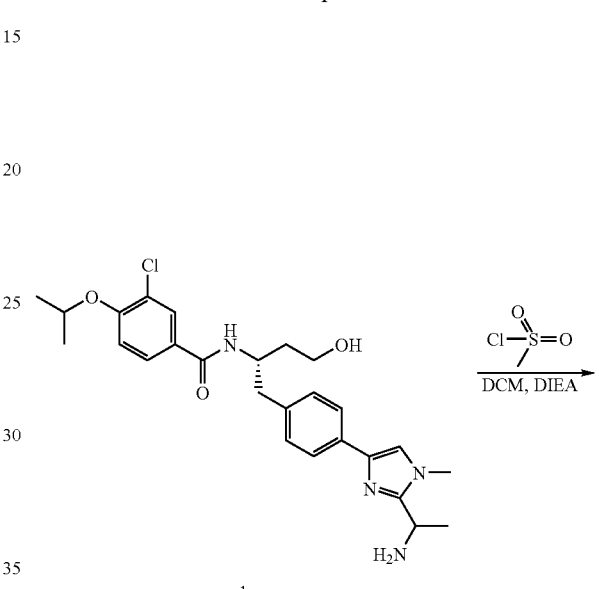

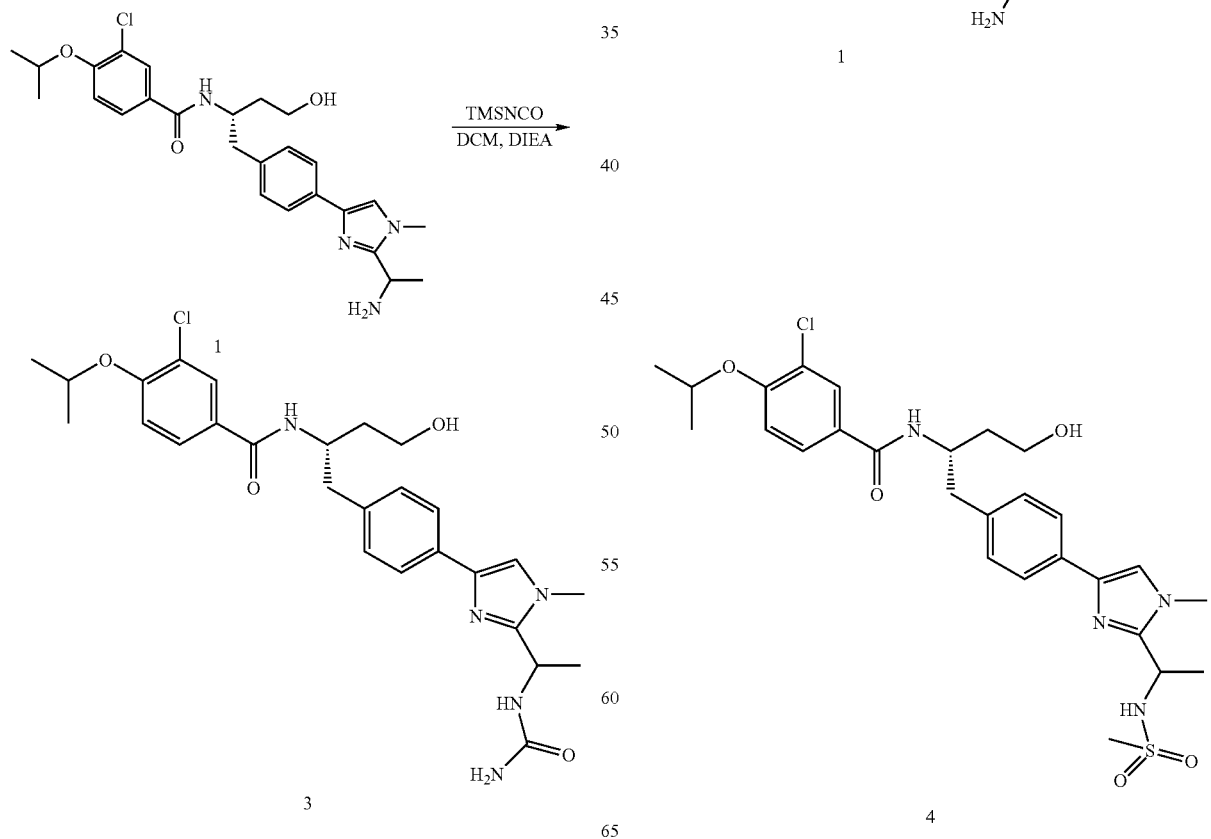

To a solution of amine 1 (150 mg, 0.309 mmol), DCM (2 mL) and DIEA (53.8 uL, 0.309 mmol) was added methanesulfonyl chloride (24 uL, 0.309 mmol). The resulting solution was stirred at room temperature for 30 minutes. The solvent was evaporated, and the remaining residue was purified on Prep-HPLC (Acetonitrile/Water) to provide 4 (18.4 mg, 10.6%). MS (MW+1): 563.1

Example 90

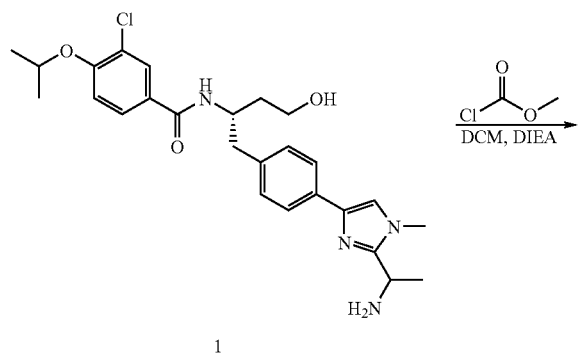

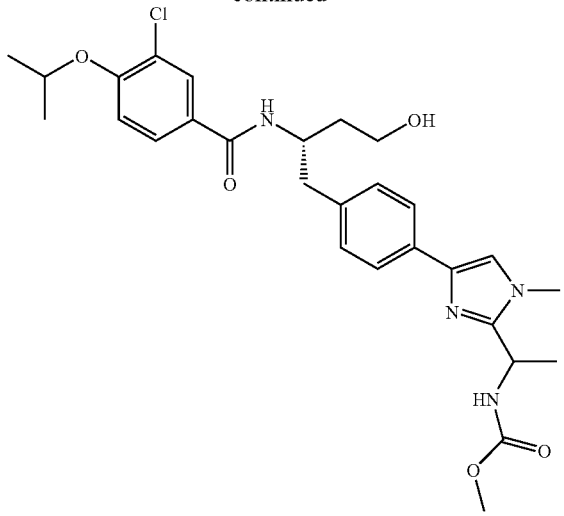

To a solution of amine 1 (150 mg, 0.309 mmol), DCM (2 mL) and DIEA (53.8 uL, 0.309 mmol) was added methyl chloroformate (24 uL, 0.309 mmol). The resulting solution was stirred at room temperature for 30 minutes. The solvent was evaporated, and the remaining residue was purified on reverse phase Prep-HPLC (Acetonitrile/Water) to provide 5 (CK1828648) (25.7 mg, 15.3%). MS (MW+1): 543.1

Example 91

(S)-3-chloro-N-(4-hydroxy-1-(4-(2-(1-(methoxyimino)ethyl)-1-methyl-1H-imidazol-4-yl)phenyl)butan-2-yl)-4-isopropoxybenzamide 2:

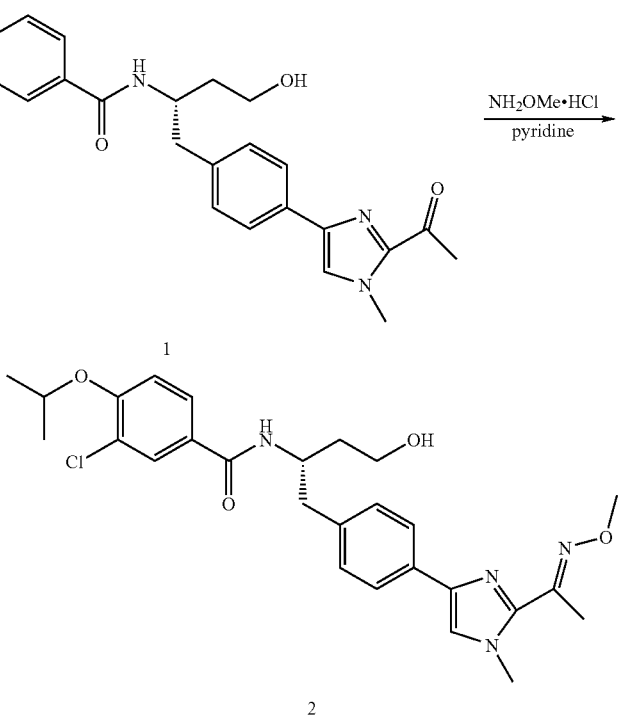

80 mg (0.031 mmol) of (S)—N-(1-(4-(2-acetyl-1-methyl-1H-imidazol-4-yl)phenyl)-4-hydroxybutan-2-yl)-3-chloro-4-isopropoxybenzamide in 2 mL of pyridine was treated with 27.6 mg (0.033 mmol) of hydroxylamine methyl ether hydrochloride. The reaction was stirred overnight after which the solvents were evaporated and the residue purified via reverse phase HPLC (acetonitrile/water). 11.2 mg (70% yield) of 2 was obtained and characterized by LCMS and HNMR.

Example 92

(S)-3-chloro-N-(4-hydroxy-1-(4-(2-(1-(hydroxyimino)ethyl)-1-methyl-1H-imidazol-4-yl)phenyl)butan-2-yl)-4-isopropoxybenzamide 3:

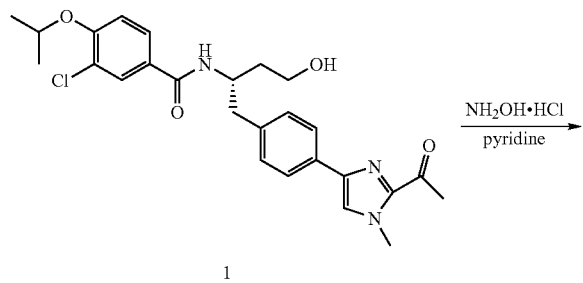

1

-continued

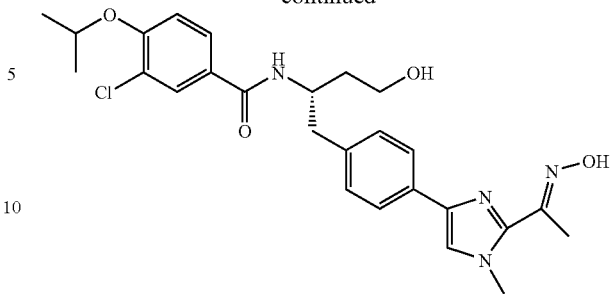

3

100 mg (0.21 mmol) of (S)—N-(1-(4-(2-acetyl-1-methyl-1H-imidazol-4-yl)phenyl)-4-hydroxybutan-2-yl)-3-chloro-4-isopropoxybenzamide in 2 mL of pyridine was treated with 71.8 mg (1.0 mmol) of hydroxylamine hydrochloride. The reaction was stirred overnight after which the solvents were evaporated and the residue purified via reverse phase HPLC (acetonitrile/water). 69.7 mg (67% yield) of 3 was obtained and characterized by LCMS and HNMR.

Example 93

(S)-3-chloro-N-(4-hydroxy-1-(4-(1-methyl-2-(2-methyl-1,3-dioxolan-2-yl)-1H-imidazol-4-yl)phenyl)butan-2-yl)-4-isopropoxybenzamide 4:

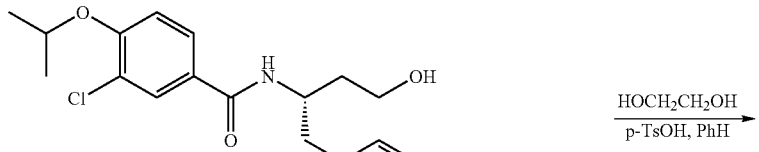

1

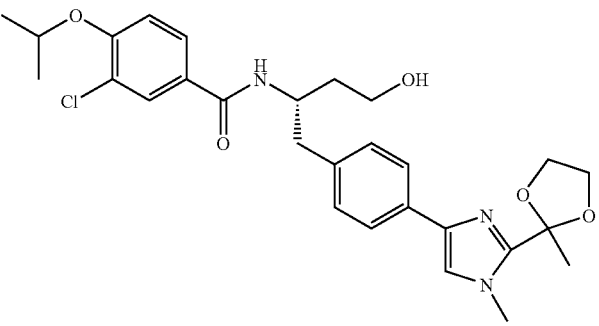

4

150 mg (0.31 mmol) of (S)—N-(1-(4-(2-acetyl-1-methyl-1H-imidazol-4-yl)phenyl)-4-hydroxybutan-2-yl)-3-chloro-4-isopropoxybenzamide in 2 mL of benzene was treated with 34.6 uL (0.62 mmol) of ethane-1,2-diol and 59 mg (0.31 mmol) of p-toluenesulfonic acid monohydrate. The reaction was stirred at 70° C. for 2 h after which the solvents were evaporated and the residue purified via reverse phase HPLC (acetonitrile/water). 25.5 mg (16% yield) of 4 was obtained and characterized by LCMS and HNMR.

Example 94

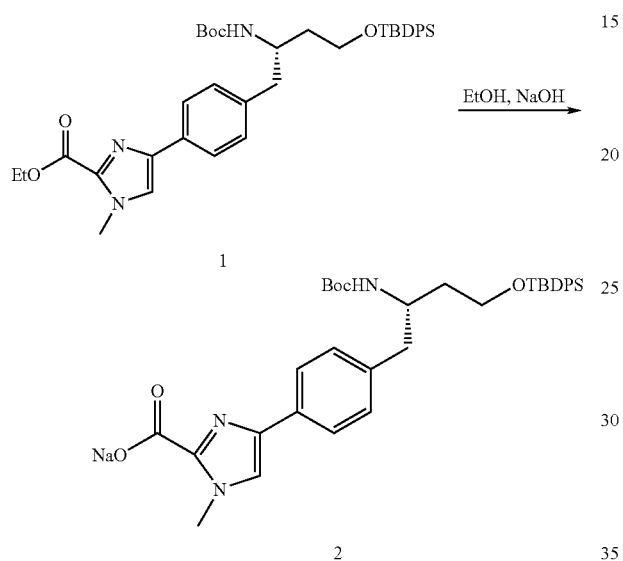

To a solution of 1 (1.5 g, 2.29 mmol), in ethanol (5.0 mL) was added NaOH in water (1.0 M, 3.7 mL, 2.80 mmol). The reaction mixture was stirred at ambient temperature for 2 hours. After the reaction was done it was concentrated to give 2 (1.49 g) which was used directly in the next step without further purification.

To a solution of 2 (1.49 g, 2.29 mmol), HBTU (1.3 g, 3.44 mmol), HOBt (530 mg, 3.44 mmol), and N, O-dimethylhydroxylamine HCl salt (340 mg, 3.44 mmol) in DMF (20 mL) was added DIEA (785 uL, 4.58 mmol). The resulting mixture was stirred at room temperature for 2 hours. The reaction mixture was concentrated. The resulting residue was purified using silica gel (Hexanes/EtOAc=1:3) to give pure compound 3 (1.20 g, 78%) as an off-white, foamy solid.

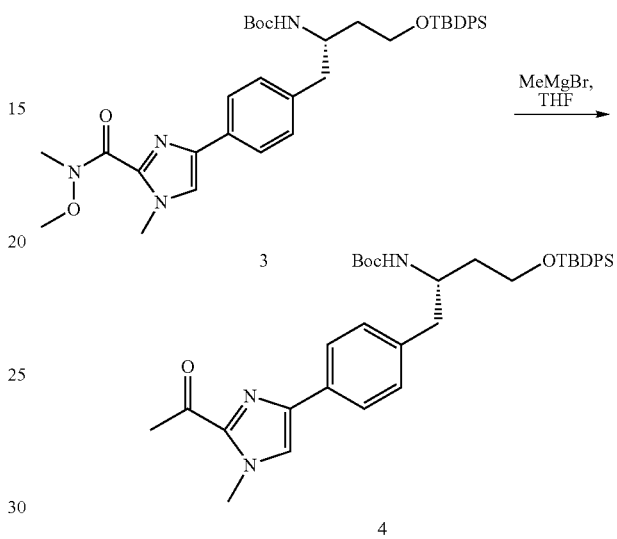

To a 0° C. solution of 3 (1.20 g, 1.79 mmol) in anhydrous THF (20 mL) was added Methylmagnesium bromide (3 M in Et$_2$O, 2.38 mL). The reaction mixture was stirred at 0° C. for 1 hour. The reaction mixture was quenched with saturated NH$_4$Cl (5 mL) and water (20 mL). EtOAc (50 mL) was added, and the layers were separated. The aqueous phase was extracted with additional EtOAc (50 mL×2). The organic phases were combined, dried (Na$_2$SO$_4$) and concentrated to a crude oil which was purified using silica gel (50% EtOAc/Hexanes). The desired compound 4 (0.82 g, 73%) was a viscous oil which became a white foamy solid while drying under high vacuum.

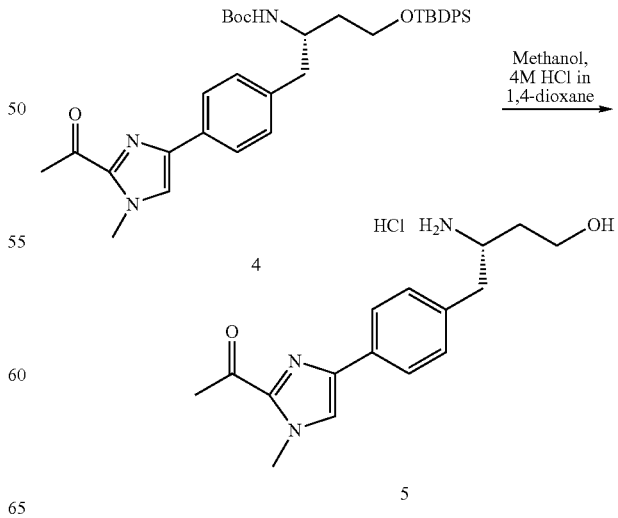

To a solution of 4 (0.82 g, 1.31 mmol) in Methanol (10 mL) was added HCl (4 M in 1,4-dioxane, 20 mL). The reaction was stirred at room temperature overnight. The mixture was concentrated, and dried under high vacuum to give 5, which was used in the following step without further purification.

To a solution of 5 (350 mg, 1.09 mmol) in DMF (5 mL) was added DIEA (280 uL, 1.63 mmol) and ester H (472 mg, 1.09 mmol). The resulting solution was stirred at room temperature for 1 hour. The crude solution was filtered and then purified by reverse phase chromatography (using a mixture of acetonitrile and water) to provide CK1904250 as a foamy white solid (400 mg, 68%). LRMS (M+H$^+$) m/z 538.1.

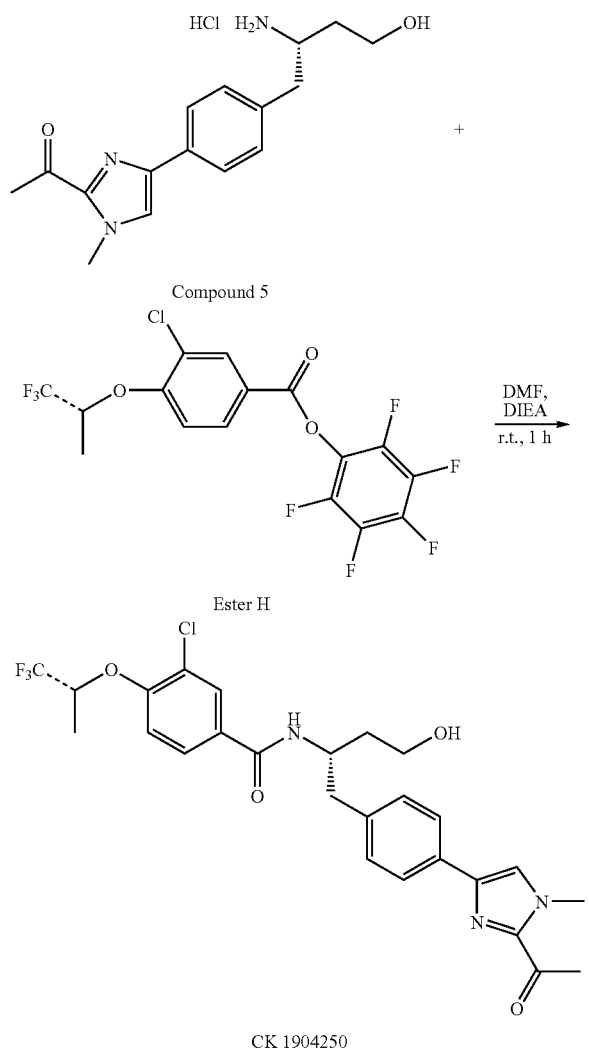

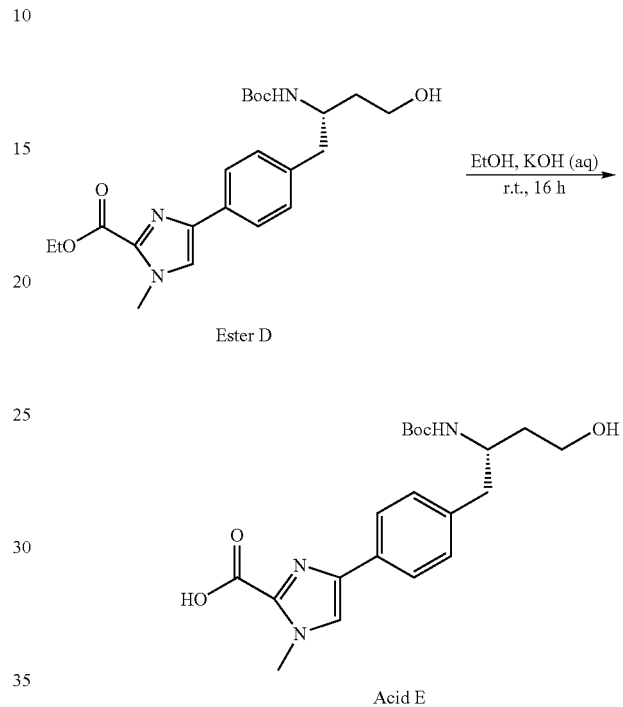

Ester D (10.2 g, 24.5 mmol) was dissolved in EtOH (150 mL) and water (50 mL). Potassium hydroxide (4.1 g, 73.5 mmol) was added, and the reaction was stirred at room temperature overnight. The reaction mixture was cooled to 0 C and neutralized with concentrated HCl. Great care was taken to not allow the pH to become <7 during the neutralization. The solvents were evaporated in vauco, and the residue was dried under high vacuum. Acid E (9.5 g, 24.5 mmol) was used in the next step without further purification.

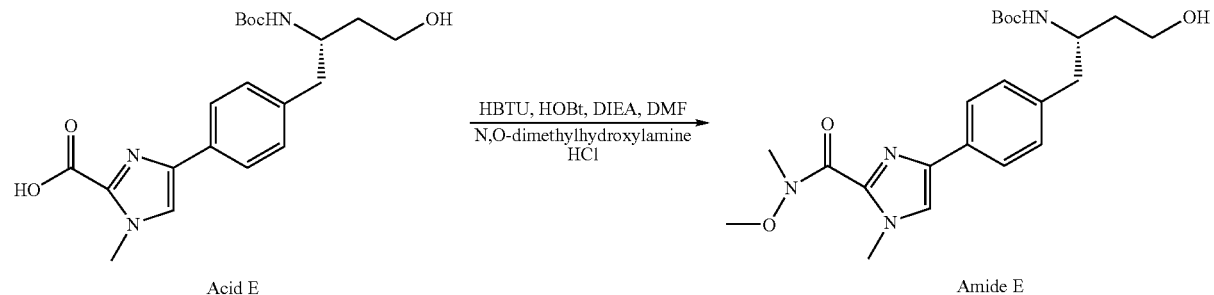

Acid E (9.5 g, 24.5 mmol) was combined with HBTU (18.5 g, 48.7 mmol), HOBt (6.6 g, 48.7 mmol), and N,O-dimethylhydroxylamine HCl (4.8 g, 48.7 mmol). To the solids were added DMF (150 mL) and DIEA (12.7 mL, 73.1 mmol). The resulting mixture was stirred at room temperature for 4 hours. Most of the DMF was evaporated, and the remaining residue was diluted with ethyl acetate (300 mL) and water (300 mL). The layers were separated, and the aqueous phase was extracted with EtOAc (1×200 mL). The organic phases were combined, washed with saturated aqueous sodium bicarbonate (2×250 mL), and dried over Na$_2$SO$_4$. Concentration under reduced pressure provided crude amide E which was purified using silica gel (3% MeOH/DCM) to give pure amide E (6.73 g, 17.4 mmol) as an off-white, foamy solid.

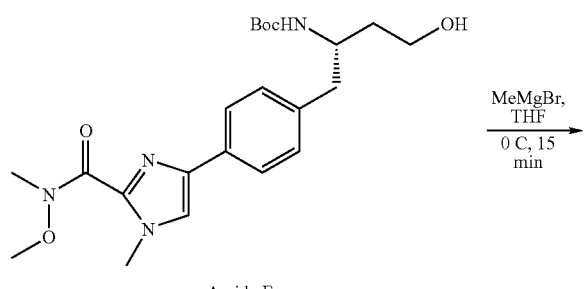

Amide E

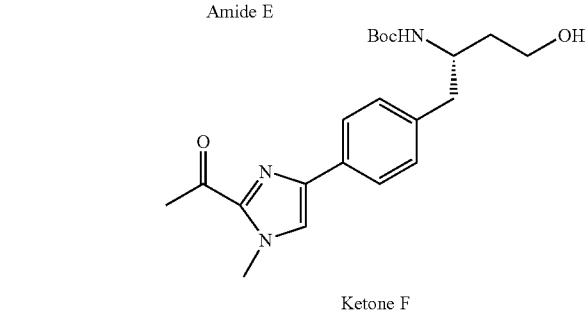

Ketone F

A solution of amide E (6.73 g, 17.4 mmol) in anhydrous THF (250 mL) was cooled to 0 C with an ice bath. Methylmagnesium bromide (3 M in diethyl ether, 52.2 mL, 156.6 mmol) was added, and the reaction was stirred at 0 C for 15 minutes. The reaction was carefully quenched with saturated ammonium chloride solution (20 mL) and water (100 mL). EtOAc (200 mL) was added, and the layers were separated. The aqueous phase was extracted with additional EtOAc (2×200 mL). The organic phases were combined, dried (Na$_2$SO$_4$) and concentrated to a crude oil which was purified using silica gel (50% EtOAc/Hexanes). The desired ketone F (4.45 g, 11.5 mmol) was a viscous oil which became a white foamy solid while drying under high vacuum.

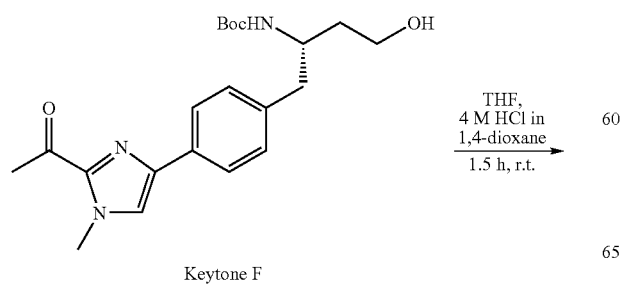

Keytone F

-continued

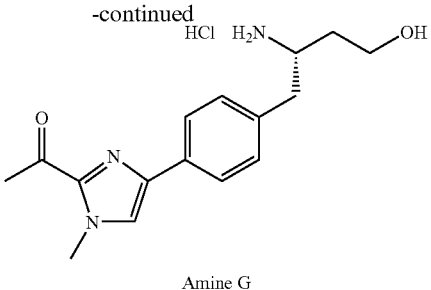

Amine G

Ketone F (4.45 g, 11.5 mmol) was dissolved in THF (25 mL) and 4 M HCl in 1,4-dioxane was added (75 mL). The reaction was stirred at room temperature for 1.5 hours. The solvents were evaporated in vacuo, and the residue was thoroughly dried under high vacuum to provide amine G. Amine G was used in the following step without further purification.

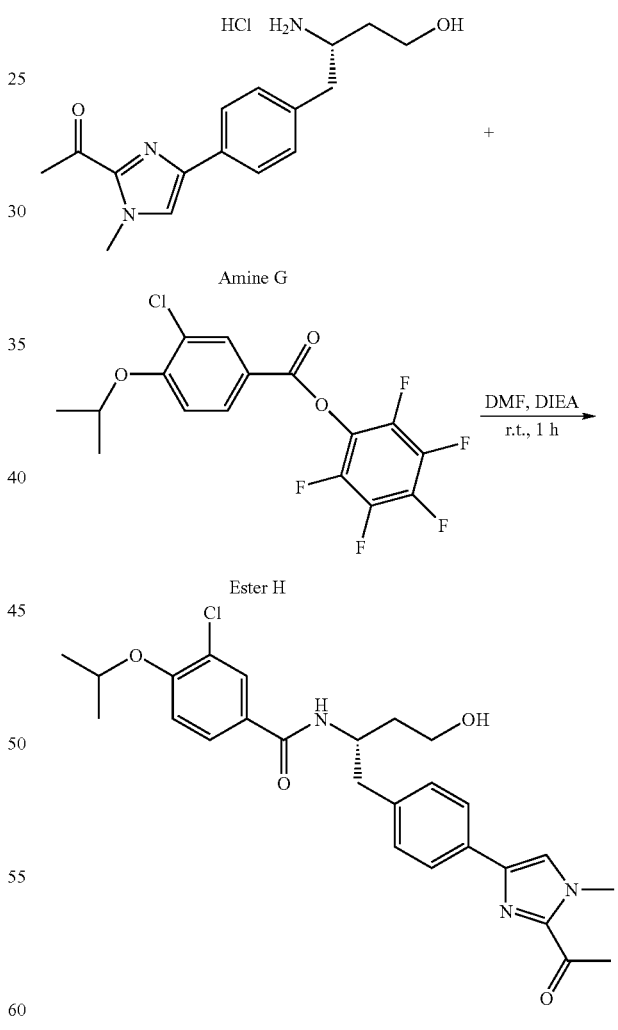

To a solution of amine G (3.30 g, 11.5 mmol) in DMF (50 mL) was added DIEA (8.0 mL, 46.0 mmol) and ester H (5.25 g, 13.8 mmol). The resulting solution was stirred at room temperature for 1 hour. Most of the DMF was evaporated, and the remaining residue was diluted with EtOAc (250 mL) and water (200 mL). The layers were separated, and the organic phase was washed with additional water (2×150 mL) and brine (2×150 mL). The organic phase was dried ($Na_2SO_4$) and concentrated. The remaining crude, viscous oil was purified using silica gel (100% EtOAc) to provide CK1317644 as a foamy white solid (2.98 g, 6.2 mmol).

Example 95

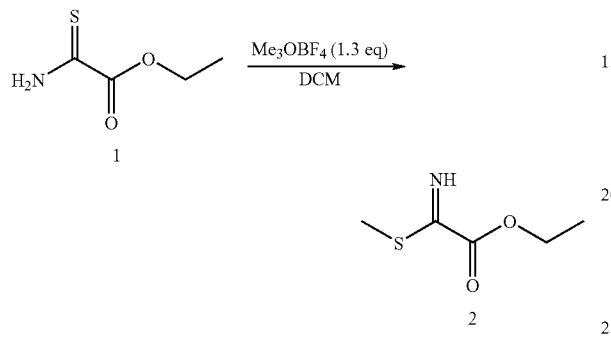

To a solution of ethyl thiooxamate (10.0 g, 75 mmol) in dichloromethane (400 mL) was slowly added trimethyloxonium tetrafluoroborate (13.1 g, 89 mmol) at 0° C. After 10 min the ice bath was removed, and the reaction mixture was stirred overnight. The solvent was removed to give 18.0 g of product 2 as white solid, which was used without further purification.

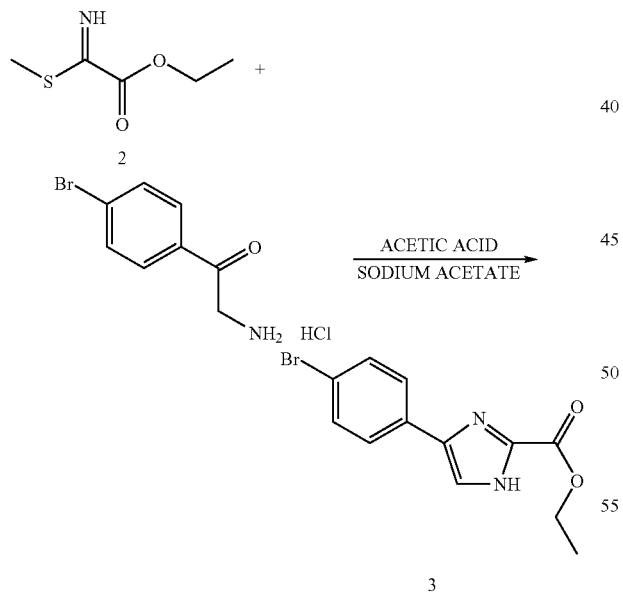

A mixture of 2-amino-4'-bromoacetophene hydrochloride (10.0 g, 40 mmol), sodium acetate (16.4 g, 200 mmol), acetic acid (11.5 mL, 200 mmol) and compound 2 (19.2 g, 80 mmol) in dioxane (70 mL) was stirred at 65° C. until TLC showed no compound 2 left (about 2 h). The reaction mixture was carefully neutralized with saturated $NaHCO_3$ solution and extracted with ethyl acetate. The organic solution was dried over $Na_2SO_4$ and concentrated. Purification with flash column chromatography (EtOAc:Hexs 1:1) gave product 3 (9.11 g, 79%) as a white solid.

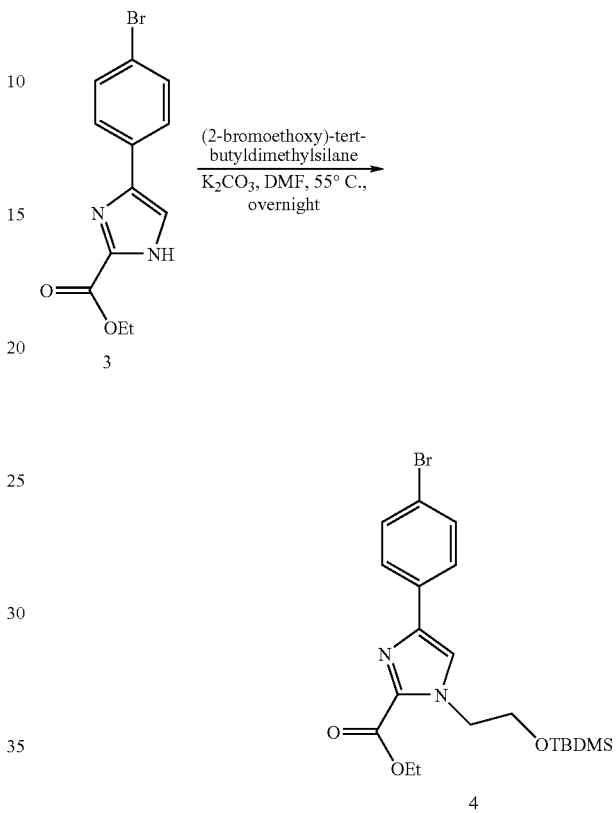

To a solution of compound 3 (3.174 g, 10.8 mmol) in DMF (15 mL) was added $K_2CO_3$ (4.478 g, 32.4 mmol) and (2-bromoethoxy)-tert-butyldimethylsilane (2.780 mL, 13.0 mmol). The resulting mixture was stirred at 55° C. overnight. The solution was concentrated, diluted with water and extracted with EtOAc (3×50 mL). The organic layers were combined and dried over $Na_2SO_4$. The solvent was removed to give a viscous oil (4.805 g, 10.6 mmol, 98.4%), which was used in the subsequent step without further purification.

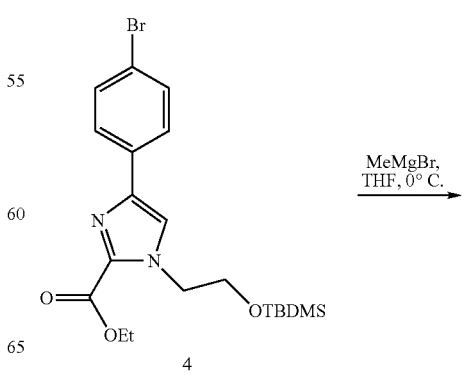

-continued

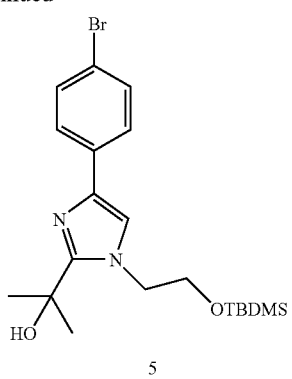

5

To a solution of compound 4 (2.174 g, 4.8 mmol) in anhydrous THF (25 mL) was added dropwise methylmagnesium bromide (4.8 mL, 3 M in diethyl ether, 14.4 mmol) under nitrogen at 0° C. The reaction was stirred at 0° C. for 15 minutes. The reaction was carefully quenched with saturated ammonium chloride solution (5 mL) and water (30 mL) and extracted with EtOAc (3×50 mL). The organic layers were combined, dried over Na$_2$SO$_4$ and concentrated to a crude oil. Purification with flash column chromatography (15% EtOAc/Hexanes) gave the desired product 5 (1.371 g, 65%) as a white amorphous solid.

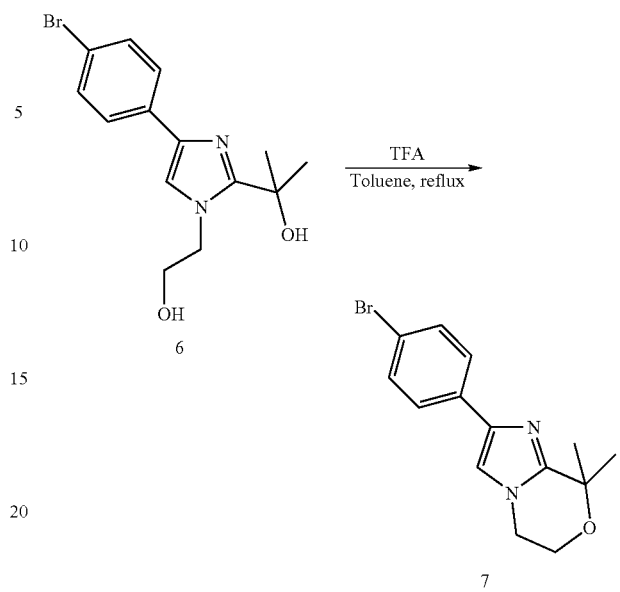

To a solution of compound 5 (1.371 g, 3.1 mmol) in THF (5 mL) was added 35 mL of HCl (4 M in 1,4-dioxane). The resulting solution was stirred at room temperature overnight. The solvents were removed to give the product 6 (1.0 g, 99%) as white solid.

A mixture of compound 6 (0.5 g, 1.54 mmol) and 1 mL of TFA in toluene (60 mL) was refluxed overnight. The solid 6 did not dissolve until around the boiling point of toluene. The solvent was removed. The residue was diluted with EtOAc, washed with NaHCO$_3$ aqueous solution, dried over Na$_2$SO$_4$, and concentrated. Purification with flash column chromatography (EtOAc:Hexanes 1:1) gave the product 7 (0.348 g, 74%) as a white solid.

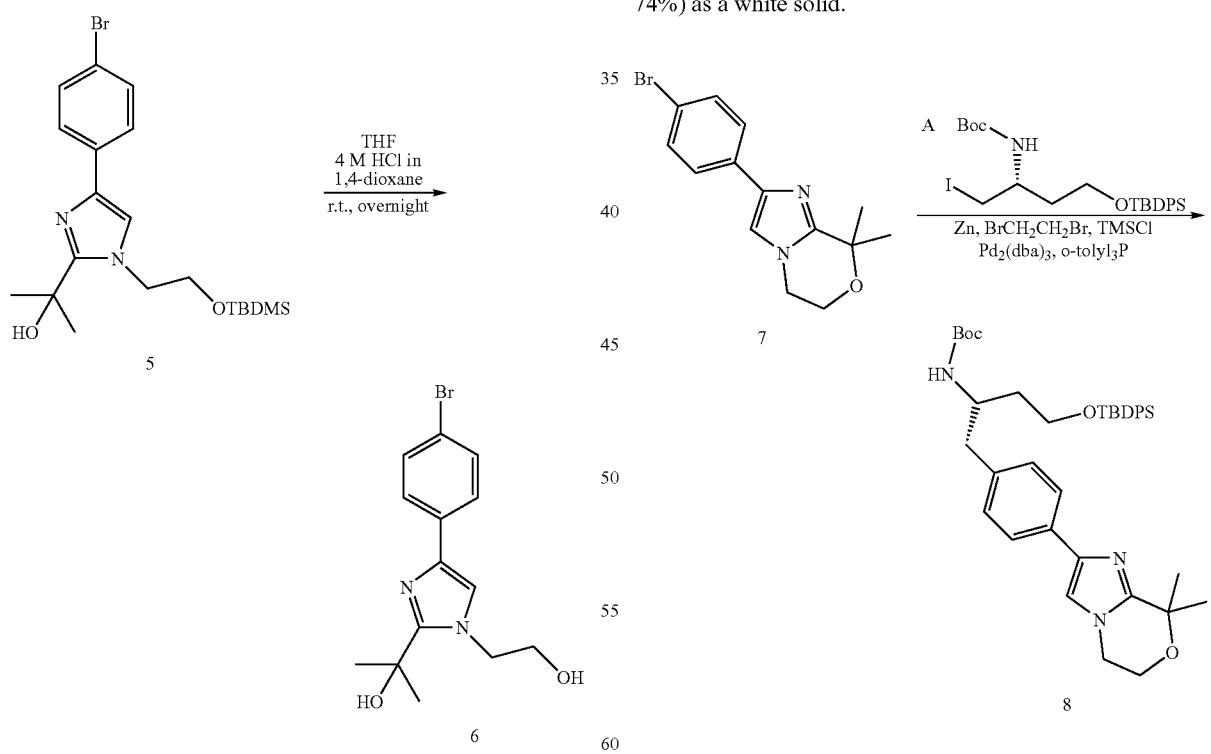

To a suspension of zinc powder (255 mg, 3.9 mmol) in dry degassed DMF (15 mL) was added 1,2 dibromoethane (0.020 mL, 0.23 mmol) under nitrogen. The mixture was heated using a heat gun for about 30 seconds until gas starts to evolve from the solution, indicating the activation of the zinc. The mixture was then allowed to cool to room temperature followed by the addition of TMSCl (6 uL, 0.05 mmol), and allowed to stir at room temperature for 30 min. A solution of iodo compound A in degassed DMF was added to the zinc solution, and the reaction mixture was stirred for 1 hour at room temperature. Then a solution of compound 7 (200 mg, 0.65 mmol) in degassed DMF was added via a syringe, followed by the addition of $Pd_2(dba)_3$ (14.9 mg, 0.016 mmol) and tri-o-tolylphospine (19.8 mg, 0.065 mmol). The reaction mixture was stirred for one hour at room temperature, then at 40° C. for 2 hours. The reaction was complete as shown on TLC. The solution was quenched with brine and extracted with EtOAc (5×50 mL). The combined organic layers were dried over sodium sulfate and concentrated. Purification with flash column chromatography (EtOAc:Hex 1:1) gave the product 8 (373 mg, 88%) as a colorless oil.

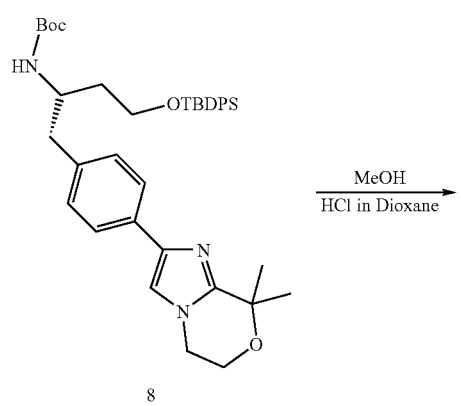

8

-continued

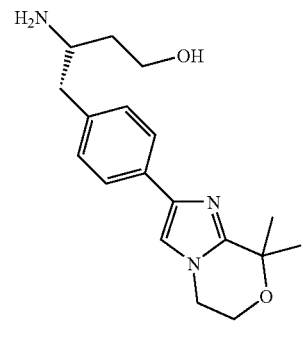

9

To a solution of compound 8 (373 mg, 0.57 mmol) in MeOH (10 mL) was added 2 mL of HCl (4.0 M in Dioxane). The solution was allowed to stir at room temperature for 2 hours. The solvent was removed to give the crude product 9 (180 mg, 99%), which was used without further purification.

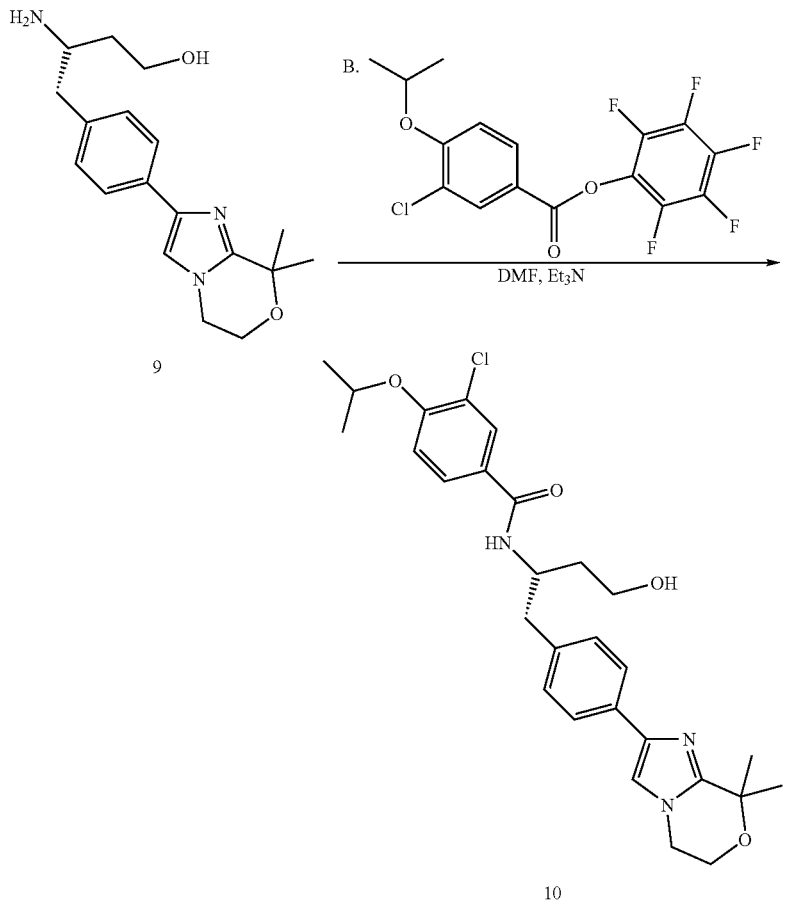

10

A mixture of compound 9 (180 mg, 0.57 mmol) and ester reagent B (260 mg, 0.68 mmol) in DMF (10 mL) containing triethylamine (0.24 mL, 1.71 mmol) was stirred at room temperature overnight. The reaction solution was diluted with brine and extracted with EtOAc (3×50 mL). The combined organic layers were dried over sodium sulfate and concentrated. Purification with HPLC (C18 column) gave the product 10 (141 mg, 50%) as a white solid.

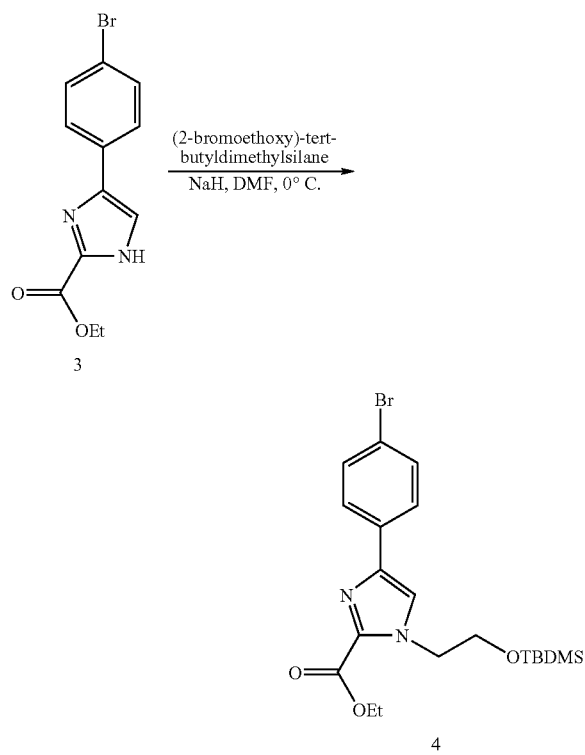

To a suspension of NaH (0.39 g, 9.3 mmol) in DMF (15 mL) was added a solution of 3 (1.9 g, 6.5 mmol) in DMF (10 mL) at 0° C. under nitrogen. The reaction was stirred for 1.5 hour, and then (2-bromoethoxy)-tert-butyldimethylsilane (2.09 mL, 9.7 mmol) was added. The reaction mixture was stirred overnight, diluted with EtOAc, quenched with aqueous ammonium chloride solution, and extracted with EtOAc (3×50 mL). The organic layers were combined and dried over Na₂SO₄. Purification with biotage (EtOAc) gave the product 4 (1.2 g, 41%) as light yellow solid.

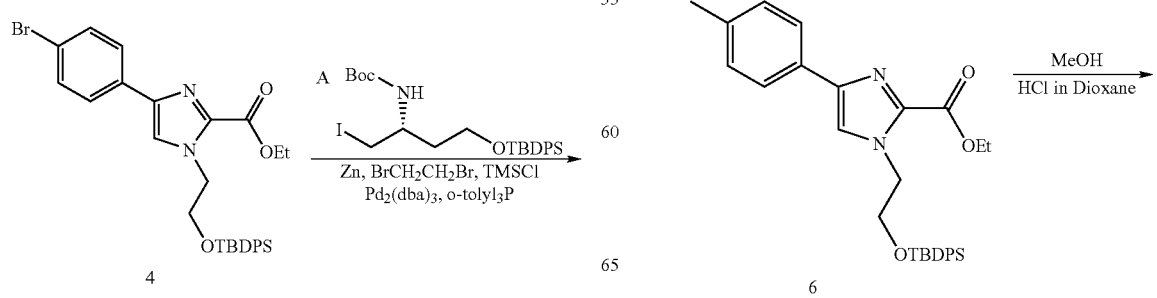

-continued

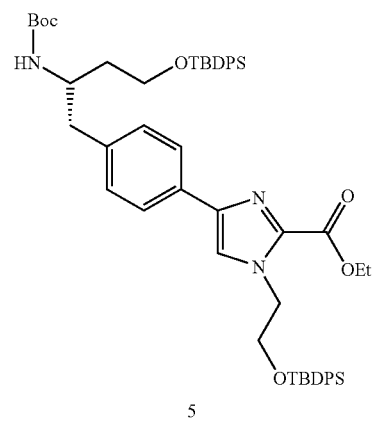

To a suspension of zinc powder (1.2 g, 18.4 mmol) in dry degassed DMF (15 mL) was added 1,2 dibromoethane (0.13 mL, 1.5 mmol) under nitrogen. The mixture was heated using a heat gun for about 30 seconds until gas starts to evolve from the solution, indicating the activation of the zinc. The mixture was then allowed to cool to room temperature followed by the addition of TMSCl (100 uL), and allowed to stir at room temperature for 30 min. A solution of iodo compound A (1.71 g, 3.1 mmol) in degassed DMF was added to the zinc solution, and the reaction mixture was stirred for 1 hour at room temperature. Then a solution of compound 4 (1.0 g, 2.2 mmol) in degassed DMF was added via a syringer, followed by the addition of Pd₂(dba)₃ (0.14 g, 0.015 mmol) and Tri-o-tolylphospine (0.18 g, 0.06 mmol). The reaction mixture was stirred for one hour at room temperature, then at 60° C. overnight. The solution was quenched with brine and extracted EtOAc (5×50 mL). The combined organic layers were dried over sodium sulfate and concentrated. Purification with flash column chromatography (EtOAc:Hex 1:1) gave the product 5 (346 mg, 20%) as colorless oil.

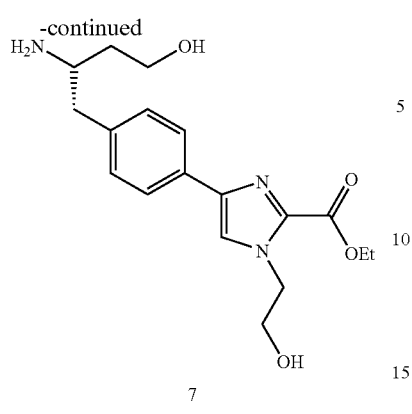

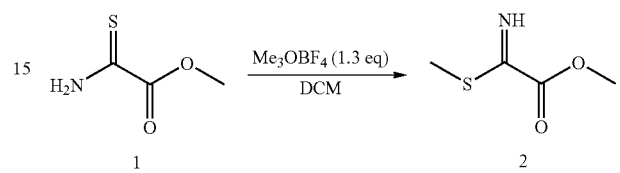

To a solution was compound 7 (346 mg) in MeOH (10 mL) was added 2 mL of HCl (4.0 M in Dioxane). The solution was allowed to stir at room temperature for 2 hour. The solvent was removed to give the crude product 7, which was used for the next step without further purification.

over sodium sulfate and concentrated. Purification with HPLC (C18 column) gave the product 8 (0.2 g, 87%) as white solid, and the lactone product 9 (15.4 mg, 7.3%) as white solid. LC-MS (CI) m/z 489.1 (MH$^+$)

Example 96

To a solution of ethyl thiooxamate (10.0 g, 75 mmol) in dichloromethane (400 mL) was slowly added trimethyloxo-

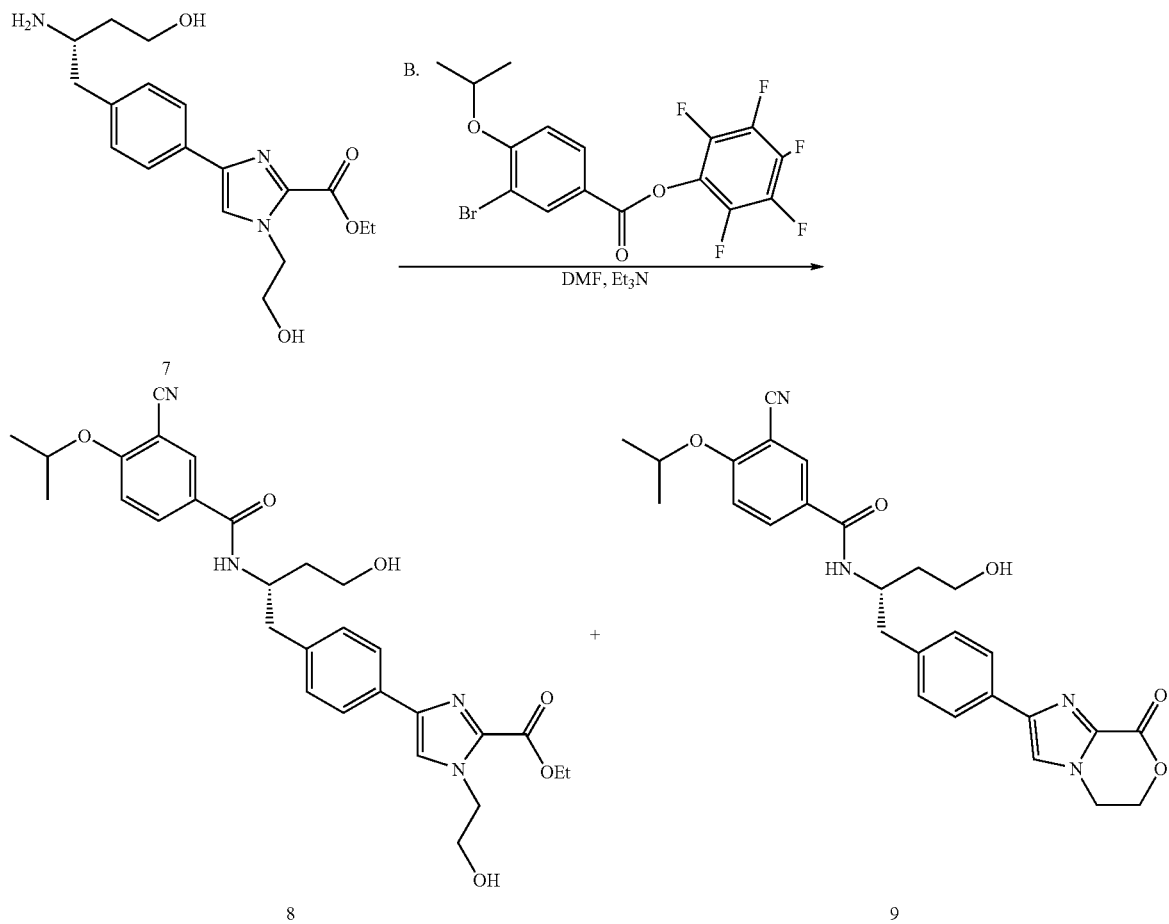

A mixture of compound 7, ester reagent B (200 mg, 0.52 mmol) in DMF (10 mL) containing triethylamine (0.15 mL, 1.08 mmol) was stirred at room temperature over night. The reaction solution was diluted with brine, extracted with EtOAc (3×50 mL). The combined organic layers were dried nium tetrafluoroborate (13.1 g, 89 mmol) at 0° C. After 10 min the ice bath was removed, and the reaction mixture was stirred overnight. The solvent was removed to give 18.0 g of product 2 as white solid, which was used without further purification.

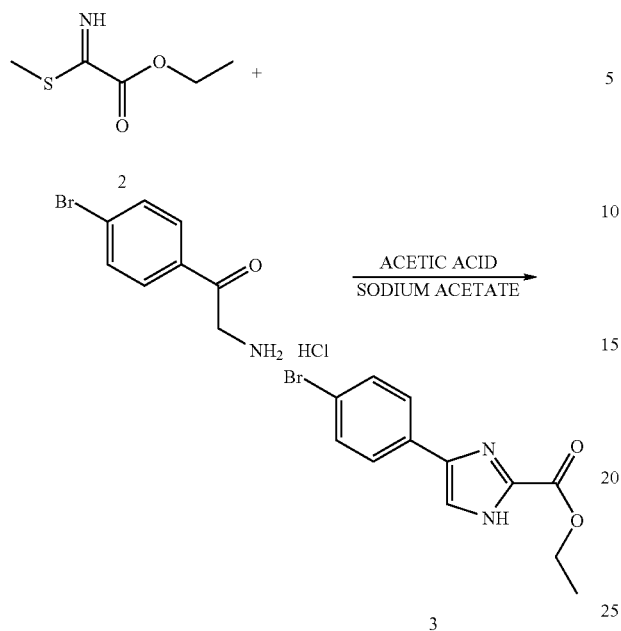

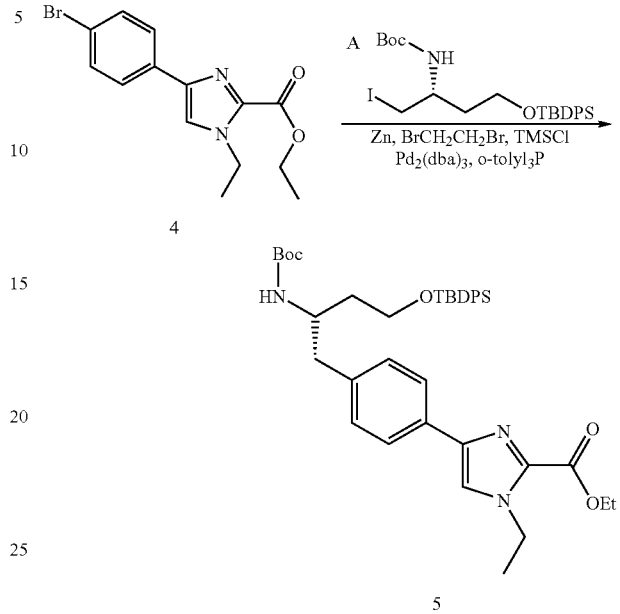

A mixture of 2-amino-4'-bromoacetophene hydrochloride (10.0 g, 40 mmol), sodium acetate (16.4 g, 200 mmol), acetic acid (11.5 mL, 200 mmol) and compound 2 (19.2 g, 80 mmol) in dioxane (70 mL) was stirred at 65° C. until TLC show no compound 2 left (about 2 h). The reaction mixture was carefully neutralized with saturated NaHCO$_3$ solution, and extracted with ethyl acetate. The organic solution was dried over Na$_2$SO$_4$ and concentrated. Purification with flash column chromatography (EtOAc:Hexs 1:1) gave product 3 (9.11 g, 79%) as white solid.

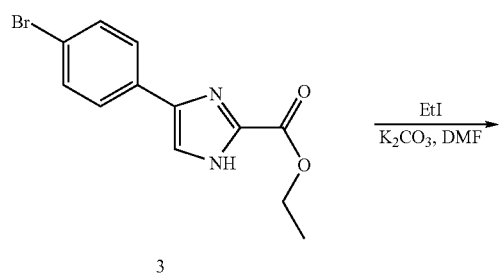

To a solution of compound 3 (5.307 g, 18 mmol) in DMF (15 mL) was added K$_2$CO$_3$ (3.73 g, 27 mmol) and iodoethane (3.5 mL, 43.2 mmol). The resulting mixture was stirred at 60° C. for three hours. The mixture was diluted with water and extracted with EtOAc (3×50 mL). The organic layers were combined, dried over Na$_2$SO$_4$, and concentrated. Purification with column chromatography (Hexanes/EtOAc 50:50) gave the product 4 (3.2 g, 55%) as white solid.

To a suspension of zinc powder (3.90 g, 59.6 mmol) in dry degassed DMF (10 mL) was added 1,2 dibromoethane (308 uL, 3.58 mmol) under nitrogen. The mixture was heated using a heat gun for about 30 seconds until gas starts to evolve from the solution, indicating the activation of the zinc. The mixture was then allowed to cool to room temperature followed by the addition of TMSCl (92 uL, 0.735 mmol), and allowed to stir at room temperature for 30 min. A solution of iodo compound A (6.6 g, 11.9 mmol) in degassed DMF was added to the zinc solution, and the reaction mixture was stirred for 1 hour at room temperature. Then a solution of compound 4 (3.2 g, 9.93 mmol) in degassed DMF was added via a syringe, followed by the addition of Pd$_2$(dba$_3$) (223 mg, 0.244 mmol) and Tri-o-tolylphospine (302 mg, 0.992 mmol). The reaction mixture was stirred for one hour at room temperature, then at 60° C. for 2 hours. The reaction was complete as shown on TLC. The solution was quenched with brine and extracted EtOAc (3×80 mL). The combined organic layers were dried over sodium sulfate and concentrated. Purification with flash column chromatography (EtOAc:Hex 1:1) gave the product 5 (5.43 mg, 82%) as colorless oil.

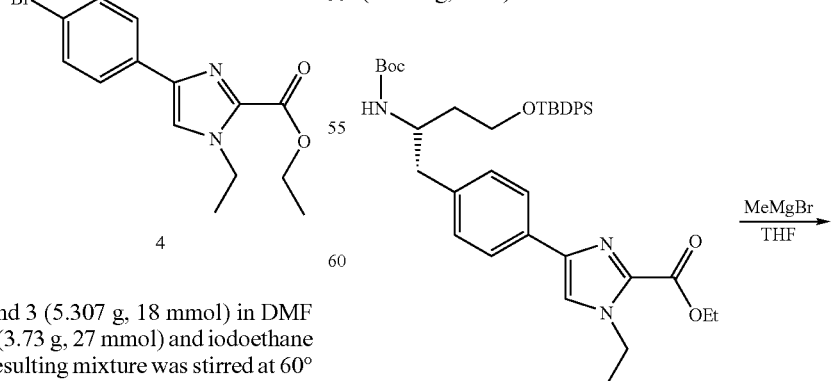

-continued

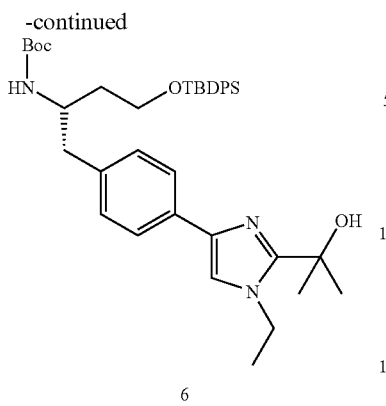

6

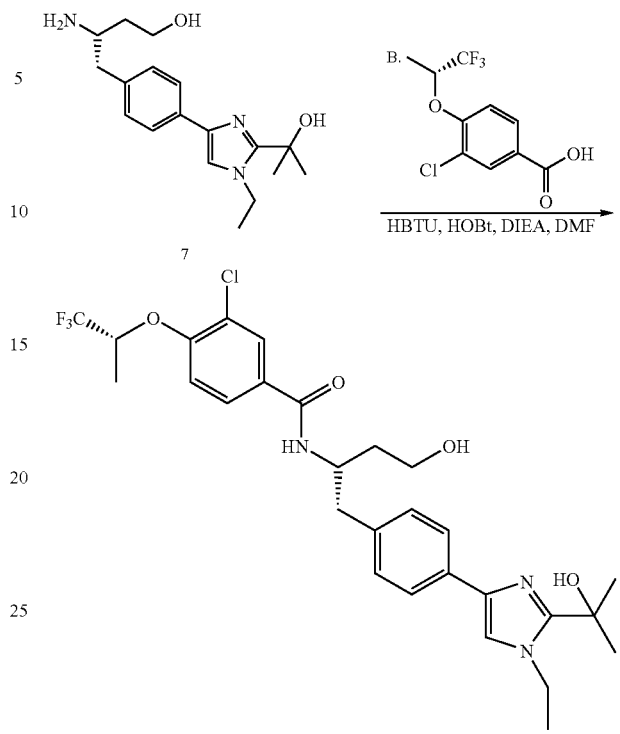

To a solution of compound 5 (5.43 g, 8.1 mmol) in THF (50 mL) was added dropwise a solution of MeMgBr bromide in ether (9.0 mL, 27 mmol) at 0° C. under nitrogen. The reaction was complete in 10 min via TLC. The solution was quenched by aqueous ammonium chloride solution while in ice, extracted with EtOAc (3×60 mL). The combined organic layers were dried over sodium sulfate and concentrated. Purification with column chromatography (Hexanes/EtOAc 1:1) gave the product 6 (4.86 g, 91%) as colorless oil.

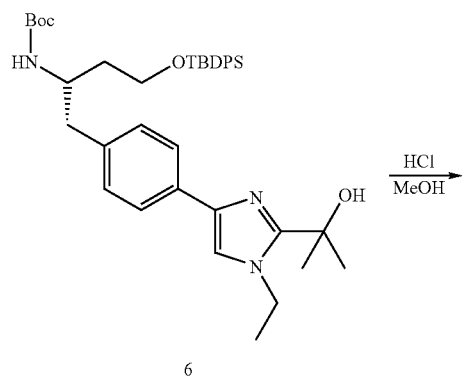

A mixture of compound 6 (4.86 g, 7.4 mmol), and 18 mL of HCl (4M in Dioxane) in MeOH (10.0 mL) was stirred at room temperature for 1 hour, followed by heating at 60° C. for 30 min. The reaction was complete via TLC and LC/MS. The solvent was removed to give the product 7, which was directly used for the next step.

A mixture of acid B (677 mg, 2.51 mmol), HBTU (3.6 g, 9.49 mmol), HOBT. (1.45 g, 9.46 mmol) and DIEA (2.20 mL, 12.6 mmol) in DMF (40 mL) was stir at room temperature for 1 min followed by the addition of 7 (1.0 g, 3.14 mmol). The reaction was complete in one hour via TLC and LC/MS. The solution was partitioned in EtOAc and brine, and extracted with EtOAc. The combined organic layers were dried over sodium sulfate and concentrated down. Purification with HPLC gave product 8 (390 mg) as white solid.

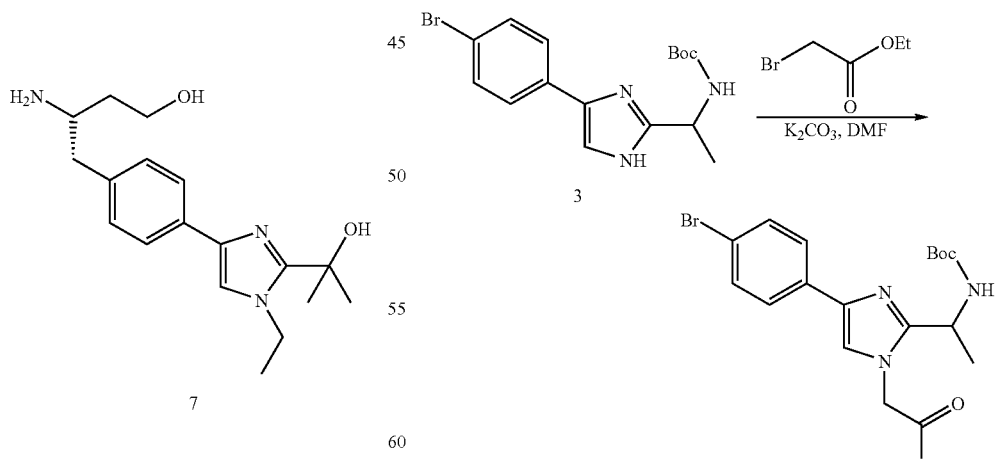

To a solution of compound 3 (2.66 g, 7.27 mmol) in DMF (15 mL) was added K$_2$CO$_3$ (2.00 g, 15 mmol) and ethyl bromoacetate (1.61 mL, 14.5 mmol). The resulting mixture was stirred at 60° C. for three hours. The mixture was diluted with water and extracted with EtOAc (3×50 mL). The organic layers were combined, dried over Na₂SO₄, and concentrated. Purification with column chromatography (Hexanes/EtOAc 50:50) gave the product 4 (3.02 g, 91%).

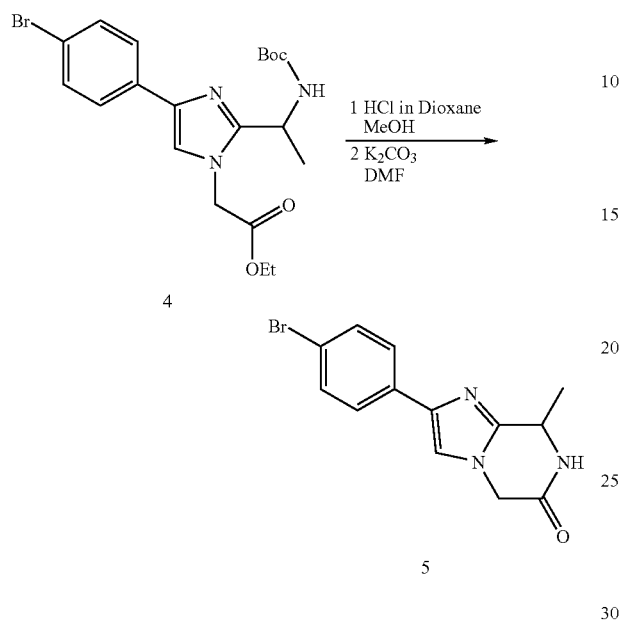

To a solution of compound 4 (3.02 g, 6.7 mmol) in MeOH (20 mL) was added HCl (4.0 M) in Dioxane (7.0 mL) and stirred at 60° C. for one hours. The mixture was concentrated and no purification was done. The resulting oil was dissolved in DMF (15 mL), added K₂CO₃ (2.0 g, 14.7 mmol) was added, and stirred at 60° C. for overnight. The mixture was diluted with water and extracted with EtOAc (3×50 mL). The organic layers were combined, dried over Na₂SO₄, and concentrated. Purification with column chromatography (Hexanes/EtOAc 50:50) gave the product 5 (1.80 g, 88%).

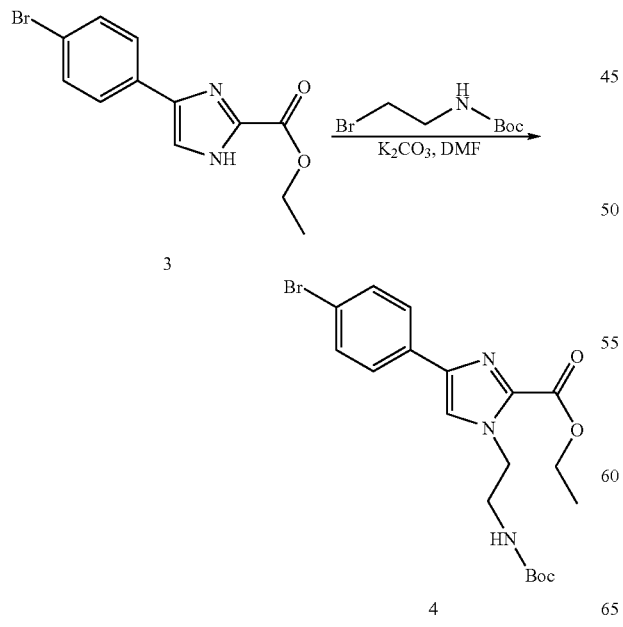

To a solution of compound 3 (5.000 g, 17 mmol) in DMF (15 mL) was added K₂CO₃ (3.51 g, 26 mmol) and Boc-2-amino ethyl bromide (4.56 g, 20.35 mmol). The resulting mixture was stirred at 60° C. for three hours. The mixture was diluted with water and extracted with EtOAc (3×50 mL). The organic layers were combined, dried over Na₂SO₄, and concentrated. Purification with column chromatography (Hexanes/EtOAc 50:50) gave the product 4 (4.08 g, 55%) as white solid.

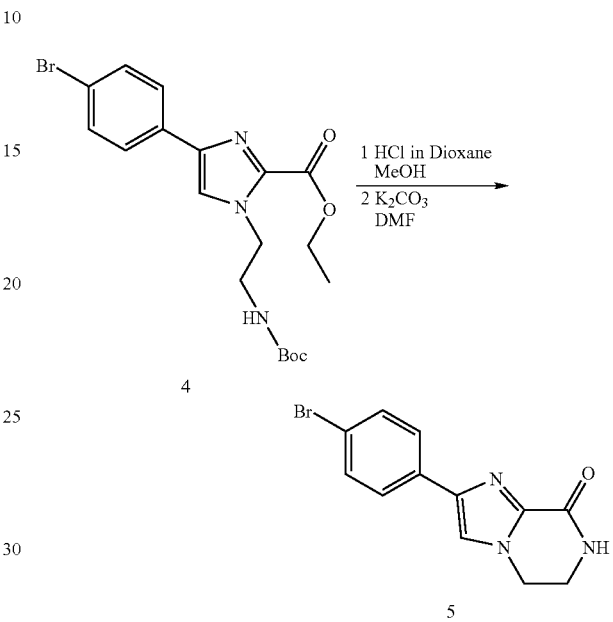

Example 97

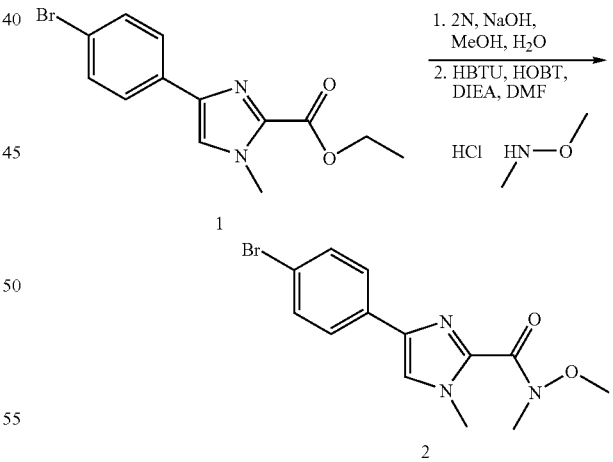

To a solution of 1 (10.7 g, 34.6 mmol) in MeOH/H₂O (60 mL/20 mL) was added NaOH (2N, 20.8 ml, 41.6 mmol). After the mixture was stirred at 50° C. for 2 h, the solution then was concentrated and under high vacuum to yield 10.3 g of light yellow solid (LRMS (M−H⁺) m/z 278.9), which was used for the next step without further purification. To a solution of the crude mixture in DMF (50 mL) were successively added N,O-dimethylhydroxylamine hydrochloride (4.0 g, 40.7 mmol), HBTU (4.0 g, 40.7 mmol), HOBT (6.2 g, 40.7 mmol) and DIEA (6.0 ml, 40.7 mmol). The mixture was stirred at rt overnight. The solution then was partitioned between EtOAc and H₂O. The organic layer was washed with NaOH (1 N), brine, dried over Na₂SO₄, filtered and concentrated. The residue was purified by flash column chromatography using a mixture of hexanes and EtOAc to give 2 (8 g, 72%). LRMS (M+H⁺) m/z 324.0.

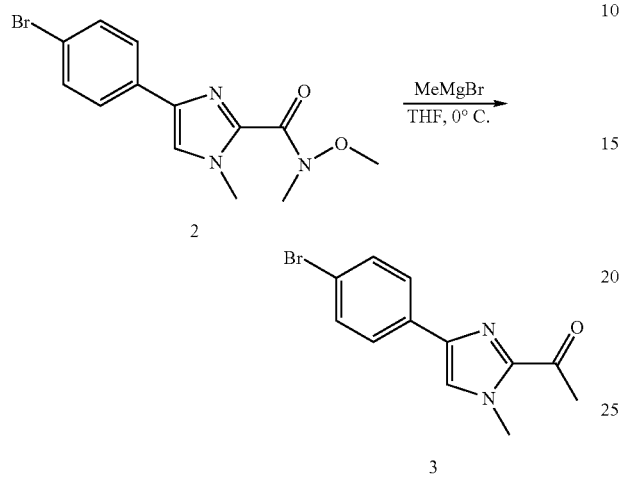

To a solution of 2 (3.7 g, 11.4 mmol) in THF (40 mL) was added dropwise MeMgBr in Et₂O (3M, 11.4 ml, 34.2 mmol) at 0° C. The mixture was stirred at 0° C. for 30 min. The solution was quenched by saturated NH₄Cl at 0° C. and diluted between EtOAc and H₂O. The organic layer was washed with brine, dried over Na₂SO₄, filtered and concentrated to give 3 (3.0 g, 94%) without further purification. LRMS (M+H⁺) m/z 279.0.

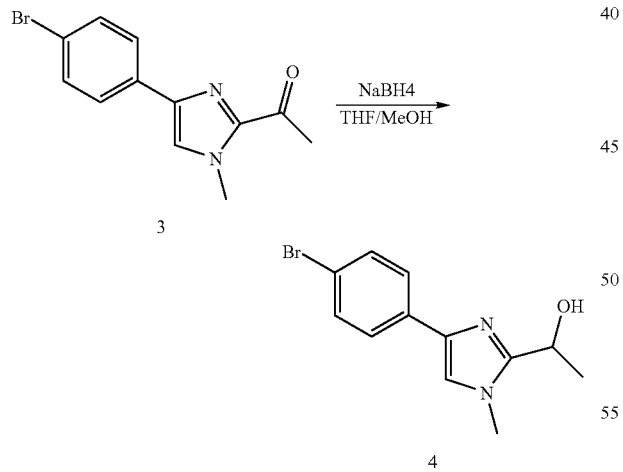

To a solution of 3 (3.0 g, 10.8 mmol) in THF/MeOH (10 mL/10 mL) was slowly added NaBH₄ (407 mg, 10.8 mmol). The mixture was stirred for 10 min, quenched by saturated NH₄Cl and partitioned between EtOAc and H₂O. The organic layer was washed with Sat NaHCO₃, brine, dried over Na₂SO₄, filtered and concentrated to give 4 (3.0 g, 99%), which was used without further purification. LRMS (M+H⁺) m/z 281.0.

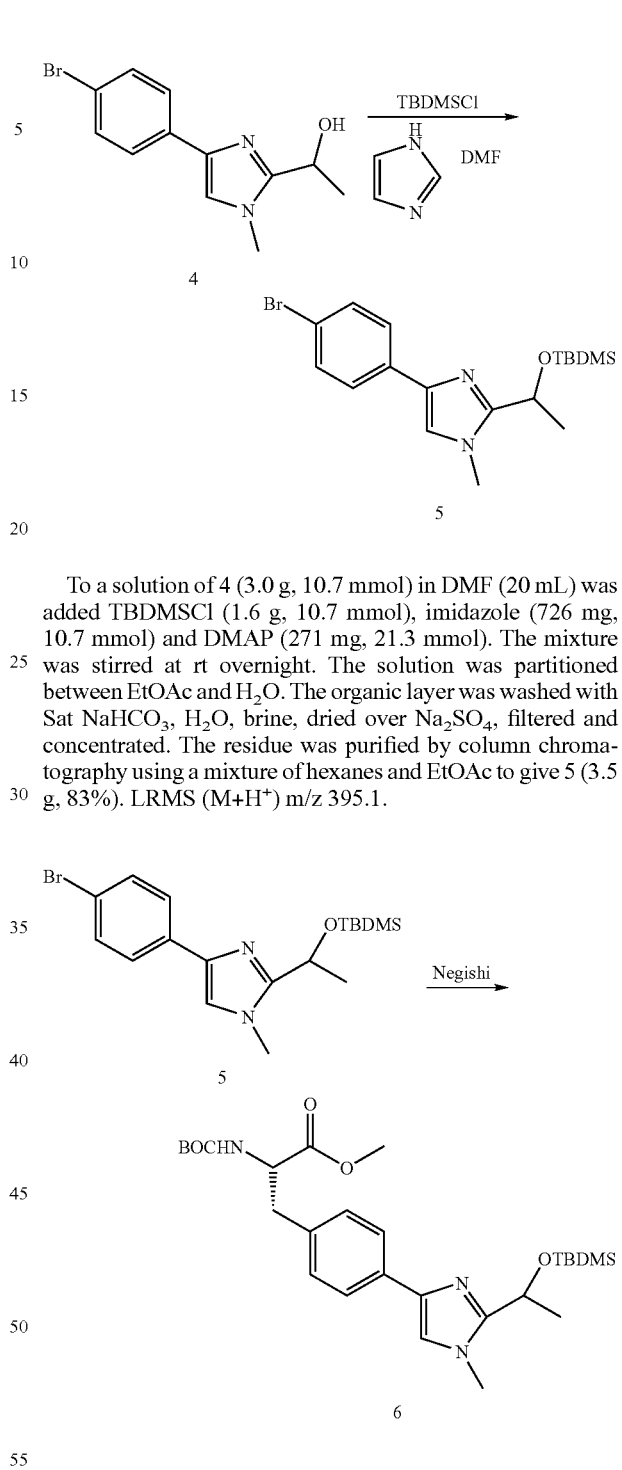

To a solution of 4 (3.0 g, 10.7 mmol) in DMF (20 mL) was added TBDMSCl (1.6 g, 10.7 mmol), imidazole (726 mg, 10.7 mmol) and DMAP (271 mg, 21.3 mmol). The mixture was stirred at rt overnight. The solution was partitioned between EtOAc and H₂O. The organic layer was washed with Sat NaHCO₃, H₂O, brine, dried over Na₂SO₄, filtered and concentrated. The residue was purified by column chromatography using a mixture of hexanes and EtOAc to give 5 (3.5 g, 83%). LRMS (M+H⁺) m/z 395.1.

To a suspension of Zn (4.8 g, 74.4 mmol) in DMF (20 mL) was added BrCH₂CH₂Br (320 μL, 3.7 mmol). The mixture was heated by heat gun for 4 min. After the solution was cooled down, trimethylchlorosilane (95 μL, 0.74 mmol) was added. After 30 min, BOC-β-iodo-Ala-OMe (5.2 g, 16.0 mmol) was added, and reaction mixture was stirred at rt for 1 h. To this mixture then were added Pd₂(dba)₃ (243 mg, 0.27 mmol), (O-Tol)₃P (269 mg, 0.88 mmol) and 5 (3.5 g, 8.9 mmol). The mixture was heated at 50° C. for 2 h, cooled down and filtered through celite. The solution was partitioned between EtOAc and H₂O. The organic layer was washed with brine, dried over Na₂SO₄, filtered and concentrated. The residue was purified by column chromatography using a mixture of hexanes and EtOAc to give 6 (3.3 g, 72%). LRMS (M+H) m/z 518.2.

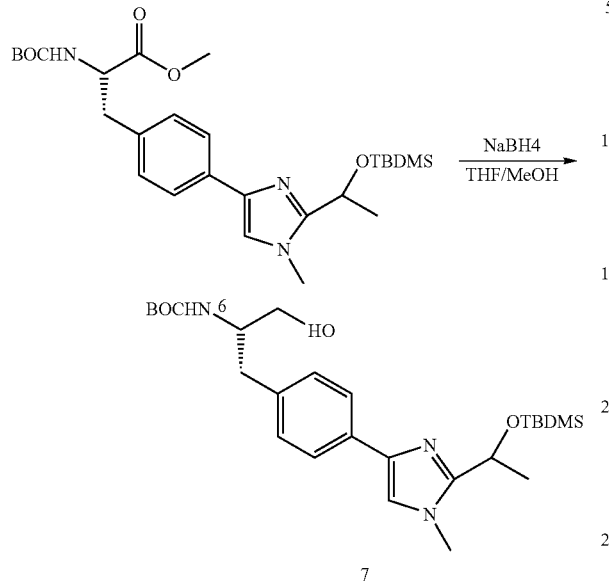

To a solution of 6 (3.3 g, 6.4 mmol) in THF (20 ml) was slowly added LAH (1 M, 6.4 mL, 6.4 mmol) at 0° C. The mixture was stirred at 0° C. in 20 min, quenched by H$_2$O (240 μL), NaOH (3N, 240 μL), H$_2$O (720 μL), filtered. The organic layer was dried over Na$_2$SO$_4$, filtered and concentrated. The residue was purified by column chromatography using a mixture of hexanes and EtOAc to give 7 (1.57 g, 50%). LRMS (M+H$^+$) m/z 490.2.

To a solution of 7 (1.57 g, 3.2 mmol) in THF (20 mL) were added PPh3 (1.0 g, 3.9 mmol), DIAD (746 μL, 3.9 mmol) and phthalimide (567 mg, 3.9 mmol). After the solution was stirred at rt for 4 hours, which was monitored by LCMS, the reaction was partitioned between EtOAc and H$_2$O. The organic layer was washed with brine, dried over Na$_2$SO$_4$, filtered and concentrated. The residue was purified by column chromatography using a mixture of hexanes and EtOAc to give 8 (2.0 g, 99%). LRMS (M+H$^+$) m/z 619.2.

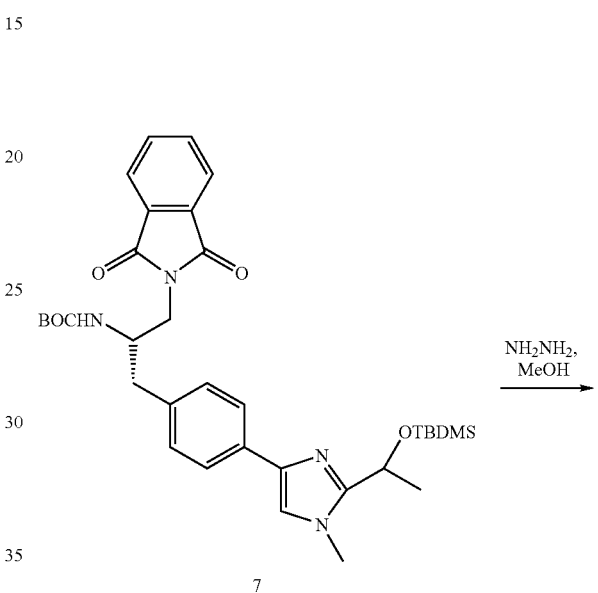

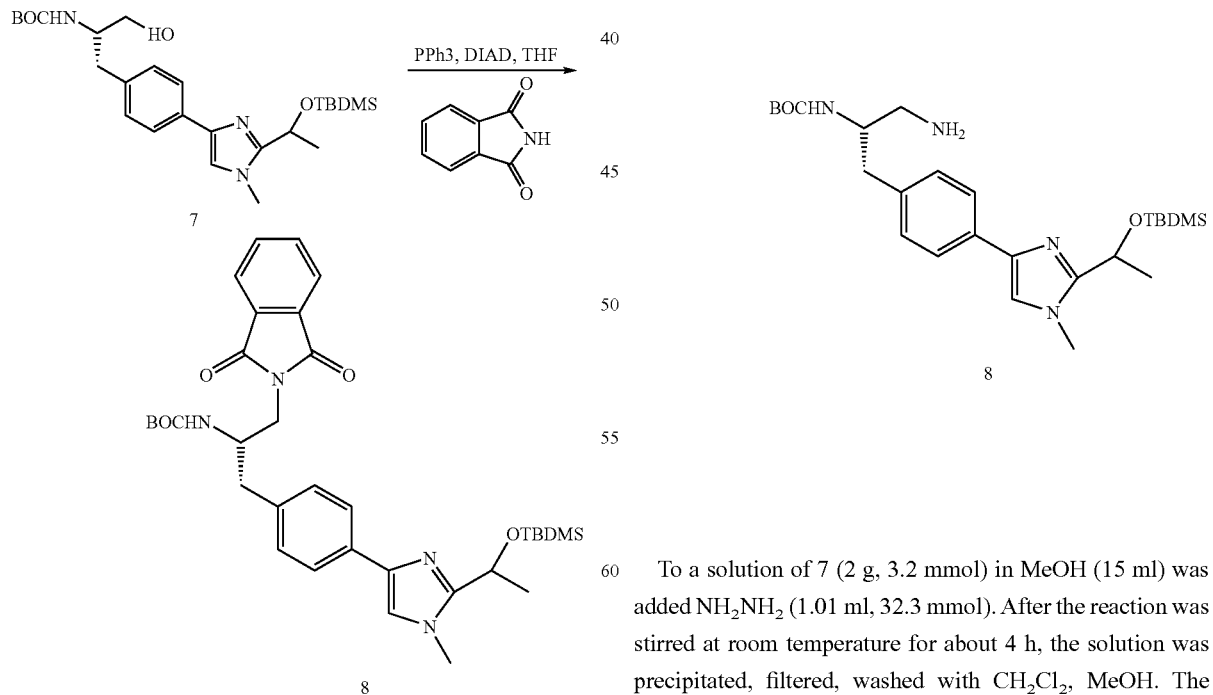

To a solution of 7 (2 g, 3.2 mmol) in MeOH (15 ml) was added NH$_2$NH$_2$ (1.01 ml, 32.3 mmol). After the reaction was stirred at room temperature for about 4 h, the solution was precipitated, filtered, washed with CH$_2$Cl$_2$, MeOH. The organic layer was concentrated to give 8 (2.5 g), which was used without further purification. LRMS (M+H$^+$) m/z 489.2.

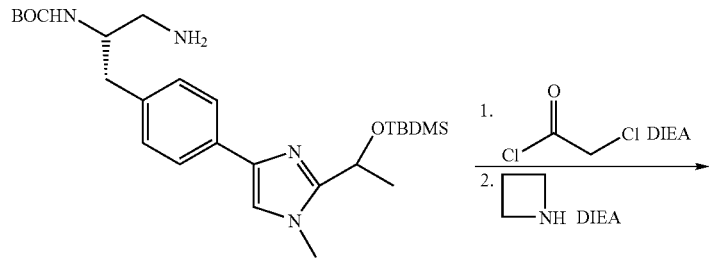

8

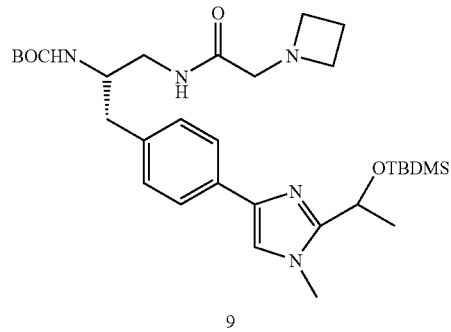

9

To a solution of 8 (1.5 g, 3.1 mmol) in CH₂Cl₂/CH₃CN (15 ml/15 ml) were added DIEA (588 µL, 3.4 mmol) and chloroacetyl chloride (269 µL, 3.4 mmol). After the reaction was stirred at rt for 10 min, azetidine (2 ml, 30.7 mmol) and DIEA (2.7 ml, 15.3 mmol) were added. The reaction mixture was stirred overnight. The solution was concentrated and diluted between EtOAc and H₂O. The organic layer was washed with brine, dried over Na₂SO₄, filtered and concentrated. The residue was purified by column chromatography using a mixture of hexanes and EtOAc to give 9 (900 mg, 51%) LRMS (M+H⁺) m/z 586.3.

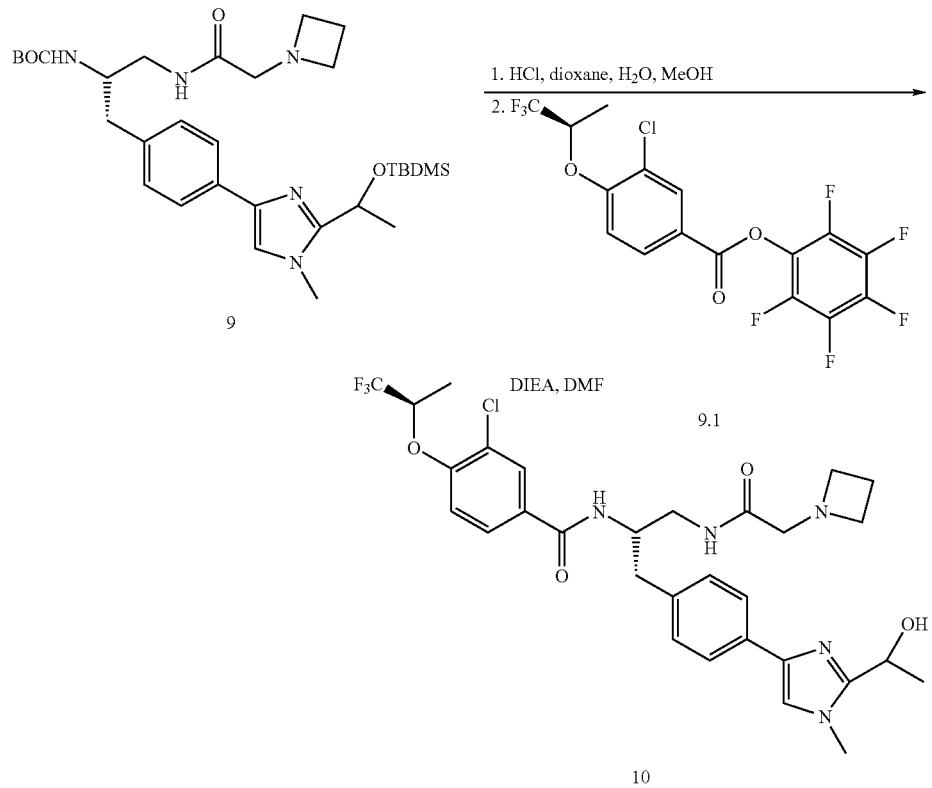

To a solution of 9 (900 mg, 1.53 mmol) in MeOH (1 mL) were added HCl in dioxane (4 N, 2 ml) and HCl in H$_2$O (2 N, 1 ml). The solution was stirred at rt overnight, concentrated to give white solid and directed for the next coupling step. To a DMF (10 ml) solution of the crude compound were added 9.1 (665 mg, 1.53 mmol) and DIEA (800 ul, 4.59 mmol). The mixture was stirred at rt for 1 h and partitioned between EtOAc and H$_2$O. The organic layer was washed with brine, dried over Na$_2$SO$_4$, filtered and concentrated. The residue was purified by reverse-phase HPLC to give 10 (600 mg, 63%). LRMS (M+H$^+$) m/z 622.2.

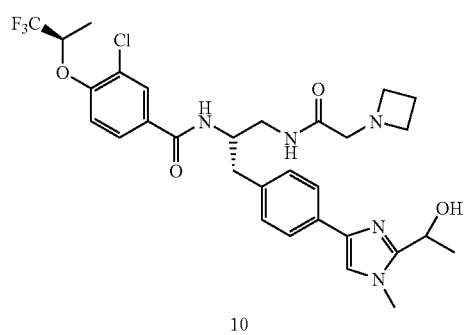

10

MnO$_2$, CH$_2$Cl$_2$

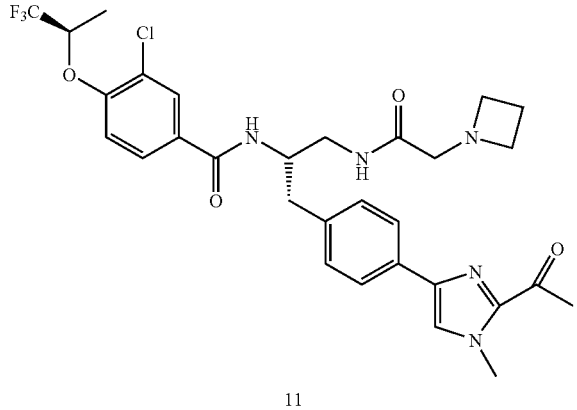

11

To a solution of 10 (160 mg, 0.24 mmol) in DCM (10 mL) was added MnO$_2$ (416 mg, 4.8 mmol). The suspension was stirred for 14 h. The reaction mixture was filtered, and the filtrate was concentrated and purified on reverse-phase HPLC using a mixture of acetonitrile and H$_2$O to give 11 (90 mg, 60%). LRMS (M+H$^+$) m/z 620.1.

Example 98

The following compounds were prepared using the procedures described above:

| Name | MS (m/z) |
|---|---|
| N-(1-{4-[2-(1-Acetylamino-ethyl)-1-ethyl-1H-imidazol-4-yl]-benzyl}-3-hydroxy-propyl)-3-chloro-4-(2,2,2-trifluoro-1-methyl-ethoxy)-benzamide | 498.1 |
| N-{1-[4-(8-isopropenyl-imidazo[1,2-a]pyridin-2-yl)-benzyl]-3-hydroxy-propyl}-3-cyano-4-isopropoxy-benzamide | 555.2 |
| N-(1-{4-[2-(1-Acetylamino-propyl)-1-ethyl-1H-imidazol-4-yl]-benzyl}-3-hydroxy-propyl)-3-chloro-4-(isopropoxy)-benzamide | 541.2 |
| N-[1-(4-{2-[1-(Acetyl-methyl-amino)-ethyl]-1-ethyl-1H-imidazol-4-yl}-benzyl)-3-hydroxy-propyl]-3-chloro-4-(2,2,2-trifluoro-1-methyl-ethoxy)-benzamide | 555.2 |
| N-(1-{4-[2-[1-(Acetyl-methyl-amino)-ethyl]-1-ethyl-1H-imidazol-4-yl]-benzyl}-3-hydroxy-propyl)-3-cyano-4-isopropoxy-benzamide | 546.2 |
| N-{1-[4-(8-Bromo-imidazo[1,2-a]pyridin-2-yl)-benzyl]-3-hydroxy-propyl}-3-chloro-4-isopropoxy-benzamide | 555.3 |
| N-(1-{4-[2-(1-Acetylamino-ethyl)-1-isopropyl-1H-imidazol-4-yl]-benzyl}-3-hydroxy-propyl)-3-chloro-4-isopropoxy-benzamide | 595.2 |
| N-(1-{4-[2-(1-Acetylamino-ethyl)-1-ethyl-1H-imidazol-4-yl]-benzyl}-3-hydroxy-propyl)-3-chloro-4-(2,2,2-trifluoro-1-methyl-ethoxy)-benzamide | 610.2 |
| N-(2-(2-dimethylamino-acetylamino)-1-{4-[8-methyl-imidazo[1,2-a]pyridin-2-yl]-benzyl}-ethyl)-3-cyano-4-isopropoxy-benzamide | 489.2 |
| N-(1-{4-[2-(1-Acetylamino-2-methyl-propyl)-1-ethyl-1H-imidazol-4-yl]-benzyl}-3-hydroxy-propyl)-3-chloro-4-(2,2,2-trifluoro-1-methyl-ethoxy)-benzamide | 629.2 |
| N-{1-[4-(8-chloro-imidazo[1,2-a]pyridin-2-yl)-benzyl]-3-hydroxy-butyl}-3-cyano-4-isopropoxy-benzamide | 639.2 |
| N-(2-(2-dimethylamino-acetylamino)-1-{4-[8-(1-hydroxy-ethyl)-imidazo[1,2-a]pyridin-2-yl]-benzyl}-ethyl)-3-chloro-4-isopropoxy-benzamide | 567.2 |
| N-(2-(2-amino-2-methyl-propionylamino)-1-{4-[8-bromo-imidazo[1,2-a]pyridin-2-yl]-benzyl}-ethyl)-3-cyano-4-isopropoxy-benzamide | 527.2 |
| N-(1-{3-fluoro-4-[2-(1-methyl-1hydroxy-ethyl)-1-ethyl-1H-imidazol-4-yl]-benzyl}-3-hydroxy-propyl)-3-chloro-4-isopropoxy-benzamide | 532.2 |
| N-{1-[2-fluoro-4-(8-methyl-imidazo[1,2-a]pyridin-2-yl)-benzyl]-3-hydroxy-propyl}-3-cyano-4-isopropoxy-benzamide | 528.2 |
| N-{1-[4-(8-acetyl-5-methyl-imidazo[1,2-a]pyridin-2-yl)-benzyl]-3-hydroxy-propyl}-3-cyano-4-isopropoxy-benzamide | 569.2 |
| N-(1-{4-[2-(1-Acetylamino-2-methyl-propyl)-1-ethyl-1H-imidazol-4-yl]-benzyl}-3-hydroxy-propyl)-3-chloro-4-isopropoxy-benzamide | 595.1 |
| N-(1-{4-[2-t-butyl-1-ethyl-1H-imidazol-4-yl]-benzyl}-3-hydroxy-propyl)-3-cyano-4-isopropoxy-benzamide | 503.3 |

-continued

| Name | MS (m/z) |
|---|---|
| N-(2-(2-dimethylamino-acetylamino)-1-{4-[8-bromo-imidazo[1,2-a]pyridin-2-yl]-benzyl}-ethyl)-3-cyano-4-isopropoxy-benzamide | 582.2 |
| N-(1-{4-[2-acetyl-1-methyl-1H-imidazol-4-yl]-benzyl}-3-carbamoyl-propyl)-3-chloro-4-isopropoxy-benzamide | 512.1 |
| N-(1-{4-[2-isobutyryl-1-methyl-1H-imidazol-4-yl]-benzyl}-3-hydroxy-propyl)-3-chloro-4-isopropoxy-benzamide | 514.3 |
| N-(1-{3-fluoro-4-[2-acetyl-1-methyl-1H-imidazol-4-yl]-benzyl}-3-hydroxy-propyl)-3-cyano-4-isopropoxy-benzamide | 533.3 |
| N-[1-[4-(8-Bromo-imidazo[1,2-a]pyridin-2-yl)-benzyl]-2-(2-oxo-tetrahydro-pyrimidin-1-yl)-ethyl]-3-cyano-4-isopropoxy-benzamide | 568.2 |
| N-(1-{4-[2-acetyl-1-methyl-1H-imidazol-4-yl]-benzyl}-3-hydroxy-propyl)-3-cyano-4-(2,2,2-trifluoro-1-methyl-ethoxy)-benzamide | 527.1 (Negative) |
| N-(1-{4-[2-(1-hydroxy-1-methyl-ethyl)-1-(2,2,2-trifluoroethyl)-1H-imidazol-4-yl]-benzyl}-3-hydroxy-propyl)-3-chloro-4-isopropoxy-benzamide | 541.2 |
| N-[1-[4-(2-acetyl-1-ethyl-1H-imidazol-4-yl)-benzyl]-2-(2-hydroxy-acetylamino)-ethyl]-3-chloro-4-isopropoxy-benzamide | 568.2 |
| N-(1-{4-[2-acetyl-1-(2-methoxyethyl)-1H-imidazol-4-yl]-benzyl}-3-hydroxy-propyl)-3-chloro-4-isopropoxy-benzamide | 528.2 |
| N-(2-(2-amino-propionylamino)-1-{4-[8-(1-hydroxy-ethyl)-imidazo[1,2-a]pyridin-2-yl]-benzyl}-ethyl)-3-chloro-4-isopropoxy-benzamide | 503.2 |
| N-(1-{4-[2-acetyl-1-methyl-1H-imidazol-4-yl]-benzyl}-3-hydroxy-propyl)-3-cyano-4-isopropoxy-benzamide | 512.2 |
| N-(1-{4-(8-methyl-5,6,7,8-tetrahydro-imidazo[1,2-a]pyridin-2-yl)-benzyl}-3-hydroxy-propyl)-3-cyano-4-isopropoxy-benzamide | 511.1 |
| N-(1-{4-[2-acetyl-1-propyl-1H-imidazol-4-yl]-benzyl}-3-hydroxy-propyl)-3-chloro-4-isopropoxy-benzamide | 512.2 |
| N-(1-{4-[2-acetyl-1-methyl-1H-imidazol-4-yl]-benzyl}-3-hydroxy-propyl)-3-chloro-4-isopropoxy-benzamide | 484.1 |
| N-(2-(2-amino-propionylamino)-1-{4-[8-methyl-imidazo[1,2-a]pyridin-2-yl]-benzyl}-ethyl)-3-cyano-4-isopropoxy-benzamide | 582.2 |
| N-(1-{4-[2-(1-hydroxy-2-methyl-propyl)-1-ethyl-1H-imidazol-4-yl]-benzyl}-3-hydroxy-propyl)-3-chloro-4-(2,2,2-trifluoro-1-methyl-ethoxy)-benzamide | 586.1 |
| N-(1-{3-fluoro-4-[2-(1-hydroxy-1-methyl-ethyl)-1-ethyl-1H-imidazol-4-yl]-benzyl}-3-hydroxy-propyl)-3-chloro-4-(2,2,2-trifluoro-1-methyl-ethoxy)-benzamide | 513.1 |
| N-(1-{4-[2-(1-hydroxy-1-methyl-ethyl)-1-(2,2,2-trifluoroethyl)-1H-imidazol-4-yl]-benzyl}-3-hydroxy-propyl)-3-cyano-4-isopropoxy-benzamide | 559.2 |
| N-(1-{4-[2-(1-formylamino-ethyl)-1-methyl-1H-imidazol-4-yl]-benzyl}-3-hydroxy-propyl)-3-chloro-4-isopropoxy-benzamide | 489.2 |
| N-(2-(2-hydroxy-acetylamino)-1-{4-[8-(1-hydroxy-ethyl)-imidazo[1,2-a]pyridin-2-yl]-benzyl}-ethyl)-3-chloro-4-isopropoxy-benzamide | 527.1 |
| N-(1-{4-[2-t-butyl-1-methyl-1H-imidazol-4-yl]-benzyl}-3-hydroxy-propyl)-3-cyano-4-isopropoxy-benzamide | 490.2 |
| N-{1-[4-(8-methyl-imidazo[1,2-a]pyridin-2-yl)-benzyl]-3-carbamoyl-propyl}-3-chloro-4-isopropoxy-benzamide | 505.2 |
| N-(1-{4-[2-(1-hydroxy-1-methyl-ethyl)-1-ethyl-1H-imidazol-4-yl]-benzyl}-3-hydroxy-propyl)-3-cyano-4-isopropoxy-benzamide | 502.1 |
| N-(1-{4-[2-acetyl-1-methyl-1H-imidazol-4-yl]-benzyl}-3-carbamoyl-propyl)-3-chloro-4-isopropoxy-benzamide | 516.1 |
| N-(1-{3-fluoro-4-[2-acetyl-1-ethyl-1H-imidazol-4-yl]-benzyl}-3-hydroxy-propyl)-3-chloro-4-isopropoxy-benzamide | 498.1 |
| N-(1-{4-[2-propionyl-1-methyl-1H-imidazol-4-yl]-benzyl}-3-hydroxy-propyl)-3-chloro-4-isopropoxy-benzamide | 537.1 |
| N-(2-(2-hydroxy-acetylamino)-1-{4-[8-methyl-imidazo[1,2-a]pyridin-2-yl]-benzyl}-ethyl)-3-cyano-4-isopropoxy-benzamide | 499.1 |
| N-(1-{4-[2-(3-hydroxy-pent-3-yl)-1-ethyl-1H-imidazol-4-yl]-benzyl}-3-hydroxy-propyl)-3-chloro-4-isopropoxy-benzamide | 542.3 |
| N-(2-(2-dimethylamino-acetylamino)-1-{4-[8-methyl-imidazo[1,2-a]pyridin-2-yl]-benzyl}-ethyl)-3-chloro-4-isopropoxy-benzamide | 552.1 |
| N-{1-[4-(8-methyl-imidazo[1,2-a]pyridin-2-yl)-benzyl]-3-carbamoyl-propyl}-3-chloro-4-isopropoxy-benzamide | 514.2 |
| N-(1-{4-[2-(1-hydroxypropyl)-1-ethyl-1H-imidazol-4-yl]-benzyl}-3-hydroxy-propyl)-3-chloro-4-isopropoxy-benzamide | 497.1 |
| N-(2-(2-hydroxy-acetylamino)-1-{4-[8-methyl-imidazo[1,2-a]pyridin-2-yl]-benzyl}-ethyl)-3-chloro-4-isopropoxy-benzamide | 538.1 |
| N-(1-{4-[2-acetyl-1-methyl-1H-imidazol-4-yl]-benzyl}-3-hydroxy-propyl)-3-chloro-4-(2,2,2-trifluoro-1-methyl-ethoxy)-benzamide | 526.2 |
| N-{1-[4-(8-(1-hydroxy-ethyl)-imidazo[1,2-a]pyridin-2-yl)-benzyl]-3-carbamoyl-propyl}-3-chloro-4-isopropoxy-benzamide | 514.2 |
| N-{1-[2-fluoro-4-(8-methyl-imidazo[1,2-a]pyridin-2-yl)-benzyl]-3-hydroxy-propyl}-3-chloro-4-isopropoxy-benzamide | 559.2 |
| N-{1-[4-(8-methyl-imidazo[1,2-a]pyridin-2-yl)-benzyl]-3-hydroxy-propyl}-3-chloro-4-(2,2,2-trifluoro-1-methyl-ethoxy)-benzamide | 546.1 |

| Name | MS (m/z) |
|---|---|
| N-(1-{4-[2-(1-hydroxy-1-methyl-ethyl)-1-ethyl-1H-imidazol-4-yl]-benzyl}-3-hydroxy-propyl)-3-cyano-4-(2,2,2-trifluoro-1-methyl-ethoxy)-benzamide | 527.2 |
| N-(1-{2,3,5,6-tetrafluoro-4-[2-t-butyl-1-methyl-1H-imidazol-4-yl]-benzyl}-3-hydroxy-propyl)-3-cyano-4-isopropoxy-benzamide | 493.2 |
| N-(1-{4-[2-t-butyl-1-methyl-1H-imidazol-4-yl]-benzyl}-3-hydroxy-propyl)-3-chloro-4-isopropoxy-benzamide | 568.1 |
| N-{1-[4-(8-(1-hydroxy-ethyl)-imidazo[1,2-a]pyridin-2-yl)-benzyl]-3-carbamoyl-propyl}-3-cyano-4-isopropoxy-benzamide | 473.3 |
| N-(1-{4-[2-(1-hydroxy-2-methyl-propyl)-1-ethyl-1H-imidazol-4-yl]-benzyl}-3-hydroxy-propyl)-3-chloro-4-isopropoxy-benzamide | 500.2 |
| N-(1-{4-[2-(1-hydroxy-1-methyl-ethyl)-1-methyl-1H-imidazol-4-yl]-benzyl}-3-hydroxy-propyl)-3-chloro-4-isopropoxy-benzamide | 528.2 |
| N-(1-{4-[2-acetyl-1-isopropyl-1H-imidazol-4-yl]-benzyl}-3-hydroxy-propyl)-3-chloro-4-isopropoxy-benzamide | 512.2 |
| N-(1-{4-[2-trifluoromethyl-1-methyl-1H-imidazol-4-yl]-benzyl}-3-hydroxy-propyl)-3-cyano-4-isopropoxy-benzamide | 512.2 |
| N-(1-hydroxy-1-{4-[2-t-butyl-1-methyl-1H-imidazol-4-yl]-phenyl}-4-hydroxy-butyl)-3-chloro-4-isopropoxy-benzamide | 539.2 |
| N-[1-[4-(8-bromo-imidazo[1,2-a]pyridin-2-yl)-benzyl]-2-(3-methyl-ureido)-ethyl]-3-cyano-4-isopropoxy-benzamide | 491.2 |
| N-(1-{4-[2-(1-hydroxy-1methyl-ethyl)-1-methyl-1H-imidazol-4-yl]-benzyl}-3-hydroxy-propyl)-3-cyano-4-isopropoxy-benzamide | 610.2 |
| N-[1-[4-(2-t-butyl-1-methyl-1H-imidazol-4-yl)-benzyl]-2-(3-methyl-ureido)-ethyl]-3-cyano-4-isopropoxy-benzamide | 501.3 |
| N-(1-{4-[2-t-butyl-1-methyl-1H-imidazol-4-yl]-benzyl}-3-hydroxy-propyl)-3-cyano-4-cyclobutoxy-benzamide | 527.2 |
| N-(1-{4-[2-(methylsulfonyl)-1-methyl-1H-imidazol-4-yl]-benzyl}-3-hydroxy-propyl)-3-cyano-4-isopropoxy-benzamide | 570.1 |
| N-[1-[4-(8-bromo-imidazo[1,2-a]pyridin-2-yl)-benzyl]-2-ureido-ethyl]-3-cyano-4-isopropoxy-benzamide | 527.2 |
| N-(1-{4-[2-(1-hydroxy-2,2-dimethyl-propyl)-1-methyl-1H-imidazol-4-yl]-benzyl}-3-hydroxy-propyl)-3-cyano-4-isopropoxy-benzamide | 513.1 |
| N-(1-{4-[2-(1-hydroxy-1methyl-ethyl)-1-methyl-1H-imidazol-4-yl]-benzyl}-3-hydroxy-propyl)-3-chloro-4-(2,2,2-trifluoro-1-methyl-ethoxy)-benzamide | 554.1 |
| N-(2-(2-amino-propionylamino)-1-{4-[8-bromo-imidazo[1,2-a]pyridin-2-yl]-benzyl}-ethyl)-3-chloro-4-isopropoxy-benzamide | 568.2 |
| N-(2-(2-hydroxy-propionylamino)-1-{4-[8-methyl-imidazo[1,2-a]pyridin-2-yl]-benzyl}-ethyl)-3-cyano-4-isopropoxy-benzamide | 593.2 |
| N-{1-[4-(8-methyl-imidazo[1,2-a]pyridin-2-yl)-benzyl]-3-hydroxy-propyl}-2,3-dichhloro-4-isopropoxy-benzamide | 552.1 |
| N-(1-{4-[2-acetyl-1-ethyl-1H-imidazol-4-yl]-benzyl}-3-hydroxy-propyl)-3-chloro-4-(2,2,2-trifluoro-1-methyl-ethoxy)-benzamide | 547.1 |
| N-{1-[4-(5-methyl-imidazo[1,2-a]pyridin-2-yl)-benzyl]-3-hydroxy-propyl}-3-cyano-4-isopropoxy-benzamide | 474.2 |
| N-(1-{4-[2-acetyl-1-methyl-1H-imidazol-4-yl]-benzyl}-3-hydroxy-propyl)-3-cyano-4-(isopropylamino)-benzamide | 478.1 |
| N-(1-{4-[2-t-butyl-1-methyl-1H-imidazol-4-yl]-benzyl}-3-hydroxy-propyl)-2-amino-3-chloro-4-isopropoxy-benzamide | 622.2 |
| N-{1-[4-(8-(1-methyl-1-hydroxy-ethyl)-imidazo[1,2-a]pyridin-2-yl)-benzyl]-3-hydroxy-propyl}-3-cyano-4-isopropoxy-benzamide | 543.1 |
| N-(1-{4-[2-(1-(methoxycarbonylamino)-ethyl)-1-methyl-1H-imidazol-4-yl]-benzyl}-3-hydroxy-propyl)-3-chloro-4-isopropoxy-benzamide | 611.2 |
| N-(2-(2-hydroxy-acetylamino)-1-{4-[8-(1-hydroxy-ethyl)-imidazo[1,2-a]pyridin-2-yl]-benzyl}-ethyl)-3-cyano-4-isopropoxy-benzamide | 625.2 |
| N-{1-[4-(imidazo[1,2-a]pyridin-2-yl)-benzyl]-3-hydroxy-propyl}-3-cyano-4-isopropoxy-benzamide | 511.2 |
| N-{1-[4-(8-methyl-imidazo[1,2-a]pyridin-2-yl)-benzyl]-3-hydroxy-propyl}-3-chloro-4-(isopropylamino)-benzamide | 491.1 |
| N-(2-(3-amino-propionylamino)-1-{4-[8-bromo-imidazo[1,2-a]pyridin-2-yl]-benzyl}-ethyl)-3-chloro-4-isopropoxy-benzamide | 513.3 |
| N-{1-[2,6-difluoro-4-(8-methyl-5,6,7,8-tetrahydro-imidazo[1,2-a]pyridin-2-yl)-benzyl]-3-hydroxy-propyl}-3-chloro-4-isopropoxy-benzamide | 579.1 |
| N-[1-[4-(8-bromo-imidazo[1,2-a]pyridin-2-yl)-benzyl]-2-(2-oxo-imidazolidinyl)-ethyl]-3-chloro-4-isopropoxy-benzamide | 556.2 |
| N-[1-[4-(2-(1-hydroxy-1-methyl-ethyl)-1-methyl-1H-imidazol-4-yl)-benzyl]-2-(2-amino-propionylamino)-ethyl]-3-chloro-4-isopropoxy-benzamide | 526.2 |
| N-(1-{4-[2-acetyl-1-butyl-1H-imidazol-4-yl]-benzyl}-3-hydroxy-propyl)-3-chloro-4-isopropoxy-benzamide | 554.2 |
| N-(1-{4-[2-(1-acetylamino-ethyl)-1-ethyl-1H-imidazol-4-yl]-benzyl}-2-carbamoyl-ethyl)-3-chloro-4-isopropoxy-benzamide | 475.5 |
| N-(1-{4-[4-t-butyl-1H-imidazol-2-yl]-benzyl}-3-hydroxy-propyl)-3-cyano-4-isopropoxy-benzamide | 503.3 |
| N-(2-(2-hydroxy-propionylamino)-1-{4-[8-(1-hydroxy-ethyl)-imidazo[1,2-a]pyridin-2-yl]-benzyl}-ethyl)-3-cyano-4-isopropoxy-benzamide | 566.1 |

-continued

| Name | MS (m/z) |
|---|---|
| N-(1-{4-[2-isobutyryl-1-methyl-1H-imidazol-4-yl]-benzyl}-3-hydroxy-propyl)-3-chloro-4-(2,2,2-trifluoro-1-methyl-ethoxy)-benzamide | 518.2 |
| N-(1-{4-[2-t-butyl-1-(2-aminoethyl)-1H-imidazol-4-yl]-benzyl}-3-hydroxy-propyl)-3-cyano-4-isopropoxy-benzamide | 513.1 |
| N-(2-(2-dimethylamino-acetylamino)-1-{4-[8-carbamoyl-imidazo[1,2-a]pyridin-2-yl]-benzyl}-ethyl)-3-cyano-4-isopropoxy-benzamide | 556.1 |
| N-(2-(2-amino-acetylamino)-1-{4-[8-bromo-imidazo[1,2-a]pyridin-2-yl]-benzyl}-ethyl)-3-cyano-4-isopropoxy-benzamide | 513.2 |
| N-(2-{4-[2-acetyl-1-methyl-1H-imidazol-4-yl]-phenyl}-1-(5-methyl-[1,2,4]oxadiazol-3-yl)-ethyl)-3-cyano-4-isopropoxy-benzamide | 530.3 |
| N-[1-[4-(2-t-butyl-1-methyl-1H-imidazol-4-yl)-benzyl]-2-hydroxy-3-azido-propyl]-3-cyano-4-isopropoxy-benzamide | 489.2 |
| N-{1-[4-(8-(1-hydroxy-ethyl)-imidazo[1,2-a]pyridin-2-yl)-benzyl]-3-hydroxy-propyl}-3-cyano-4-isopropoxy-benzamide | 498.1 |
| N-(1-{4-[5-t-butyl-4-methyl-1H-imidazol-2-yl]-benzyl}-3-hydroxy-propyl)-3-chloro-4-isopropoxy-benzamide | 581.1 |
| N-{1-[4-(8-methyl-imidazo[1,2-a]pyridin-2-yl)-benzyl]-3-hydroxy-butyl}-3-cyano-4-isopropoxy-benzamide | 489.2 |
| N-(2-(2-amino-propionylamino)-1-{4-[8-bromo-imidazo[1,2-a]pyridin-2-yl]-benzyl}-ethyl)-3-chloro-4-isopropoxy-benzamide | 483.2 |
| N-(1-{4-[2-acetyl-1-methyl-1H-imidazol-4-yl]-benzyl}-3-hydroxy-propyl)-3-chloro-4-isopropylamino-benzamide | 475.5 |

Example 99

Inhibition of Cellular Viability in Tumor Cell Lines Treated with Mitotic Kinesin Inhibitors Materials and Solutions:
Cells: SKOV3, Ovarian Cancer (human).
Media: Phenol Red Free RPMI+5% Fetal Bovine Serum+2 mM L-glutamine.
Colorimetric Agent for Determining Cell Viability: Promega MTS tetrazolium compound.
Control Compound for max cell kill: Topotecan, 1 µM.
Procedure: Day 1—Cell Plating:
Adherent SKOV3 cells are washed with 10 mLs of PBS followed by the addition of 2 mLs of 0.25% trypsin and incubation for 5 minutes at 37° C. The cells are rinsed from the flask using 8 mL of media (phenol red-free RPMI+5% FBS) and transferred to fresh flask. Cell concentration is determined using a Coulter counter and the appropriate volume of cells to achieve 1000 cells/100 µL is calculated. 100 µL of media cell suspension (adjusted to 1000 cells/100 µL) is added to all wells of 96-well plates, followed by incubation for 18 to 24 hours at 37° C., 100% humidity, and 5% $CO_2$, allowing the cells to adhere to the plates.

Procedure: Day 2—Compound Addition:
To one column of the wells of an autoclaved assay block are added an initial 2.5 µL of test compound(s) at 400× the highest desired concentration. 1.25 µL of 400× (400 µM) Topotecan is added to other wells (ODs from these wells are used to subtract out for background absorbance of dead cells and vehicle). 500 µL of media without DMSO are added to the wells containing test compound, and 250 µL to the Topotecan wells. 250 µL of media+0.5% DMSO is added to all remaining wells, into which the test compound(s) are serially diluted. By row, compound-containing media is replica plated (in duplicate) from the assay block to the corresponding cell plates. The cell plates are incubated for 72 hours at 37° C., 100% humidity, and 5% $CO_2$.

Procedure: Day 4—MTS Addition and OD Reading:
The plates are removed from the incubator and 40 µl MTS/PMS is added to each well. Plates are then incubated for 120 minutes at 37° C., 100% humidity, 5% $CO_2$, followed by reading the ODs at 490 nm after a 5 second shaking cycle in a ninety-six well spectrophotometer.

Data Analysis
The normalized % of control (absorbance-background) is calculated and an XLfit is used to generate a dose-response curve from which the concentration of compound required to inhibit viability by 50% is determined. The compounds of the present invention show activity when tested by this method.

Example 100

Application of a Mitotic Kinesin Inhibitor

Human tumor cells Skov-3 (ovarian) were plated in 96-well plates at densities of 4,000 cells per well, allowed to adhere for 24 hours, and treated with various concentrations of the test compounds for 24 hours. Cells were fixed in 4% formaldehyde and stained with antitubulin antibodies (subsequently recognized using fluorescently-labeled secondary antibody) and Hoechst dye (which stains DNA).

Visual inspection revealed that the compounds caused cell cycle arrest.

Example 101

Inhibition of Cellular Proliferation in Tumor Cell Lines Treated with Mitotic Kinesin Inhibitors Cells were plated in 96-well plates at densities from 1000-2500 cells/well of a 96-well plate and allowed to adhere/grow for 24 hours. They were then treated with various concentrations of drug for 48 hours. The time at which compounds are added is considered $T_0$. A tetrazolium-based assay using the reagent 3-(4,5-dimethylthiazol-2-yl)-5-(3-carboxymethoxyphenyl)-2-(4-sulfophenyl)-2H-tetrazolium (MTS) (U.S. Pat. No. 5,185,450) (see Promega product catalog #G3580, CellTiter 96® AQ$_{ueous}$ One Solution Cell Proliferation Assay) was used to determine the number of viable cells at To and the number of cells remaining after 48 hours compound exposure. The number of cells remaining after 48 hours was compared to the number of viable cells at the time of drug addition, allowing for calculation of growth inhibition.

The growth over 48 hours of cells in control wells that had been treated with vehicle only (0.25% DMSO) is considered 100% growth and the growth of cells in wells with compounds is compared to this. Mitotic kinesin inhibitors inhibited cell proliferation in human ovarian tumor cell lines (SKOV-3).

A $Gi_{50}$ was calculated by plotting the concentration of compound in µM vs the percentage of cell growth of cell growth in treated wells. The $Gi_{50}$ calculated for the compounds is the estimated concentration at which growth is inhibited by 50% compared to control, i.e., the concentration at which:

$$100 \times [(Treated_{48} - T_0)/(Control_{48} - T_0)] = 50.$$

All concentrations of compounds are tested in duplicate and controls are averaged over 12 wells. A very similar 96-well plate layout and $Gi_{50}$ calculation scheme is used by the National Cancer Institute (see Monks, et al., J. Natl. Cancer Inst. 83:757-766 (1991)). However, the method by which the National Cancer Institute quantitates cell number does not use MTS, but instead employs alternative methods.

Example 102

Calculation of $IC_{50}$

Measurement of a composition's $IC_{50}$ uses an ATPase assay. The following solutions are used: Solution 1 consists of 3 mM phosphoenolpyruvate potassium salt (Sigma P-7127), 2 mM ATP (Sigma A-3377), 1 mM IDTT (Sigma D-9779), 5 µM paclitaxel (Sigma T-7402), 10 ppm antifoam 289 (Sigma A-8436), 25 mM Pipes/KOH pH 6.8 (Sigma P6757), 2 mM MgCl2 (VWR JT400301), and 1 mM EGTA (Sigma E3889). Solution 2 consists of 1 mM NADH (Sigma N8129), 0.2 mg/ml BSA (Sigma A7906), pyruvate kinase 7 U/ml, L-lactate dehydrogenase 10 U/ml (Sigma P0294), 100 nM motor domain of a mitotic kinesin, 50 µg/ml microtubules, 1 mM DTT (Sigma D9779), 5 µM paclitaxel (Sigma T-7402), 10 ppm antifoam 289 (Sigma A-8436), 25 mM Pipes/KOH pH 6.8 (Sigma P6757), 2 mM MgCl2 (VWR JT4003-01), and 1 mM EGTA (Sigma E3889). Serial dilutions (8-12 two-fold dilutions) of the composition are made in a 96-well microtiter plate (Corning Costar 3695) using Solution 1. Following serial dilution each well has 50 µl of Solution 1. The reaction is started by adding 50 µl of solution 2 to each well. This may be done with a multichannel pipettor either manually or with automated liquid handling devices. The microtiter plate is then transferred to a microplate absorbance reader and multiple absorbance readings at 340 nm are taken for each well in a kinetic mode. The observed rate of change, which is proportional to the ATPase rate, is then plotted as a function of the compound concentration. For a standard $IC_{50}$ determination the data acquired is fit by the following four parameter equation using a nonlinear fitting program (e.g., Grafit 4):

$$y = \frac{Range}{1 + \left(\frac{x}{IC_{50}}\right)^s} + Background$$

where y is the observed rate and x the compound concentration.

Other chemical entities of this class were found to inhibit cell proliferation, although $GI_{50}$ values varied, $GI_{50}$ values for the chemical entities tested ranged from 200 nM to greater than the highest concentration tested. By this we mean that although most of the chemical entities that inhibited mitotic kinesin activity biochemically did inhibit cell proliferation, for some, at the highest concentration tested (generally about 20 µM), cell growth was inhibited less than 50%. Many of the chemical entities have $GI_{50}$ values less than 10 µM, and several have $GI_{50}$ values less than 1 µM. Anti-proliferative compounds that have been successfully applied in the clinic to treatment of cancer (cancer chemotherapeutics) have $GI_{50}$'s that vary greatly. For example, in A549 cells, paclitaxel $GI_{50}$ is 4 nM, doxorubicin is 63 nM, 5-fluorouracil is 1 and hydroxyurea is 500 µM (data provided by National Cancer Institute, Developmental Therapeutic Program. Therefore, compounds that inhibit cellular proliferation at virtually any concentration may be useful.

What is claimed is:

1. A compound of Formula V

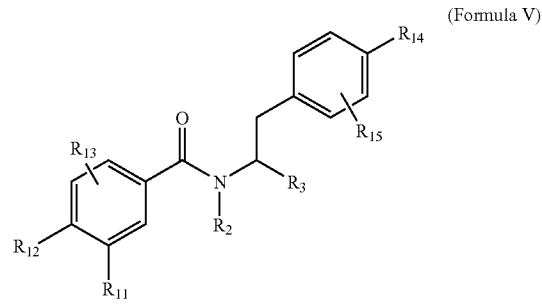

(Formula V)

or a pharmaceutically acceptable salt thereof, wherein
$R_2$ is hydrogen or lower alkyl;
$R_3$ is lower alkyl substituted with a hydroxyl or a phosphate ester thereof;
$R_{11}$ is hydrogen, cyano, nitro, or halo; sulfonyl
$R_{12}$ is lower alkoxy or 2,2,2-trifluoro-1-methyl-ethoxy;
$R_{13}$ is hydrogen;
$R_{14}$ is 1H-imidazol-2-yl, pyrazol-3-yl, or 1H-imidazol-4-yl, each of which is optionally substituted with one, two, or three groups chosen from lower alkyl, halo, acyl, sulfonyl, cyano, nitro, amino, heteroaryl, trifluoromethyl, trifluoroethyl, lower alkyl substituted with hydroxy or lower alkoxy, and lower alkyl substituted with an amino group wherein the amino group is further optionally substituted with a lower alkyl group and/or a group —C(O)$R^b$ wherein $R^b$ is chosen from hydrogen, lower alkoxy, amino, (lower alkyl)amino, di-(lower alkyl)amino, $C_1$-$C_6$ alkyl, aryl, and heteroaryl; and
$R_{15}$ is chosen from hydrogen, halo, hydroxyl, and lower alkyl.

2. The compound of claim 1, or a pharmaceutically acceptable salt thereof, wherein $R_{15}$ is hydrogen.

3. The compound of claim 1, or a pharmaceutically acceptable salt thereof, wherein $R_{11}$ is chloro or cyano.

4. The compound of claim 1, or a pharmaceutically acceptable salt thereof, wherein $R_{12}$ is propoxy or 2,2,2-trifluoro-1-methyl-ethoxy.

5. The compound of claim 1, or a pharmaceutically acceptable salt thereof, wherein $R_2$ is hydrogen.

6. A composition comprising a pharmaceutical excipient and a compound of claim 1, or a pharmaceutically acceptable salt thereof.

7. The compound of claim 1, or a pharmaceutically acceptable salt thereof, wherein $R_{14}$ is chosen from 1H-imidazol-2- yl, and 1H-imidazol-4-yl, each of which is optionally substituted with one or two groups chosen from lower alkyl, lower alkyl substituted with hydroxy, and lower alkyl substituted with an amino group wherein the amino group is further substituted with a group —C(O)R$^b$ wherein R$^b$ is C$_1$-C$_6$ alkyl.

8. The compound of claim 1, or a pharmaceutically acceptable salt thereof, wherein R$_{14}$ is chosen from
- 2-(1-Acetylamino-ethyl)-1-ethyl-1H-imidazol-4-yl;
- 2-acetyl-1-ethyl-1H-imidazol-4-yl;
- 2-(1-Acetylamino-propyl)-1-ethyl-1H-imidazol-4-yl;
- 2-(1-Acetylamino-ethyl)-1-ethyl-1H-imidazol-4-yl;
- 2-[1-(Acetyl-methyl-amino)-ethyl]-1-ethyl-1H-imidazol-4-yl;
- 2-(1-Acetylamino-ethyl)-1-propyl-1H-imidazol-4-yl;
- 2-(1-Acetylamino-ethyl)-1-ethyl-1H-imidazol-4-yl;
- 2-[1-(3-methyl-ureido)-ethyl]-1-ethyl-1H-imidazol-4-yl;
- 2-(1-Acetylamino-ethyl)-1-isopropyl-1H-imidazol-4-yl
- 2-(1-Acetylamino-2-methyl-propyl)-1-ethyl-1H-imidazol-4-yl;
- 2-(1-(isopropoxycarbonylamino)-ethyl)-1-ethyl-1H-imidazol-4-yl;
- 2-(1-formylamino-ethyl)-1-ethyl-1H-imidazol-4-yl;
- 2-(1-methyl-1-hydroxy-ethyl)-1-ethyl-1H-imidazol-4-yl;
- 2-acetyl-1-(3-hydroxypropyl)-1H-imidazol-4-yl;
- 2-t-butyl-1-ethyl-1H-imidazol-4-yl;
- 2-t-butyl-1-methyl-1H-imidazol-4-yl;
- 2-acetyl-1-methyl-1H-imidazol-4-yl;
- 2-isobutyryl-1-methyl-1H-imidazol-4-yl;
- 2-acetyl-1-(2-hydroxy-ethyl)-1H-imidazol-4-yl;
- 2-(1-methyl-1-hydroxy-ethyl)-1-ethyl-1H-imidazol-4-yl;
- 2-(3-hydroxy-pent-3-yl)-1-ethyl-1H-imidazol-4-yl;
- 2-(1-hydroxy-1-methyl-ethyl)-1-(2,2,2-trifluoroethyl)-1H-imidazol-4-yl;
- 2-acetyl-1-(2-methoxyethyl)-1H-imidazol-4-yl;
- 2-acetyl-1-propyl-1H-imidazol-4-yl;
- 2-(1-hydroxy-2-methyl-propyl)-1-ethyl-1H-imidazol-4-yl;
- 2-(1-hydroxy-1-methyl-ethyl)-1-ethyl-1H-imidazol-4-yl;
- 2-propionyl-1-methyl-1H-imidazol-4-yl;
- 2-(1-hydroxy-1-methyl-ethyl)-1-(2,2,2-trifluoroethyl)-1H-imidazol-4-yl;
- 2-(1-formylamino-ethyl)-1-methyl-1H-imidazol-4-yl;
- 2-(1-hydroxy-1-methyl-ethyl)-1-methyl-1H-imidazol-4-yl;
- 2-(1-acetylamino-ethyl)-1-methyl-1H-imidazol-4-yl;
- 2-(1-hydroxy-1-methyl-ethyl)-1-ethyl-1H-imidazol-4-yl; and
- 2-(3-hydroxy-pent-3-yl)-1-ethyl-1H-imidazol-4-yl.

9. The compound of claim 8, or a pharmaceutically acceptable salt thereof, wherein R$_{14}$ is chosen from
- 2-(1-Acetylamino-ethyl)-1-ethyl-1H-imidazol-4-yl;
- 2-(1-methyl-1-hydroxy-ethyl)-1-ethyl-1H-imidazol-4-yl; and
- 2-(1-hydroxy-1-methyl-ethyl)-1-methyl-1H-imidazol-4-yl.

10. The compound of claim 1, or a pharmaceutically acceptable salt thereof, wherein R$_3$ is —CH$_2$CH$_2$OH.

* * * * *